(12) United States Patent
Beckett et al.

(10) Patent No.: US 10,702,418 B2
(45) Date of Patent: Jul. 7, 2020

(54) NEGATIVE PRESSURE WOUND THERAPY APPARATUS

(71) Applicant: Smith & Nephew PLC, Watford, Hertfordshire (GB)

(72) Inventors: Trevor John Beckett, Cambridge (GB); Iacopo Claudio Ferrari, Milan (IT); Christopher John Fryer, York (GB); Alexander David Norman, Cambridge (GB); Christian Riva, Milan (IT); Gary Stacey, Cambridge (GB)

(73) Assignee: Smith & Nephew PLC, Watford (GB)

( * ) Notice: Subject to any disclaimer, the term of this patent is extended or adjusted under 35 U.S.C. 154(b) by 281 days.

(21) Appl. No.: 15/406,585

(22) Filed: Jan. 13, 2017

(65) Prior Publication Data
US 2017/0181894 A1    Jun. 29, 2017

Related U.S. Application Data

(63) Continuation of application No. 14/401,356, filed as application No. PCT/IB2013/001513 on May 15, 2013, now Pat. No. 9,545,465.
(Continued)

(51) Int. Cl.
*A61M 1/00* (2006.01)
*A61F 13/00* (2006.01)
(Continued)

(52) U.S. Cl.
CPC ....... *A61F 13/00068* (2013.01); *A61M 1/009* (2014.02); *A61M 1/0072* (2014.02);
(Continued)

(58) Field of Classification Search
CPC .............. A61F 13/00068; A61F 1/0072; A61F 1/0088; A61M 1/009; A61M 2209/088;
(Continued)

(56) References Cited

U.S. PATENT DOCUMENTS 3,787,882 A   1/1974   Fillmore et al.
3,972,328 A   8/1976   Chen
(Continued)

FOREIGN PATENT DOCUMENTS

CN   101676563   3/2010
DE   34 43 101   5/1986
(Continued)

OTHER PUBLICATIONS

U.S. Appl. No. 61/828,604, filed May 29, 2013, Collinson et al.
(Continued)

*Primary Examiner* — Kai H Weng
(74) *Attorney, Agent, or Firm* — Knobbe, Martens, Olson & Bear LLP

(57) ABSTRACT

Some embodiments disclosed herein are directed to a pump assembly comprising a voice coil, a magnet and a diaphragm, wherein the voice coil is configured to move the diaphragm to pump a fluid through the pump assembly in response to a drive signal applied to the voice coil. Some embodiments disclosed herein are directed to an apparatus for applying negative pressure to a wound comprising a source of negative pressure configured to be coupled to a dressing, the source of negative comprising a voice coil actuator and a diaphragm, and a controller configured to produce a drive signal for the voice coil actuator.

26 Claims, 303 Drawing Sheets

Related U.S. Application Data

(60) Provisional application No. 61/791,984, filed on Mar. 15, 2013, provisional application No. 61/729,288, filed on Nov. 21, 2012, provisional application No. 61/678,563, filed on Aug. 1, 2012, provisional application No. 61/647,397, filed on May 15, 2012.

(51) Int. Cl.
  *F04B 49/06* (2006.01)
  *A61M 27/00* (2006.01)
  *F04B 43/00* (2006.01)
  *F04B 43/04* (2006.01)
  *F04B 45/047* (2006.01)
  *F04B 53/10* (2006.01)

(52) U.S. Cl.
  CPC .......... *A61M 1/0088* (2013.01); *A61M 27/00* (2013.01); *F04B 43/0054* (2013.01); *F04B 43/04* (2013.01); *F04B 45/047* (2013.01); *F04B 49/06* (2013.01); *F04B 53/10* (2013.01); *A61F 2013/00174* (2013.01); *A61M 2205/42* (2013.01); *A61M 2205/8206* (2013.01); *A61M 2209/088* (2013.01)

(58) Field of Classification Search
  CPC ..... A61M 27/00; F04B 43/0054; F04B 43/04; F04B 45/047; F04B 53/10
  See application file for complete search history.

(56) References Cited

U.S. PATENT DOCUMENTS

| | | |
|---|---|---|
| 4,015,912 A | 4/1977 | Kofink |
| 4,293,609 A | 10/1981 | Erickson |
| 4,321,020 A | 3/1982 | Mittal |
| 4,460,642 A | 7/1984 | Errede et al. |
| 4,578,060 A | 3/1986 | Huck et al. |
| 4,585,397 A | 4/1986 | Crawford et al. |
| 4,599,052 A | 7/1986 | Langen et al. |
| 4,604,313 A | 8/1986 | McFarland et al. |
| 4,643,641 A | 2/1987 | Clausen et al. |
| 4,846,164 A | 7/1989 | Martz |
| 4,969,880 A | 11/1990 | Zamierowski |
| 4,979,944 A | 12/1990 | Luzsicza |
| 4,988,345 A | 1/1991 | Reising |
| 5,115,801 A | 5/1992 | Cartmell et al. |
| 5,160,328 A | 11/1992 | Cartmell et al. |
| 5,197,945 A | 3/1993 | Cole et al. |
| 5,222,714 A | 6/1993 | Morinigo et al. |
| 5,238,732 A | 8/1993 | Krishnan |
| 5,246,353 A | 9/1993 | Sohn |
| 5,291,822 A | 3/1994 | Alsobrooks et al. |
| 5,336,219 A | 8/1994 | Krantz |
| 5,349,896 A | 9/1994 | Connelly et al. |
| 5,354,261 A | 10/1994 | Clark et al. |
| 5,358,494 A | 10/1994 | Svedman |
| 5,360,445 A | 11/1994 | Goldowsky |
| 5,364,381 A | 11/1994 | Soga et al. |
| 5,380,294 A | 1/1995 | Persson |
| 5,391,179 A | 2/1995 | Mezzoli |
| 5,417,743 A | 5/1995 | Dauber |
| 5,447,492 A | 9/1995 | Cartmell et al. |
| 5,449,003 A | 9/1995 | Sugimura |
| 5,449,347 A | 9/1995 | Preen et al. |
| 5,456,660 A | 10/1995 | Reich et al. |
| 5,466,229 A | 11/1995 | Elson |
| 5,470,585 A | 11/1995 | Gilchrist |
| 5,480,377 A | 1/1996 | Cartmell et al. |
| 5,492,313 A | 2/1996 | Pan et al. |
| 5,497,788 A | 3/1996 | Inman et al. |
| 5,538,500 A | 7/1996 | Peterson |
| 5,545,151 A | 8/1996 | O'Connor et al. |
| 5,549,584 A | 8/1996 | Gross |
| 5,562,107 A | 10/1996 | Lavender et al. |
| 5,579,765 A | 12/1996 | Cox et al. |
| 5,591,297 A | 1/1997 | Ahr |
| 5,603,946 A | 2/1997 | Constantine |
| 5,630,855 A | 5/1997 | Lundback |
| 5,634,391 A | 6/1997 | Eady |
| 5,636,643 A | 6/1997 | Argenta et al. |
| 5,637,080 A | 6/1997 | Geng |
| 5,645,081 A | 7/1997 | Argenta et al. |
| 5,662,599 A | 9/1997 | Reich et al. |
| 5,676,525 A | 10/1997 | Berner et al. |
| 5,685,214 A | 11/1997 | Neff et al. |
| 5,687,633 A | 11/1997 | Eady |
| 5,688,516 A | 11/1997 | Raad et al. |
| 5,693,013 A | 12/1997 | Geuder |
| 5,702,356 A | 12/1997 | Hathman |
| 5,704,905 A | 1/1998 | Jensen et al. |
| 5,707,173 A | 1/1998 | Cottone et al. |
| 5,713,384 A | 2/1998 | Roach et al. |
| 5,730,587 A | 3/1998 | Snyder et al. |
| 5,743,170 A | 4/1998 | Forman et al. |
| 5,759,570 A | 6/1998 | Arnold |
| 5,762,638 A | 6/1998 | Shikani et al. |
| 5,769,608 A | 6/1998 | Seale |
| 5,785,508 A | 7/1998 | Bolt |
| 5,827,213 A | 10/1998 | Jensen |
| 5,840,052 A | 11/1998 | Johns |
| 5,843,025 A | 12/1998 | Shaari |
| 5,863,184 A | 1/1999 | Juterbock et al. |
| 5,882,743 A | 3/1999 | McConnell |
| 5,897,296 A | 4/1999 | Yamamoto et al. |
| 5,897,541 A | 4/1999 | Uitenbrock et al. |
| 5,950,523 A | 9/1999 | Reynolds |
| 6,040,493 A | 3/2000 | Cooke et al. |
| 6,056,519 A | 5/2000 | Morita et al. |
| 6,068,588 A | 5/2000 | Goldowsky |
| 6,071,267 A | 6/2000 | Zamierowski |
| 6,075,177 A | 6/2000 | Bahia et al. |
| 6,080,685 A | 6/2000 | Eady |
| 6,102,205 A | 8/2000 | Greff et al. |
| 6,102,680 A | 8/2000 | Fraser et al. |
| 6,124,520 A | 9/2000 | Roberts |
| 6,124,521 A | 9/2000 | Roberts |
| 6,138,550 A | 10/2000 | Fingar, Jr. |
| 6,142,982 A | 11/2000 | Hunt et al. |
| 6,145,430 A | 11/2000 | Able et al. |
| 6,158,327 A | 12/2000 | Huss |
| 6,162,194 A | 12/2000 | Shipp |
| 6,174,136 B1 | 1/2001 | Kilayko et al. |
| 6,174,306 B1 | 1/2001 | Fleischmann |
| 6,227,825 B1 | 5/2001 | Vay |
| 6,230,609 B1 | 5/2001 | Fingar |
| 6,231,310 B1 | 5/2001 | Tojo et al. |
| 6,249,198 B1 | 6/2001 | Clark et al. |
| 6,297,423 B1 | 10/2001 | Schoenfeldt et al. |
| 6,323,568 B1 | 11/2001 | Zabar |
| 6,327,960 B1 | 12/2001 | Heimueller et al. |
| 6,343,539 B1 | 2/2002 | Du |
| 6,362,390 B1 | 3/2002 | Carlucci et al. |
| 6,388,417 B1 | 5/2002 | Keith |
| 6,413,057 B1 | 7/2002 | Hong et al. |
| 6,506,175 B1 | 1/2003 | Goldstein |
| 6,514,047 B2 | 2/2003 | Burr et al. |
| 6,528,696 B1 | 3/2003 | Ireland |
| 6,540,490 B1 | 4/2003 | Lilie |
| 6,589,028 B1 | 7/2003 | Eckerbom et al. |
| 6,604,908 B1 | 8/2003 | Bryant et al. |
| 6,613,953 B1 | 9/2003 | Altura |
| 6,618,221 B2 | 9/2003 | Gillis et al. |
| 6,623,255 B2 | 9/2003 | Joong et al. |
| 6,626,891 B2 | 9/2003 | Ohmstede |
| 6,638,035 B1 | 10/2003 | Puff |
| 6,652,252 B2 | 11/2003 | Zabar |
| 6,655,257 B1 | 12/2003 | Meyer |
| 6,673,036 B1 | 1/2004 | Britto |
| 6,685,681 B2 | 2/2004 | Lockwood et al. |
| 6,719,742 B1 | 4/2004 | McCormack et al. |
| 6,752,794 B2 | 6/2004 | Lockwood et al. |
| 6,764,459 B1 | 7/2004 | Donaldson |
| 6,776,769 B2 | 8/2004 | Smith |

(56) References Cited

U.S. PATENT DOCUMENTS

| | | |
|---|---|---|
| 6,800,074 B2 | 10/2004 | Henley et al. |
| 6,815,846 B2 | 11/2004 | Godkin |
| 6,823,905 B1 | 11/2004 | Smith et al. |
| 6,824,533 B2 | 11/2004 | Risk, Jr. et al. |
| 6,877,419 B2 | 4/2005 | Ohrle et al. |
| 6,885,116 B2 | 4/2005 | Knirck |
| 6,886,116 B1 | 4/2005 | MacLellan et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,033,148 B2 | 4/2006 | Bunner et al. |
| 7,041,057 B1 | 5/2006 | Faupel et al. |
| 7,049,478 B1 | 5/2006 | Smith et al. |
| 7,108,683 B2 | 9/2006 | Zamierowski |
| 7,128,735 B2 | 10/2006 | Weston |
| 7,151,348 B1 | 12/2006 | Ueda et al. |
| 7,294,752 B1 | 11/2007 | Propp |
| 7,361,184 B2 | 4/2008 | Joshi |
| 7,363,850 B2 | 4/2008 | Becker |
| 7,374,409 B2 | 5/2008 | Kawamura |
| 7,381,859 B2 | 6/2008 | Hunt et al. |
| 7,401,703 B2 | 7/2008 | McMichael et al. |
| 7,447,327 B2 | 11/2008 | Kitamura et al. |
| 7,524,315 B2 | 4/2009 | Blott et al. |
| 7,550,034 B2 | 6/2009 | Janse Van Rensburg et al. |
| 7,553,306 B1 | 6/2009 | Hunt et al. |
| 7,569,742 B2 | 8/2009 | Haggstrom et al. |
| 7,615,036 B2 | 11/2009 | Joshi et al. |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,785,247 B2 | 8/2010 | Tatum et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,909,805 B2 | 3/2011 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,105,295 B2 | 1/2012 | Blott et al. |
| 8,118,794 B2 | 2/2012 | Weston |
| 8,152,785 B2 | 4/2012 | Vitaris |
| 8,162,907 B2 | 4/2012 | Heagle |
| 8,167,869 B2 | 5/2012 | Wudyka |
| 8,186,978 B2 | 5/2012 | Tinholt et al. |
| 8,188,331 B2 | 5/2012 | Barta et al. |
| 8,192,409 B2 | 6/2012 | Hardman et al. |
| 8,207,392 B2 | 6/2012 | Haggstrom et al. |
| 8,215,929 B2 | 7/2012 | Shen et al. |
| 8,241,015 B2 | 8/2012 | Lillie |
| 8,241,261 B2 | 8/2012 | Randolph et al. |
| 8,257,327 B2 | 9/2012 | Blott et al. |
| 8,257,328 B2 | 9/2012 | Augustine et al. |
| 8,267,918 B2 | 9/2012 | Johnson et al. |
| 8,282,611 B2 | 10/2012 | Weston |
| 8,294,586 B2 | 10/2012 | Pidgeon et al. |
| 8,303,552 B2 | 11/2012 | Weston |
| 8,323,264 B2 | 12/2012 | Weston et al. |
| 8,350,116 B2 | 1/2013 | Lockwood et al. |
| 8,363,881 B2 | 1/2013 | Godkin |
| 8,366,692 B2 | 2/2013 | Weston |
| 8,372,049 B2 | 2/2013 | Jaeb et al. |
| 8,372,050 B2 | 2/2013 | Jaeb et al. |
| 8,398,614 B2 | 3/2013 | Blott et al. |
| 8,404,921 B2 | 3/2013 | Lee et al. |
| 8,409,157 B2 | 4/2013 | Haggstrom et al. |
| 8,409,160 B2 | 4/2013 | Locke et al. |
| 8,414,519 B2 | 4/2013 | Hudspeth et al. |
| 8,425,478 B2 | 4/2013 | Olson |
| 8,429,778 B2 | 4/2013 | Receveur et al. |
| 8,444,612 B2 | 5/2013 | Patel et al. |
| 8,449,267 B2 | 5/2013 | Debrito et al. |
| 8,460,255 B2 | 6/2013 | Joshi et al. |
| 8,535,296 B2 | 9/2013 | Blott et al. |
| 8,545,464 B2 | 10/2013 | Weston |
| 8,545,466 B2 | 10/2013 | Andresen et al. |
| 8,569,566 B2 | 10/2013 | Blott et al. |
| 8,617,129 B2 | 12/2013 | Hartwell |
| 8,622,981 B2 | 1/2014 | Hartwell et al. |
| 8,628,505 B2 | 1/2014 | Weston |
| 8,641,691 B2 | 2/2014 | Fink et al. |
| 8,646,479 B2 | 2/2014 | Jaeb et al. |
| 8,663,198 B2 | 3/2014 | Buan et al. |
| 8,708,984 B2 | 4/2014 | Robinson et al. |
| 8,715,256 B2 | 5/2014 | Greener |
| 8,734,131 B2 | 5/2014 | McCrone et al. |
| 8,764,732 B2 | 7/2014 | Hartwell |
| 8,791,316 B2 | 7/2014 | Greener |
| 8,795,243 B2 | 8/2014 | Weston |
| 8,808,274 B2 | 8/2014 | Hartwell |
| 8,827,983 B2 | 9/2014 | Braga et al. |
| 8,829,263 B2 | 9/2014 | Haggstrom et al. |
| 8,834,451 B2 | 9/2014 | Blott et al. |
| 8,843,327 B2 | 9/2014 | Vernon-Harcourt et al. |
| 8,905,985 B2 | 12/2014 | Allen et al. |
| 8,945,074 B2 | 2/2015 | Buan et al. |
| 8,956,336 B2 | 2/2015 | Haggstrom et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,127,665 B2 | 9/2015 | Locke et al. |
| 9,199,012 B2 | 12/2015 | Vitaris et al. |
| 9,220,822 B2 | 12/2015 | Hartwell |
| 9,227,000 B2 | 1/2016 | Fink et al. |
| 9,427,505 B2 | 8/2016 | Askem et al. |
| 9,446,178 B2 | 9/2016 | Blott et al. |
| 9,506,463 B2 | 11/2016 | Locke et al. |
| 9,518,575 B2 | 12/2016 | Felber |
| 2001/0001278 A1 | 5/2001 | Drevet |
| 2001/0033795 A1 | 10/2001 | Humpheries |
| 2001/0043870 A1 | 11/2001 | Song |
| 2002/0026946 A1 | 3/2002 | McKay |
| 2002/0122732 A1 | 9/2002 | Oh et al. |
| 2002/0161317 A1 | 10/2002 | Risk et al. |
| 2002/0164255 A1 | 11/2002 | Burr et al. |
| 2003/0035743 A1 | 2/2003 | Lee et al. |
| 2003/0065292 A1 | 4/2003 | Darouiche |
| 2003/0095879 A1 | 5/2003 | Oh et al. |
| 2003/0097100 A1 | 5/2003 | Watson |
| 2003/0099558 A1 | 5/2003 | Chang |
| 2003/0108430 A1 | 6/2003 | Yoshida et al. |
| 2003/0110939 A1 | 6/2003 | Able et al. |
| 2003/0133812 A1 | 7/2003 | Puff et al. |
| 2003/0161735 A1 | 8/2003 | Kim et al. |
| 2003/0162071 A1 | 8/2003 | Yasuda |
| 2003/0175125 A1 | 9/2003 | Kwon et al. |
| 2003/0175135 A1 | 9/2003 | Heo et al. |
| 2003/0230191 A1 | 12/2003 | Ohrle et al. |
| 2004/0005222 A1 | 1/2004 | Yoshida et al. |
| 2004/0021123 A1 | 2/2004 | Howell et al. |
| 2004/0054338 A1 | 3/2004 | Bybordi et al. |
| 2004/0066097 A1 | 4/2004 | Kobayashi et al. |
| 2004/0071568 A1 | 4/2004 | Hyeon |
| 2004/0071572 A1 | 4/2004 | Greter et al. |
| 2004/0115076 A1 | 6/2004 | Lilie et al. |
| 2004/0116551 A1 | 6/2004 | Terry |
| 2004/0118460 A1 | 6/2004 | Stinson |
| 2004/0126250 A1 | 7/2004 | Tsuchiya et al. |
| 2004/0155741 A1 | 8/2004 | Godin |
| 2004/0156527 A1 | 8/2004 | Stiles et al. |
| 2004/0156730 A1 | 8/2004 | Lilie et al. |

(56) References Cited

U.S. PATENT DOCUMENTS

| | | |
|---|---|---|
| 2004/0163713 A1 | 8/2004 | Schulze et al. |
| 2004/0182237 A1 | 9/2004 | Headley et al. |
| 2004/0189103 A1 | 9/2004 | Duncan et al. |
| 2004/0219059 A1 | 11/2004 | Barringer et al. |
| 2005/0031470 A1 | 2/2005 | Lee |
| 2005/0098031 A1 | 5/2005 | Yoon et al. |
| 2005/0100450 A1 | 5/2005 | Bryant et al. |
| 2005/0110190 A1 | 5/2005 | Giardini |
| 2005/0111987 A1 | 5/2005 | Yoo et al. |
| 2005/0123422 A1 | 6/2005 | Lilie |
| 2005/0124966 A1 | 6/2005 | Karpowicz et al. |
| 2005/0129540 A1 | 6/2005 | Puff |
| 2005/0135946 A1 | 6/2005 | Kang et al. |
| 2005/0142007 A1 | 6/2005 | Lee et al. |
| 2005/0142008 A1 | 6/2005 | Jung et al. |
| 2005/0155657 A1 | 7/2005 | Kack et al. |
| 2005/0163635 A1 | 7/2005 | Berwanger et al. |
| 2005/0209560 A1 | 9/2005 | Boukhny et al. |
| 2005/0251117 A1 | 11/2005 | Anderson et al. |
| 2005/0271526 A1 | 12/2005 | Chang et al. |
| 2005/0272142 A1 | 12/2005 | Horita |
| 2005/0276706 A1 | 12/2005 | Radue |
| 2006/0009744 A1 | 1/2006 | Erdman et al. |
| 2006/0017332 A1 | 1/2006 | Kang et al. |
| 2006/0018771 A1 | 1/2006 | Song et al. |
| 2006/0019144 A1 | 1/2006 | Hidaka et al. |
| 2006/0024181 A1 | 2/2006 | Kim |
| 2006/0029675 A1 | 2/2006 | Ginther |
| 2006/0039806 A1 | 2/2006 | Becker |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0073036 A1 | 4/2006 | Debrito et al. |
| 2006/0110259 A1 | 5/2006 | Puff et al. |
| 2006/0118190 A1 | 6/2006 | Takehana et al. |
| 2006/0122558 A1 | 6/2006 | Sherman et al. |
| 2006/0191575 A1 | 8/2006 | Naesje |
| 2006/0192259 A1 | 8/2006 | Silverbrook |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0245947 A1 | 11/2006 | Seto et al. |
| 2006/0251523 A1 | 11/2006 | Lee et al. |
| 2006/0271020 A1 | 11/2006 | Huang et al. |
| 2006/0282174 A1 | 12/2006 | Haines |
| 2006/0287632 A1 | 12/2006 | Sarangapani |
| 2007/0016152 A1 | 1/2007 | Karpowicz et al. |
| 2007/0032741 A1 | 2/2007 | Hibner et al. |
| 2007/0040454 A1 | 2/2007 | Freudenberger et al. |
| 2007/0041856 A1 | 2/2007 | Hansen et al. |
| 2007/0052144 A1 | 3/2007 | Knirck et al. |
| 2007/0055209 A1 | 3/2007 | Patel et al. |
| 2007/0078444 A1 | 4/2007 | Larsson |
| 2007/0091614 A1 | 4/2007 | Kaisser et al. |
| 2007/0179460 A1 | 8/2007 | Adahan |
| 2007/0196214 A1 | 8/2007 | Bocchiola |
| 2007/0219532 A1 | 9/2007 | Karpowicz et al. |
| 2007/0225663 A1 | 9/2007 | Watt et al. |
| 2007/0256428 A1 | 11/2007 | Unger et al. |
| 2007/0260226 A1 | 11/2007 | Jaeb et al. |
| 2007/0282283 A1 | 12/2007 | Kaern et al. |
| 2007/0292286 A1 | 12/2007 | Hell et al. |
| 2007/0295201 A1 | 12/2007 | Dadd |
| 2008/0008607 A1 | 1/2008 | Schade et al. |
| 2008/0015526 A1 | 1/2008 | Reiner et al. |
| 2008/0020178 A1 | 1/2008 | Oehrle et al. |
| 2008/0051708 A1 | 2/2008 | Kumar et al. |
| 2008/0071234 A1 | 3/2008 | Kelch et al. |
| 2008/0071235 A1 | 3/2008 | Locke et al. |
| 2008/0082040 A1 | 4/2008 | Kubler et al. |
| 2008/0089796 A1 | 4/2008 | Schade et al. |
| 2008/0094753 A1 | 4/2008 | Brodkin et al. |
| 2008/0110336 A1 | 5/2008 | Bovill et al. |
| 2008/0125697 A1 | 5/2008 | Gao |
| 2008/0125698 A1 | 5/2008 | Gerg et al. |
| 2008/0132821 A1 | 6/2008 | Propp et al. |
| 2008/0191399 A1 | 8/2008 | Chang |
| 2008/0211435 A1 | 9/2008 | Imagawa |
| 2008/0234641 A1 | 9/2008 | Locke et al. |
| 2008/0240942 A1 | 10/2008 | Heinrich et al. |
| 2008/0260551 A1 | 10/2008 | Simmons |
| 2008/0267797 A1 | 10/2008 | Hell et al. |
| 2008/0281281 A1 | 11/2008 | Meyer et al. |
| 2008/0306456 A1 | 12/2008 | Riesinger |
| 2008/0310980 A1 | 12/2008 | Ramsdorf et al. |
| 2009/0012441 A1 | 1/2009 | Mulligan |
| 2009/0028733 A1 | 1/2009 | Duwel |
| 2009/0053081 A1 | 2/2009 | Griffiths |
| 2009/0054855 A1 | 2/2009 | Blott et al. |
| 2009/0060750 A1 | 3/2009 | Chen et al. |
| 2009/0071551 A1 | 3/2009 | Chalich |
| 2009/0081049 A1 | 3/2009 | Tian et al. |
| 2009/0087323 A1 | 4/2009 | Blakey et al. |
| 2009/0114293 A1 | 5/2009 | Kanai et al. |
| 2009/0125004 A1 | 5/2009 | Shen et al. |
| 2009/0129955 A1 | 5/2009 | Schubert |
| 2009/0129986 A1 | 5/2009 | Wimberger-Friedl et al. |
| 2009/0148320 A1 | 6/2009 | Lucas |
| 2009/0149821 A1 | 6/2009 | Scherson et al. |
| 2009/0166411 A1 | 7/2009 | Kramer et al. |
| 2009/0169402 A1 | 7/2009 | Stenberg |
| 2009/0206778 A1 | 8/2009 | Roh et al. |
| 2009/0234306 A1 | 9/2009 | Vitaris |
| 2009/0292263 A1 | 11/2009 | Hudspeth et al. |
| 2009/0292264 A1 | 11/2009 | Hudspeth et al. |
| 2009/0299251 A1 | 12/2009 | Buan |
| 2009/0299306 A1 | 12/2009 | Buan |
| 2009/0304534 A1 | 12/2009 | Richter |
| 2009/0312725 A1 | 12/2009 | Braga |
| 2010/0042059 A1 | 2/2010 | Pratt et al. |
| 2010/0068820 A1 | 3/2010 | Meathrel et al. |
| 2010/0074775 A1* | 3/2010 | Yamamoto ............ F04B 43/028 417/413.2 |
| 2010/0098566 A1 | 4/2010 | Kang |
| 2010/0125258 A1 | 5/2010 | Coulthard et al. |
| 2010/0145289 A1 | 6/2010 | Line et al. |
| 2010/0160876 A1 | 6/2010 | Robinson et al. |
| 2010/0160881 A1 | 6/2010 | Lin et al. |
| 2010/0191178 A1 | 7/2010 | Ross et al. |
| 2010/0204663 A1 | 8/2010 | Wudyka |
| 2010/0211030 A1 | 8/2010 | Turner et al. |
| 2010/0244780 A1 | 9/2010 | Turner |
| 2010/0265649 A1 | 10/2010 | Singh et al. |
| 2010/0268179 A1 | 10/2010 | Kelch et al. |
| 2010/0280435 A1 | 11/2010 | Raney et al. |
| 2010/0305526 A1 | 12/2010 | Robinson et al. |
| 2010/0318052 A1 | 12/2010 | Ha et al. |
| 2010/0318071 A1 | 12/2010 | Wudyka |
| 2010/0320659 A1 | 12/2010 | Chen et al. |
| 2011/0000069 A1 | 1/2011 | Ramsdorf et al. |
| 2011/0004172 A1 | 1/2011 | Eckstein et al. |
| 2011/0015587 A1 | 1/2011 | Tumey et al. |
| 2011/0020588 A1 | 1/2011 | Kinugawa et al. |
| 2011/0038741 A1 | 2/2011 | Lissner et al. |
| 2011/0043055 A1 | 2/2011 | Chiang |
| 2011/0071415 A1 | 3/2011 | Karwoski et al. |
| 2011/0081267 A1 | 4/2011 | McCrone et al. |
| 2011/0098600 A1 | 4/2011 | Matsumura et al. |
| 2011/0103984 A1 | 5/2011 | Santa |
| 2011/0112492 A1 | 5/2011 | Bharti et al. |
| 2011/0118683 A1 | 5/2011 | Weston |
| 2011/0169348 A1 | 7/2011 | Park |
| 2011/0171044 A1 | 7/2011 | Flanigan |
| 2011/0176945 A1 | 7/2011 | Drevet |
| 2011/0176946 A1 | 7/2011 | Drevet |
| 2011/0184341 A1 | 7/2011 | Baker et al. |
| 2011/0186765 A1 | 8/2011 | Jaeb et al. |
| 2011/0196321 A1 | 8/2011 | Wudyka |
| 2011/0205646 A1 | 8/2011 | Sato et al. |
| 2011/0205647 A1 | 8/2011 | Osaka et al. |
| 2011/0224631 A1 | 9/2011 | Simmons |
| 2011/0229352 A1 | 9/2011 | Herbert |

(56) References Cited

U.S. PATENT DOCUMENTS

| | | |
|---|---|---|
| 2011/0236265 A1 | 9/2011 | Hasui et al. |
| 2011/0236277 A1 | 9/2011 | Lee et al. |
| 2011/0237863 A1 | 9/2011 | Ricci et al. |
| 2011/0251569 A1 | 10/2011 | Turner et al. |
| 2011/0257572 A1 | 10/2011 | Locke et al. |
| 2011/0311379 A1 | 12/2011 | Hale et al. |
| 2012/0000208 A1 | 1/2012 | Hon et al. |
| 2012/0008817 A1 | 1/2012 | Grinker et al. |
| 2012/0016323 A1 | 1/2012 | Robinson et al. |
| 2012/0034109 A1 | 2/2012 | Tout et al. |
| 2012/0046625 A1 | 2/2012 | Johannison |
| 2012/0051956 A1 | 3/2012 | Grip |
| 2012/0053543 A1 | 3/2012 | Miau et al. |
| 2012/0095380 A1 | 4/2012 | Gergeley et al. |
| 2012/0109083 A1 | 5/2012 | Coulthard et al. |
| 2012/0160091 A1 | 6/2012 | Dadd et al. |
| 2012/0177513 A1 | 7/2012 | Lilie et al. |
| 2012/0184930 A1 | 7/2012 | Johannison |
| 2012/0220960 A1 | 8/2012 | Ruland |
| 2012/0251359 A1 | 10/2012 | Neelakantan et al. |
| 2012/0259299 A1 | 10/2012 | Ryu et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0289914 A1 | 11/2012 | Eckstein et al. |
| 2012/0301341 A1 | 11/2012 | Ota et al. |
| 2013/0017110 A1 | 1/2013 | Villagomez et al. |
| 2013/0042753 A1 | 2/2013 | Becker et al. |
| 2013/0085462 A1 | 4/2013 | Nip et al. |
| 2013/0090613 A1 | 4/2013 | Kelch et al. |
| 2013/0116635 A1 | 5/2013 | Fleischmann |
| 2013/0118622 A1 | 5/2013 | Patzold et al. |
| 2013/0123755 A1 | 5/2013 | Locke et al. |
| 2013/0138054 A1 | 5/2013 | Fleischmann |
| 2013/0144230 A1 | 6/2013 | Wu et al. |
| 2013/0150814 A1 | 6/2013 | Buan |
| 2013/0165878 A1 | 6/2013 | Heagle |
| 2013/0209277 A1 | 8/2013 | Locke et al. |
| 2013/0209278 A1 | 8/2013 | Locke et al. |
| 2013/0209279 A1 | 8/2013 | Locke et al. |
| 2013/0209281 A1 | 8/2013 | Locke et al. |
| 2013/0213506 A1 | 8/2013 | Chen et al. |
| 2013/0223979 A1 | 8/2013 | Locke et al. |
| 2013/0267917 A1 | 10/2013 | Pan et al. |
| 2013/0274688 A1 | 10/2013 | Weston |
| 2013/0276906 A1 | 10/2013 | Locke et al. |
| 2013/0280113 A1 | 10/2013 | Miranda et al. |
| 2013/0331822 A1 | 12/2013 | Patel et al. |
| 2013/0340870 A1 | 12/2013 | Ito et al. |
| 2014/0010673 A1 | 1/2014 | Locke et al. |
| 2014/0017093 A1 | 1/2014 | Locke et al. |
| 2014/0018753 A1 | 1/2014 | Joshi |
| 2014/0072149 A1 | 3/2014 | Yan et al. |
| 2014/0100516 A1 | 4/2014 | Hunt et al. |
| 2014/0114236 A1 | 4/2014 | Gordon |
| 2014/0114237 A1 | 4/2014 | Gordon |
| 2014/0114268 A1 | 4/2014 | Auguste et al. |
| 2014/0163490 A1 | 6/2014 | Locke et al. |
| 2014/0194835 A1 | 7/2014 | Ehlert |
| 2014/0228791 A1 | 8/2014 | Hartwell |
| 2014/0236106 A1 | 8/2014 | Locke et al. |
| 2014/0276487 A1 | 9/2014 | Locke et al. |
| 2014/0303551 A1 | 10/2014 | Germain et al. |
| 2014/0316359 A1 | 10/2014 | Collinson et al. |
| 2014/0323906 A1 | 10/2014 | Peatfield et al. |
| 2015/0025482 A1 | 1/2015 | Begin et al. |
| 2015/0032035 A1 | 1/2015 | Banwell et al. |
| 2015/0051560 A1 | 2/2015 | Askem |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0100045 A1 | 4/2015 | Allen et al. |
| 2015/0159066 A1 | 6/2015 | Hartwell et al. |
| 2016/0319957 A1 | 11/2016 | Jaeb et al. |
| 2016/0367737 A1 | 12/2016 | Askem et al. |
| 2019/0307611 A1 | 10/2019 | Askem et al. |

FOREIGN PATENT DOCUMENTS

| | | |
|---|---|---|
| DE | 39 16 648 | 9/1990 |
| DE | 90 17 289 | 4/1992 |
| DE | 198 44 355 | 4/2000 |
| DE | 10 2005 007016 | 8/2006 |
| EP | 0 208 395 | 1/1987 |
| EP | 0 411 564 | 2/1991 |
| EP | 0 541 251 | 5/1993 |
| EP | 0 578 999 | 6/1993 |
| EP | 0 604 953 | 7/1994 |
| EP | 0 759 521 | 2/1997 |
| EP | 0 775 825 | 5/1997 |
| EP | 0 759 521 | 7/1997 |
| EP | 0 793 019 | 9/1997 |
| EP | 0 809 028 | 11/1997 |
| EP | 0 909 895 | 10/1998 |
| EP | 0 898 076 | 2/1999 |
| EP | 0 941 726 | 9/1999 |
| EP | 0 688 189 | 9/2000 |
| EP | 1 114 933 | 7/2001 |
| EP | 1 153 218 | 11/2001 |
| EP | 1 897 569 | 8/2002 |
| EP | 0 909 895 | 12/2002 |
| EP | 0 708 620 | 5/2003 |
| EP | 0 993 317 | 9/2003 |
| EP | 1 406 020 | 9/2003 |
| EP | 1 554 737 | 5/2004 |
| EP | 1 556 942 | 5/2004 |
| EP | 1 430 588 | 6/2004 |
| EP | 1 449 971 | 8/2004 |
| EP | 1 452 156 | 9/2004 |
| EP | 1 476 217 | 11/2004 |
| EP | 1 556 942 | 5/2005 |
| EP | 1 554 737 | 7/2005 |
| EP | 1 757 809 | 8/2005 |
| EP | 1 469 580 | 12/2005 |
| EP | 1 850 005 | 10/2007 |
| EP | 1 430 588 | 6/2008 |
| EP | 1 460 270 | 6/2008 |
| EP | 1 791 579 | 7/2009 |
| EP | 1 513 478 | 12/2009 |
| EP | 2 129 915 | 12/2009 |
| EP | 2 145 636 | 1/2010 |
| EP | 2 161 011 | 3/2010 |
| EP | 2 161 448 | 3/2010 |
| EP | 1 932 481 | 6/2010 |
| EP | 2 216 573 | 8/2010 |
| EP | 2 253 353 | 11/2010 |
| EP | 2 302 127 A1 | 3/2011 |
| EP | 1 956 242 | 4/2011 |
| EP | 2 366 721 | 9/2011 |
| EP | 1 169 071 | 2/2012 |
| EP | 2 462 908 | 6/2012 |
| EP | 2 531 160 | 12/2012 |
| EP | 2 531 761 | 12/2012 |
| EP | 2 577 062 | 4/2013 |
| EP | 1 875 081 | 12/2013 |
| EP | 2 616 116 | 12/2014 |
| EP | 2 544 642 | 1/2015 |
| EP | 2 648 668 | 1/2015 |
| EP | 2 830 555 | 2/2015 |
| EP | 2 836 711 | 2/2015 |
| FR | 1 163 907 | 10/1958 |
| FR | 2 939 320 | 6/2010 |
| GB | 1039145 | 8/1966 |
| GB | 1220857 | 1/1971 |
| GB | 2099306 | 12/1982 |
| GB | 2235877 | 3/1991 |
| GB | 2273133 | 6/1994 |
| GB | 2306580 | 5/1997 |
| GB | 2433298 | 3/2007 |
| GB | 2435422 | 8/2007 |
| JP | 52-040804 | 3/1977 |
| JP | 2000-220570 | 8/2000 |

(56) References Cited

FOREIGN PATENT DOCUMENTS

| | | |
|---|---|---|
| JP | 2006-233925 | 9/2006 |
| RU | 62504 | 4/2007 |
| WO | WO 1987/07683 | 12/1987 |
| WO | WO 1994/21312 | 9/1994 |
| WO | WO 1994/23677 | 10/1994 |
| WO | WO 1995/04511 | 2/1995 |
| WO | WO 1995/14451 | 6/1995 |
| WO | WO 1996/21410 | 7/1996 |
| WO | WO 1997/11658 | 4/1997 |
| WO | WO 1999/39671 | 8/1999 |
| WO | WO 2000/000743 | 1/2000 |
| WO | WO 2000/07653 | 2/2000 |
| WO | WO 2000/22298 | 4/2000 |
| WO | WO 2000/42957 | 7/2000 |
| WO | WO 2000/49968 | 8/2000 |
| WO | WO 2000/56378 | 9/2000 |
| WO | WO 2000/079154 | 12/2000 |
| WO | WO 2001/16488 | 3/2001 |
| WO | WO 2001/79693 | 10/2001 |
| WO | WO 2002/17840 | 3/2002 |
| WO | WO 2002/26180 | 4/2002 |
| WO | WO 2002/38096 | 5/2002 |
| WO | WO 2002/076379 | 10/2002 |
| WO | WO 2002/087058 | 10/2002 |
| WO | WO 2002/090772 | 11/2002 |
| WO | WO 2003/018098 | 3/2003 |
| WO | WO 2003/057071 | 7/2003 |
| WO | WO 2003/057307 | 7/2003 |
| WO | WO 2003/085810 | 10/2003 |
| WO | WO 2003/101508 | 12/2003 |
| WO | WO 2004/007960 | 1/2004 |
| WO | WO 2004/060225 | 7/2004 |
| WO | WO 2004/073566 | 9/2004 |
| WO | WO 2004/081421 | 9/2004 |
| WO | WO 2005/001286 | 1/2005 |
| WO | WO 2005/001287 | 1/2005 |
| WO | WO 2005/009488 | 2/2005 |
| WO | WO 2005/046761 | 5/2005 |
| WO | WO 2005/123170 | 12/2005 |
| WO | WO 2006/046060 | 5/2006 |
| WO | WO 2006/052839 | 5/2006 |
| WO | WO 2006/058801 | 6/2006 |
| WO | WO 2006/059098 | 6/2006 |
| WO | WO 2006/062276 | 6/2006 |
| WO | WO 2006/069875 | 7/2006 |
| WO | WO 2006/069884 | 7/2006 |
| WO | WO 2006/069885 | 7/2006 |
| WO | WO 2006/092333 | 9/2006 |
| WO | WO 2006/233925 | 9/2006 |
| WO | WO 2006/111775 | 10/2006 |
| WO | WO 2006/117207 | 11/2006 |
| WO | WO 2006/122268 | 11/2006 |
| WO | WO 2007/030601 A2 | 3/2007 |
| WO | WO 2007/049876 | 5/2007 |
| WO | WO 2007/055642 | 5/2007 |
| WO | WO 2007/067359 | 6/2007 |
| WO | WO 2007/087810 | 8/2007 |
| WO | WO 2007/087811 | 8/2007 |
| WO | WO 2008/013896 | 1/2008 |
| WO | WO 2008/027449 | 3/2008 |
| WO | WO 2008/031418 | 3/2008 |
| WO | WO 2008/048527 | 4/2008 |
| WO | WO 2008/049277 | 5/2008 |
| WO | WO 2008/100440 | 8/2008 |
| WO | WO 2008/110022 | 8/2008 |
| WO | WO 2008/131895 | 11/2008 |
| WO | WO 2008/135997 | 11/2008 |
| WO | WO 2009/019415 | 2/2009 |
| WO | WO 2009/047524 | 4/2009 |
| WO | WO 2009/066104 | 5/2009 |
| WO | WO 2009/071935 | 6/2009 |
| WO | WO 2009/089390 | 7/2009 |
| WO | WO 2009/095170 | 8/2009 |
| WO | WO 2009/124100 | 10/2009 |
| WO | WO 2009/126103 | 10/2009 |
| WO | WO 2009/146441 | 12/2009 |
| WO | WO 2009/158128 | 12/2009 |
| WO | WO 2010/039481 | 4/2010 |
| WO | WO 2010/051068 | 5/2010 |
| WO | WO 2010/056977 | 5/2010 |
| WO | WO 2010/079359 | 7/2010 |
| WO | WO 2010/082872 | 7/2010 |
| WO | WO 2010/089448 | 8/2010 |
| WO | WO 2010/093753 | 8/2010 |
| WO | WO 2010/126444 | 11/2010 |
| WO | WO 2010/139926 | 12/2010 |
| WO | WO 2010/142959 | 12/2010 |
| WO | WO 2011/003163 | 1/2011 |
| WO | WO 2011/023650 | 3/2011 |
| WO | WO 2011/068310 | 6/2011 |
| WO | WO 2011/082461 | 7/2011 |
| WO | WO 2011/087871 | 7/2011 |
| WO | WO 2011/097361 | 8/2011 |
| WO | WO 2011/097362 | 8/2011 |
| WO | WO 2011/103890 | 9/2011 |
| WO | WO 2011/130542 | 10/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2011/146535 | 11/2011 |
| WO | WO 2011/148188 | 12/2011 |
| WO | WO 2011/150529 | 12/2011 |
| WO | WO 2012/009370 | 1/2012 |
| WO | WO 2012/034238 | 3/2012 |
| WO | WO 2012/048179 | 4/2012 |
| WO | WO 2012/074512 | 6/2012 |
| WO | WO 2012/088572 | 7/2012 |
| WO | WO 2012/095245 | 7/2012 |
| WO | WO 2012/131237 | 10/2012 |
| WO | WO 2012/140180 | 10/2012 |
| WO | WO 2012/140378 | 10/2012 |
| WO | WO 2012/142002 | 10/2012 |
| WO | WO 2012/143665 | 10/2012 |
| WO | WO 2012/146656 | 11/2012 |
| WO | WO 2012/150235 | 11/2012 |
| WO | WO 2013/006932 | 1/2013 |
| WO | WO 2013/007973 | 1/2013 |
| WO | WO 2013/010907 | 1/2013 |
| WO | WO 2013/019017 | 2/2013 |
| WO | WO 2013/064852 | 5/2013 |
| WO | WO 2013/065423 | 5/2013 |
| WO | WO 2013/083800 | 6/2013 |
| WO | WO 2013/090810 | 6/2013 |
| WO | WO 2013/117945 | 8/2013 |
| WO | WO 2013/118447 | 8/2013 |
| WO | WO 2013/119854 | 8/2013 |
| WO | WO 2013/133652 | 9/2013 |
| WO | WO 2013/136181 | 9/2013 |
| WO | WO 2013/149078 | 10/2013 |
| WO | WO 2013/158897 | 10/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/022440 | 2/2014 |
| WO | WO 2014/108476 | 7/2014 |
| WO | WO 2014/113253 | 7/2014 |
| WO | WO 2015/022334 | 2/2015 |
| WO | WO 2015/022340 | 2/2015 |
| WO | WO 2015/023515 | 2/2015 |
| WO | WO 2015/031216 | 3/2015 |

OTHER PUBLICATIONS

U.S. Appl. No. 61/829,187, filed May 30, 2013, Collinson et al.
U.S. Appl. No. 61/906,865, filed Nov. 20, 2013, Collinson et al.
U.S. Appl. No. 61/907,350, filed Nov. 21, 2013, Collinson et al.
International Partial Search Report and Invitation to Pay, re PCT Application No. PCT/IB2013/001513, dated Sep. 30, 2013, in 7 pages.
International Search Report in International Application No. PCT/IB2013/001513, dated Nov. 2, 2014 in 5 pages.

(56) References Cited

OTHER PUBLICATIONS

Morcos, Anthony C.; Voice Coil Actuators & Their Use in Advanced Motion Control Systems; Motion; Jul./Aug. 1995; pp. 25-27.
Park et al., "Design and Analysis of a VCA for Fuel Pump in Automobile," World of Academy of Science, Engineering and Technology; 80 2011; pp. 573-576.
Protz, Kerstin: "Modern Wundauflagen unterstutzen Heilungsprozess", Wundversorgung: Indikation und Anwendung, Geriatrie Journal, Apr. 2005, pp. 3333-3339, with translation.
Chinese Office Action, re CN Application No. 201380037737.4, dated Apr. 20, 2017.
European Exam Report, re EP Application No. 13 740 361.4, dated Nov. 17, 2015.
International Preliminary Report, re PCT Application No. PCT/IB2013/001513, dated Nov. 27, 2014.
Mexican Office Action, re MX Application No. MX/a/2014/013963, dated Jun. 8, 2017.
Russian Office Action, re RU Application No. 2014149280, dated Apr. 11, 2017.
Russian Office Action and Search Report, re RU Application No. 2014149280, dated Aug. 8, 2017.

\* cited by examiner

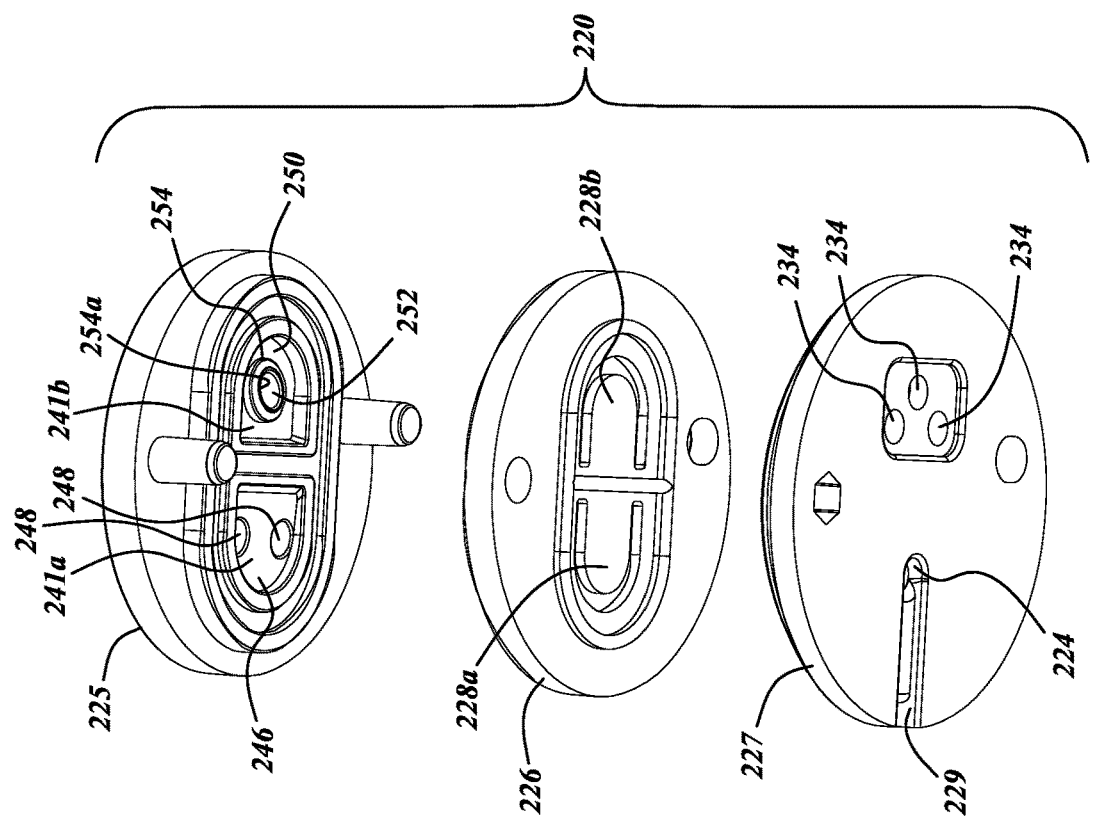
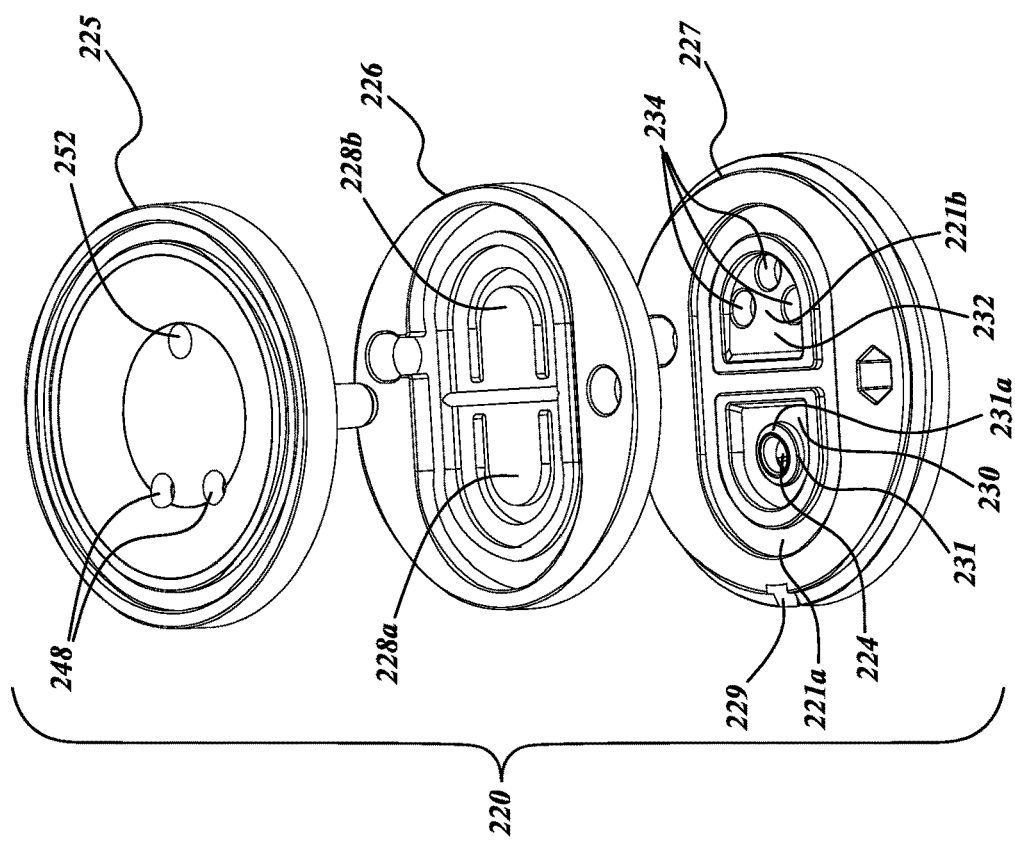
FIG. 14
FIG. 13

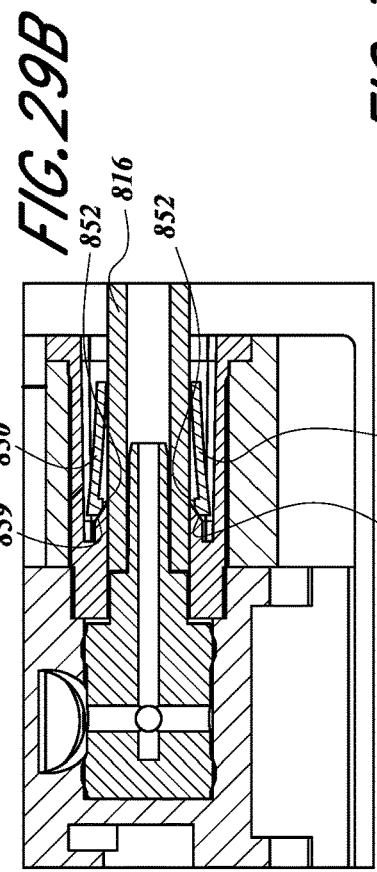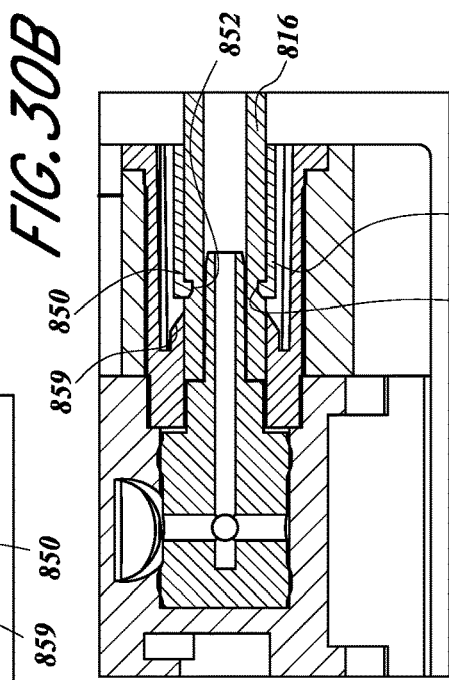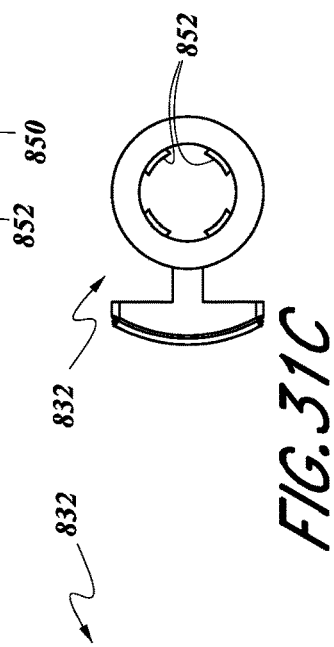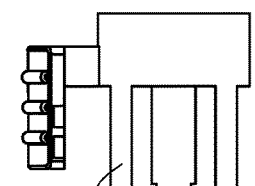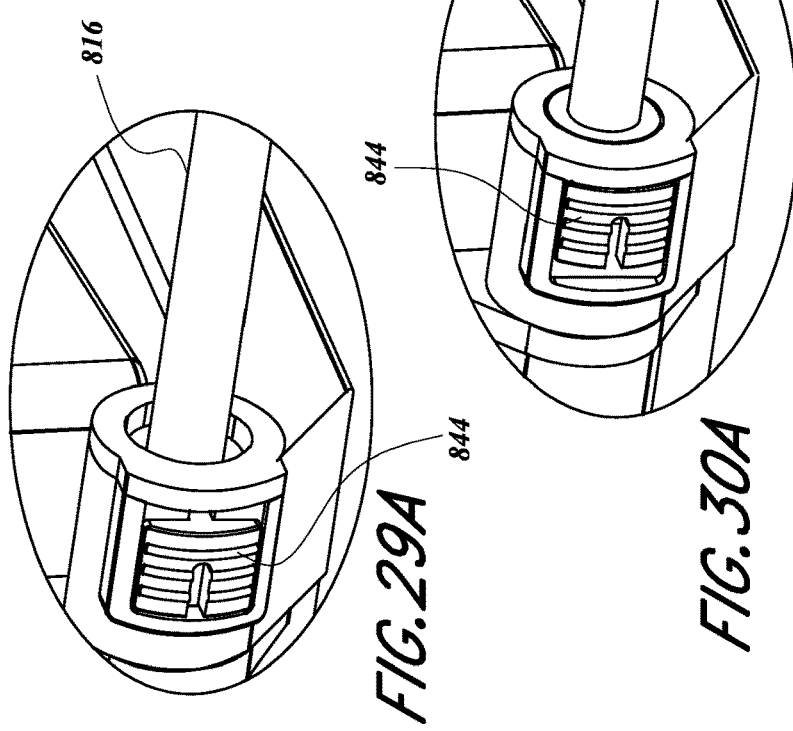

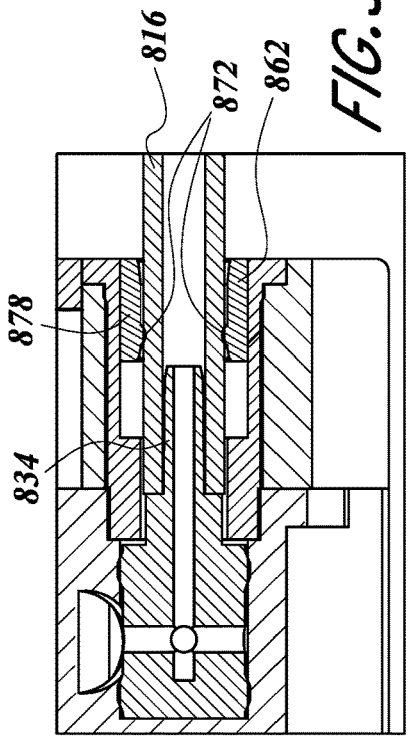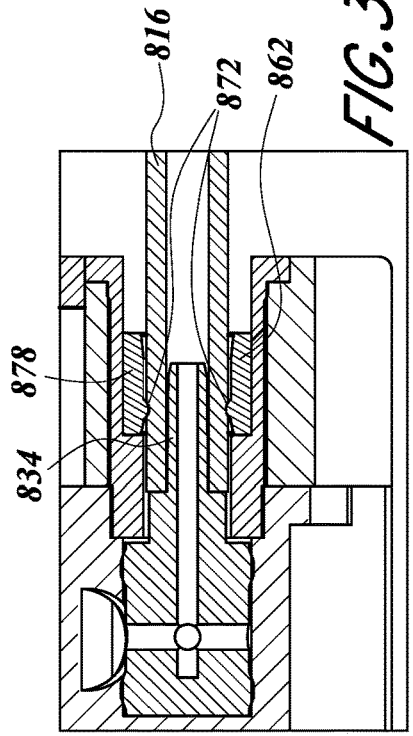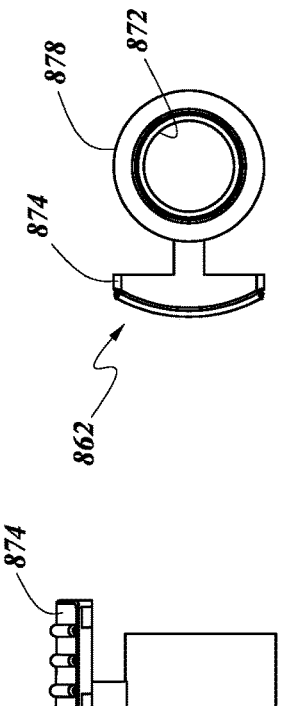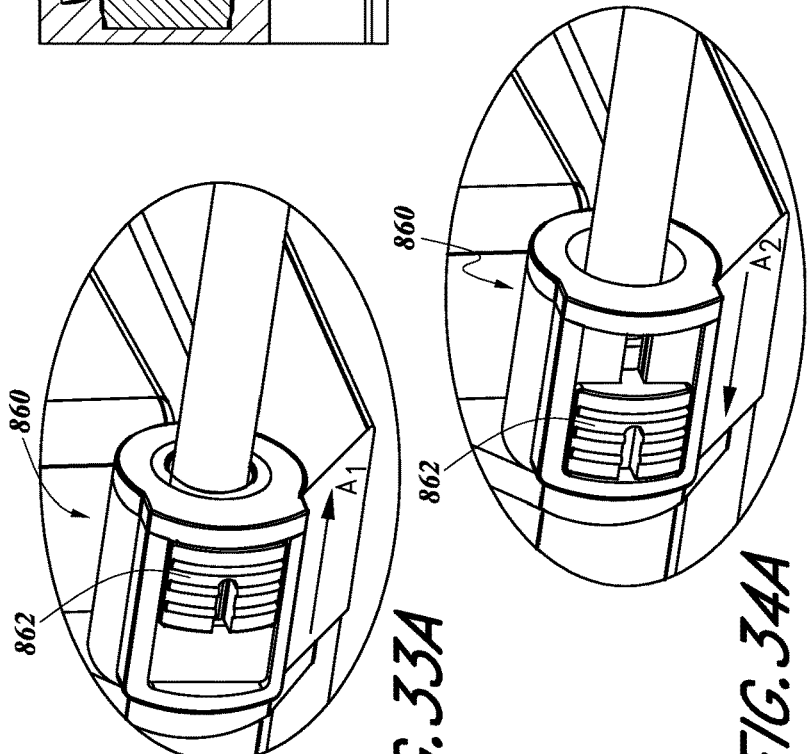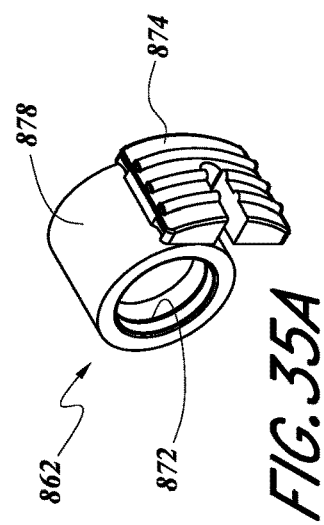

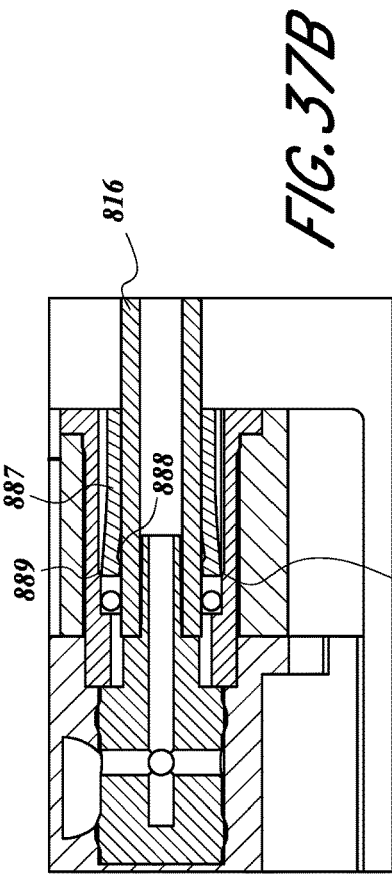
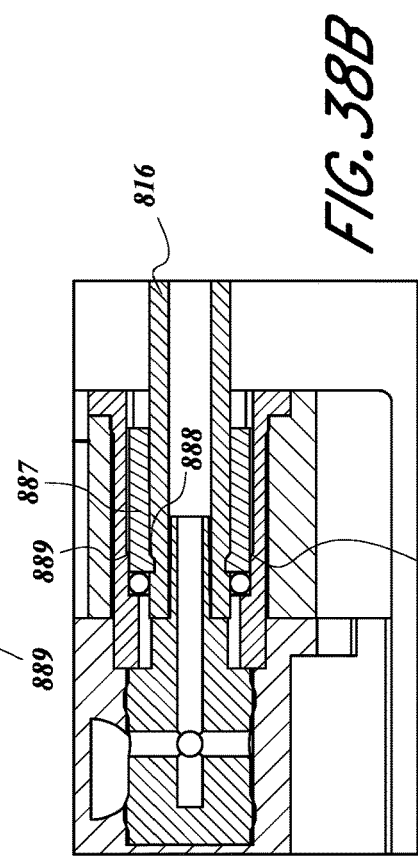
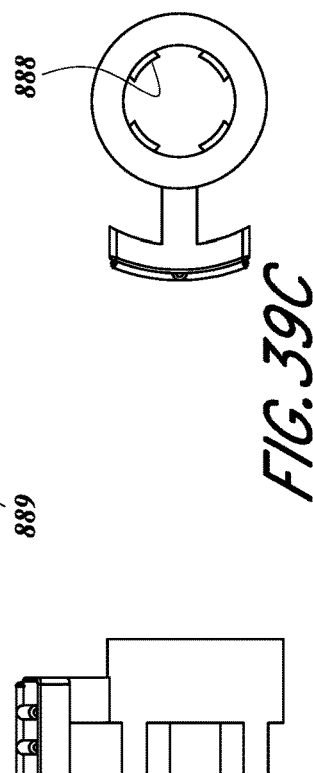
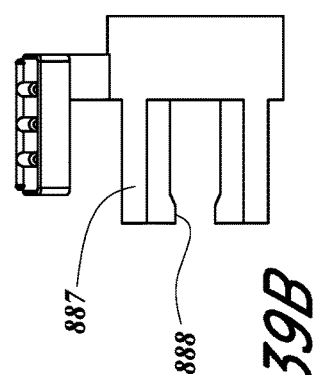
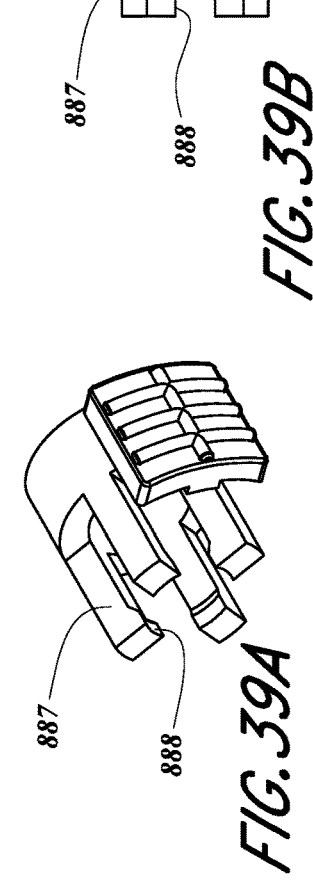
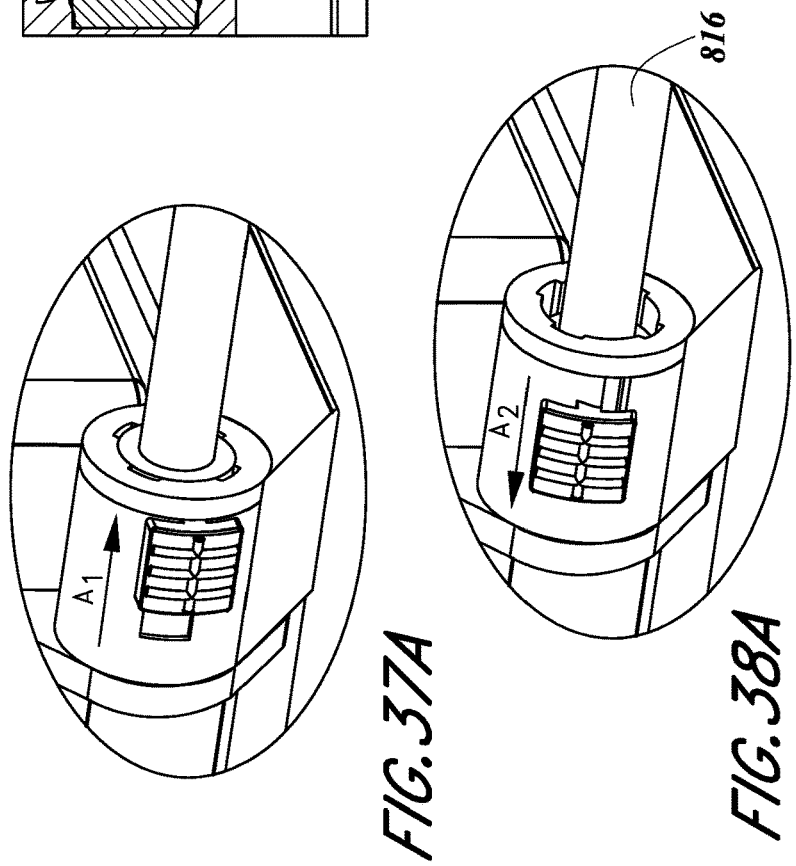

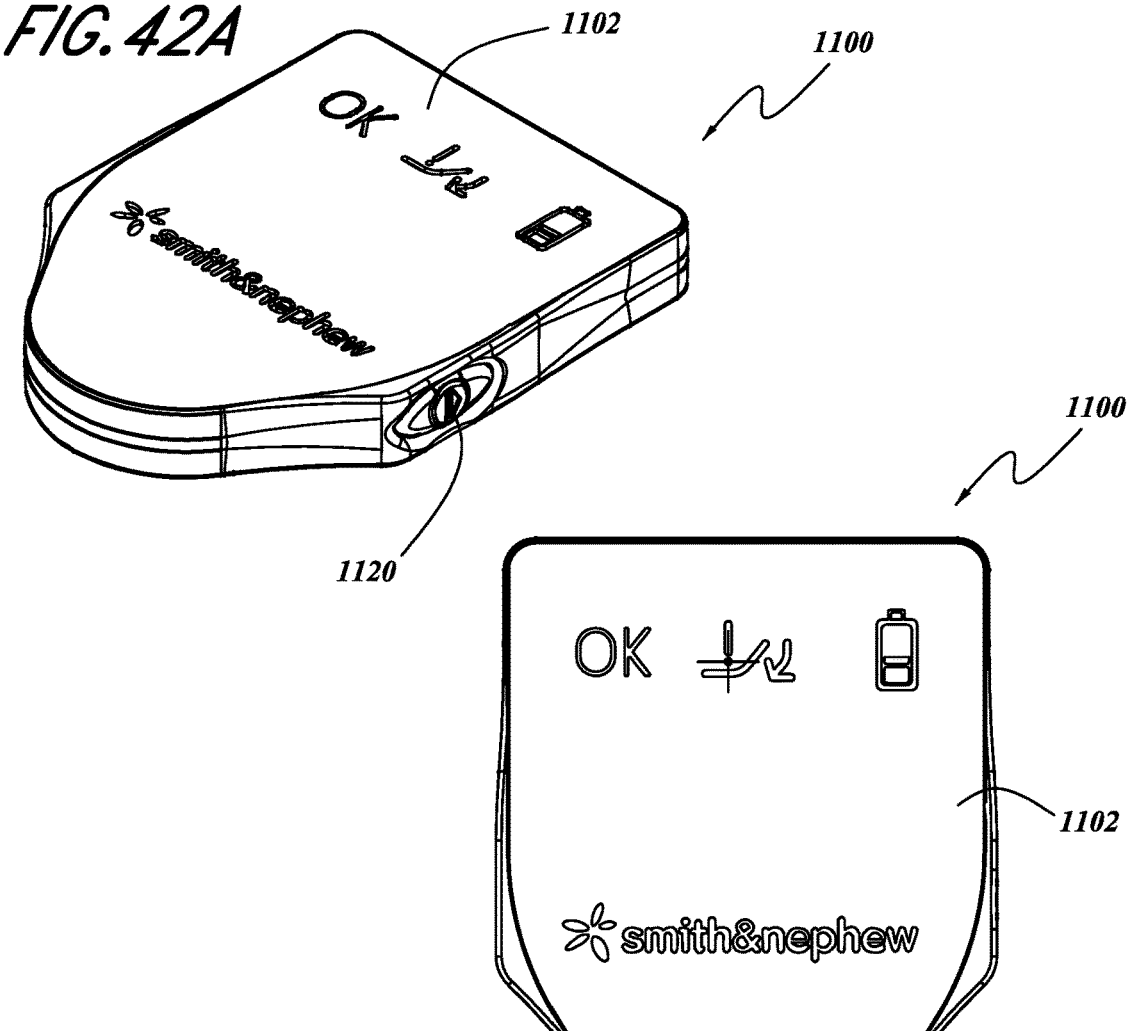
FIG. 42A
FIG. 42B
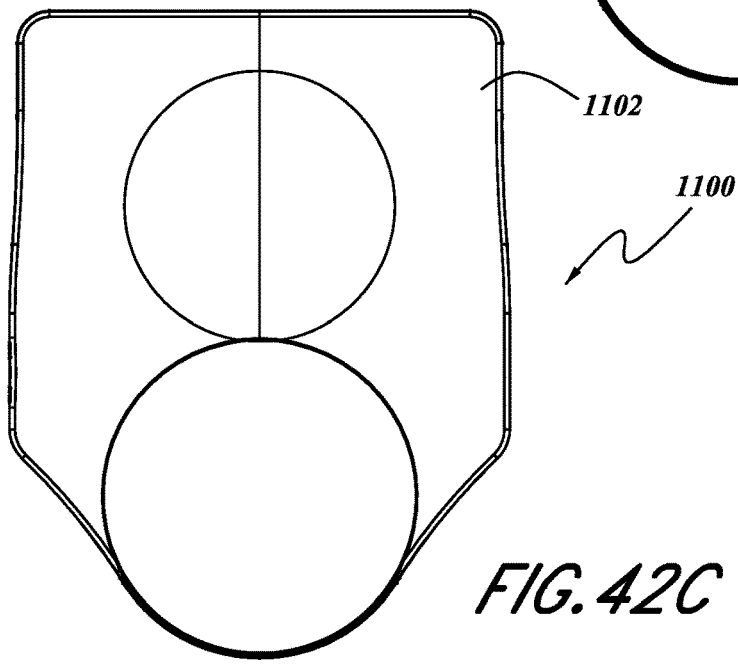
FIG. 42C

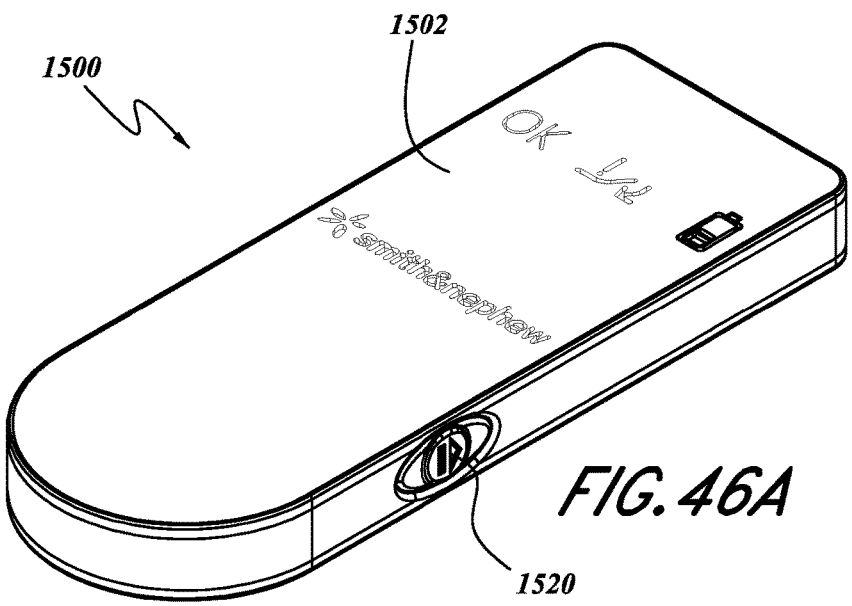
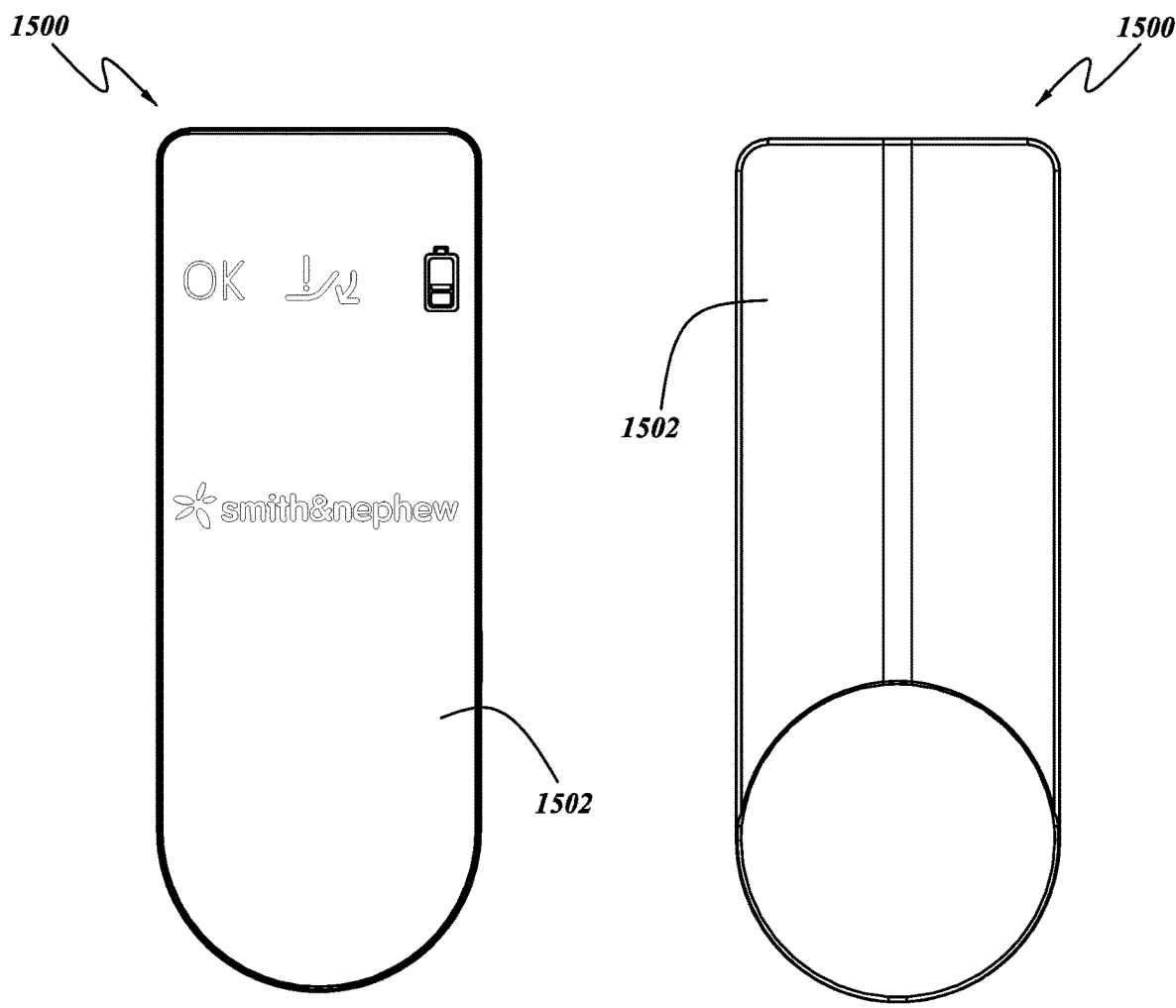
FIG. 46A
FIG. 46B
FIG. 46C

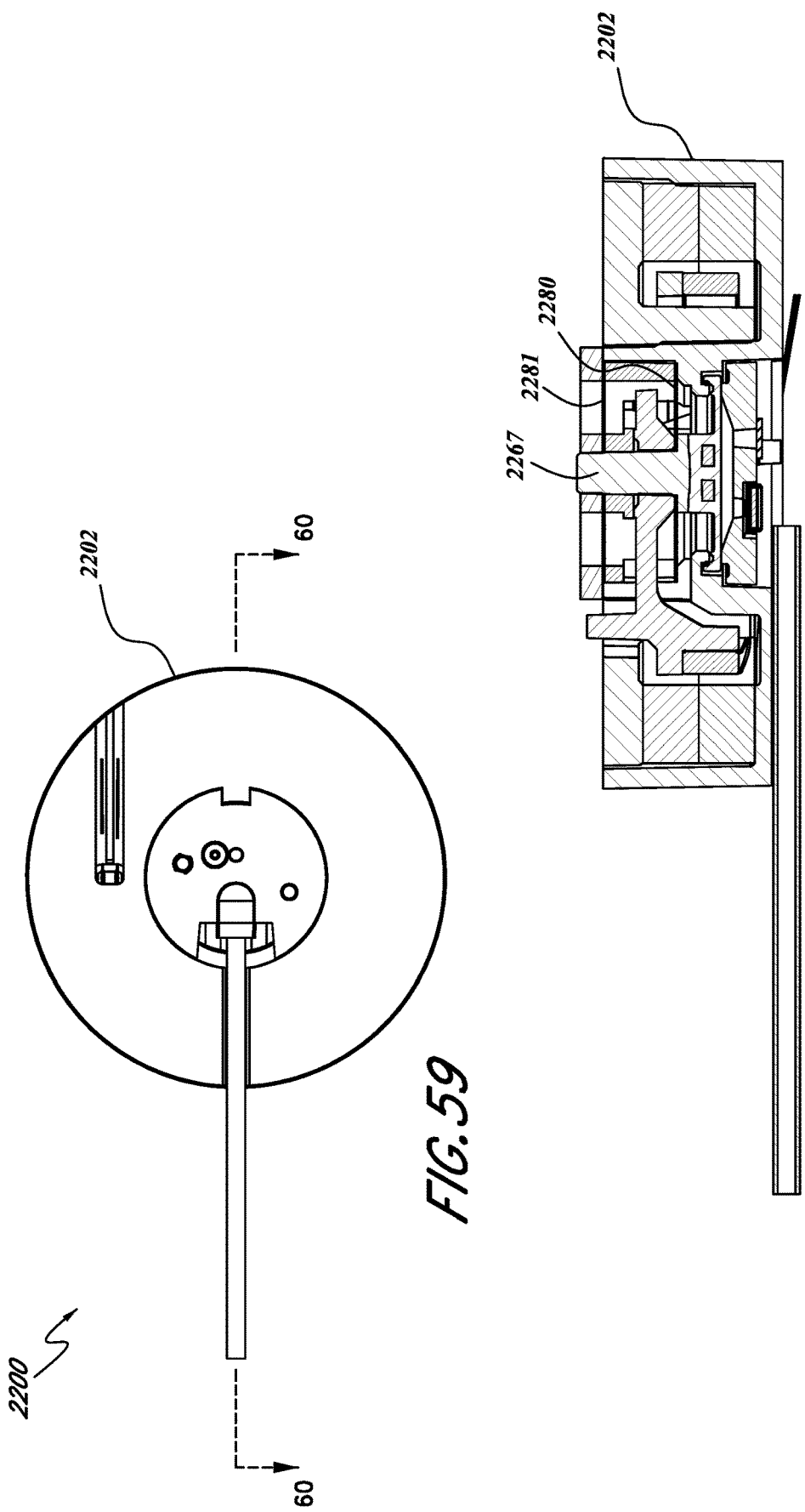

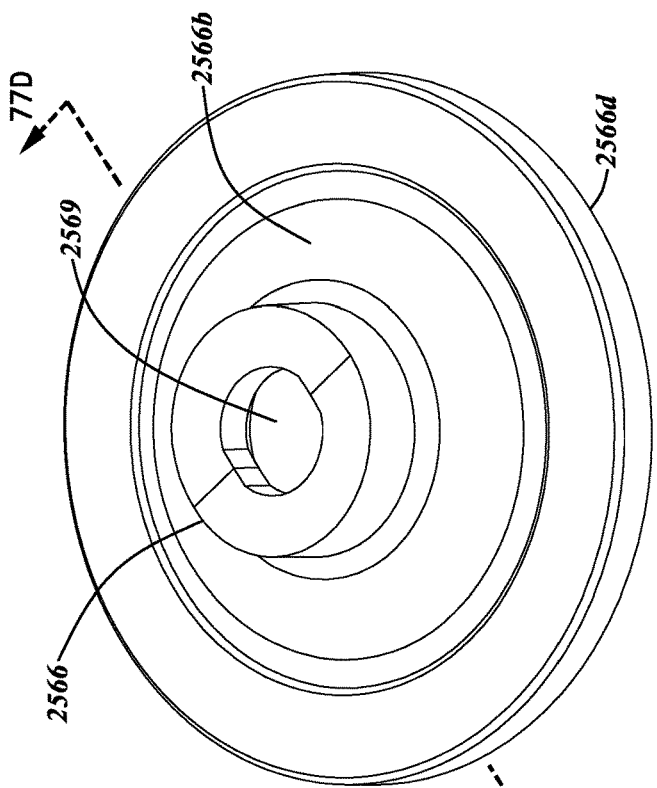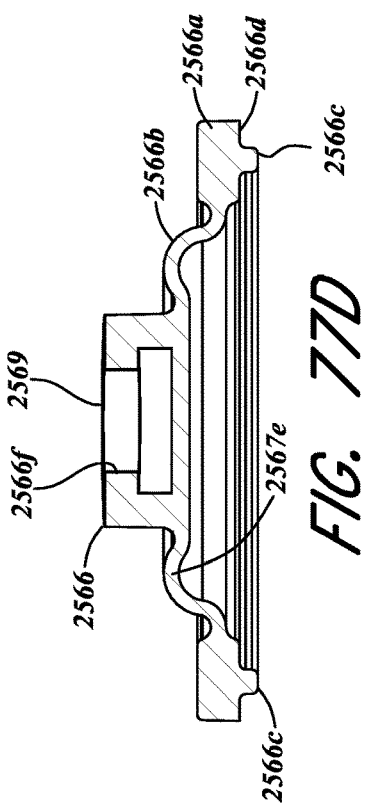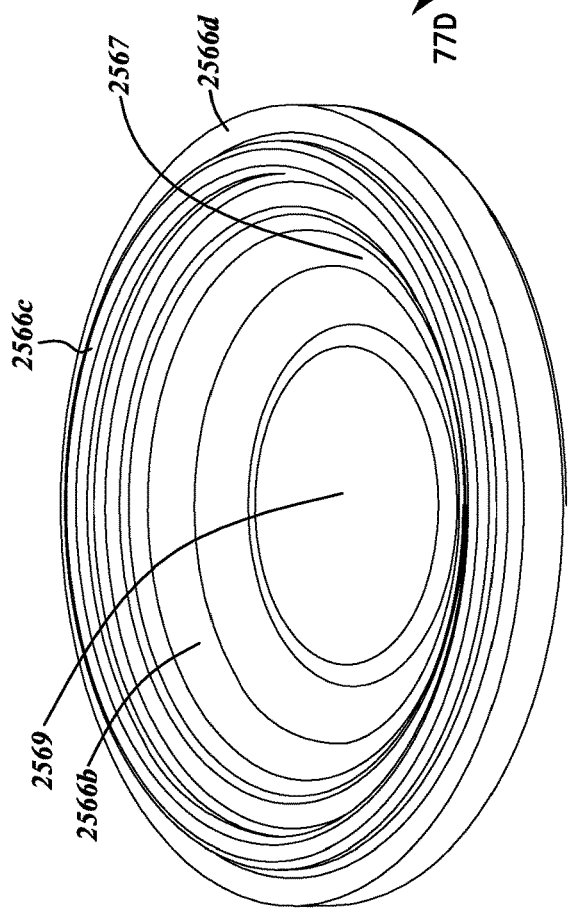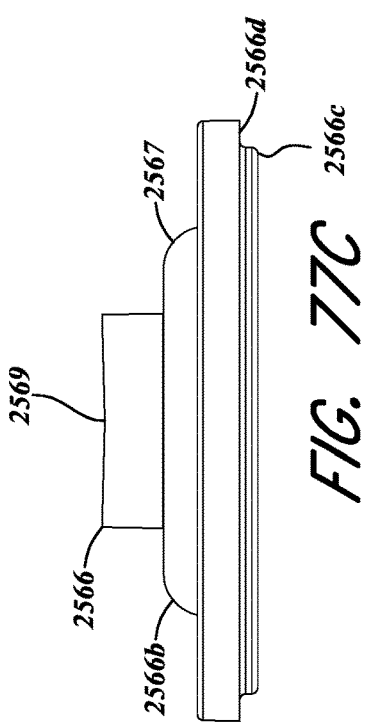
FIG. 77A
FIG. 77B
FIG. 77C
FIG. 77D

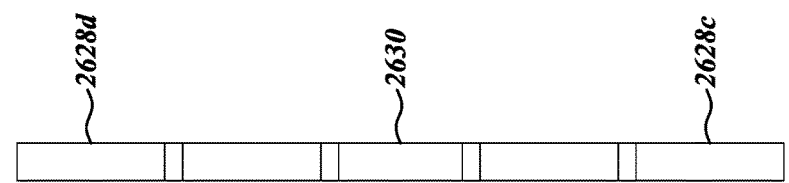
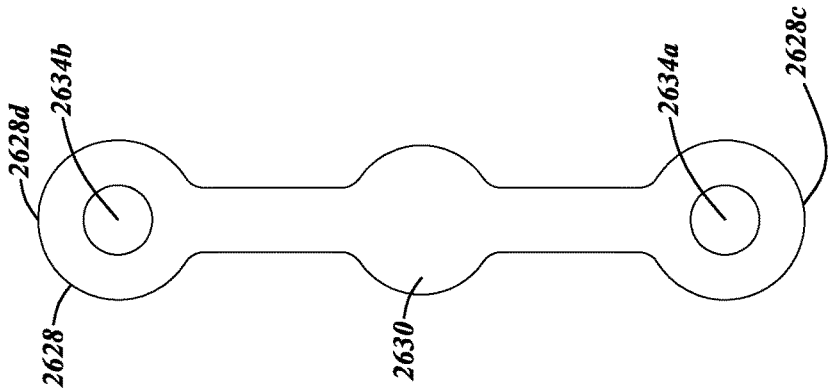
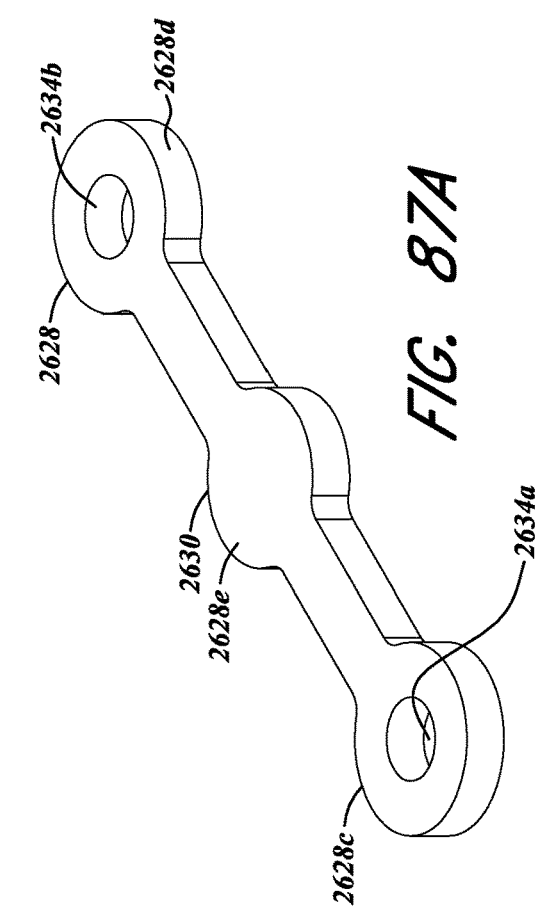
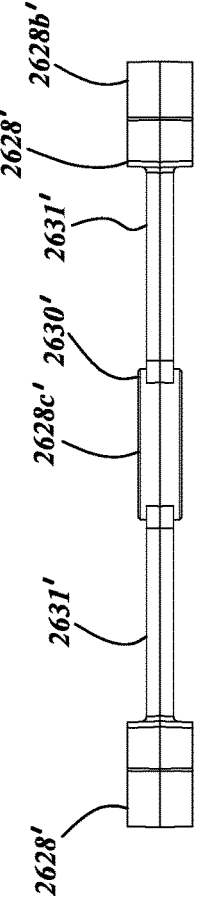
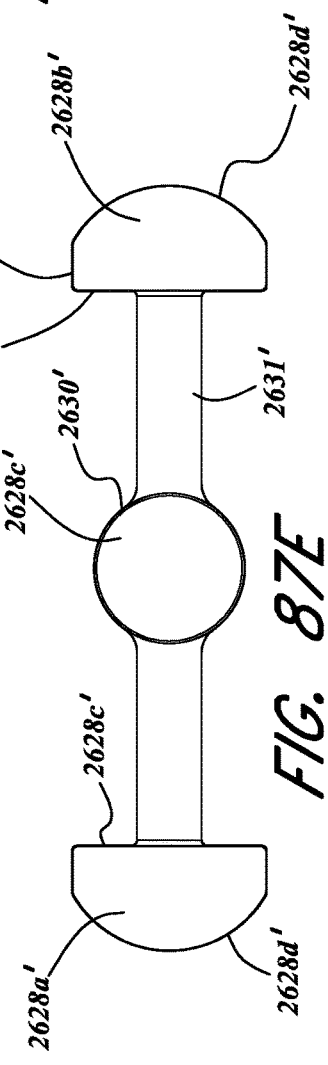

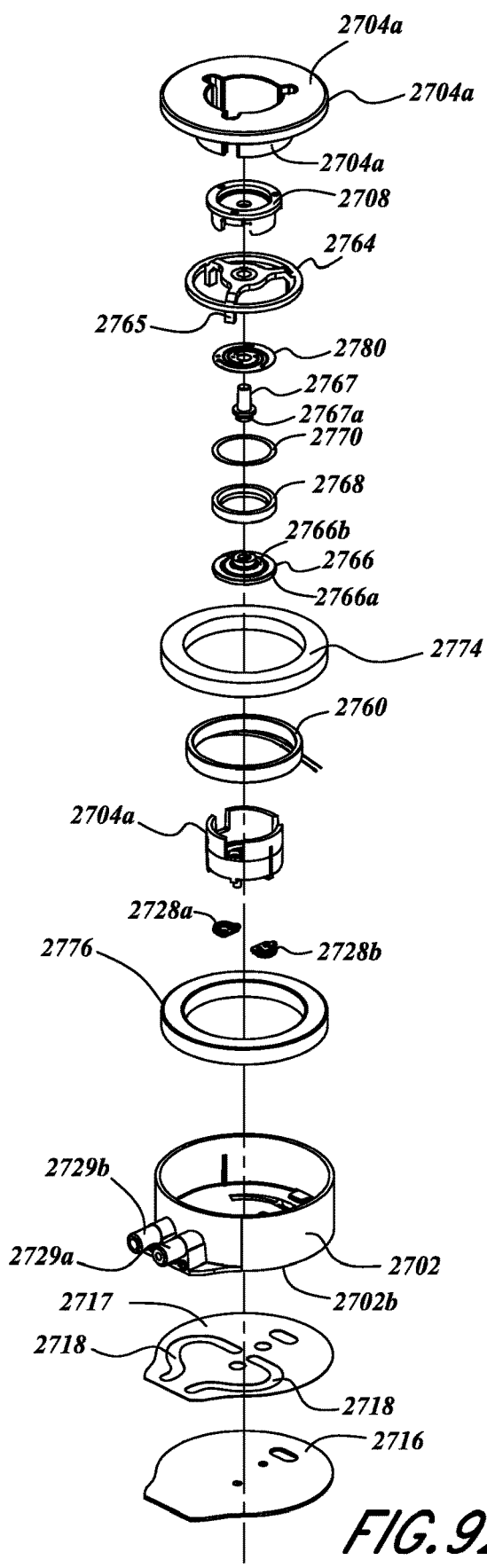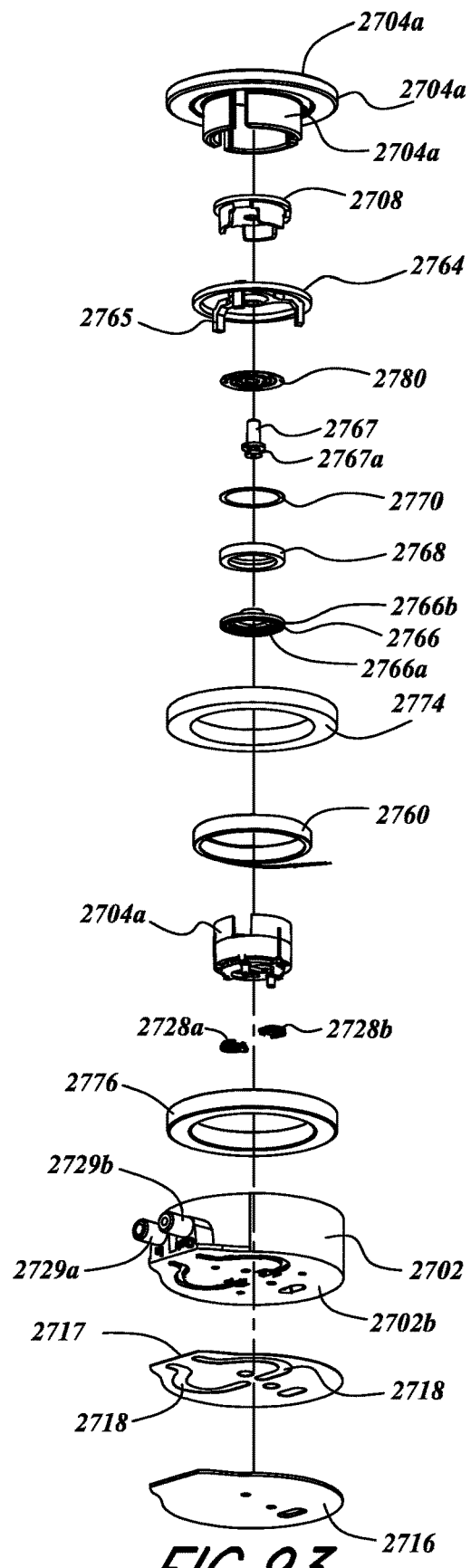

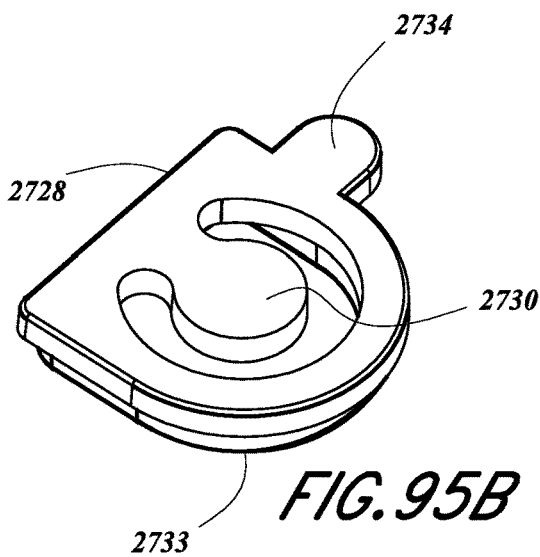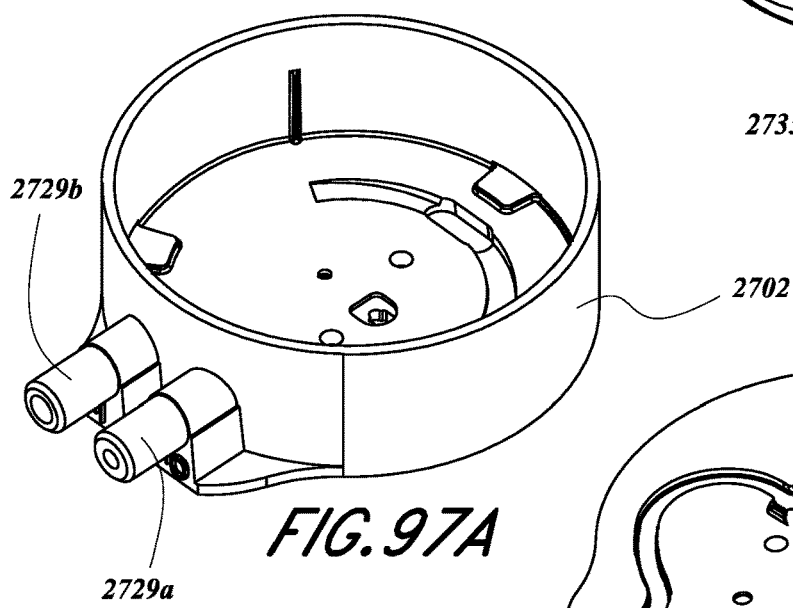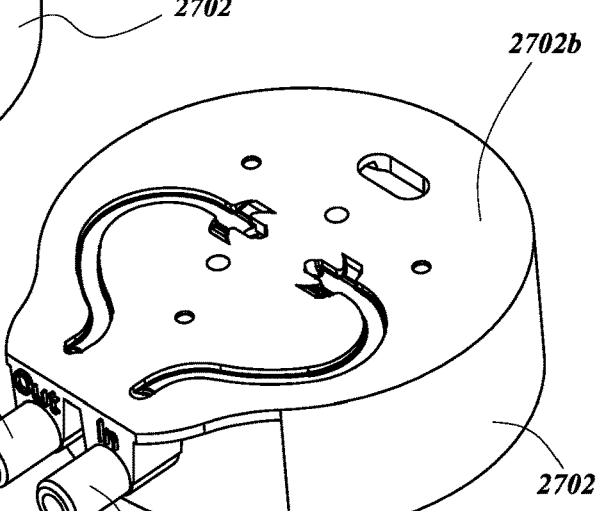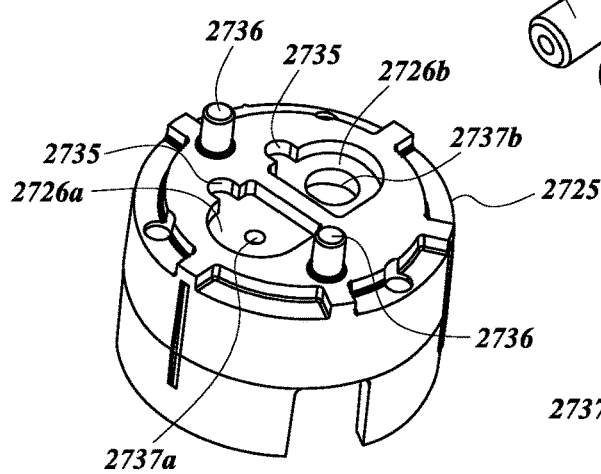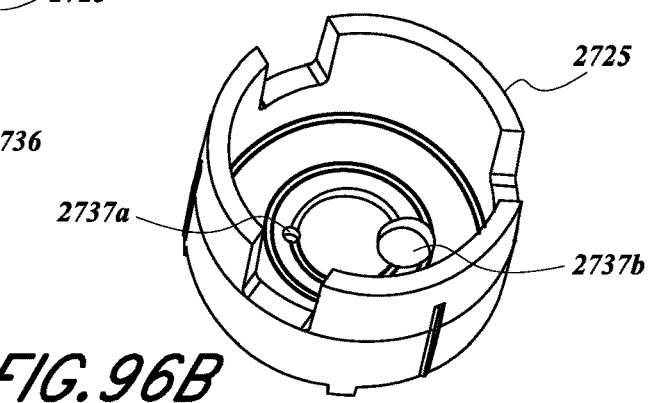

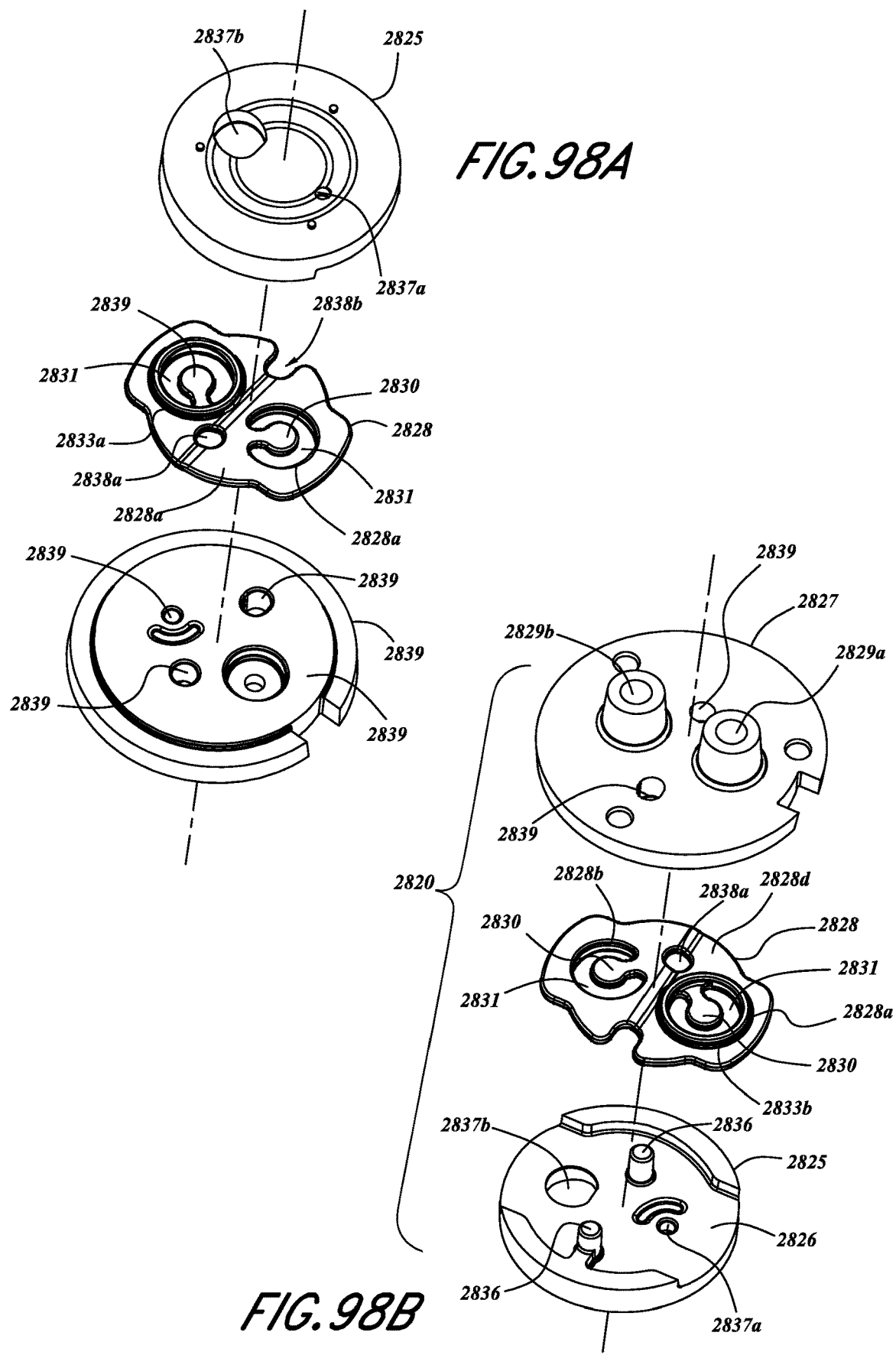

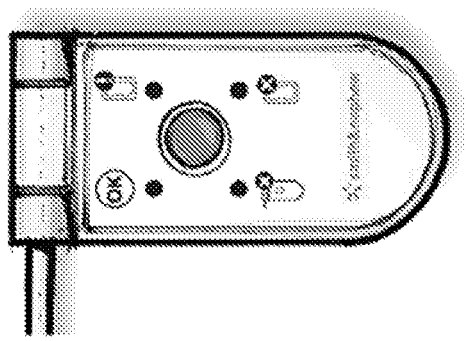
Layout of interface features
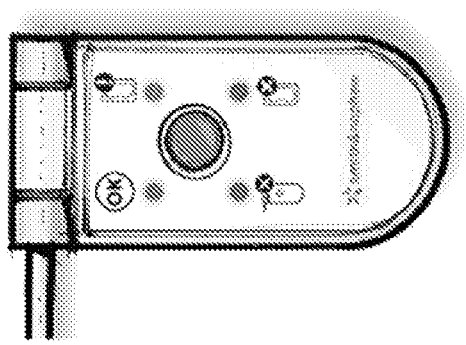
All interface indicators illuminated
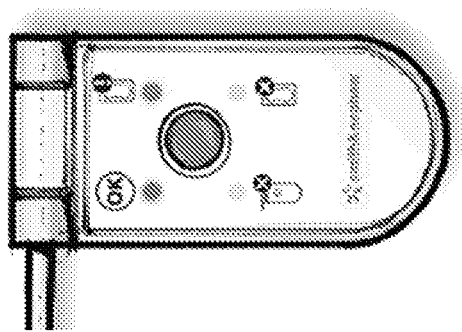
Most common indicator state when device is operational
FIG. 119

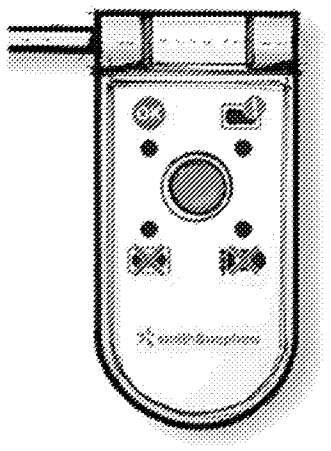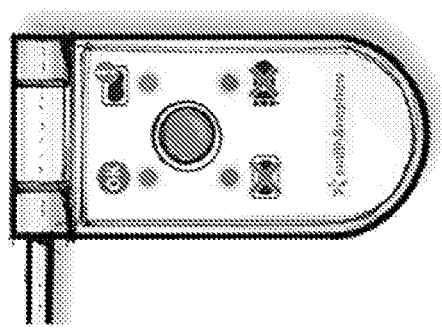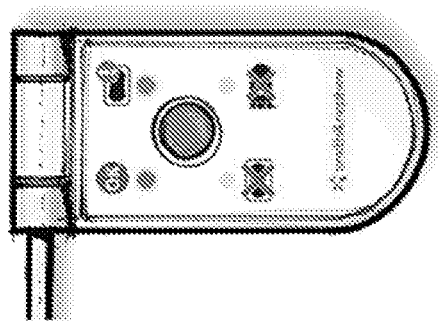
FIG. 120

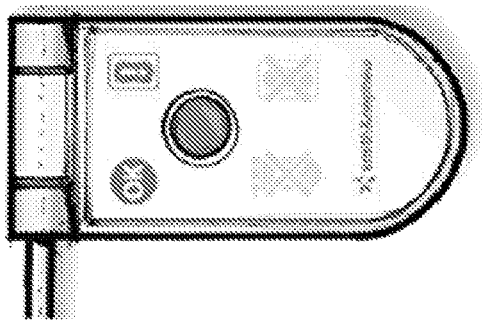
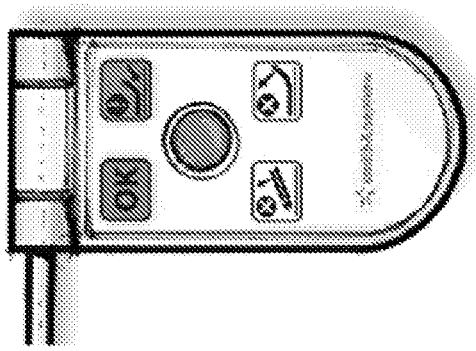
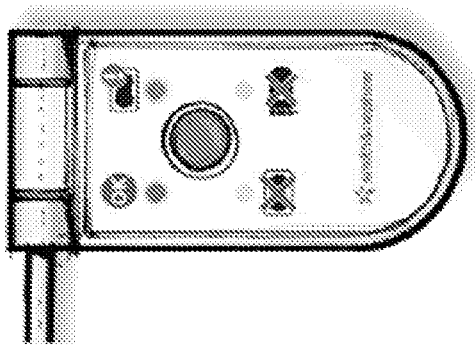
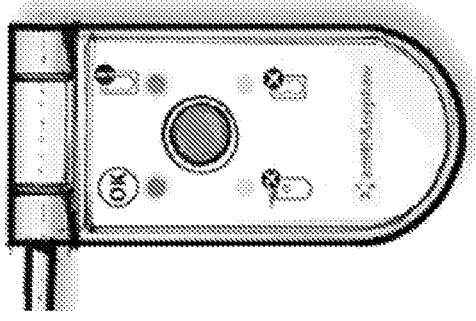
FIG. 123

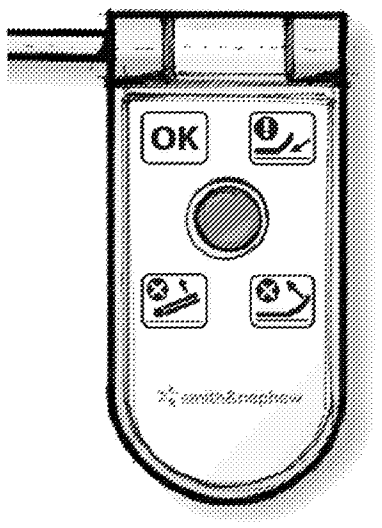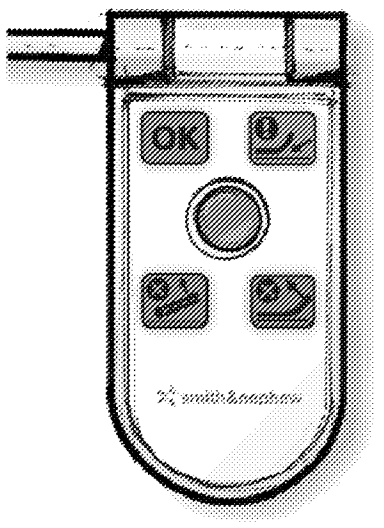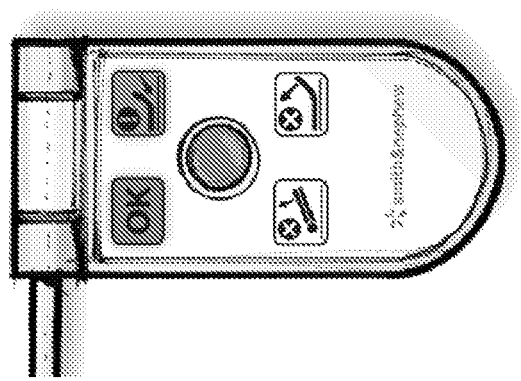
FIG. 128

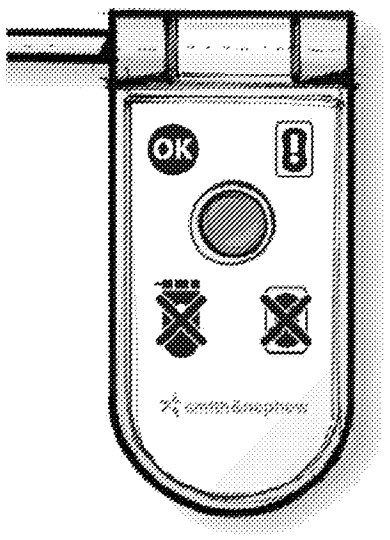
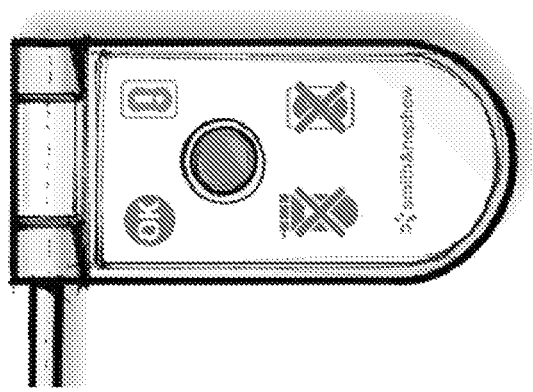
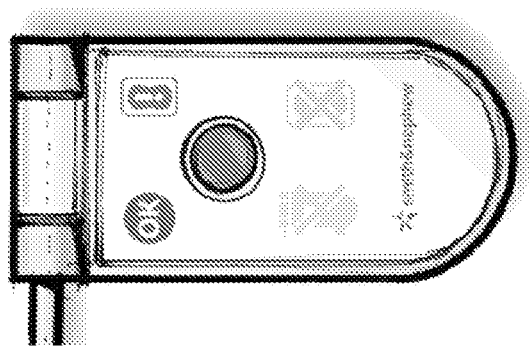
FIG. 129

Initial Concepts
OK' Icon
Illuminates green (pulsing) when product is running normally
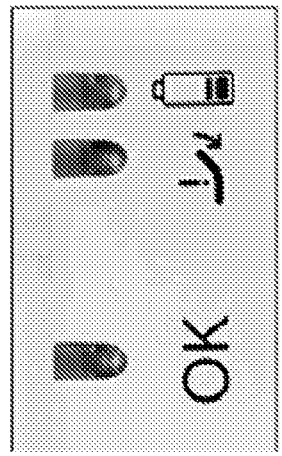
FIG. 130

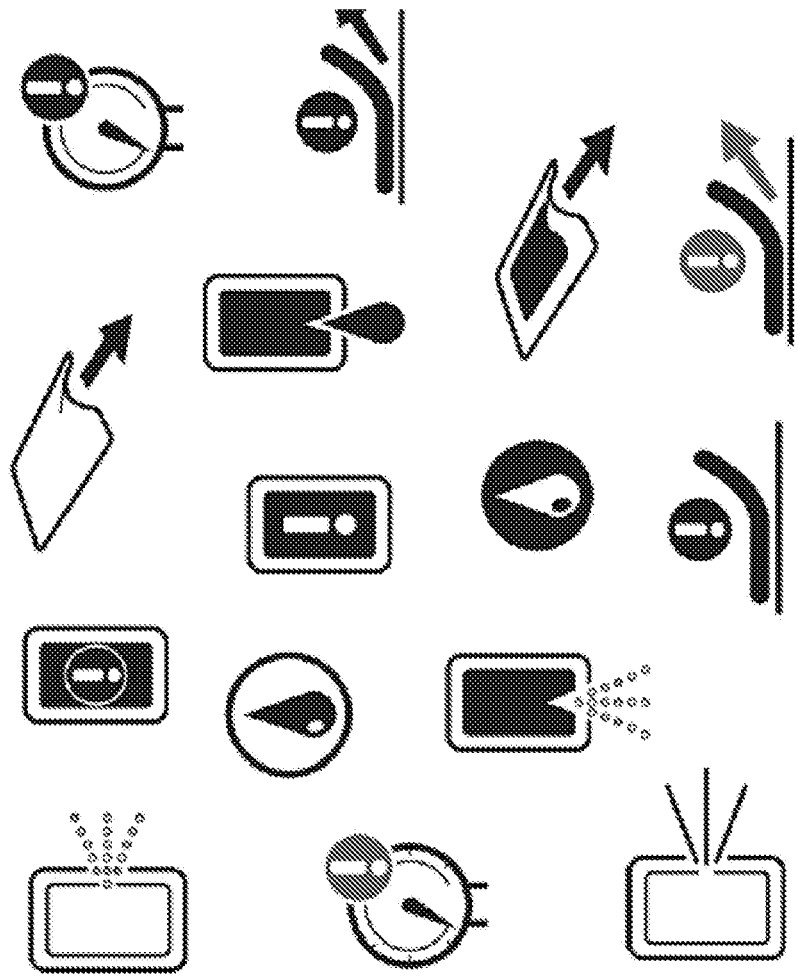
FIG. 131
'Dressing Leak' Icon
- Indicated pressure loss due to incomplete sealing of the dressing
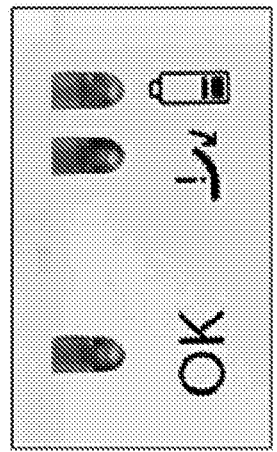

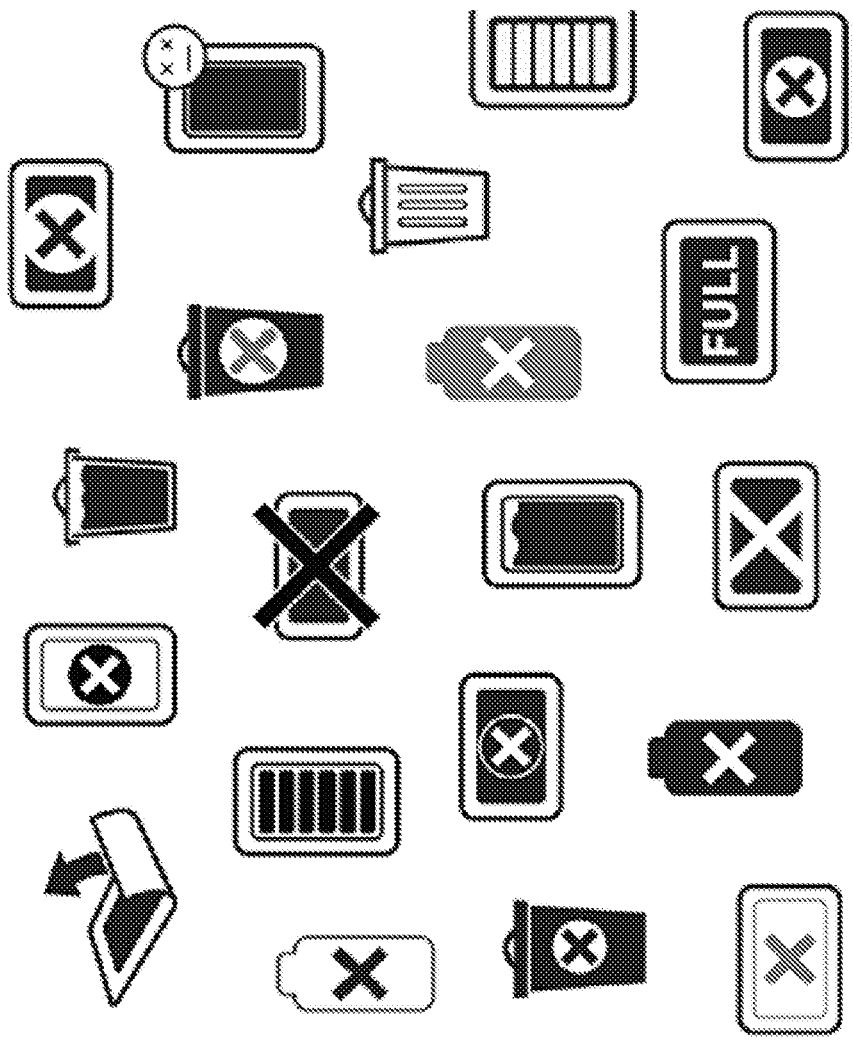
FIG. 132
'End of Life' Icon
- Illuminates to indicate when device is within 7 days of end of life or illuminates when the 7 day life has expired?
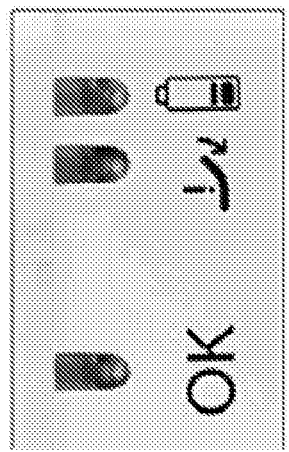

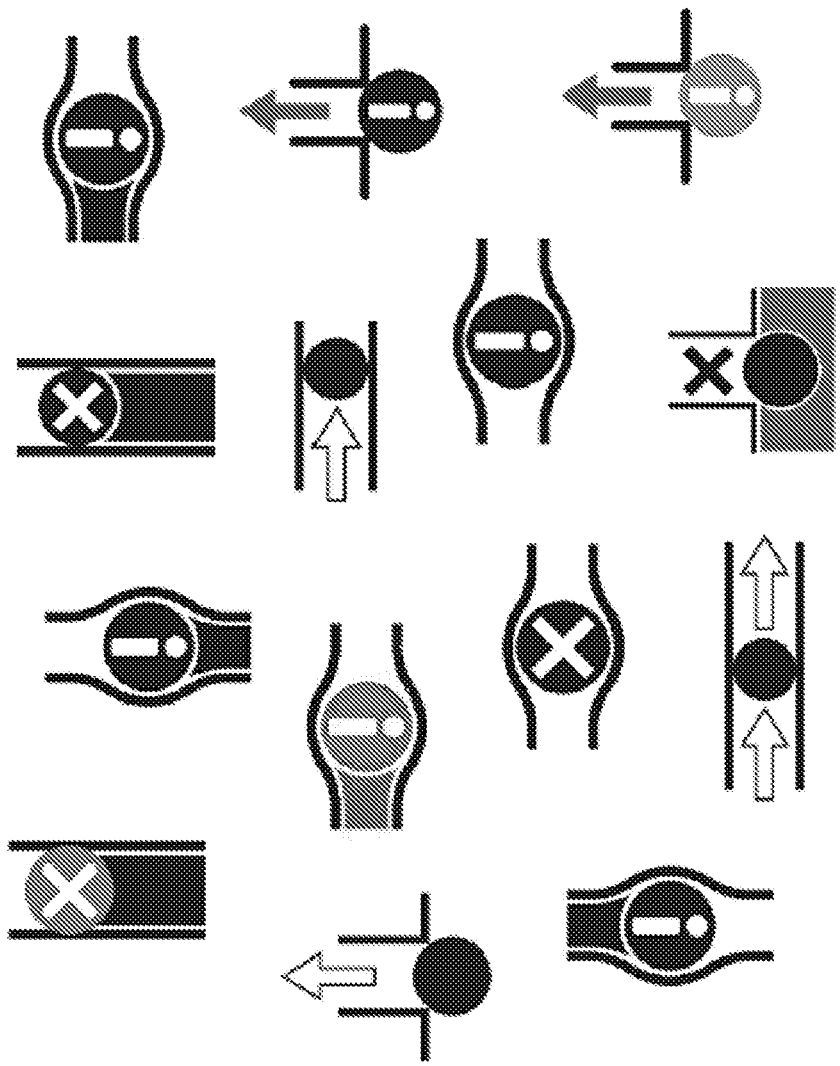
FIG. 133
'Blockage' Icon
- Illuminates to indicate when the dressing filter is blocked and the dressing requires changing.
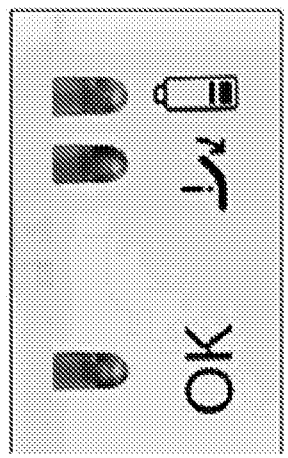

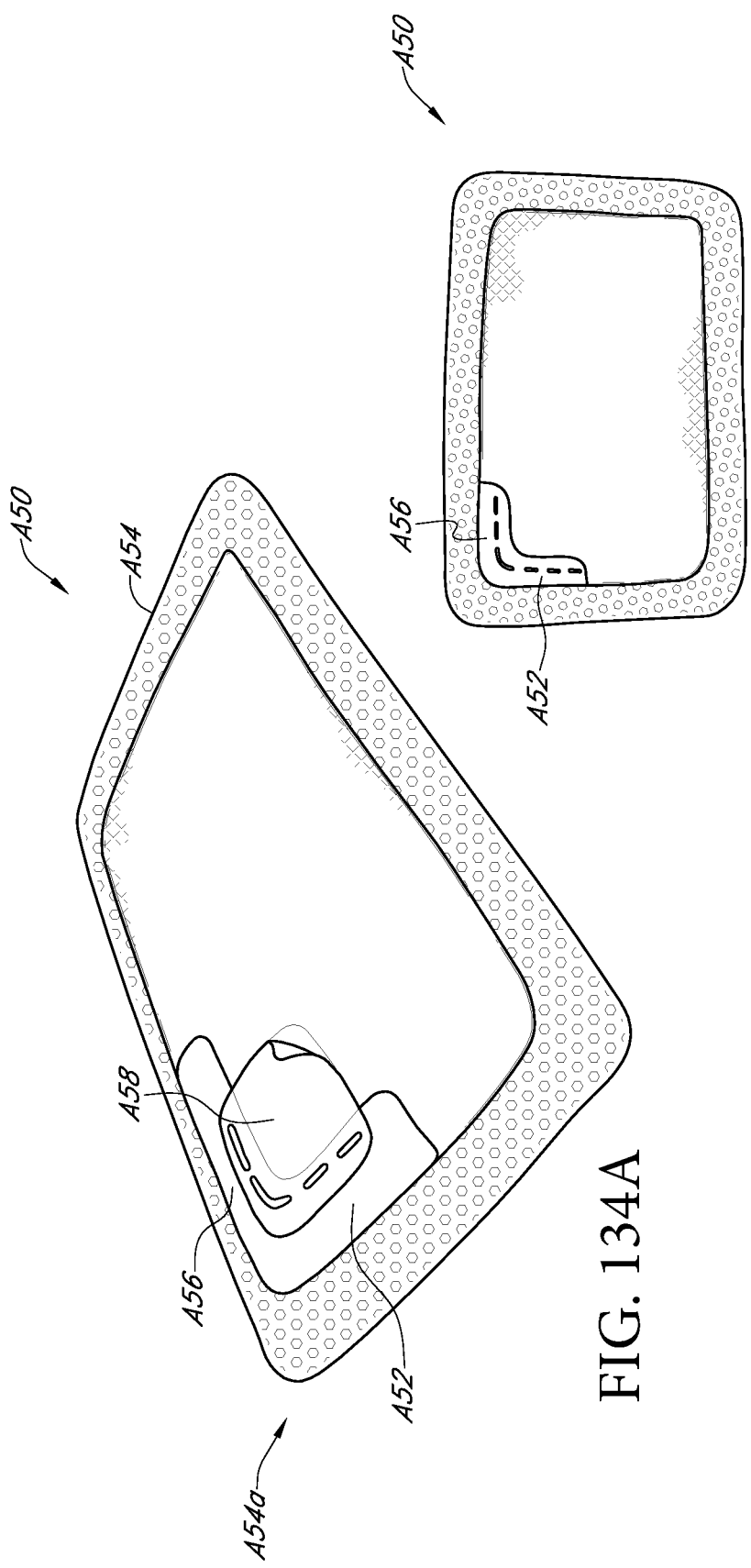

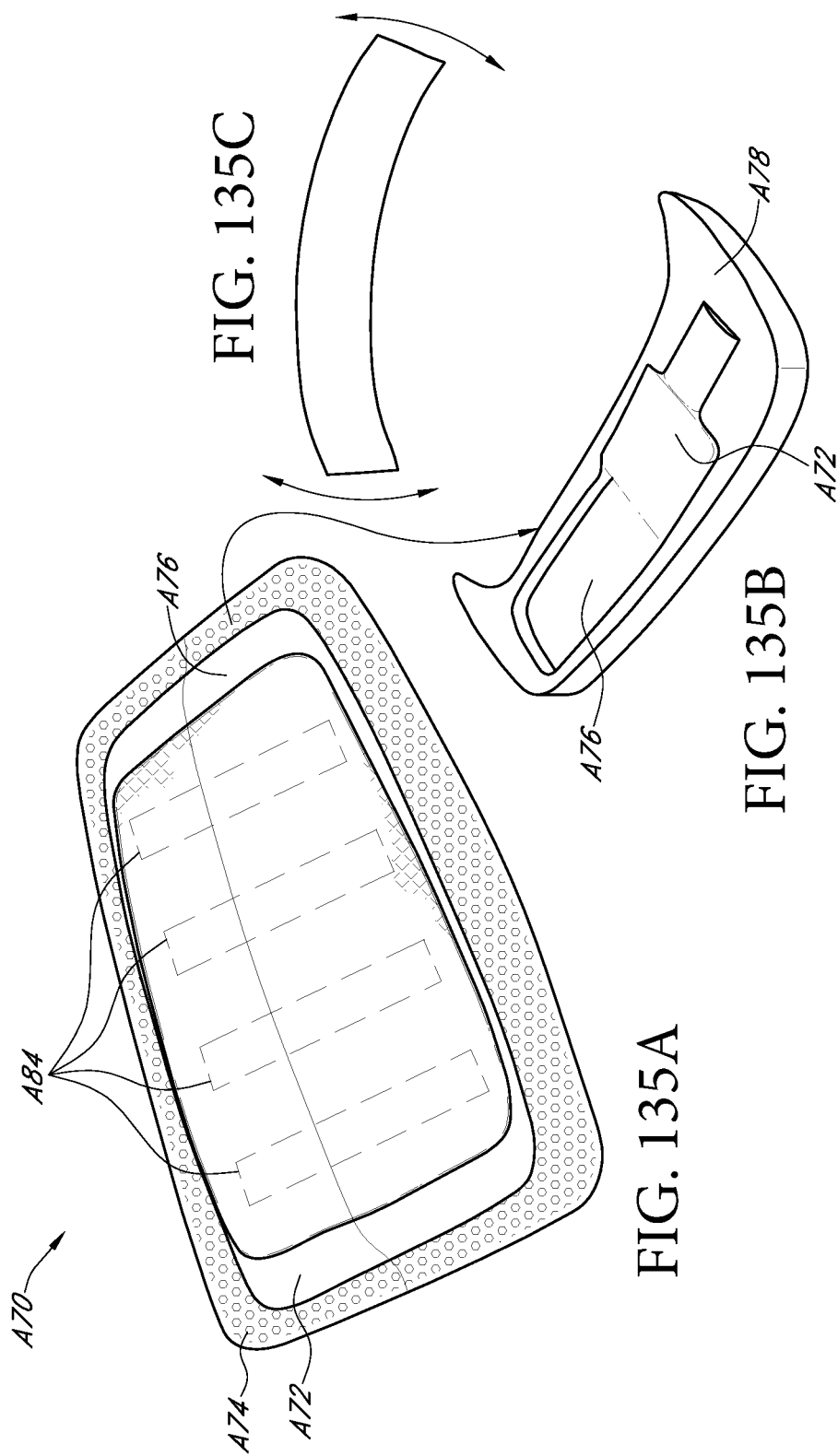

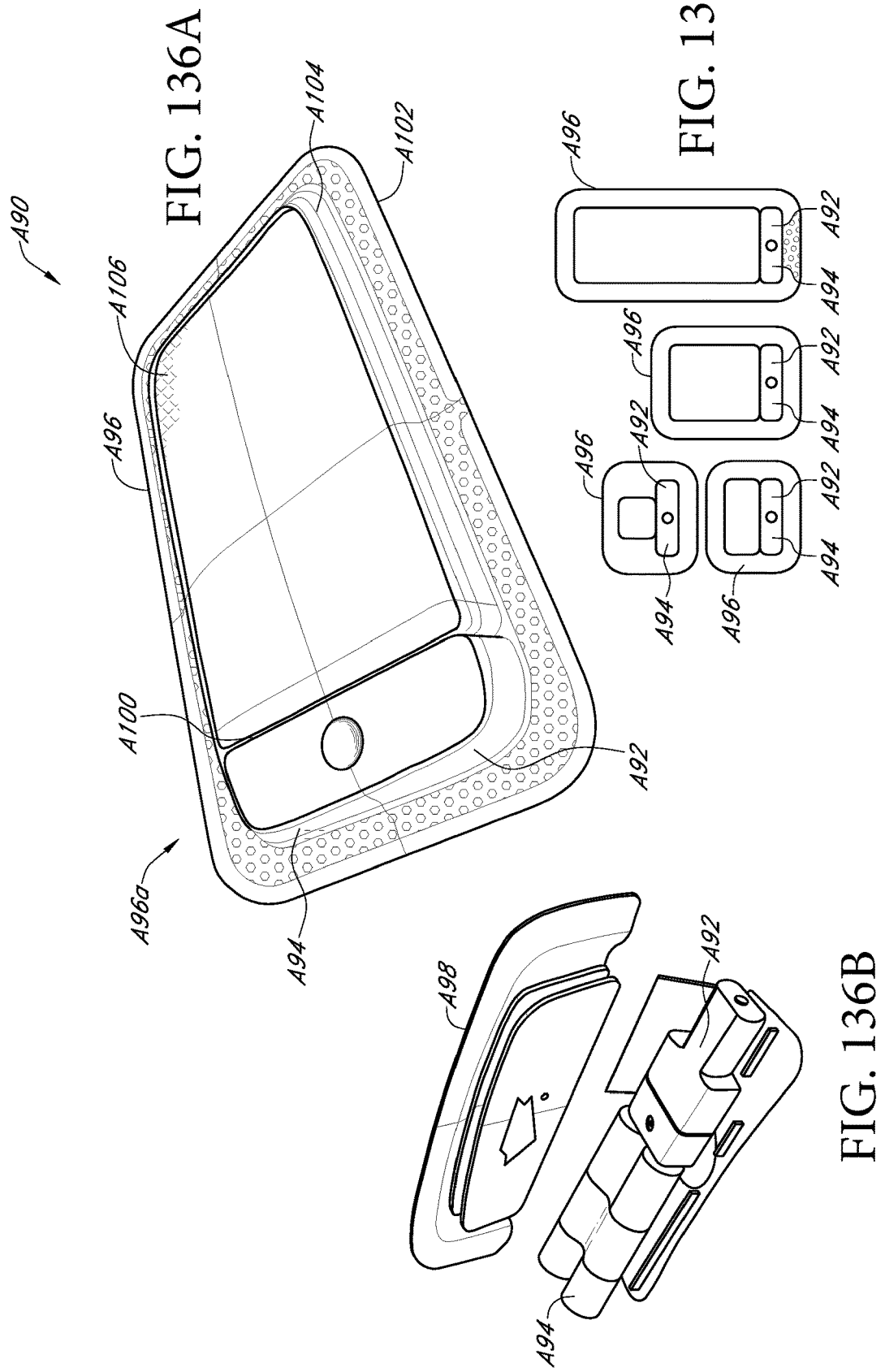

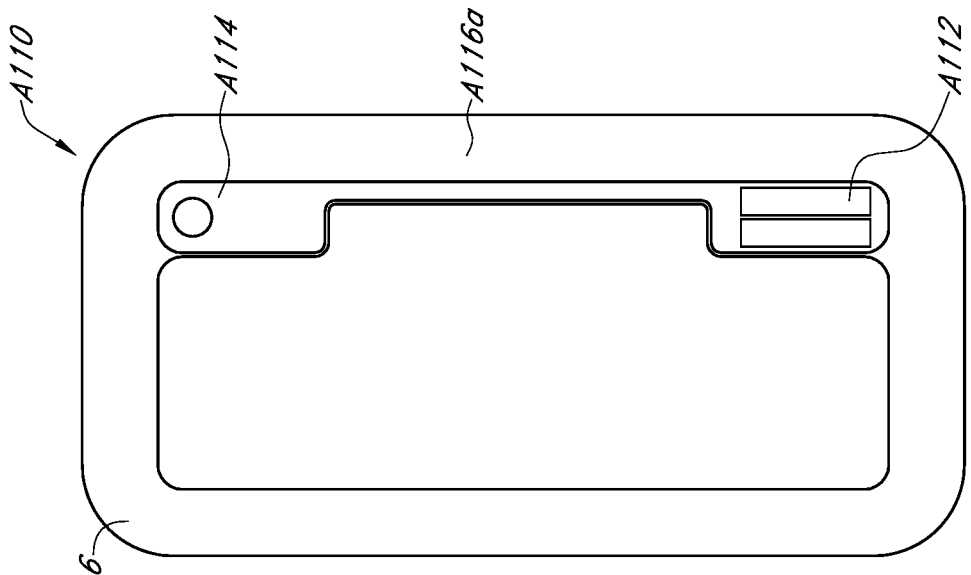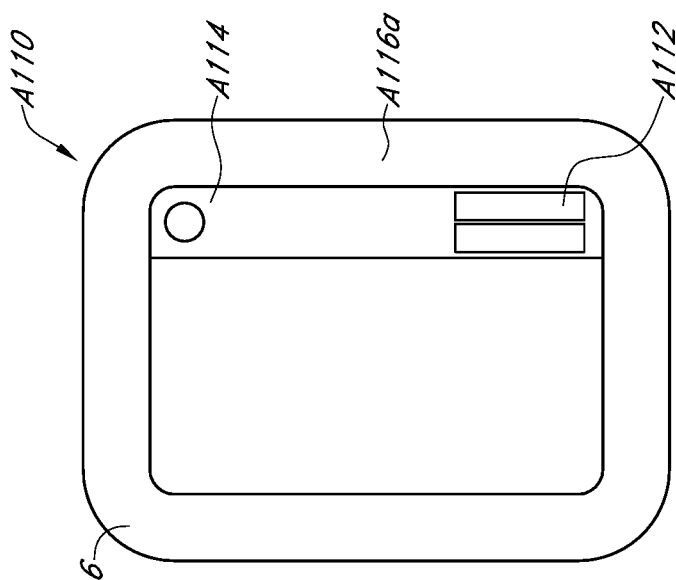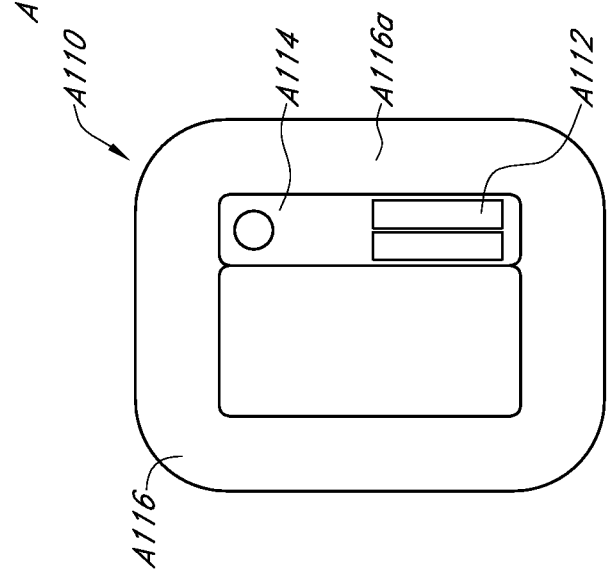

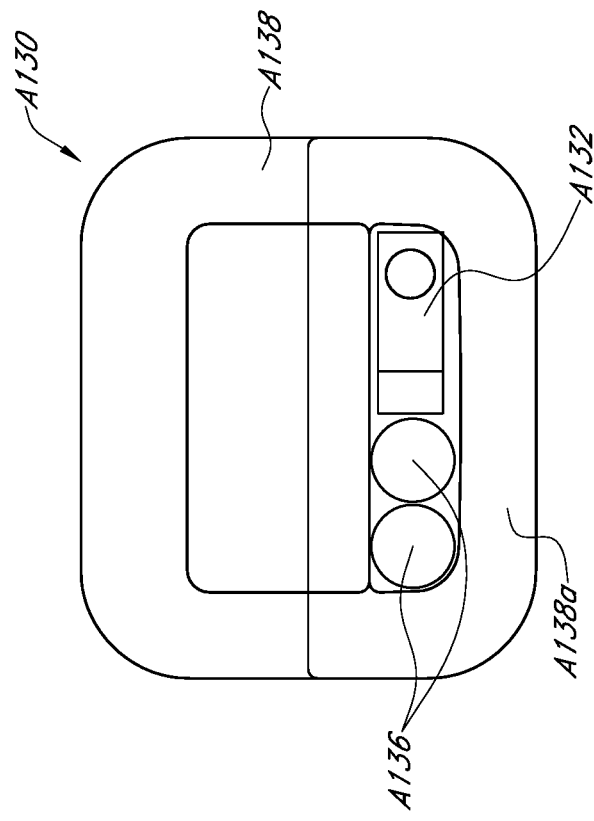
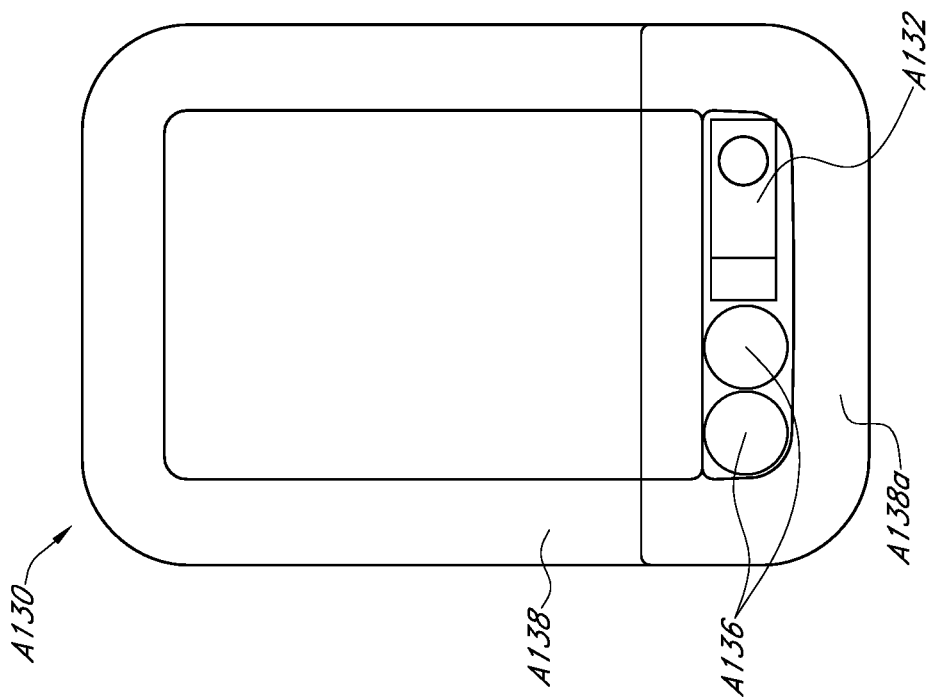
FIG. 138B
FIG. 138A

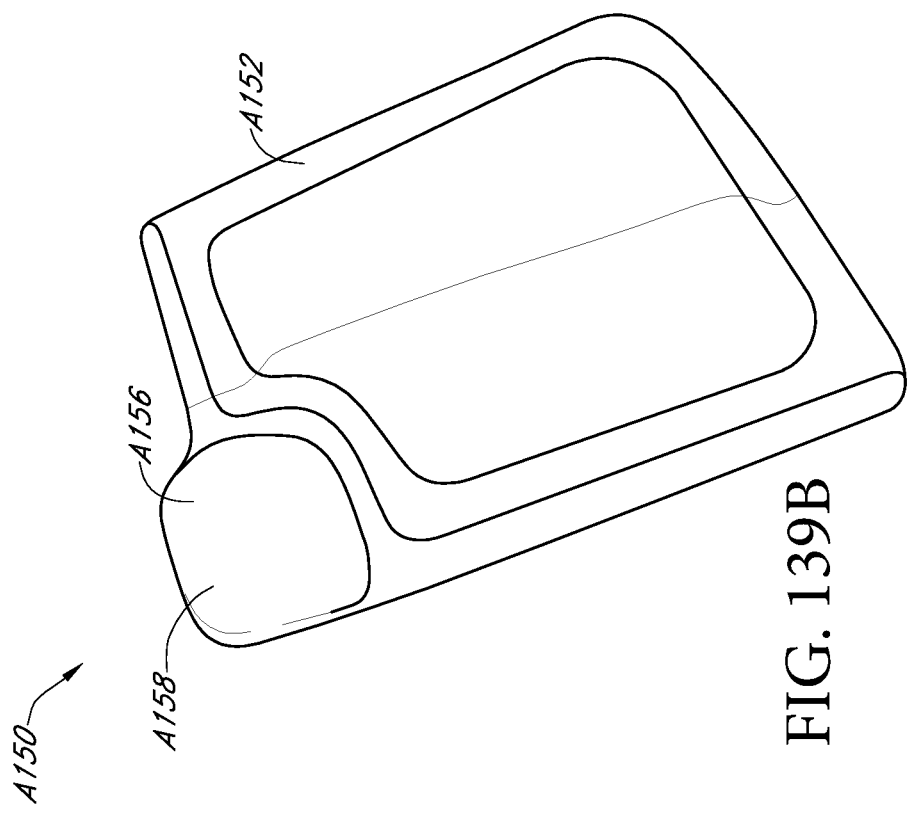
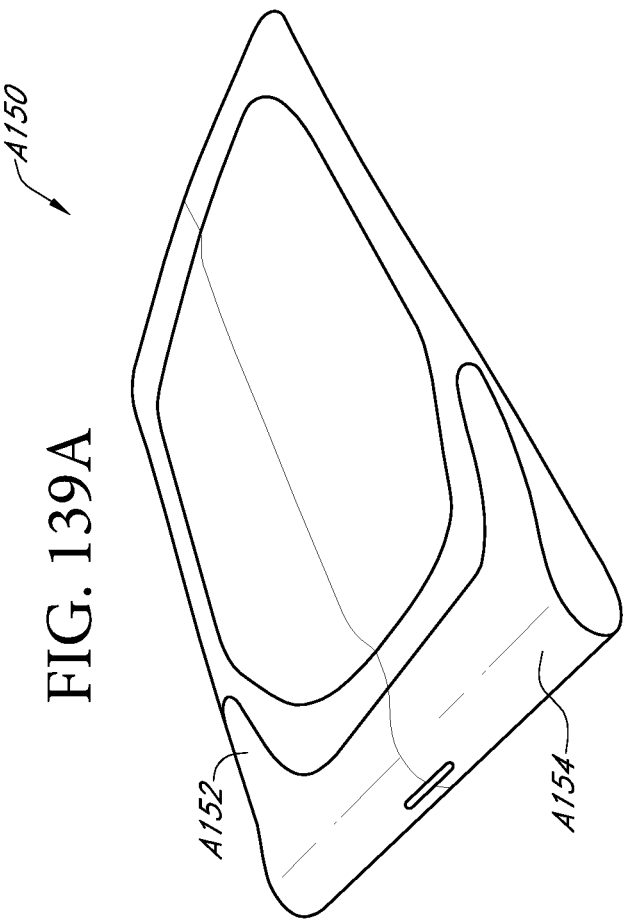

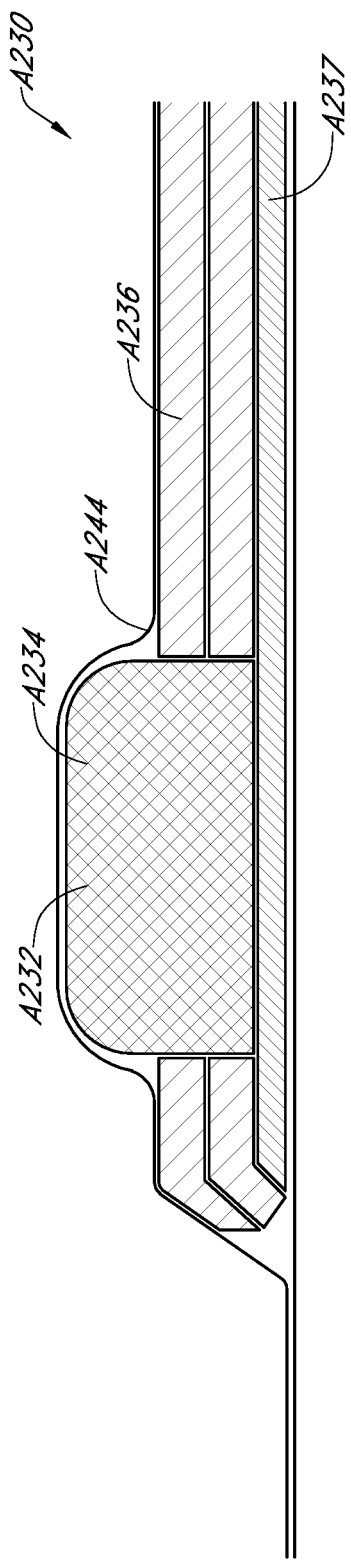

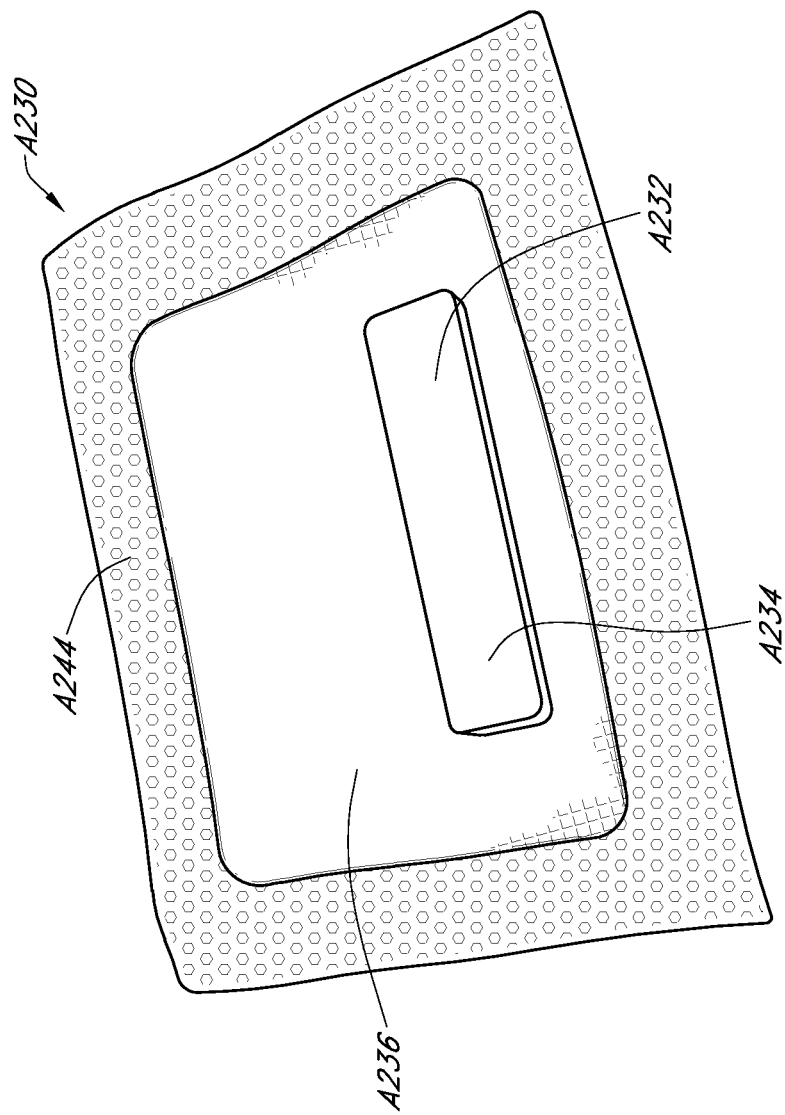

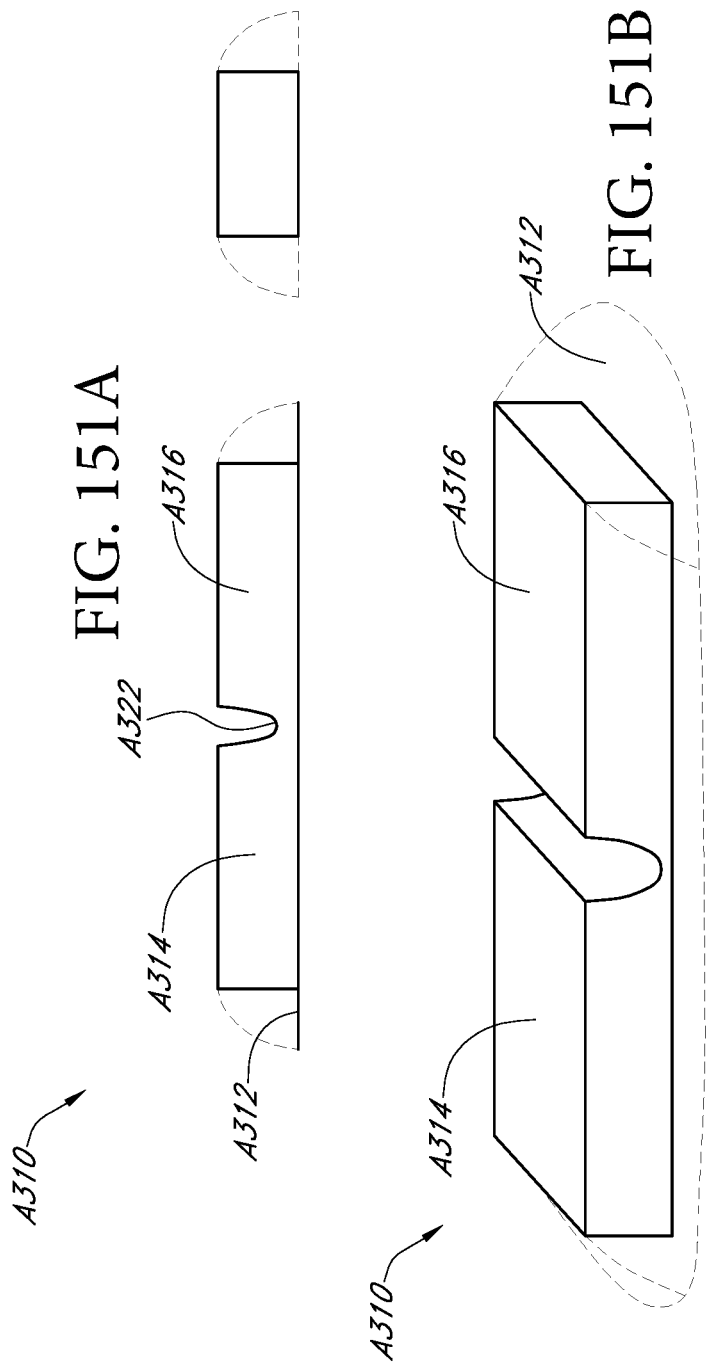

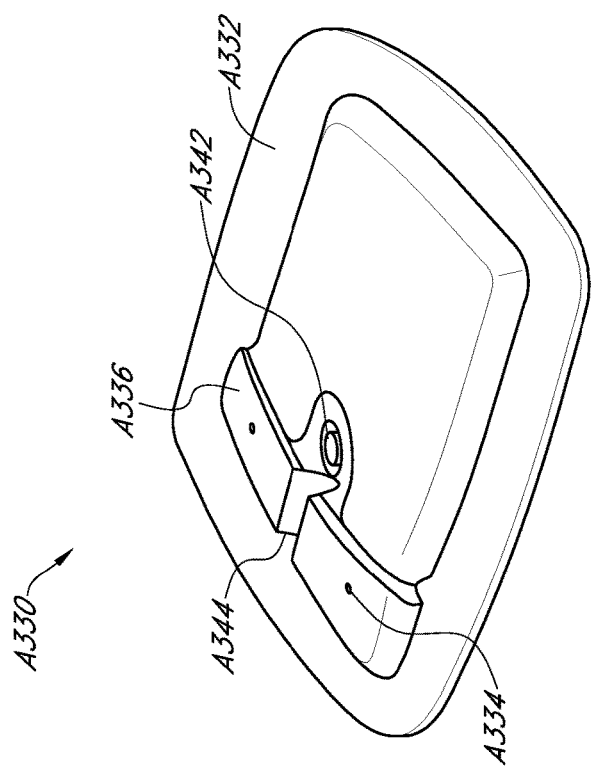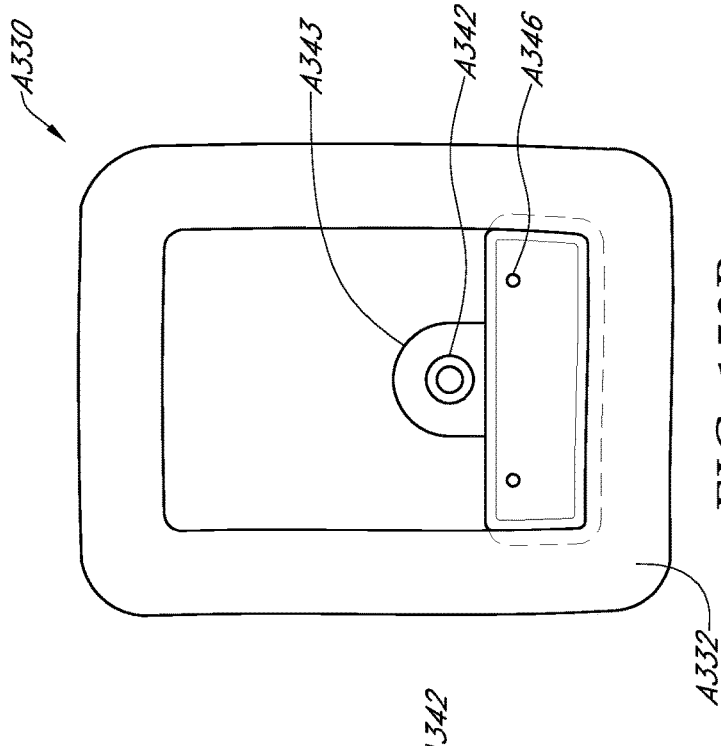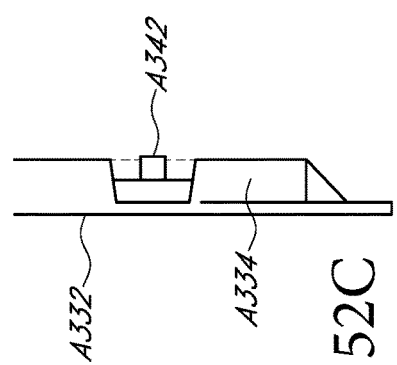
FIG. 152A
FIG. 152B
FIG. 152C

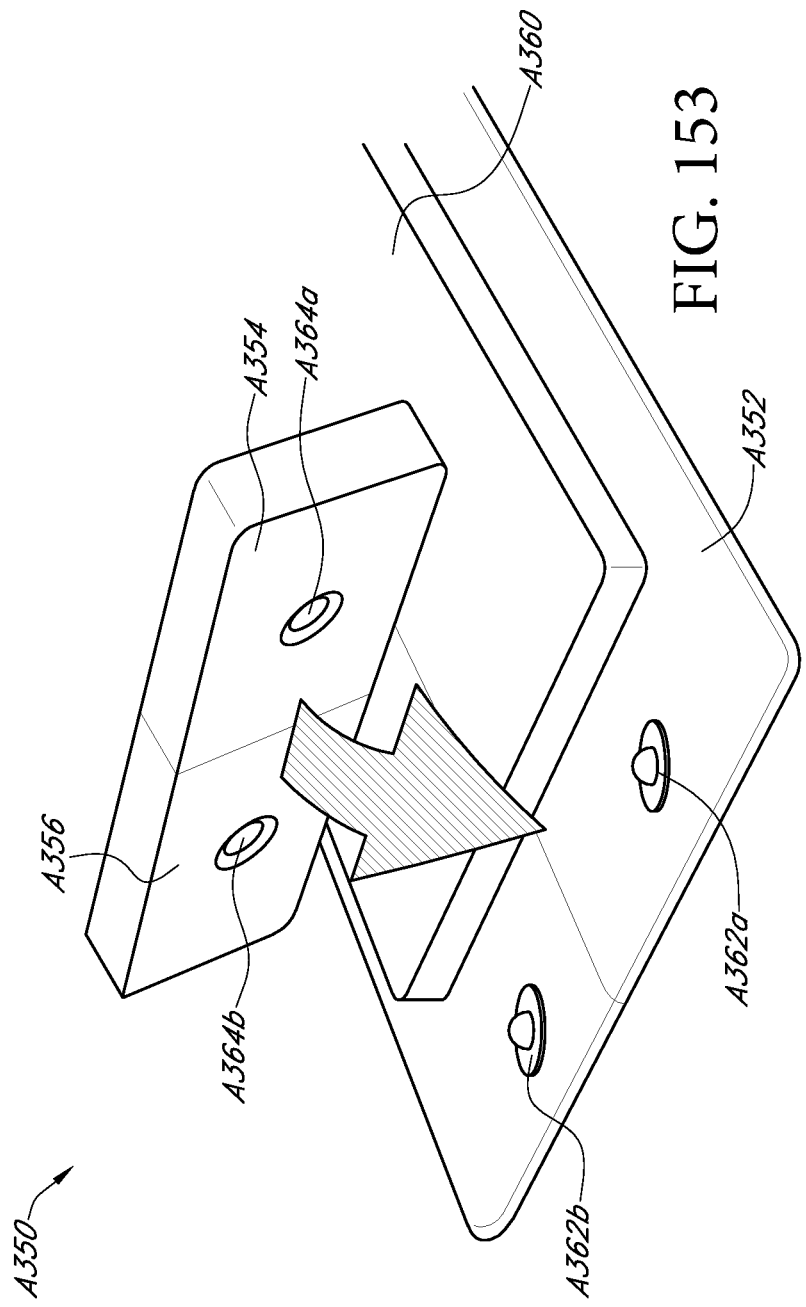

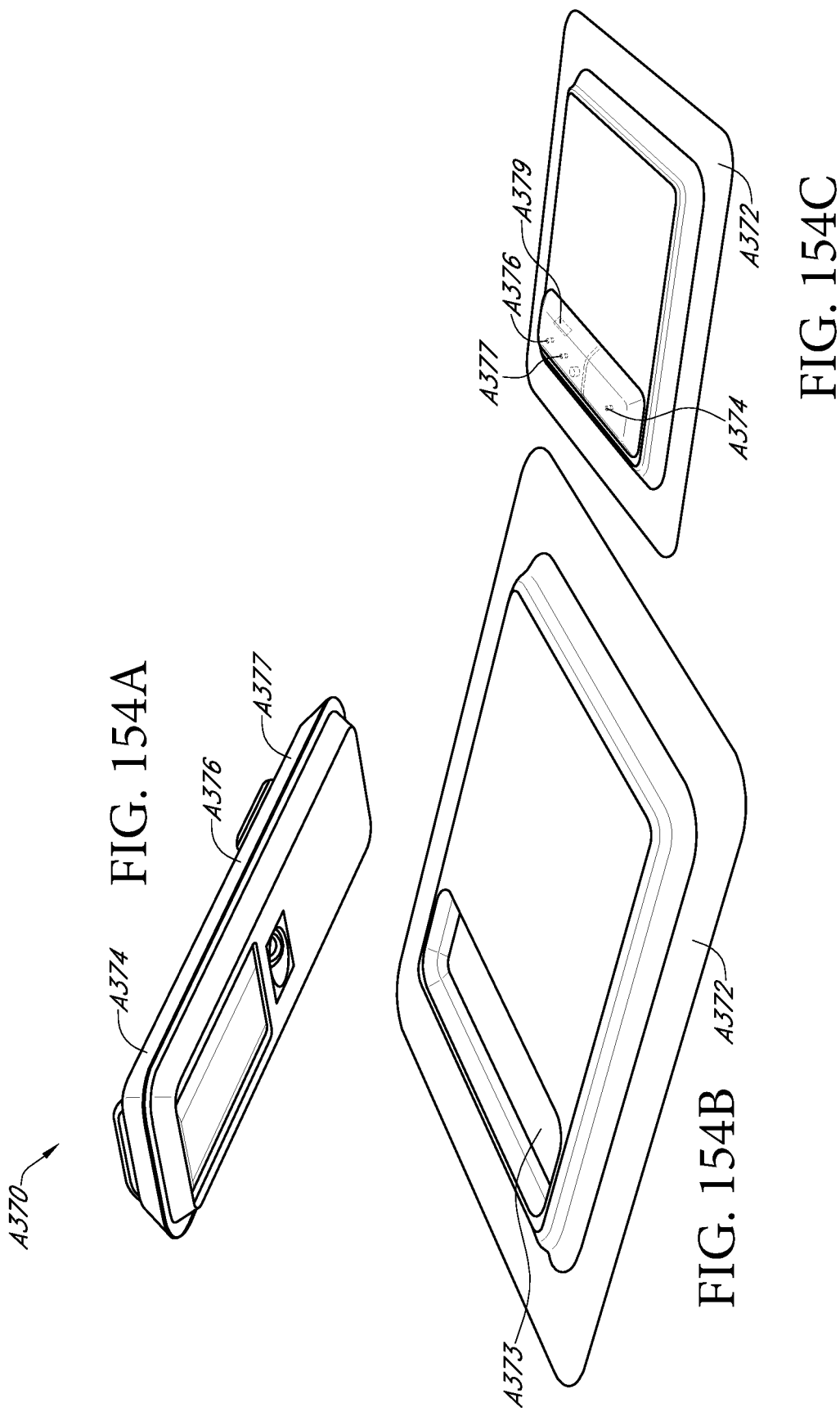

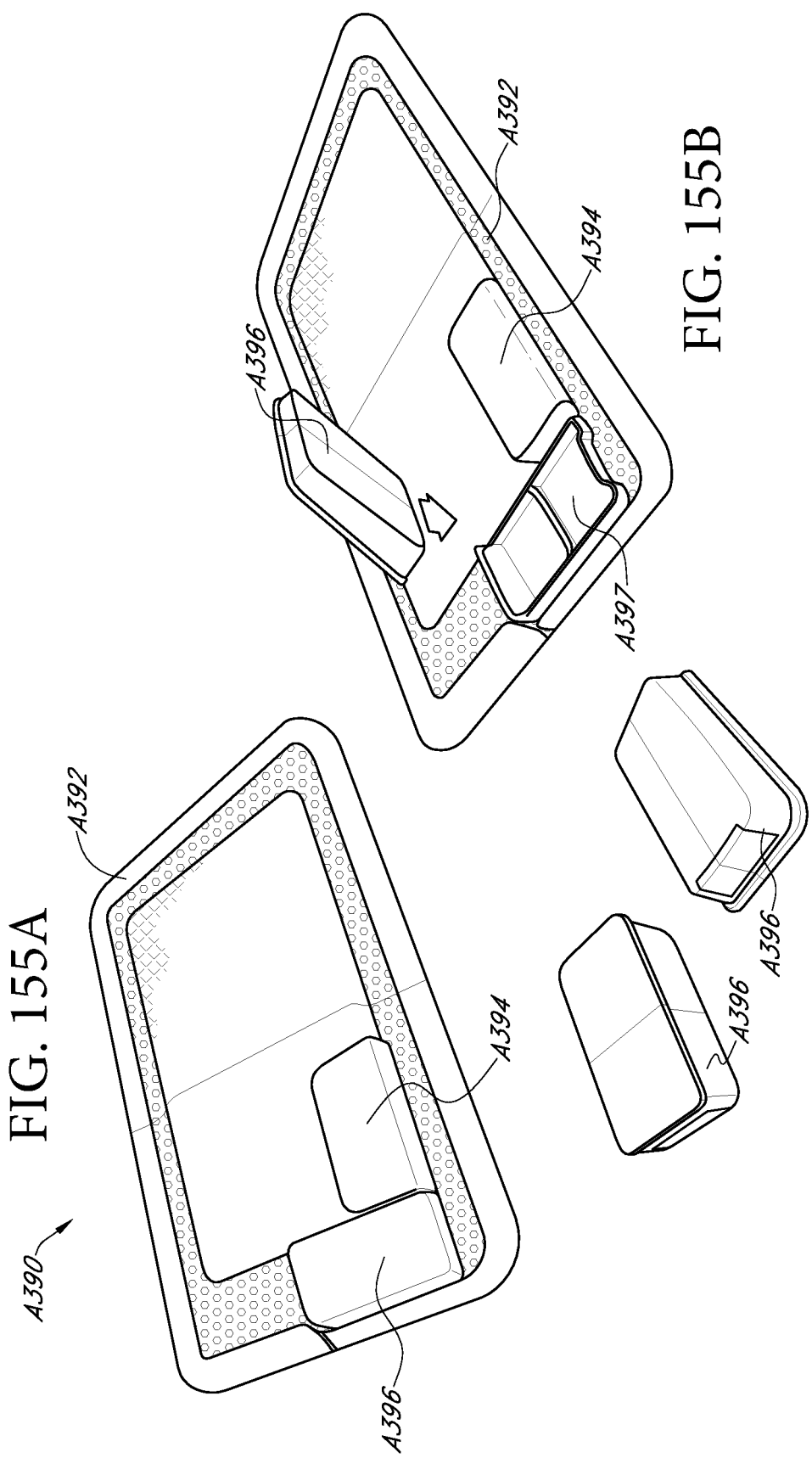

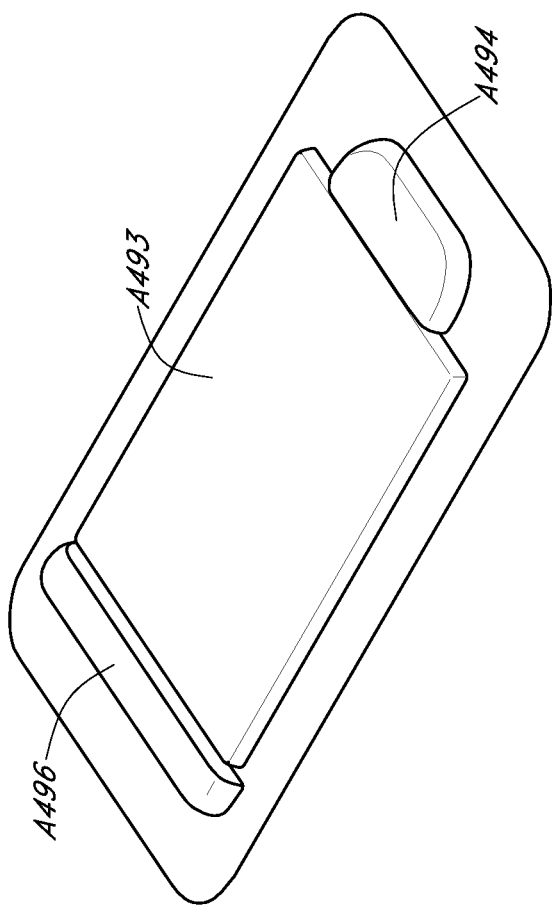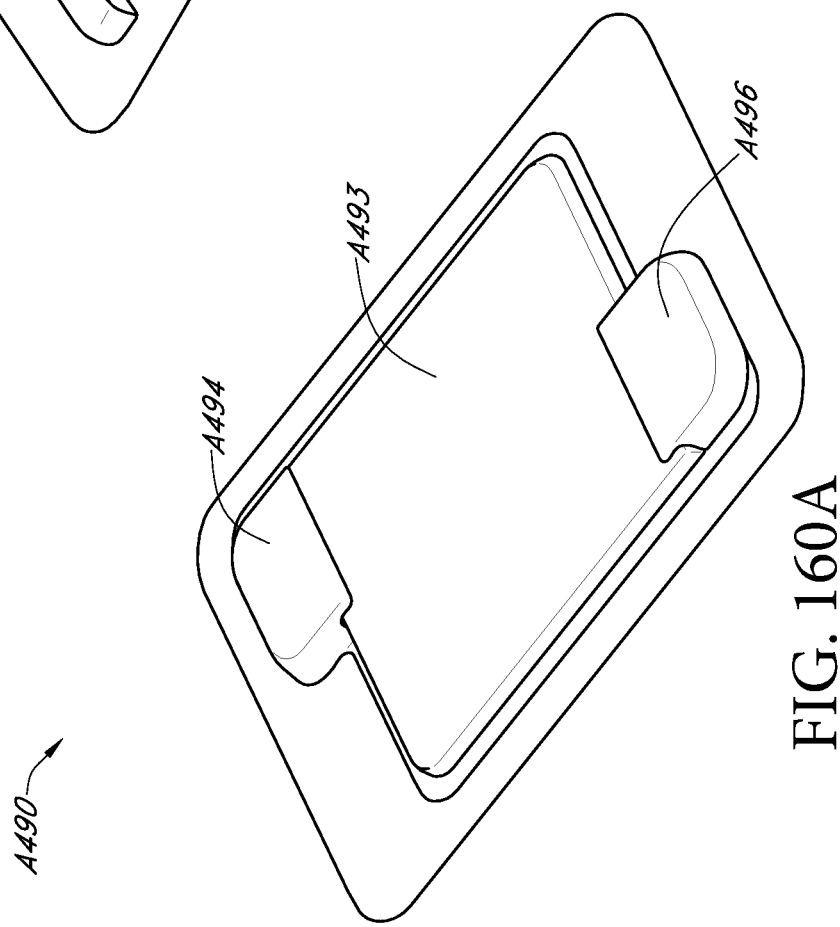

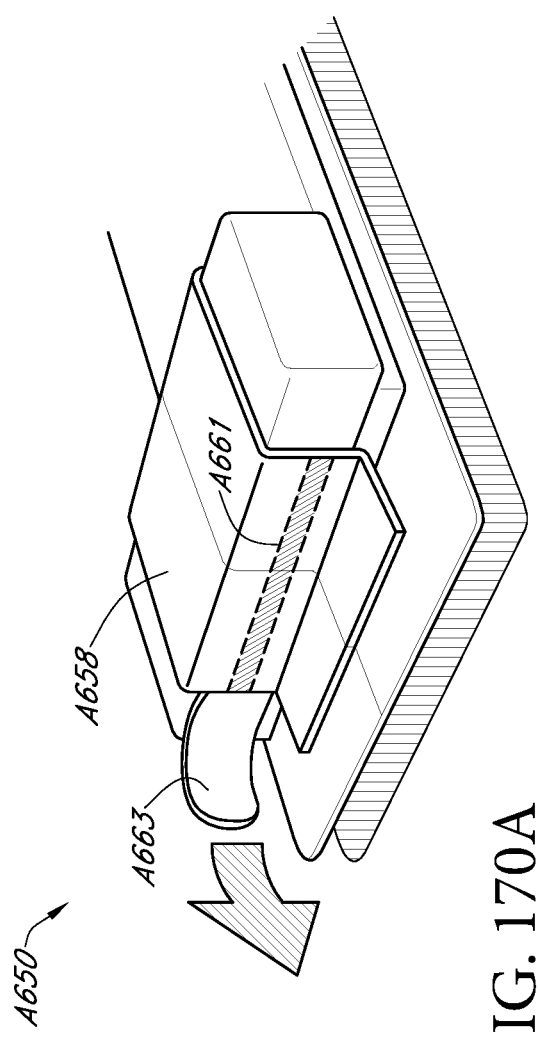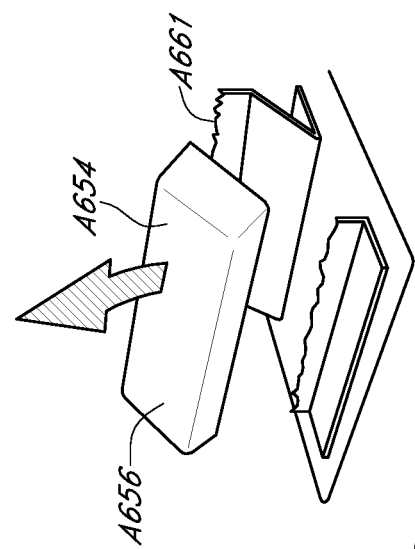
FIG. 170A
FIG. 170B

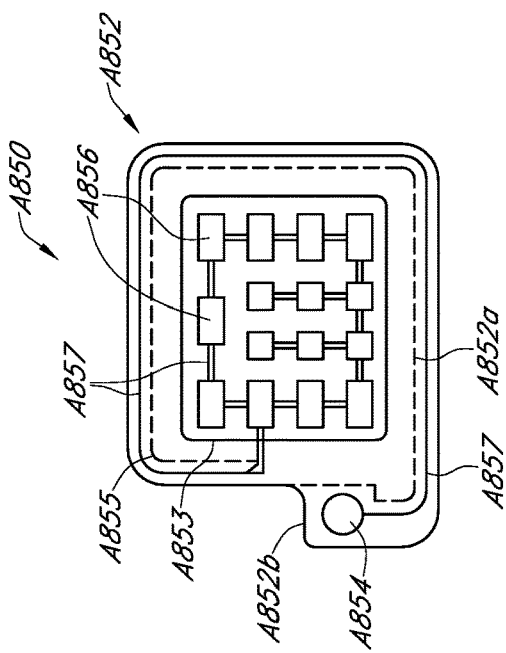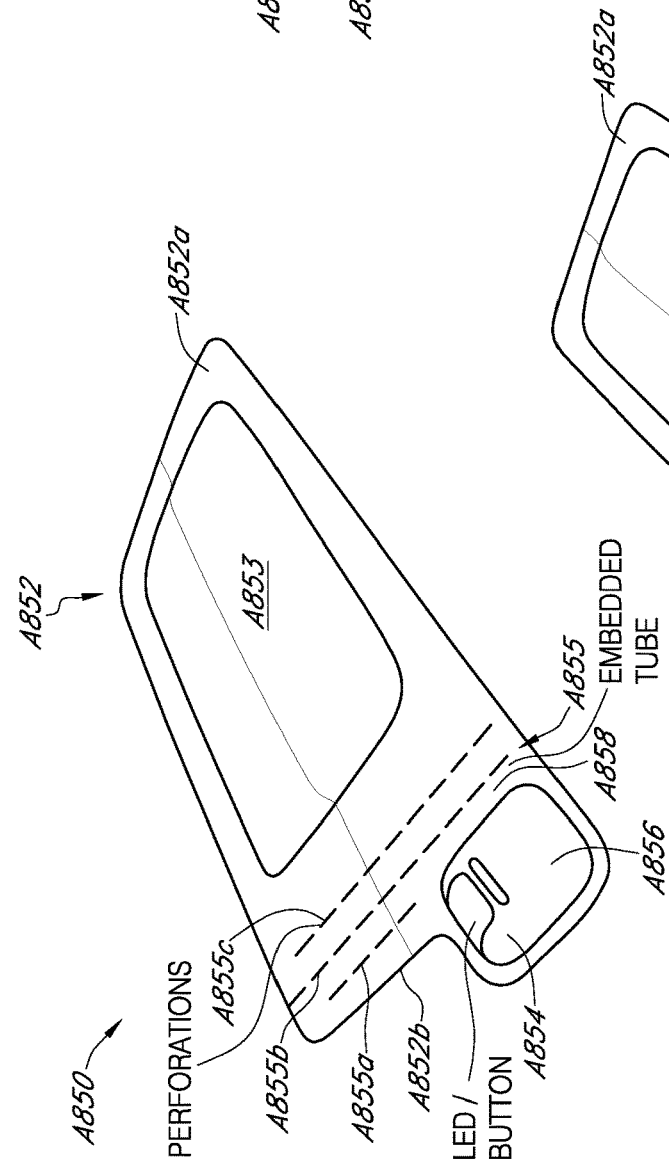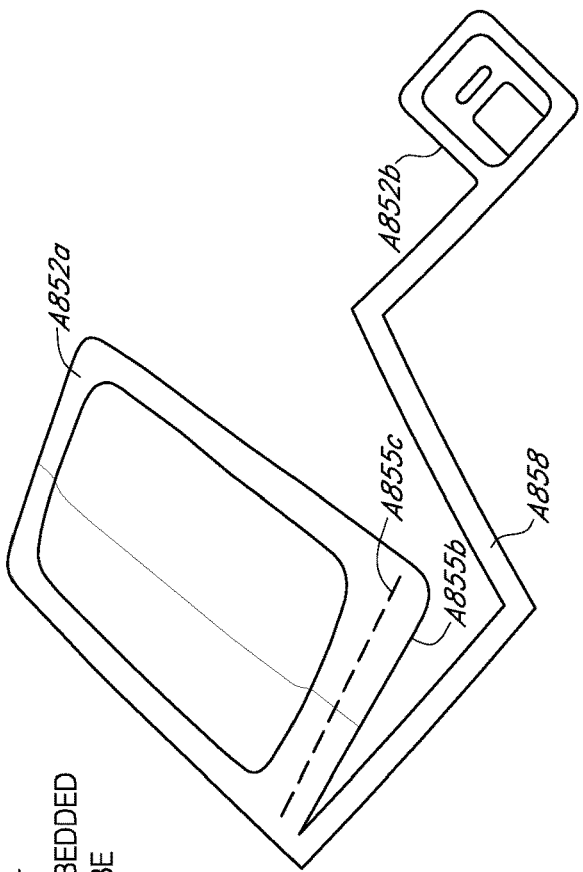

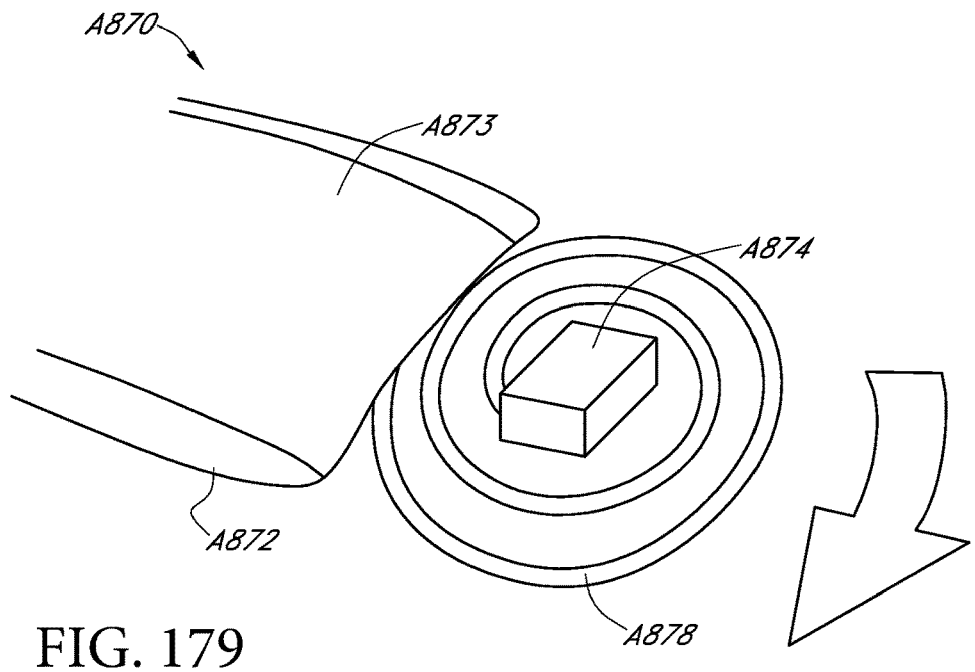
FIG. 179
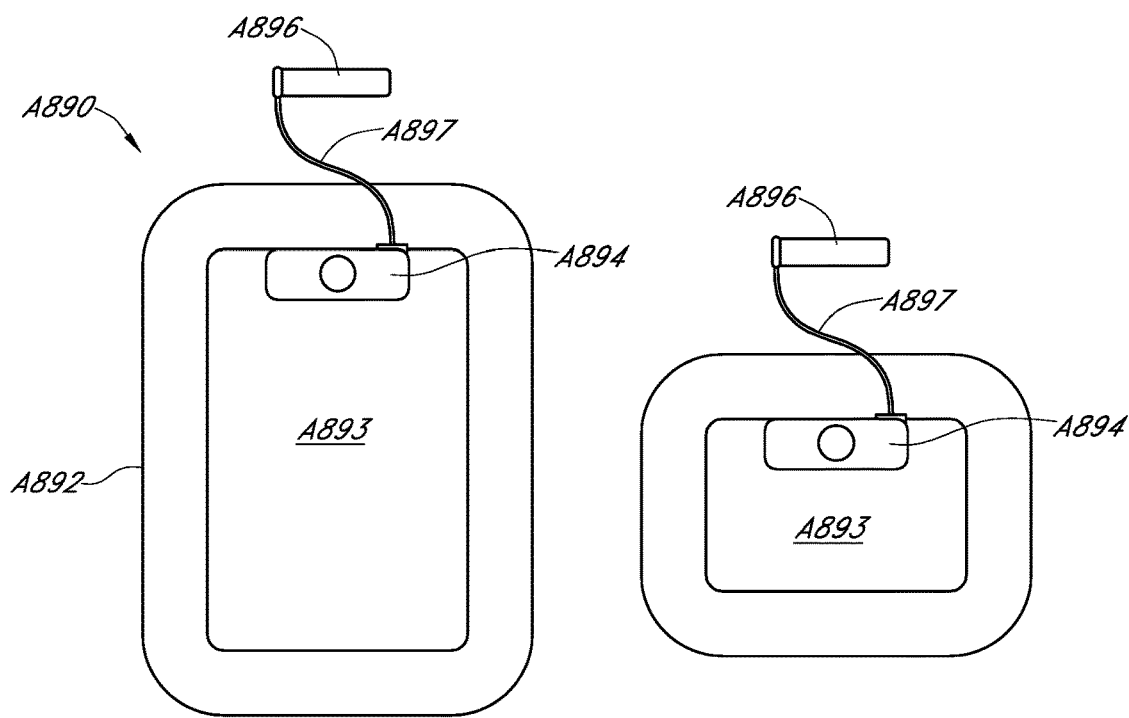
FIG. 180A
FIG. 180B

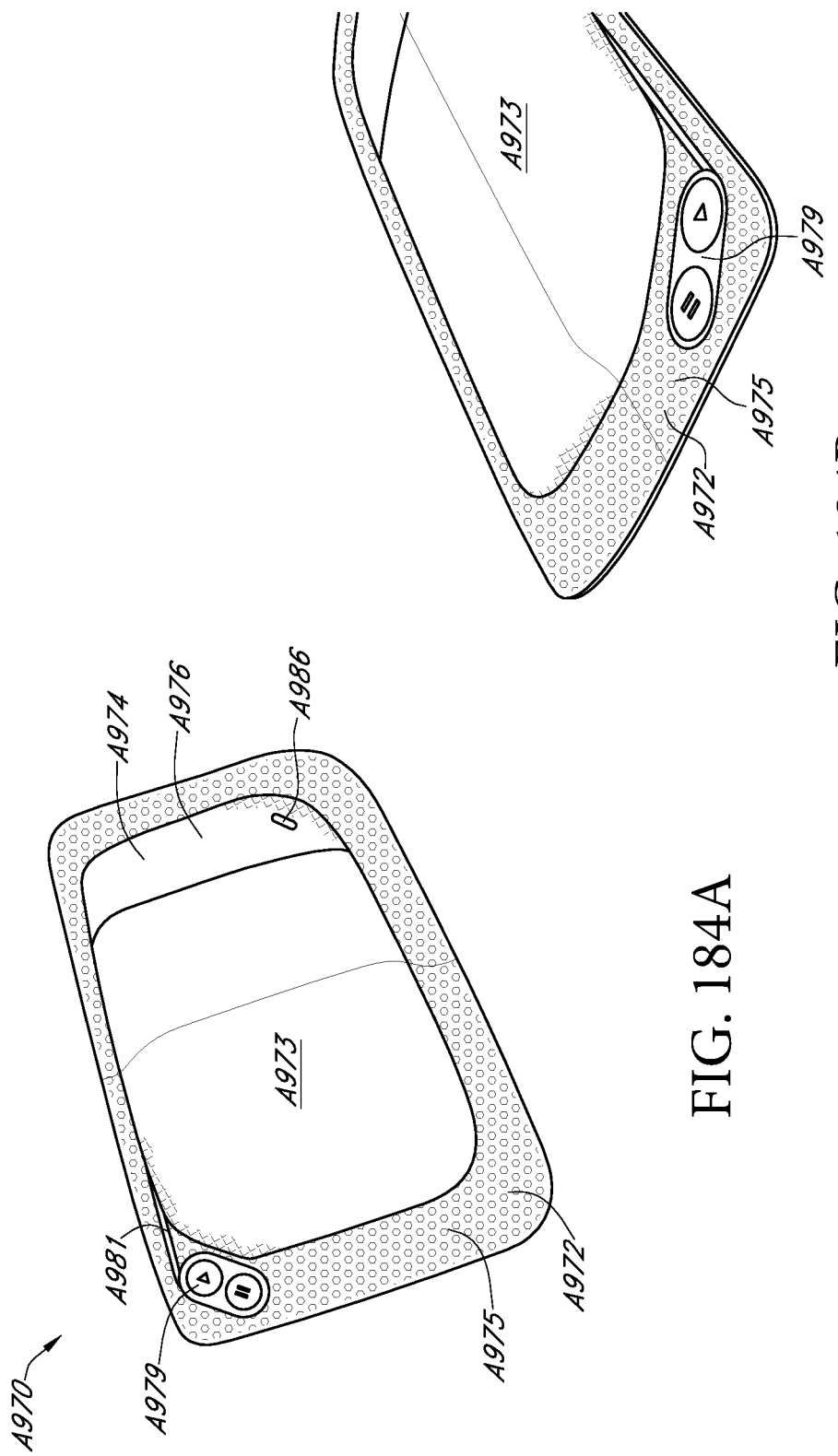

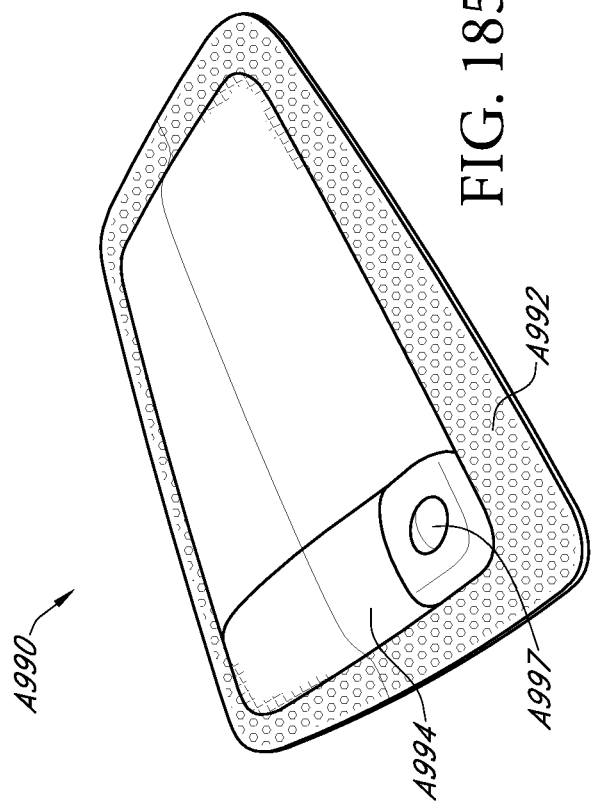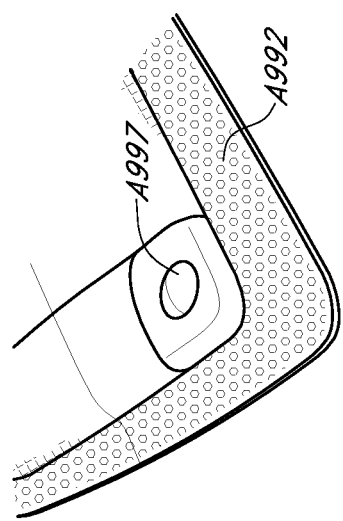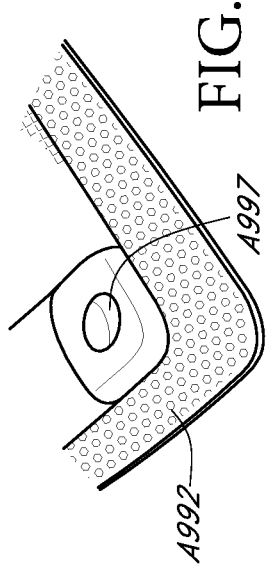
FIG. 185A
FIG. 185B
FIG. 185C

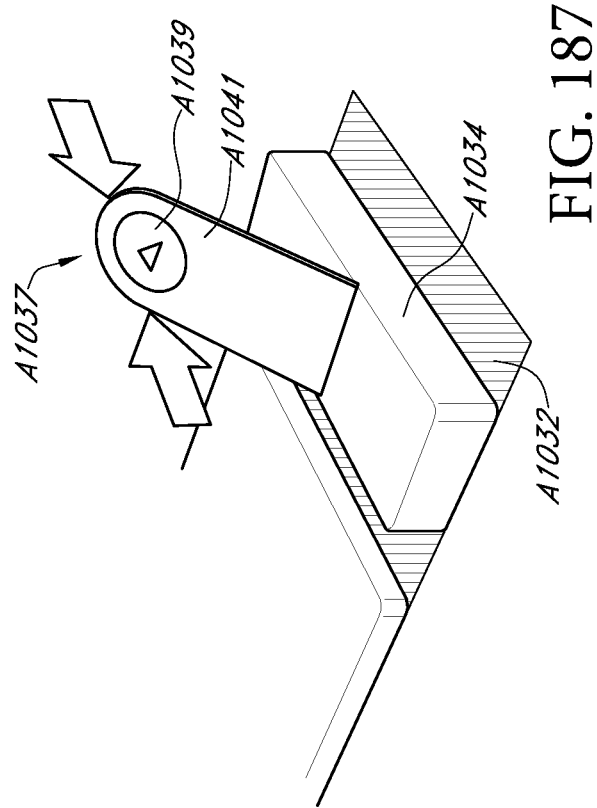
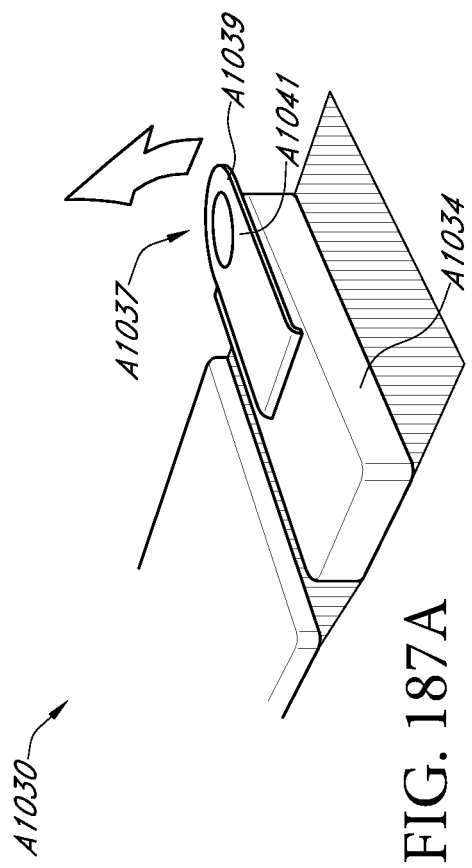
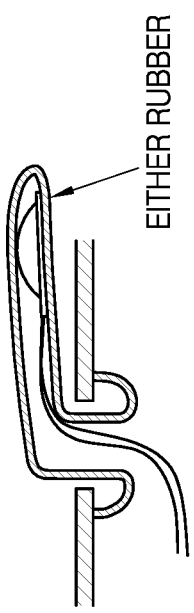
FIG. 187A
FIG. 187B
FIG. 187C

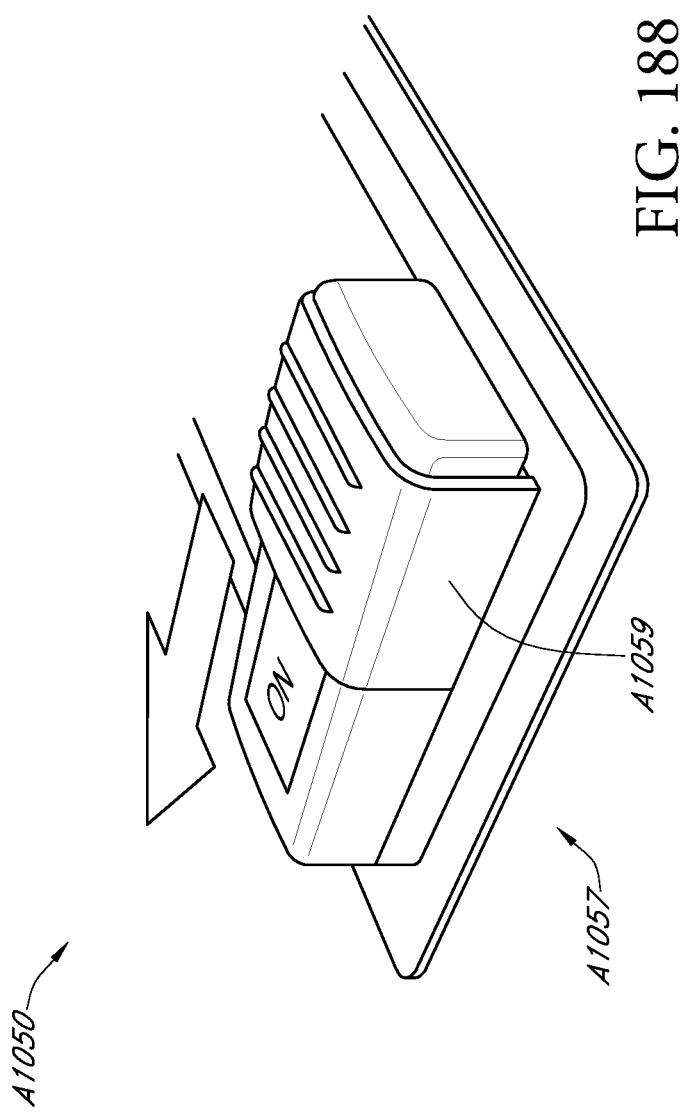

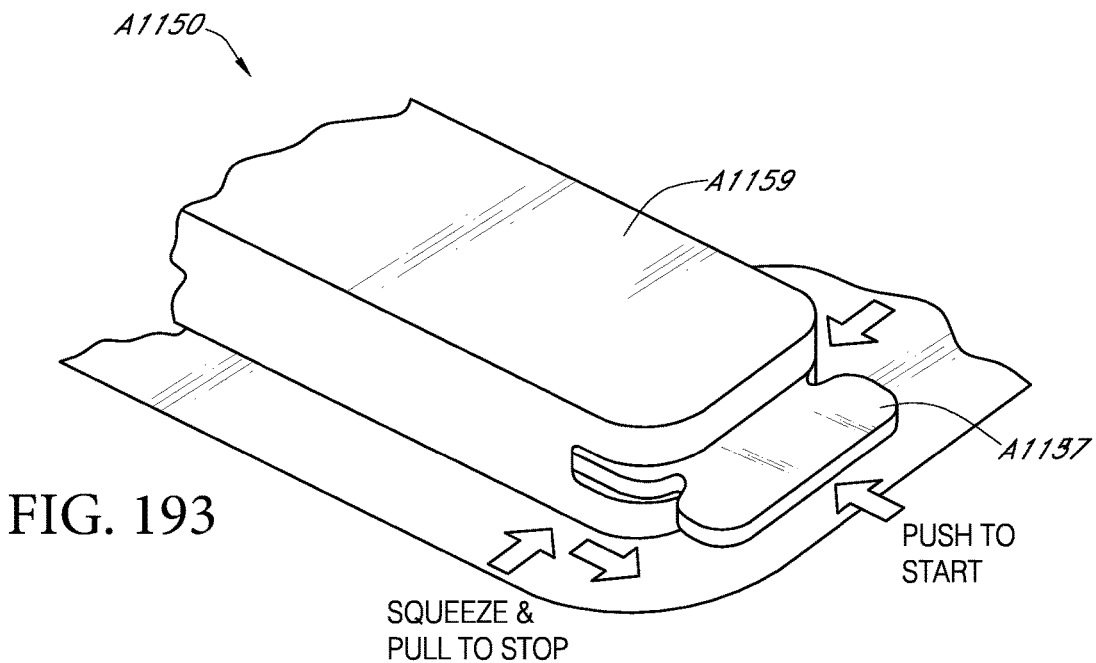
FIG. 193
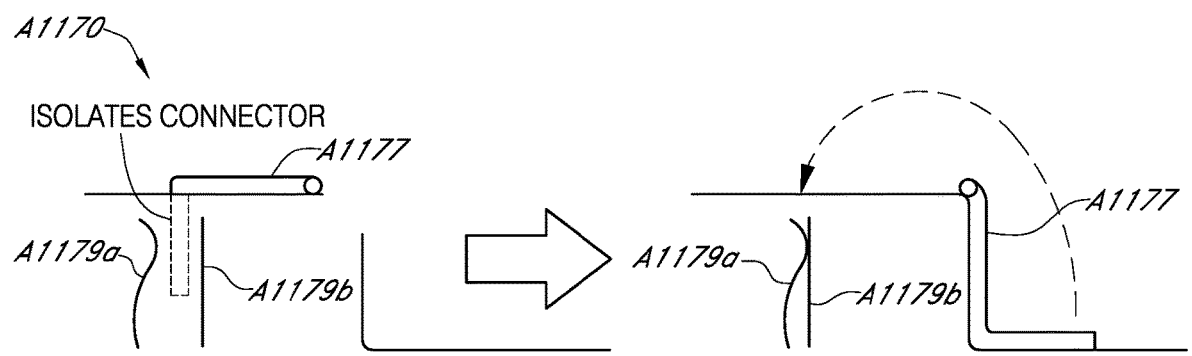
FIG. 194A
FIG. 194B

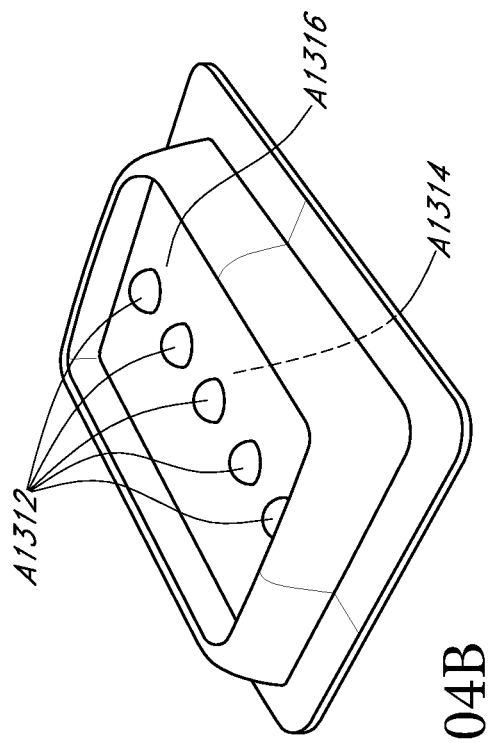
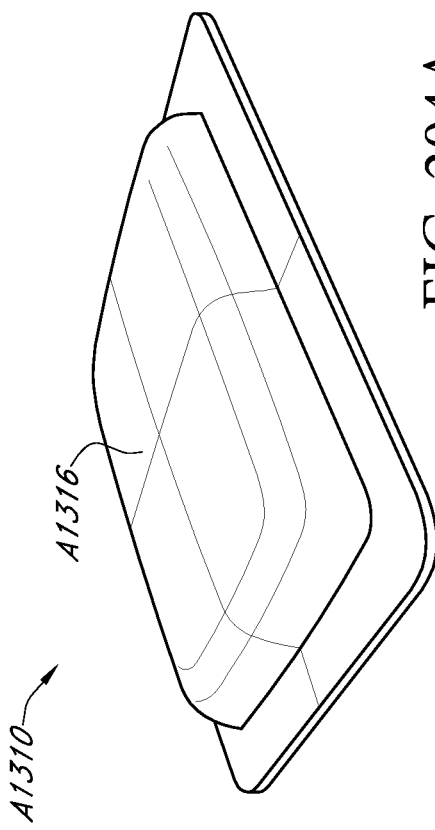
FIG. 204A
FIG. 204B

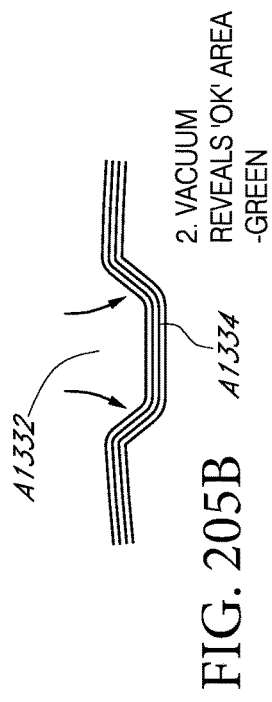
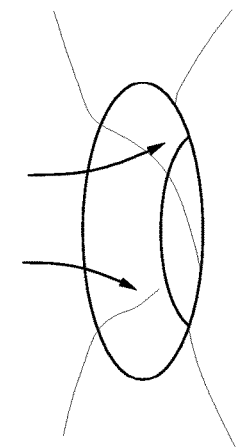
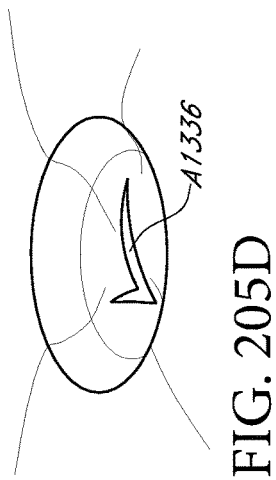
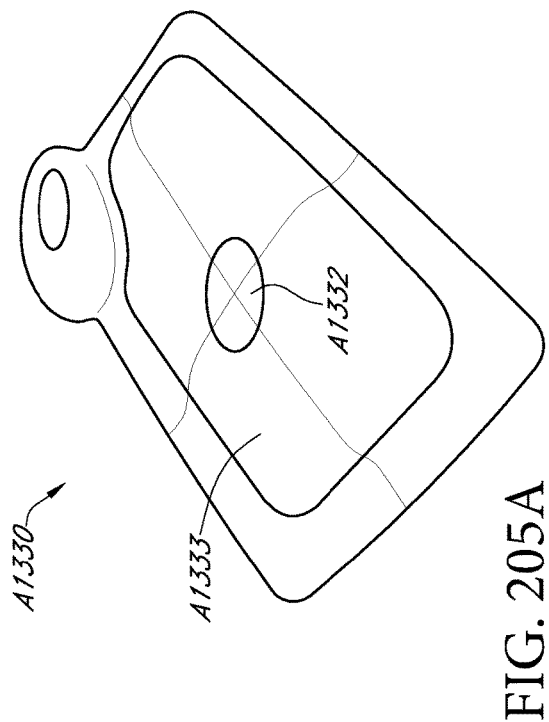

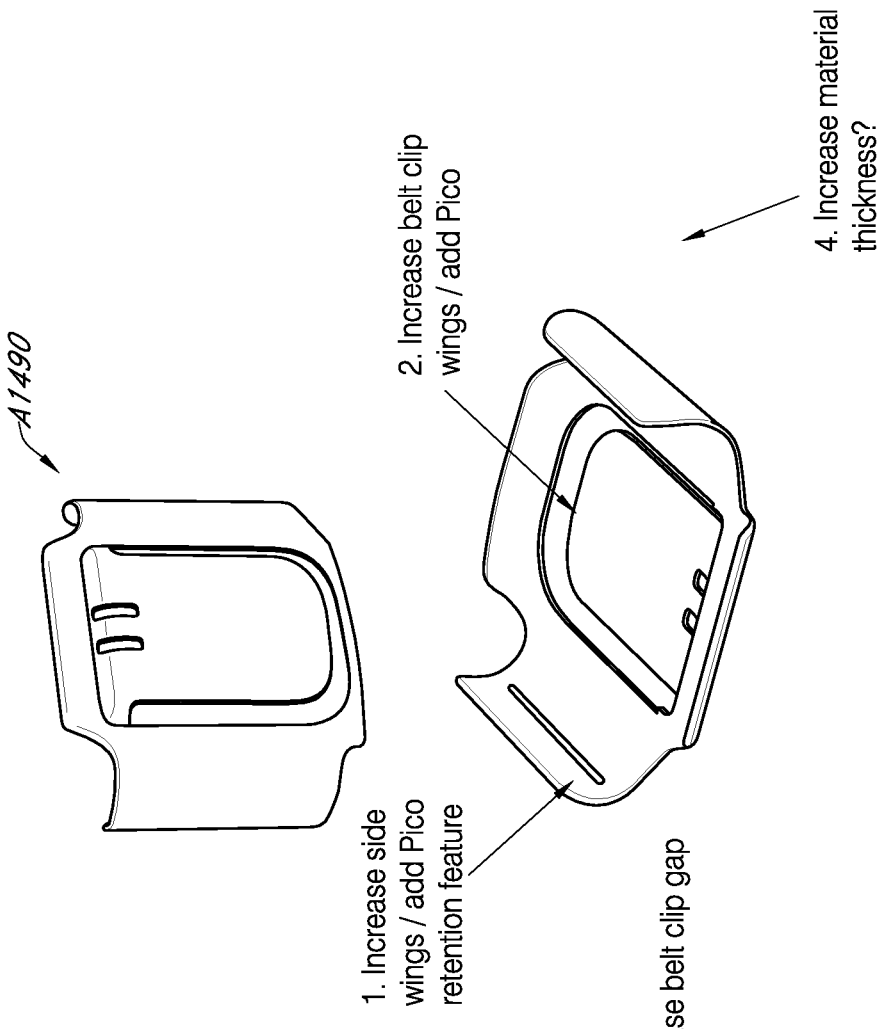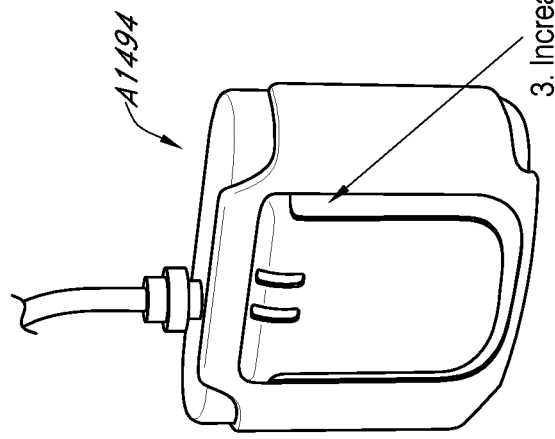

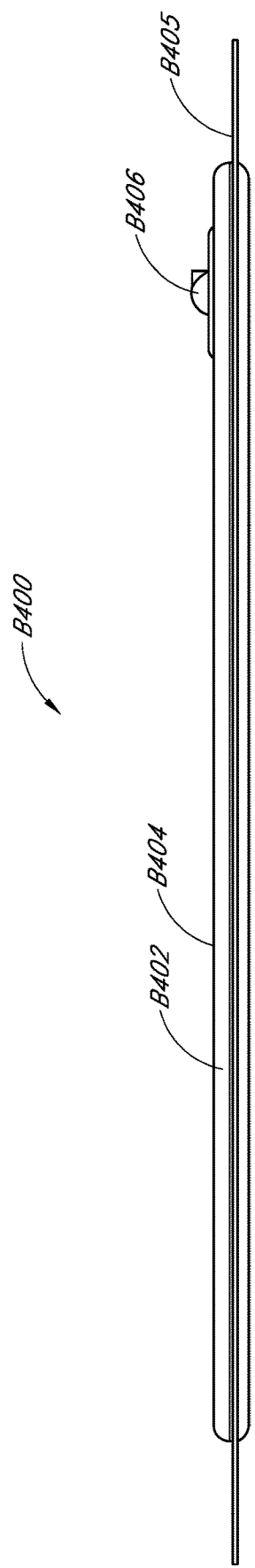

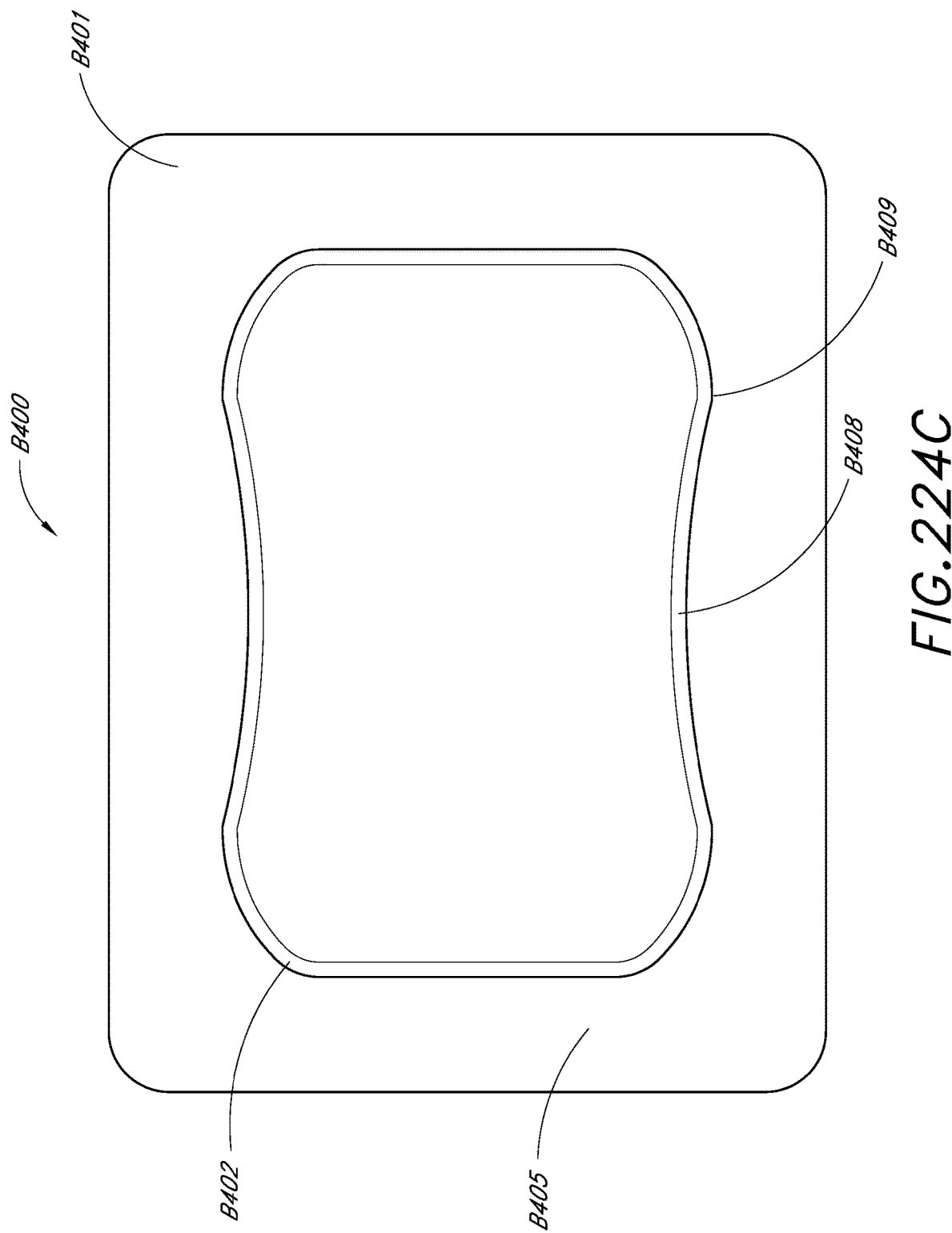

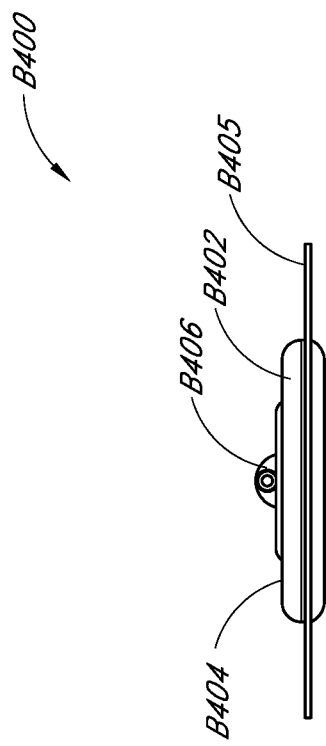
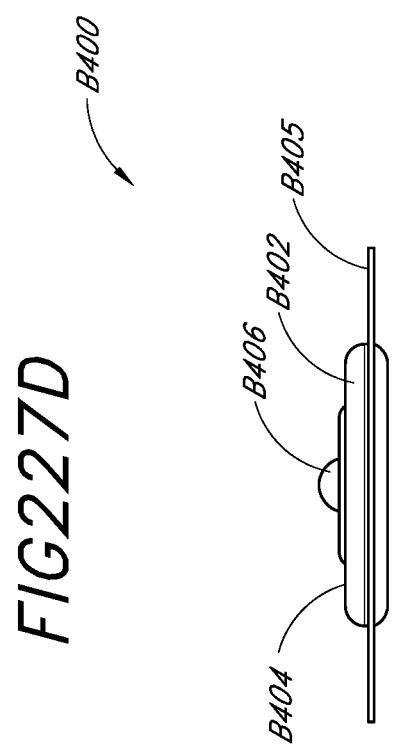

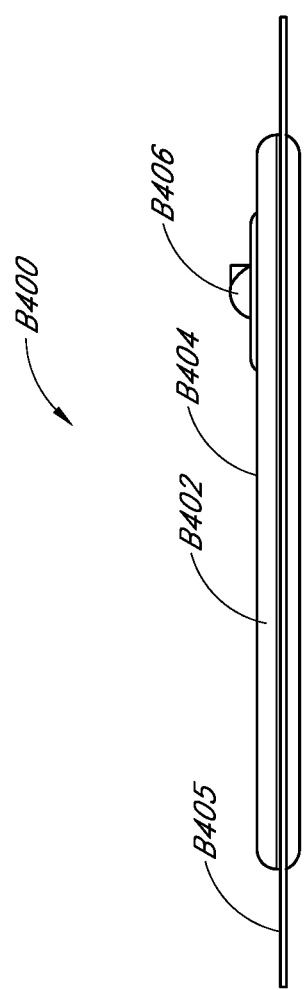

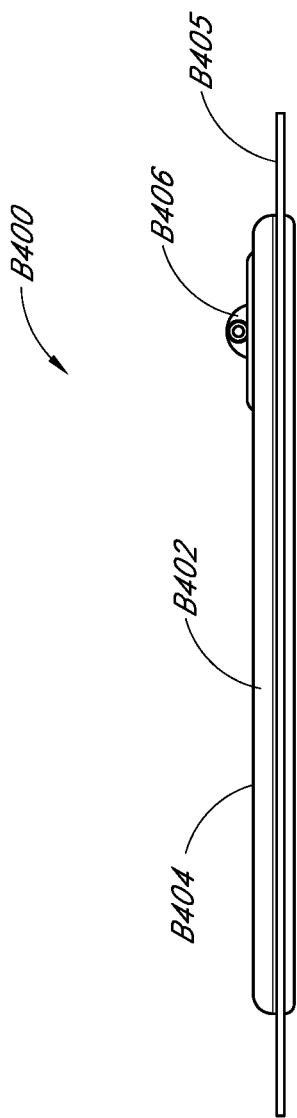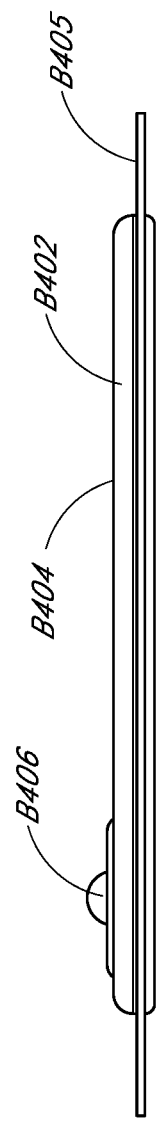
FIG.228D
FIG.228E

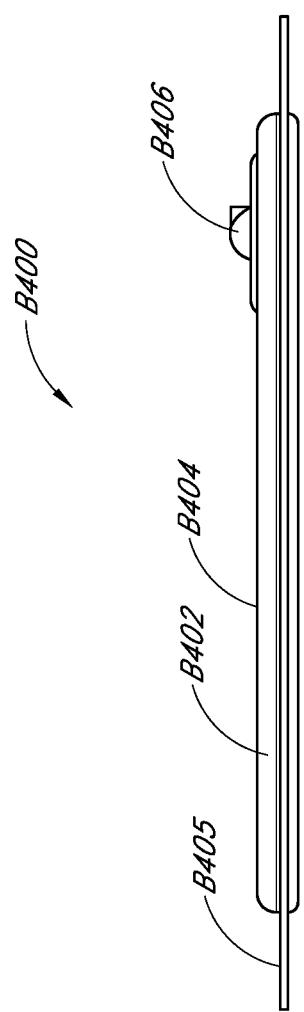

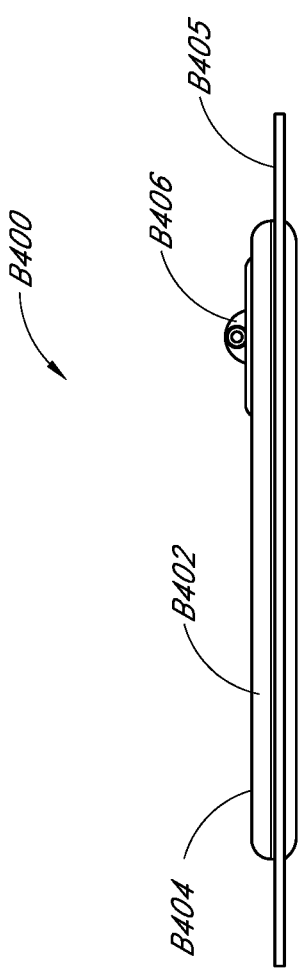
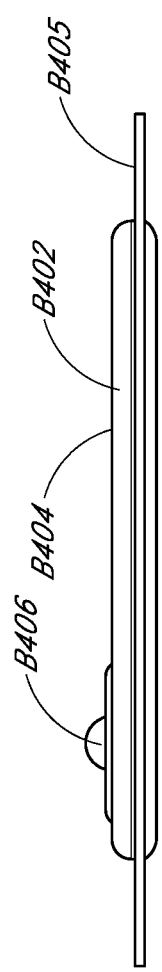
FIG. 229D
FIG. 229E

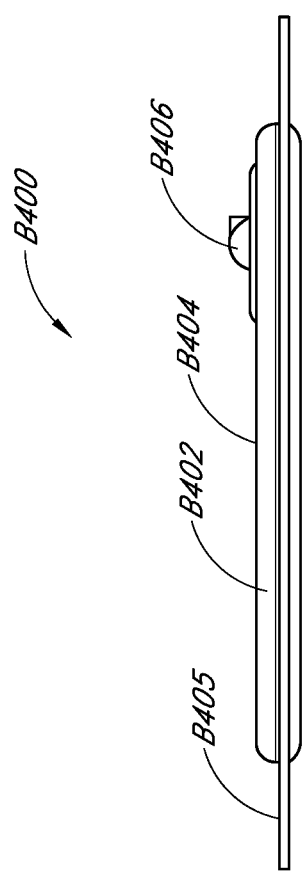

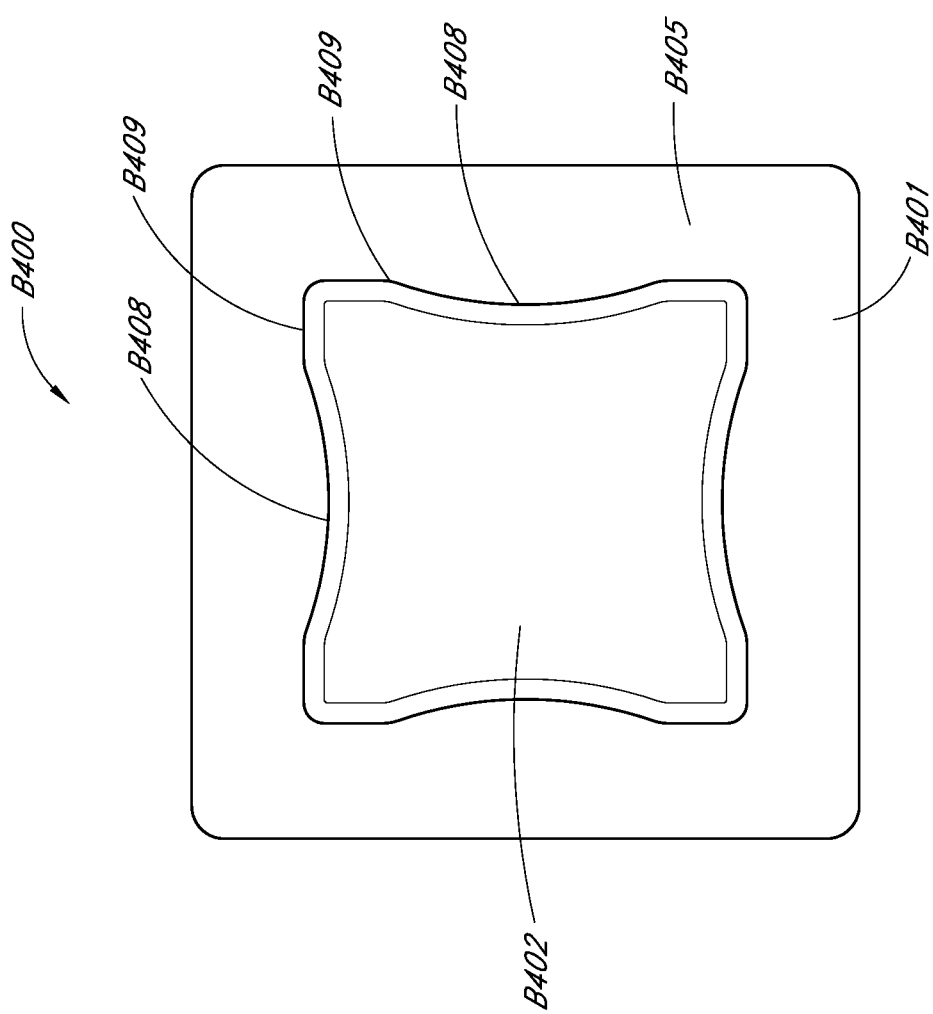

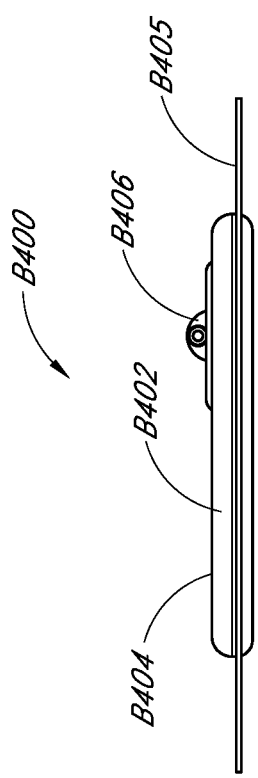
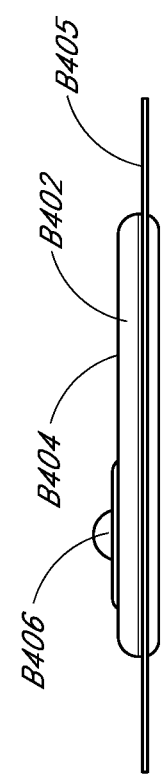
FIG. 230D
FIG. 230E

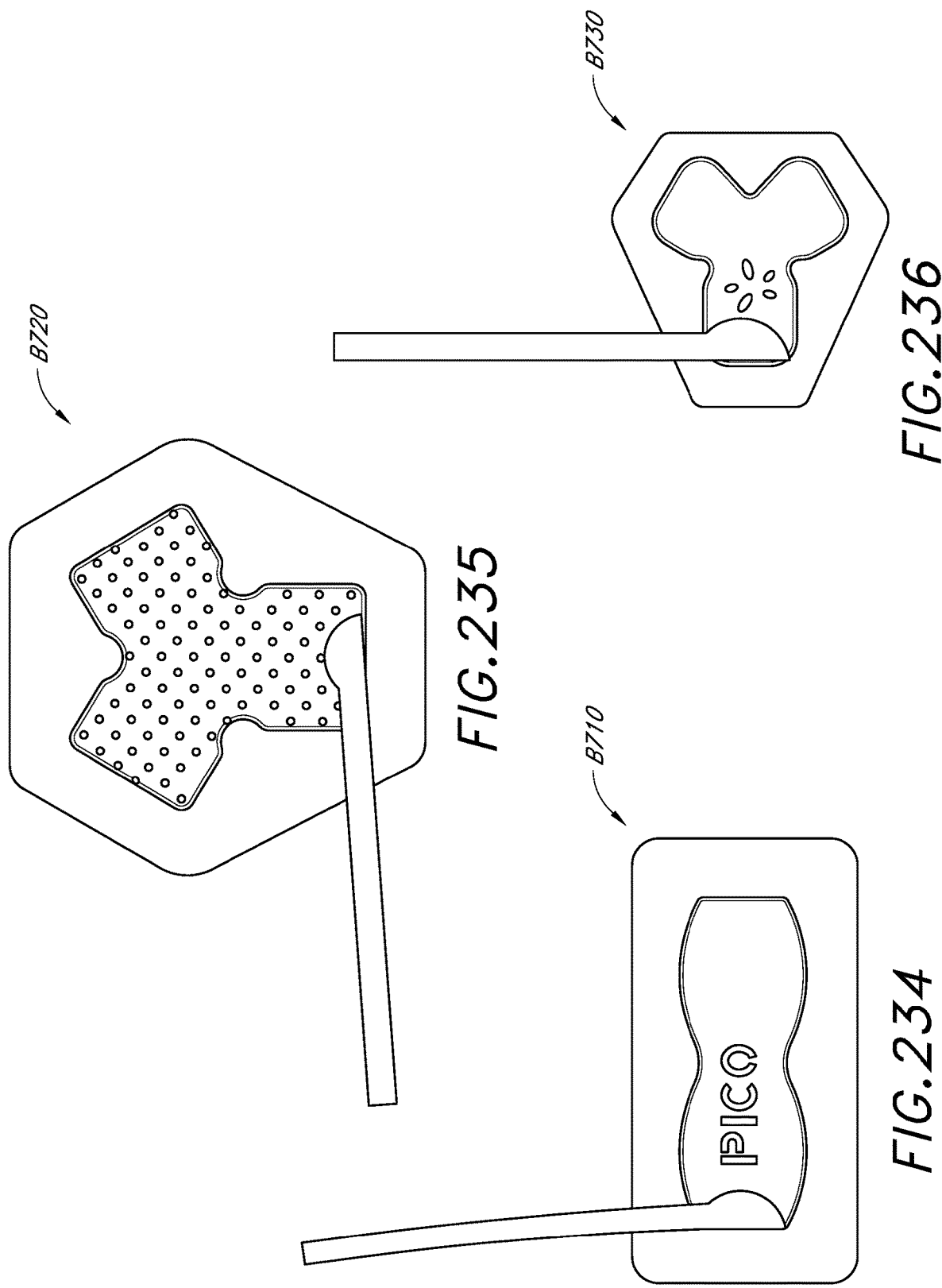

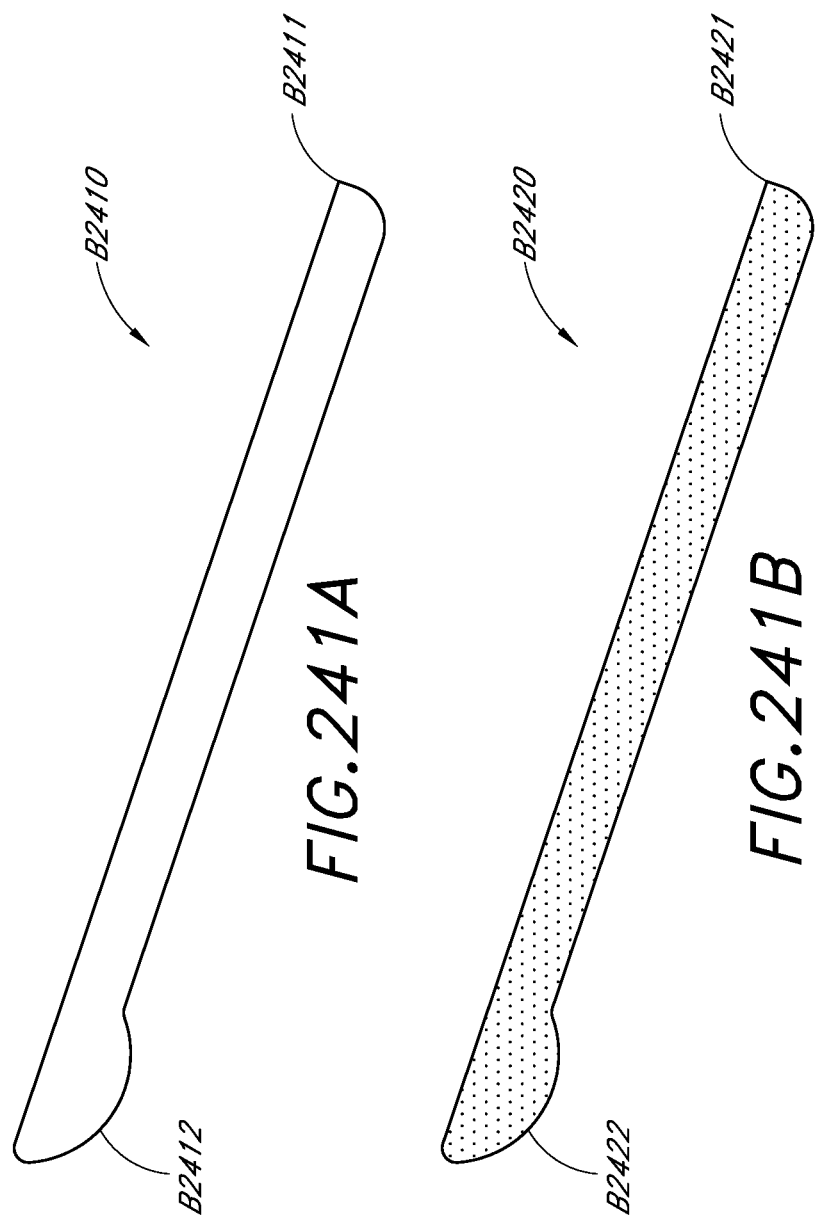

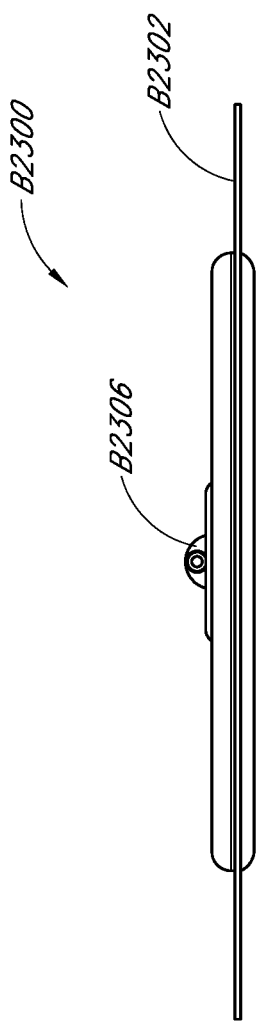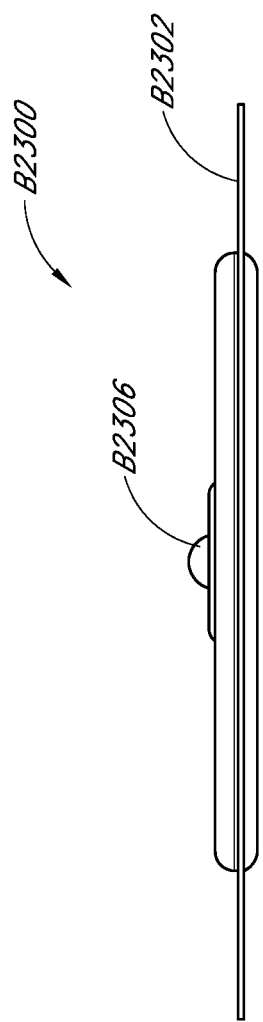

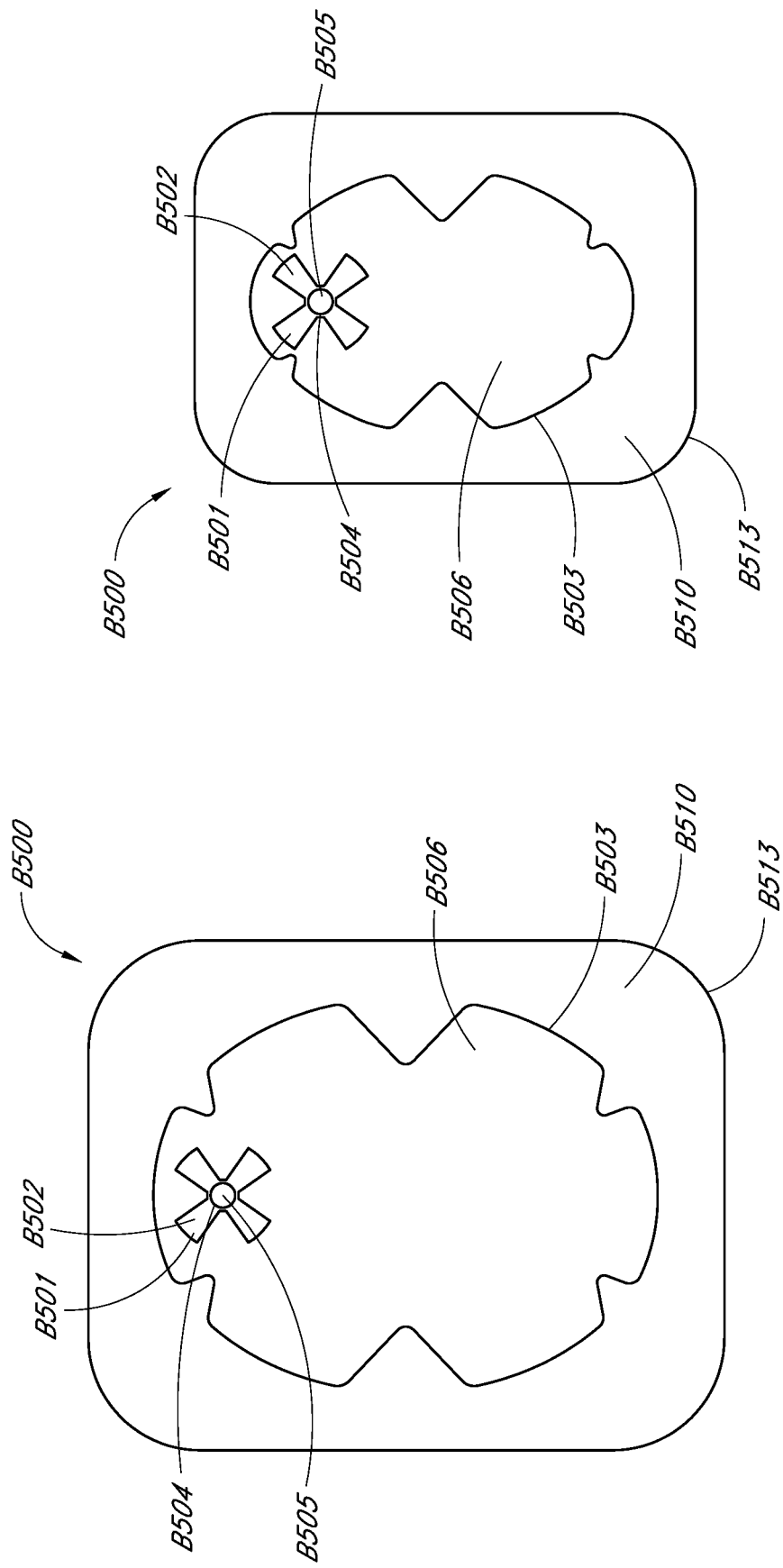

NEGATIVE PRESSURE WOUND THERAPY APPARATUS

CROSS-REFERENCE TO RELATED APPLICATIONS

This application is continuation of U.S. patent application Ser. No. 14/401,356, filed Nov. 14, 2014, titled "NEGATIVE PRESSURE WOUND THERAPY APPARATUS," which is a national stage application of International Patent Application No. PCT/IB2013/001513, filed on May 15, 2013, which claims the benefit of U.S. Provisional Application Nos. 61/647,397, filed May 15, 2012, 61/678,563, filed Aug. 1, 2012, 61/729,288, filed Nov. 21, 2012, and 61/791,984, filed Mar. 15, 2013, the contents of each of the above-mentioned applications are hereby incorporated by reference in their entirety as if fully set forth herein and should be considered a part of this specification.

INCORPORATION BY REFERENCE

Further components, features, and details of pump assemblies, wound dressings, wound treatment apparatuses and kits, and negative pressure wound treatment methods that may be used with any of the embodiments disclosed in this application are found in the following applications and/or patents, which are hereby incorporated by reference in their entireties as if fully set forth herein:

U.S. patent application Ser. No. 13/287,897, filed Nov. 2, 2011, entitled REDUCED PRESSURE THERAPY APPARATUSES AND METHODS OF USING SAME;

U.S. patent application Ser. No. 13/092,042 (U.S. Patent Publication No. 2011/0282309), filed Apr. 21, 2011, entitled WOUND DRESSING AND METHOD OF USE;

U.S. patent application Ser. No. 11/922,894 (U.S. Patent Publication No. 2009/0123513), filed May 21, 2008, entitled ANTIMICROBIAL BIGUANIDE METAL COMPLEXES;

U.S. Provisional Application No. 61/511,950, entitled METHODS AND APPARATUSES FOR DETECTING LEAKS AND CONTROLLING PUMP OPERATION IN A NEGATIVE PRESSURE WOUND THERAPY SYSTEM, filed Jul. 26, 2011;

PCT Patent Application No. PCT/GB11/000622 (WO/2011/135284), entitled WOUND DRESSING, filed on Apr. 21, 2011;

PCT Patent Application No. PCT/GB11/000621 (WO/2011/144888), entitled WOUND PROTECTION, filed on Apr. 21, 2011, PCT Patent Application No. PCT/GB11/000625 (WO/2011/135285), entitled WOUND DRESSING, filed on Apr. 21, 2011;

PCT Patent Application No. PCT/GB11/000626 (WO/2011/135286), entitled MULTIPORT DRESSING, filed on Apr. 21, 2011;

PCT Patent Application No. PCT/GB11/000628 (WO/2011/135287), entitled SUCTION PORT, filed on Apr. 21, 2011;

PCT Patent Application No. PCT/GB11/051745 (WO/2012/038724), entitled PRESSURE CONTROL APPARATUS, filed on Sep. 16, 2011; and U.S. Patent Application No. 61/678,563, filed Aug. 1, 2011, entitled NEGATIVE PRESSURE WOUND THERAPY APPARATUS.

U.S. patent application Ser. No. 13/287,959 (U.S. Patent Publication No. 2012/0136325), entitled "SYSTEMS AND METHODS FOR CONTROLLING OPERATION OF A REDUCED PRESSURE THERAPY SYSTEM," filed on Nov. 2, 2011;

PCT Patent Application No. PCT/US2011/059016 (WO/2013/015827), entitled "SYSTEMS AND METHODS FOR CONTROLLING OPERATION OF A REDUCED PRESSURE THERAPY SYSTEM," filed on Nov. 2, 2011;

U.S. patent application Ser. No. 13/092,042 (U.S. Patent Publication No. 2011/0282309), entitled "WOUND DRESSING AND METHOD OF USE," filed on Apr. 21, 2011;

PCT International Application No. PCT/IB2013/000847 (previously PCT/US13/30541), filed Mar. 12, 2013, entitled REDUCED PRESSURE APPARATUS AND METHODS; and U.S. Provisional Patent Application No. 61/785,054, entitled "WOUND DRESSING AND METHOD OF TREATMENT," filed on Mar. 14, 2013.

Each and all of the foregoing patent applications are hereby incorporated by reference in their entireties and made part of this disclosure.

BACKGROUND OF THE DISCLOSURE

Field of the Disclosure

Embodiments or arrangements disclosed herein relate to methods and apparatuses for dressing and treating a wound with topical negative pressure (TNP) therapy. For example but without limitation, any embodiments disclosed herein relate to treating a wound with reduced pressure provided from a pump kit. Although not required, any embodiments of the pump kit can be sterile. As another non-limiting example, any embodiments disclosed herein relate to apparatuses and methods for controlling the operation of a TNP system.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates and may reduce bacterial load and thus, infection to the wound. Furthermore, TNP therapy permits less outside disturbance of the wound and promotes more rapid healing.

SUMMARY OF SOME EMBODIMENTS

Embodiments of the present disclosure relate to apparatuses and methods for wound treatment. Some of the wound treatment apparatuses described herein comprise a pump assembly for proving negative pressure to a wound site. Wound treatment apparatuses may also comprise wound dressings that may be used in combination with the pump assemblies described herein, and connectors for connecting the wound dressings to the pump assemblies.

In some embodiments, a pump assembly for reduced pressure wound therapy comprises a housing, a pump motor supported within or by the housing, and a flow pathway through the pump assembly. Though not required, any embodiments may have a one-way flow valve in fluid communication with the pump motor and supported within or by the housing. Any embodiments of the one-way flow valve can be configured to substantially prevent a flow of gas through the flow pathway in a direction of flow away from the pump motor. The pump assembly can have a motor, an inlet and an outlet, a first valve supported by the pump motor or housing and configured to control a flow of a fluid through the inlet, and a second valve supported by the pump motor or housing and configured to control a flow of a fluid through the outlet.

In any embodiments disclosed herein, the pump assembly can form part of a wound treatment apparatus that also includes a wound dressing. In some embodiments, the pump assembly and/or a wound dressing can have one or more sensors therein. For example, in any embodiments disclosed herein, the pump assembly and/or dressing can have a pressure monitor configured to monitor the pressure within the pump housing, dressing, or conduit or chambers within the pump assembly or between the pump assembly and the dressing, or in any combination of such. Additionally, some pump embodiments disclosed herein can use orifices or other features or components to control a flow or rate of flow of fluid through the pump assembly.

Any embodiments disclosed herein may also relate to a negative pressure therapy kit for reduced pressure wound therapy. The negative pressure therapy kit in some embodiments may comprise a pump assembly comprising a housing, a pump motor supported within the housing, and a controller supported within or by the housing. In some embodiments, at least one switch or button may be supported by the housing. The at least one switch or button can be in communication with the controller and can be accessible to a user so as to permit a user to control one or more modes of operation of the pump assembly.

In any embodiments disclosed herein, though not required, the negative pressure therapy kit can comprise a dressing configured to form a substantially fluid tight seal over a wound, a conduit coupleable with the dressing and the pump assembly and configured to provide a substantially or completely enclosed fluid flow pathway from the pump assembly to the dressing, and a first packaging element for packaging the pump assembly, one or more batteries, the dressing, and the conduit.

In any embodiments disclosed herein, a controller can be configured to control an operation of the pump motor, valve, and other components of the pump assembly. Any embodiments of the negative pressure therapy kit can be configured such that the negative pressure therapy kit has been sterilized. The negative pressure therapy kit can be sterilized such that at least an inside and an outside of the housing, the at least one valve, the pump motor, the controller, and the at least one switch or button have been sterilized.

The pump assembly embodiments disclosed herein are not required to be sterilized. However, sterilizing the reduced pressure pump assembly before use and providing the pump assembly and/or dressing or pump kit components in a sterile condition can permit the use of the pump assembly in an operating room (also referred to as an operating theater) or any other location where sterility of the devices is required. For example and without limitation, some embodiments are directed to a sterile pump or dressing kit comprising a sterile pump assembly, a sterile dressing, and a sterile conduit connectable to the dressing and the pump assembly that can be used in an operating room.

Some embodiments disclosed herein relate to a canisterless pump assembly for reduced pressure wound therapy, comprising a housing, a flow pathway through the housing or through the pump assembly, one or more valves in communication with the flow pathway, and a pump motor supported within or by the housing, wherein the pump assembly is canisterless. Some embodiments disclosed herein relate to a canisterless pump assembly for reduced pressure wound therapy, comprising a housing and a pump motor supported within or by the housing. The pump assembly can have a motor, an inlet and an outlet, a first valve supported by the pump assembly and configured to control a flow of a fluid through the inlet, and a second valve supported by the pump and configured to control a flow of a fluid through the outlet. The pump or pump assembly can be canisterless. Further, though not required for all embodiments disclosed herein, and the first and second valves can each have a leakage rate of from approximately 0.1 mL/min to approximately 10 mL/min at nominal working pressures and/or during nominal sterilization pressures, or from 0.1 mL/min or less to 5 mL/min or more, or from 1 mL/min or less to 3 mL/min or more, or between any two values in any of the foregoing ranges at nominal working pressures. In any embodiments disclosed herein, the leakage rate can be from approximately 0.4 mL/min to 0.7 mL/min at nominal working pressures and/or during nominal sterilization pressures.

Some embodiments disclosed herein relate to a sterile pump kit, comprising any of the pump embodiments disclosed herein, a dressing, a conduit coupleable with the dressing and the sterile pump and configured to provide a fluid pathway of reduced pressure to the dressing, one or more batteries, and a first packaging element and a second packaging element configured to be removably coupled with the first packaging element. In any embodiments disclosed herein, at least one of the first and second packaging elements can have recesses for receiving the sterile pump, a dressing, a conduit coupleable with the dressing and the sterile pump and configured to provide a fluid pathway of reduced pressure to the dressing. The sterile pump kit can be been sterilized after the pump, the dressing, the conduit, and the one or more batteries have been supported inside at least one of the first packaging element and the second packaging element.

Any embodiments provide the advantage that the wound dressing can be used to collect wound exudate generated during a negative pressure therapy process. A pump remote from the wound dressing or supported thereby can be connected to the wound dressing and reused (or can be disposable) whilst the wound dressing itself is used to collect wound exudate and may then be disposed of after use. The pump or other source of negative pressure can be connected to the wound dressing through a flexible tubing or conduit. In this arrangement, negative pressure can draw wound exudate and other fluids or secretions away from the wound site. Any of the embodiments disclosed herein are suitable for use with and, hence, can be used with a negative pressure wound therapy system to aid in wound closure and healing in which wound exudate drawn from a wound site during the therapy is collected and stored in a wound dressing and/or in a collection canister.

Some dressing embodiments disclosed herein are configured to have an increased capacity for absorbing wound exudate reducing the frequency with which the dressings must be changed, and to manage the movement of wound exudate through a dressing to avoid blockages occurring that lead to reduced life of the dressing. Some embodiments are configured to provide a wound dressing able to be used with topical negative pressure therapy which helps maintain an open flow path so that therapy can be continued unhindered by blockages caused by build-up of solid matter.

Some embodiments disclosed herein are directed toward the treatment of wounds with negative pressure wound therapy. In particular, any of the dressing embodiments disclosed herein can be used for absorbing and storing wound exudate in conjunction with a pump, such as any of the pump embodiments disclosed herein. Any of the wound dressing embodiments disclosed herein can further comprise a transmission layer configured to transmit wound exudates to an absorbent layer disposed in the wound dressing. Additionally, any of the wound dressing embodiments disclosed herein can be adapted to provide for a port or other fluidic connector configured to retain wound exudate within the wound dressing while transmitting negative pressure to the wound dressing, though such a feature is not required.

According to an embodiment of the present disclosure there is provided a wound treatment apparatus comprising:
  any of the dressing embodiments disclosed herein;
  any of the pump embodiments disclosed herein; and/or
  a suction port for applying negative pressure to the wound dressing for the application of topical negative pressure at a wound site, the suction port comprising:
    a connector portion for connecting the suction port to the pump;
    a sealing surface for sealing the suction port to the cover layer of the wound dressing; and
    a liquid impermeable gas permeable filter element arranged to prevent a liquid from entering the connector portion.

According to another embodiment of the present disclosure there is provided a method for the treatment of a wound comprising:
  providing a wound dressing comprising any of the features or combination of features of any of the dressing embodiments disclosed herein,
  positioning the dressing over a wound site to form a sealed cavity over the wound site; and
  applying negative pressure to the wound site to draw fluid through the transmission layer into the absorbent layer.
In some embodiments, the wound dressing may comprise a transmission layer comprising a 3D knitted or fabric material, an absorbent layer for absorbing wound exudate, the absorbent layer overlying the transmission layer, and a cover layer overlying the absorbent layer and comprising an orifice, wherein the cover layer is moisture vapor permeable;

According to another embodiment of the present disclosure, there is provided a wound dressing for providing protection at a wound site, comprising any of the features or combination of features of any of the dressing embodiments disclosed herein, and/or:
  a transmission layer comprising a first surface and a further surface spaced apart from the first surface by a relax distance in a relaxed mode of operation; and
  a plurality of spacer elements extending between the first and further surfaces and, in a forced mode of operation, locatable whereby the first and further surfaces are spaced apart by a compression distance less than the relax distance.

According to another embodiment of the present disclosure there is provided a method for providing protection at a wound site, comprising:
  locating a wound dressing comprising any of the components or features of any of the wound dressing embodiments disclosed herein, and/or a transmission layer over a wound site; and
  responsive to a force on the wound dressing, displacing a plurality of spacer elements extending between a first surface and a further surface of the transmission layer whereby;
  a distance between the first and further surfaces is reduced as the spacer elements are displaced.

According to another embodiment of the present disclosure there is provided an apparatus for dressing a wound for the application of topical negative pressure at a wound site, comprising a wound dressing comprising any of the components or features of any of the wound dressing embodiments disclosed herein, and/or:
  a liquid and gas permeable transmission layer;
  an absorbent layer for absorbing wound exudate, the absorbent layer overlying the transmission layer;
  a gas impermeable cover layer overlying the absorbent layer and comprising a first orifice, wherein the cover layer is moisture vapor permeable.

According to a further embodiment of the present disclosure there is provided a method of applying TNP at a wound site, comprising:
  applying negative pressure at an orifice of a cover layer of any wound dressing embodiment disclosed herein, a peripheral region around the wound site being sealed with the wound dressing, such that air and wound exudate are drawn towards the orifice;
  collecting wound exudate, drawn from the wound site, through a transmission layer of the wound dressing, in an absorbent layer of the wound dressing; and
  transpiring a water component of the wound exudate collected in the absorbent layer through the cover layer of the wound dressing.

According to an additional embodiment of the present disclosure there is provided apparatus for dressing a wound for the application of topical negative pressure at a wound site, comprising a wound dressing comprising any of the components or features of any wound dressing embodiment disclosed herein, and/or:
  a liquid and gas permeable transmission layer;
  an absorbent layer for absorbing wound exudate;
  a gas impermeable cover layer overlying the absorbent layer and the transmission layer, the cover layer comprising an orifice connected to the transmission layer; and
  at least one element configured to reduce the rate at which wound exudate moves towards the orifice when a negative pressure is applied at the orifice.

According to another embodiment of the present disclosure there is provided a method of applying TNP at a wound site, comprising:
  applying negative pressure at an orifice of a cover layer of a wound dressing comprising any of the components or features of any wound dressing embodiment disclosed herein, a peripheral region around the wound site being sealed with the wound dressing such that air and wound exudate move towards the orifice;
  collecting wound exudate, from the wound site, through a transmission layer of the wound dressing, in an absorbent layer of the wound dressing; and
  reducing the rate at which wound exudate moves towards the orifice.

According to still another embodiment of the present disclosure there is provided an apparatus for dressing a wound for the application of topical negative pressure at a wound site, comprising a wound dressing comprising any of the components or features of any wound dressing embodiment disclosed herein and/or:

an absorbent layer for absorbing wound exudate;
a gas impermeable cover layer overlying the absorbent layer the cover layer comprising at least one orifice configured to allow negative pressure to be communicated through the cover layer in at least two spaced apart regions.

According to an additional embodiment of the present disclosure there is provided a method of applying TNP at a wound site, comprising:
 sealing a cover layer of a wound dressing comprising any of the components or features of any wound dressing embodiment disclosed herein around the wound site;
 applying negative pressure at at least one orifice in the cover layer, said at least one orifice configured to allow negative pressure to be communicated through the cover layer in at least two spaced apart regions; and
 collecting wound exudate, from the wound site, in an absorbent layer of the wound dressing.

According to another embodiment of the present disclosure there is provided a suction port for applying negative pressure to a wound dressing of any of the embodiments disclosed herein or having any of the components or features of any wound dressing embodiment disclosed herein for the application of topical negative pressure at a wound site, the suction port comprising:
 a connector portion for connecting the suction port to a source of negative pressure;
 a sealing surface for sealing the suction port to a cover layer of a wound dressing; and
 a liquid impermeable gas permeable filter element arranged to prevent a liquid entering the connector portion.

According to an additional embodiment of the present disclosure there is provided a method of communicating negative pressure comprising a wound dressing of any of the embodiments disclosed herein or having any of the components or features of any wound dressing embodiment disclosed herein for the application of topical negative pressure at a wound site, comprising:
 applying negative pressure at a connecting portion of a suction port sealed around a perimeter of an orifice in a cover layer of the wound dressing;
 filtering gas drawn from within the wound dressing through a liquid impermeable gas permeable filter element of the suction port.

According to another embodiment of the present disclosure there is provided a method of manufacturing a suction port for applying negative pressure to a wound dressing for the application of topical negative pressure at a wound site, the suction port having a connector portion for connecting the suction port to a source of negative pressure and a sealing surface for sealing the suction port to a cover layer of a wound dressing of any of the embodiments disclosed herein or having any of the components or features of any wound dressing embodiment disclosed herein, the method comprising:
 disposing a liquid impermeable gas permeable filter element of the suction port at a location to prevent a liquid entering the connector portion.

According to yet another embodiment of the present disclosure there is provided an apparatus for the application of TNP therapy to a wound site, comprising:
 a first layer comprising a plurality of openings each having a first open area;
 a further layer spaced apart from the first layer comprising a plurality of further openings each having a further open area; and
 an air impermeable, moisture vapor permeable cover layer over the first and further layers; wherein
 a region between the first and further layers comprises a portion of a flow path for air and/or wound exudate flowing from a wound site and said first open area is less than said further open area.

According to still another embodiment of the present disclosure there is provided a method of applying TNP therapy to a wound site, comprising:
 via a vacuum pump in fluid communication with a wound dressing of any of the embodiments disclosed herein or having any of the components or features of any wound dressing embodiment disclosed herein located over a wound site, applying a negative pressure at the wound site; and
 as liquid evaporates through a cover layer of the dressing, preventing blockage of a fluid flowpath region of the wound dressing.

Some embodiments provide a wound dressing of any of the embodiments disclosed herein or having any of the components or features of any wound dressing embodiment disclosed herein able to disconnect shear forces applied to the dressing from the wound site covered by the dressing. As a result damage to the wound can be wholly or at least partially avoided.

Some embodiments provide the advantage that a wound site can be covered with a wound dressing of any of the embodiments disclosed herein or having any of the components or features of any wound dressing embodiment disclosed herein which is simultaneously able to deliver negative pressure wound therapy to a wound site, collect exudate and provide protection from forces operating on the dressing.

Some embodiments provide the advantage that a wound dressing of any of the embodiments disclosed herein or having any of the components or features of any wound dressing embodiment disclosed herein can be used to collect wound exudate generated during a negative pressure therapy process, whilst extending the useful lifetime of the dressing by transpiring a water component of the wound exudate. A pump remote from the wound dressing or adjacent to or supported by the wound dressing can be connected to the wound dressing and reused whilst the wound dressing itself is used to collect wound exudate and may then be disposed of after use.

Some embodiments provide a wound dressing and/or method of applying topical negative pressure in which a flowpath through a wound dressing of any of the embodiments disclosed herein or having any of the components or features of any wound dressing embodiment disclosed herein is kept open so that therapy can be continued for as long as desired by a care giver.

Some embodiments prevent solid material, which may cause a blockage, from entering a flowpath region in a wound dressing of any of the embodiments disclosed herein or having any of the components or features of any wound dressing embodiment disclosed herein by using a layer of the dressing to act as a bar to such material.

Some embodiments prevent build-up of solid material in a flowpath region of a wound dressing of any of the embodiments disclosed herein or having any of the components or features of any wound dressing embodiment disclosed herein by ensuring that any solid material that enters into that flowpath region can always escape into a further region of the dressing.

Some embodiments provide the advantage that the build-up of solid material in a flowpath in a wound dressing of any of the embodiments disclosed herein or having any of the components or features of any wound dressing embodiment disclosed herein is avoided by having an absorbent layer close to the flowpath region store liquid over time. This helps keep the environment of the flowpath region moist which helps avoid crusting.

Some embodiments provide the advantage that a wound dressing of any of the embodiments disclosed herein or having any of the components or features of any wound dressing embodiment disclosed herein can be used to collect wound exudate generated during a negative pressure therapy process, whilst extending the useful lifetime of the dressing by transpiring a water component of the wound exudate. A pump remote from the wound dressing can be connected to the wound dressing and reused whilst the wound dressing itself is used to collect wound exudate and may then be disposed of after use.

Additional embodiments disclosed herein relate to methods and apparatuses for dressing and treating a wound with topical negative pressure (TNP) therapy, any parts, features, or components of which can be used with any of the pump assembly or housing embodiments disclosed or incorporated by reference herein, any of the pump components, features, or any of the indicator lights and alarms disclosed herein. For example but without limitation, some additional embodiments disclosed herein relate to treating a wound with reduced pressure provided from a pump kit. Although not required, any embodiments of the pump kit disclosed herein can be integral to any of the dressing kit or dressing member embodiments disclosed here, wherein the pump is mounted to or otherwise supported by or adjacent to the dressing. Any reference to a pump in any of the dressing embodiments disclosed herein is meant to refer to any of the pump embodiments disclosed herein, including without limitation any of the voice coil actuated pumps, crank pumps, or any of the other pump embodiments disclosed or incorporated by reference herein. Any reference to objects disclosed herein is meant to refer also to any objects incorporated by reference herein, as such objects are meant to form a part of this disclosure.

Additionally, although not required, any embodiments of the pump kit and/or dressing kit or dressing member can be sterile. As another non-limiting example, some embodiments disclosed herein relate to apparatuses, features, and methods for controlling the operation of a TNP system and/or apparatuses, features, and methods for detecting one or more conditions or parameters of the dressing, such as pressure, temperature, or saturation level, and, although not required, controlling the operation of the pump or other components of the dressing kit accordingly. As another non-limiting example, any embodiments disclosed herein can be configured to provide a visual indication of one or more conditions or parameters of the dressing, such as pressure, temperature, or saturation level.

As used throughout this specification, the phrase "some embodiments," "any embodiments," "any embodiments disclosed herein" or the like is meant to refer to any embodiment described, illustrated, incorporated by reference, or otherwise disclosed herein.

In some embodiments, an apparatus for use in negative pressure wound therapy comprises a pump assembly, comprising an electrically conductive coil, a magnet; and a diaphragm. The coil is directly or indirectly coupled with the diaphragm and is configured to move at least a portion of the diaphragm to pump a fluid through the pump assembly in response to a drive signal applied to the coil. The pump assembly may comprise an electrically conductive upper pole, an electrically conductive lower pole, and one or more valves, wherein the magnet is positioned between at least a portion of the upper pole and the lower pole, and wherein the coil is directly or indirectly coupled with the diaphragm and is configured to axially displace at least a middle portion of the diaphragm to pump a fluid through the pump assembly in response to a drive signal applied to the coil. The drive signal may comprise an offset square wave drive signal or an offset sinusoidal wave drive signal. The upper pole may have a first portion and a second portion, the first pole portion extending in a generally planar direction and the second portion extending in a first direction away from the first portion. The second portion of the upper pole may extend through an opening in the coil so as to shift the magnetic field of the voice coil actuator in the first direction, wherein the first direction is toward the lower pole.

In some embodiments, the apparatus for use in negative pressure wound therapy may further comprise a wound dressing configured to sealingly surround a wound. The wound dressing maybe be configured to sealingly surround a wound and a conduit may be provided configured to communicate a source of reduced pressure from the pump assembly to the wound dressing. The pump assembly may be supported on, by, partially within, or fully within a wound dressing.

In some embodiments, the apparatus for use in negative pressure wound therapy may comprise a flat spring member, wherein a periphery of the spring member is supported within the pump assembly so as to be in a fixed position relative to the diaphragm, and a middle portion of the spring member is configured to deflect relative to the periphery of the spring member when a middle portion of the diaphragm axially deflects. The spring member may be configured to directly or indirectly exert a force on a middle portion of the diaphragm so as to displace the middle portion of the diaphragm when the apparatus is in an assembled state but before an electrical current has been applied to the coil. The spring member may be configured to alter a resonant oscillation frequency of the diaphragm member, thereby permitting the adjustment of the resonant frequency of the pump assembly to improve efficiency of the pump assembly.

In some embodiments, the pump assembly may comprise a first flap valve and a second flap valve, wherein the first flap valve is configured to prevent air from flowing out of a valve chamber defined by the diaphragm during an intake cycle but to permit air to flow out of the valve chamber and through an outlet port during an exhaust cycle, and the second flap valve is configured to prevent air from flowing into the valve chamber through an inlet port during the exhaust cycle but to permit air to flow into the valve chamber during the intake cycle. The at least one of the first flap valve and the second flap valve may comprise a flap portion surrounded by a frame portion, the flap portion being configured to deflect away from a relaxed position of the flap portion to block passage of air through an opening adjacent to the flap portion in response to a pressure differential between a first main surface and a second main surface of the flap portion. The flap portion may comprise a base portion and a body portion, the body portion being supported in cantilever and the flap portion being configured to deflect about the base portion, and wherein the base portion has a smaller cross-sectional area than the body portion. The at least one of the first flap valve and the second flap valve may comprise a bridge valve, the bridge valve being fixed to a support member at a first end and a second opposite end of the bridge valve, and having a middle portion configured to deflect away from a relaxed position of the middle portion to block passage of air through an opening adjacent to the flap portion in response to a pressure differential between a first main surface and a second main surface of the middle portion.

In some embodiments, the apparatus for use in negative pressure wound therapy may comprise a first valve support and a second valve support, wherein the one or more valves are positioned between the first and second valve supports. The first valve support may be attached to the second valve support using one or more welds such as laser welds or ultrasonic welds, clamps, screws, adhesive, or other similar methods.

In some embodiments, the apparatus for use in negative pressure wound therapy may further comprise a packaging element, wherein the pump assembly is sterile within the packaging element. The pump assembly may be supported within a casing having a user interface screen and at least one operation button. A controller may be configured to produce a drive signal for the coil. A filter may be configured to filter the drive signal, wherein the drive signal comprises a first pulse-width modulation drive signal and a second pulse-width modulation drive signal, the first and second pulse-width modulation drive signals having different magnitudes. The filter may be further configured to filter the first pulse-width modulation drive signal to produce a first sinusoidal wave and filter the second pulse-width modulation drive signal to produce a second sinusoidal wave, and the controller may be further configured to combine the first and second sinusoidal waves to produce the sinusoidal drive signal. In some embodiments, the voice coil actuator comprises the filter. In some embodiments, the first and second sinusoidal waves are phase shifted by about 180 degrees.

In some embodiments, a method of operating an apparatus as described herein for use in negative pressure wound therapy, comprises placing a dressing over a wound to create a substantially fluid tight seal over the wound, connecting the dressing to the pump assembly; and driving the coil so that negative pressure is provided to the dressing. The drive may comprise driving the voice coil actuator with a sinusoidal wave drive signal. The sinusoidal wave drive signal may comprises an offset sinusoidal wave drive signal. The method may further comprise generating a pulse-width modulation drive signal, and generating the offset sinusoidal wave drive signal from the pulse-width modulation drive signal. Generating the offset sinusoidal wave drive signal from the pulse-width modulation drive signal may comprise filtering a first pulse-width modulation drive signal and a second pulse-width modulation drive signal, the first and second pulse-width modulation drive signals having different magnitudes. The filter may further comprise filtering the first pulse-width modulation drive signal to produce a first sinusoidal wave, filtering the second pulse-width modulation drive signal to produce a second sinusoidal wave, and combining the first and second sinusoidal waves to generate the offset sinusoidal drive signal. The first and second sinusoidal waves may be phase shifted by about 180 degrees.

Any of the features, components, or details of any of the arrangements or embodiments disclosed in this application, including without limitation any of the pump embodiments (for example, any of the voice coil pump embodiments) and any of the negative pressure wound therapy embodiments disclosed below, are interchangeably combinable with any other features, components, or details of any of the arrangements or embodiments disclosed herein to form new arrangements and embodiments. With that, the following additional arrangements are also disclosed herein:

1. An apparatus for applying negative pressure to a wound, comprising:
   a source of negative pressure configured to be coupled to a dressing, the source of negative comprising a voice coil actuator and a diaphragm; and
   a controller configured to produce a drive signal for the voice coil actuator.

2. The apparatus of Arrangement 1, wherein the drive signal comprises an offset square wave drive signal.

3. The apparatus of Arrangement 1, wherein the drive signal comprises an offset sinusoidal wave drive signal.

4. The apparatus of any one of Arrangements 1-3, further comprising a filter configured to filter the drive signal, wherein the drive signal comprises a first pulse-width modulation drive signal and a second pulse-width modulation drive signal, the first and second pulse-width modulation drive signals having different magnitudes.

5. The apparatus of Arrangement 4, wherein:
   the filter is further configured to filter the first pulse-width modulation drive signal to produce a first sinusoidal wave and filter the second pulse-width modulation drive signal to produce a second sinusoidal wave; and
   the controller is further configured to combine the first and second sinusoidal waves to produce the sinusoidal drive signal.

6. The apparatus of any one of Arrangements 4-5, wherein the voice coil actuator comprises the filter.

7. The apparatus of any one of Arrangement 5, wherein the first and second sinusoidal waves are phase shifted by about 180 degrees.

8. A method of operating a negative pressure wound therapy apparatus, the method comprising:
   placing a dressing over a wound to create a substantially fluid tight seal over the wound;
   connecting the dressing to a source of negative pressure, the source of negative pressure comprising a voice coil actuator and a diaphragm; and
   driving the voice coil actuator so that negative pressure is provided to the dressing.

9. The method of Arrangement 8, wherein the driving further comprises driving the voice coil actuator with a sinusoidal wave drive signal.

10. The method of Arrangement 9, wherein the sinusoidal wave drive signal comprises an offset sinusoidal wave drive signal.

11. The method of any one of Arrangements 9-10, further comprising generating a pulse-width modulation drive signal, and generating the offset sinusoidal wave drive signal from the pulse-width modulation drive signal.

12. The method of any one of Arrangements 9-11, wherein generating the offset sinusoidal wave drive signal from the pulse-width modulation drive signal comprises filtering a first pulse-width modulation drive signal and a second pulse-width modulation drive signal, the first and second pulse-width modulation drive signals having different magnitudes.

13. The method of Arrangement 12, wherein the filtering further comprises:
   filtering the first pulse-width modulation drive signal to produce a first sinusoidal wave;
   filtering the second pulse-width modulation drive signal to produce a second sinusoidal wave; and
   combining the first and second sinusoidal waves to generate the offset sinusoidal drive signal.

14. The method of Arrangement 12 or 13, wherein the first and second sinusoidal waves are phase shifted by about 180 degrees.

15. A method of treating a wound, comprising;
placing a wound dressing of any one of the arrangements described herein over a wound;
applying negative pressure to the wound from any of the pump assemblies described herein.

16. A wound dressing kit, comprising a pump assembly and/or pump housing of any of the embodiments disclosed or illustrated herein, and/or comprising any of the features, components, or details of any of the pump assembly embodiments disclosed herein or any combination of the features, components, or details of any of the pump assembly embodiments or housing embodiments disclosed herein.

17. A wound dressing kit, comprising a means for applying reduced or negative pressure to any of the dressing embodiments disclosed herein.

18. The wound dressing kit of Arrangement 17, wherein the means for applying reduced or negative pressure to any of the dressing embodiments disclosed herein comprises any of the pump assembly or pump housing embodiments disclosed and/or illustrated herein or any of the embodiments disclosed herein, and/or comprising any of the features, components, or details of any of the pump assembly embodiments disclosed herein, and/or any combination of the features, components, or details of any of the pump assembly embodiments disclosed herein.

19. The wound dressing kit of any of the previous Arrangements, comprising a voice coil actuated pump assembly of any of the embodiments disclosed herein.

20. The wound dressing kit of any of the previous Arrangements, comprising a pump assembly of any of the embodiments disclosed or illustrated herein, wherein the pump assembly is supported by, mounted on, integrated in, or otherwise coupled with the wound dressing member.

BRIEF DESCRIPTION OF THE DRAWINGS

Embodiments of the present disclosure will now be described hereinafter, by way of example only, with reference to the accompanying drawings in which:

FIG. 13 is an exploded view of a valve assembly of the pump assembly embodiment illustrated in FIG. 9, showing the top of the valve assembly.

FIG. 14 is an exploded view of the valve assembly of the pump assembly embodiment illustrated in FIG. 9, showing the bottom of the valve assembly.

FIGS. 27H-27I are a side view and an isometric view of the pump assembly embodiment shown in FIG. 27A, respectively, showing a housing of the pump assembly in a partially open position.

FIG. 29A is an enlarged isometric view of a portion of the embodiment of a pump assembly shown in FIG. 28, showing a slider member of an embodiment of a conduit connector in a first, open position.

FIG. 29B is a section view of a portion of the embodiment of a pump assembly shown in FIG. 28, showing a slider member in the first, open position.

FIG. 30A is an enlarged isometric view of a portion of the embodiment of a pump assembly shown in FIG. 28, showing a slider member in a second, closed position.

FIG. 30B is a section view of a portion of the embodiment of a pump assembly shown in FIG. 28, showing a slider member in the second, closed position.

FIGS. 31A, 31B, and 31C are an isometric, side, and end view of an embodiment of a slide member.

FIG. 33A is an enlarged isometric view of a portion of the embodiment of a pump assembly shown in FIG. 32, showing a slider member of an embodiment of a conduit connector in a first, open position.

FIG. 33B is a section view of a portion of the embodiment of a pump assembly shown in FIG. 32, showing a slider member in the first, open position.

FIG. 34A is an enlarged isometric view of a portion of the embodiment of a pump assembly shown in FIG. 32, showing a slider member in a second, closed position.

FIG. 34B is a section view of a portion of the embodiment of a pump assembly shown in FIG. 32, showing a slider member in the second, closed position.

FIGS. 35A, 35B, and 35C are an isometric, side, and end view of another embodiment of a slide member.

FIG. 37A is an enlarged isometric view of a portion of the embodiment of a pump assembly shown in FIG. 36, showing a slider member of an embodiment of a conduit connector in a first, open position.

FIG. 37B is a section view of a portion of the embodiment of a pump assembly shown in FIG. 36, showing a slider member in the first, open position.

FIG. 38A is an enlarged isometric view of a portion of the embodiment of a pump assembly shown in FIG. 36, showing a slider member in a second, closed position.

FIG. 38B is a section view of a portion of the embodiment of a pump assembly shown in FIG. 36, showing a slider member in the second, closed position.

FIGS. 39A, 39B, and 39C are an isometric, side, and end view of another embodiment of a slide member.

FIGS. 42A-42G are an isometric view, a top view, a bottom view, a top end view, a bottom end view, a first side view, and a second side view, respectively, of another embodiment of a pump assembly.

FIGS. 46A-46G are an isometric view, a top view, a bottom view, a top end view, a bottom end view, a first side view, and a second side view, respectively, of another embodiment of a pump assembly.

FIGS. 59 and 60 are a top view and a section view of another embodiment of a pump assembly.

FIGS. 77A-77D are a first isometric view, a second isometric view, a side view, and a section view of an embodiment of a diaphragm member of the pump assembly embodiment shown in FIG. 72.

FIGS. 87A-87C are an isometric, top, and side view, respectively, of an embodiment of a diaphragm member of the pump assembly embodiment shown in FIG. 82.

FIGS. 87D-87E are a first and a second isometric view of another embodiment of a valve member that can be used with the pump assembly embodiment shown in FIG. 82.

FIGS. 92 and 93 are exploded views of the pump assembly embodiment illustrated in FIG. 90, showing the top and the bottom of the pump assembly, respectively.

FIGS. 95A-95B are isometric views of an embodiment of a valve member of the pump assembly embodiment shown in FIG. 90.

FIGS. 96A-96B are isometric views of an embodiment of a first valve support of the pump assembly embodiment shown in FIG. 90.

FIGS. 97A-97B are isometric views of an embodiment of a housing member of the pump assembly embodiment shown in FIG. 90.

FIGS. 98A-98B are isometric views of another embodiment of a valve assembly that can be used with the pump assembly embodiment shown in FIG. 72 or any pump assembly embodiment disclosed herein.

FIGS. 114-133 illustrate a variety of indicator lights that can be included with any pump assembly disclosed herein.

FIGS. 134A-134B illustrate an embodiment of a dressing kit for negative pressure wound therapy.

FIGS. 135A-135C illustrate additional embodiments of a dressing kit for negative pressure wound therapy.

FIGS. 136A-136C illustrate additional embodiments of a dressing kit for negative pressure wound therapy.

FIGS. 137A-137C illustrate additional embodiments of dressing kits for negative pressure wound therapy, showing three different exemplifying sizes of such embodiment.

FIGS. 138A-138B illustrate additional embodiments of a dressing kit for negative pressure wound therapy, showing two different exemplifying sizes of such embodiment.

FIGS. 139A-139B illustrate additional embodiments of a dressing kit for negative pressure wound therapy.

FIGS. 145A-145B illustrate additional embodiments of a dressing kit for negative pressure wound therapy, showing such dressing kit schematically in section and isometrically.

FIG. 149 illustrates an additional embodiment of a dressing kit for negative pressure wound therapy.

FIG. 150 illustrates an additional embodiment of a dressing kit for negative pressure wound therapy.

FIGS. 151A-151C illustrate additional embodiments of a dressing kit for negative pressure wound therapy.

FIGS. 152A-152C illustrate additional embodiments of a dressing kit for negative pressure wound therapy.

FIG. 153 illustrates an additional embodiment of a dressing kit for negative pressure wound therapy.

FIGS. 154A-154C illustrate an additional embodiment of a dressing kit for negative pressure wound therapy.

FIGS. 155A-155C illustrate an additional embodiment of a dressing kit for negative pressure wound therapy.

FIGS. 156A-156C illustrate an additional embodiment of a dressing kit for negative pressure wound therapy.

FIGS. 157A-157F illustrate an additional embodiment of an activation switch of a dressing kit for negative pressure wound therapy.

FIGS. 158A-181B respectively illustrate additional embodiments of a dressing kit for negative pressure wound therapy.

Figure 182:
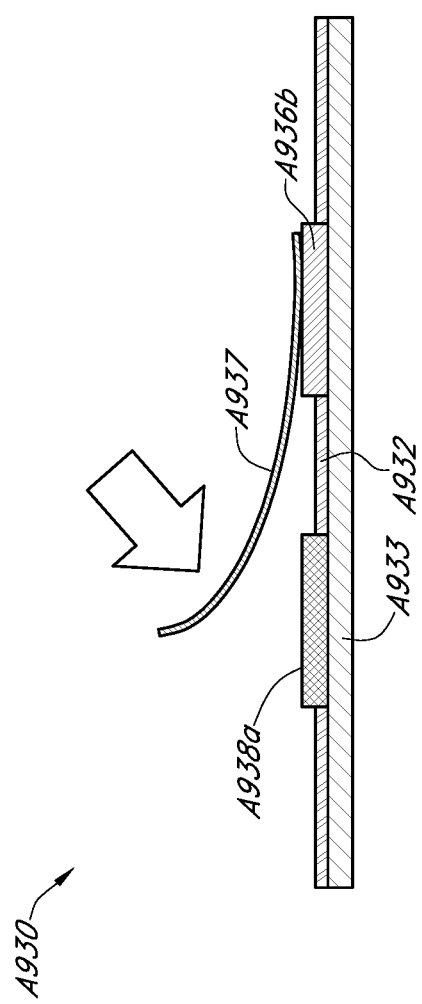

FIG. 182 illustrates an embodiment of a switch or activation mechanism.

FIGS. 183A-183D illustrate an embodiment of a switch or activation mechanism.

FIGS. 184A-184B illustrate an additional embodiment of a dressing kit for negative pressure wound therapy.

FIGS. 185A-185C illustrate an additional embodiment of a dressing kit for negative pressure wound therapy.

FIGS. 186A-188 respectively illustrate additional embodiments of an activation switch of a dressing kit for negative pressure wound therapy.

Figures 189A, 189B:
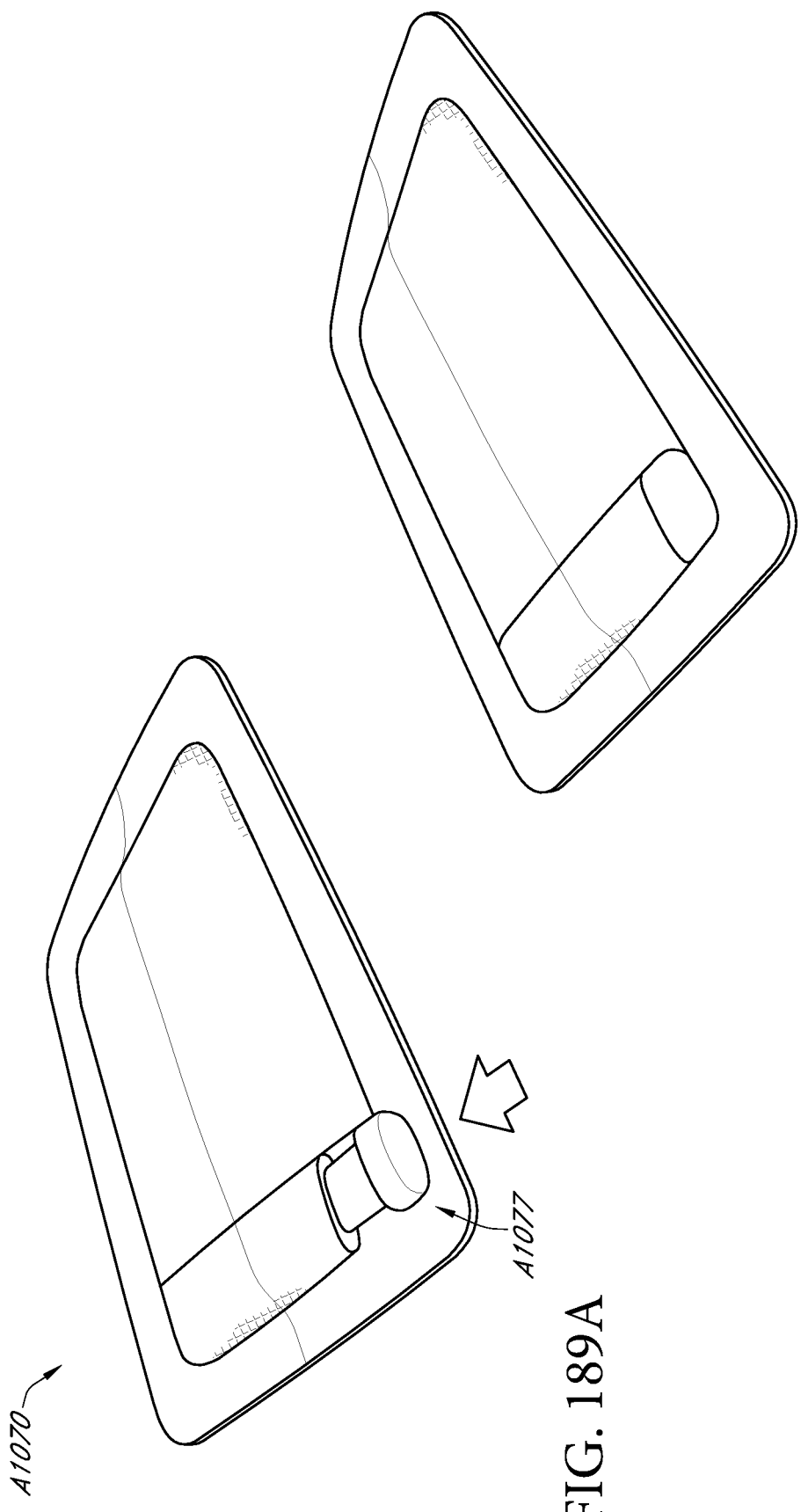

FIGS. 189A-189B illustrate an additional embodiment of an indicator light of a dressing kit for negative pressure wound therapy.

Figure 190:
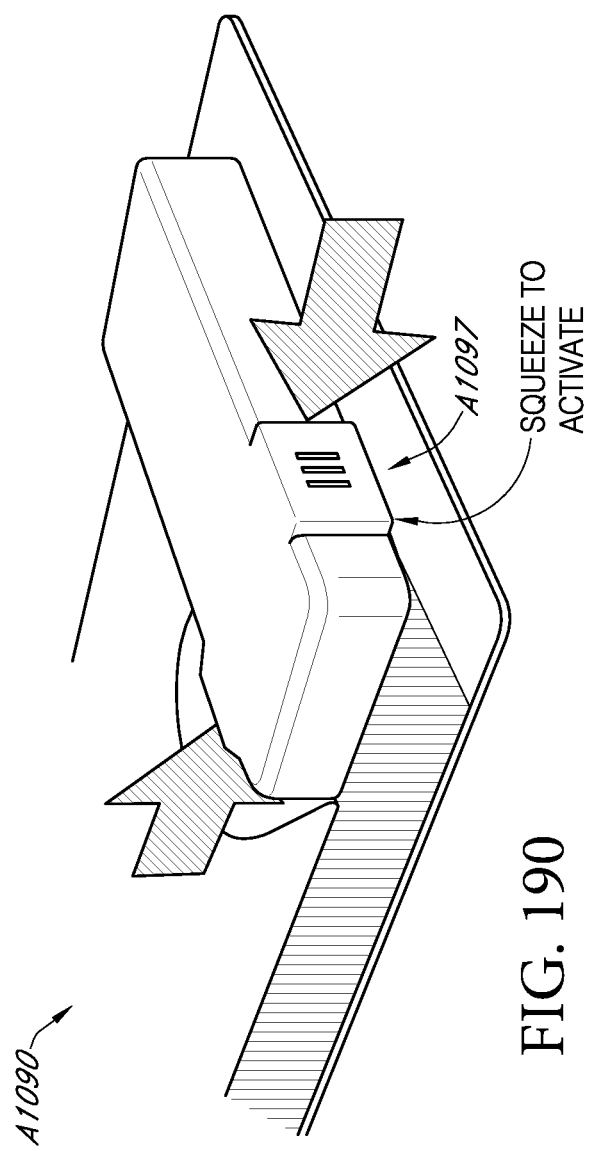

FIG. 190 illustrates an additional embodiment of an activation switch of a dressing kit for negative pressure wound therapy.

Figure 191:
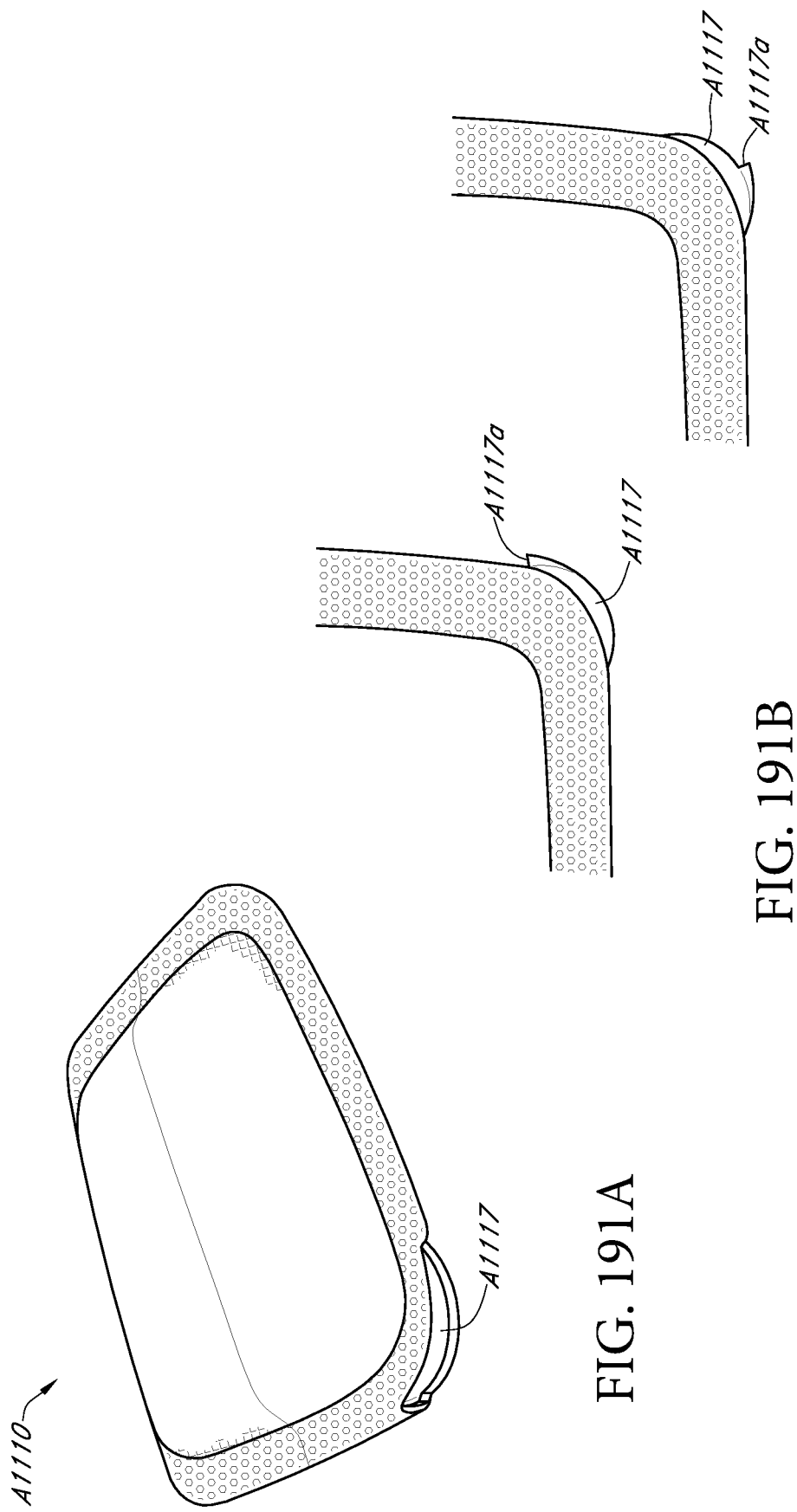

FIGS. 191A-191C illustrate an additional embodiment of an activation switch of a dressing kit for negative pressure wound therapy.

Figure 192:
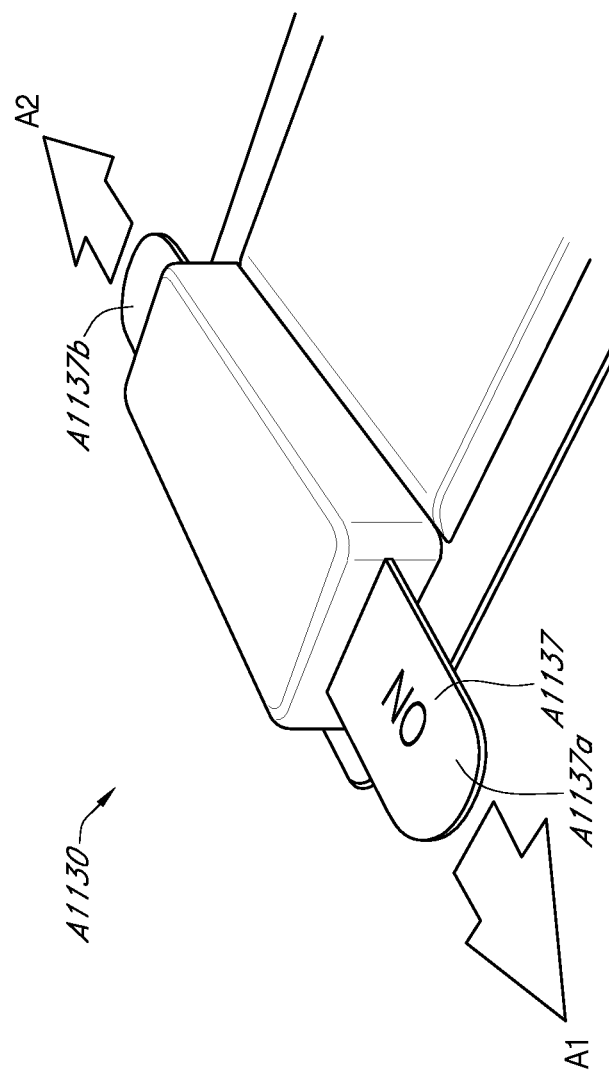

FIG. 192 illustrates an additional embodiment of an activation switch of a dressing kit for negative pressure wound therapy.

FIG. 193 illustrates an additional embodiment of an activation switch of a dressing kit for negative pressure wound therapy.

FIGS. 194A-194B illustrate an additional embodiment of an activation switch of a dressing kit for negative pressure wound therapy.

Figure 195:
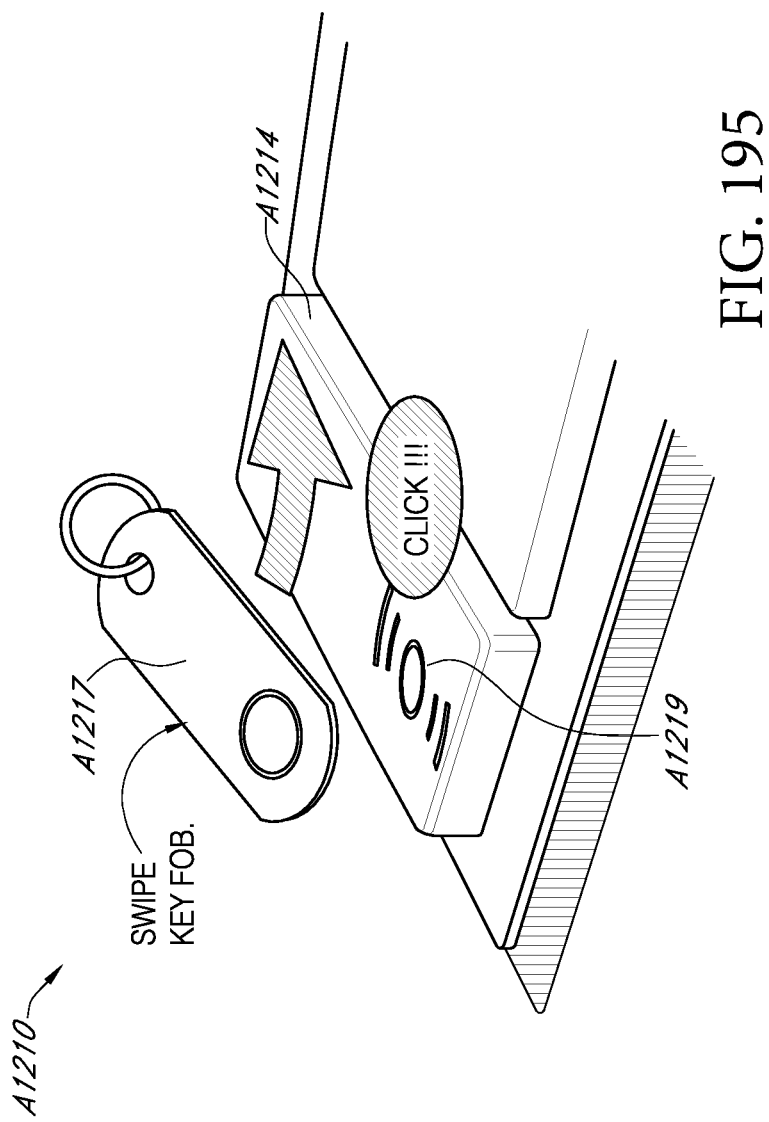

FIG. 195 illustrates an additional embodiment of an activation switch of a dressing kit for negative pressure wound therapy.

Figure 196:
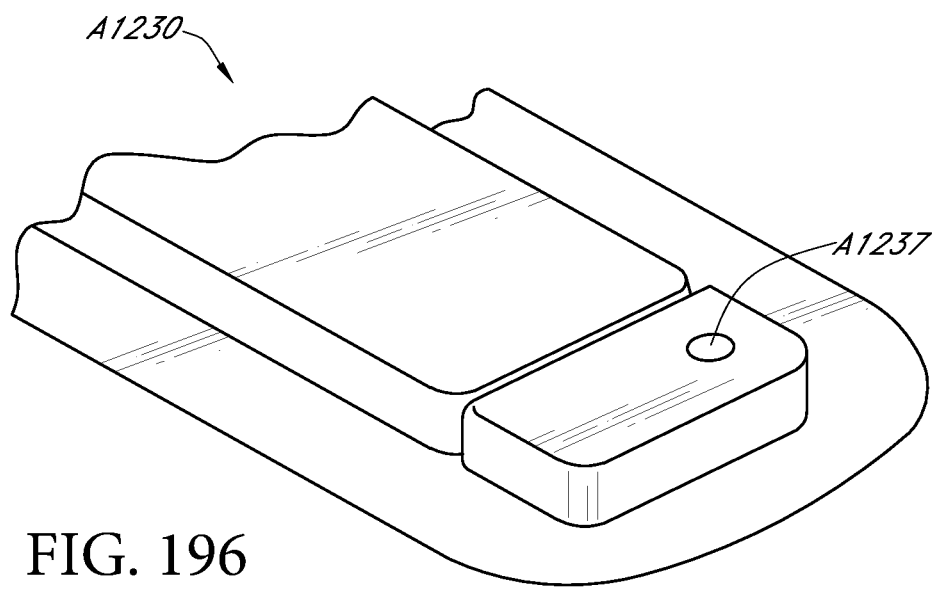

FIG. 196 illustrates an additional embodiment of a dressing kit for negative pressure wound therapy.

Figures 197A, 197B:
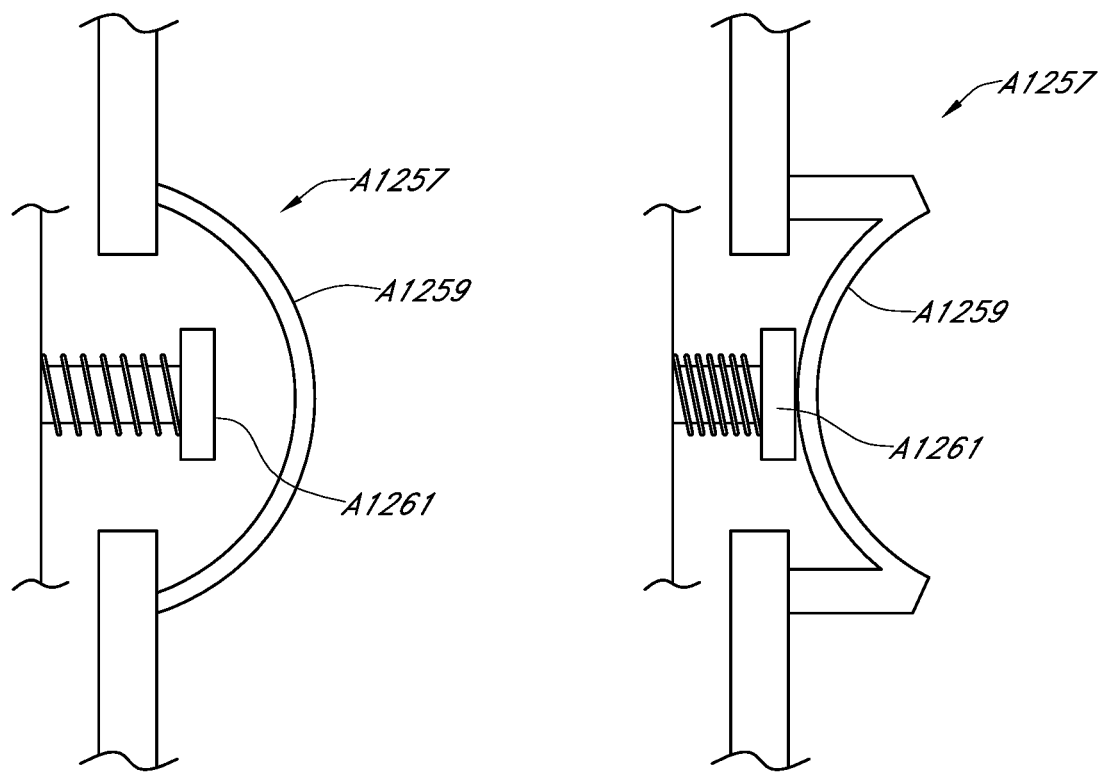

FIGS. 197A-197B illustrate an additional embodiment of a dressing kit for negative pressure wound therapy.

Figure 198A:
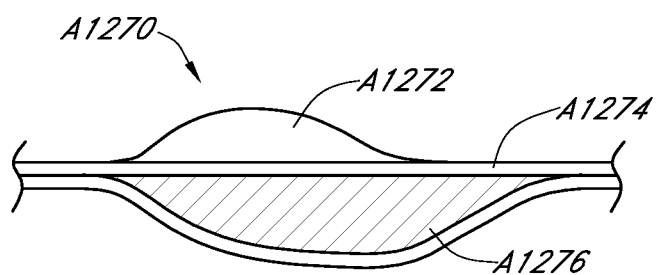
Figure 198B:
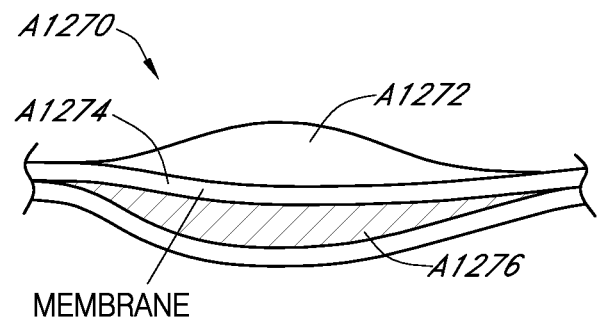

FIGS. 198A-198B illustrate several embodiments of a pressure indicator of a dressing kit for negative pressure wound therapy.

Figure 199A:
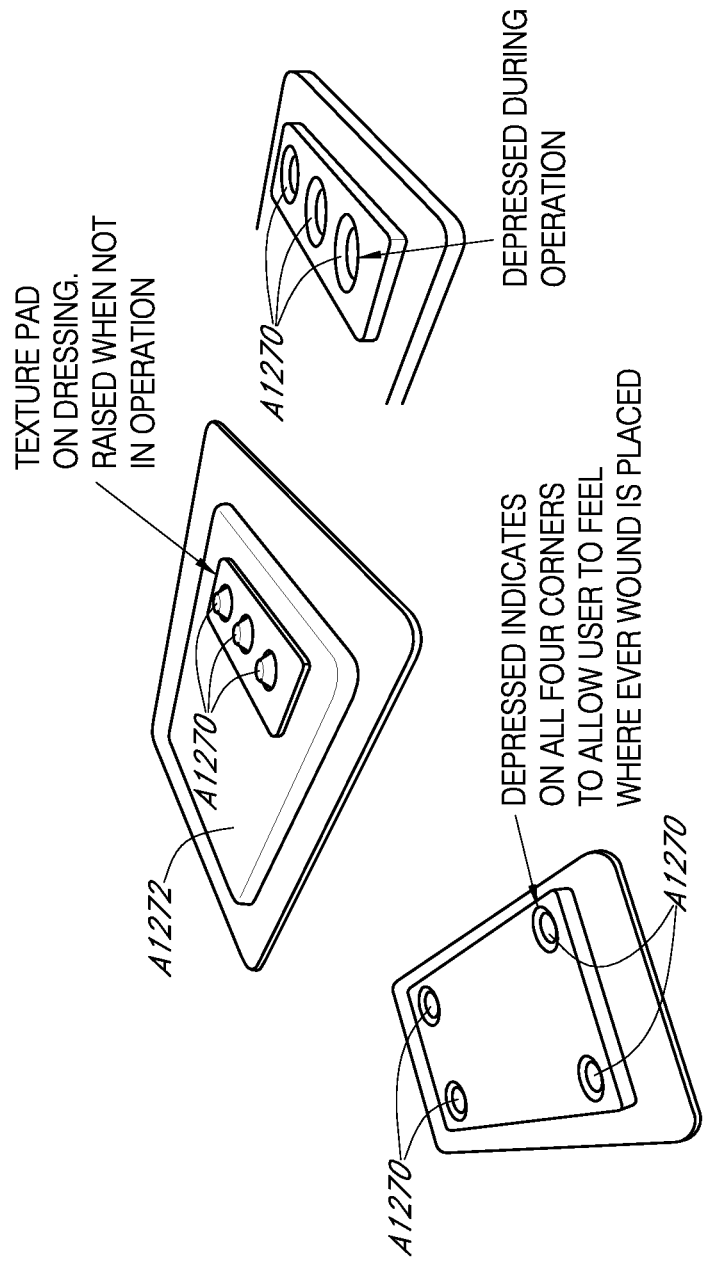
Figure 199B:
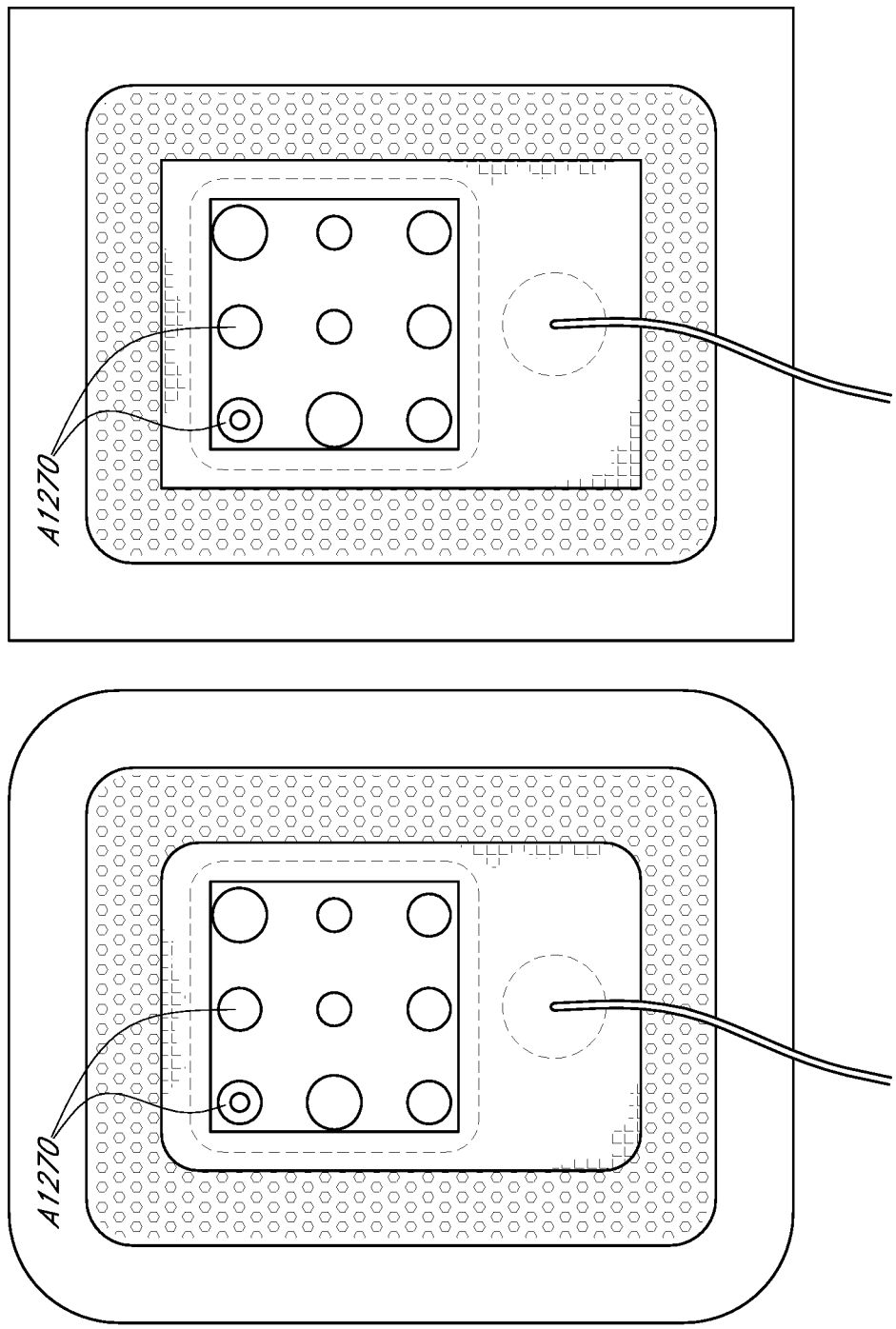
Figure 199C:
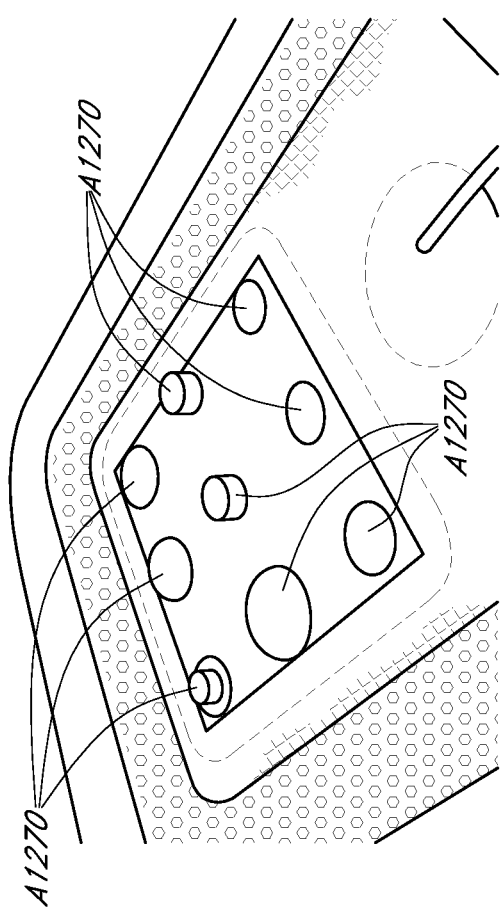
Figure 200:
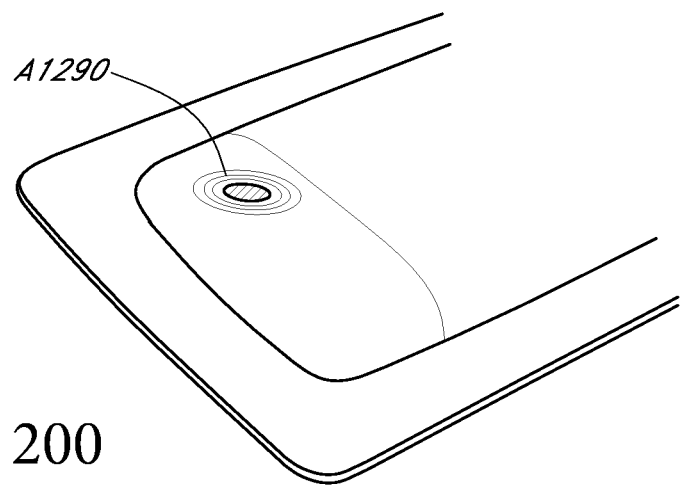

FIGS. 199A-199C illustrate additional embodiments of a dressing kit for negative pressure wound therapy.

FIGS. 200-203 illustrate additional embodiments of dressing kits for negative pressure wound therapy having one or more indicator lights thereon.

FIGS. 204A-205D illustrate additional embodiments of a dressing kit for negative pressure wound therapy having one or more pressure indicators thereon.

Figure 206:
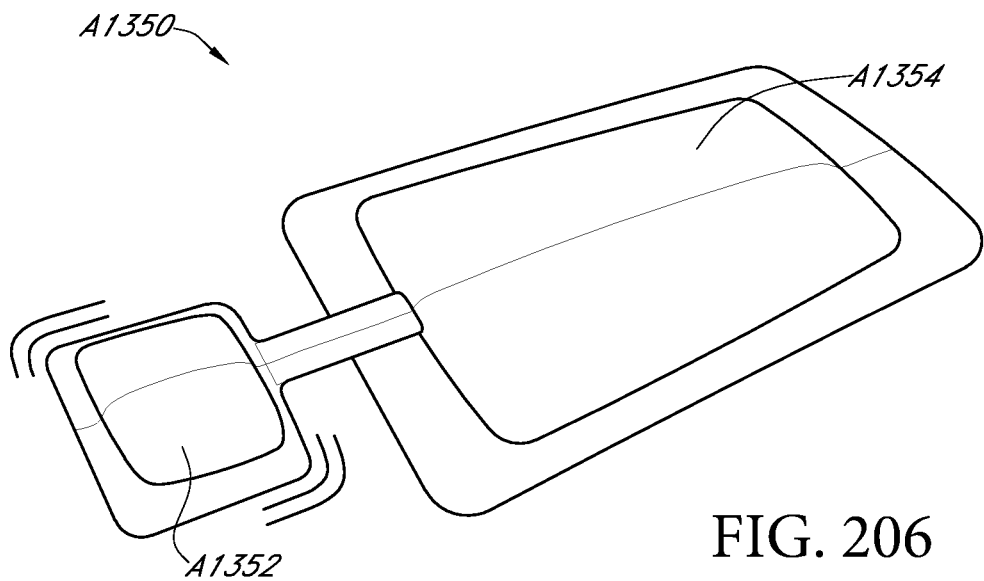
Figure 207:
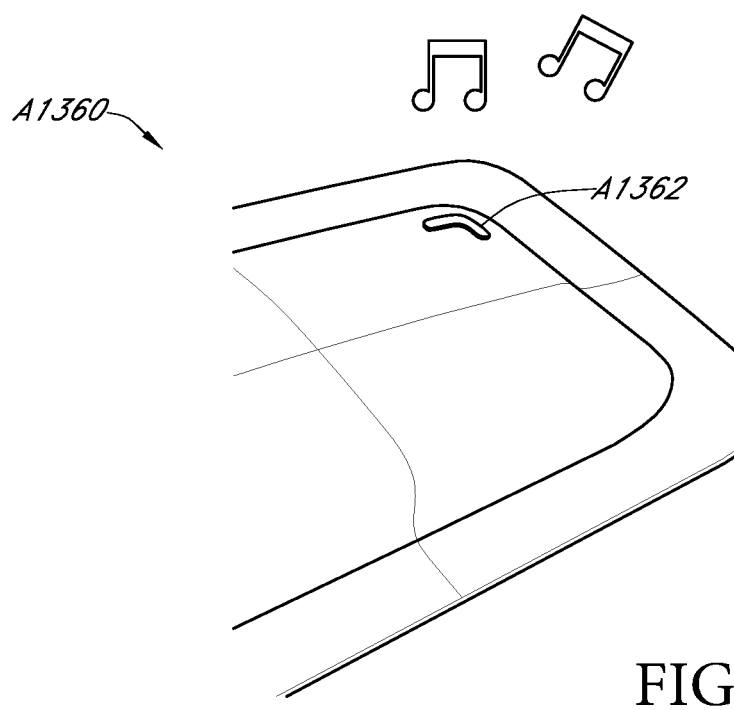

FIGS. 206-207 illustrate additional embodiments of a dressing kit for negative pressure wound therapy.

Figure 208:
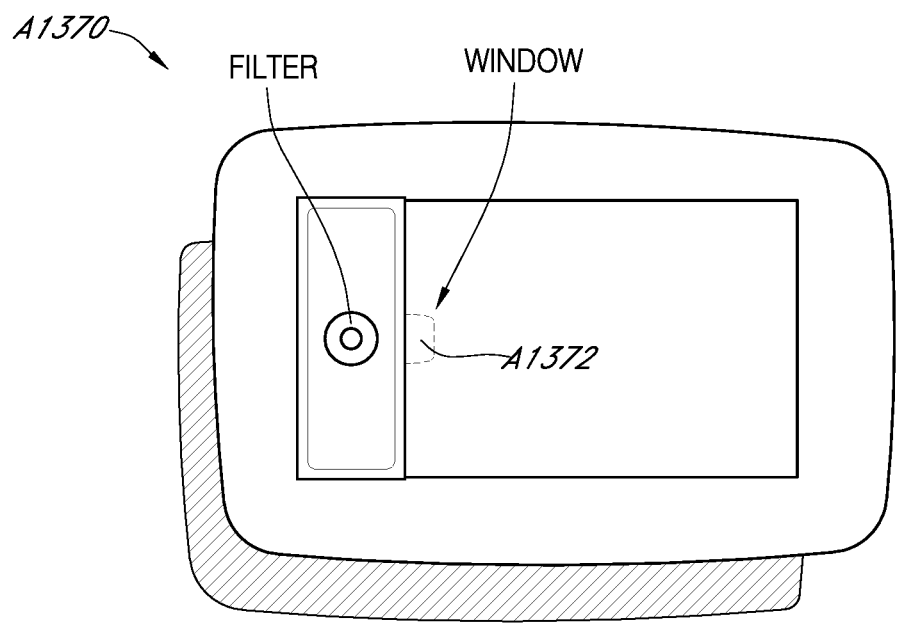
Figure 209:
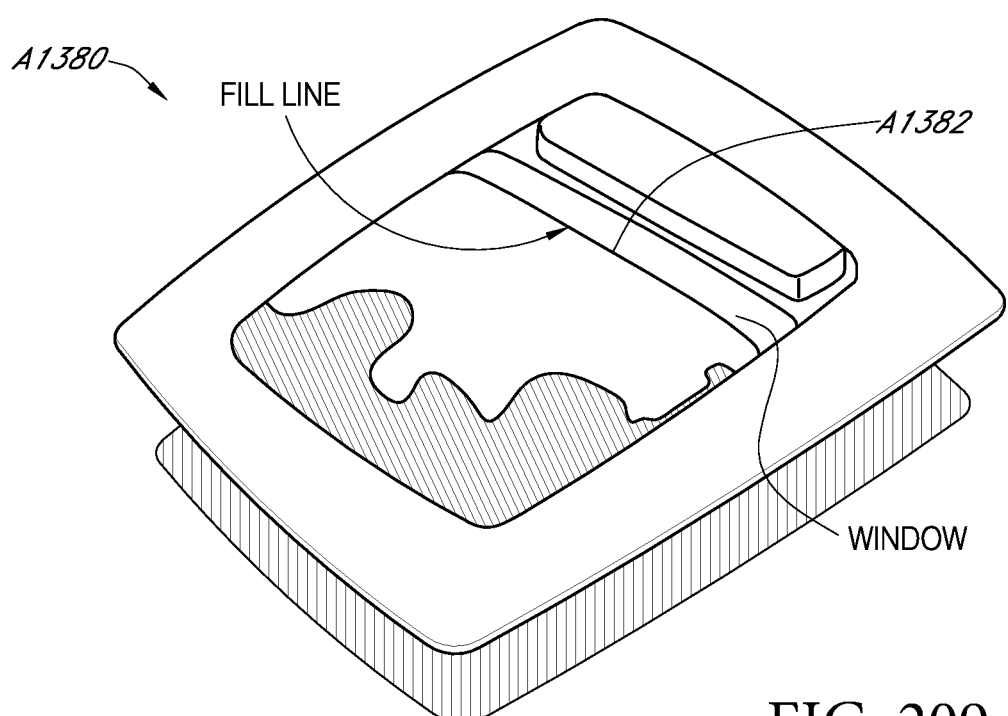
Figure 210:
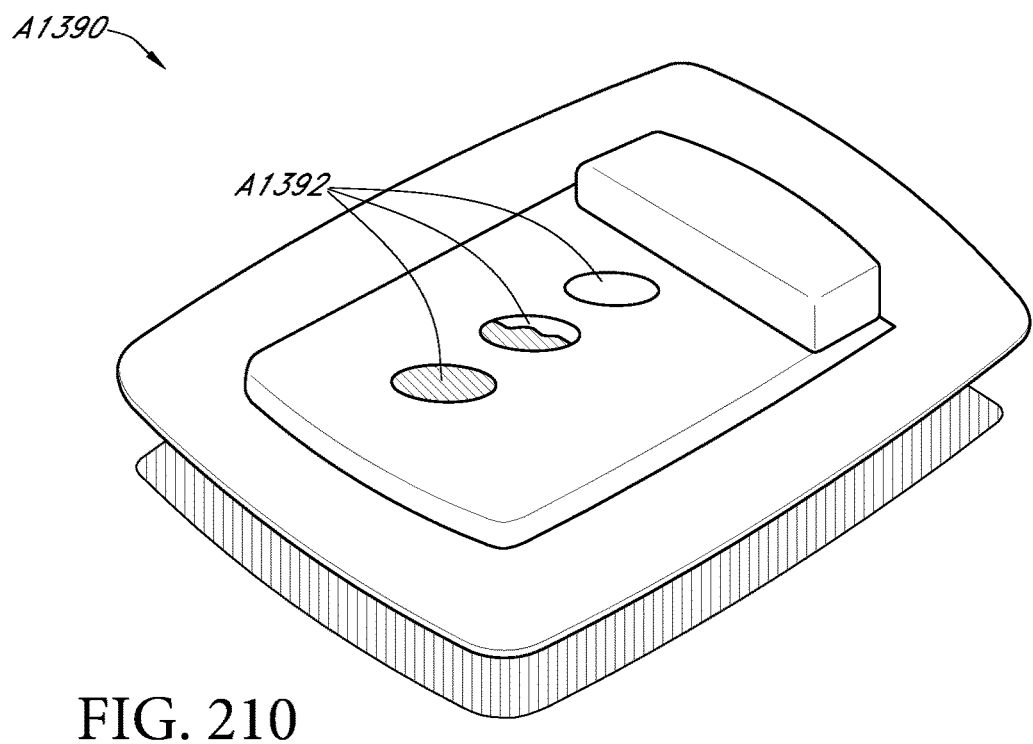

FIGS. 208-210 illustrate additional embodiments of a dressing kit for negative pressure wound therapy having one or more fill indicators thereon.

Figure 211:
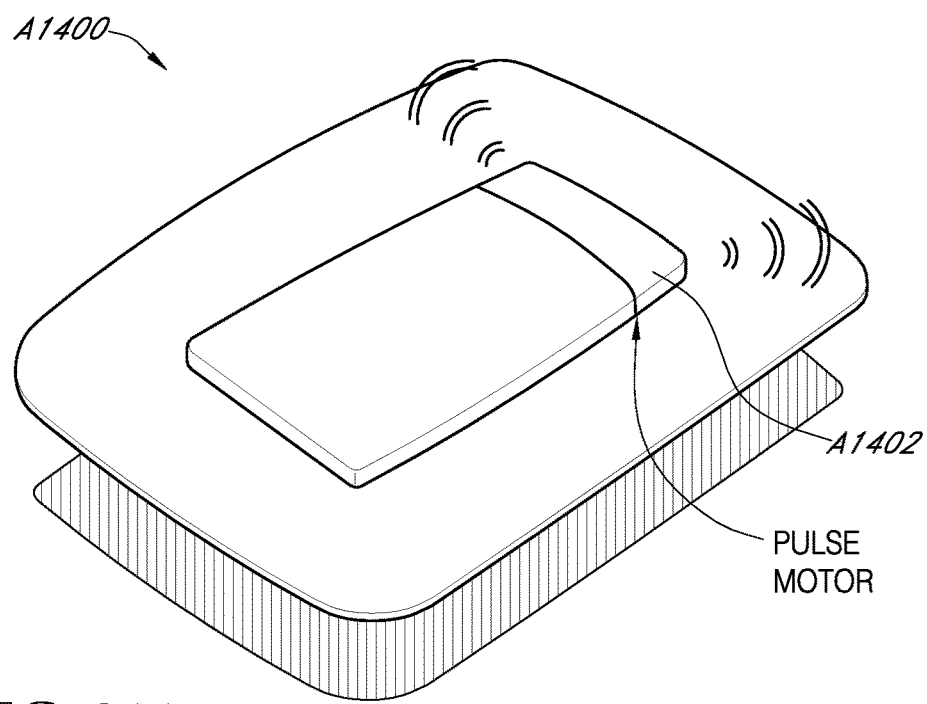

FIG. 211 illustrates an additional embodiment of a dressing kit for negative pressure wound therapy.

Figure 212A:
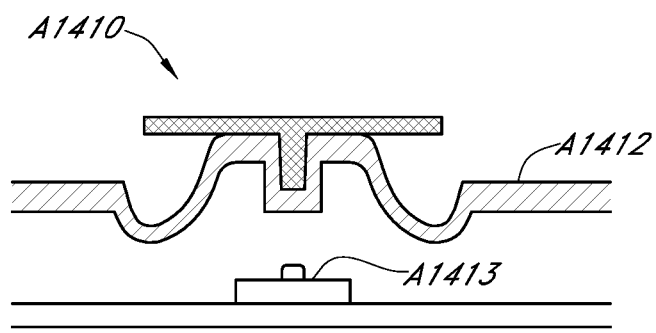
Figure 212B:
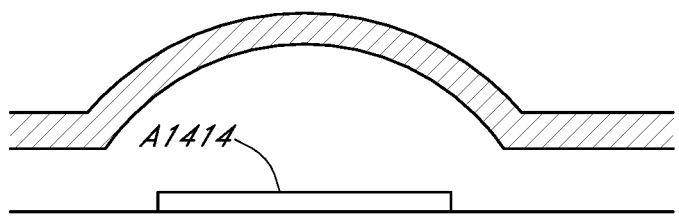

FIGS. 212A-212B illustrate an additional embodiment of an activation switch and/or pressure indicator for a dressing kit for negative pressure wound therapy.

Figure 213A:
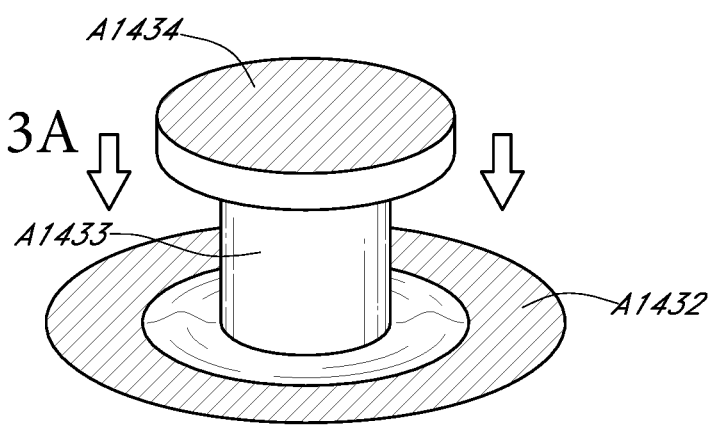
Figure 213B:
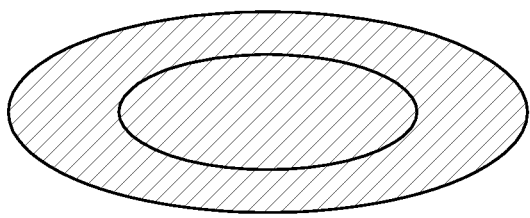

FIGS. 213A-213B illustrate an additional embodiment of a pressure indicator for a dressing kit for negative pressure wound therapy.

Figure 214A:
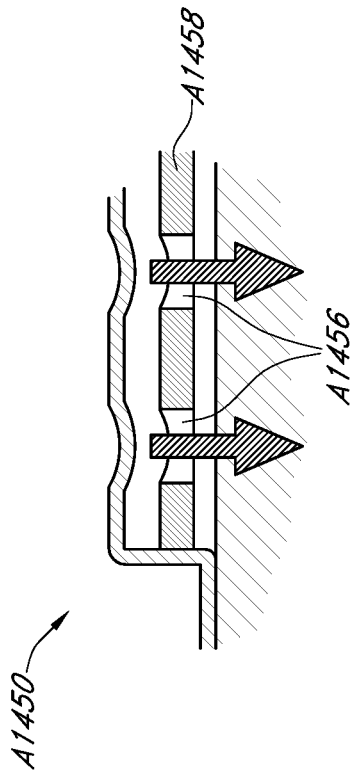
Figure 214B:
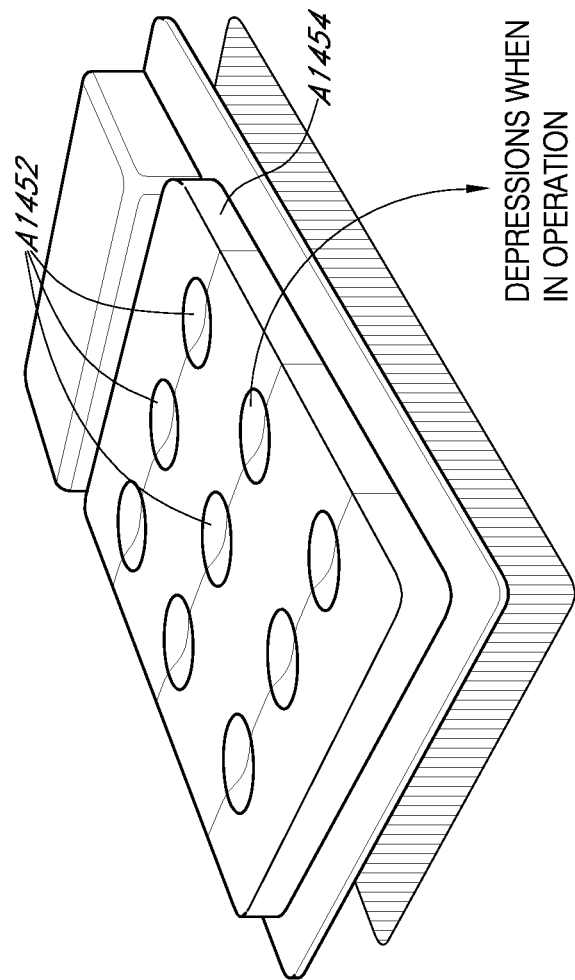

FIGS. 214A-214B illustrate an additional embodiment of a dressing kit for negative pressure wound therapy having one or more pressure indicators thereon.

Figure 215B:
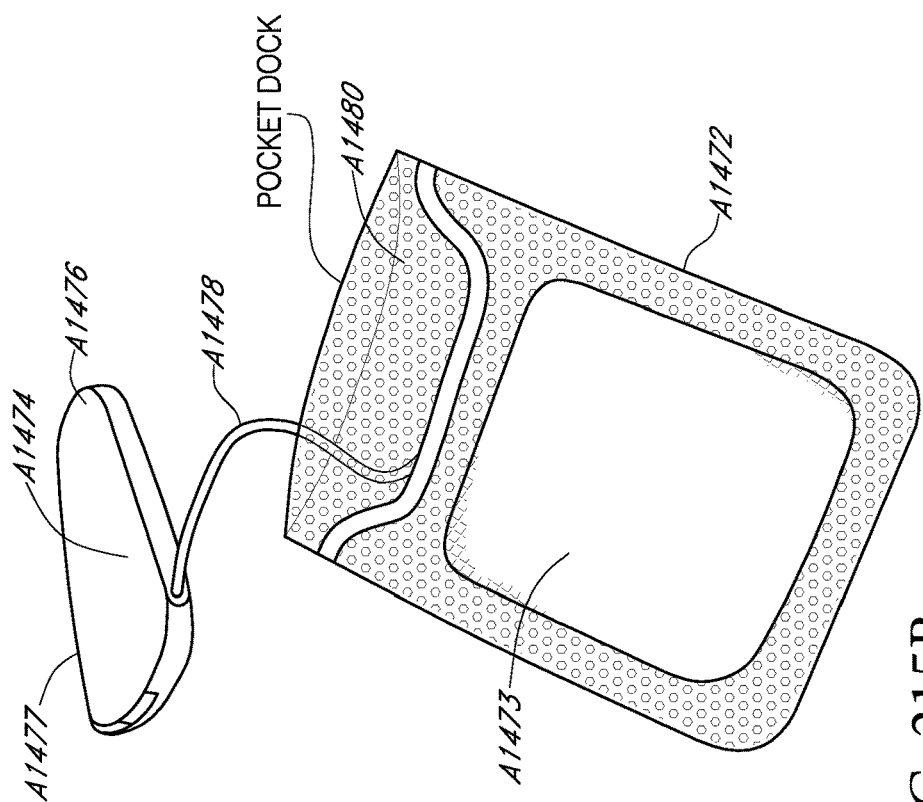
Figure 215A:
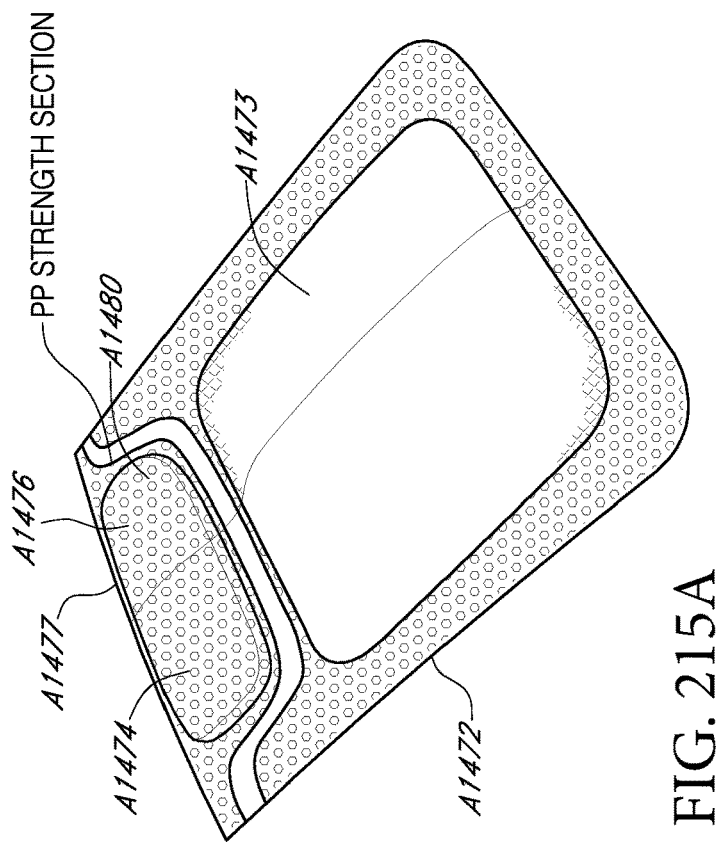

FIGS. 215A-215B illustrate an additional embodiment of a dressing kit for negative pressure wound therapy.

FIGS. 216A-216C illustrate an additional embodiment of a dressing kit for negative pressure wound therapy.

Figure 217A:
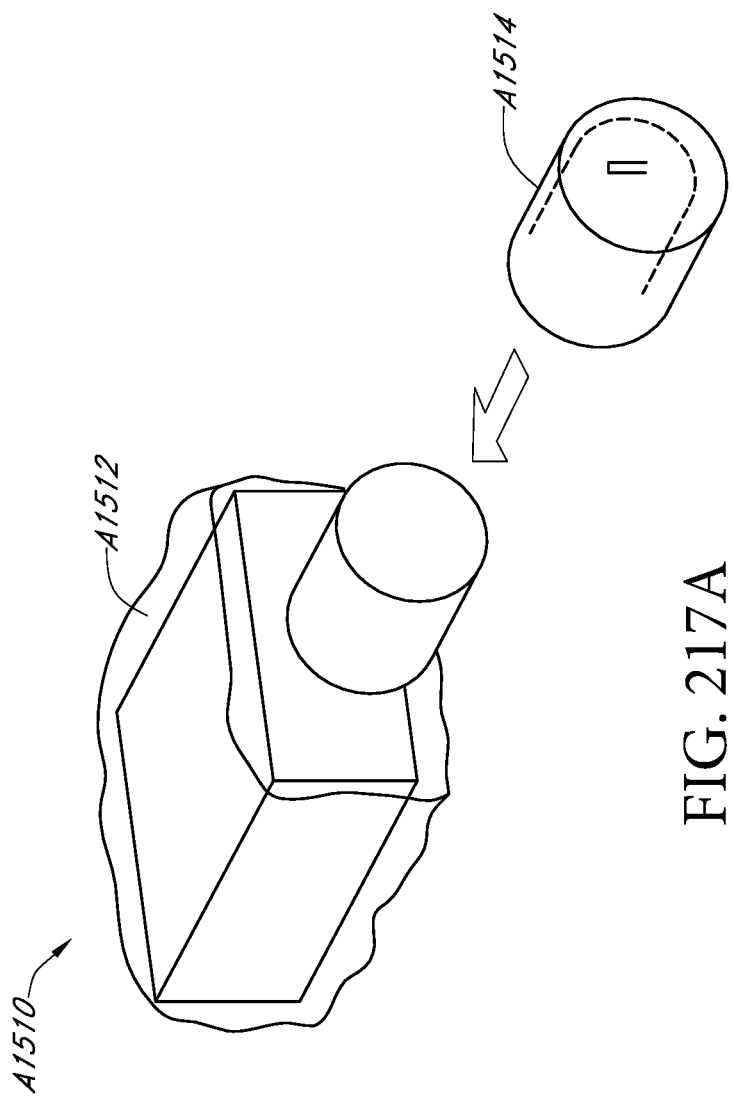
Figure 217B:
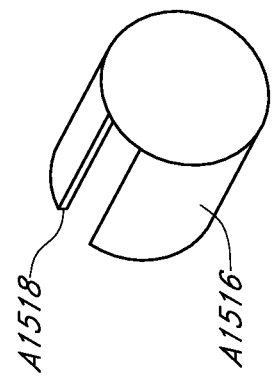
Figure 218B:
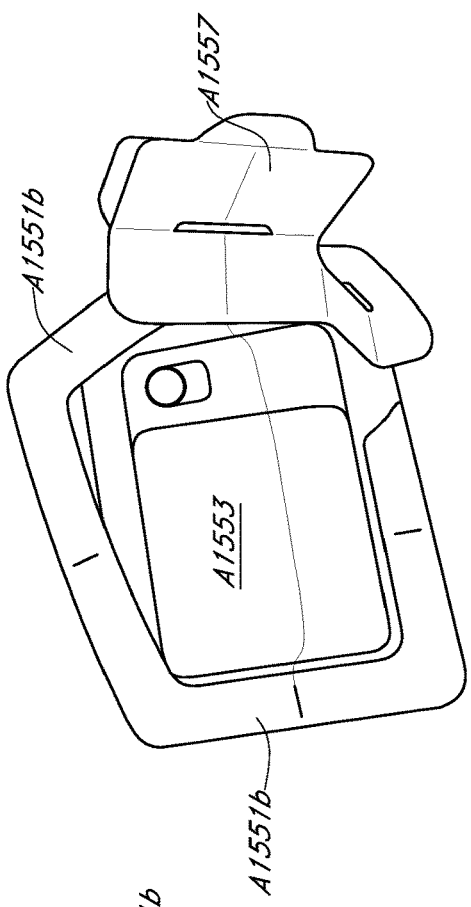
Figure 218A:
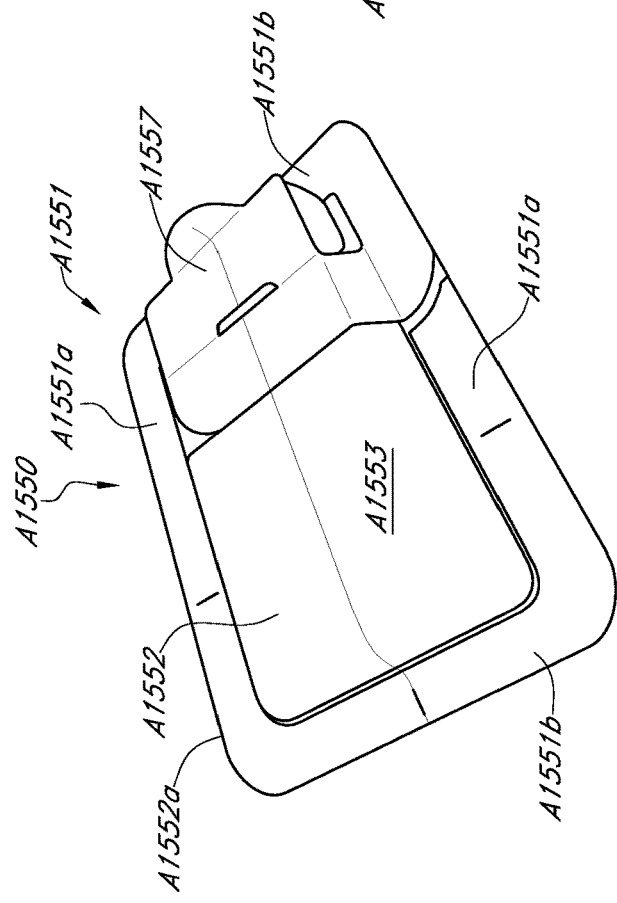
Figure 218D:
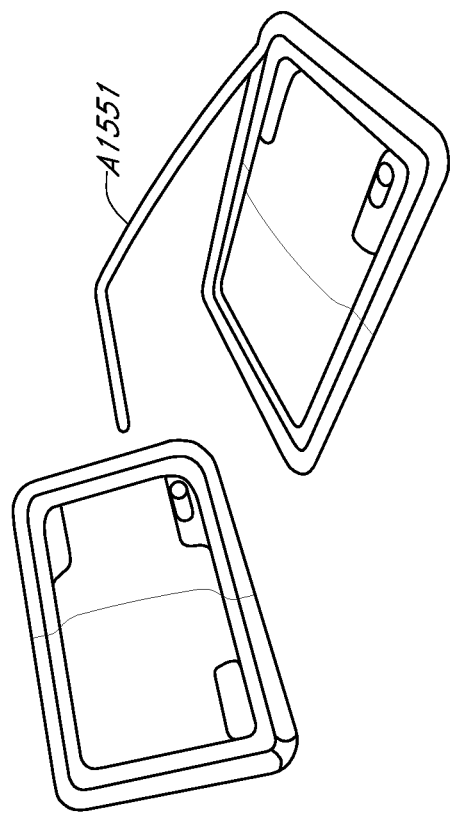
Figure 218C:
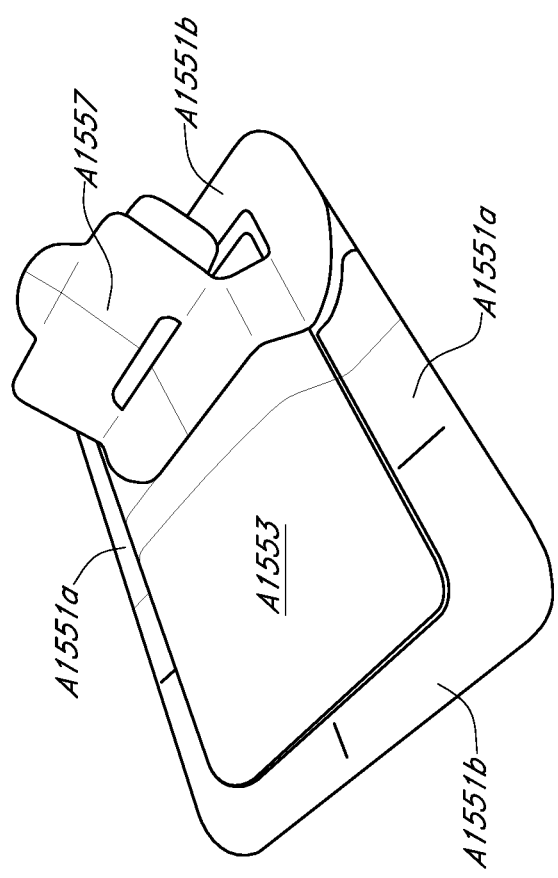

FIGS. 217A-217B illustrate an additional embodiment of a dressing kit for negative pressure wound therapy.

FIGS. 218A-218D illustrate an additional embodiment of a dressing kit for negative pressure wound therapy.

Figure 219:
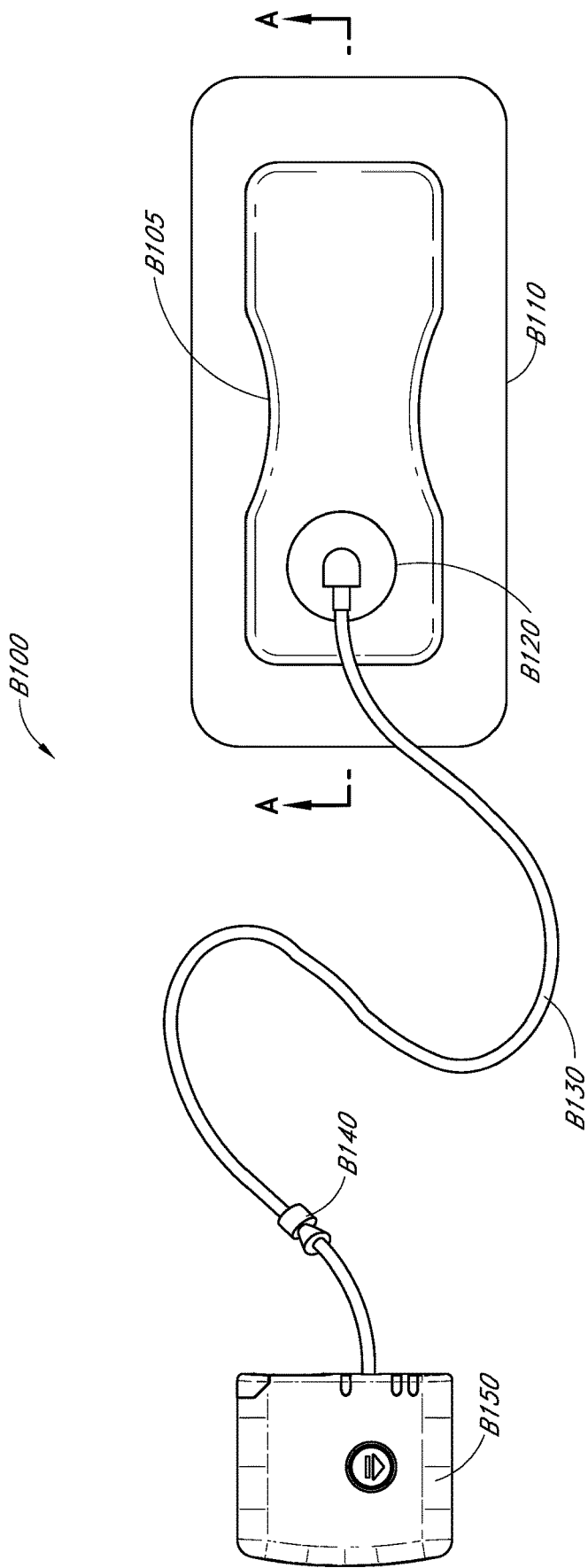

FIG. 219 illustrates an embodiment of a wound treatment system.

FIGS. 220A-D illustrate the use and application of an embodiment of a wound treatment system onto a patient.

Figure 221A:
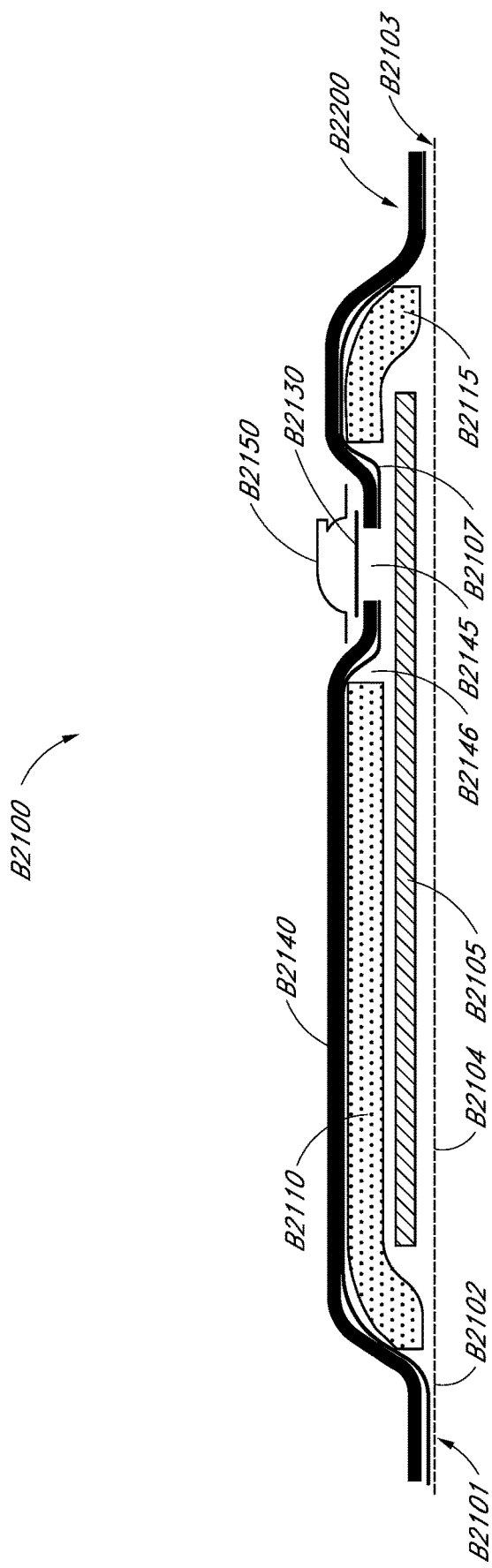

FIG. 221A illustrates an embodiment of a wound dressing in cross-section.

Figure 221B:
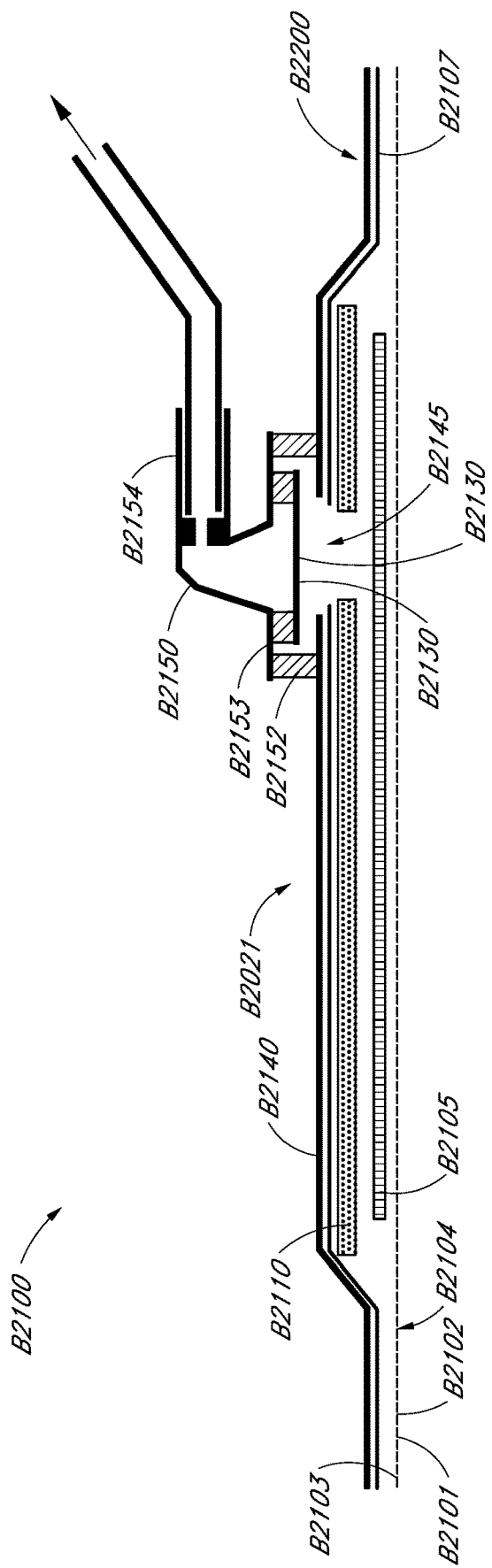

FIG. 221B illustrates another embodiment of a wound dressing in cross-section.

Figure 221C:
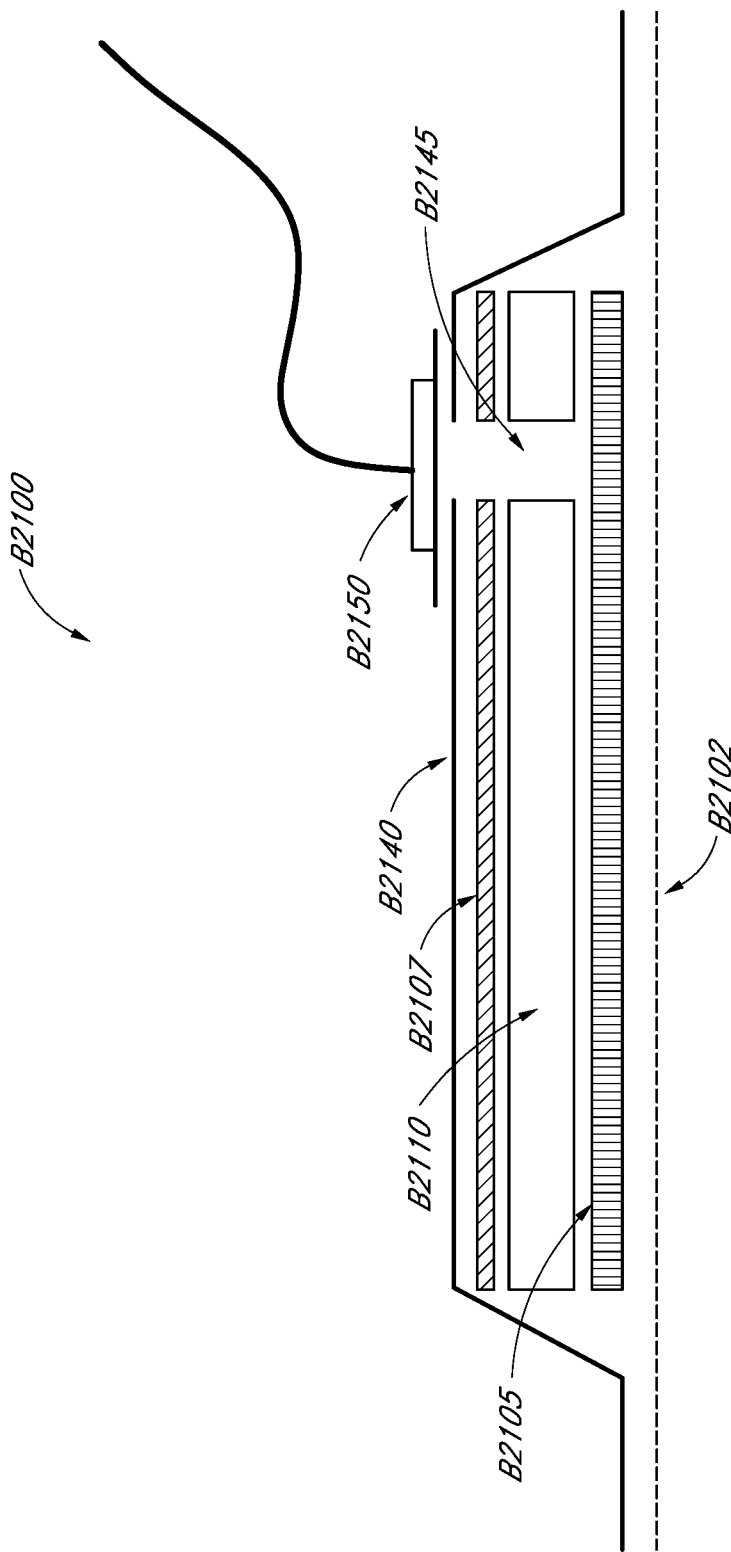

FIG. 221C illustrates another embodiment of a wound dressing in cross-section.

Figure 222A:
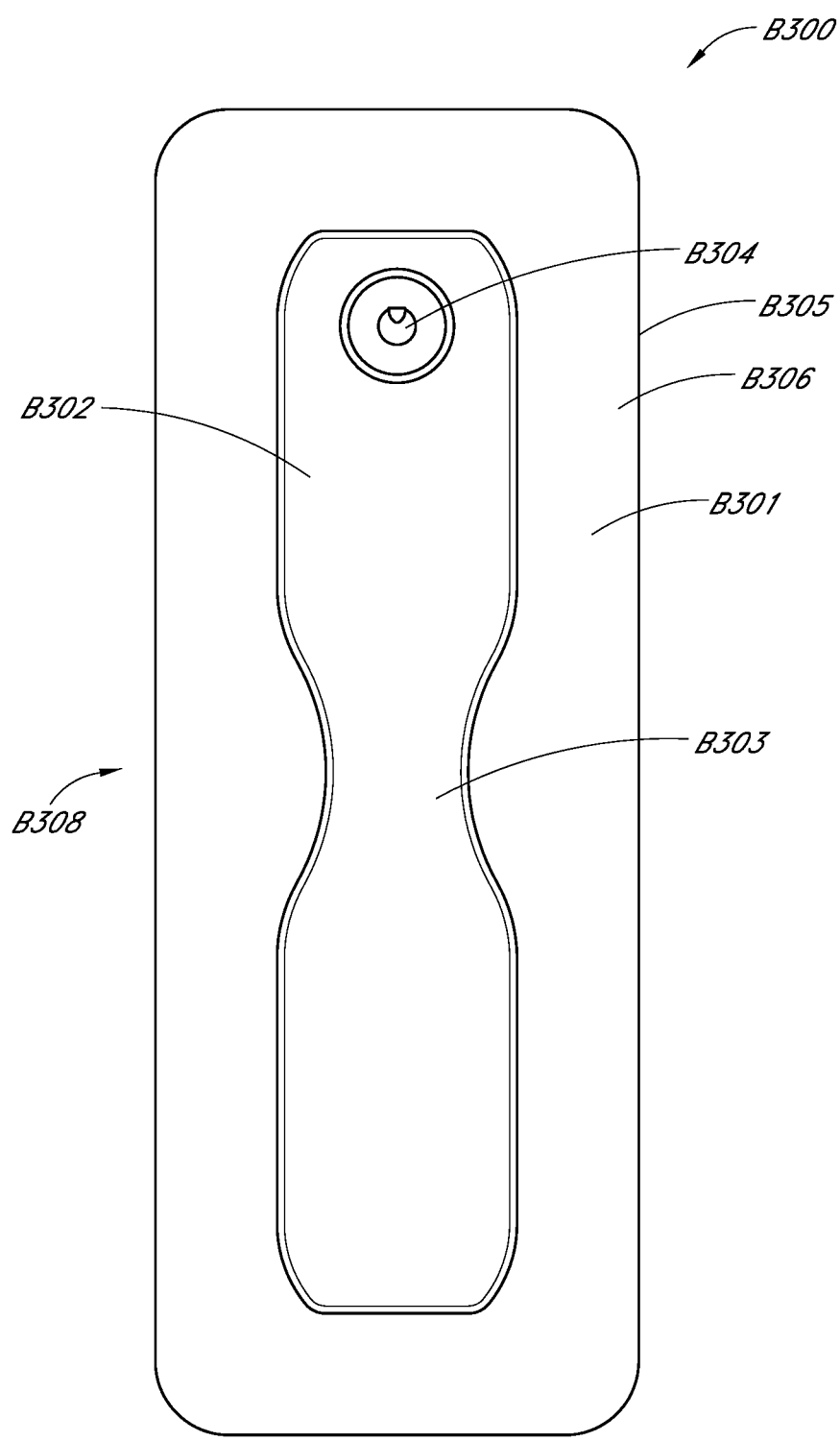
Figure 222B:
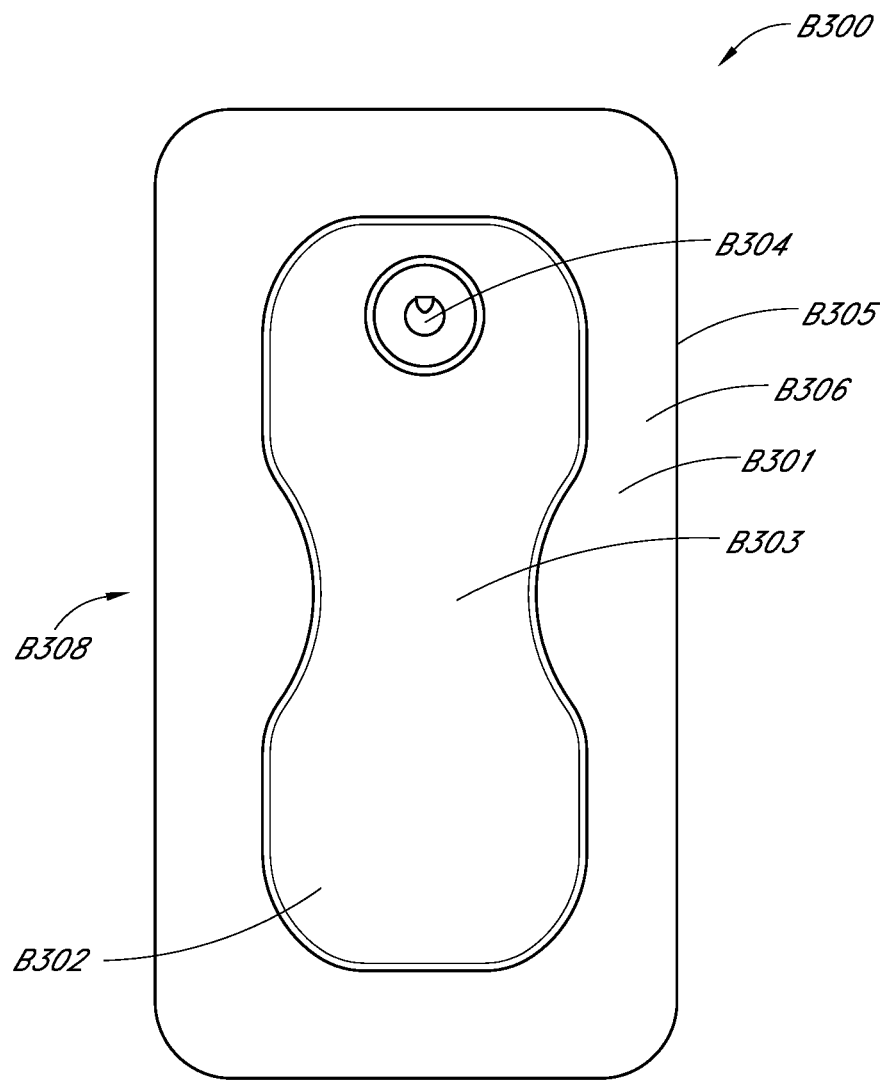
Figure 222C:
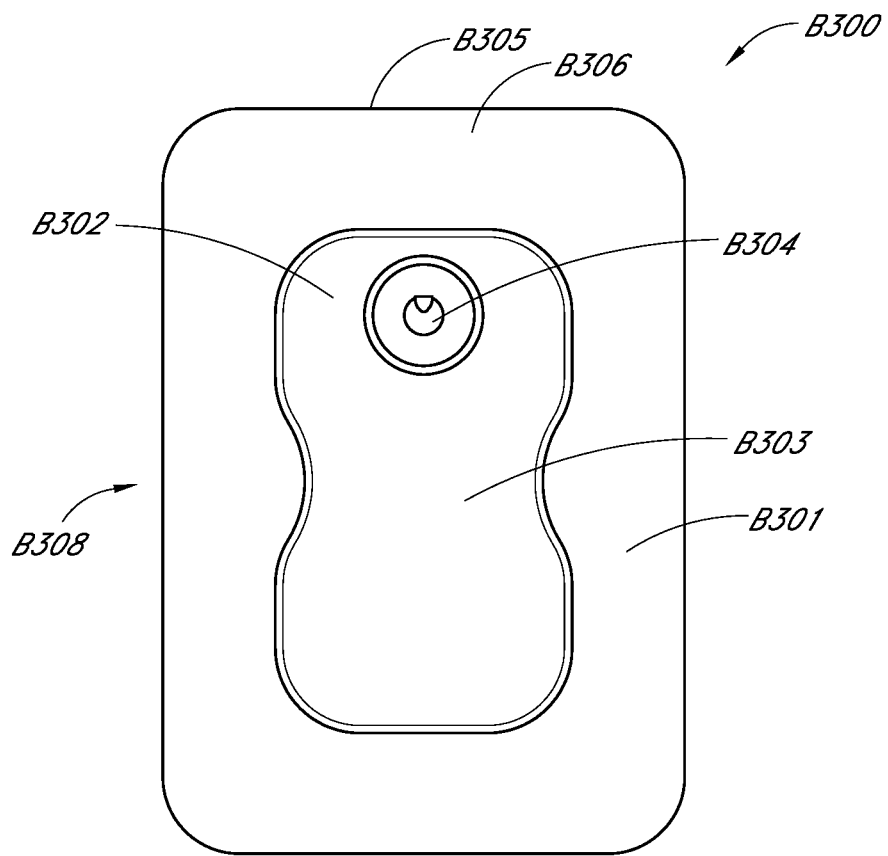

FIGS. 222A-C illustrate a top view of an embodiment of a wound dressing with a narrow central portion.

FIGS. 223A-230F illustrate a perspective view, a top view, a bottom view, a front view, a back view, and a side view, respectively, of embodiments of a wound dressing including an obscuring layer and viewing windows.

Figures 231A, 231B:
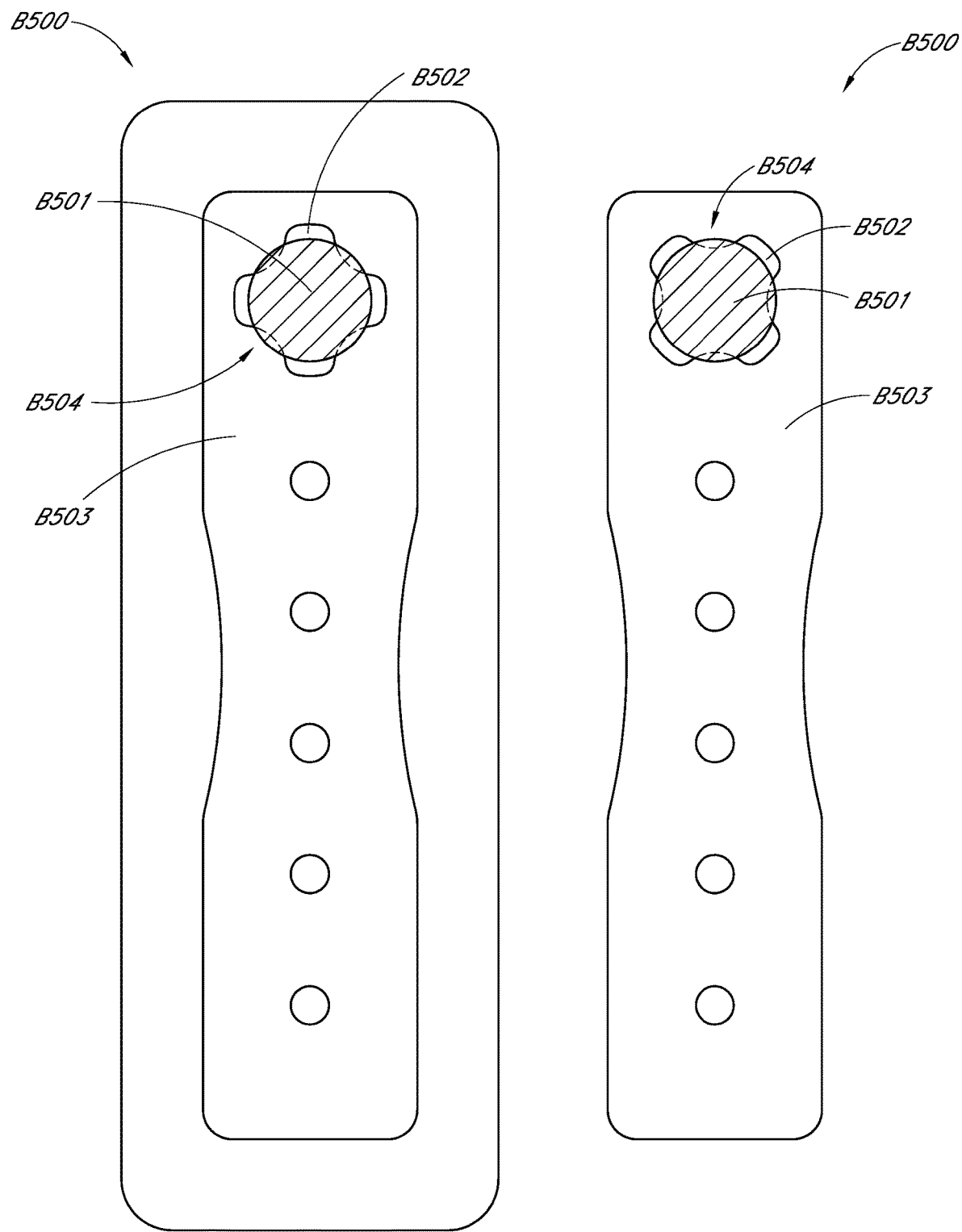
Figure 232:
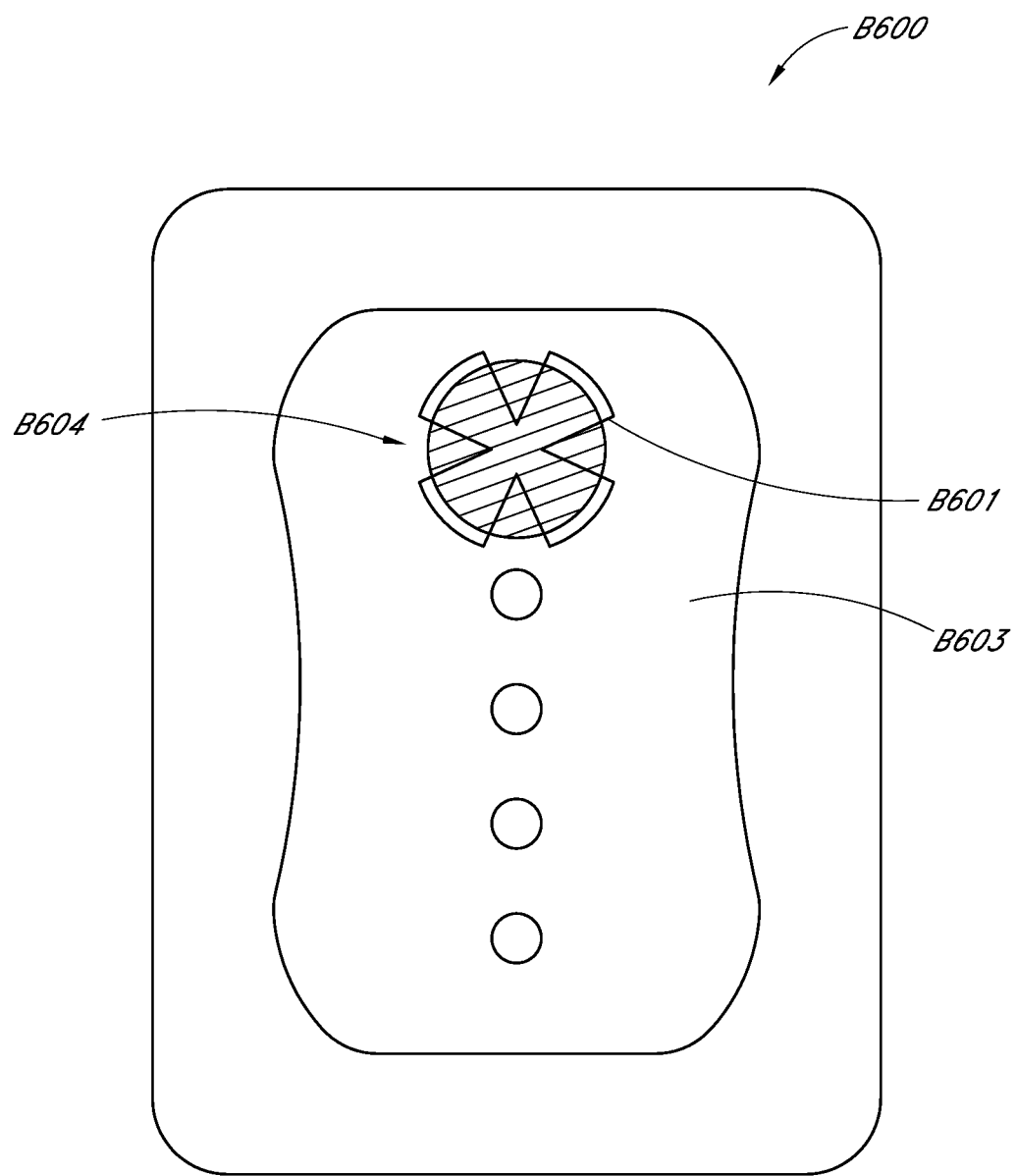

FIGS. 231A-B and 232 illustrate a top view of an embodiment of a wound dressing including a cross-shaped viewing window.

Figure 233A:
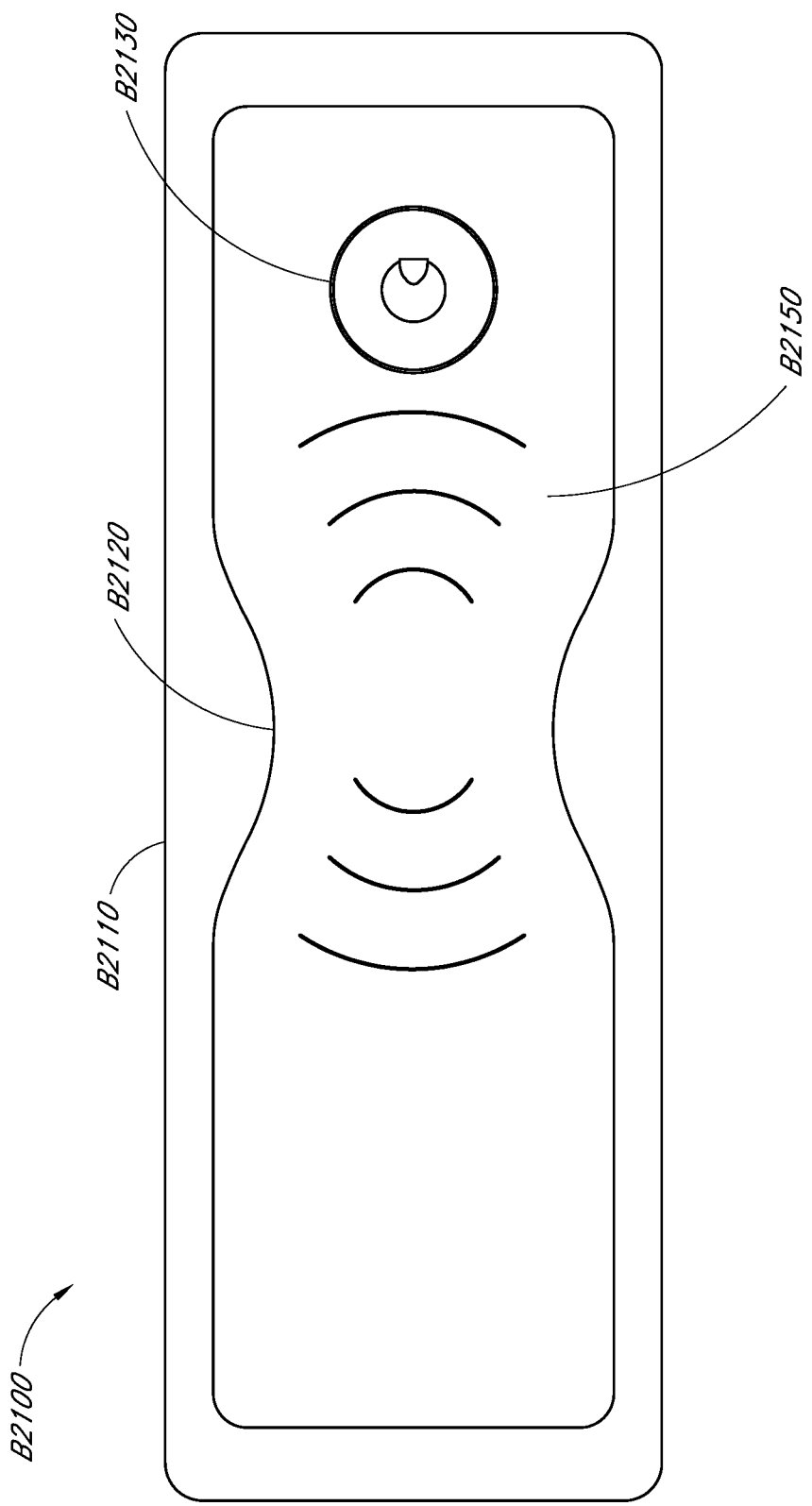
Figure 233B:
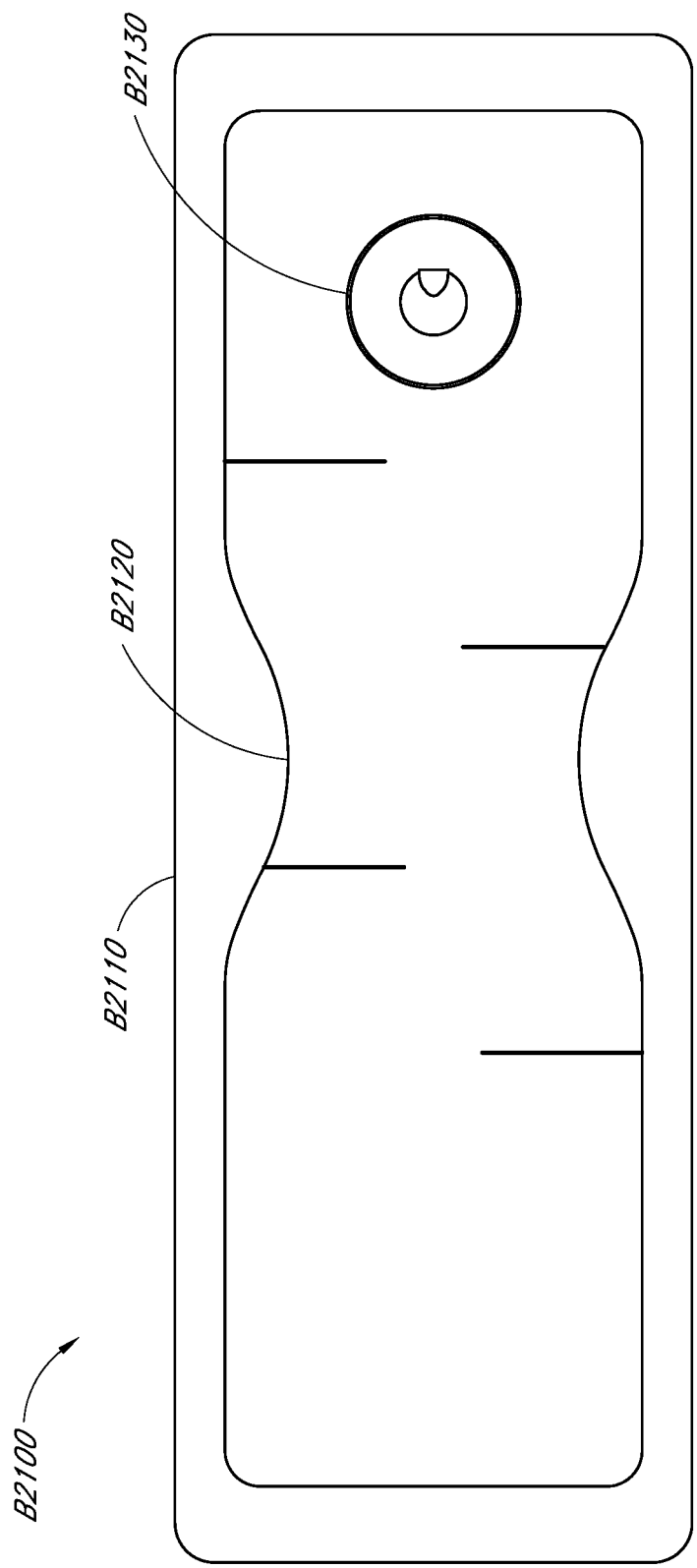

FIGS. 233A-B illustrate a top view of an embodiment of a wound dressing including slits in the wound dressing.

FIG. 234 illustrates an embodiment of a dressing comprising a viewing window in the shape of a trademarked brand name.

FIG. 235 illustrates a top view of an embodiment of a three-lobe configuration of a wound dressing and a dot pattern of viewing windows.

FIG. 236 illustrates a top view of an embodiment of a three-lobe configuration of a wound dressing and viewing windows in the shape of a logo.

Figure 237:
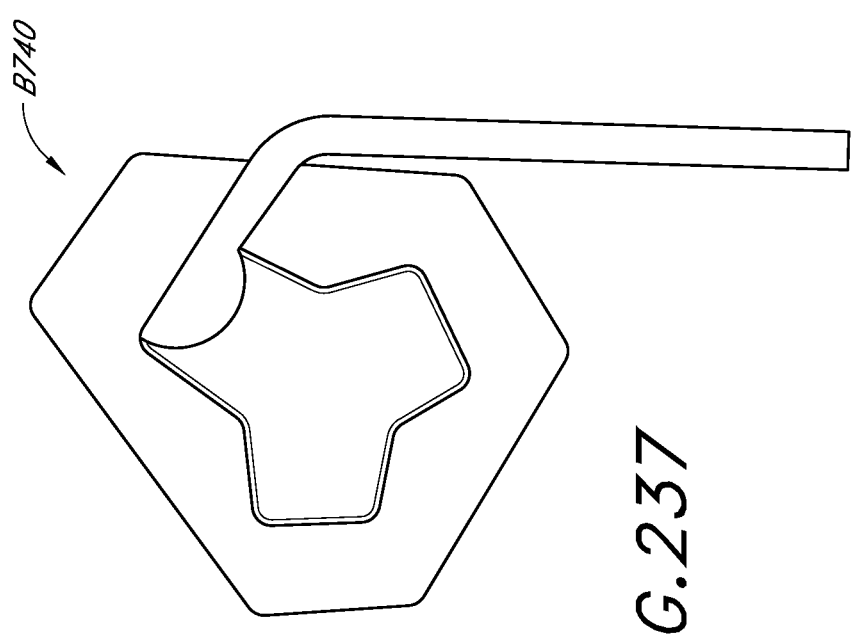

FIG. 237 illustrates a top view of an embodiment of a three-lobe wound dressing.

Figure 238:
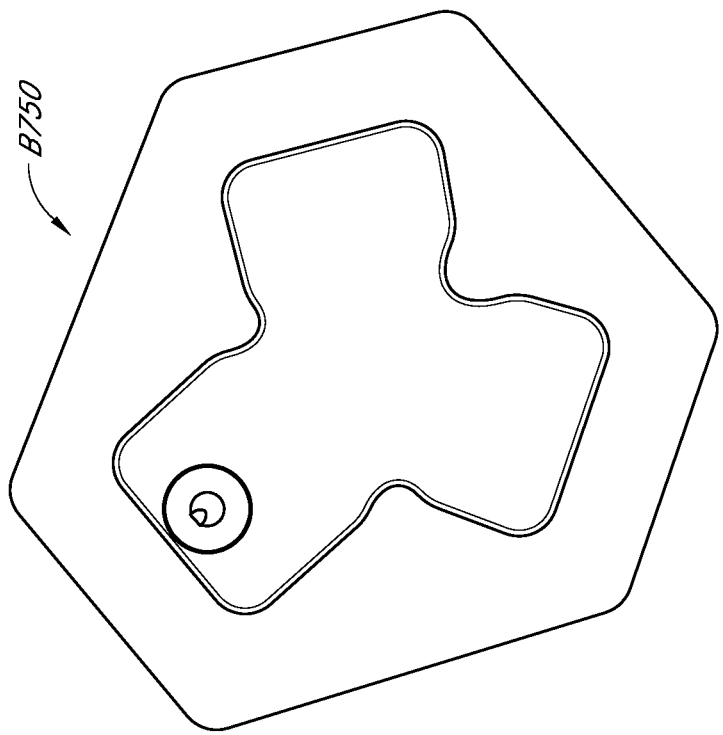

FIG. 238 illustrates a top view of an embodiment of a three-lobe wound dressing with flared ends on each lobe.

Figure 239A:
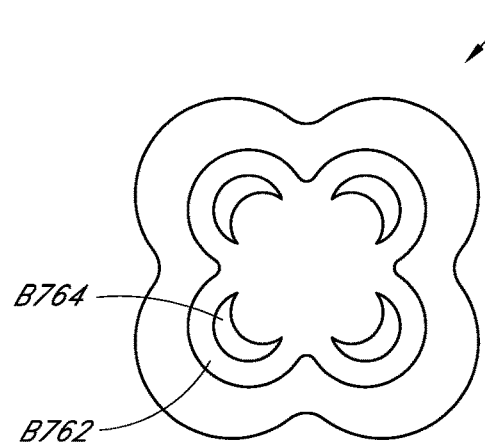

FIG. 239A illustrates a top view of an embodiment of a four-lobe wound dressing with crescent shaped cut-outs as viewing windows.

Figure 239B:
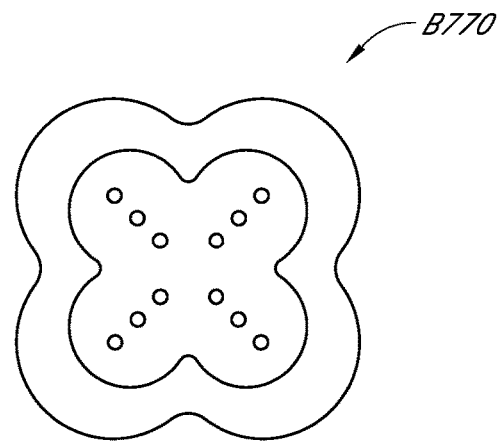

FIG. 239B illustrates a top view of an embodiment of a four-lobe wound dressing with an array of dots at viewing windows.

Figure 239C:
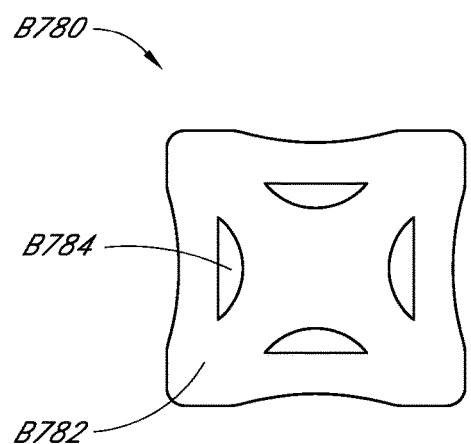

FIG. 239C illustrates a top view of an embodiment of a four-lobe wound dressing with viewing windows.

Figure 240:
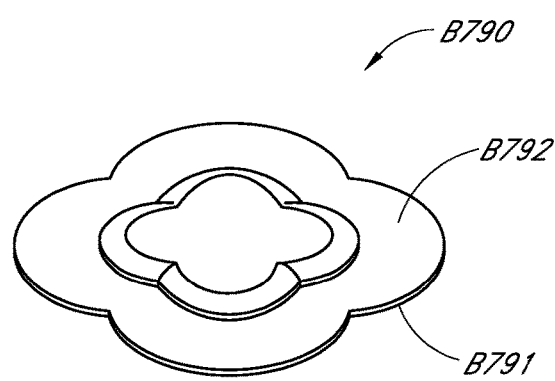

FIG. 240 illustrates a perspective view of an embodiment of a four-lobe wound dressing.

FIG. 241A-B illustrate embodiments of white and colored fluidic connectors, respectively.

FIGS. 242A-F illustrate a perspective view, a top view, a bottom view, a front view, a back view, and a side view, respectively, of an embodiment of an oval-shaped wound dressing.

FIGS. 243-250 illustrate embodiments of a wound dressing including an obscuring layer and viewing windows including an orifice viewing window.

FIGS. 251A-B illustrate embodiments of an oval-shaped wound dressing comprising an obscuring layer and an orifice viewing window.

Figure 252A:
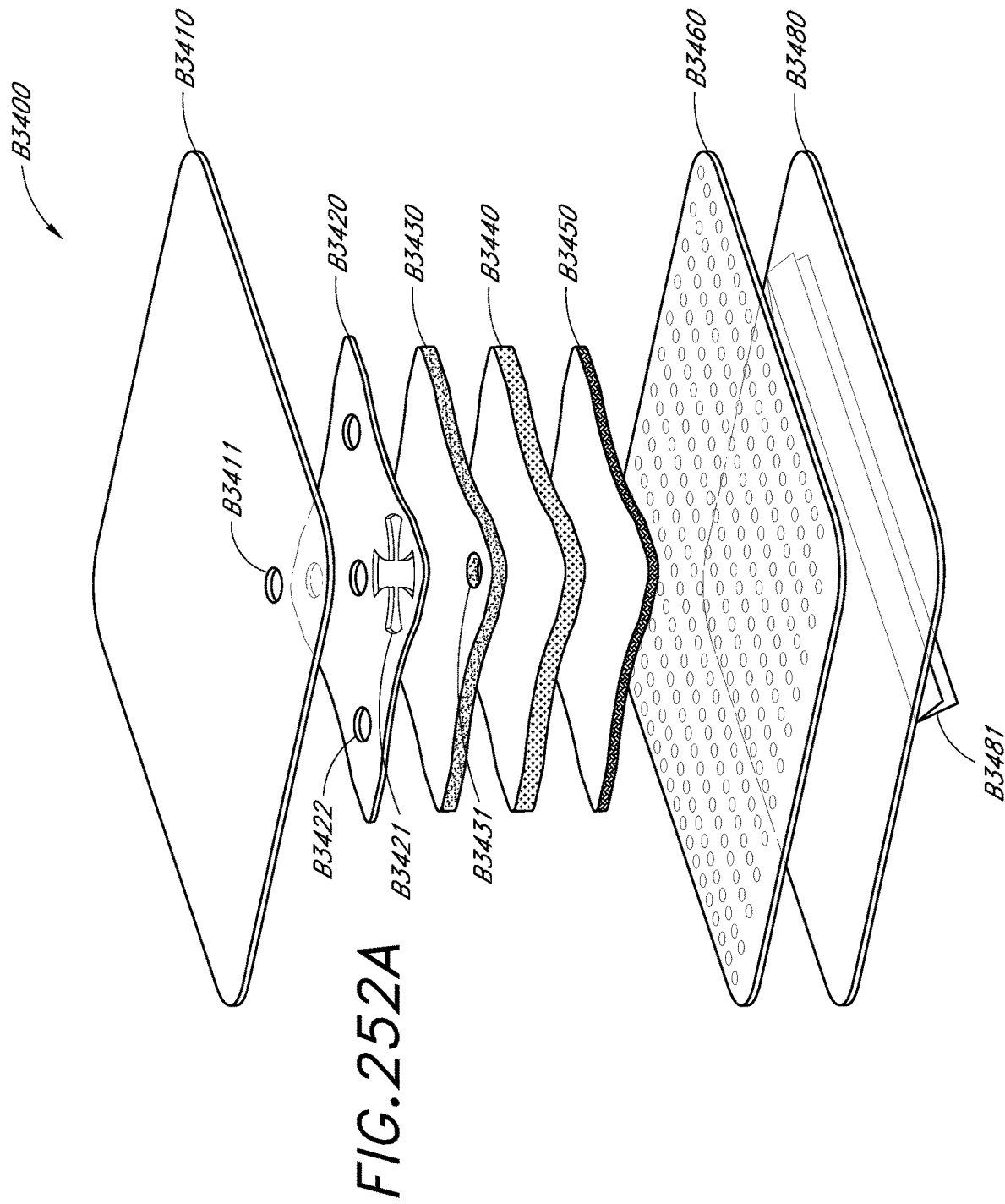

FIG. 252A illustrates an exploded view of an embodiment of a wound dressing.

Figure 252B:
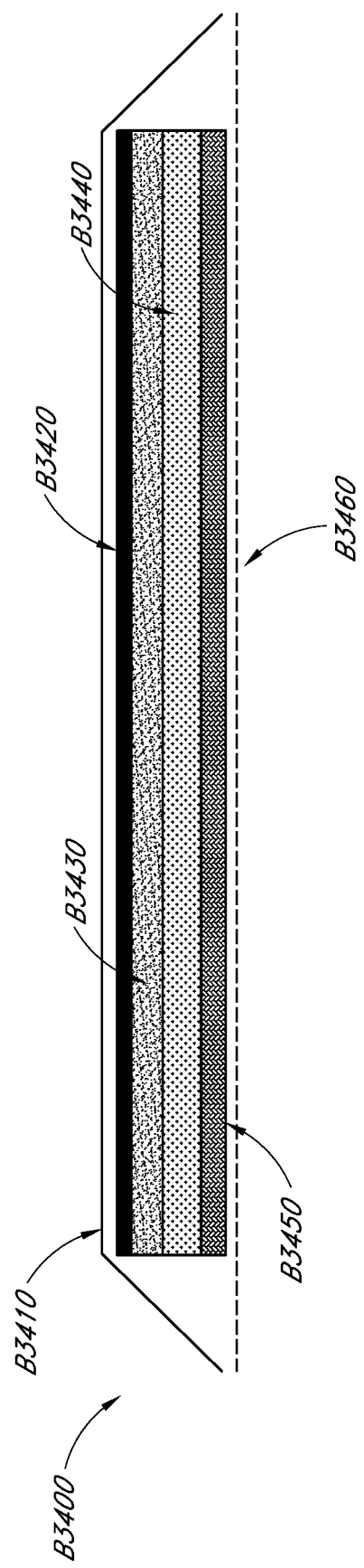

FIG. 252B illustrates a cross sectional view of an embodiment of a wound dressing.

Figure 253:
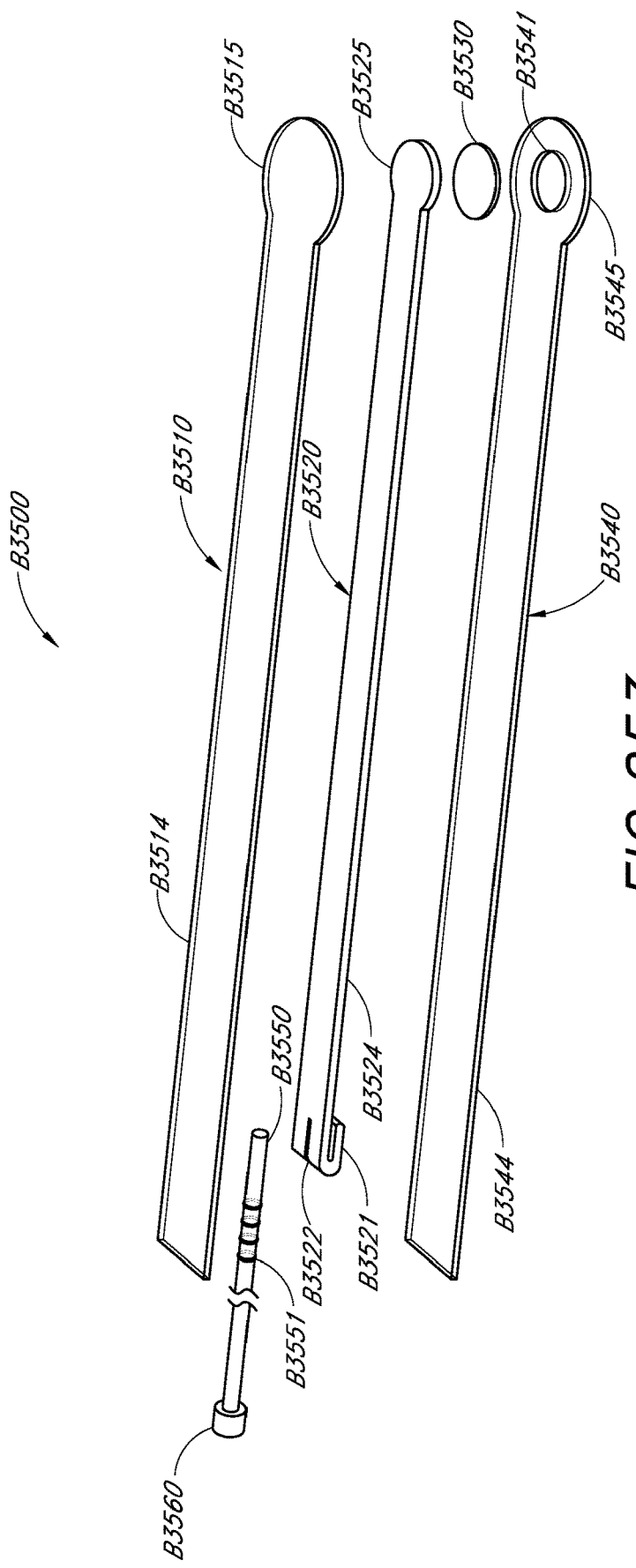

FIG. 253 illustrates an exploded view of an embodiment of a soft or flexible port for transmitting negative pressure to a wound dressing.

Figure 254:
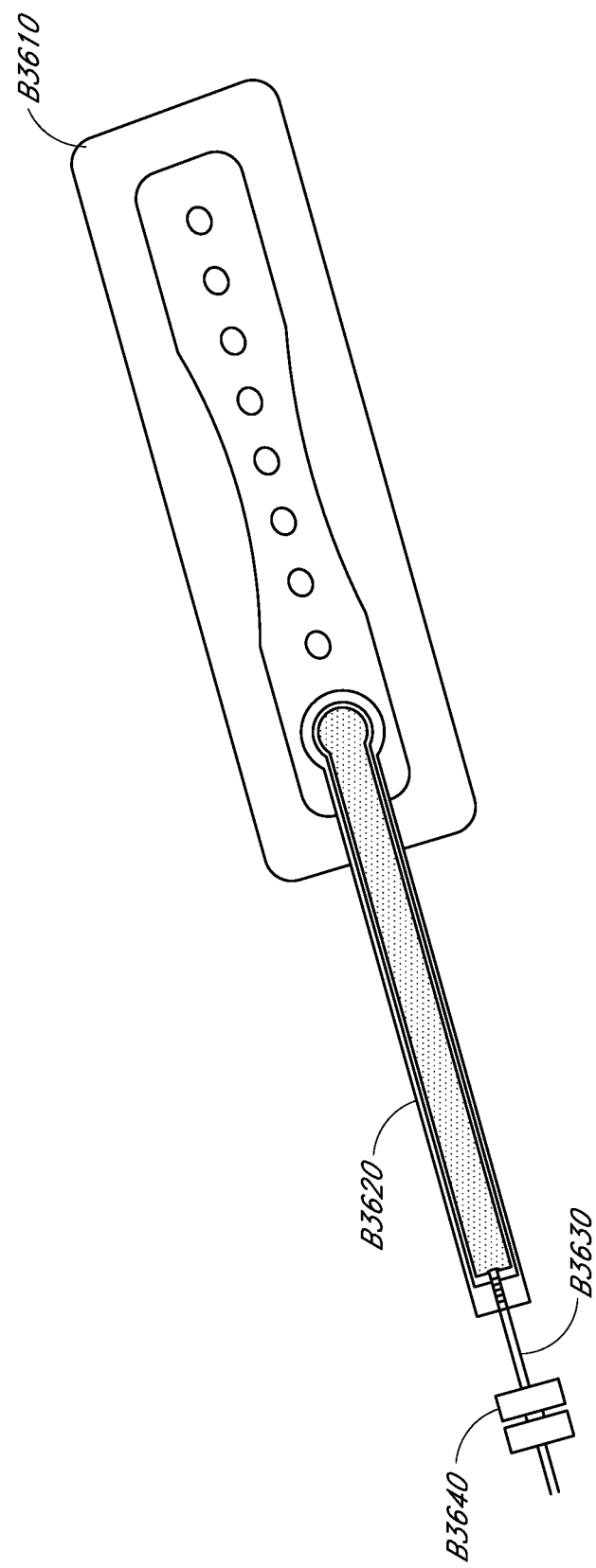

FIG. 254 illustrates an embodiment of a soft or flexible port attached to a wound dressing.

Figure 255A:
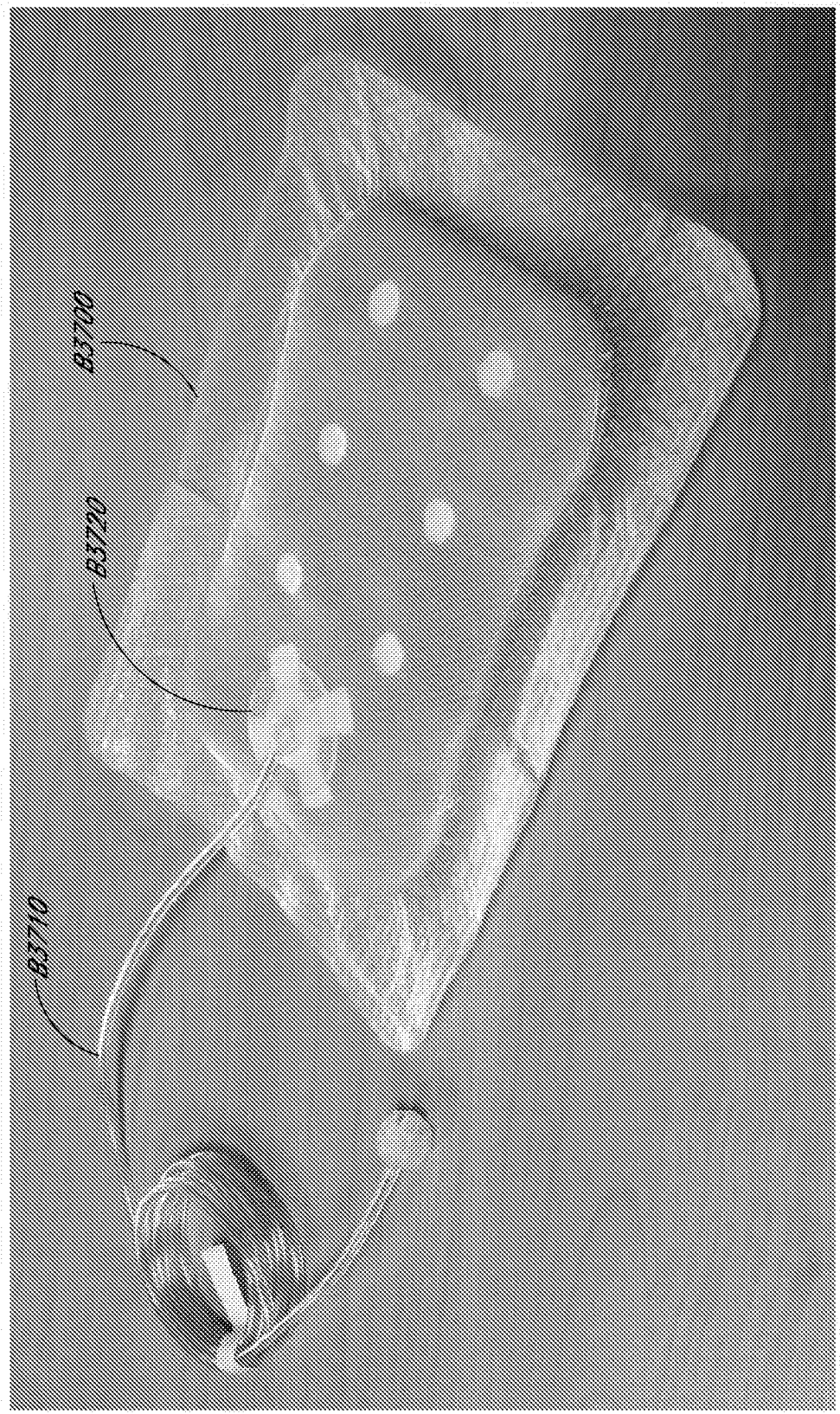

FIG. 255A illustrates a perspective view of a wound dressing.

Figure 255B:
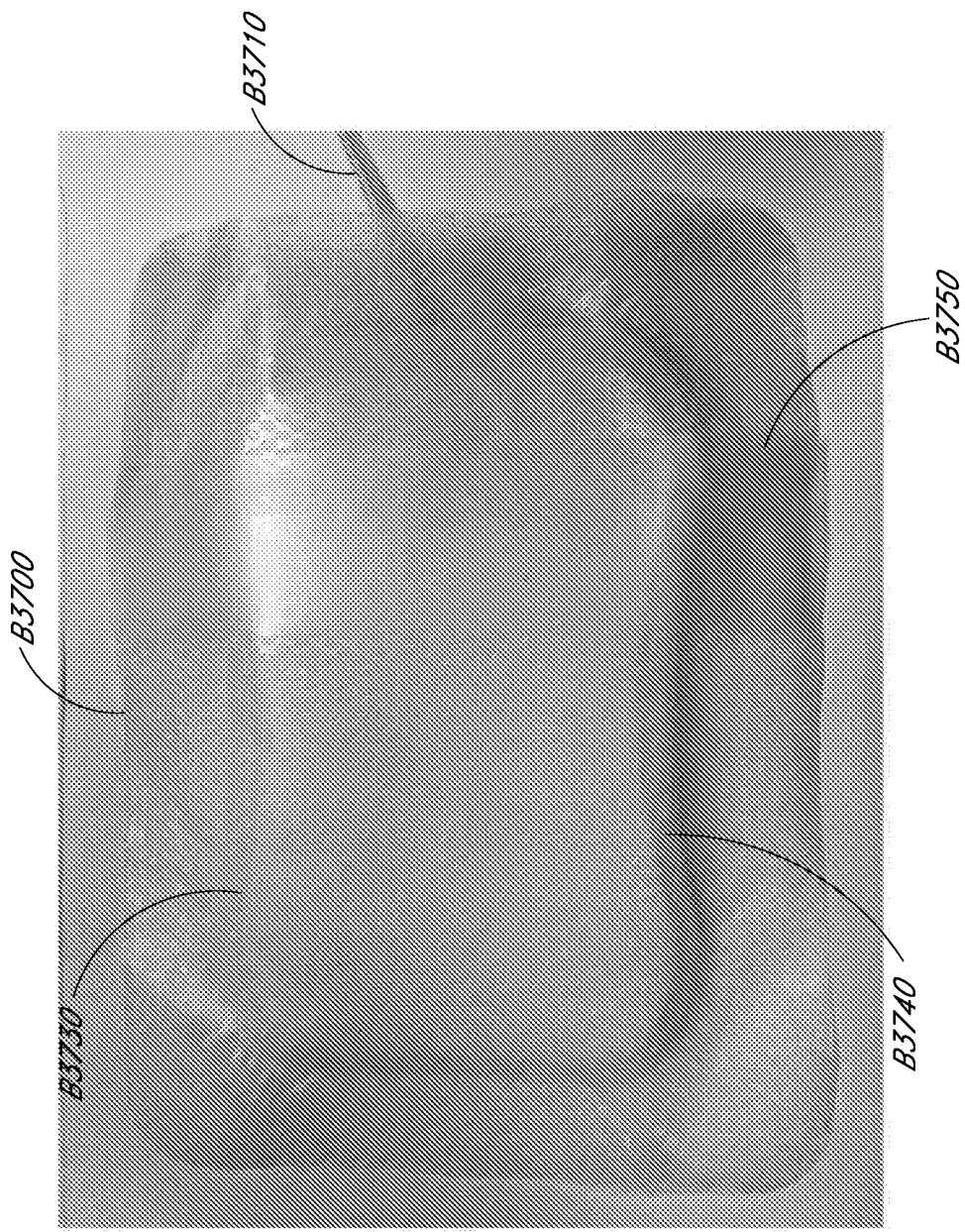

FIG. 255B illustrates a bottom view of the wound dressing of FIG. 255A.

Figure 256:
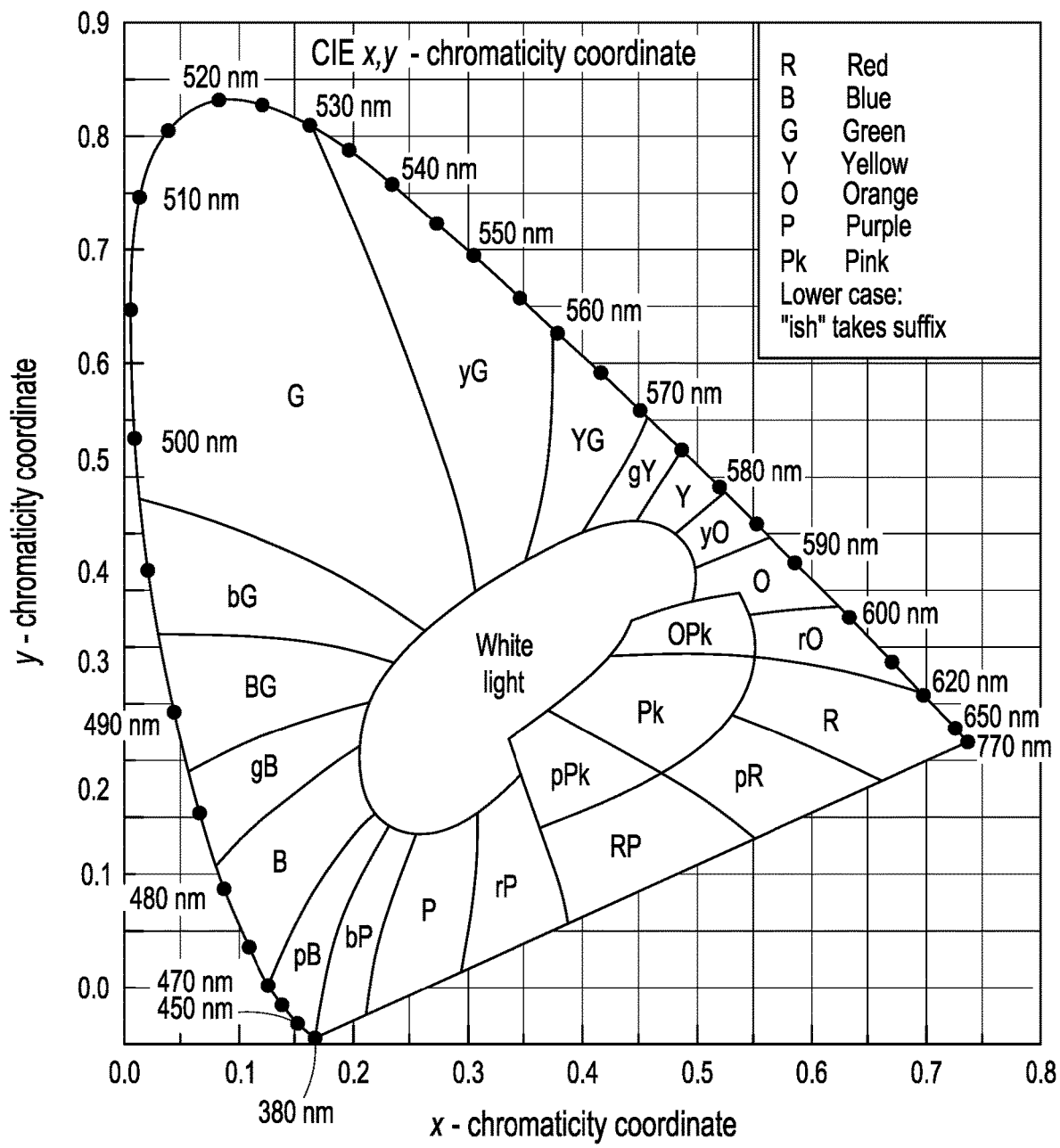

FIG. 256 illustrates a CIE chromacity scale.

Figure 257A:
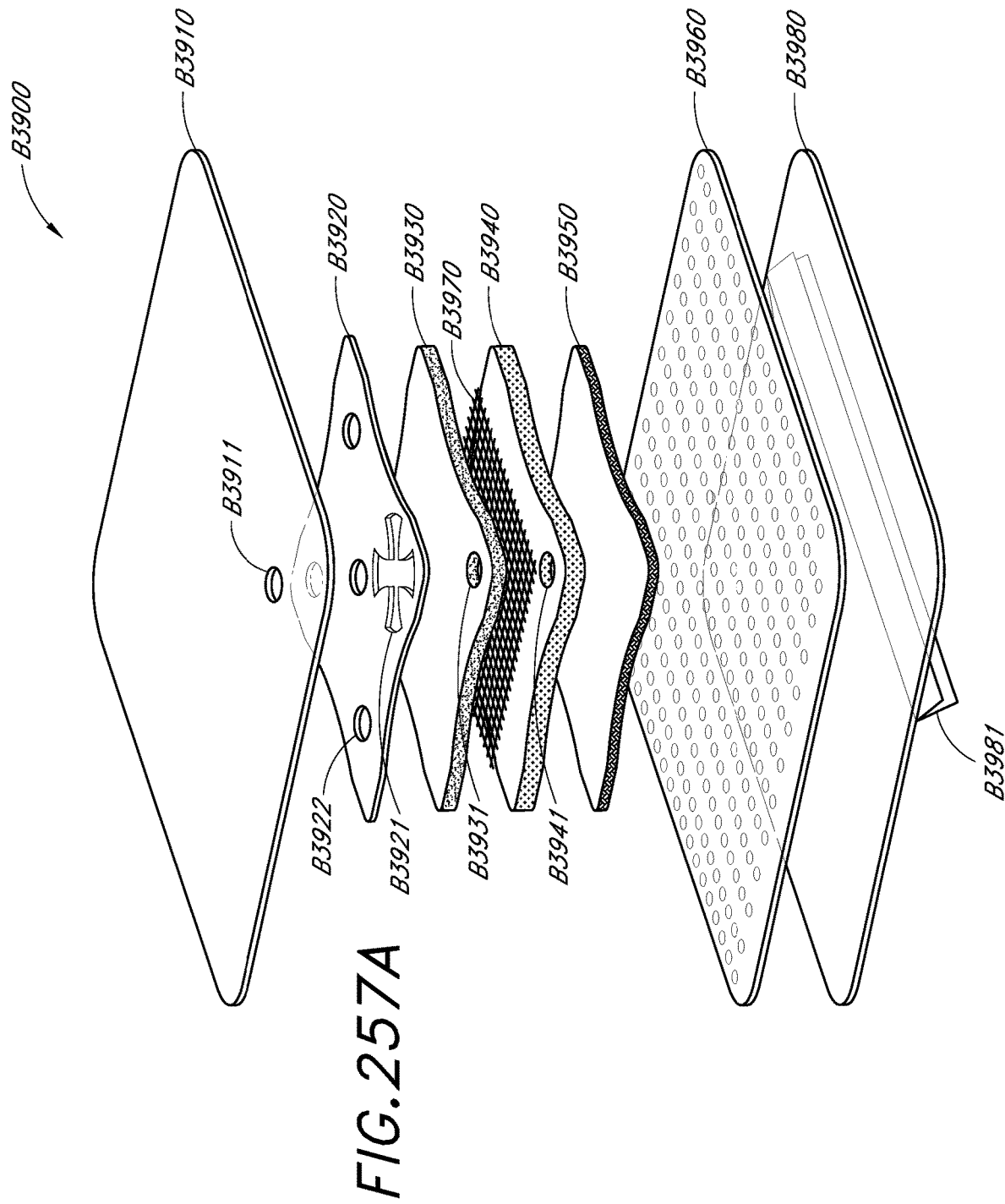

FIG. 257A illustrates an exploded view of another embodiment of a wound dressing.

Figure 257B:
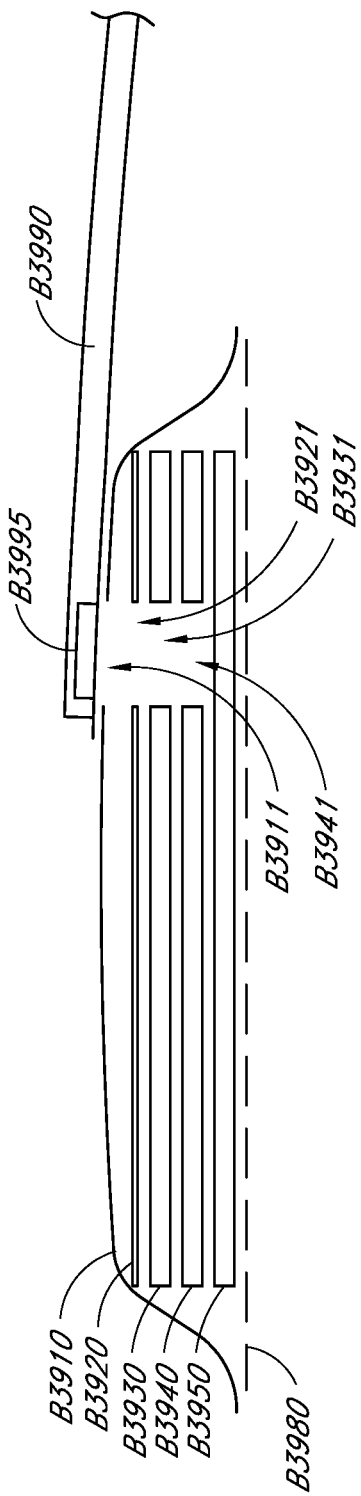

FIG. 257B illustrates a cross-sectional view of the wound dressing of FIG. 257A.

DETAILED DESCRIPTION OF SOME EMBODIMENTS

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In any embodiments disclosed herein, the components of the TNP system described herein can be particularly suited for incisional wounds that exude a small amount of wound exudate.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for any embodiments of the present disclosure can be approximately −80 mmHg, or between about −20 mmHg and −200 mmHg. Note that these pressures are relative to normal ambient atmospheric pressure thus, −200 mmHg would be about 560 mmHg in practical terms. In any embodiments disclosed herein, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even 150 mmHg, can be supplied by the negative pressure apparatus. Other details regarding the operation of the pump assembly are set forth in U.S. patent application Ser. No. 13/092,042, and such embodiments, configurations, details, and illustrations thereof are hereby incorporated by reference in their entireties as if made part of this disclosure.

Any of the embodiments disclosed herein can comprise a pump and/or a pump and dressing kit. However, the pump apparatuses and embodiments of the present disclosure are not limited to use with a dressing or for wound therapy. Any of the pump embodiments disclosed herein can be used independently of the dressing components disclosed herein. Further, any of the pump embodiments disclosed herein can be used, or can be adapted for use, for other purposes outside of negative pressure wound therapy. As such, any of the pump embodiments disclosed herein can be used, or can be adapted for use, to move fluids (gaseous and/or liquid) in any system or application.

Figure 1:
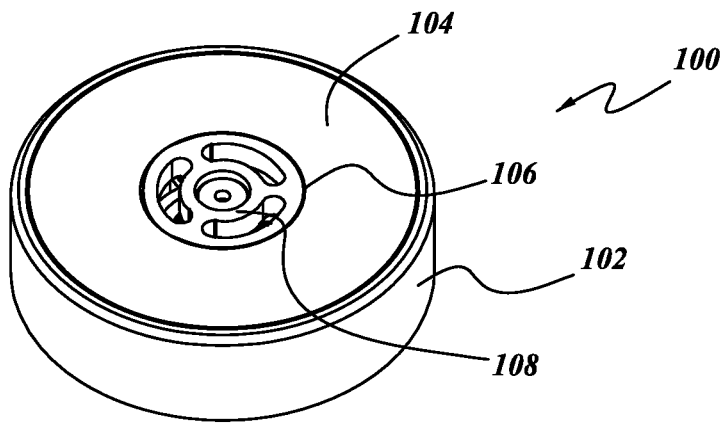
FIGS. 1 and 2 are isometric views of an embodiment of a pump assembly that can be used to move fluids, showing a top surface of the pump assembly.
Figure 2:
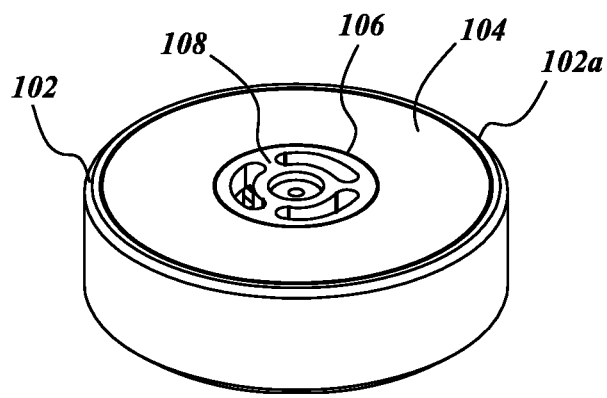
Figure 3:
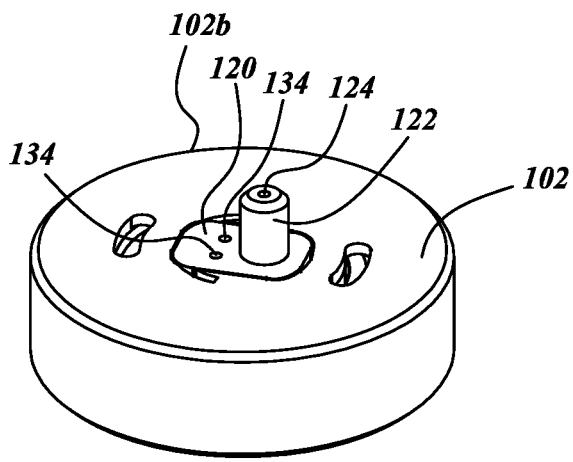
FIG. 3 is an isometric view of the pump assembly embodiment illustrated in FIG. 1, showing a bottom surface of the pump assembly.
Figure 4:
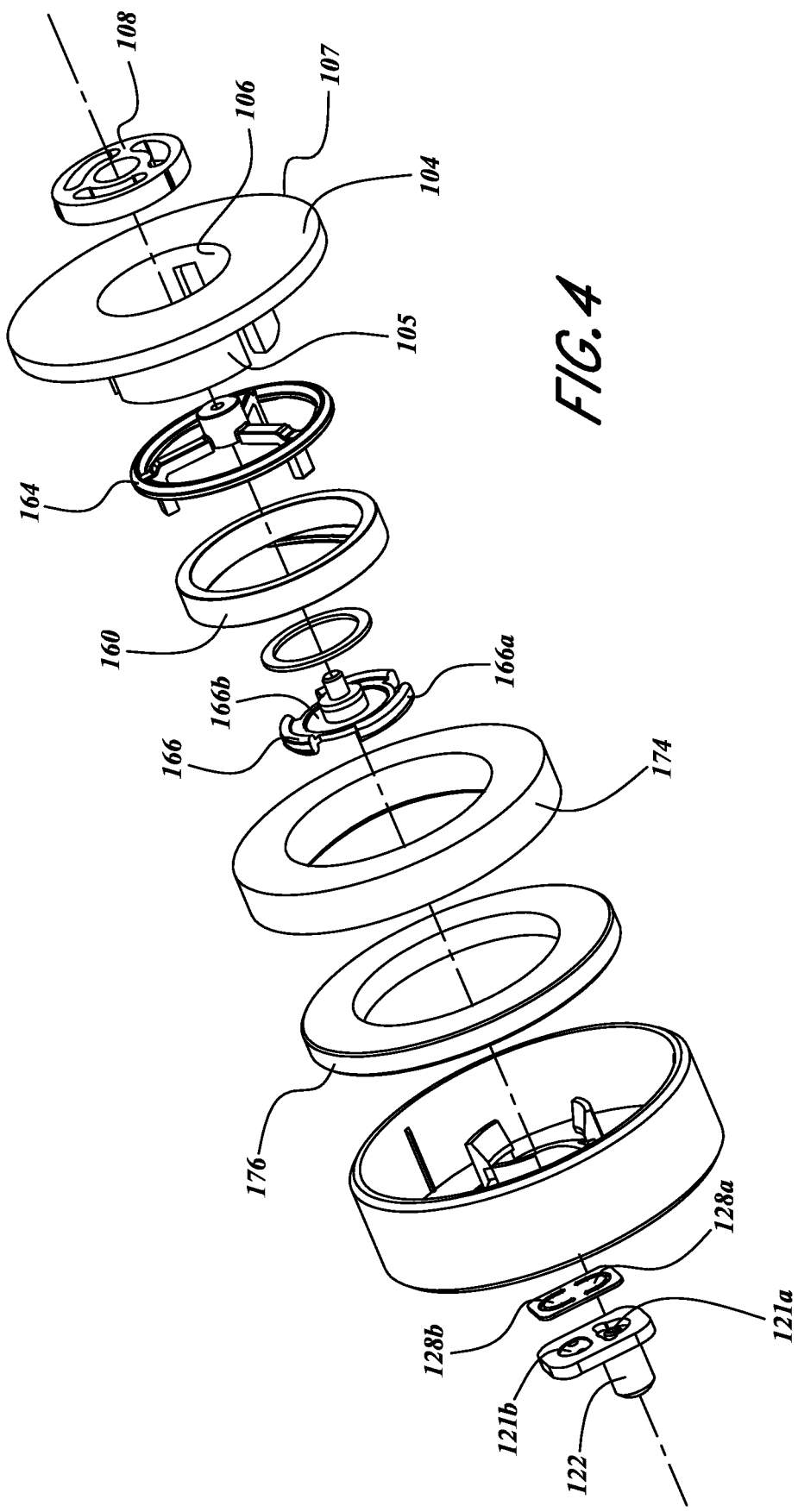
FIG. 4 is an exploded view of the pump assembly embodiment illustrated in FIG. 1.
Figure 5:
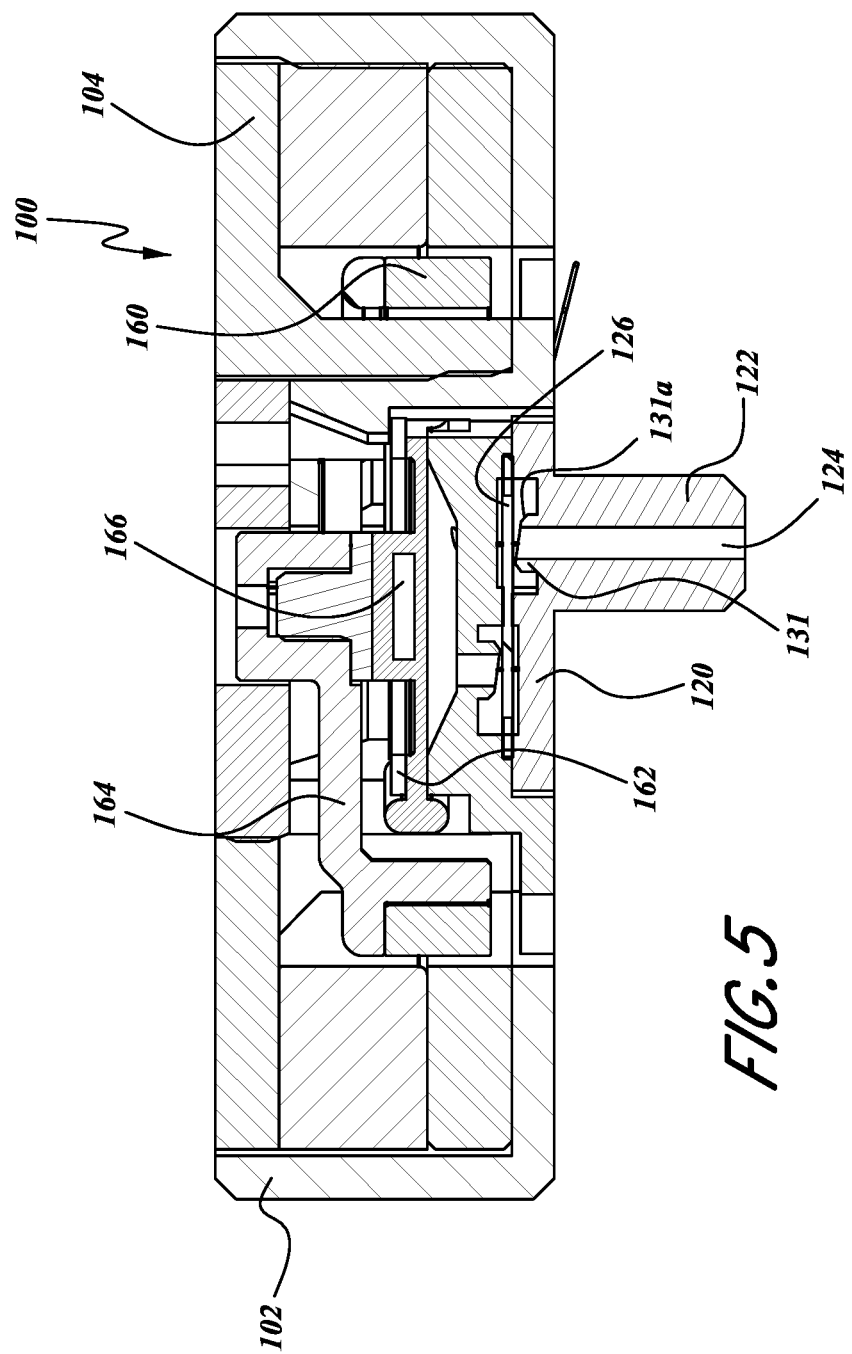
FIG. 5 is a section view of the pump assembly embodiment illustrated in FIG. 1, taken through the axial centerline of the pump assembly embodiment.

FIG. 1 is a scaled photograph of an embodiment of a pump assembly 100 that can be used to move fluids. FIGS. 2 and 3 are isometric views of the pump assembly embodiment illustrated in FIG. 1, showing a top surface of the pump assembly and the bottom surface of the pump assembly, respectively. FIGS. 4 and 5 are an exploded view and a section view of such pump assembly embodiment, the section view being taken through the axial centerline of the pump assembly embodiment.

The pump assembly embodiment 100 can have a compact, small size. In any embodiments disclosed herein, the pump assembly embodiment 100 can have a diameter or lateral size in the range of approximately 26 mm to approximately 27 mm, or between approximately 22 mm or smaller and approximately 28 mm. In any embodiments disclosed herein, the pump assembly embodiment 100 can have a thickness or height of approximately 8 mm, or from approximately 6 and approximately 10 mm. The pump assembly embodiment 100 can be any miniaturized size that is manufacturable, and the overall power output and efficiency meet the needed requirements for the desired application, within or outside of wound therapy. For example, in some pump assembly embodiments that may be suitable for applications requiring miniaturized pumps, the pump can have a diameter or lateral size of approximately 10 mm or less to approximately 15 mm, and a thickness or height of from approximately 3 mm and approximately 6 mm. The sizes and ranges listed herein can apply to any pump embodiment disclosed in this application. Only manufacturing technology limits the lower end of the size scale, although fluid power output and overall efficiency will decrease with decreasing size— but a smaller pump would still be useful in other applications.

As used herein, efficiency can be defined as (fluid power out)/(electrical power in). Additionally, as used herein, unless otherwise specified, the term approximately, as applied to measures of length, weight, time, efficiency rates, percentages, and other similar measures, is meant to refer to a range of plus or minus 15% of the stated value. This embodiment and arrangement of the pump assembly embodiment can be referred to as a "drum" type pump.

The pump assembly embodiment 100 can be produced for a low cost and can operate at high efficiencies, making it beneficial for portable, disposable, and/or single use applications. This pump can be used in an ultra-portable single-use negative-pressure wound therapy (NPWT) device. In any embodiments disclosed herein, the pump assembly embodiment 100 can run for a week on a small primary cell without the need for battery replacement or recharging. Any embodiments of the pump assembly can run up to a week on a 1200 mAh cell, assuming the pump is working for about 20% of the time. Any pump embodiments disclosed herein can be powered by two 1.5 volt, 1500 mAh batteries connected in parallel.

Any pump assembly embodiments disclosed herein can be configured to be capable of producing approximately 118 ml/min of fluid displacement for a power draw of 94 mW. The drive electronics can include a buck-boost convertor to supply a constant voltage from the battery, and a chip to both control the overall system logic and to generate the drive signal for the voice coil actuator (VCA), some pump embodiments disclosed herein will produce a battery life of approximately 7.04 days from the soft-pack $Li/MnO_2$, model CF502445.

In any embodiments disclosed herein, as mentioned, the pump assembly embodiment 100 can be used for negative pressure wound therapy. However, the pump assembly embodiment 100 is not limited to use in NPWT systems. The pump assembly embodiment can be adapted and configured for use in any reduced pressure system or in any system or application in which the movement of gaseous and liquid fluids is desired.

As an overview, the pump assembly embodiment 100 can be configured as a small diaphragm pump with passive valves (such as, but not limited to, flap valves) that can be driven by a VCA. The pump can be designed to work at pressures of 60-80 mm Hg, and can be configured to produce a flow rate of approximately 100 ml min-1, with a minimum efficiency of 15%, in order for the NPWT device to run for a week on a specified battery capacity. In any embodiments disclosed herein, the pump assembly embodiment 100 can be adapted to operate at efficiency levels in excess of 25%.

With reference to FIGS. 1-5, the pump assembly embodiment 100 can have a housing 102 adapted to support and protect many of the components of the pump assembly embodiment 100. An upper pole 104 can be supported at one end (for example, a first end) 102a of the housing 102. In any embodiments disclosed herein, the upper pole 104 can have an opening 106 formed through an axial centerline of the upper pole 104. A bearing 108 can be supported by the upper pole 104, within the opening 106. The bearing 108 or any other components disclosed in this application can be formed by stereolithography, selective laser sintering, molding, or by other suitable processes. Two or more electrical wires 114 can be connected to the pump assembly embodiment 100, configured to provide power to the pump assembly embodiment 100. In particular, the wires 114 can be used to provide electrical current to the coil of the pump assembly. The electrical wires 114 can be routed through one or more openings formed in the housing 102 or other components of the pump assembly embodiment 100.

The housing 102 can support a valve support member 120 at an end (for example, a second end 102b) of the housing 102. The valve support member 120 can support a boss member 122 that can receive a conduit therein or thereover, the boss member 122 having an opening 124 therethrough. The opening 124 can be in fluid communication with one or more passageways inside the pump assembly embodiment 100.

With reference to FIG. 4, the valve support member 120 can support one side of two valve chambers 121, a first inlet valve chamber 121a and a first outlet valve chamber 121b, which will be described in greater detail below. The valve support member 120 can support a flexible valve plate 126 having two flaps 128, one per chamber. The valve plate 126 can have a first flap 128a and a second flap 128b configured to deflect away from the relaxed position of the flaps 128 shown in FIGS. 4-5. In any embodiments disclosed herein, the valve plate 126 and flaps 128, or any other valve plate or flap embodiment disclosed herein, can be formed from a silicone rubber. Any of the valve plate embodiments disclosed in relation to any pump embodiment disclosed herein (meaning, anywhere within this application) can be formed, print-cut, or dye cut from silicone sheet material, or cast or molded from silicone or other suitable materials, molded, machined, or otherwise formed from plastic, aluminum, metal, or any composite material, and can have any of the following shore hardness values: 20 A, 40 A, 50 A, 60 A and 80 A. Any of the flap valves disclosed herein can have one or more score lines therein to improve flexibility and bendability of the deflectable portion of the flap valve.

Figure 6:
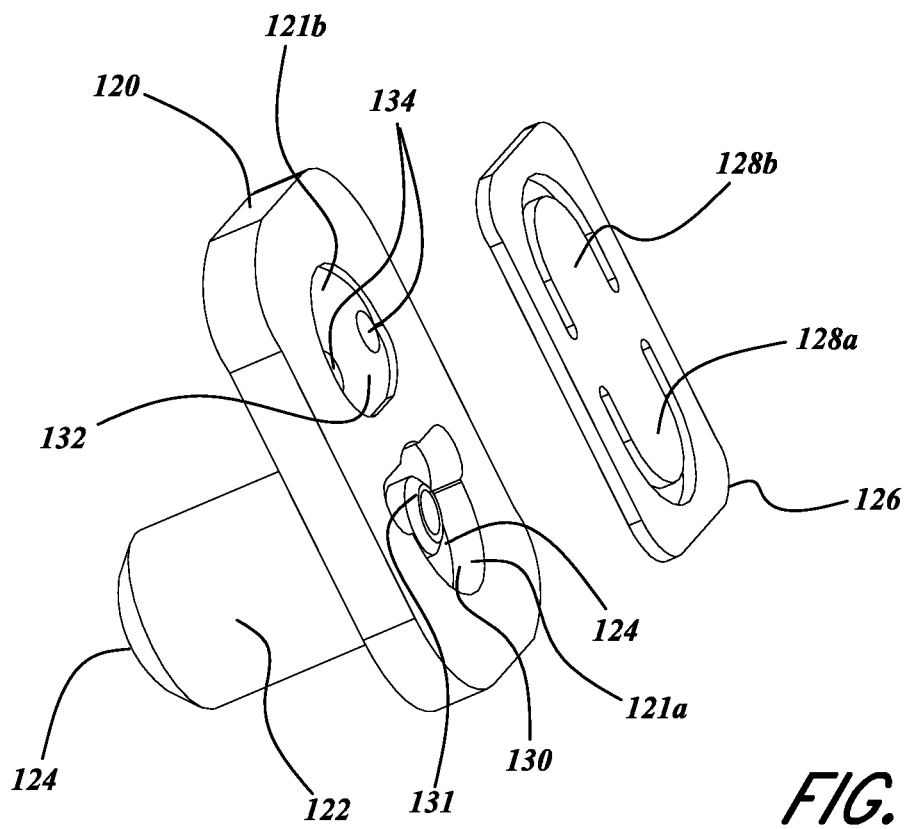
FIG. 6 is an isometric view of the valve support member and the valve plate of the pump assembly embodiment illustrated in FIG. 1.
Figure 7:
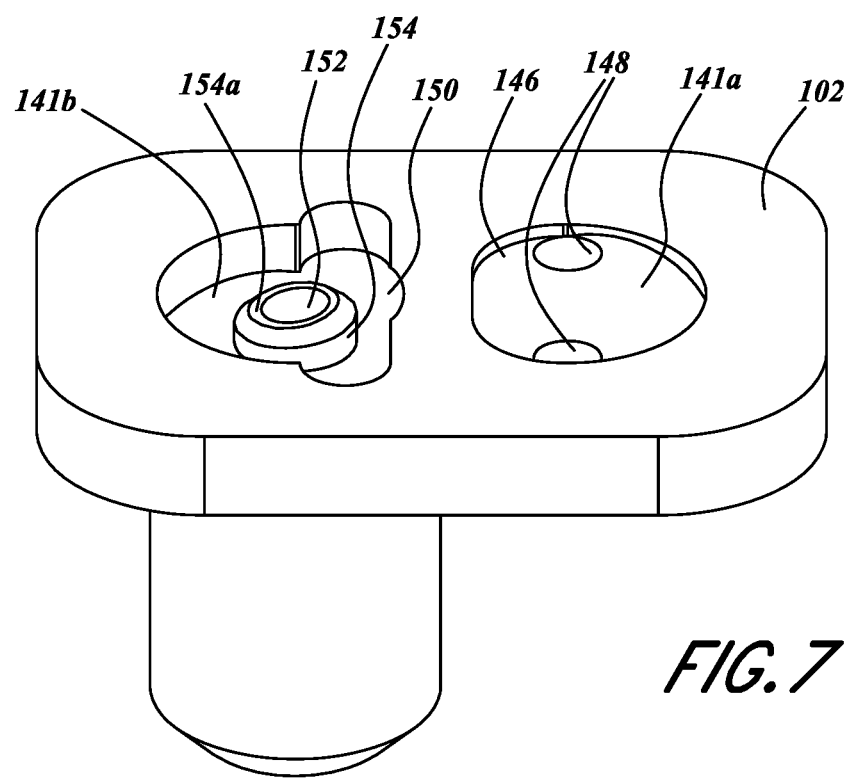
FIG. 7 is an isometric view of a second half or portion of a valve housing that could be formed on the housing, to complete the valve chamber.

FIG. 6 is an isometric view of the valve support member 120 and the valve plate 126 of the embodiment of the pump assembly embodiment 100 illustrated in FIG. 1. FIG. 7 is an isometric view of a second half or portion of a valve housing that could be formed on the housing 102, to complete the valve chamber.

With reference to FIG. 6, the first inlet valve chamber 121a of the valve support member 120 can have a cavity or depression 130 and one or more openings, such as opening 124 in communication with the depression 130 to permit the passage of air from a conduit connected to the boss 122 into the pump assembly embodiment 100 when the flap valve 128a is in an open position (for example, not sealingly covering the opening 124). A boss 131 can be formed within the depression 130 surrounding the opening 124 to provide a sealing surface for the valve flap 128 to selectively seal the opening 124. In any embodiments disclosed herein, the boss 131 can have an angled or curved surface 131a (as shown in FIG. 5) configured to substantially match the profile of the valve flap 128a as the valve flap 128a is deflected from its relaxed position to a position against the surface of the boss 131. This arrangement can improve the seal between the valve flap 128a and the boss 131 to increase the efficiency of the pump assembly embodiment 100.

As shown in FIG. 6, the first outlet valve chamber 121b can have a cavity or depression 132 and one or more openings 134 configured to allow the passage or exit of air from the inside of the depression 132 and the pump assembly embodiment 100 when the valve flap 128b is in an open position. In the embodiment shown in FIG. 6, the valve support member 120 has two openings 134 formed in the first outlet valve chamber 121b.

The housing 102 can have a similar arrangement of inlet and outlet valve chambers as compared to the first inlet and outlet valve chambers 121a, 121b.

With reference to FIG. 7, a second inlet valve chamber 141a supported or defined by the housing 102 can have a cavity or depression 146 and one or more openings 148 in communication with the depression 146 to permit the passage of air from the first inlet valve chamber 121a into the second inlet valve chamber 146 when the valve flap 128a is in an open position. One or more openings 148 (two being shown) can be formed in the second inlet valve chamber 141a to permit air to pass from the second inlet valve chamber 146 into the inside of the pump assembly embodiment 100. In any of the pump embodiments disclosed herein, the inlet valve chamber and/or the outlet valve chamber, on either side of the flap valve, can have one, two, three, ore more openings configured to permit air to pass therethrough.

Similarly, a second outlet valve chamber 141b can be supported or defined by the housing 102. The second outlet valve chamber 141b can have a depression 150 formed therein and an opening 152 in communication with the second outlet valve chamber 141b. A boss 154 can be formed within the depression 150 surrounding the opening 152 to provide a sealing surface for the valve flap 128b to selectively seal the opening 152. In any embodiments disclosed herein, similar to the boss 131, the boss 152 can have an angled or curved surface 154a configured to substantially match the profile of the valve flap 128b as the valve flap 128b is deflected from its relaxed position to a position against the surface of the boss 154a. This arrangement can improve the seal between the valve flap 128b and the boss 1154 to increase the efficiency of the pump assembly embodiment 100. When the valve flap 128b is in an open position, air or other fluid within the pump assembly embodiment 100 can pass through the opening 152 into the first outlet valve chamber 121b and exit the pump assembly embodiment 100 through the one or more openings 134.

In any embodiments disclosed herein, valve flaps 128a, 128b can be configured to be unstressed in a neutral position, neither fully open nor fully closed. Therefore, rather than there being a 'cracking pressure' required to open them, In any embodiments disclosed herein, a small back-pressure (e.g., approx. 30 mbar or more) can be used to hold valve flaps 128a, 128b closed. This can improve efficiency by reducing the pressure force that must be generated by the VCA during the suction stroke. The configuration of the pump assembly embodiment 100 can eliminate or reduce the need for a check valve or other one-way flow restrictor. In any of the embodiments disclosed herein, the valve flaps can operate at a frequency in the range of approximately 120 to approximately 150 Hz.

With reference again to FIG. 4, the pump assembly embodiment 100 can have a coil 160, a retainer 162, and a support 164. The support member 164 or any other components disclosed in this application can be formed by stereolithography, selective laser sintering, molding, or by other suitable processes. The coil 160 can be formed from a length of wound conductive wire, such as without limitation copper wire or amethyst. In any embodiments disclosed herein, the coil 160 or any coil disclosed herein can be formed by winding approximately 160 turns of wire, or from approximately 100 turns or less to 200 turns or more of wire, which can be but is not required to be, 42 gauge (approximately 0.102 mm diameter) wire. The wire used can be self-bonding wire that bonds to adjacent sections of wire upon application of heat. The wire can also be non-self-bonding wire. In any embodiments disclosed herein, approximately 200 turns of wire, or up to approximately 260 turns of wire, can be used to form the coil. Increasing the number of turns of wire In any embodiments disclosed herein of the pump assembly could reduce ohmic losses and could improve the overall efficiency of the pump by between approximately 22% and approximately 24%. As the number of turns of wire is increased, thereby increasing the efficiency of the pump, the size or thickness of the magnet can be decreased, thereby reducing the magnetic field outside of the pump that can potentially interfere with the function of pacemakers and other implanted cardiac devices (ICDs). It was generally determined during experimentation that increasing the number of turns of wire increased the suction stroke and improved the flow rate of the pump assembly.

In operation, the coil 160 is configured to move within a magnetic circuit, and is connected or supported via the support member 164 to a pump diaphragm assembly 166. The diaphragm 166 can be supported and/or fixed at its peripheral portion 166a, wherein an interior portion 166b of the diaphragm assembly 166 is permitted to flex and deflect in either direction away from the relaxed position of the diaphragm assembly 166. In any embodiments disclosed herein, the diaphragm can be clamped and compressed between two rigid surfaces to provide such support. The rigid surfaces can define an annular shape. For example, any embodiments of the diaphragm 166 (or any other diaphragm disclosed herein) can have a moulding and a separate compression ring (made from a rigid plastic, aluminium or other metal, or any other suitable material or composite material). Additionally, any embodiments of the diaphragm 166 (or any other diaphragm disclosed herein) can have one plastic or other frame or moulding on each side of the flexible diaphragm membrane. The mouldings and the flexible diaphragm membrane can be held together with adhesive, mechanical connections between the mouldings, ultrasonically welding, or by any other suitable method. In any embodiments disclosed herein, the diaphragm can have a single frame or moulding having a channel therein configured to receive and support a peripheral edge of the flexible diaphragm membrane. Additionally, In any embodiments disclosed herein, the diaphragm 166 can be sealed at its outer perimeter 166a. The diaphragm assembly 166 is configured to elastically return the coil 160 to its relaxed position.

The configuration of the pump assembly embodiment 100 can be similar to that used in low fidelity loudspeakers, which fit a significant amount of magnetic material into a very compact space. With reference to the figures, the pump assembly embodiment 100 can have a magnet 174 positioned between a lower pole 176 and the upper pole 104. In any embodiments disclosed herein, the magnet 174 can be made from sintered Neodymium-Iron-Boron (NdFeB), Neodymium N33, or any other suitable material. This material can be used to maximize field strength and minimize losses, thereby increasing the efficiency of the pump assembly embodiment 100. However, In any embodiments disclosed herein, the magnet 174 can be formed from any suitable magnetic material.

Any of the magnets in any of the embodiments disclosed herein can have any suitable thickness and size, which can depend on the size of one or more of the other components of the pump assembly. For example, In any embodiments disclosed herein, the magnet 174 can have an approximately 25.65 mm outer diameter, an approximately 15 mm inner diameter, and be approximately 6 mm thick. Further, the magnet 174 of any embodiments can have an approximately 25.65 mm outer diameter, an approximately 17 mm inner diameter, and be approximately 3.5 mm thick. The thickness of the magnet In any embodiments disclosed herein can be as small as 2.5 mm.

Additionally, in any embodiments disclosed herein, the upper pole 104 can have a body portion 105 extending away from a planar portion 107 of the upper pole 104. With reference to the cross-sectional view in FIG. 7, the body portion 105 can extend in an axial direction through an axial opening formed in the coil 160, the magnet 174, and the lower pole 176. As will be described in greater detail below, in any embodiments, the body portion can improve the magnetic field of the voice coil actuator and improve the efficiency of the voice coil pump.

Additionally, In any embodiments disclosed herein, shielding components or materials configured to attenuate the magnetic field outside of the pump assembly can be used. For example, materials with very high nickel content (for example, from 50-80%) can be used for magnetic shielding. MuMetal is one material that can be used for this purpose.

Figure 8A:
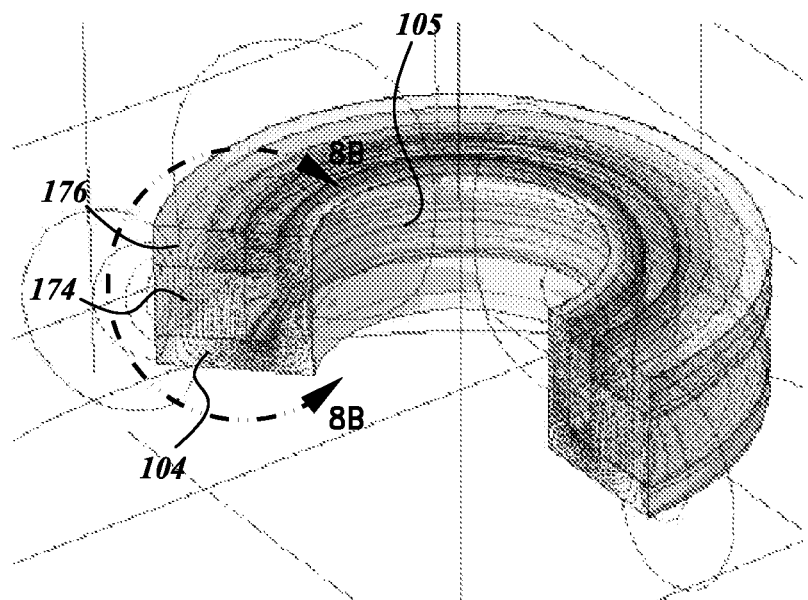
FIG. 8A illustrates one arrangement of a magnetic circuit of the pump assembly embodiment illustrated in FIG. 1.
Figure 8B:
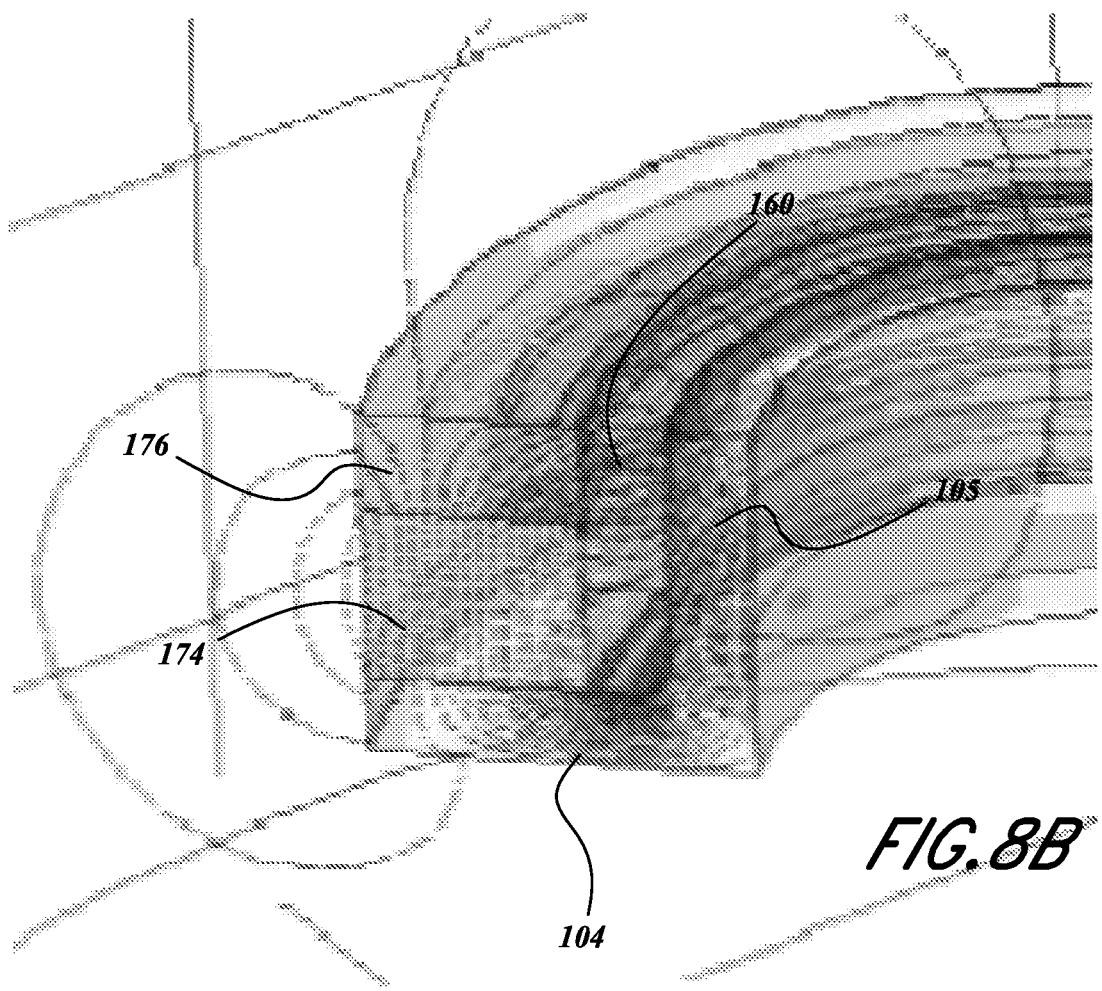
FIG. 8B is an enlarged view of a portion of the arrangement of the magnetic circuit illustrated in FIG. 8A.

One arrangement of a magnetic circuit is shown in FIG. 8. FIG. 8 is a partial cut-away of the an arrangement of a magnetic circuit, with contours of simulated radial magnetic field strength.

Strong magnetic fields can disrupt the function of pacemakers and other ICDs. Boston Scientific, a pacemaker manufacturer, states that 10 Gauss (G) is the maximum safe field that will not interfere with pacemakers. (Boston Scientific, *Portable media players and implantable pacemakers and defibrillators*, http://www.bostonscientific.com/templatedata/imports/HTML/CRM/A_Closer_Look/pdfs/ACL_Portable_MultiMedia_Players_030609.pdf, March 2009). Medtronic, another manufacturer, state that 5 G is the safe field. One paper states that a magnetic field strength of 5-10 G at the pacemaker or ICD has the potential to interact with the device. S. Lee, B. Ransford, K. Fu, K. Tadayoshi, and W. H. Maisel, *Electromagnetic interference (EMI) of implanted cardiac devices by MP3 player headphones*, American Heart Association's Scientific Sessions 2008. A fact sheet from the Swiss Federal Office of Public Health (http://www.bag.admin.ch/themen/strahlung/00053/00673/05059/index.html?lang=en) states that modern devices are immune to static fields of up to 10 G, but that older devices with a lower immunity threshold (5-10 G) are still in use.

The thin drum prototype described in greater detail below was measured to have a field strength of approximately 0.7 kG at the surface, dropping to 5 G at a distance of around 55 mm, as measured with a Gauss meter. In its current state, therefore, the pump should not be used within this distance from a pacemaker. If this distance can be reduced significantly (to, e.g., under 1 inch), that would be beneficial.

The arrangement of the pump assembly embodiment 100 can be configured to differ from a typical low fidelity loudspeaker. For example, some embodiments of the pump assembly 100 can differ in the following ways. In the pump assembly embodiment 100, the coil 160 can be configured to underhang below the end of the magnetic circuit. For example, the coil 160 can be configured such that it does not extend above the magnetic circuit. This can improve the efficiency and reduce the overall height of the pump assembly embodiment 100, but can result in the degradation of the linearity of response of the pump assembly embodiment 100.

The coil 160 can have a relatively high number of turns. For example, any coil embodiments disclosed herein, including but not limited to coils 160 and 260 (described below), can have approximately 100 or more turns of wire (which can be copper), or less than 100 turns or wire, or between approximately 100 turns and approximately 160 turns of wire. Some embodiments can fit into the space left by the magnetic circuit, based on available or practical wire thicknesses. Generally, the electrical efficiency of the pump assembly will be increased as the number of turns is increased. In any embodiments disclosed herein, the density of the copper can be maximized for the available space, or per unit volume of copper wire in the coil. In any of the embodiments described herein, the wire used for the coil can have a round, flat, square, rectangular, or diamond cross-section. The non-circular cross section shaped wire can result in a more dense copper wire packing and higher electrical efficiency.

Having a relatively high number of turns can give the coil 160 greater structural rigidity and, as mentioned, can maximize the efficiency of the pump assembly embodiment 100. Having a relatively high number of turns in the coil 160 can also limit the frequency of oscillation. The impact of limiting the frequency of oscillation should not affect the performance of the pump assembly embodiment 100 because, In any embodiments disclosed herein, the operating frequency of the pump assembly embodiment 100 can be limited by the responsiveness of the valves, for example, by the responsiveness of the valve flaps 128*a*, 128*b*.

Additionally, the pump assembly embodiment 100 will not have a speaker cone that is typically in a low fidelity speaker, which normally serves to control coil motion. In the pump assembly embodiment 100, the diaphragm can be used to center the coil 160, and a linear bearing 108 can be used to limit any wobble of the coil 160 by controlling the movement of the support member 164.

The housing 102, support 114, valve support member 120, retainer 162, and/or support member 164 can be made of a plastic or hard rubber material, metal, or any other suitable material or combination of materials. Such components can be formed by any suitable methods such as casting, any molding process such as injection molding, forging, sintering, machining, or any other suitable process.

Figure 105:
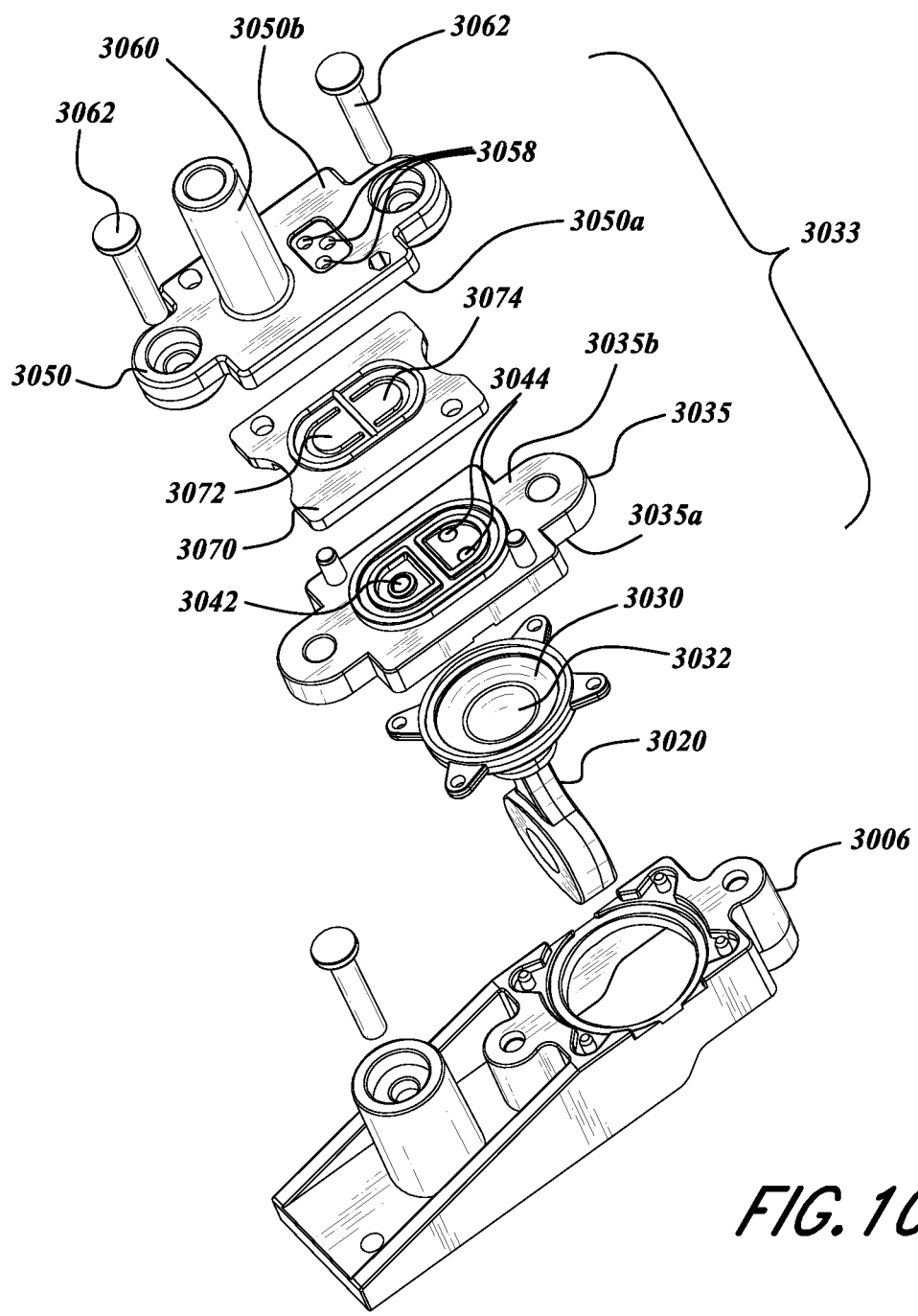
FIG. 105 is an exploded view of some components of the pump assembly embodiment shown in FIG. 99.
Figure 106:
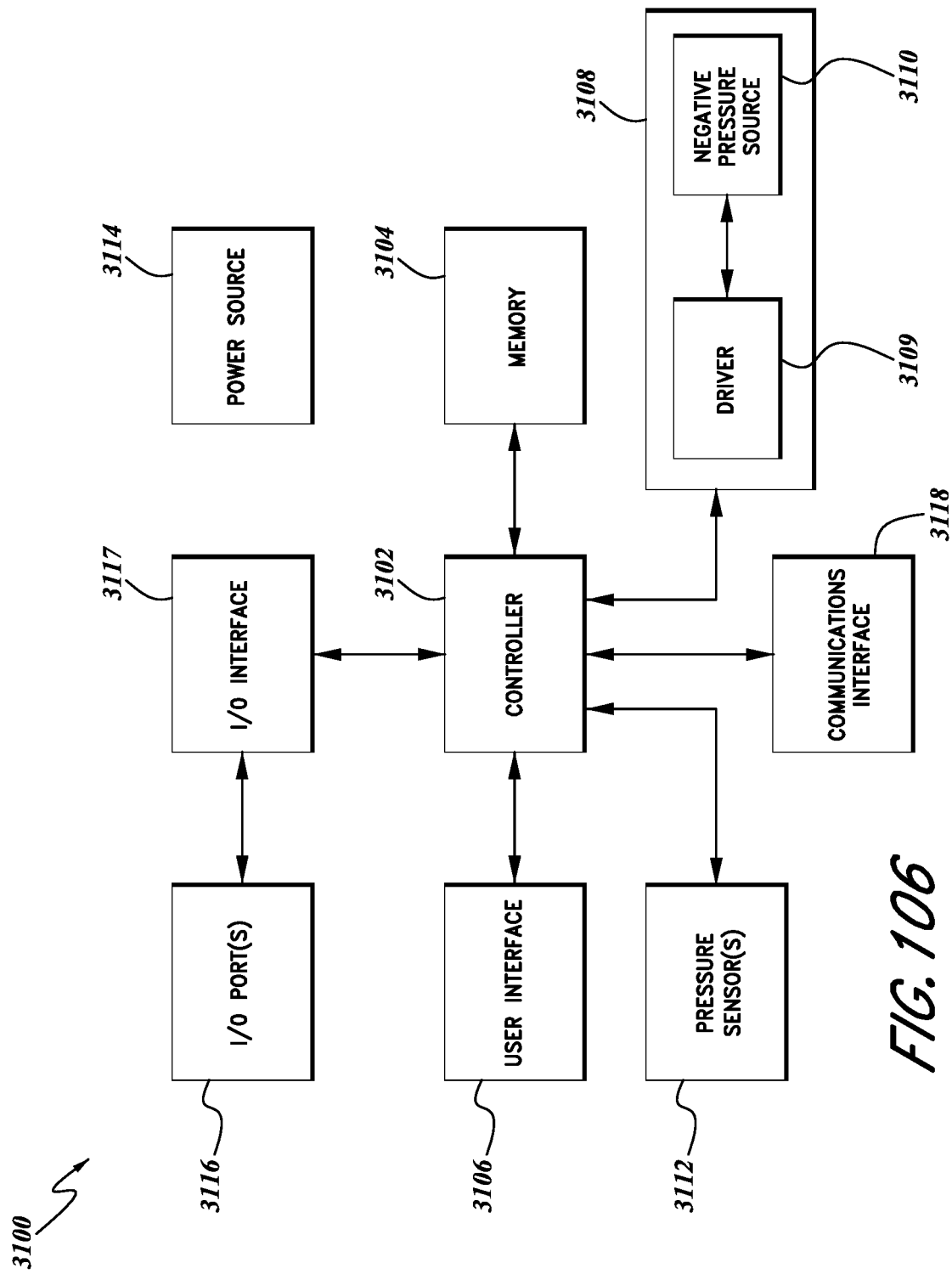
FIG. 106 is an electrical component schematic of an embodiment of a pump assembly.
Figure 107:
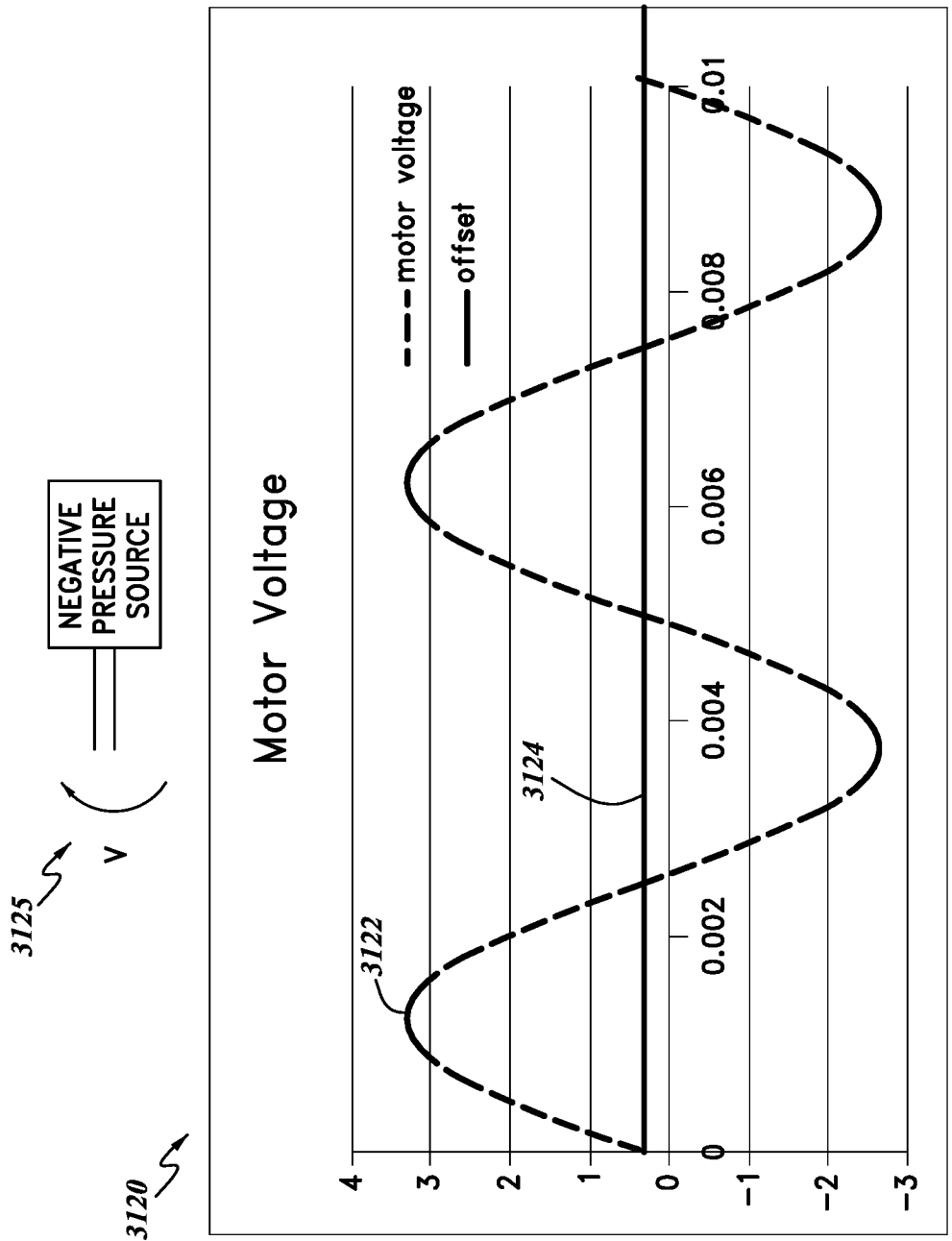
FIGS. 107-110 illustrate sinusoidal waveforms for driving a diaphragm according to some embodiments.
Figure 108:
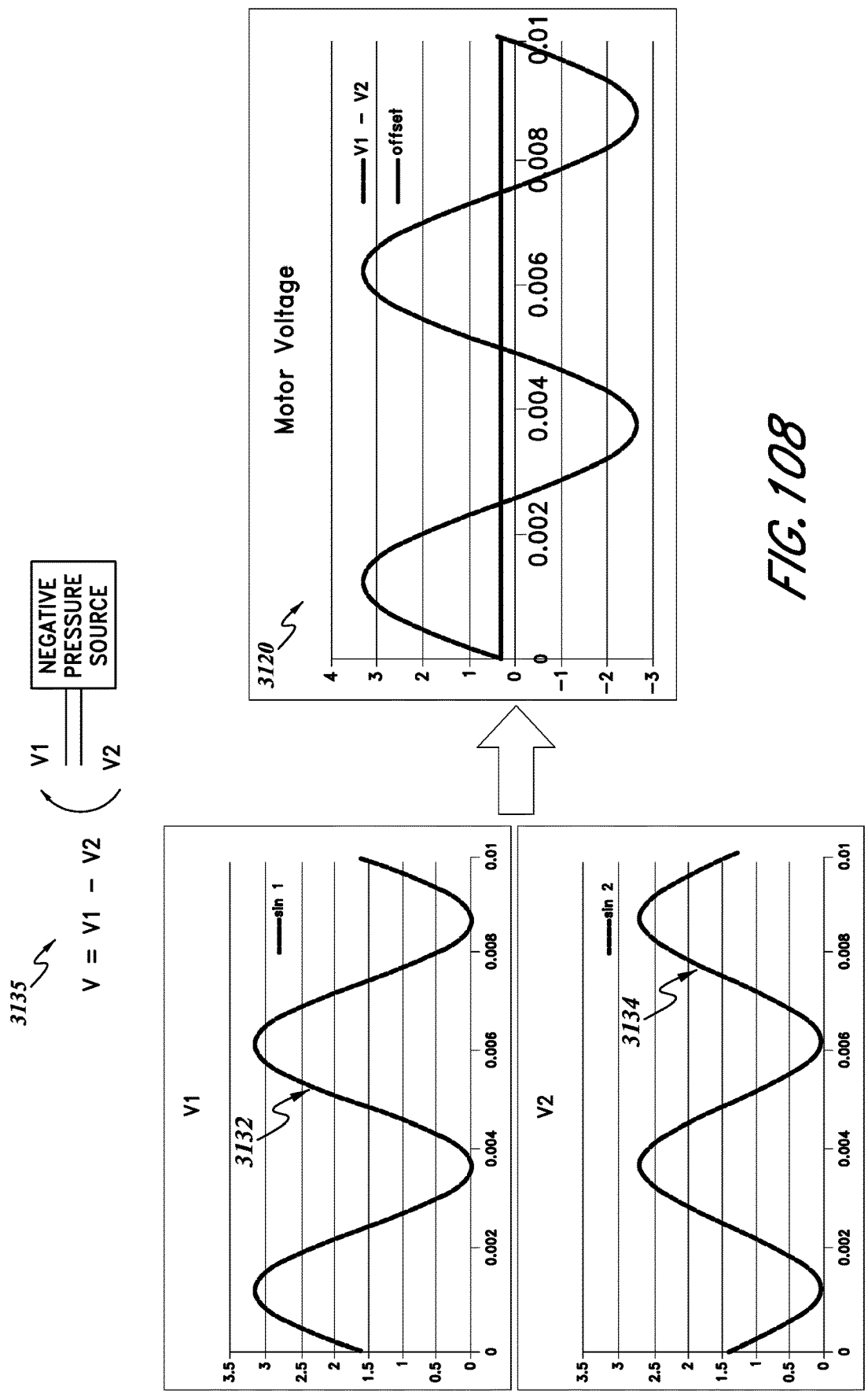
Figure 109:
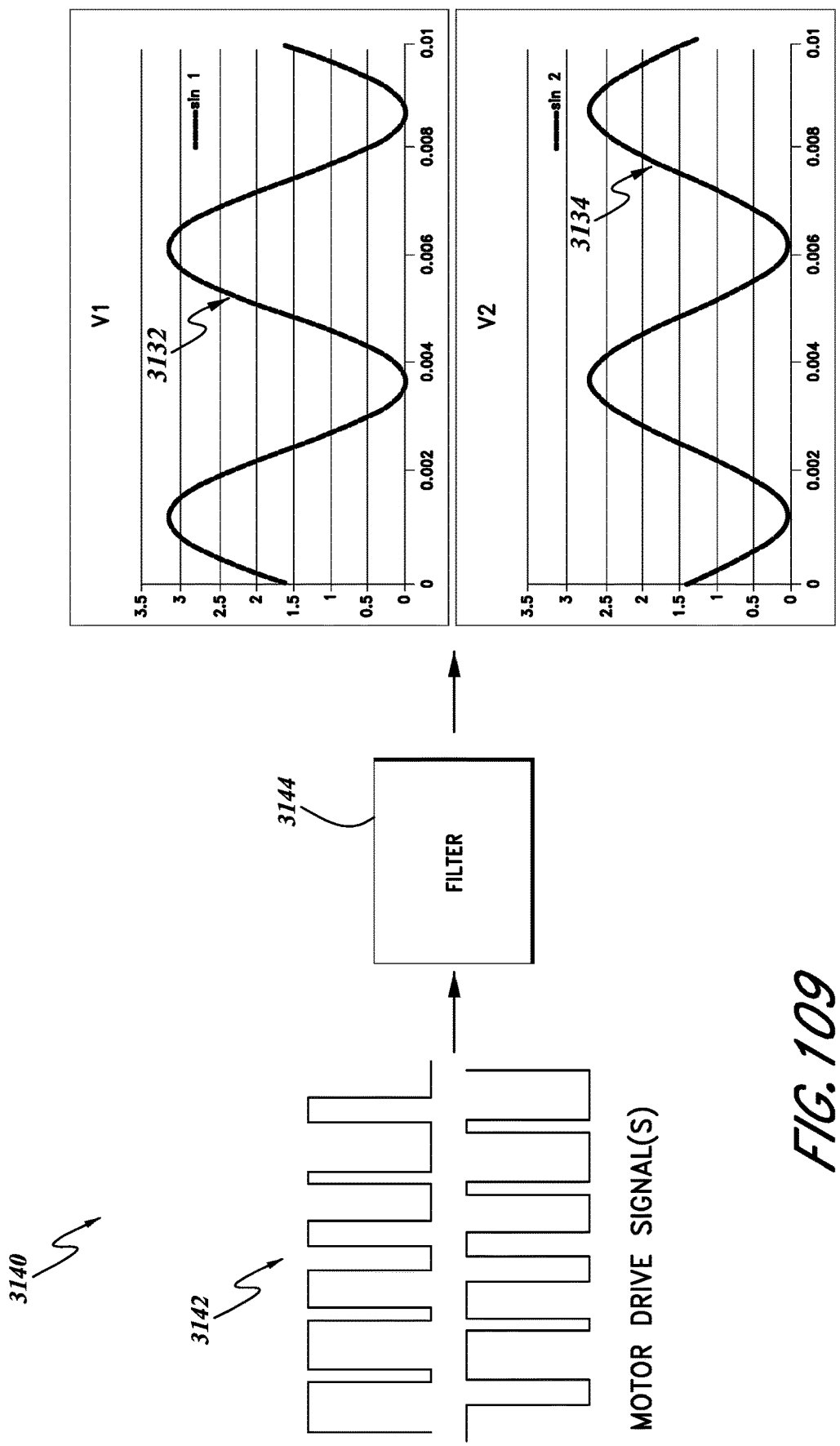
Figure 110:
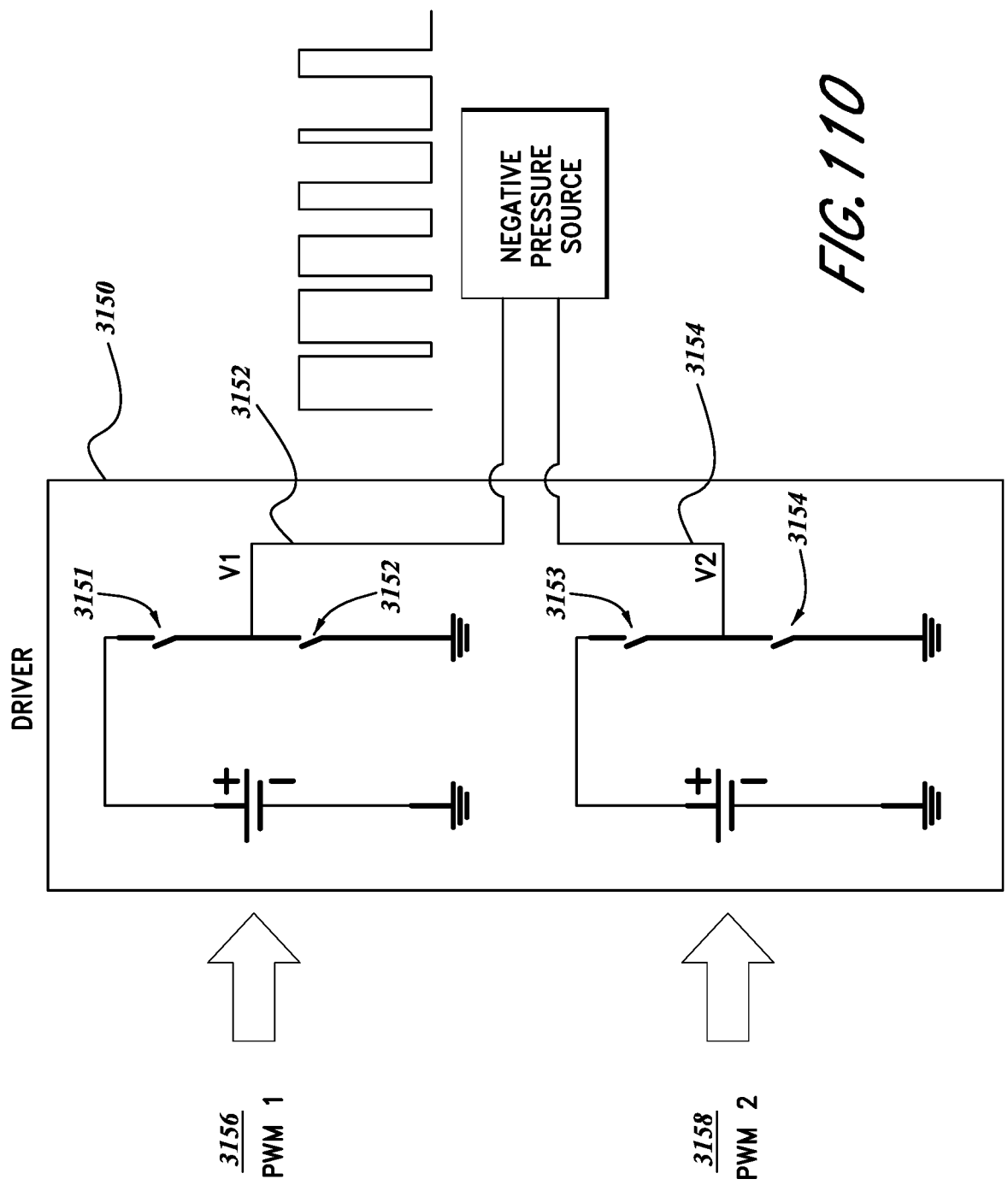
Figure 111:
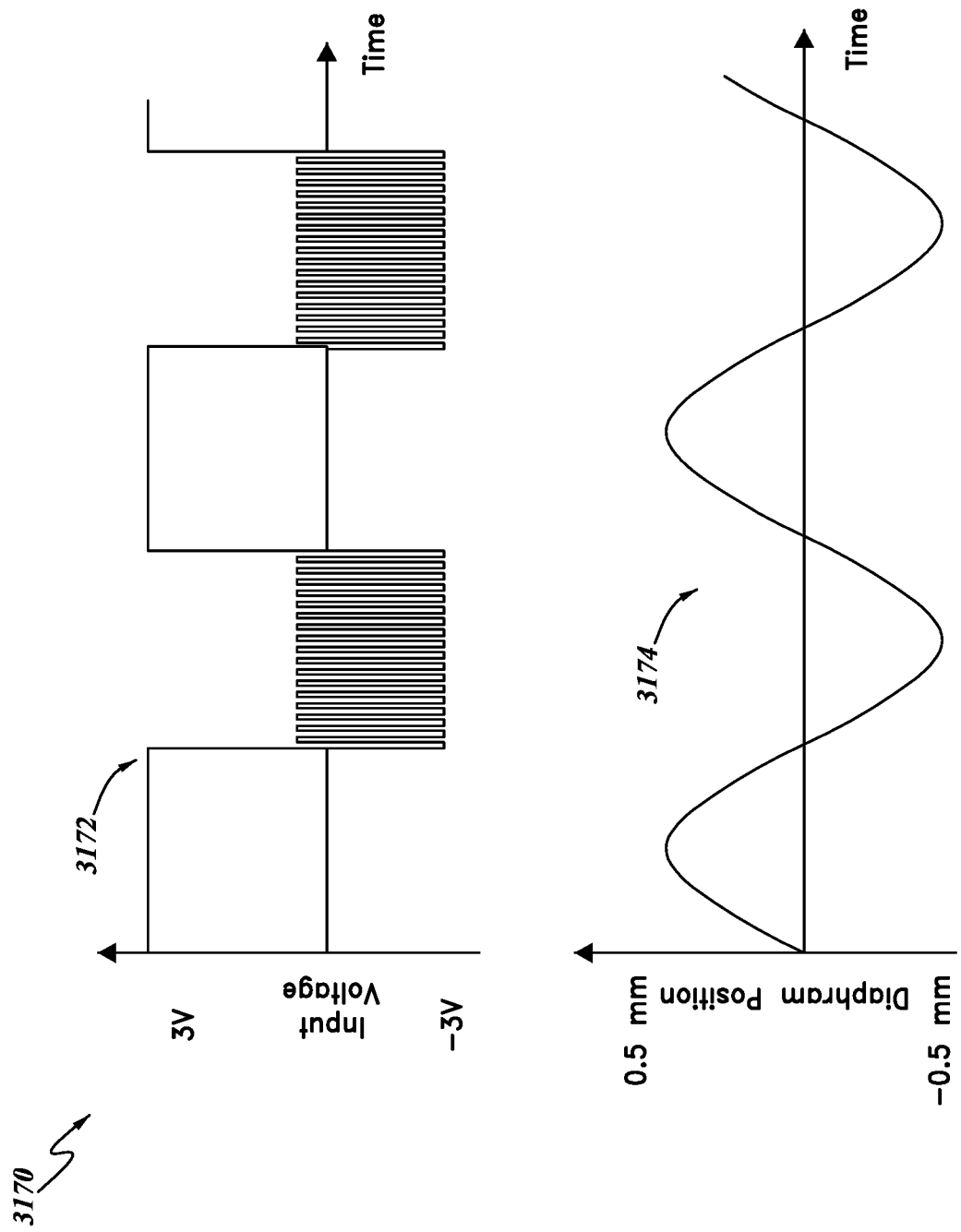
FIG. 111 illustrates a position of a diaphragm according to an embodiment of a pump assembly.
Figure 112:
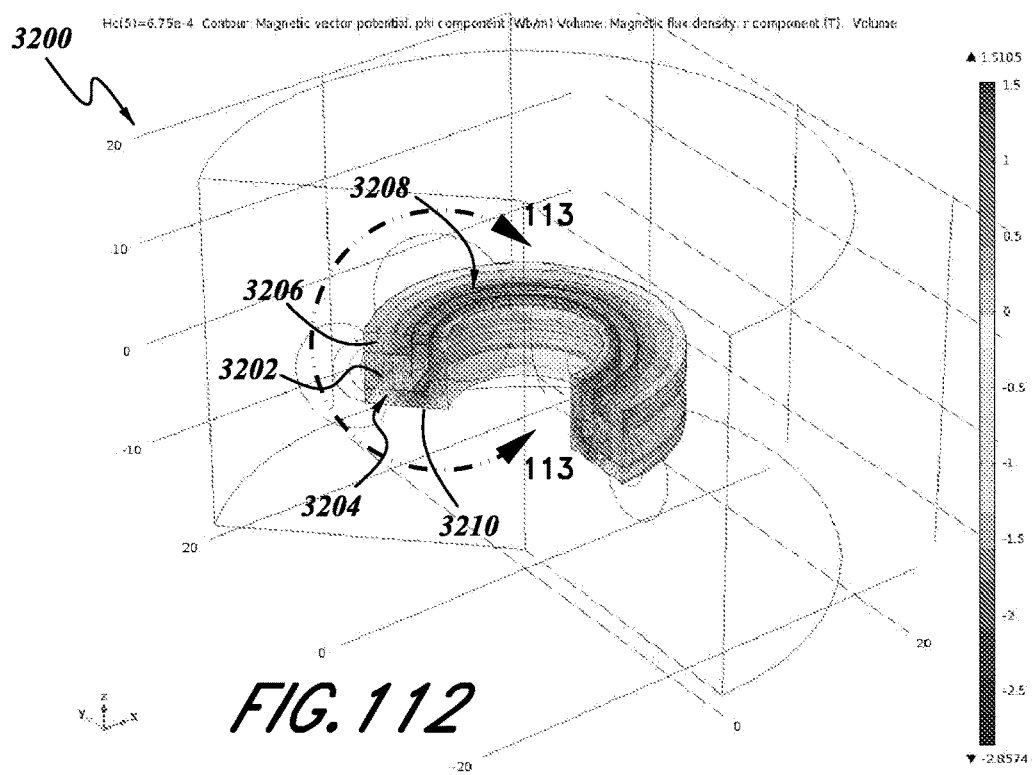
FIG. 112 illustrates another arrangement of a magnetic circuit of the pump assembly embodiment illustrated in FIG. 1.
Figure 113:
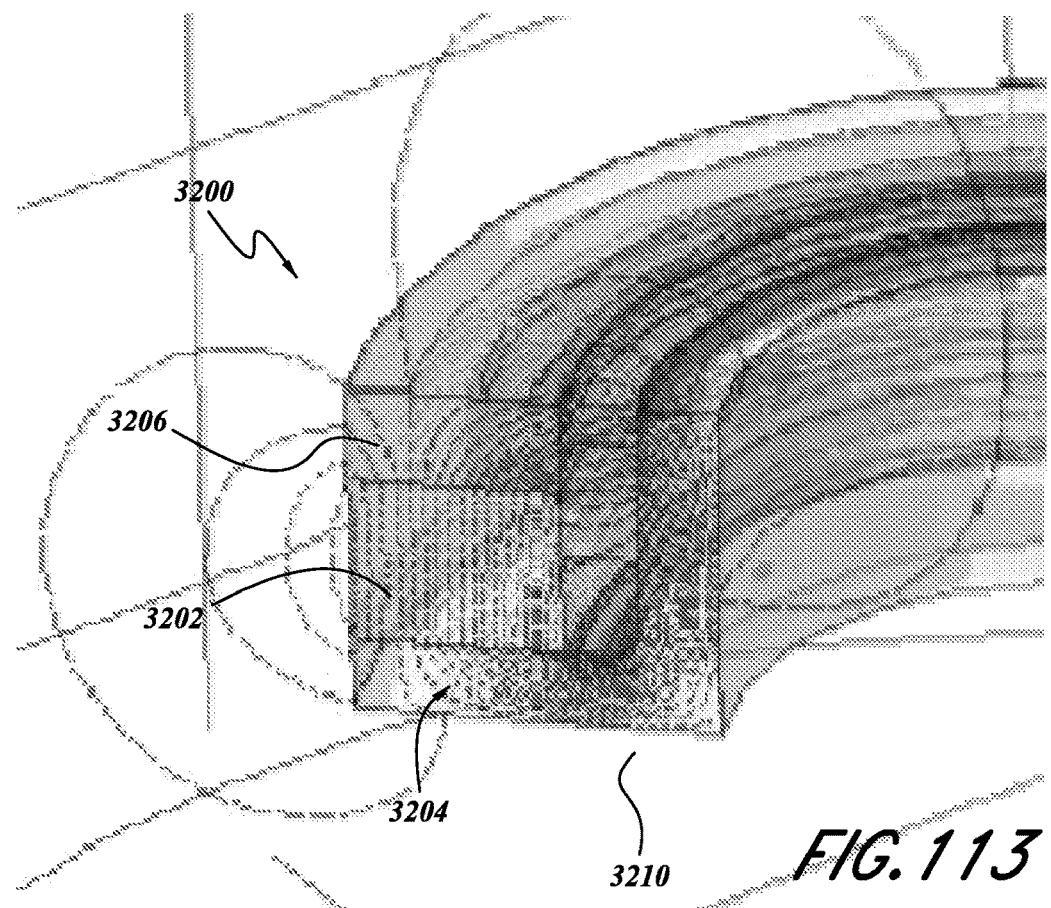
FIG. 113 is enlarged portion of the arrangement of the magnetic circuit of the pump assembly embodiment illustrated in FIG. 1.
Figure 114:
Figure 115:
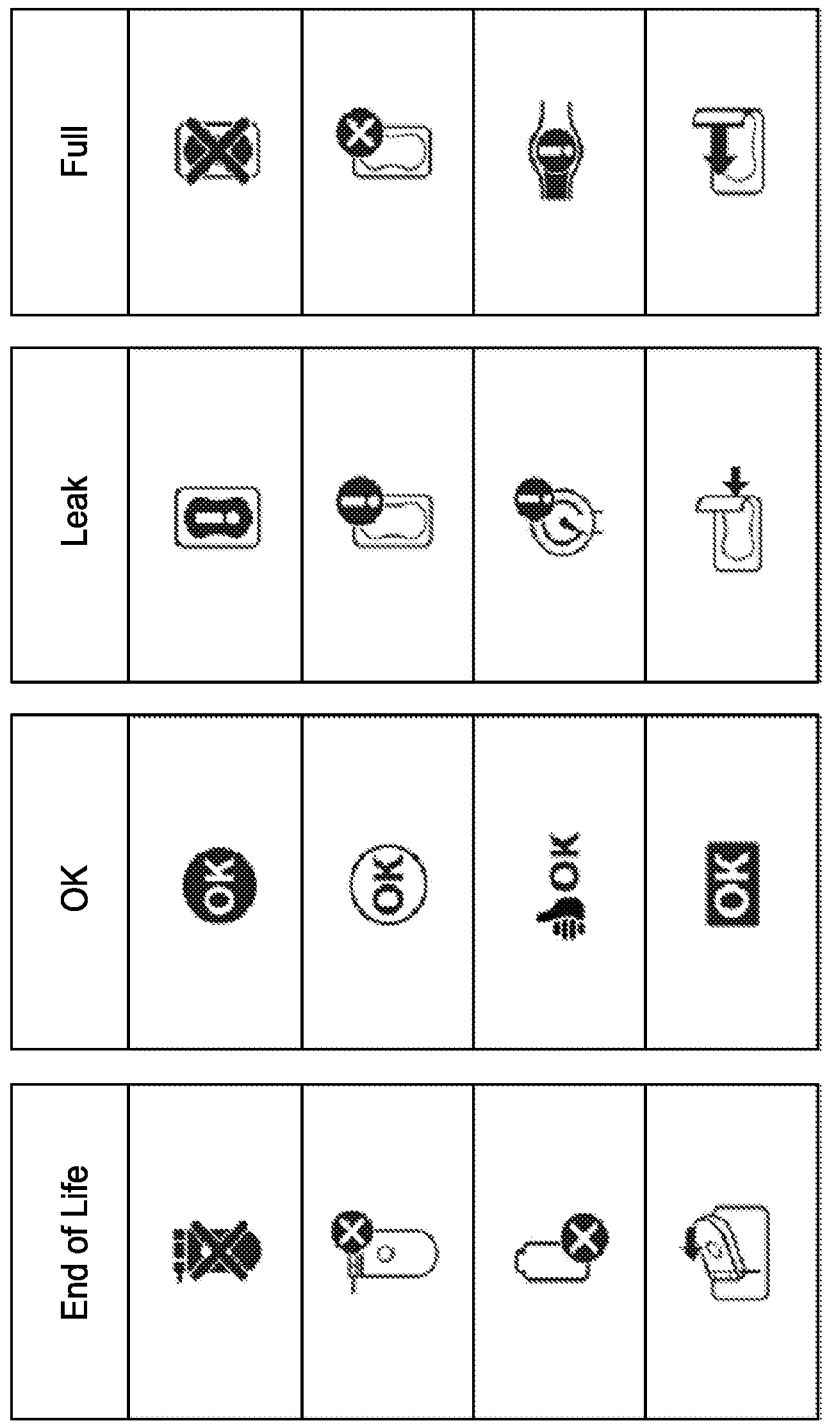
Figure 116:
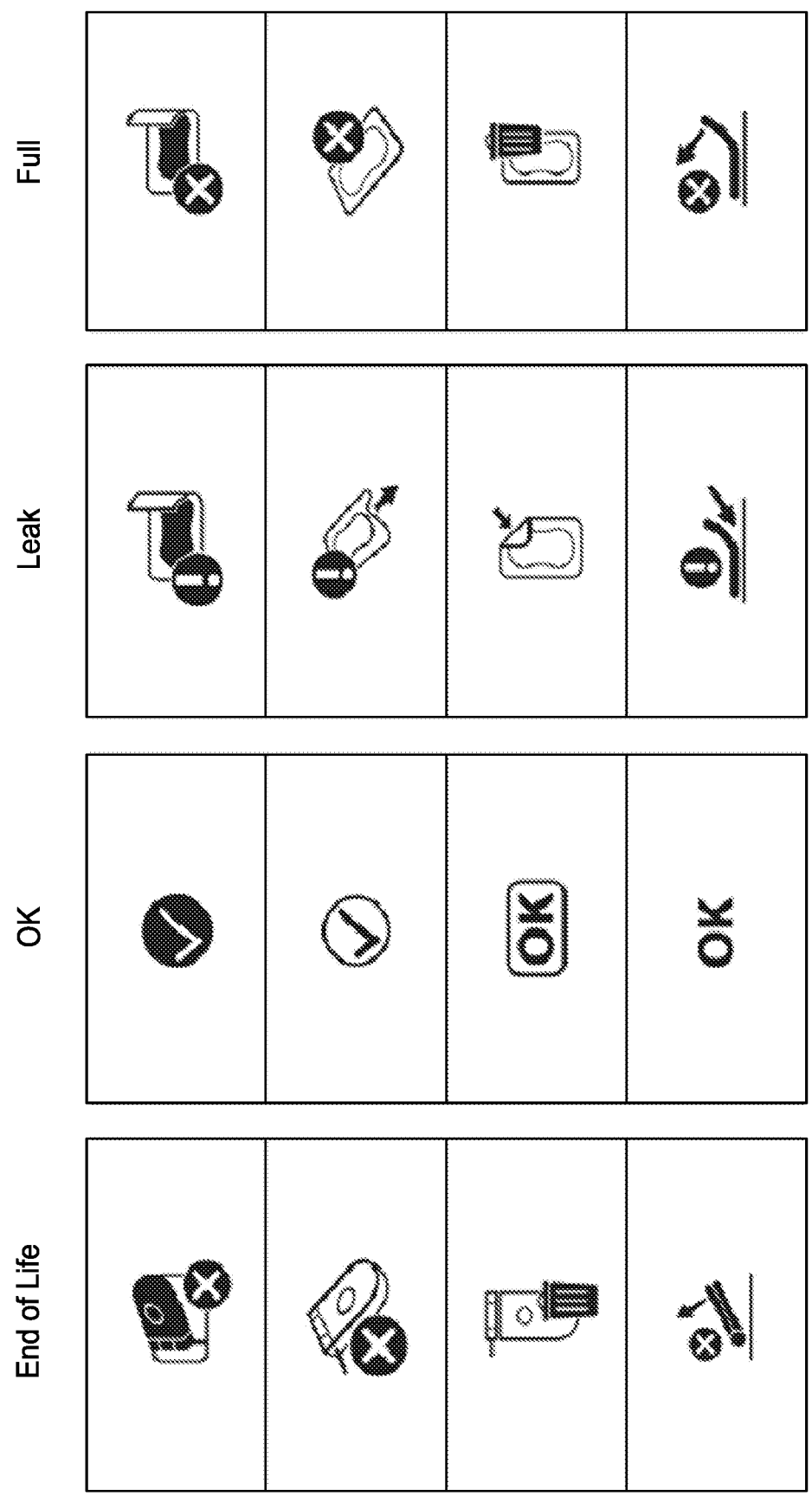
Figure 117:
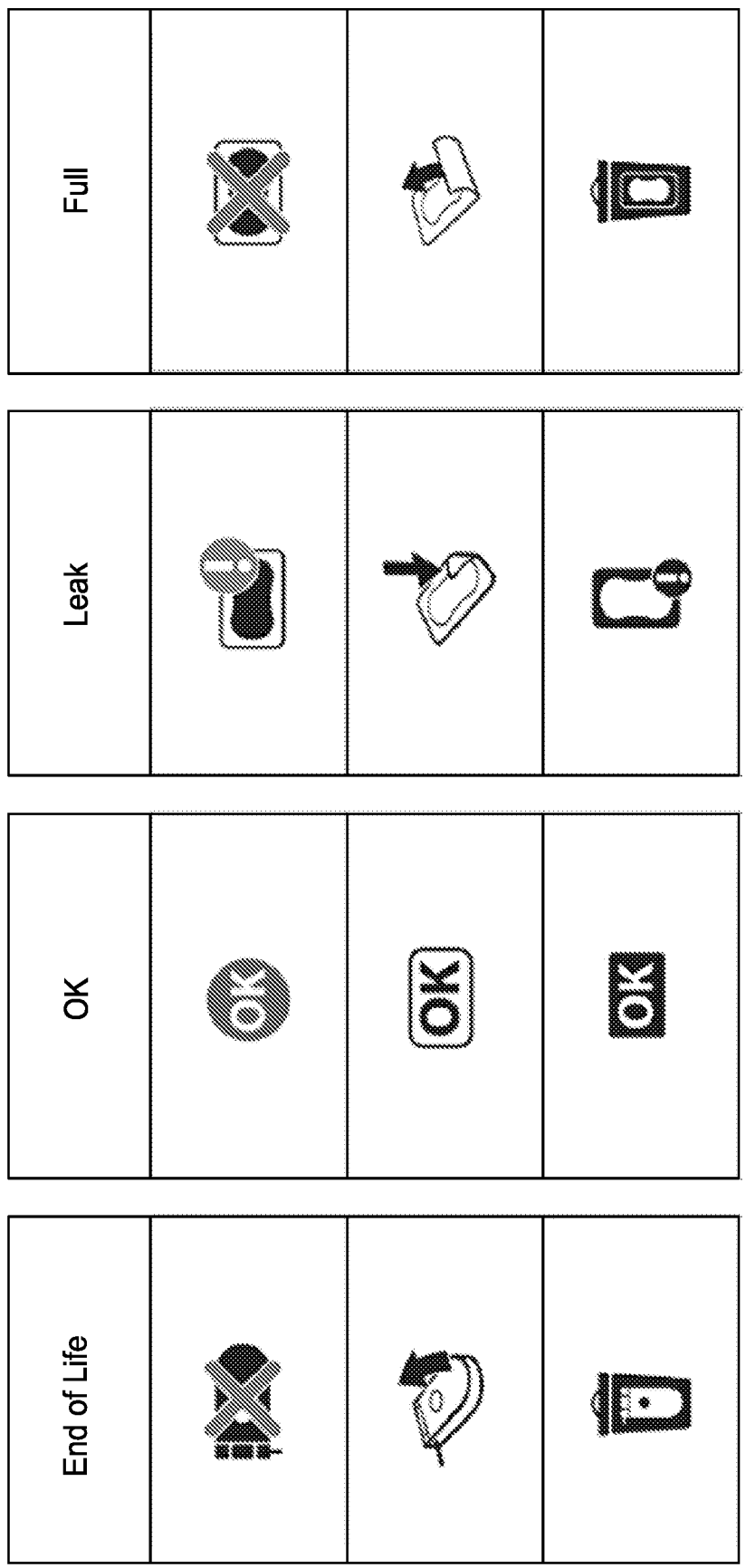
Figure 118:
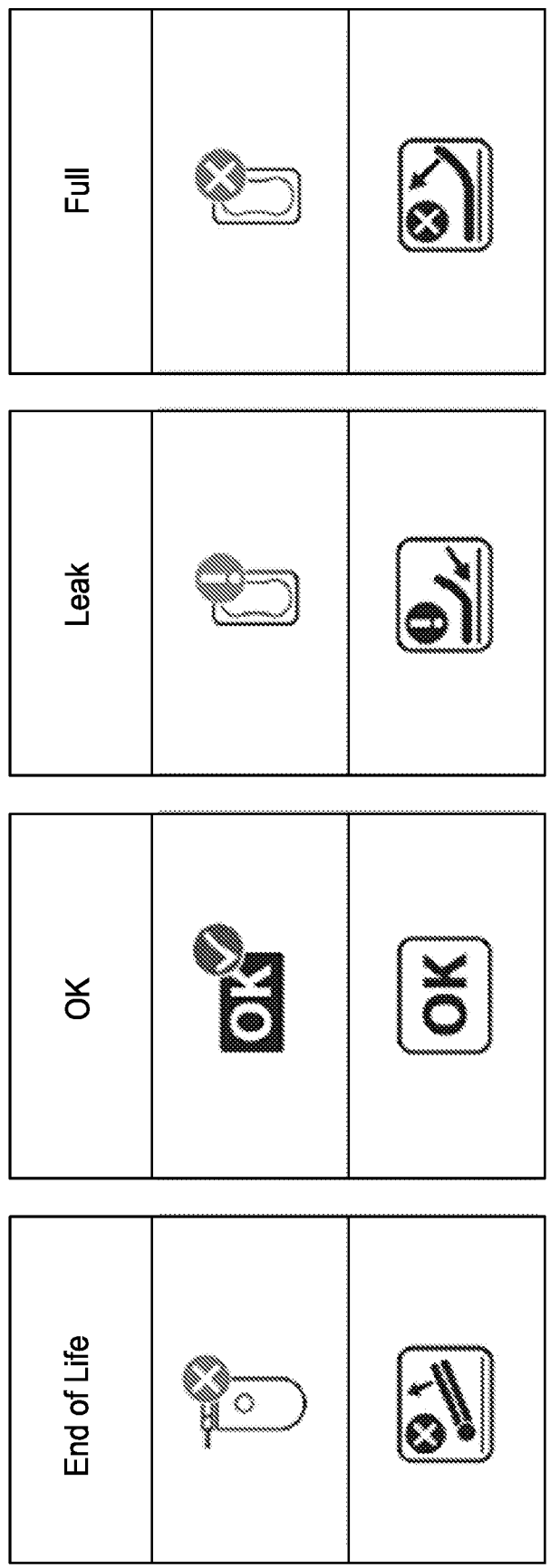
Figure 121:
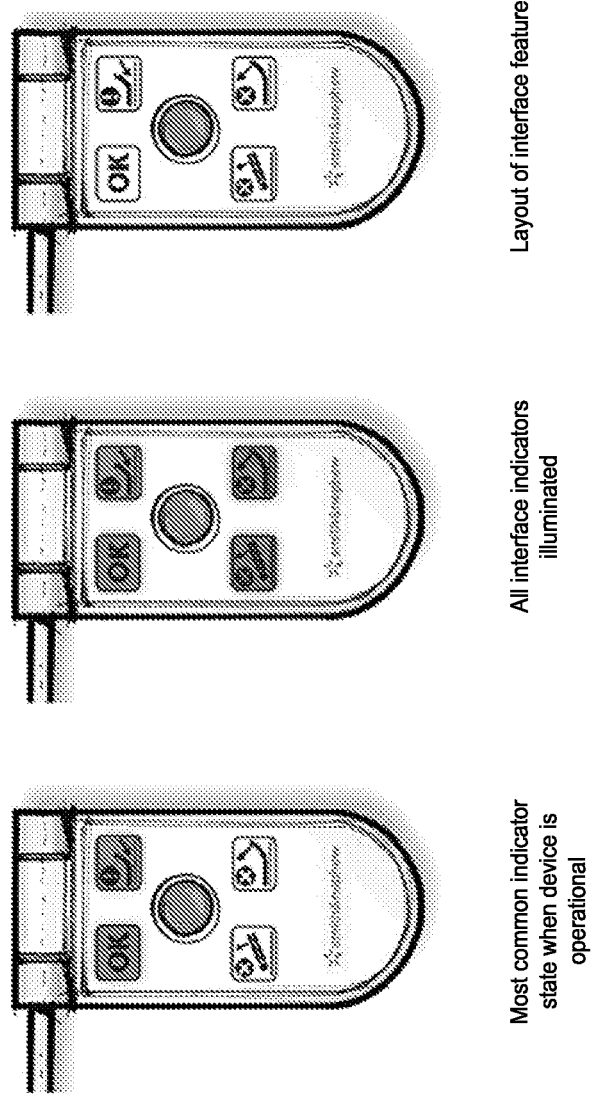
Figure 122:
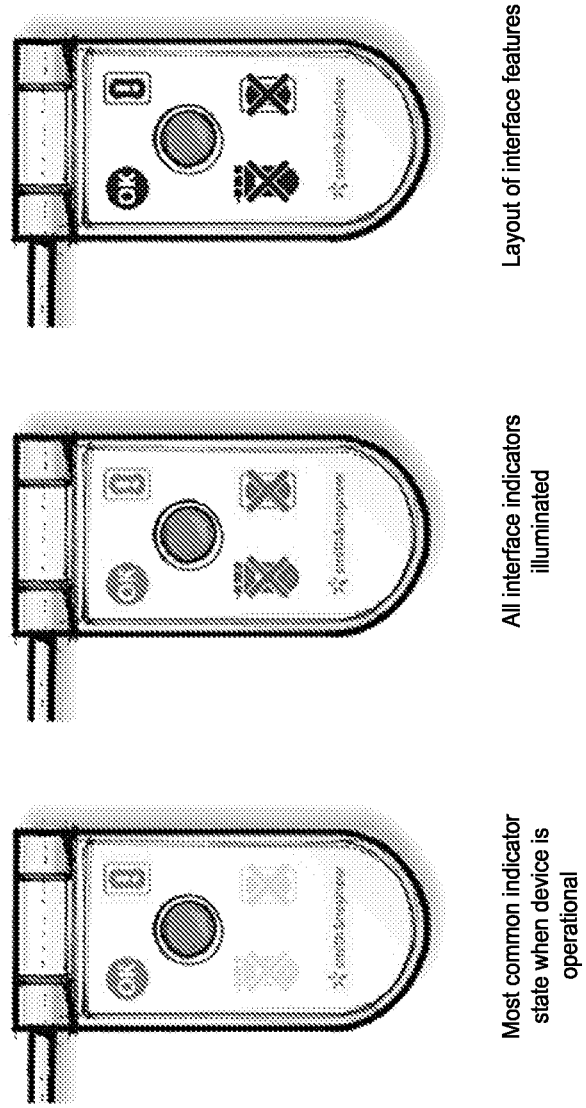
Figure 124:
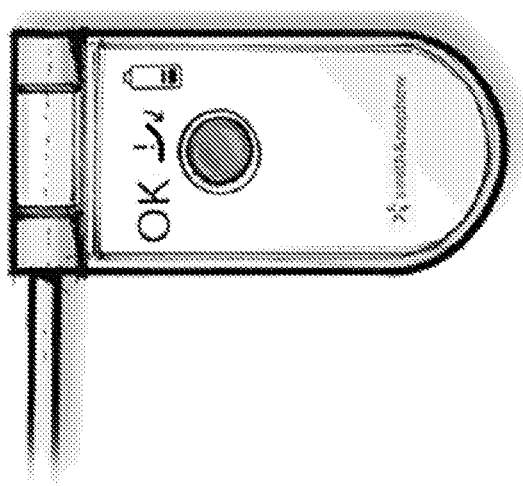
Figure 125:
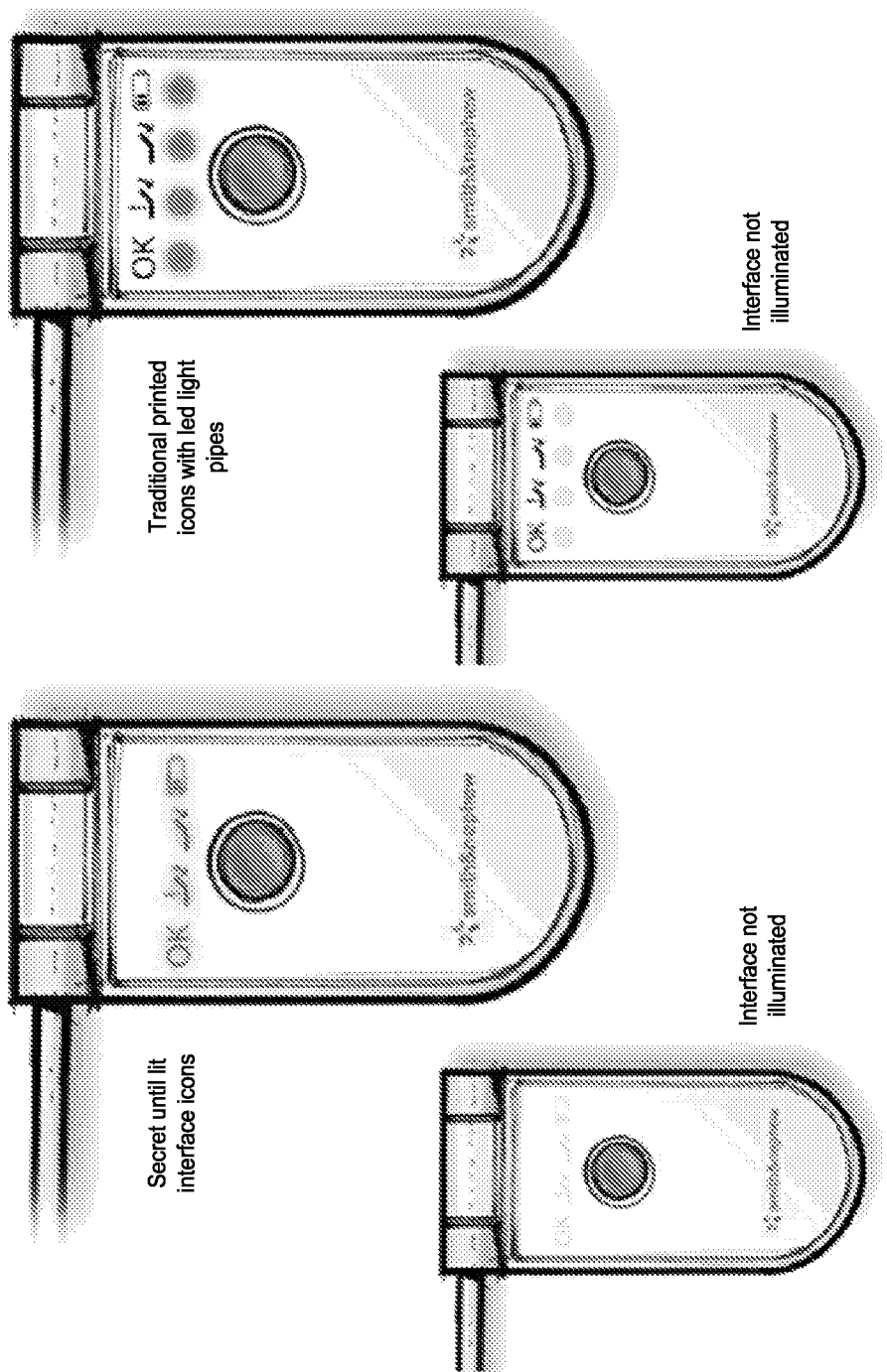
Figure 126:
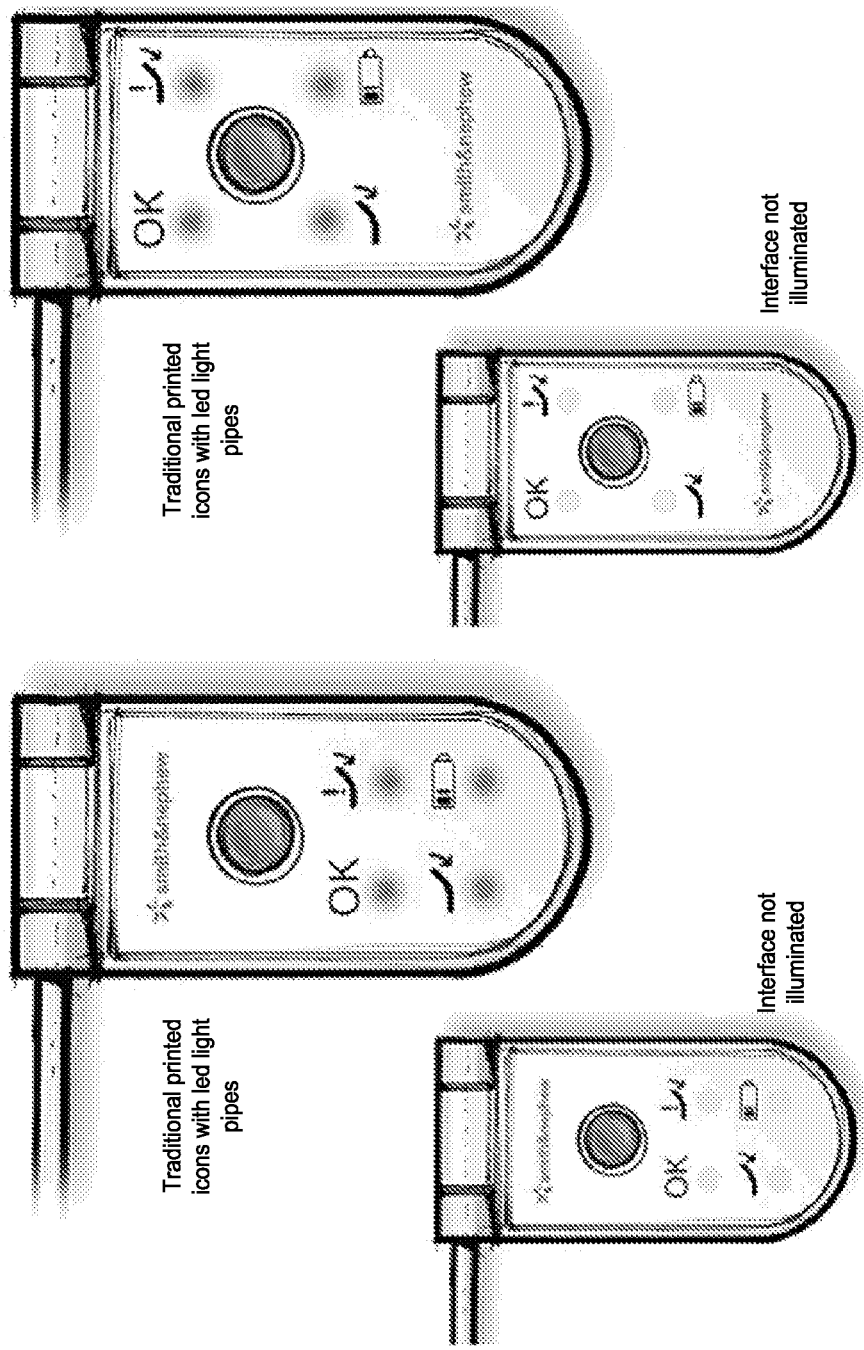
Figure 127:
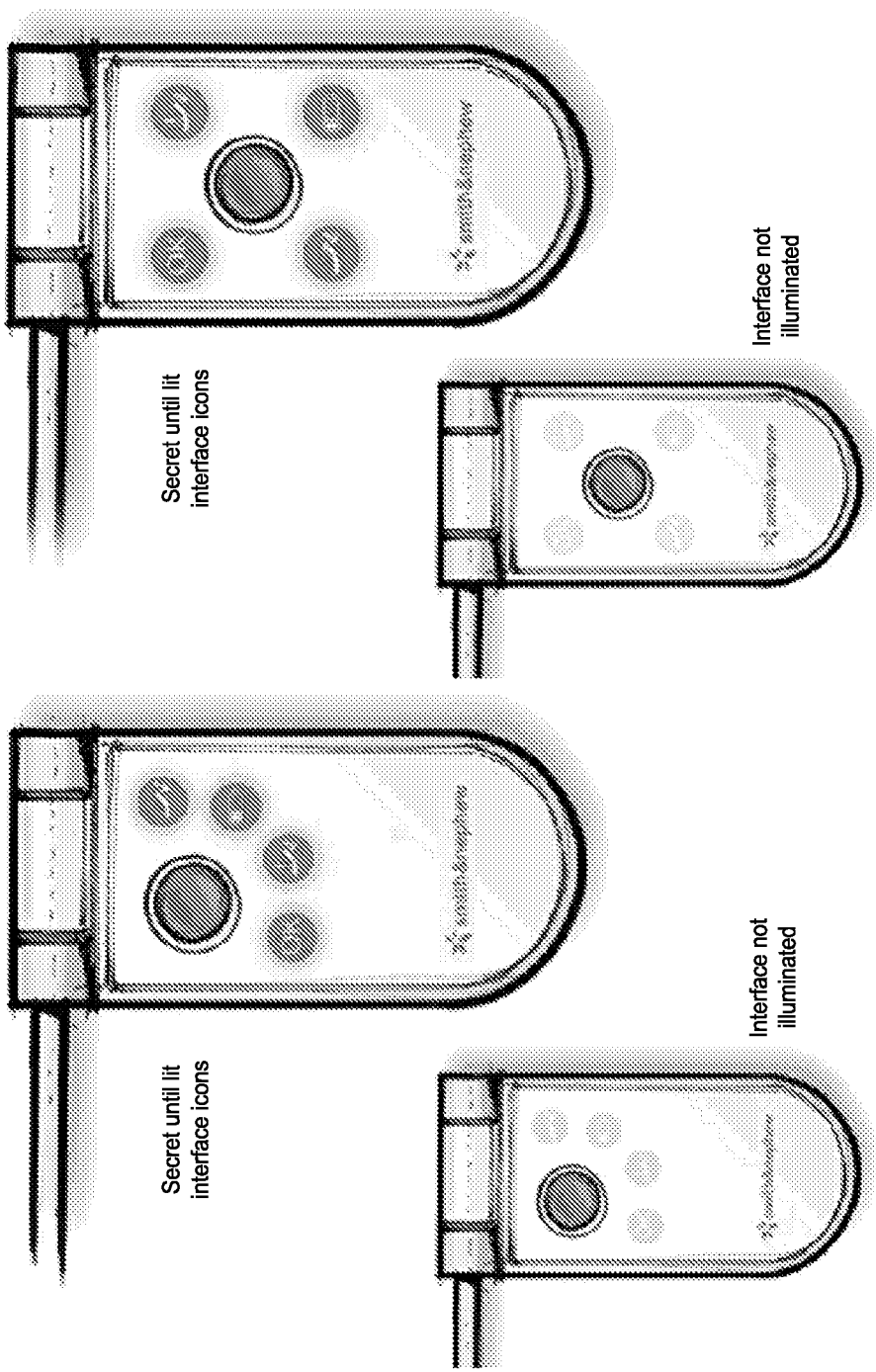

FIG. 105 illustrates an arrangement of a magnetic circuit 3200 according to some embodiments. FIG. 105 is a partial cut-away of the an arrangement of the magnetic circuit 3200, with contours of simulated radial magnetic field strength (e.g., in Tesla). This arrangement can be similar to the arrangement illustrated in FIG. 8. The circuit 3200 can include a magnet 3202 positioned between a lower pole 3206 and an upper pole 3204. A coil 3208 can be positioned in a groove in which the coil moves. In any embodiments disclosed herein, the magnetic field can have a north orientation at the bottom of the diagram and a south orientation at the top of the diagram in FIG. 105. In certain embodiments, these directions can be reversed.

As is illustrated, the upper and lower pole pieces 3204 and 3206 are not symmetrical with respect to the coil 3208. In any embodiments disclosed herein, this arrangement of the upper and lower pole pieces can act as a magnetic field "guide" that places the magnetic flux symmetrically with the coil 3208. As is illustrated, the magnetic flux is at its strongest in region 3210 as is evidenced by the density of the flux lines in region 3210. Accordingly, the magnetic field of the magnet 3202, which would normally be centered around the magnet, is shifted to be aligned with the coil 3208. In any embodiments disclosed herein, the entire arrangement illustrated in FIG. 105 contributes to aligning the magnetic field with the coil 3208. In various embodiments, the arrangement and/or placement of the upper pole piece 3204 contributes to aligning the magnetic field with the coil 3208. In any embodiments disclosed herein, such alignment of the magnetic field with the coil 3208 improves efficiency of the voice coil pump.

Figure 9:
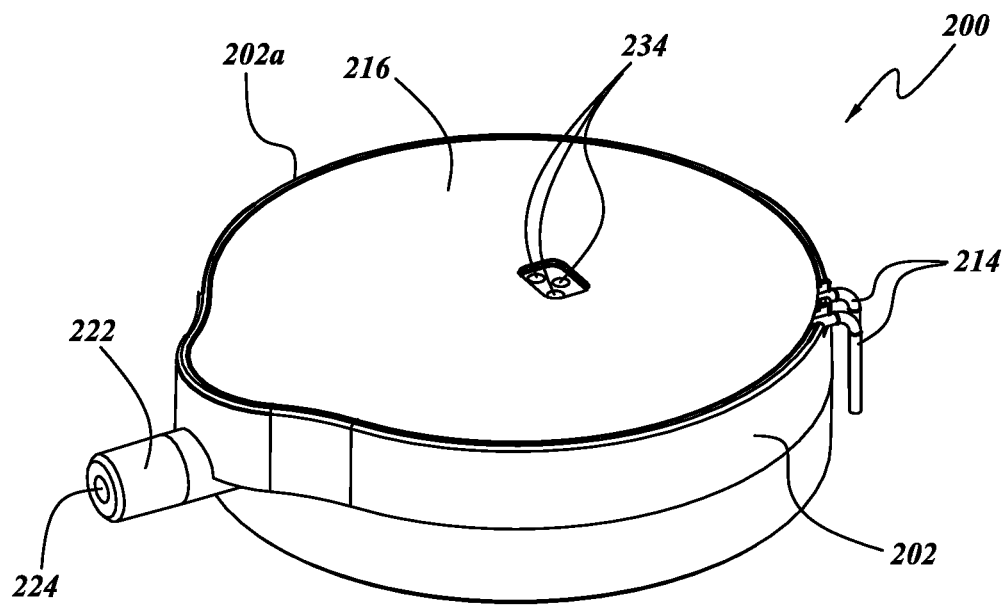
FIG. 9 is an isometric view of another embodiment of a pump assembly, showing a top surface of the pump assembly.
Figure 10:
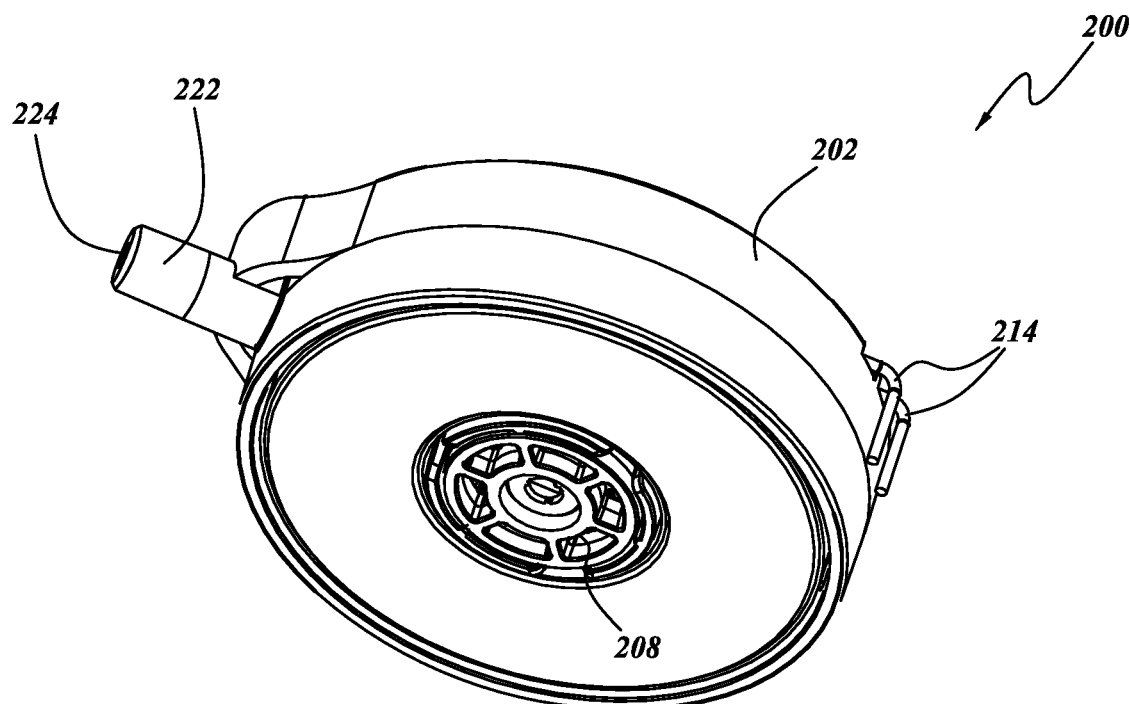
FIG. 10 is an isometric view of the pump assembly embodiment illustrated in FIG. 9, showing a bottom surface of the pump assembly.
Figure 11:
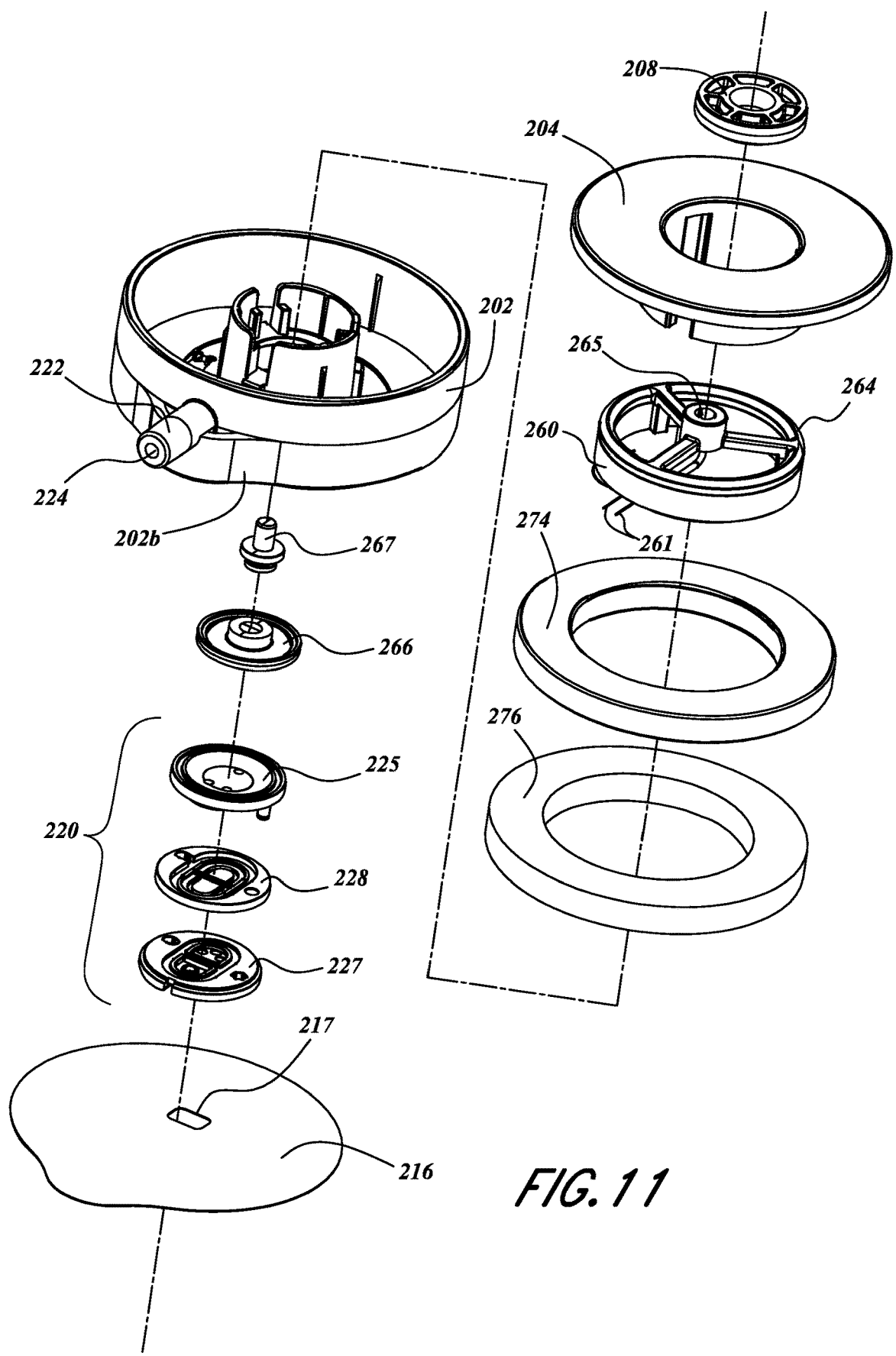
FIG. 11 is an exploded view of the pump assembly embodiment illustrated in FIG. 9, showing the top of the pump assembly.
Figure 12:
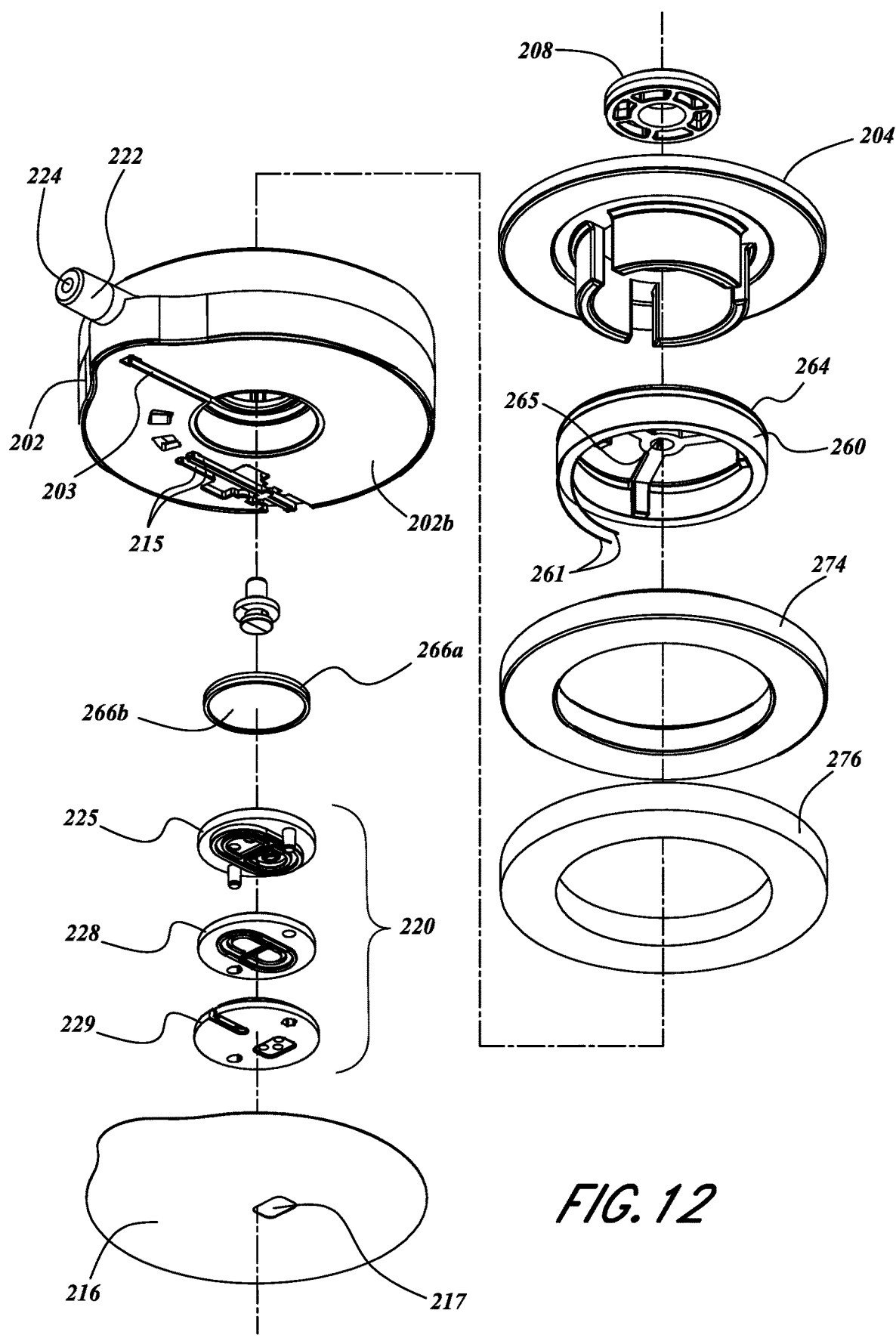
FIG. 12 is an exploded view of the pump assembly embodiment illustrated in FIG. 9, showing the bottom of the pump assembly.

FIGS. 9 and 10 are isometric views of another pump assembly embodiment 200, showing a top surface of the pump assembly and the bottom surface of the pump assembly, respectively. FIGS. 11 and 12 are exploded views of the pump assembly embodiment illustrated in FIG. 9, showing the top of the pump assembly and the bottom of the pump assembly, respectively. The pump assembly embodiment 200 can have a compact, small size and can have any of the same features, components, materials, or other details of the pump assembly embodiment 100 described above, or any of the other pump assembly embodiments disclosed herein.

In any embodiments disclosed herein, the pump assembly embodiment 200 can have a diameter or lateral size in the range of approximately 26-29 mm, or between approximately 25 and approximately 28 mm. In any embodiments disclosed herein, the pump assembly embodiment 200 can have a thickness or height of approximately 8 mm, or between approximately 6 mm and approximately 10 mm. Similar to the pump assembly embodiment 100 above, this embodiment and arrangement of the pump assembly embodiment can also be referred to as a "drum" type pump.

The pump assembly embodiment 200 can be produced for a low cost and can operate at high efficiencies, making it beneficial for portable, disposable, and/or single use applications. In any embodiments disclosed herein, the pump assembly embodiment 200 can run for a week on a small primary cell without the need for battery replacement or recharging. This pump can be used in an ultra-portable single-use negative-pressure wound therapy (NPWT) device, but is not so limited. In any embodiments disclosed herein, as mentioned, the pump assembly embodiment 200 can be used for negative pressure wound therapy. However, the pump assembly embodiment 200 is not limited to use in negative pressure wound therapy systems. The pump assembly embodiment can be adapted and configured for use in any reduced pressure system or in any system or application in which the movement of gaseous and liquid fluids is desired.

The pump assembly embodiment 200 can be designed to work at pressures of 60-80 mm Hg, and can be configured to produce a flow rate of approximately 200 ml min-1, with a minimum efficiency of 15%, in order for the NPWT device to run for a week on a specified battery capacity. In any embodiments disclosed herein, the pump assembly embodiment 200 can be adapted to operate at efficiency levels in excess of 25%.

With reference to FIGS. 9-12, the pump assembly embodiment 200 can have a housing 202 adapted to support and protect many of the components of the pump assembly embodiment 200. An upper pole 204, which can be made from any suitable materials such as mild steel or sintered steel, can be supported at one end (for example, a first end) 202a of the housing 202. In any embodiments disclosed herein, the upper pole 204 can have an opening 206 formed through an axial centerline of the upper pole 204. A bearing 208 can be supported by the upper pole 204, within the opening 206. Two or more electrical wires 214 can be connected to the pump assembly embodiment 200, configured to provide power to the pump assembly embodiment 200. In particular, the wires 214 can be used to provide electrical current to the coil 260 of the pump assembly. The electrical wires 214 can be routed through one or more openings or channels formed in the housing 202, such as channels 215 shown in FIG. 12.

A cover 216 can be positioned over the electrical wires 214 after the electrical wires have been advanced through the channels 215. The cover 216 can be an adhesive backed foil, film, paper, plastic sheet or label, or other similar object. An opening 217 can be formed in the cover 216 to permit air, gas, or other fluid to be exhausted from the pump through the outlet manifold.

Additionally, In any embodiments disclosed herein, the cover 216 can be configured to complete the inlet vacuum channel. In other words, the cover 216 can be configured to separate or seal the vacuum created by the pump from atmosphere. Using a thin label in place of a thicker plastic molded part or otherwise can decrease the height or thickness of the pump as much as possible. Alternatively, any embodiments of the pump assembly can have a thicker cover that can be molded, cast, machined, or formed by any other suitable method.

The housing 202 can support a valve assembly 220 at an end (for example, a second end 202b) of the housing 202. The housing 202 can support a boss member 222 that can receive a conduit therein or thereover, the boss member 222 having an opening 224 therethrough. The opening 224 can be in fluid communication with one or more passageways inside the pump assembly embodiment 200, such as air passageway 203 formed (that can be covered by the cover 216) in the housing 202 that communicates with the air passageway 229 formed in the valve assembly 220.

Figure 15:
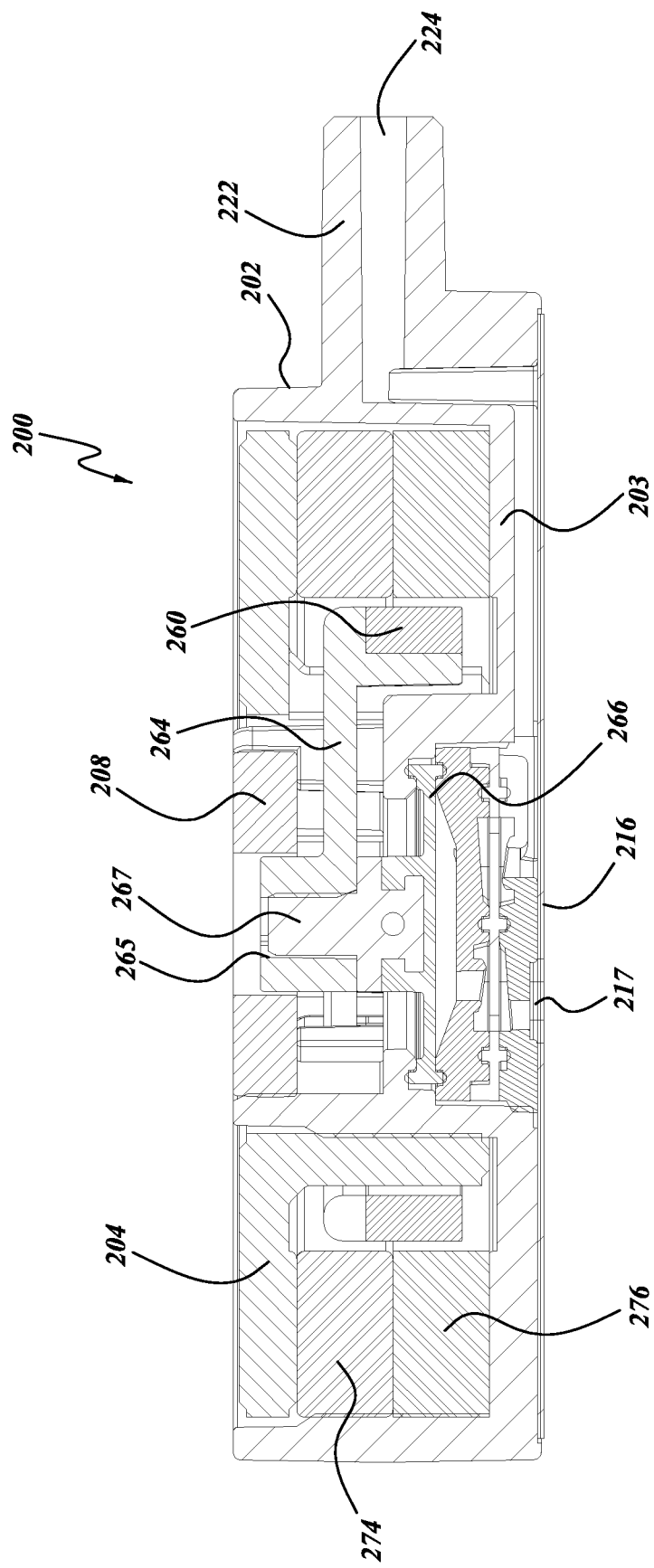
FIG. 15 is a section view of the pump assembly embodiment illustrated in FIG. 9, the section being taken through the center of the pump assembly embodiment.

FIGS. 13 and 14 are exploded views of the valve assembly of the pump assembly embodiment 200 illustrated in FIG. 9, showing the top of the valve assembly and the bottom of the valve assembly, respectively. FIG. 15 is a section view of the pump assembly embodiment 200 illustrated in FIG. 9, the section being taken through the center of the pump assembly embodiment 200. With reference to FIGS. 13 and 14, the valve assembly 220 can have a first valve member 225, a second valve member 227, and a valve plate 226. The valve plate 226 can support two flexible valve flaps 228, a first valve flap 228a for the inlet valve chamber and a second valve flap 228b for the outlet valve chamber. The first flap 228a and the second flap 228b can be configured to deflect away from the relaxed position of the flaps 228 shown in FIGS. 4-5.

The first inlet valve chamber 221a of the second valve member 227 can have a cavity or depression 230 and one or more openings, such as opening 224 in communication with the depression 230 to permit the passage of air from the channel 229 into the pump assembly embodiment 200 when the flap valve 228a is in an open position. A boss 231 can be formed within the depression 230 surrounding the opening 224 to provide a sealing surface for the valve flap 228 to selectively seal the opening 224. In any embodiments disclosed herein, the boss 231 can have an angled or curved surface 231a (as shown in FIG. 5) configured to substantially match the profile of the valve flap 228a as the valve flap 228a is deflected from the relaxed position against the surface of the boss 231. This arrangement can improve the seal between the valve flap 228a and the boss 231 to increase the efficiency of the pump assembly embodiment 200.

In use, for any of the embodiments disclosed herein, as the voltage supplied to the coil oscillates between a positive voltage and a negative voltage, the coil (which can be fixed to the support member and the diaphragm) can oscillate up and down in the pump between the two poles. The oscillation of the diaphragm can cause the volume within the pump to increase or decrease and, hence, cause the pressure within the pump to decrease or increase. A pressure decrease within the pump chamber can draw air into the pump chamber and open the inlet manifold (or flap), while the flap on the outlet manifold can seal the outlet manifold closed. Then, as the diaphragm returns toward the valve support, the volume of airspace decreases, causing the air pressure to increase. This forces air out of the chamber through the outlet valve, while the inlet valve is sealed closed.

The first outlet valve chamber 221b of the second valve member 227 can have a cavity or depression 232 and one or more openings 234 configured to allow the passage or exit of air from the inside of the depression 232 and the pump assembly embodiment 200 when the valve flap 228b is in an open position. In the embodiment shown in FIGS. 9-14, the valve assembly 220 has three openings 234 formed in the first outlet valve chamber 221b. The housing 202 can have a similar arrangement of inlet and outlet valve chambers as compared to the first inlet and outlet valve chambers 221a, 221b.

With reference to FIGS. 13 and 14, a second inlet valve chamber 241a supported by the first valve member 225 can have a cavity or depression 246 and one or more openings 248 in communication with the depression 246 to permit the passage of air from the first inlet valve chamber 221a into the second inlet valve chamber 246 when the valve flap 228a is in an open position (e.g., not sealingly covering the opening 224). One or more openings 248 (two being shown) can be formed in the second inlet valve chamber 241a to permit air to pass from the second inlet valve chamber 246 into the inside of the pump assembly embodiment 200. In any of the pump embodiments disclosed herein, the inlet valve chamber and/or the outlet valve chamber, on either side of the flap valve, can have one, two, three, ore more openings configured to permit air to pass therethrough.

Similarly, a second outlet valve chamber 241b can be supported by first valve member 225. The second outlet valve chamber 241b can have a depression 250 formed therein and an opening 252 in communication with the second outlet valve chamber 241b. A boss 254 can be formed within the depression 250 surrounding the opening 252 to provide a sealing surface for the valve flap 228b to selectively seal the opening 252. In any embodiments disclosed herein, similar to the boss 231, the boss 252 can have an angled or curved surface 254a configured to substantially match the profile of the valve flap 228b as the valve flap 228b is deflected from the relaxed position against the surface of the boss 254a. This arrangement can improve the seal between the valve flap 228b and the boss 254 to increase the efficiency of the pump assembly embodiment 200. When the valve flap 228b is in an open position, air or other fluid within the pump assembly embodiment 200 can pass through the opening 252 into the first outlet valve chamber 221b and exit the pump assembly embodiment 200 through the one or more openings 234.

In any embodiments disclosed herein, valve flaps 228a, 228b can be configured to be unstressed in a neutral position, neither fully open nor fully closed. Therefore, rather than there being a 'cracking pressure' required to open them, In any embodiments disclosed herein, a small back-pressure (for example, approx. 30 mbar or more) can be used to hold valve flaps 228a, 228b closed. This improves efficiency by reducing the pressure force that must be generated by the VCA during the suction stroke.

The pump assembly embodiment 200 can have a coil 260 comprising electrical wires 261, a retainer 264, and a support 264. The coil 260 can be formed from a length of wound conductive wire, such as without limitation copper wire. In operation, the coil 260 is configured to move within a magnetic circuit, and is connected or supported via the support member 264 to a pump diaphragm assembly 266. In any embodiments disclosed herein, an opening 265 formed in the support member 264 can be configured to receive a boss or protrusion 267 of the diaphragm assembly 266 so the pump diaphragm assembly 266 can be coupled with the support member 264. The diaphragm 266 can be supported and fixed at its peripheral portion 266a, wherein an interior portion 266b of the diaphragm assembly 266 is permitted to flex and deflect in either direction away from the relaxed position of the diaphragm assembly 266. The diaphragm assembly 266 is configured to elastically return the coil 260 to its relaxed position.

The diaphragm 266 can be supported and/or fixed along all or a portion of its peripheral portion 266a, wherein an interior portion 266b of the diaphragm assembly 266 is permitted to flex and deflect in either direction away from the relaxed position of the diaphragm assembly 266. In any embodiments disclosed herein, the diaphragm can be clamped and compressed between two rigid surfaces to provide such support. The rigid surfaces can define an annular shape. For example, any embodiments of the diaphragm 266 (or any other diaphragm disclosed herein) can have a moulding and a separate compression ring (made from a rigid plastic, aluminium or other metal, or any other suitable material or composite material). Additionally, any embodiments of the diaphragm 266 (or any other diaphragm disclosed herein) can have one plastic or other frame or moulding on each side of the flexible diaphragm membrane. The mouldings and the flexible diaphragm membrane can be held together with adhesive, mechanical connections between the mouldings, ultrasonically welding, or by any other suitable method. In any embodiments disclosed herein, the diaphragm can have a single frame or moulding having a channel therein configured to receive and support a peripheral edge of the flexible diaphragm membrane. Additionally, In any embodiments disclosed herein, the diaphragm 266 can be sealed at its outer perimeter 266a. The diaphragm assembly 266 is configured to elastically return the coil 160 to its relaxed position. Any of the pump embodiments disclosed herein (i.e., in this application) can be formed from cast or molded silicone, polyurethane, thermoplastic polyurethane, and/or other suitable materials, having a hardness value of approximately 20 A, 30 A, 40 A, 50 A, 55 A, or more.

The configuration of the pump assembly embodiment 200 can be similar to that used in low fidelity loudspeakers, which fit a significant amount of magnetic material into a very compact space. With reference to the figures, the pump assembly embodiment 200 can have a magnet 274 positioned between a lower pole 276 and the upper pole 204. In any embodiments disclosed herein, the magnet 274 can be made from sintered Neodymium-Iron-Boron (NdFeB). This material can be used to maximize field strength and minimize losses, thereby increasing the efficiency of the pump assembly embodiment 200. However, In any embodiments disclosed herein, the magnet 274 can be formed from any suitable magnetic material. In any embodiments disclosed herein, the lower pole can be approximately 1.5-2.0 mm thick and can be made from any suitable material, such as mild steel.

One arrangement of a magnetic circuit is shown in FIG. 8. FIG. 8 is a cut-away of an arrangement of a magnetic circuit, with contours of simulated radial magnetic field strength.

The arrangement of the pump assembly embodiment 200 can be configured to differ from a typical low fidelity loudspeaker. For example, some embodiments of the pump assembly 200 can differ in the following ways. In the pump assembly embodiment 200, the coil 260 can be configured to underhang below the end of the magnetic circuit. For example, the coil 260 can be configured such that it does not extend above the magnetic circuit. This can improve the efficiency and reduce the overall height of the pea 200, but can result in the degradation of the linearity of response of the pump assembly embodiment 200.

The coil 260 can have a relatively high number of turns. Having a relatively high number of turns can give the coil 260 greater structural rigidity and can maximize the efficiency of the pump assembly embodiment 200. Additionally, the pump assembly embodiment 200 will not have a speaker cone that is typically in a low fidelity speaker, which normally serves to control coil motion. In the pump assembly embodiment 200, the diaphragm can be used to center the coil 260, and a linear bearing 208 can be used to limit any wobble of the coil 260 by engaging the protrusion 267 and controlling the movement of the support member 264.

The housing 202, support 214, valve assembly 220, retainer 262, and/or support member 264 can be made of a plastic or hard rubber material, metal, or any other suitable material or combination of materials. Such components can be formed by any suitable methods such as casting, any molding process such as injection molding, forging, sintering, machining, or any other suitable process.

In any embodiments disclosed herein, as in any of the illustrated embodiments, the pump assembly can be of a sufficiently small and portable size to be supported on a user's body or in a user's clothing. For example, any of the pump assemblies disclosed herein can be sized to be attached using adhesive medical tape or otherwise to a person's skin or to a dressing in a comfortable location, adjacent to or on the dressing or otherwise. Further, any of the pump assembly embodiments disclosed herein can be sized to fit within a person's pants or shirt pocket, or can be tethered to a person's body using a lanyard, pouch, or other suitable device or article.

In any embodiments disclosed herein, the pump assembly can be powered by one or more batteries (for example, two batteries, or as described in any other embodiments described herein) and can weigh less than 80 grams, including the weight of the batteries. In any embodiments disclosed herein, the pump assembly can have any desired number of batteries and can weigh from approximately 70 grams to approximately 90 grams, or from approximately 75 grams to approximately 100 grams, or between any values within the foregoing ranges. For example, the weight and/or size of the pump assembly could be reduced by reducing the battery size and/or weight (to, for example, AAA sized batteries, or smaller) or the pump size and/or weight. Any embodiments of the pump assembly can be powered by any suitable electrical source, including a main supply of electricity.

Any of the pump assemblies described herein can have a layer of open foam or other material wrapped at least partially around an outside surface of the pump to reduce the noise and/or vibration produced by the pump. One or more labels can be affixed to an outside surface of the housing of any pump assembly disclosed herein, not only to seal the internal components, but also to recite printed information. Additionally, In any embodiments disclosed herein, the pump can have one or more weights, cushions, foam (such as a viscoelastic foam), plastic (such as ABS, polyurethane, urethane, or otherwise), or other pads, panels, sheets, or segments supported by the pump or positioned adjacent to one or more outside surfaces of the pump. Any embodiments can have mass based or compliant damping materials. Such components or materials (not illustrated) can damp vibration and/or attenuate noise produced by the pump.

Any of the pump assemblies disclosed herein can have a flow manifold and a one-way flow valve in communication with a fluid flow pathway within the pump assembly. The one-way flow valve (also referred to as a check valve) can be a diaphragm valve made from silicone or any other suitable elastomeric or soft material, including without limitation, polyurethane, viton, nitrile rubber, neoprene, Teflon, and other suitable materials. Other suitable valves for the one-way flow valve are, for example and without limitation, umbrella valves, ball valves, reed valves, duckbill valves. In any embodiments disclosed herein, the leakage rate of the one-way flow valve can be approximately 0.05 mL/minute or less. In any embodiments disclosed herein, the one-way flow valve can be positioned within the pump assembly or in place of one of the valves positioned within the pump assembly.

Any of the pump assembly embodiments disclosed herein can be powered by one or more batteries. The batteries can be lithium chloride or any other suitable batteries that are suitable for exposure to ethylene dioxide and/or other sterilization gases. The batteries can be supported outside of the pump housing so as to minimize or eliminate the chance of an electrical spark which could cause an explosion in the presence of the sterilization gas or an explosive gas during the sterilization process when supported in the packaging element or elements. Additionally, where there are a plurality of batteries, the batteries can be spaced apart or otherwise separated in the packaging to prevent any power loss or sparking of the batteries during the sterilization process or otherwise before usage.

Any embodiments of the dressings disclosed herein can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. The pump can be programmed to automatically terminate therapy after a desired number of days, e.g., after seven days, further operation of the pump will not be possible. Some embodiments are designed for longer or repeated usage, and can be configured to support an exudate canister.

As described in U.S. patent application Ser. No. 13/092, 042, which disclosure is hereby incorporated by reference as if fully set forth herein, a lower surface of any of the wound dressing embodiments for use with the pump assembly disclosed herein can have an optional wound contact layer. Any of the dressing embodiments disclosed herein can be made without the wound contact layer. The wound contact layer can be a polyurethane layer or polyethylene layer or other flexible layer which can be made porous or perforated, for example via a hot pin process, laser ablation process, ultrasound process or in some other way or otherwise made permeable to liquid and gas. The perforations can enable fluid and/or gas to flow through the layer. The wound contact layer can help prevent tissue ingrowth into the other material of the wound dressing.

As mentioned, any dressing embodiments for use in the dressing kits disclosed or incorporated by reference herein can have an adhesive covered bottom (e.g., wound contacting) surface. In any embodiments disclosed herein, as mentioned, the adhesive can be a silicone adhesive including, for example, polysiloxanes or polyorganosiloxanes or other polymeric pressure sensitive silicone adhesives. For example, polydimethylsiloxane or the like can be used. The adhesive formulation may be a mixture of alkyl pendant siloxanes, which can be spread and cast as a two part mix with a catalyst such that a final polymerisation step takes place following casting or spreading. In any embodiments disclosed herein, a dressing layer can have a non-perforated silicone adhesive coating (coat weight 130 gsm nominal) and full spread acrylic adhesive (27 to 37 gsm) coated onto opposite sides of an extruded EU30 polyurethane clear film (27 to 37 gsm). Moisture vapour permeability of some embodiments of such an arrangement can be between approximately 367 $gm^{-2}/24$ hrs to approximately 405 $gm^{-2}/24$ hrs, or a mean moisture vapour permeability of 382 $gm^{-2}/24$ hrs.

Additionally, any of the dressing embodiments disclosed herein can have an anti-microbial agent or substance incorporated into the dressing or coated on one or more surfaces of the dressing. For example, without limitation, a wound contact layer of any dressing embodiments disclosed herein can have nanocrystalline silver agents, silver salts, copper salts, or gold salts such as, without limitation, those disclosed in U.S. patent application Ser. No. 11/922,894 (titled ANTIMICROBIAL BIGUANIDE METAL COMPLEXES), filed May 21, 2008, which application is incorporated by reference herein as if made part of this disclosure, PHMB, chlorohexadine, peroxide, hypochloride, or other bleaches therein or thereon. Further, an absorbent layer of any dressing embodiments disclosed herein can have silver sulphur diazine or any of the previously mentioned substances or active agents therein or thereon. These may be used separately or together. These respectively can eliminate microorganisms in the wound and micro-organisms in the absorption matrix. As a still further option, other active components, for example, pain suppressants such as ibuprofen or healing agents can be incorporated into the dressing. Also agents which enhance cell activity, such as growth factors or that inhibit enzymes, such as matrix metalloproteinase inhibitors, such as tissue inhibitors of metalloproteinase (TIMPS) or zinc chelators, can be incorporated into the dressing. Odor trapping elements such as activated carbon, cyclodextrine, zeolite or the like can also be included in the absorbent layer or other portions or components of the dressing, or above the filter layer.

Any embodiments of the wound therapy apparatuses disclosed herein can be manufactured in a wide variety of different models or versions, wherein the size of the dressing can be varied to accommodate a wide range of wound sizes. For example, without limitation, any of the embodiments disclosed herein can have any of the following sizes of dressings and wound pads or other absorbent elements.

| Approximate Dressing Size | Approximate Wound Pad Size |
| --- | --- |
| 10 cm × 30 cm (4 in × 11.75 in) | 5 cm × 20 cm (2 in × 8 in) |
| 15 cm × 15 cm (6 in × 6 in) | 10 cm × 10 cm (4 in × 4 in) |
| 15 cm × 20 cm (6 in × 8 in) | 10 cm × 15 cm (4 in × 6 in) |

-continued

| Approximate Dressing Size | Approximate Wound Pad Size |
| --- | --- |
| 10 cm × 20 cm (4 in × 8 in) | 5 cm × 10 cm (2 in × 4 in) |
| 20 cm × 20 cm (8 in × 8 in) | 15 cm × 15 cm (6 in × 6 in) |

In any embodiments disclosed herein, it may be preferable for the wound site to be filled partially or completely with a wound packing material. This wound packing material is optional, but may be desirable in certain wounds, for example deeper wounds. The wound packing material can be used in addition to the other components of overlay or overlay kit. The wound packing material generally can comprise a porous and conformable material, for example foam (including reticulated foams), and gauze. Preferably, the wound packing material is sized or shaped to fit within the wound site so as to fill any empty spaces. The wound dressing can then be placed over the wound site and wound packing material overlying the wound site. When a wound packing material is used, once the wound dressing is sealed over the wound site, TNP can be transmitted from a pump through or under the wound dressing, through the wound packing material, and to the wound site. This negative pressure draws wound exudate and other fluids or secretions away from the wound site. Any embodiments of the overlay or dressing can be substantially impervious to air flow and the flow of bacteria or other contaminants through the overlay layer, while being pervious to vapor transmission.

Any embodiments of the pump and dressing embodiments disclosed herein can be configured or adapted for sterilization before delivery to the hospital, operating room or theatre, or to the medical practitioner using such devices such that the sterile pump and/or a sterile pump/dressing kit can be applied immediately following the surgical or operating procedures. One advantage of this is that the surgeon can release the patient from the operating room knowing that the reduced pressure pump is operating and that the reduced pressure therapy has been started at the earliest point in time possible. A further advantage of applying the dressing kit immediately following the surgical or other procedure is that doing so can reduce the chance of infection by eliminating a subsequent dressing change that may otherwise be required in the ward. In other words, for those patients where a dressing (but not a pump) is applied in the operating theatre and then a problem is found thereafter, such as a leak or other issue with the dressing, if the dressing is required to be removed to be repositioned, replaced, or otherwise after the patient is released from the operating theater, the patient's wound may be exposed to infection risk when the dressing is repositioned, replaced, or otherwise outside of the operating theater.

However, with the embodiments disclosed herein, if the pump is applied and tested while the patient is in the operating theater, any issues with the dressing that may require the dressing to be removed, repositioned, or otherwise, can be handled in the sterile operating room environment, thereby significantly reducing or eliminating the risk of exposure to pathogens, bacteria, or other contaminants. Further, it is generally not possible for a hospital to sterilize a traditional pump once it has been received by the hospital, and therefore the hospital may resort to bagging the pumps in sterile bags but risk compromising the operating room sterile field with this approach, particularly once the device is turned on and pathogens, bacteria, or other contaminants that may be inside the pump are release due to the operation of the pump.

Any of the pump assembly embodiments disclosed herein can be configured to be amenable to gas sterilization, having features, components, and other characteristics that make the pump amenable to full sterilization gas exposure and penetration throughout the components of the pump. For example, without limitation, one or more pump valves or flap valves can be selected or configured to permit a sufficient flow of sterilization gas therethrough such that the entire fluid pathway within the pump can be exposed to the sterilization gas. As will be explained in greater detail below, In any embodiments disclosed herein, the pump can have other components, such as without limitation, strategically positioned one way flow valves, to complement the other valves within the pump, which can improve the efficiency of the pump by reducing leakage through the flow pathway within the pump assembly.

Additionally, where provided, the sterile pump/dressing kit can also be designed and configured to be amenable to gas sterilization. As described below, the sterile pump/dressing kit can be configured such that all of the components comprising the sterile pump/dressing kit, including the pump assembly, are packaged together in at least a first packaging element before sterilization, permitting all of the components to be sterilized together. Furthermore, as will be described, the components comprising the sterile pump/dressing kit can be arranged in the packaging such that at least some of the components can be removed in a pre-defined order, making it easier for the surgeon or medical practitioner to assemble and apply the dressing to the patient.

The pump assembly can be configured such that a sterilization gas, such as ethylene dioxide, can penetrate into the housing of the pump assembly such that the internal components of the pump assembly are exposed to the sterilization gas during normal sterilization processes. Typically, the pump will be exposed to the sterilization gas in a chamber that has been substantially evacuated of air or any other gas, so that the sterilization gas is drawn into the pump housing and into the other spaces and chambers within the pump assembly.

There are a number of benefits to being able to begin treatment of a wound in the operating theater, including without limitation providing a substantially sealed barrier over the wound while the wound is in a sterile condition and environment that will inhibit or prevent bacteria or other contaminants from getting into the wound. Additionally, initiating the reduced pressure treatment at the earliest stage possible is also advantageous to healing of the wound.

Additionally, embodiments disclosed or incorporated by reference herein, such as those disclosed in U.S. patent application Ser. No. 13/287, U.S. patent application Ser. No. 13/092,042, Great Britain Patent Application Nos. 1015656.0, 1006986.2, 1006983.9, 1006985.4, 1006988.8, and 1008347.5 comprise improved wound dressing components. All embodiments, components, features, and other details of such disclosures are hereby incorporated by reference herein as if made part of this disclosure, and can be used in place of or in combination with any of the components, features, and other details of the embodiments disclosed herein. For example, In any embodiments disclosed herein, the wound dressing can be configured to act as a buffer to help prevent compression or shear forces exerted on the wound dressing, for example due to patient movement, from harming a healing wound. Embodiments of the wound dressing may act as a waste canister to collect and store wound exudate removed from a wound site, and also relate to the management of solid build-up in a wound dressing covering a wound site whilst TNP therapy is applied. Further, embodiments disclosed herein relate to a method and suction port for applying negative pressure to a wound dressing and a method of manufacturing a suction port and wound dressing.

Moreover, some embodiments disclosed or incorporated by reference herein are directed to systems that include negative pressure therapy apparatuses and dressings, and methods and algorithms for operating such negative pressure therapy apparatuses for use with negative pressure therapy dressings. In any embodiments disclosed herein, a negative pressure therapy apparatus comprises a pump assembly configured to, inter alia, provide negative pressure to a wound. Some embodiments of pump assemblies disclosed herein comprise novel and inventive control logic configured to control the operation of the pump assembly. Any embodiments of the drum pumps disclosed herein can be configured such that their maximum pressure level produced by the pumps is less than the threshold value that is capable of injuring a user. For example, some drum pump embodiments disclosed herein can be configured so that it is impossible for the drum pump to produce vacuum levels that can harm a user.

For example, some embodiments comprise novel and inventive control logic configured to control the operation of a pump assembly in response to monitoring and detecting various operating conditions, such as presence and/or severity of a leak or leaks in the system, rate of flow of fluid (e.g., air, liquid and/or solid exudate, etc.) aspirated from a wound, and the like. In any embodiments disclosed herein, the control logic can be configured to detect a leak or leaks in a system (e.g., leak or leaks in the dressing that is in fluid communication with the pump, leak or leaks in the seal created by the dressing over the wound, etc.) as well as to control the operation of the pump assembly when such leak or leaks are detected. In any embodiments disclosed herein, the pump assembly can be configured to distinguish between at least a normal or low leak (e.g., a leak that has a relatively low flow rate), a high leak (e.g., a leak that has a relatively high flow rate), and a very high leak (e.g., a leak that has a relatively very high flow rate). Some embodiments can further be configured to also distinguish between the aforementioned leaks and an extremely high leak.

In any embodiments disclosed herein, the pump assembly can comprise a source of negative pressure, such as a miniature, disposable pump, powered by a power source, such as a battery source. The pump assembly can be configured to provide therapy for a predetermined period of time, such as approximately 1 day, 2-10 days, etc. In any embodiments disclosed herein, the pump assembly can be required to provide uninterrupted therapy for such period of time. In any embodiments disclosed herein, the pump assembly can be configured to deactivate itself a predetermined period of time (e.g., 7 days) after an initial activation. The algorithms or logic disclosed herein can help the pump assembly operate more efficiently and conserve power, for example but without limitation, battery power.

In any embodiments disclosed herein, the system can be configured to provide "play/pause" functionality and/or logic via a switch, button, etc. located on the exterior of the pump assembly's housing or any other suitable place where it can be accessed by the user. Play/pause functionality can allow the user to suspend and/or restart therapy (e.g., pause and/or restart the pump). The pump assembly can be configured to automatically restart therapy following a certain predetermined or variable pause interval. The pump assembly can be configured to automatically restart therapy upon expiration of such interval and/or indicate to the user expiration of such interval.

In any embodiments disclosed herein, the system can be configured to provide indication, alarms, etc. to the user reflecting operating conditions. The system can include visual, audible, tactile, and other types of indicators and/or alarms configured to signal to the user various operating conditions. Such conditions include system on/off, standby, pause, normal operation, dressing problem, leak, error, and the like. The indicators and/or alarms can include speakers (including a speaker made using some or all of the relevant components of the pump motor), displays, light sources, etc., and/or combinations thereof. For example, indication can be provided by activating or deactivating the source of negative pressure, reducing negative pressure level generated by the source of negative, lowering the amount of power used by the source of negative pressure, etc. or any combination thereof. Additionally, for example, the pump itself can be used to create audio alarm sounds, buzzing sensations, pulsing sensations, etc.

In any of the apparatus embodiments disclosed herein, the pump assembly can be a canisterless pump assembly (meaning that the pump assembly does not have an exudate or liquid collection canister). However, any of the pump embodiments disclosed herein can be configured to include or support a canister. Additionally, in any of the apparatus embodiments disclosed herein, any of the pump assembly embodiments can be mounted to or supported by the dressing, or adjacent to the dressing. The dressing may be placed over a wound (not illustrated) as described in greater detail in U.S. patent application Ser. No. 13/092,042, which disclosure is hereby incorporated by reference and made part of this disclosure, and a conduit may then be connected to the dressing. Any dressing disclosed herein can have any of the materials, sizes, components, or other details of any of the dressing embodiments disclosed in U.S. patent application Ser. No. 13/092,042, and such embodiments and illustrations thereof are hereby incorporated by reference in their entireties as if made part of this disclosure. The conduit or any other conduit disclosed herein can be formed from polyurethane, PVC, nylon, polyethylene, silicone, or any other suitable material.

Figure 16:
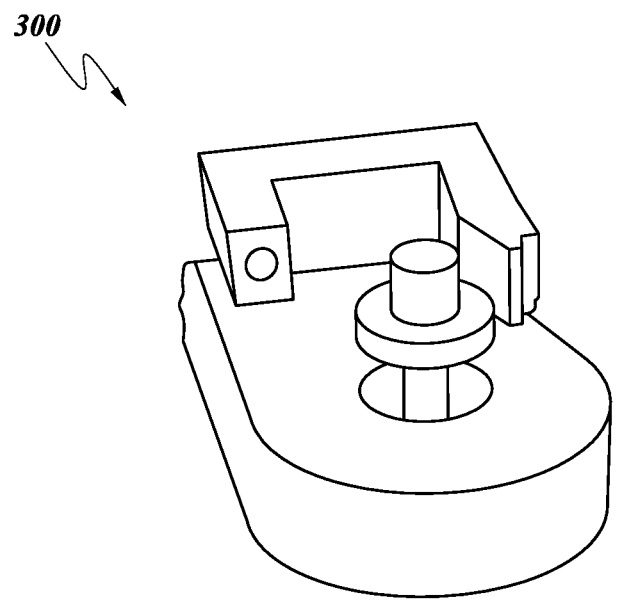
FIG. 16 is an illustration of a first drum pump (also referred to herein as a thick pump) that was built for experimental purposes.

Two examples of voice coil pump assemblies were constructed and tested. First, an embodiment of a thicker drum pump assembly 300, as illustrated in FIG. 16, was constructed. This assembly used an off-the-shelf, 25.65 mm outer diameter, 15 mm inner diameter, 6 mm high NdFeB ring magnet. The pump did not fit inside this ring, so the pump head with diaphragm and valves were separated out of the housing and separate from the magnet for this experimental setup.

Figure 17:
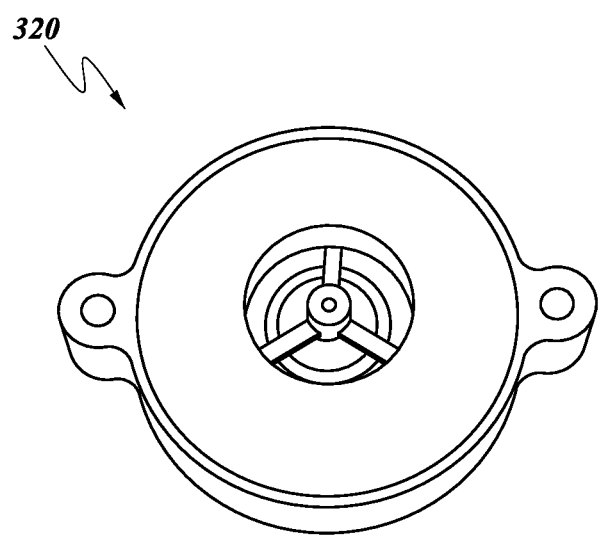
FIG. 17 is an illustration of a second drum pump (also referred to herein as a thin pump) that was built for experimental purposes.

Additionally, a thin drum style pump, such as the embodiment of the drum pump 320 as illustrated in FIG. 17, was constructed. The embodiment of the thin drum pump 320 comprises NdFeB magnets ground down to the target size. The magnets were machined using a combination of grinding and wire erosion. In both cases, the pole pieces were machined from mild steel, which has a high magnetic saturation. For this application, saturation is more important than permeability, and eddy currents are not an issue. Therefore, typical transformer steels may not be suitable or optimized for the pump embodiments disclosed herein.

In the two example voice coil pumps that were constructed, the valve chambers were machined from aluminum. Machined aluminum has a poor surface finish compared with typical high-volume injection-molded plastic parts. The poor surface finished of the aluminum parts may negatively affect the sealing performance and capabilities of the valves if not properly controlled. The valve chambers of any of the pump embodiments disclosed herein, such as those of pump assembly embodiments 100 or 200, can be made from injection molded plastic to improve the efficiency of the pumps. In addition, tolerances of machining are high compared with the total valve flap travel (which, in the constructed examples, was approximately 0.25 mm). The machined features can also deviate slightly from the ideal design for reasons of machinability.

The valve plate and diaphragm of the example pumps can be made from cast elastomers, using machined aluminum molds. Again, this may also negatively affect the surface finish of the valve flaps. Valve flaps in both silicone and polyurethane were tested, with a range of shore hardness values: 20 A, 40 A, 60 A and 80 A. Diaphragms were tested in both 30 A and 40 A silicone.

Figure 18:
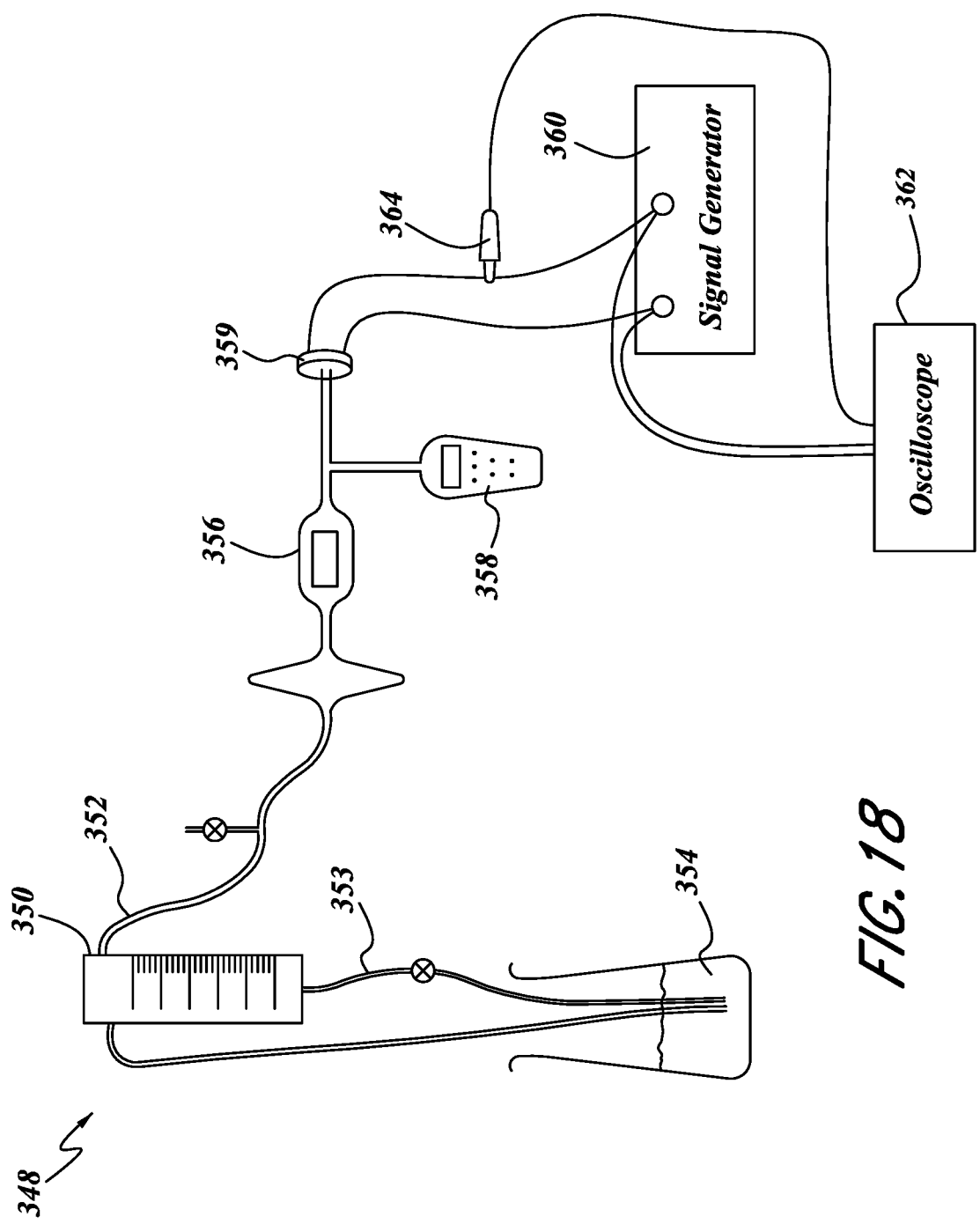
FIG. 18 shows a an illustration of the experimental test setup used to test the first, thick, and the second, thin, experimental pump assemblies.

FIG. 18 shows a schematic of the experimental test setup 348 used to test the thick experimental pump assembly embodiment 300 and the thin experimental pump assembly embodiment. A graduated cylinder 350 was used as a reservoir of air at constant pressure. Tubing 352 runs from the top of the cylinder to a water reservoir 354, and as air is drawn from the graduated cylinder 350, so water is drawn up the tubing 353 to replace it. The constant head of water maintains the pressure within the cylinder at 80 mm Hg below atmospheric pressure (approximately 10% vacuum).

The air is drawn through a TSI 4140 flow meter 356 (a thermal-mass flow meter). This flow meter 356 has an accuracy of ±5 sccm (standard cubic centimetres per minute) for flows of 10-250 sccm. In addition, the flow rate can be independently verified by measuring the rate at which water flows into the graduated cylinder, with an accuracy of ±4% (assuming flows around 100 ml min$^{-1}$, measured over approximately 1 minute). Pressure is determined by the head of water. However, it is also verified with a calibrated manometer 358, and also with a pressure meter built into the TSI 4140 flow meter. The tubing used is 6 mm ID except for the final section from manometer to pump, which is 2.5 mm ID. At the flow rates observed, and over the tubing lengths used, this does not give any significant pressure loss.

The VCA 359 is driven from a signal generator 360. The signal generator output is fed to an oscilloscope 362, monitoring the driving voltage, and a current clamp 364 monitors the current fed to the VCA 359. This data is logged by computer, which multiplies the two signals to determine instantaneous power draw, and averages the power draw over 2.5 seconds (250-500 cycles, for frequencies of 100 Hz-200 Hz, the frequencies used in testing).

The following metrics were used to evaluate pump performance:

Flow rate at approximately 80 mm Hg pressure (the maximum pressure that the NPWT system is expected to draw)

Efficiency, defined as (fluid power out)/(electrical power in). Fluid power is the product of pressure differential and flow rate.

The following experimental outputs were gathered. In both prototypes, peak flow rate was achieved with the 30 A silicone diaphragm and the 60 A polyurethane valve plate, driven by an offset square wave, and peak efficiency was achieved with the same mechanical configuration but driven by an offset sinusoidal or sine wave. The biased signal was, essentially, powering the pump in suction, and then providing a small 'nudge' to expel the air.

The drive signal in any pump embodiments disclosed herein, including those disclosed below, can be offset to increase the power of the stroke in one direction more than the other. For example, In any embodiments disclosed herein, it has been determined that the amount of force required to move the diaphragm in an air intake direction is greater than the amount of force required to move the diaphragm in an air offtake or outflow direction. Therefore, the voltage of the drive signal can be offset to supply more power to the motor during the intake portion of the stroke than the offtake portion of the stroke. Alternatively, any of the pump embodiments can be configured such that the diaphragm or one or more springs (elastomeric, plastic, metallic, or otherwise) bias the diaphragm in one direction more than another, for example, more in the intake direction than the outflow direction such that the pump can operate at optimal efficiency with a symmetrical drive signal (i.e., a non-offset drive signal).

Increasing the diaphragm hardness to 40 A made the pump behave in a more 'resonant' fashion: peak performance required an unbiased signal.

A 40 A valve plate was more tolerant of imperfections in valve housing geometry, but does not respond so quickly, and is therefore less efficient than the 60 A valve when the geometry is close enough to design. Note that the prototype valve housings were aluminium machinings, whose dimensions and surface finish are poorly controlled relative to the plastic mouldings envisaged for full production.

The 20 A valve plate did not respond quickly enough to produce a reasonable flow, and the 80 A valve plate was too stiff for the valves to operate at all.

Experimental results for the thick pump assembly are listed below in Table 1.

Peak efficiencies achieved were 28.4%, for a flow rate of 60 ml min$^{-1}$ at the target pressure. Peak flow rate at the target pressure was 105 ml min$^{-1}$, at an efficiency of 24.1%.

TABLE 1

Thick drum experimental results

|  | Peak efficiency | Peak flow rate |
| --- | --- | --- |
| Pressure/mm Hg | 78.8 | 78.8 |
| Driving signal waveform | Offset sine | Offset square |
| Frequency/Hz | 120 | 120 |
| Peak +ve voltage | 2.7 | 3.0 |
| Peak −ve voltage | 1.3 | 1.0 |
| Power draw/mW | 37 | 76 |
| Diaphragm material | 30 shore A silicone | 30 shore A silicone |
| Valve material | 60 shore A PU | 60 shore A PU |
| Flow rate/ml min$^{-1}$ | 60 | 105 |
| Efficiency | 28.4% | 24.1% |
| Flow rate per power drawn/ml min$^{-1}$ mW$^{-1}$ | 1.62 | 1.38 |

Experimental results for the thin drum pump assembly are listed below in Table 2.

Peak efficiencies achieved were 22.3%, for a flow rate of 118 ml min$^{-1}$ at the target pressure.

Peak flow rate at the target pressure was 137 ml min$^{-1}$, at an efficiency of 22.3%.

Figure 19:
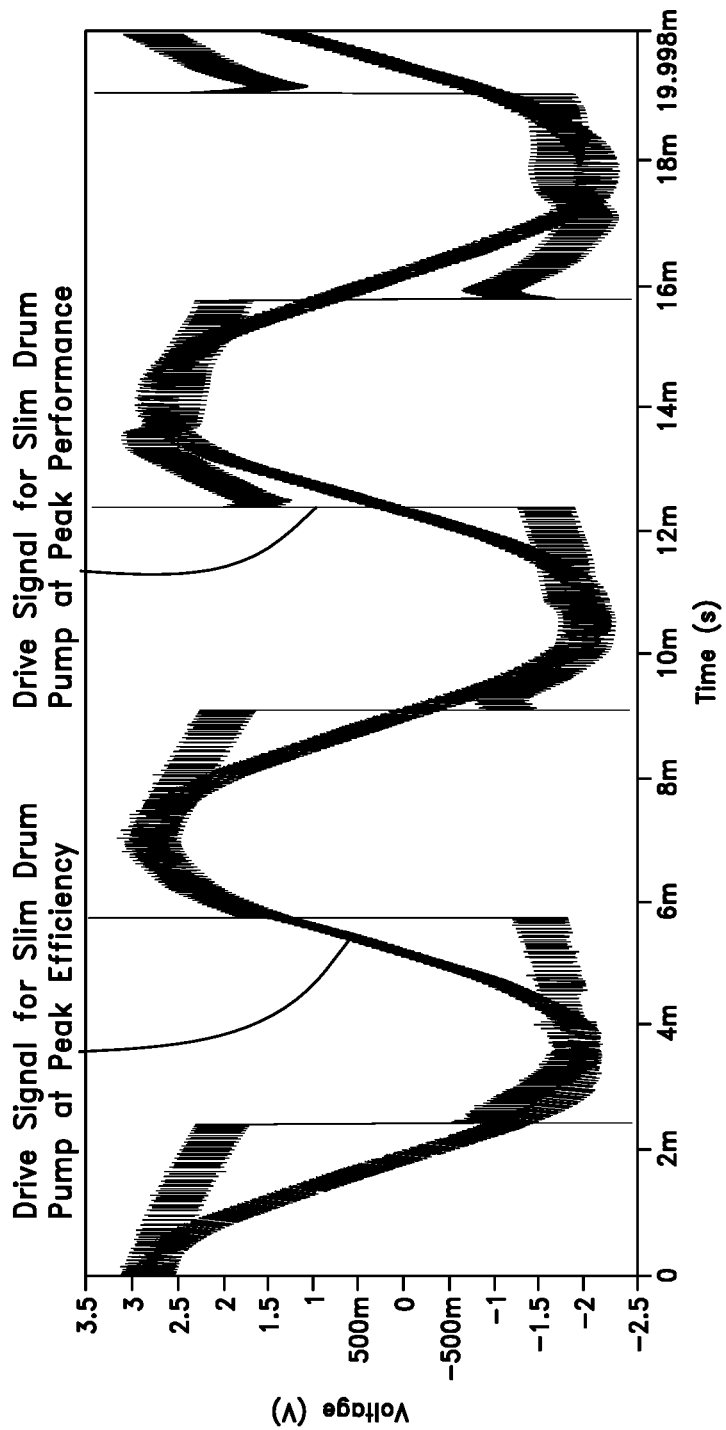
FIGS. 19 and 20 show the measured drive signal and current draw for the second thin drum pump for the two cases described in Table 2.
Figure 20:
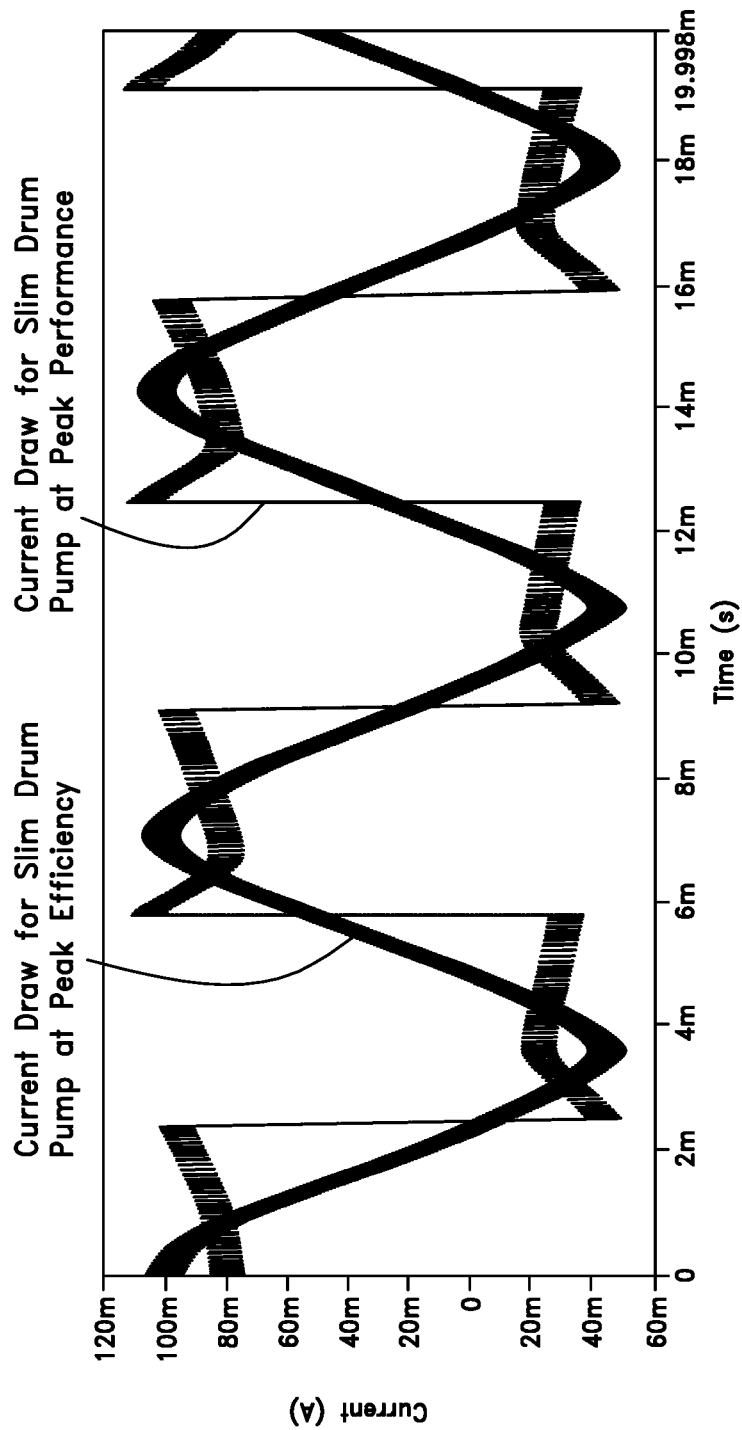
Figure 21:
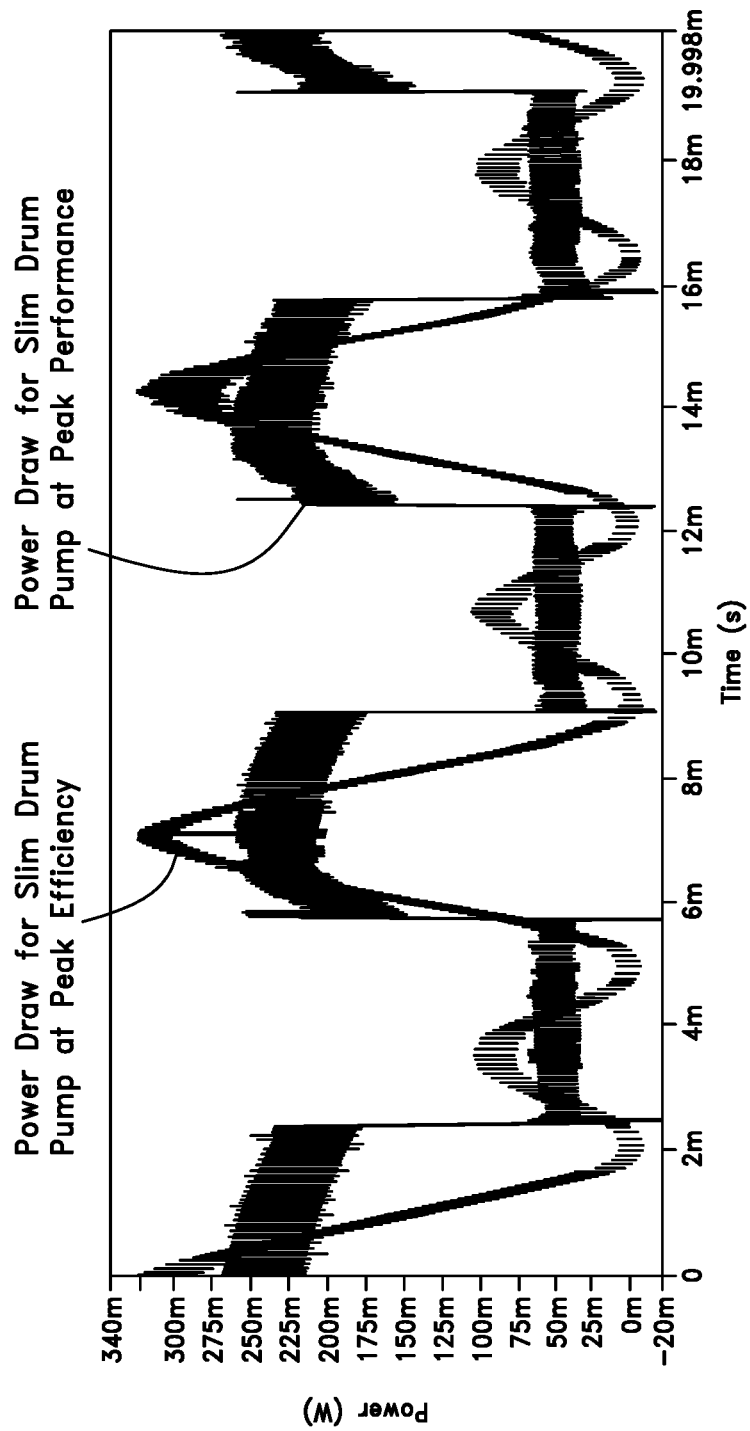
FIG. 21 shows the instantaneous power draw of the second, thin pump.

FIGS. 19 and 20 show the measured drive signal and current draw for the second, thin drum pump for the two cases described in Table 2. FIG. 21 shows the instantaneous power draw of the second, thin pump, which peaks at 320 mW for the sine signal. Note that one half of the signal contains almost all of the power draw (225 mW vs 50 mW, for the square wave signal): this is the 'suction' stroke. Expelling the air to atmosphere requires very little power.

Any of the voice coil actuated pump embodiments disclosed herein can be driven by a signal generator. For example, without limitation, any of the voice coil actuated pump embodiments disclosed herein can be driven by an offset square wave (for example, +3.0 V/−1.0 V), a square wave with a non-50-% duty cycle, an offset sine wave, a symmetric sine wave, a pulsed wave having pulses in either direction (e.g. 35% at +3.0V, 15% rest, 15% −3.0V, 35% rest), pulses in either direction with 'suck' pulse more than half the cycle (e.g. 75% at +3.0V, 25% −3.0V), or any other suitable drive signal.

Figure 22:
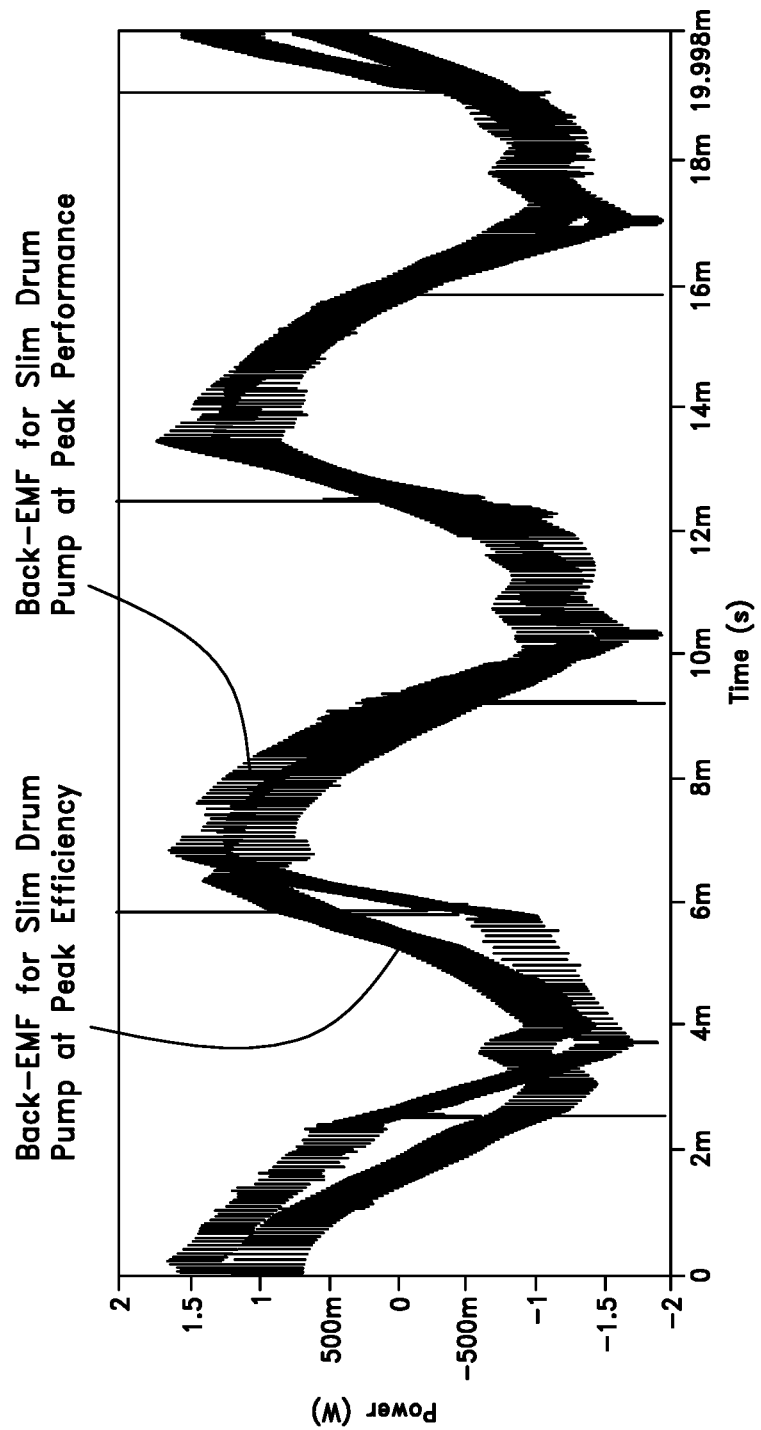
FIG. 22 illustrates the back EMF across the coil of the second, thin pump.

FIG. 22 illustrates the back EMF across the coil, based on a measured coil resistance of 19.5Ω. This is approximately proportional to instantaneous coil velocity, and shows that despite the significant difference in the power draw signal shapes, the motion of the pump is very similar in the two cases.

TABLE 2

Slim drum experimental results

|  | Peak efficiency | Peak flow rate |
| --- | --- | --- |
| Pressure/mm Hg | 80.3 | 80.3 |
| Driving signal waveform | Offset sine | Offset square |
| Frequency/Hz | 140 | 150 |
| Peak +ve voltage | 4.0 | 3.5 |
| Peak −ve voltage | 2.0 | 1.5 |
| Power draw/mW | 94 | 135 |
| Diaphragm material | 30 shore A silicone | 30 shore A silicone |
| Valve material | 60 shore A PU | 60 shore A PU |
| Flow rate/ml min$^{-1}$ | 118 | 138 |
| Efficiency | 22.3% | 18.2% |
| Flow rate per power drawn/ml min$^{-1}$ mW$^{-1}$ | 1.25 | 1.02 |

The following is a discussion of the experimental results. For both thick and thin drum embodiments, there was a single prototype, with valve mating surfaces made from machined aluminium. There were no specific alignment features to aid valve block assembly. Therefore, dismantling and reassembling the valve block typically had a large effect on performance, and it is anticipated that production surface finishes and tolerances would improve performance further.

However, the efficiencies achieved are very good for a vacuum pump on this scale, more than double the peak efficiency obtainable from the pump used in the current-generation ultra-portable NPWT device.

Further reductions in winding losses can be realised, by using production coil winding equipment. Currently, self-bonding wire is used, which is comparatively bulky. If normal insulated wire is used, the coil density can be increased by 50%, leading to a 33% reduction in resistive losses. System simulations suggest that the VCA losses are around 40% of total power draw, and therefore the peak efficiency of Fat Drum could rise to 33%, and the efficiency of Slim Drum could increase to 26%. This would be in addition to gains from improved valve performance (noted above).

Figure 99:
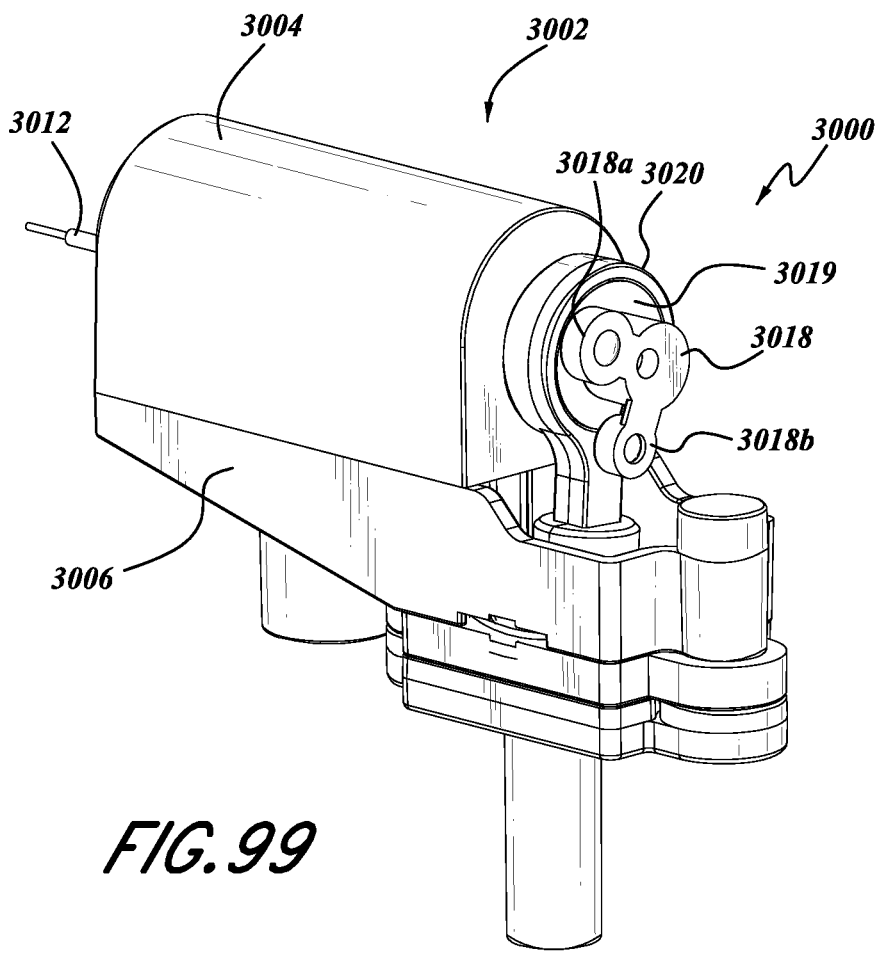
FIGS. 99 and 100 are isometric views of another embodiment of a pump assembly that can be used to provide reduced pressure to a wound dressing.

FIG. 99 is an electrical component schematic 3100 of an embodiment of the pump assembly 100 or any pump assembly embodiment disclosed herein, particularly the voice coil actuated drive pumps. Electrical components can operate to accept user input, provide output to the user, operate the pump assembly and the source of negative pressure, provide network connectivity, and so on. Electrical components can be mounted on one or more PCBs (not shown). The pump assembly can include a controller or processor 3102. In any embodiments disclosed herein, the controller 3102 can be a general purpose processor, such as a low-power processor. In other embodiments, the controller 3102 can be an application specific processor. In any embodiments disclosed herein, the controller 3102 can be configured as a "central" processor in the electronic architecture of the pump assembly, and the controller 3102 can coordinate the activity of other controllers, such as a user interface controller 3106, I/O interface controller 3117, negative pressure control module 3108, communications interface controller 3118, and the like.

The pump assembly can also include a user interface controller or processor 3106 configured to operate one or more components for accepting user input and providing output to the user, such buttons, indicators (e.g., LEDs), displays, etc. Input to the pump assembly and output from the pump assembly can controlled via one or more input/output (I/O) ports 3116 controlled by an I/O interface module or controller 3117. For example, the I/O module 3117 can receive data from one or more I/O ports 3116, such as serial, parallel, hybrid ports, expansion ports, and the like. In any embodiments disclosed herein, I/O ports 3116 include one or more of USB ports, SD ports, Compact Disc (CD) drives, DVD drives, FireWire ports, Thunderbolt ports, PCI Express ports, and the like. The controller 3102, along with other controller or processors, can store data in one or more memory modules 3104, which can be internal and/or external to the schematic 3100. Any suitable type of memory can be used, including volatile and/or non-volatile memory, such as RAM, ROM, magnetic memory, solid-state memory, Magnetoresistive random-access memory (MRAM), and the like. The pump assembly can be powered by a power source 3114, which can comprise one or more disposable or rechargeable batteries, mains, etc. The power source 3114 can be internal or external to the schematic 3100.

A negative pressure or pump control module 3108 can be configured to control the operation of a negative pressure source 3110. The negative pressure source 3110 can be a voice coil pump. Other suitable pumps include diaphragm pumps, peristaltic pumps, rotary pumps, rotary vane pumps, scroll pumps, screw pumps, liquid ring pumps, diaphragm pumps operated by a piezoelectric transducer, and the like. The pump control module 3108 can include a driver module 3109 configured to control the operation of the negative pressure source 3110. For example, the driver module 3109 can provide power to the negative pressure source 3110. Power can be provided in a form of a voltage and/or current signal. In any embodiments disclosed herein, the driver module 3109 controls the negative pressure source 3108 using pulse-width modulation (PWM). A control signal for driving the negative pressure source 3108 (or pump drive signal) can be a 0-100% duty cycle PWM signal.

The controller 3102 can receive information from one or more sensors 3112 placed in a suitable location in a fluid flow path. In any embodiments disclosed herein, the controller 3102 can measure pressure in the fluid flow path, using data received from one or more pressure sensors 3112, calculate the rate of fluid flow, and control the negative pressure source 3110 so that desired level of negative pressure is achieved in a wound cavity or under the dressing. The desired level of negative pressure can be pressure set or selected by a user. Pressure measured by the one or more sensors can be provided to the controller 3102 so that the controller can determine and adjust the pump drive signal to achieve the desired negative pressure level. In any embodiments disclosed herein, the tasks associated with controlling the negative pressure source 3110 can be offloaded to the pump control module 3108, which can include one or more controllers or processors.

In any embodiments disclosed herein, it may be advantageous to utilize multiple processors for performing various tasks. In any embodiments disclosed herein, a first processor can be responsible for user activity and a second processor can be responsible for controlling the negative pressure source. This way, the activity of controlling the negative pressure source, which may necessitate a higher level of responsiveness, can be offloaded to a dedicated processor and, thereby, will not be interrupted by user interface tasks, which may take longer to complete because of interactions with the user.

A communications interface controller or processor 3118 can be configured to provide wired and/or wireless connectivity. The communications processor 3118 can utilize one or more antennas (not shown) for sending and receiving data. In any embodiments disclosed herein, the communications processor 3118 can provide one or more of the following types of connections: Global Positioning System (GPS) technology, cellular or other connectivity, such as 2G, 3G, LTE, 4G, WiFi, Internet connectivity, Bluetooth, zigbee, RFID, and the like. Additionally, any embodiments disclosed herein can be configured to synchronize, upload, or download data to and/or from the pump apparatus to and/or from a portable data device, such as a tablet, smart phone, or other similar devices.

Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. In any embodiments disclosed herein, the communications processor 3118 can provide dual GPS/cellular functionality. Cellular functionality can, for example, be 3G functionality. In such cases, if the GPS module is not be able to establish satellite connection due to various factors including atmospheric conditions, building or terrain interference, satellite geometry, and so on, the device location can be determined using the 3G network connection, such as by using cell identification, triangulation, forward link timing, and the like. In any embodiments disclosed herein, the pump assembly can include a SIM card, and SIM-based positional information can be obtained.

In any embodiments disclosed herein, the performance and efficiency of the pump can be improved by selecting a suitable signal or waveform for driving the coil (e.g., coil 160 of the pump assembly). A suitable driving waveform can be applied to the coil by the controller (e.g., by the driver module 3109). For example, a suitable waveform can be applied to the voice coil actuator (or pump motor). In any embodiments disclosed herein, the pressure differential across a diaphragm of a pump (e.g., diaphragm 166) when the diaphragm is drawing against vacuum (or removing gas from the fluid flow pathway) can be determined as the sum of the pressure drop across the valves and the vacuum level under the dressing. For example, In any embodiments disclosed herein, the negative pressure range can be approximately −80 mmHg, which means that the vacuum level of up to 80 mm Hg can affect the pressure drop across the diaphragm. When the diaphragm is expelling removed gas (e.g., expelling removed air to the atmosphere), the pressure differential across the diaphragm can be determined as the pressure drop across the valves. In other words, when gas is being expelled, the pressure differential across the diaphragm is substantially equivalent to the pressure drop across the valves.

Figure 23:
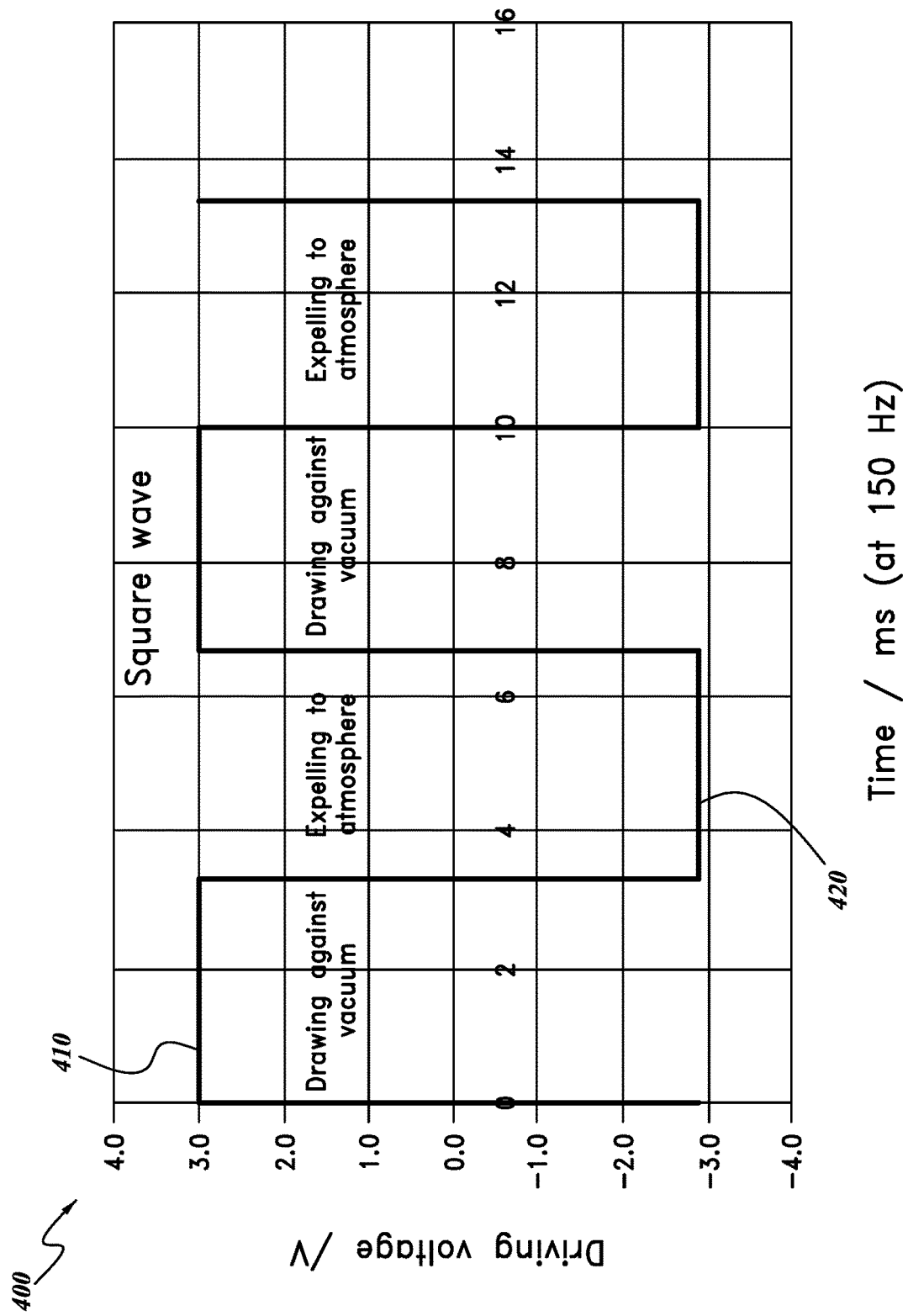
FIGS. 23-26 illustrate waveforms of various signals for driving a diaphragm.

In any embodiments disclosed herein, the force for expelling removed gas can be smaller than the force for drawing vacuum (e.g., removing gas from the fluid flow pathway). If a symmetric signal, such as a square wave or sine wave of equal positive and negative amplitude is applied to the coil, the diaphragm may oscillate about a point that is not its relaxed center state, which may reduce the total diaphragm travel. One such signal is illustrated in FIG. 23, which depicts a symmetric square wave voltage signal 400 that can be applied to the coil. In any embodiments disclosed herein, symmetric signals, such as that depicted in FIG. 23, can be used to drive the coil, which thereby causes the diaphragm to flex and deflect. Although a voltage waveform is depicted, it will be understood that waveform of current applied to the coil can be alternatively or additionally illustrated. As is shown, symmetrical voltage signal of magnitude between −3.0 V and 3.0 V is applied to the coil at a frequency of 150 Hz, which can cause the diaphragm to flex and deflect so that the diaphragm oscillates to draw vacuum (depicted as region 410) and to expel the removed gas (depicted as region 420). As is illustrated, the waveforms applied in regions 410 and 420 are identical with the exception of the reversal of voltage magnitude (e.g., so that the diaphragm oscillates in opposite directions in regions 410 and 420). In any embodiments disclosed herein, other suitable magnitudes of voltage can be used, such as between −1.0 V and 1.0V, −2.0 V and 2.0 V, −4.0 V and 4.0 V, and so on. In any embodiments disclosed herein, increasing the voltage can increase the flow rate of the pump assembly, but can result in greater energy losses in the coil, which can decrease the operating efficiency of the pump.

Any suitable frequency of the driving waveform can be used, such as frequencies less than or greater than 150 Hz.

In any embodiments disclosed herein, driving the coil with using a symmetrical waveform can reduce the performance and efficiency of the pump. Such reduction in performance and efficiency can be avoided by utilizing a stiffer diaphragm (e.g., so that deflection resulting from the vacuum level under the dressing is negligible). However, In any embodiments disclosed herein, its may be advantageous to have the natural frequency of the diaphragm-coil assembly match the frequency at which the valves perform substantially optimally. In such cases, increasing the diaphragm stiffness may require the use of valves to having a faster response or may require the use of a heavier coil (which can increase the vibration felt by a user and may also generate more operational noise). In addition, with increase in the diaphragm stiffness, more energy is put into it in each oscillation cycle, which may cause greater hysteric losses in the diaphragm elastomer.

In any embodiments disclosed herein, in order to achieve substantially optimal efficiency, a soft diaphragm can be driven by a biased drive signal(s). Such signal(s) can, In any embodiments disclosed herein, combine an oscillating force to drive the diaphragm and a constant force for countering the pressure differential due to the vacuum under the dressing. The diaphragm can achieve full travel, which can be important for effective and efficient operation of the pump.

Figure 24:
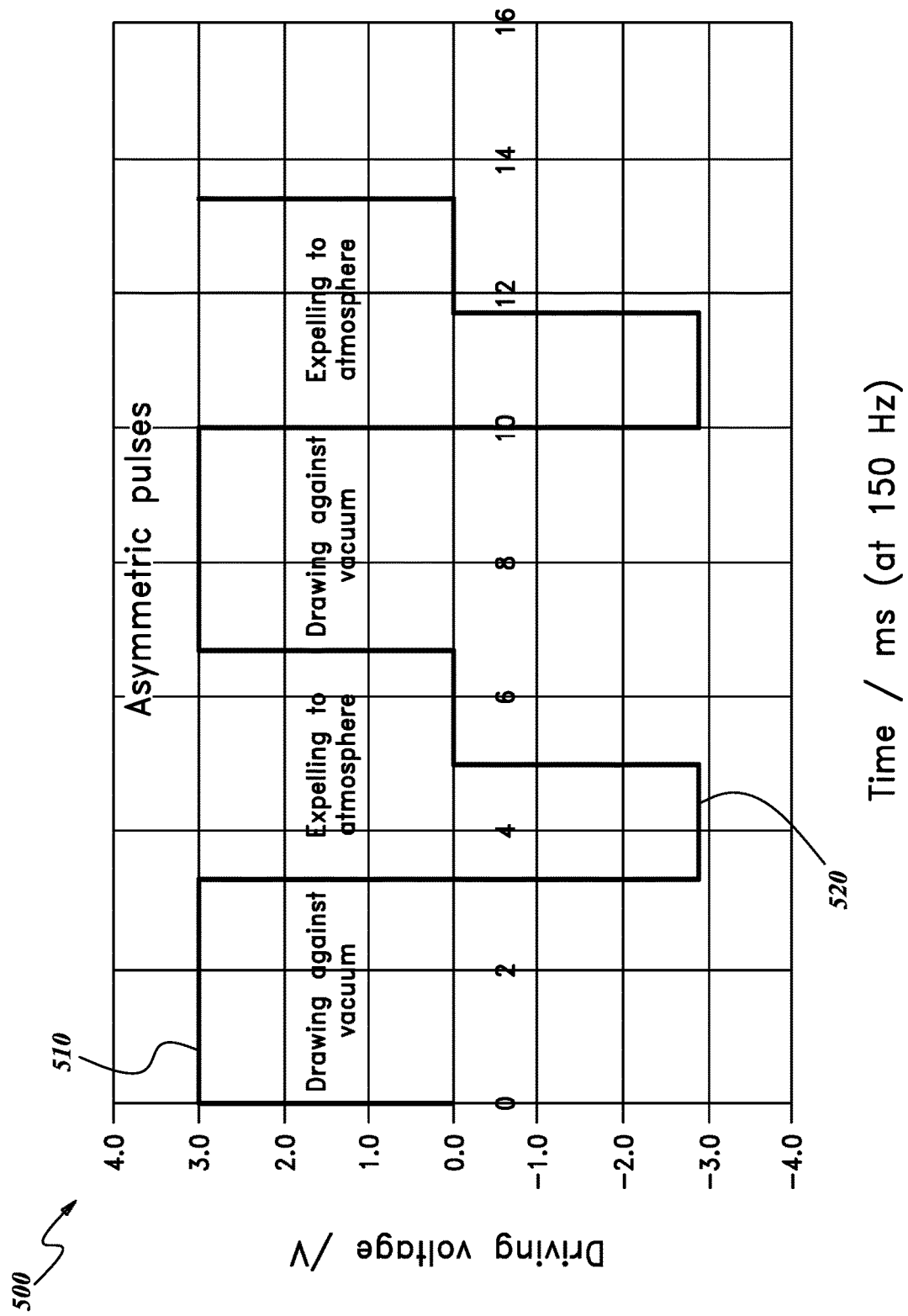
Figure 25:
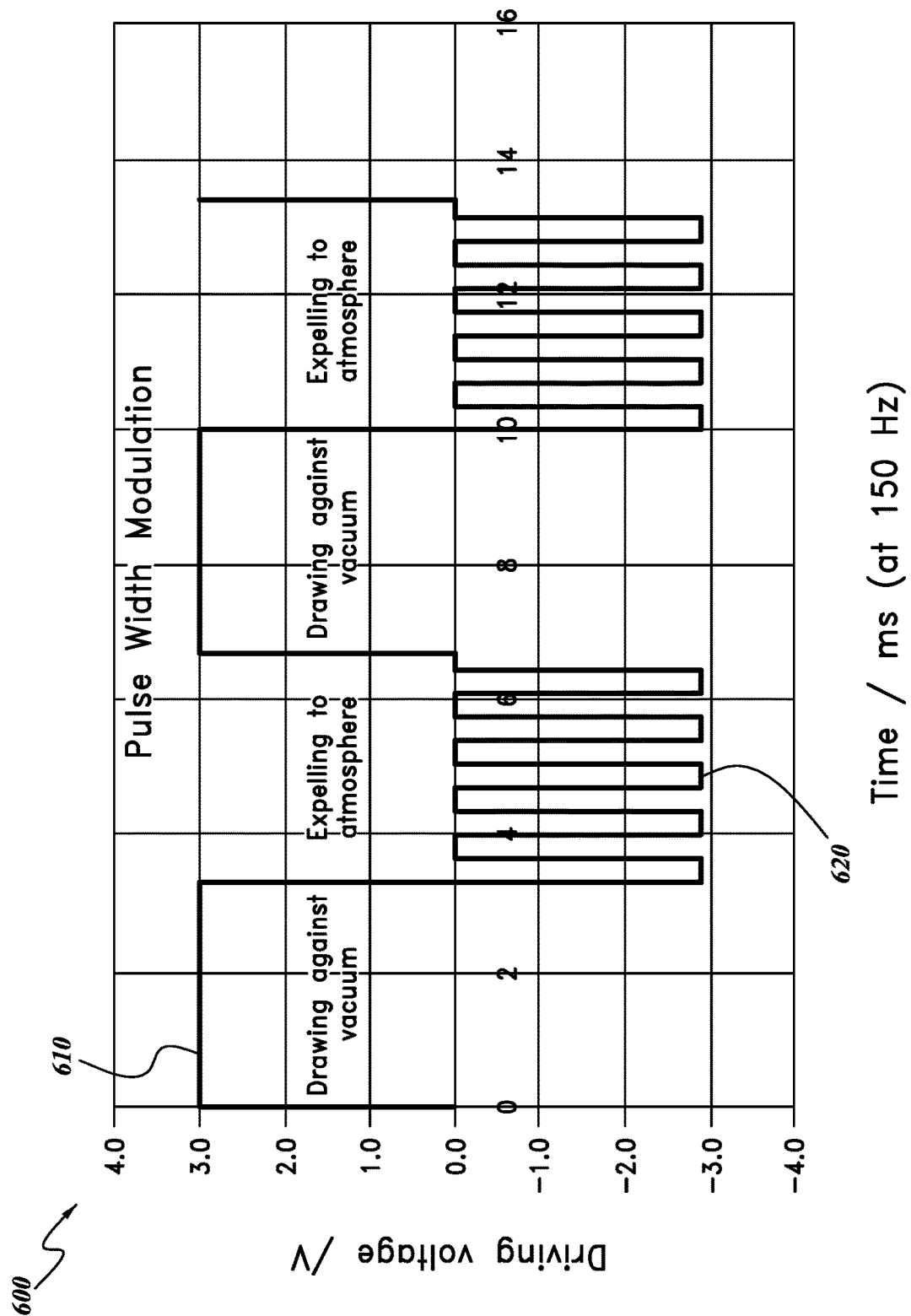
Figure 26:
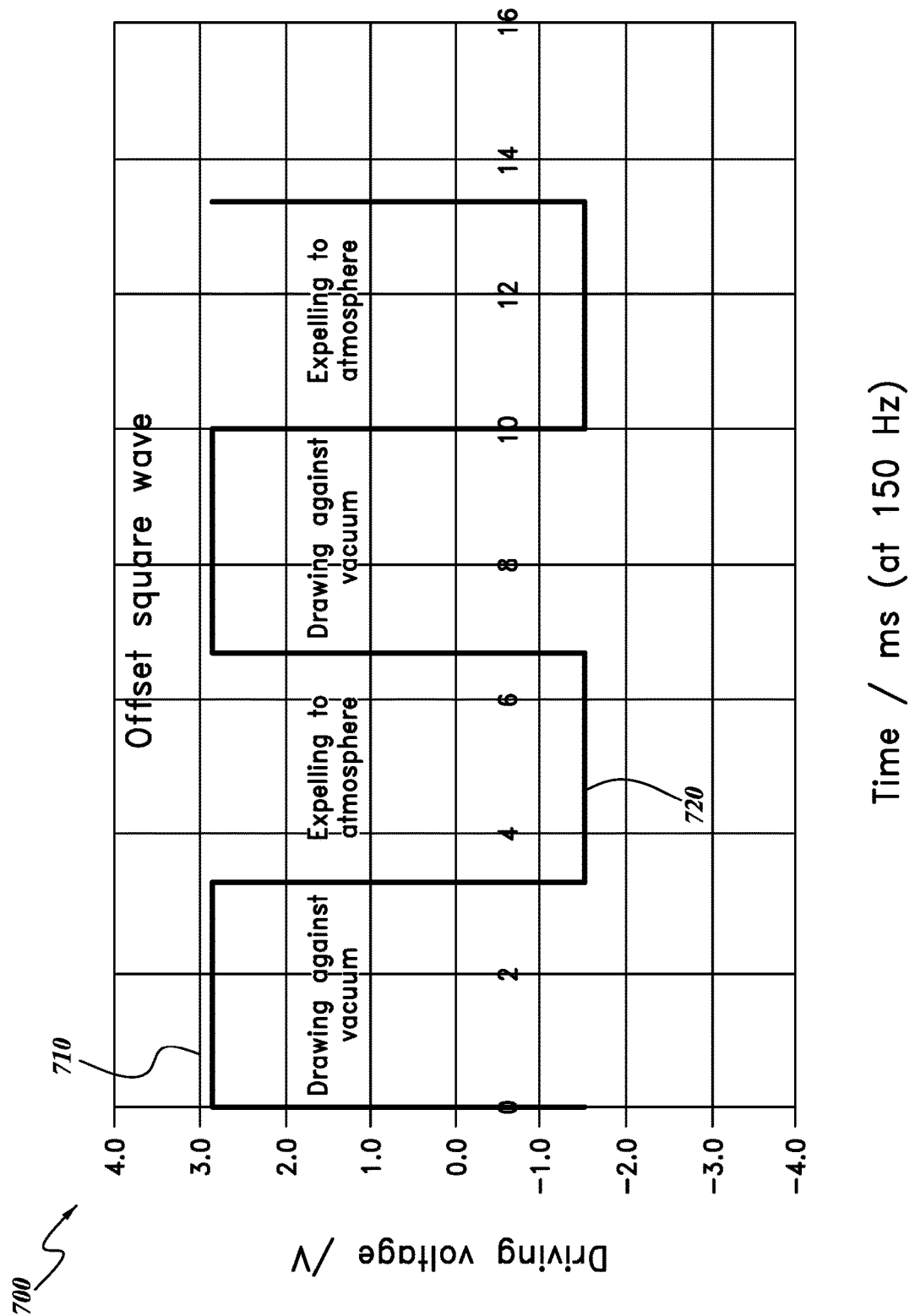

Examples of biased drive signals are illustrated in FIGS. 24-26. FIG. 24 illustrates an asymmetric pulse voltage signal 500 that can be applied to the coil. In any embodiments disclosed herein, the signal depicted in FIG. 24 can be used to drive the coil, which thereby causes the diaphragm to flex and deflect. Although a voltage waveform is depicted, it will be understood that waveform of current applied to the coil can be alternatively or additionally illustrated. As is shown, asymmetrical voltage signal of magnitude between −3.0 V and 3.0 V is applied to the coil at a frequency of 150 Hz, which can cause the diaphragm to flex and deflect so that the diaphragm oscillates to draw vacuum (depicted as region 510) and to expel the removed gas (depicted as region 520). As is illustrated, the waveforms applied in regions 510 and 520 are not the same. Less power (e.g., average power, total power, etc.) is applied to the coil in region 520 (e.g., when gas is expelled), thereby causing less force to be applied to the diaphragm when gas is expelled. In any embodiments disclosed herein, other suitable magnitudes of voltage can be used, such as between −1.0 V and 1.0V, −2.0 V and 2.0 V, −4.0 V and 4.0 V, and so on. Any suitable frequency of the driving waveform can be used, such as frequencies less than or greater than 150 Hz.

FIG. 25 illustrates a pulse width modulated voltage signal 600 that can be applied to the coil. In any embodiments disclosed herein, the signal depicted in FIG. 25 can be used to drive the coil, which thereby causes the diaphragm to flex and deflect. Although a voltage waveform is depicted, it will be understood that waveform of current applied to the coil can be alternatively or additionally illustrated. As is shown, asymmetrical voltage signal of magnitude between −3.0 V and 3.0 V is applied to the coil at a frequency of 150 Hz, which can cause the diaphragm to flex and deflect so that the diaphragm oscillates to draw vacuum (depicted as region 610) and to expel the removed gas (depicted as region 620). As is illustrated, the waveforms applied in regions 610 and 620 are not the same. Due to pulse width modulation of the waveform, less power (e.g., average power, total power, etc.) is applied to the coil in region 620 (e.g., when gas is expelled), thereby causing less force to be applied to the diaphragm when gas is expelled. In any embodiments disclosed herein, other suitable magnitudes of voltage can be used, such as between −1.0 V and 1.0V, −2.0 V and 2.0 V, −4.0 V and 4.0 V, and so on. Any suitable frequency of the driving waveform can be used, such as frequencies less than or greater than 150 Hz.

FIG. 26 illustrates an offset square wave voltage signal 700 that can be applied to the coil. In any embodiments disclosed herein, the signal depicted in FIG. 26 can be used to drive the coil, which thereby causes the diaphragm to flex and deflect. Although a voltage waveform is depicted, it will be understood that waveform of current applied to the coil can be alternatively or additionally illustrated. As is shown, asymmetrical voltage signal of magnitude between −3.0 V and 3.0 V is applied to the coil at a frequency of 150 Hz, which can cause the diaphragm to flex and deflect so that the diaphragm oscillates to draw vacuum (depicted as region 710) and to expel the removed gas (depicted as region 720). As is illustrated, the waveforms applied in regions 710 and 720 are not the same. Due to pulse width modulation of the waveform, less power (e.g., average power, total power, etc.) is applied to the coil in region 720 (e.g., when gas is expelled), thereby causing less force to be applied to the diaphragm when gas is expelled. In any embodiments disclosed herein, other suitable magnitudes of voltage can be used, such as between −1.0 V and 1.0V, −2.0 V and 2.0 V, −4.0 V and 4.0 V, and so on. Any suitable frequency of the driving waveform can be used, such as frequencies less than or greater than 150 Hz. It will be appreciated that other suitable drive signals can be used in other embodiments. For example, pulse duration modulated waveforms, offset sinusoidal waveforms, offset sawtooth waveforms, assymetric sinusoidal waveforms, asymmetrical sawtooth waveforms, etc. can be used.

Figure 100:
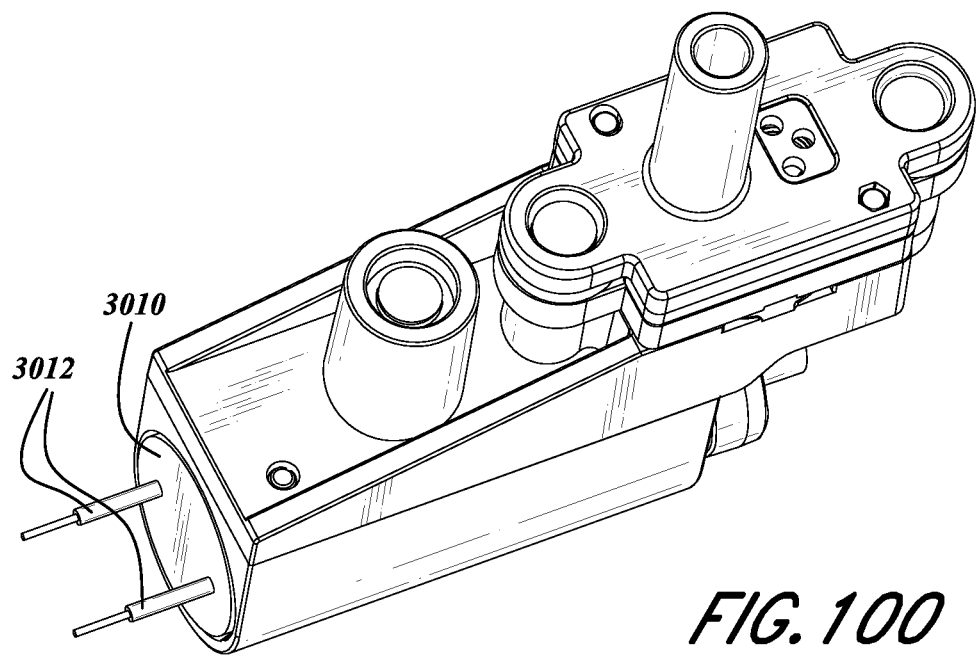

In any embodiments disclosed herein, in order to achieve a substantially optimal pumping efficiency, a soft diaphragm can be driven by an offset sinusoidal drive signal. For example, the driving signal can be applied to the voice coil actuator of the pump, thereby causing the diaphragm to flex and deflect. FIG. 100 illustrates an offset sine waveform 3120 that can be applied to the coil according to some embodiments. The x-axis represents time and the y-axis represents voltage. The sine wave 3122 is offset from 0 V as is shown by line 3124, which is about 0.4 V. Any suitable offset can be used, such as 0.05 V, 0.1 V, 0.65 V, etc. The sine wave 3122 can be applied to the pump (and the diaphragm) as is illustrated in 3125. In one embodiment, the sine wave 3122 can be applied to the voice coil actuator, thereby causing the voice coil to move and the diaphragm to flex and deflect. The sine wave 3120 can be a signal of a suitable magnitude, such as 5.3 V, less than 5.3V, or more than 5.3 V. Although the illustrated sine wave 3120 is a voltage signal, a current signal can be used for driving the diaphragm. The sine wave 3120 can be of a suitable frequency, such as from approximately 50 Hz to approximately 200 Hz, or from approximately 25 Hz or less to approximately 300 Hz or more. Other frequencies can be used, such as frequencies below 50 Hz and above 200 Hz.

In any embodiments disclosed herein, driving the diaphragm with a sine wave signal, such as the offset sine wave 3122, increases the efficiency of the negative pressure source. For example, because the sine wave 3122 has a single frequency, that frequency only stimulates a single vibrational or resonance mode of the pump (e.g., the first vibrational mode of the pump is stimulated provided that the other modes have a higher natural or resonant frequency). Efficiency can be optimized if the pump only moves or resonates at a single frequency. For instance, the axial spring stiffness of the diaphragm and the offset of the sine wave can be optimized for greater efficiency. In addition, little or no driving energy may be absorbed by components other than the diaphragm, such as rubber components. In contrast, In any embodiments disclosed herein, a square wave driving signal is more difficult to optimize because the square wave comprises decaying frequency components that are multiples of a base frequency. These higher frequency components can excite higher vibrational modes of the system, which can make the overall behaviour of the pump less predictable and more difficult to optimize. In any embodiments disclosed herein, using a square wave driving signal generates higher flow at a cost of lower efficiency.

In any embodiments disclosed herein, non-offset sine wave drive signals can be used. In various embodiments, other periodic signals such as cosine waves, tangent waves, square, triangular waves, sawtooth waves, pulse duration modulated waveform, and the like can be used to drive the diaphragm. Signals driving the diaphragm can be symmetrical or asymmetrical and/or offset or not offset. In certain embodiments, non-periodic driving signals are used.

Figure 101:
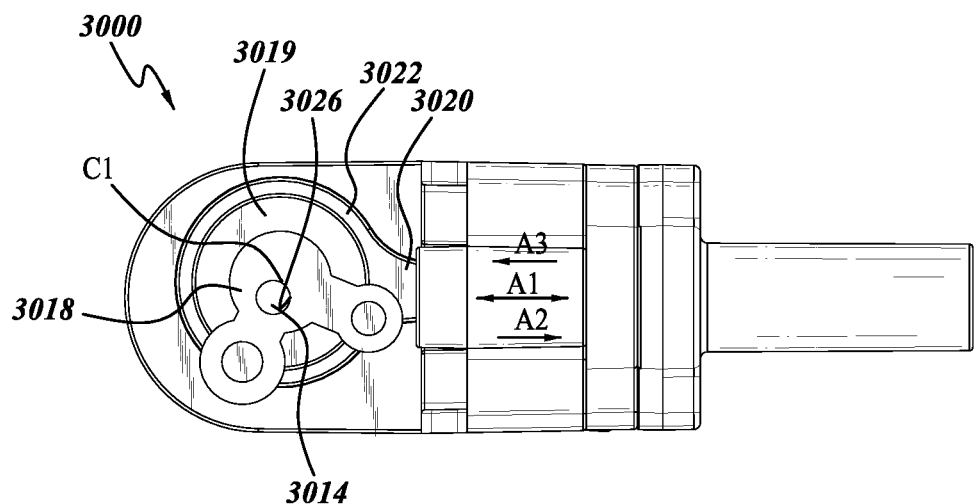
FIG. 101 is an end view of the pump assembly embodiment shown in FIG. 99.

FIG. 101 illustrates generation of the sine wave 3122 according to some embodiments. Two 180 degree phase shifted sine waves 3132 and 3134 can be combined to generate the sine wave 3122. The sine waves 3132 and 3134 can have different amplitudes, such as peak-to-peak amplitudes. In any embodiments disclosed herein, sine wave 3134 is subtracted from sine wave 3132 and applied to the diaphragm as is illustrated in 3135. In any embodiments disclosed herein, the sine waves 3132 and 3134 can be phase shifted with respect to each other with any suitable phase shift value selected from the range between 0 and 360 degrees. In various embodiments, sine waves 3132 and 3134 can be combined in any linear or non-linear manner.

Figure 102:
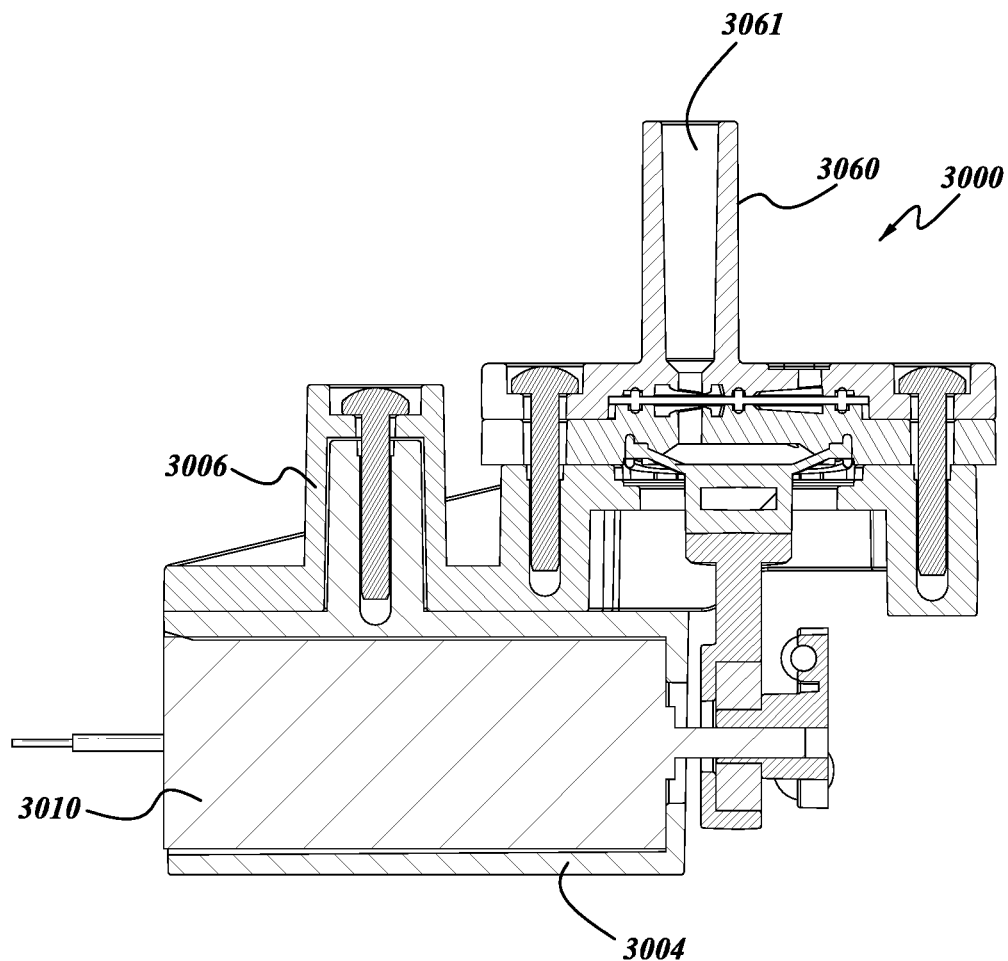
FIG. 102 is a sectional view of the pump assembly embodiment shown in FIG. 99.

FIG. 102 illustrates generation of the sine waves 3132 and 3134 according to some embodiments. One or more PWM drive signals 3142 can be generated by the driver module 3109. These signals, which can be represented as a combination of square waves at different frequencies, are filtered by a filter 3144, which can be a low-pass filter. In any embodiments disclosed herein, filtering the one or more PWM drive signals 3142 produces the sine waves 3132 and 3134. In any embodiments disclosed herein, two PWM drive signals 3142 are used to produce the sine waves 3132 and 3134. Each of the PWM drive signals 3142 can be a signal having appropriate characteristics, such as amplitude, for generating the respective sine wave signal 3132 or 3134.

In any embodiments disclosed herein, the voice coil actuator or motor is used as the filter 3144. The voice coil motor can behave as a resonant circuit, such as an LC or RLC circuit, that has low-pass filter characteristics. In one embodiment, the motor can have the following characteristics: resistance R=20Ω, inductance L=1 mH, and time constant τ=50 μs. In any embodiments disclosed herein, a suitable separate filter 3144 can be used. In certain embodiments, the filter 3144 can have high pass, band pass, band stop, and/or notch characteristics. In any embodiments disclosed herein, the sine wave 3122 can be generated directly from the one or more PWM signals.

Figure 103:
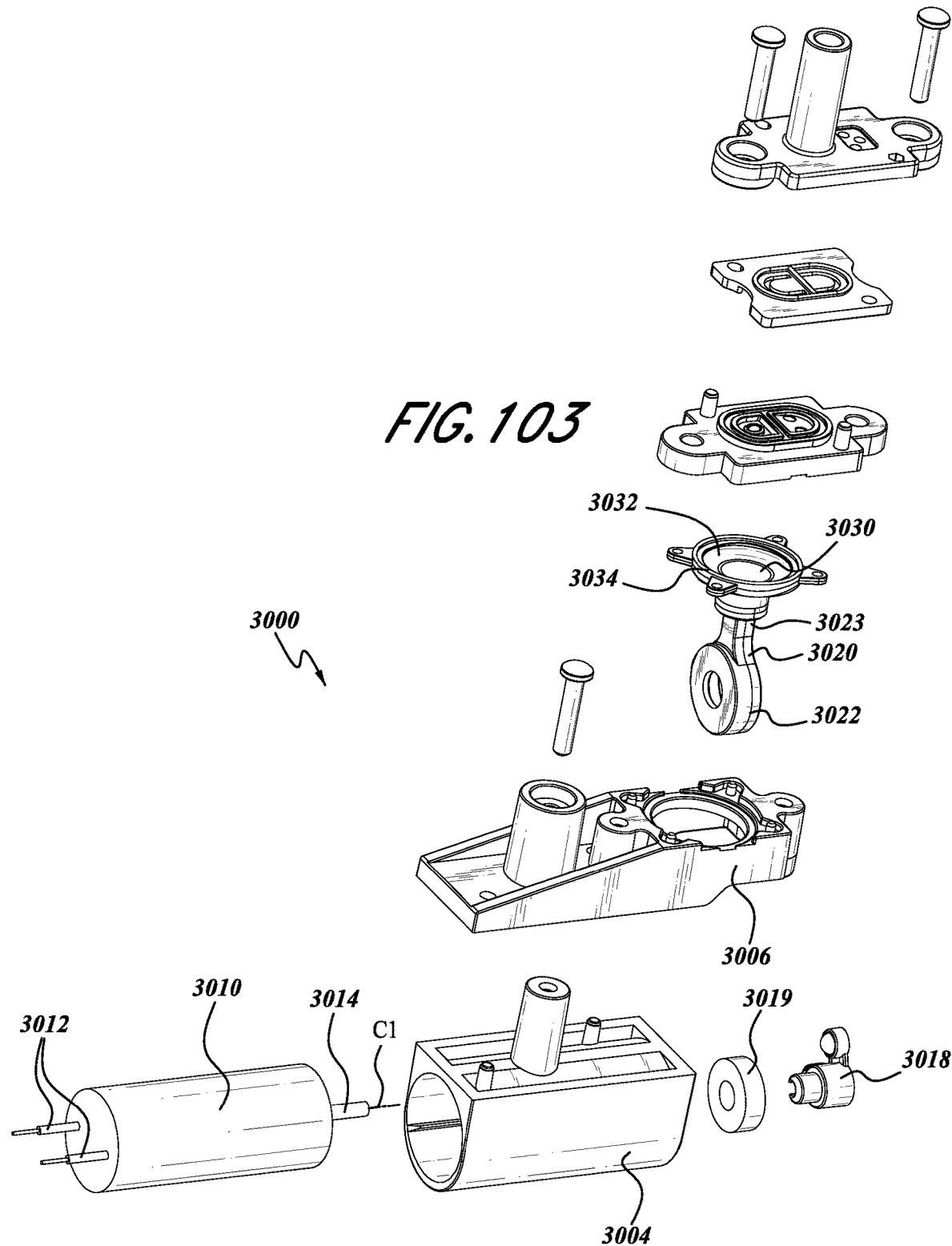
FIG. 103 is an exploded view of the pump assembly embodiment shown in FIG. 99.

FIG. 103 illustrates a circuit 3150 for generating one or more PWM drive signals, such as signals 3142, used to generate the sine waves 3132 and 3134 according to some embodiments. The circuit 3150 can be part of the driver module 3109. The circuit 3150 includes switches 3151, 3152, 3153, and 3154, which can be transistor switches. Two PWM control signals 3156 and 3158 are used to drive the respective pair of switches 3151, 3152 and 3153, 3154. The PWM control signals 3156 and 3158 can cause the switches to toggle, which produces the desired one or more PWM drive signals for driving the pump. PWM control signals 3156 and 3158 can be generated by the controller 3102. In any embodiments disclosed herein, the circuit 3150 can be an H bridge circuit. In various embodiments, using the circuit 3150 results in pumping efficiency of approximately 90% or higher.

In any embodiments disclosed herein, linear driving can be used to generate the one or more PWM signals used to generate the sine waves 3132 and 3134. One example of linear driving is using a digital-to-analog converter (DAC) in conjunction with an amplifier, such as an audio amplifier (e.g., class A, class B, class C, class D, etc. amplifier). A digital controller, such as the controller 3102, can generate a digital control signal, such as a PWM signal, that is converted into an analog signal by the DAC. The analog signal output by the DAC can be amplified by the amplifier and can be used for driving the motor. In any embodiments disclosed herein, using switching driving, such as that illustrated in circuit 3150, provides a higher efficiency than that achieved with linear driving.

Figure 104:
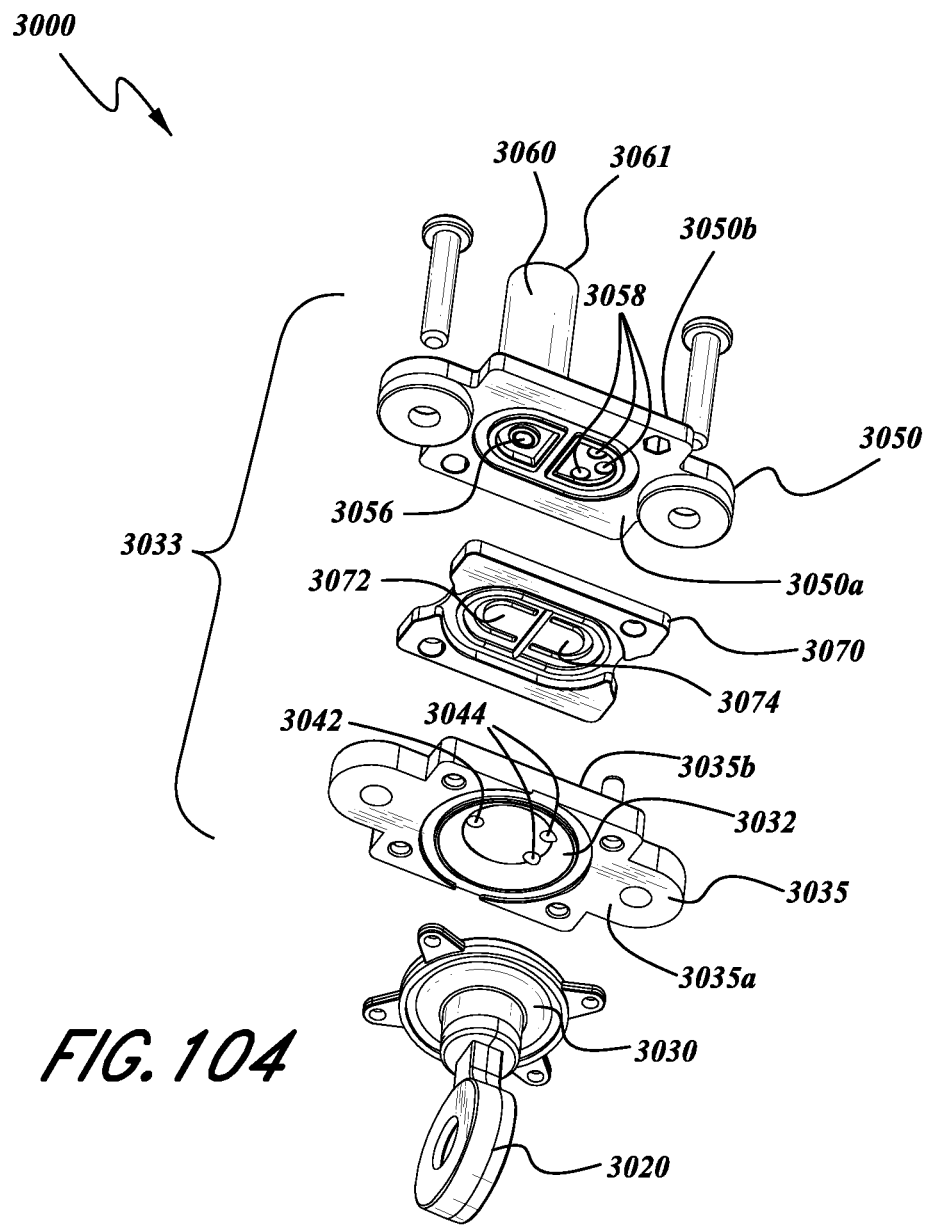
FIG. 104 is an exploded view of some components of the pump assembly embodiment shown in FIG. 99.

FIG. 104 illustrates a diagram 3170 of a position of the diaphragm according to an embodiment of a pump assembly. Graph 3172 illustrates a driving signal applied to the pump. In any embodiments disclosed herein, the driving signal is offset as is illustrated in graph 3172. For example, the positive portion of the driving signal can have a peak amplitude of +3 V, and the negative portion of the driving signal can have a peak amplitude of −1.5 V. As explained above, In any embodiments disclosed herein, the force for expelling removed gas can be smaller than the force for drawing vacuum, and using an offset driving signal can improve pumping efficiency. In certain embodiments, a non-offset driving signal is used. In any embodiments disclosed herein, applying the driving signal 3172 results in the diaphragm moving as is illustrated by 3174. The diaphragm oscillates between +0.5 mm and −0.5 mm with respect to a resting position. In any embodiments disclosed herein, the diaphragm can oscillate between any other suitable position, such as positions greater or lesser than +0.5 mm and −0.5 mm.

FIGS. 27A-27G are an isometric view, a top view, a bottom view, a top end view, a bottom end view, a first side view, and a second side view, respectively, of an embodiment of a pump assembly 800. The pump assembly 800 can have a casing 802 that can be used or adapted to support any suitable type of pump motor or actuator. This can include, without limitation, any of the voice coil actuated pump embodiments disclosed herein (such as, without limitation, pump disclosed above), a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combination of the foregoing pumps. In any embodiments disclosed herein, the pump housing 802 can be configured to support the components of the pump directly therein such that some or a portion of the components of the pump housing that may otherwise be on the pump can be eliminated, with the housing 802 providing the necessary support for pump components. Any of the pump assembly embodiments disclosed herein, including without limitation pump assembly 800, can be used with any of the dressing embodiments disclosed herein or otherwise.

In any of the pump assembly embodiments disclosed herein, as in the embodiment illustrated in FIGS. 27A-27G, the pump assembly can be a canisterless pump assembly (meaning that the pump assembly does not have an exudate or liquid collection canister). However, any of the pump embodiments disclosed herein can be configured to include or support a canister, either within the pump casing, attached to or supported by the pump casing, or otherwise. Additionally, in any of the apparatus embodiments disclosed herein, any of the pump assembly embodiments can be mounted to or supported by the dressing, or adjacent to the dressing. The dressing may be positioned and sealed over any suitable wound, as described in greater detail in U.S. patent application Ser. No. 13/092,042, which disclosure is hereby incorporated by reference and made part of this disclosure, and a conduit may then be connected to the dressing.

Dressing embodiments that are usable with the pump assembly 800, or any other pump assembly embodiment disclosed herein, can have any of the materials, sizes, components, or other details of any of the dressing embodiments disclosed in U.S. patent application Ser. No. 13/092, 042, and such embodiments and illustrations thereof are hereby incorporated by reference in their entireties as if made part of this disclosure. The conduit used to communicate the reduced pressure from the pump assembly to the dressing, or any other conduit disclosed herein, can be formed from polyurethane, PVC, nylon, polyethylene, silicone, or any other suitable material.

As mentioned, some embodiments of the apparatus are designed to operate without the use of an exudate canister. The dressing can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. The pump can be programmed to automatically terminate therapy after a desired number of days, e.g., after seven days, further operation of the pump will not be possible. Some embodiments are designed for longer or repeated usage, and can be configured to support an exudate canister.

In any embodiments disclosed herein, as in the illustrated embodiment, the pump assembly 800 can be of a sufficiently small and portable size to be supported on a user's body or in a user's clothing. For example, the pump assembly 800 can be sized to be attached using adhesive medical tape or otherwise to a person's skin in a comfortable location, adjacent to or on the dressing or otherwise. Further, the pump assembly 800 can be sized to fit within a person's pants or shirt pocket, or can be tethered to a person's body using a lanyard, pouch, or other suitable device or article.

Figure 27A:
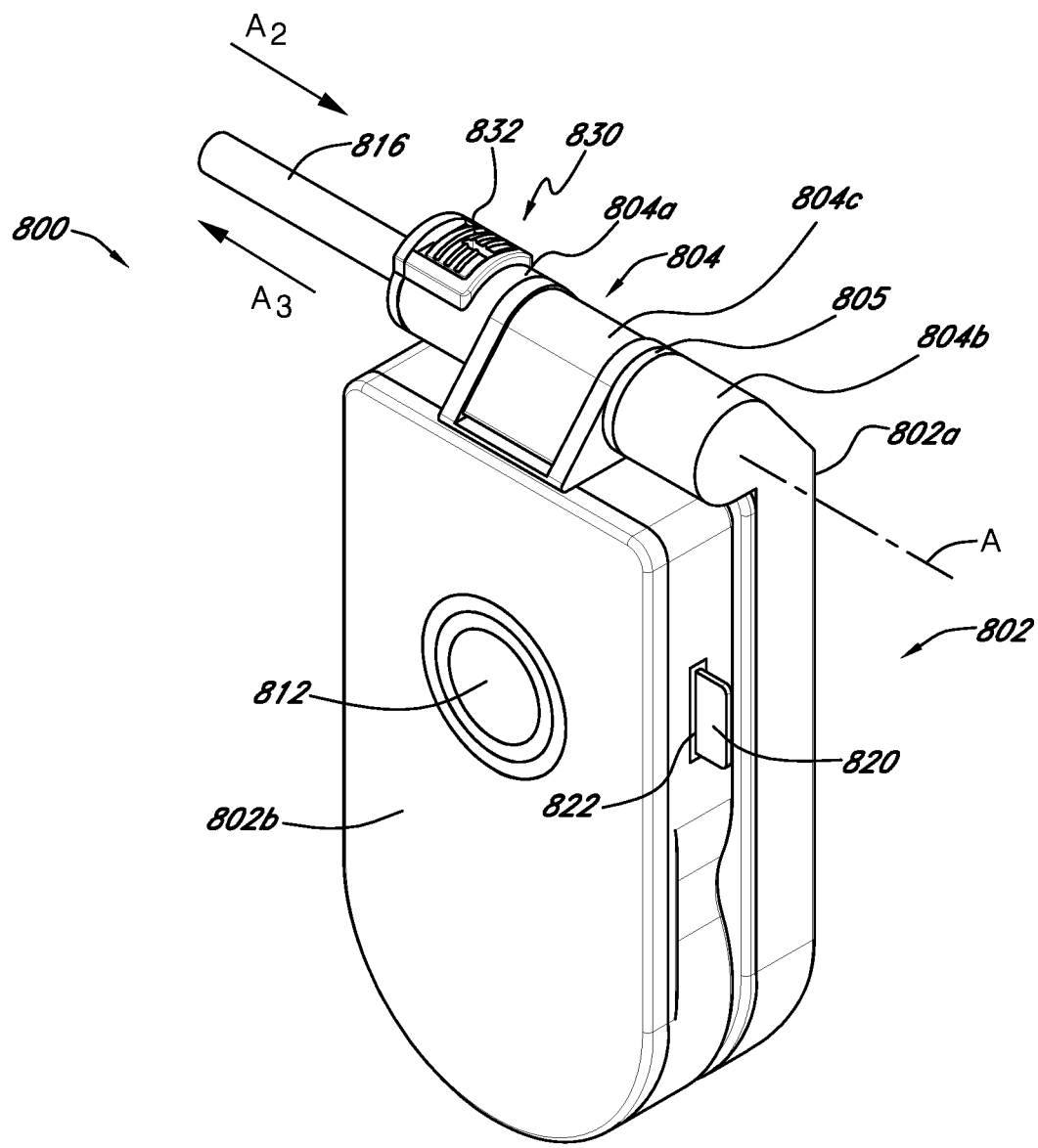
FIGS. 27A-27G are an isometric view, a top view, a bottom view, a top end view, a bottom end view, a first side view, and a second side view, respectively, of an embodiment of a pump assembly.
Figure 27B:
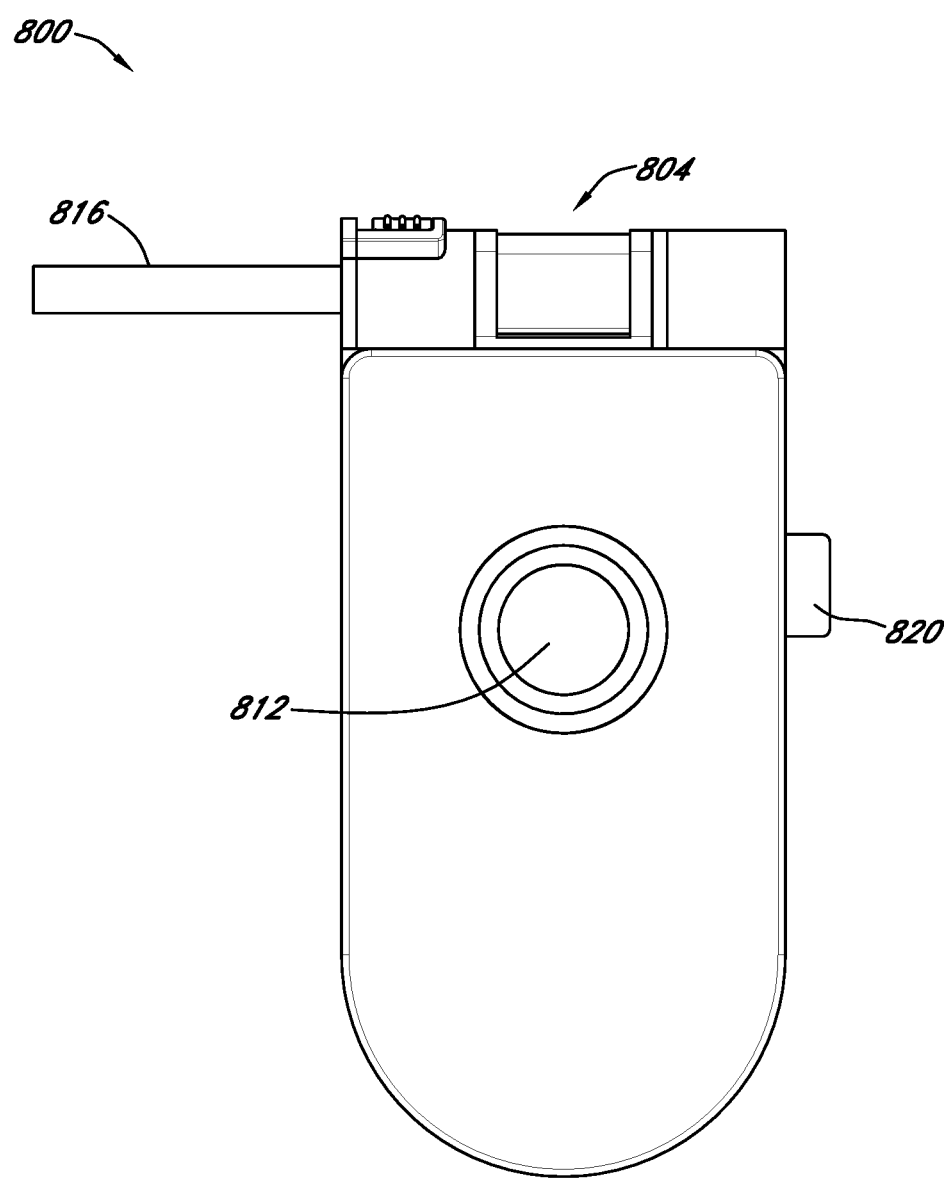
Figure 27C:
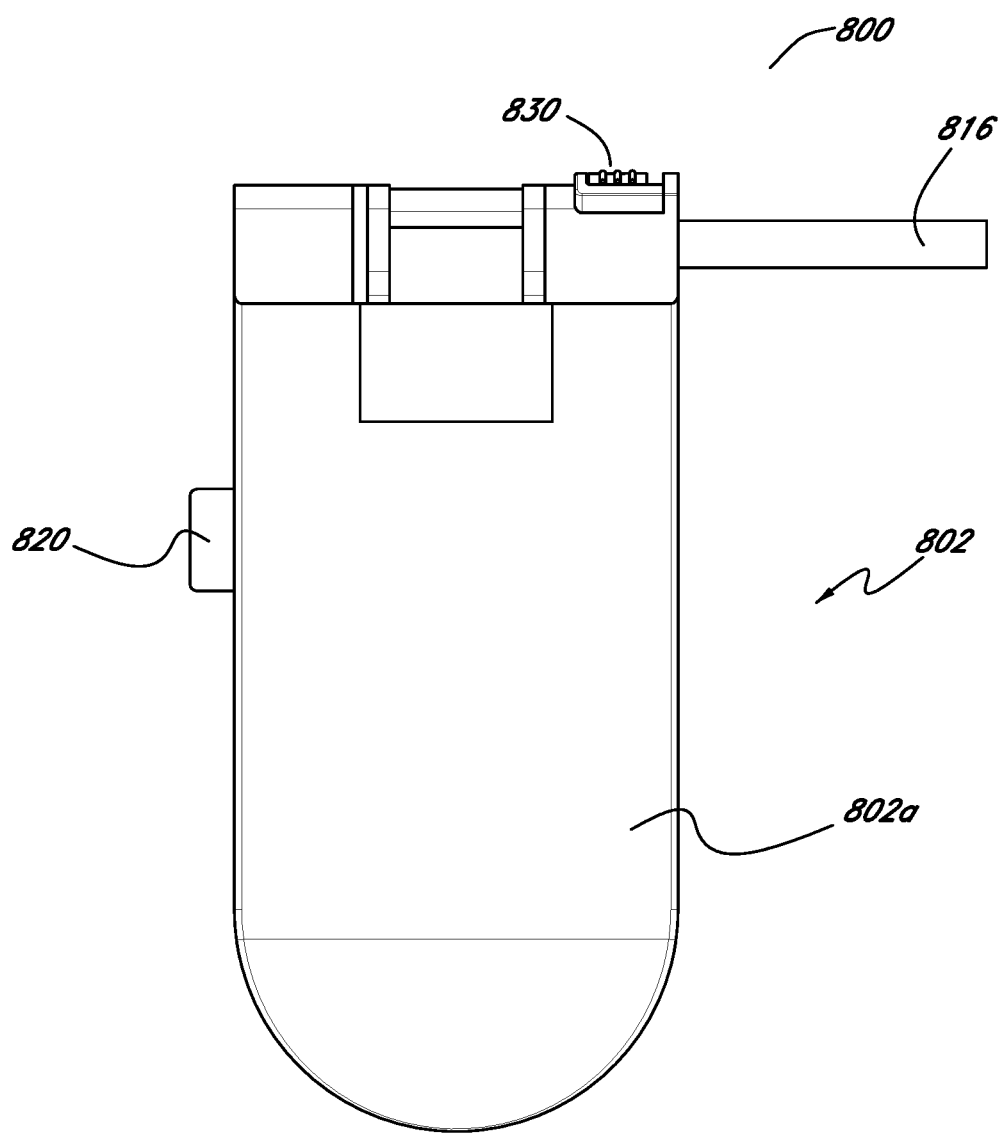
Figure 27D:
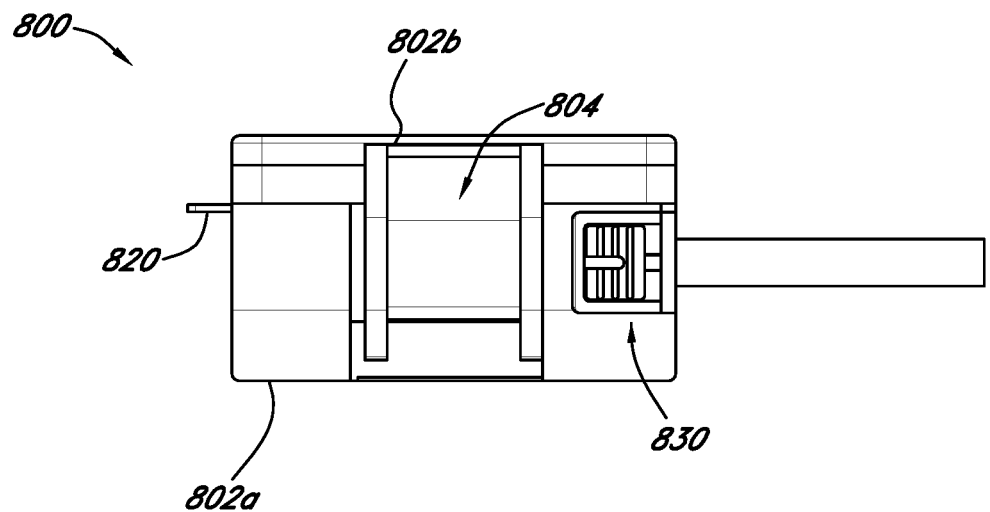
Figure 27E:
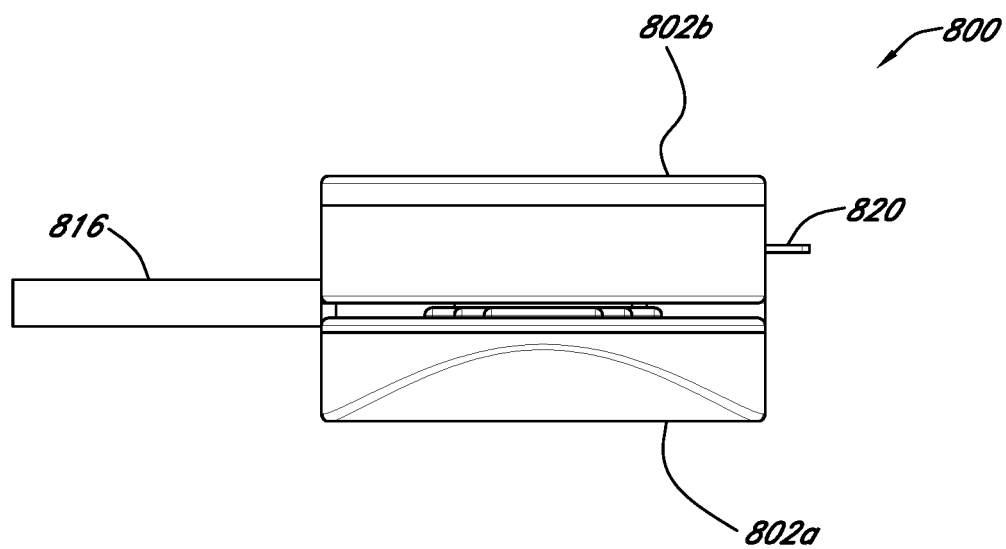
Figure 27F:
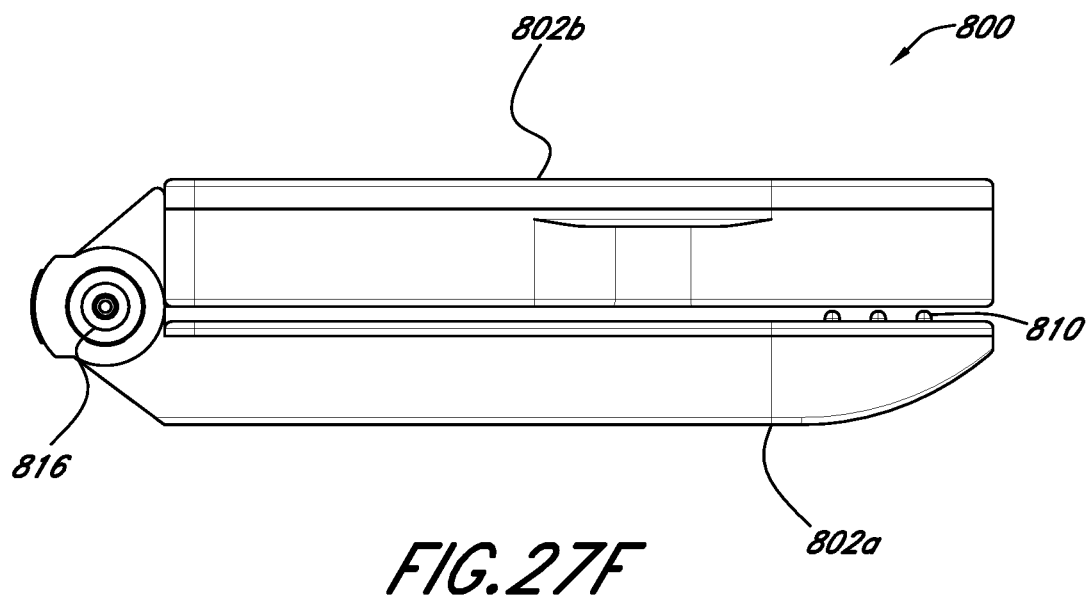
Figure 27G:
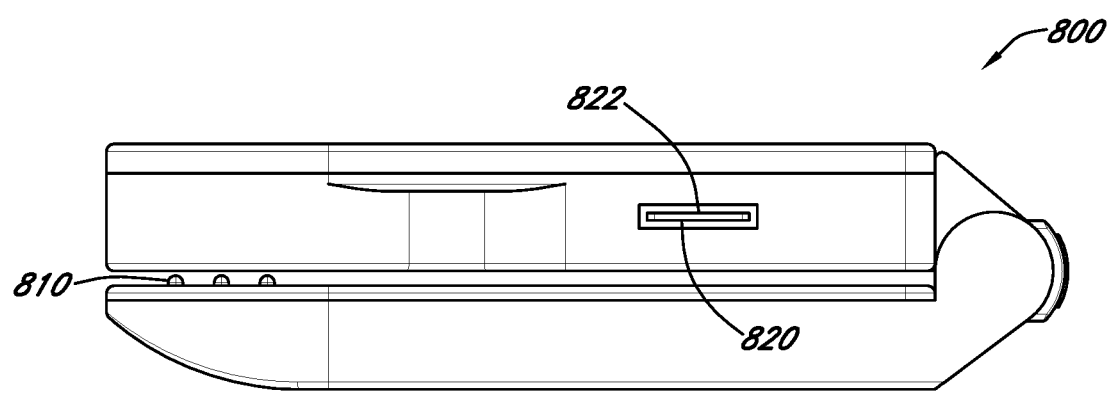
Figure 27H:
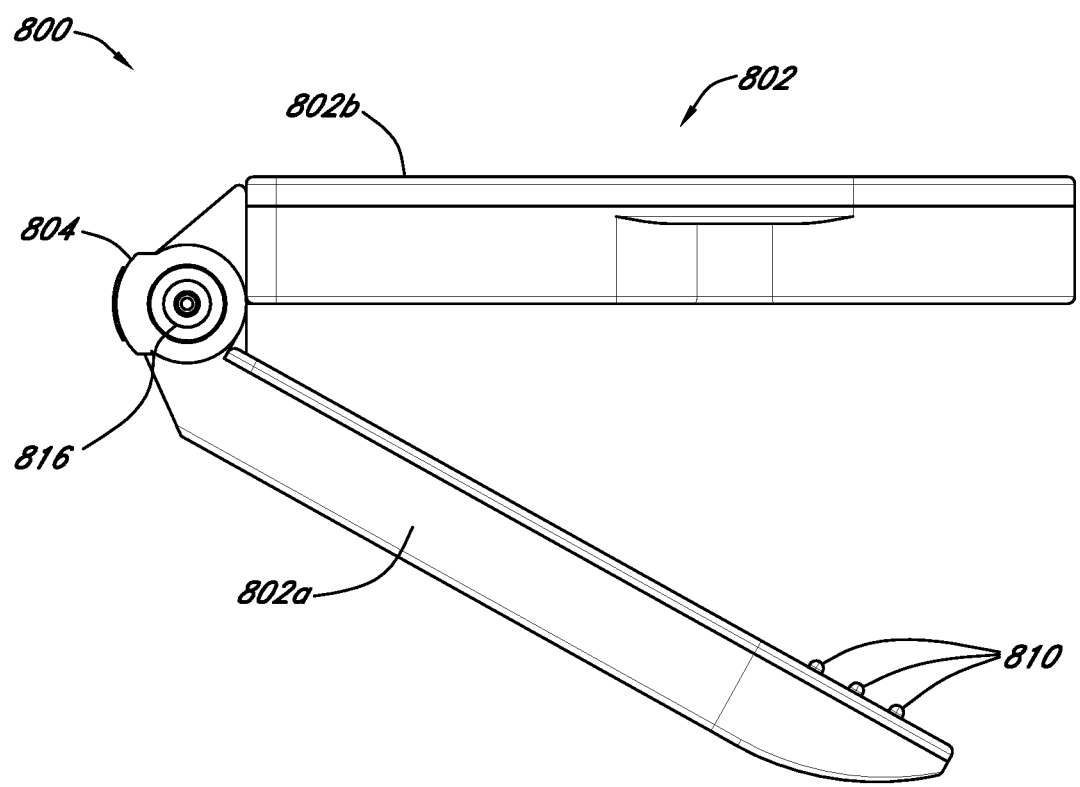
Figure 271:
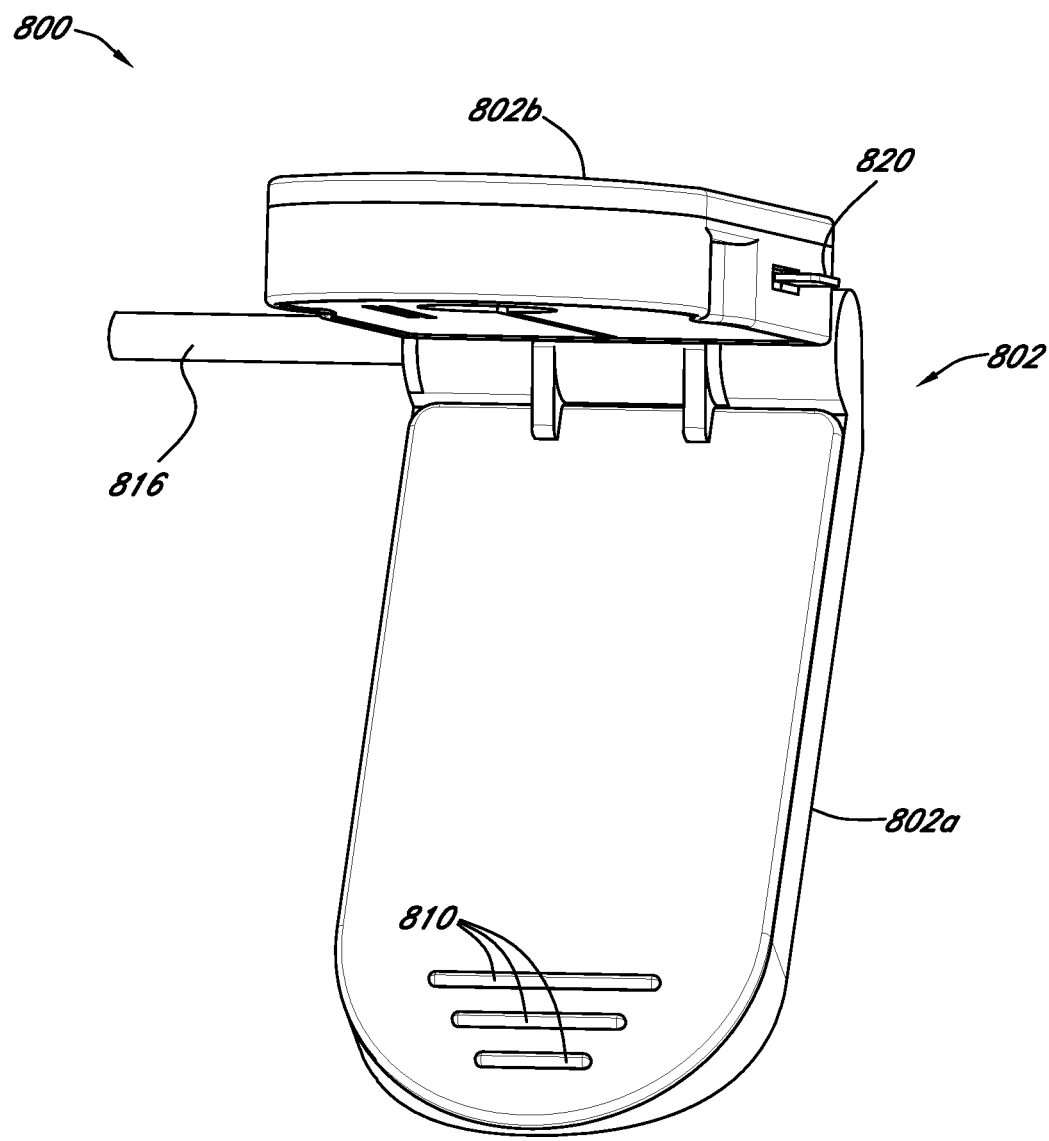

The housing 802 of the pump assembly 800 can have a first portion or element 802a and a second portion or element 802b. With reference to FIGS. 27H-27I, the first portion 802a and the second portion 802b of the housing 802 can be rotatably connected to one another by a hinge 804. The hinge 804 can permit the first portion 802a to rotate about an axis A within a particular angular range relative to the second portion 802b. The hinge 804 can be biased toward a closed position, as illustrated in FIG. 27A, such that the two portions 802a, 802b form a clip or a clamp. In this configuration, the housing 802 can be clipped to a person's clothing, such as in a pocket, over a belt, to a flap or in a pouch or a pocket on the dressing, or otherwise. For example, the first portion 802a can be positioned on the inside of a pouch, pocket, or otherwise, and the second portion 802b can be positioned outside of the pouch, pocket, or otherwise. The bias can be created with a coil spring, a bent spring, or otherwise, and can cause the housing 802 to grip the flap or pocket. The clamping force can be low enough that a user can open the housing from the clamped position, but strong enough so that it will remain clamped about the pocket, flap, or other material.

The hinge 804 can have a first hinge portion 804a and a second hinge portion 804b supported by the first housing portion 802a. A complementary hinge 804c supported by the second housing portion 802b can be positioned between the first and second hinge portions 804a, 804b and rotatable about axis A1 relative to one another.

One or both of the first portion 802a and the second portion 802b can have gripping features to help prevent the pump housing from sliding off of the flap or other material that the pump housing 802 is clipped onto. For example and without limitation, with reference to FIGS. 27H-27I, a plurality of protrusions 810 can be supported by or molded onto the first housing portion 802a and/or the second housing portion 802b to help grip the flap or other material that the housing is clipped to or clamped over.

A control button 812 can be used to control the operation of the pump assembly 800. For example, the button 812 can be used to activate the pump motor, pause the pump motor, clear indication or alarm signals, or be used for any other suitable purpose for controlling an operation of the pump assembly 800. The button can be a push style button that can be positioned on an outside, front surface of the housing.

Additionally, the housing can have any combination of indication lights, as described more fully below. The lights, which can be LED lights, can be configured to alert a user to a variety of operating and/or failure conditions of the pump assembly 800, including alerting the user to normal or proper operating conditions, pump failure, power supplied to the pump or power failure, the condition or voltage level of the batteries, detection of a leak within the dressing or flow pathway, suction blockage, or any other similar or suitable conditions or combinations thereof. The indicator lights can be positioned on an outside, front surface of the housing.

The pump assembly 800 can be configured to receive and support a conduit 816 used to communicate the reduced pressure provided by the pump housing 800 to the dressing. In any embodiments disclosed herein, the conduit 816 can be supported by the housing 800 such that the conduit cannot be removed by the user, so as to prevent the user from inadvertently disconnecting the conduit from the pump housing 800 or from inadvertently causing a leak with the tubing. In any embodiments disclosed herein, the conduit 816 can be removably supported by an opening in the housing or by the tube connector features and embodiments described herein. For example, any pump assembly embodiments disclosed herein can have a tube connector configured to removably or non-removably secure the conduit to the pump assembly.

In any pump embodiments disclosed herein, a tubing connector can be supported by the housing 802, such as tubing connector 830. In any embodiments, the tubing connector 830 can be configured to securely attach an end of the tubing 816 to the housing 802.

Figure 28:
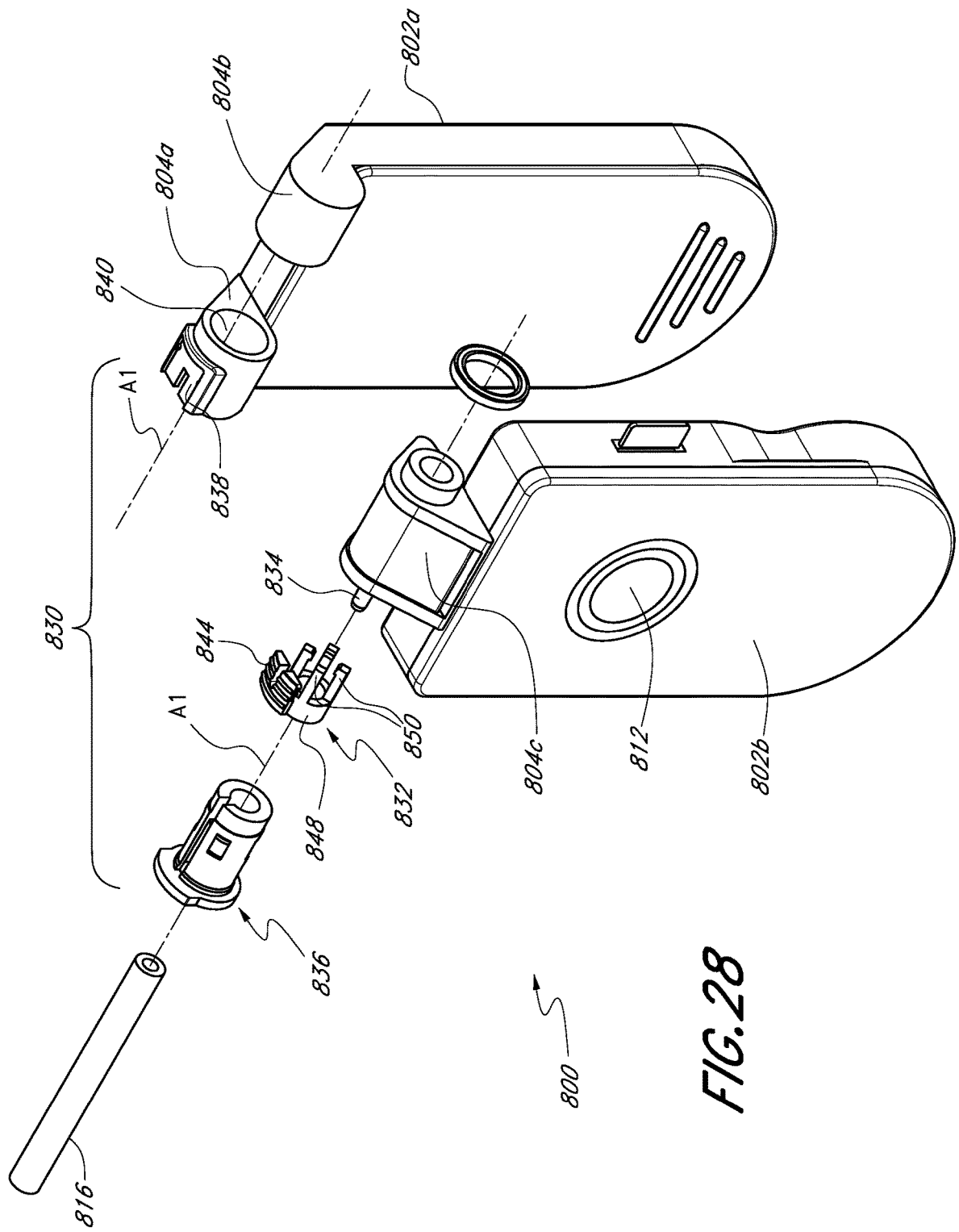
FIG. 28 is an exploded view of a portion of an embodiment of a pump assembly.

For example, as shown in FIG. 28, which is an exploded view of a portion of the pump assembly embodiment 800 shown in FIG. 27A, any pump assembly embodiments disclosed herein can have a tube connector 830 comprising a slider member 832, a boss 834 that can be supported by the third hinge portion 804c, a support member 836 for supporting the slider member 832, and a receiving element 838 formed on or supported by the first hinge portion 804a. In an assembled state, the slider member 832 and the support member 836 can be supported within an opening 840 formed in the first hinge portion 804a. The boss member 834 can be configured to receive an end portion of the conduit, such as but not limited to round tubing. A pad portion 844 of the slider member 832 can be configured to translate in the receiving portion 838. With reference to FIG. 27A, moving the slider member 832 in a first direction (represented by arrow A2 in FIG. 27A) will put the connector 830 in a second, locked position over the conduit 816, such that the conduit is securely attached to the housing 802, or at least inhibited from being removed from the housing 802. Moving the slider member 832 in a second, opposite direction (represented by arrow A3 in FIG. 27A) will put the connector 830 in an open or first position over the conduit 816, such that the conduit can be removed. The connector 830 is shown in the open or first position in FIG. 27A.

FIGS. 29A and 29B are an isometric and section view, respectively, of a portion of the embodiment of a pump assembly 800 shown in FIG. 28, showing a slider member 832 of an embodiment of a conduit connector 830 in a first, open position. With reference to FIGS. 29A and 29B, when the slide member 832 is in a first position, the one or more legs 850 of the slide member 832 can be forced against the inclined surfaces 859 so as to spread radially away from the conduit member 816 such that the protrusions 852 at the distal ends of the legs 850 are forced radially away from the conduit member, thereby permitting the conduit member 816 to be removed from the connector 830.

FIGS. 30A and 30B are an isometric and section view, respectively, of a portion of the embodiment of a pump assembly 800 shown in FIG. 28, showing a slider member 832 in a second, closed position. In this position, because the protrusions or tabs 852 at the ends of the one or more legs 850 have been moved apart from the inclined surfaces 859, the protrusions 852 can squeeze against the tubing or conduit 816 to hold or secure the conduit in the connector 830. The legs 850 can be biased to exert a radial inward force on the tubing 816 when no external force is applied to the legs 850.

Figure 32:
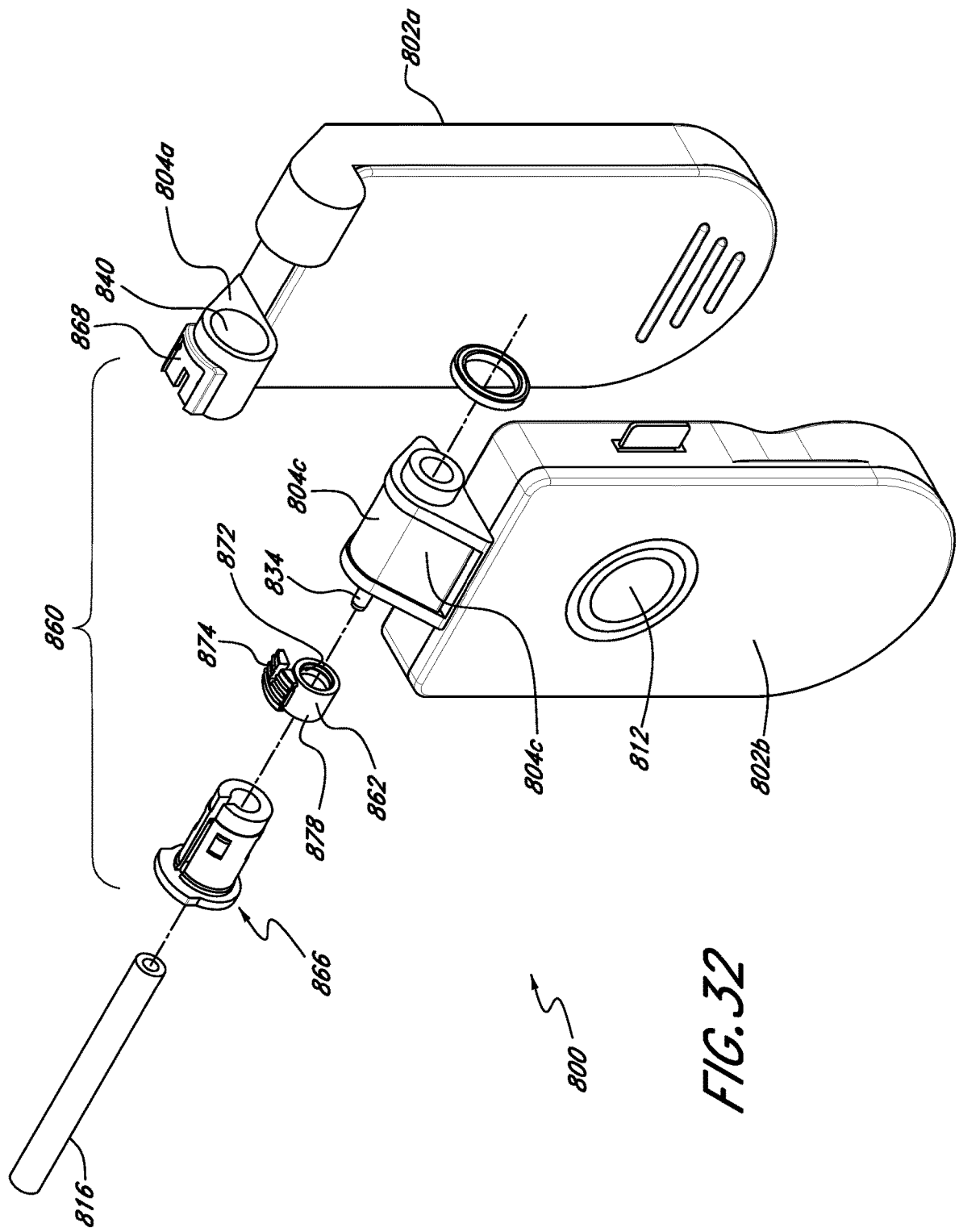
FIG. 32 is an exploded view of a portion of another embodiment of a pump assembly having another embodiment of a conduit connector.

Additionally, as shown in FIG. 32, which is an exploded view of a portion of the pump assembly embodiment 800 shown in FIG. 27A, any pump assembly embodiments disclosed herein can have a tube connector 860 comprising a slider member 862, a boss 834 that can be supported by the third hinge portion 804c, a support member 866 for supporting the slider member 832, and a receiving element 868 formed on or supported by the first hinge portion 804a. In an assembled state, the slider member 862 and the support member 866 can be supported within an opening 840 formed in the first hinge portion 804a. The boss member 864 can be configured to receive an end portion of the conduit, such as but not limited to round tubing. A pad portion 874 of the slider member 862 can be configured to translate in the receiving portion 868.

FIGS. 33A and 33B are an isometric and section view, respectively, of a portion of the embodiment of a pump assembly 800 shown in FIG. 32, showing a slider member 832 of an embodiment of a conduit connector 830 in a first, open position. With reference to FIG. 33A, moving the slider member 862 in a first direction (represented by arrow A1 in FIG. 33A) will put the connector 860 in a second, locked position over the conduit 816, such that the conduit is securely attached to the housing 802, or at least inhibited from being removed from the housing 802. Moving the slider member 862 in a second, opposite direction (represented by arrow A2 in FIG. 34A) will put the connector 860 in an open or first position over the conduit 816, such that the conduit can be removed. The connector 860 is shown in the open or first position in FIG. 33A.

With reference to FIGS. 33A and 33B, when the slide member 832 is in a first position, a protrusion (such as the annular protrusion 872 formed on the body 878) will be positioned so as to not surround the boss 834. FIGS. 34A and 34B are an isometric and section view, respectively, of a portion of the embodiment of a pump assembly 800 shown in FIG. 32, showing a slider member 862 in a second, closed position. In this position, because the protrusions or tabs 872 supported by the body portion 878 of the slider member 862 have been moved so as to surround the conduit positioned over the boss 834, the protrusions 834 can squeeze against the conduit and squeeze the wall of the conduit between the boss 834 and the tabs 872 to secure the conduit to the boss 834.

Figure 36:
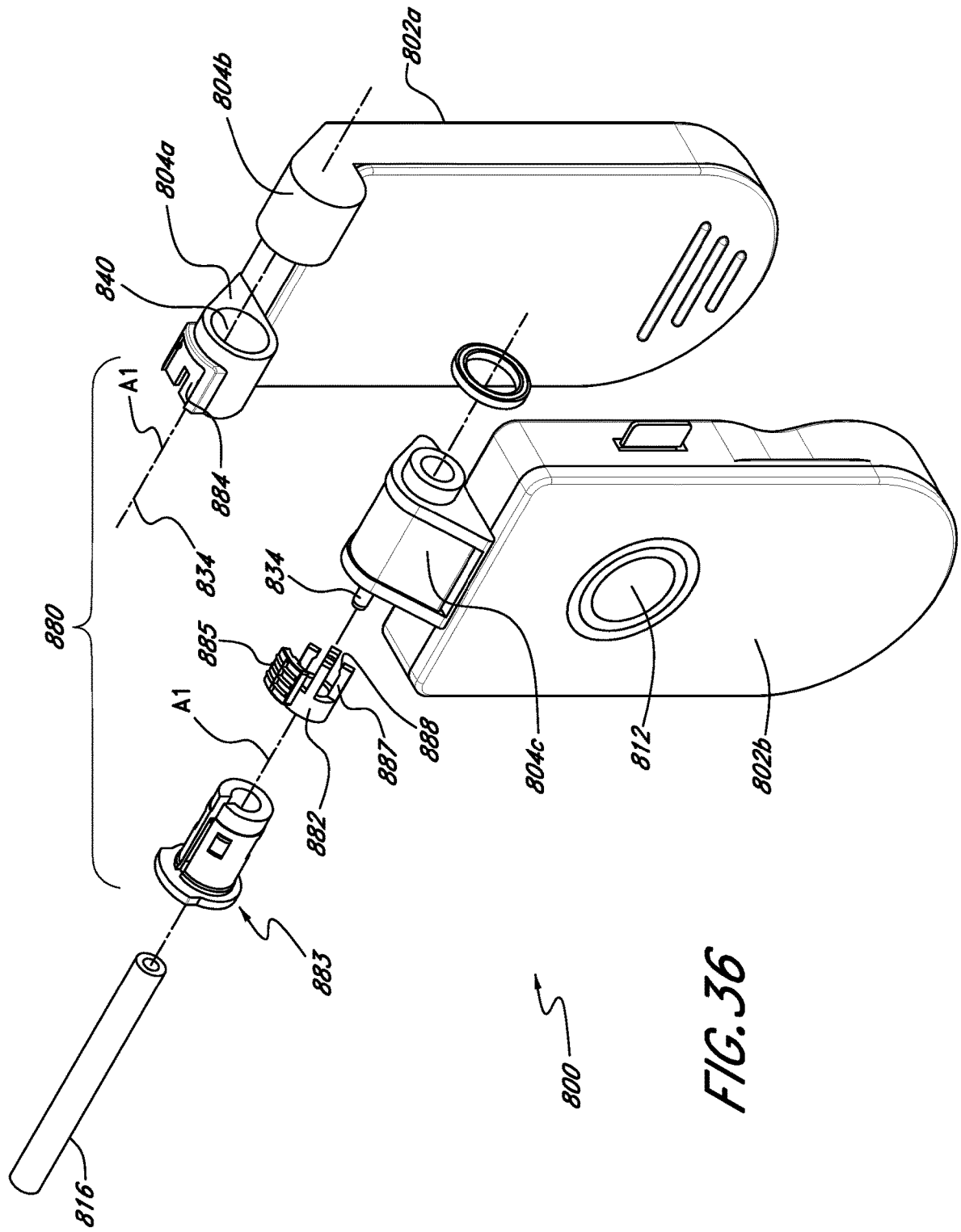
FIG. 36 is an exploded view of a portion of another embodiment of a pump assembly having another embodiment of a conduit connector.

Additionally, as shown in FIG. 36, which is an exploded view of a portion of the pump assembly embodiment 800 shown in FIG. 27A, any pump assembly embodiments disclosed herein can have a tube connector 880 comprising a slider member 882, a boss 834 that can be supported by the third hinge portion 804c, a support member 883 for supporting the slider member 882, and a receiving element 884 formed on or supported by the first hinge portion 804a. In an assembled state, the slider member 882 and the support member 883 can be supported within an opening 840 formed in the first hinge portion 804a. The boss member 834 can be configured to receive an end portion of the conduit, such as but not limited to round tubing. A pad portion 885 of the slider member 882 can be configured to translate in the receiving portion 884. With reference to FIG. 37A, moving the slider member 882 in a first direction (represented by arrow A1 in FIG. 27A) will put the connector 880 in a second, locked position over the conduit 816, such that the conduit is securely attached to the housing 802, or at least inhibited from being removed from the housing 802. Moving the slider member 882 in a second, opposite direction (represented by arrow A2 in FIG. 38A) will put the connector 880 in an open or first position over the conduit 816, such that the conduit can be removed. The connector 880 is shown in the open or first position in FIG. 37A.

FIGS. 37A and 37B are an isometric and section view, respectively, of a portion of the embodiment of a pump assembly 800 shown in FIG. 28, showing a slider member 882 of an embodiment of a conduit connector 880 in a first, open position. With reference to FIGS. 37A and 37B, when the slide member 882 is in a first position, the one or more legs 887 of the slide member 882 can be spaced apart from the inclined surfaces 889 so as to permit the legs 887 to remain in a relaxed position relative to the conduit 816 such that the protrusions 888 at the distal ends of the legs 887 are relaxed and do not substantially engage the conduit 816, thereby permitting the conduit member 816 to be removed from the connector 880.

FIGS. 38A and 38B are an isometric and section view, respectively, of a portion of the embodiment of a pump assembly 800 shown in FIG. 28, showing a slider member 882 (shown in more detail in FIGS. 39A-39C) in a second, closed position. In this position, because the protrusions or tabs 888 at the ends of the one or more legs 887 have been forced against the inclined surface 889, the inclined surface can force the ends of the 887, having the protrusions 888 thereon, radially inward against the conduit 816 such that the protrusions 888 can squeeze against the tubing or conduit 816 to hold or secure the conduit in the connector 880. The legs 887 can be biased to extend radially outward away from the tubing 816 when no external force is applied to the legs 887.

The operation or activation of any of the pump embodiments disclosed herein can be alternatively or additionally controlled by the use of one or more pull tabs, sliding switches, or other similar features coupled with one or more switches, buttons, controllers, etc. of the pump assembly. For example, with reference to FIGS. 27A-27I, in any embodiments disclosed herein, a pull tab 820 can be supported by an opening 822 formed in the housing 802. In this arrangement, the pull tab 820 can be configured to be positioned between the battery terminals and batteries, or between other components in the electrical circuit. In any embodiments disclosed herein, the packaging supporting the dressing can be configured such that such tab or isolator must be positioned between the components in the electrical circuit to ensure that the batteries are not electrically connected to the pump assembly or other components during sterilization or prior to activation. The pump assembly 800 can be configured such that, the pump cannot be operated or activated when the pull tab 820 is positioned within the opening 822 (so as to open a portion of the electrical or power circuit that necessary for the operation of the pump). To use the pump, the user must remove the pull tab 820 from the opening 822. The pump can then be operated automatically, or can be operated by depressing one or more buttons (such as button 812) or moving one or more switches.

The pump assembly 800 or any pump assembly embodiment disclosed herein can be configured such that the pump device (such as, without limitation, a voice coil actuated pump device) is supported in the first housing portion 802a. The battery can be supported in the first or the second housing portion 802a, or, in the case of multiple batteries supported by the pump device, in both. In other words, one battery can be supported in the first housing portion 802a and one batter can be supported in the second housing portion 802b. When two or more batteries are used, such batteries can provide power simultaneously or sequentially, or both. The housing 802 can be configured such that a user can access and replace the batteries without the use of tools. In any embodiments disclosed herein, the housing 802 can be configured such that a user cannot gain access to the batteries without the use of tools or without opening the housing.

A control board, such as a printed circuit board assembly (PCBA), can be configured to mechanically support and electrically connect various electrical/electronic components of the pump assembly, including the battery or batteries, the pump device, the control button, a pressure monitor in communication with the pump device or the conduit or otherwise, and/or any indicator lights or audible alarms. The PCBA can be single-sided or double-sided. The control board can be supported within the first or the second housing portion 802a, 802b.

In any embodiments disclosed herein, as in the illustrated embodiment, the pump device and the control board can be supported in the first housing portion 802a and the battery can be supported in the second housing portion 802b. In any embodiments disclosed herein, the pump device can be supported in the first housing portion 802a, the control board can be supported in the second housing portion 802b, and the battery can be supported in the second housing portion 802b. Electrical wires or connectors can be routed from the first to the second housing portion through the hinge 804.

In any embodiments disclosed herein, though not required, the pump assembly can be configured such that a sterilization gas, such as ethylene dioxide, can penetrate into the housing 802 to expose the internal components of the pump assembly 800 to the sterilization gas during normal sterilization processes. Typically, the pump will be exposed to the sterilization gas in a chamber that has been substantially evacuated of air or any other gas, so that the sterilization gas is drawn into the pump housing 802 and into the other spaces, channels, and chambers within the pump assembly 800.

In any embodiments disclosed herein, the pump assembly can be powered by one or more batteries (for example, two batteries) and can weigh approximately 84 grams, or less than 90 grams, including the weight of the batteries. In any embodiments disclosed herein, the pump assembly 800 can have any desired number of batteries and can weigh from approximately 80 grams to approximately 90 grams, or from approximately 75 grams to approximately 100 grams, or between any values within the foregoing ranges. For example, the weight and/or size of the pump assembly 800 could be reduced by reducing the battery size and/or weight by using, for example, AAA sized batteries, lithium batteries, printed or flexible batteries, or smaller), or by reducing the pump size and/or weight.

Further, any embodiments of the pump assembly 800 (or any pump assembly embodiments disclosed herein) can be sized to have a total volume defined by an outside surface of the pump of approximately 92.5 cubic centimeters (approximately 5.6 cubic inches), or 92.5 cubic centimeters (5.6 cubic inches) or less, or between 75 cubic centimeters or less and 115 cubic centimeters or more, or between 85 cubic centimeters and 100 cubic centimeters. Additionally, the pump assembly 800 can be further miniaturized using techniques known to one of ordinary skill in the art to sizes in the range of approximately 40 cubic centimeters, or 40 cubic centimeters or less, or between 30 cubic centimeters or less and 60 cubic centimeters or more. Any pump assembly embodiments disclosed herein can be sized to have a total volume of between 2 cubic inches or less and 6.5 cubic inches or more, or from approximately 4 cubic inches to approximately 6 cubic inches, or between any values within the foregoing ranges.

The pump assembly 800 can have an overall outside size that is approximately 7.2 cm×approximately 6.4 cm×approximately 2.1 cm (or 7.2 cm×6.4 cm×2.1 cm), or a maximum of approximately 8.5 cm×approximately 8.5 cm×approximately 3 cm. Additionally, the pump assembly 800 can have an overall outside size that is approximately 5.5 cm×approximately 4.8 cm×approximately 1.5 cm (or 5.5 cm×4.8 cm×1.5 cm). As mentioned, the size and weight of the pump assembly 800 can be optimized, as it is in the embodiments disclosed herein, to make it more comfortable to wear or carry by the user, thereby affording increased mobility.

The negative pressure range for any embodiments of the present disclosure can be approximately −80 mmHg, or between about −20 mmHg and −200 mmHg. Note that these pressures are relative to normal ambient atmospheric pressure thus, −200 mmHg would be about 560 mmHg in practical terms. In any embodiments disclosed herein, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even 150 mmHg, can be supplied by the pump assembly. Other details regarding the operation of the pump assembly 800 are set forth in U.S. patent application Ser. No. 13/092,042, and such embodiments, configurations, details, and illustrations thereof are hereby incorporated by reference in their entireties as if made part of this disclosure.

As mentioned, the pump assembly 800 can be powered by one or more batteries. The batteries can be lithium chloride or any other suitable batteries that are suitable for exposure to ethylene dioxide and/or other sterilization gases. The batteries can be supported outside of the pump housing 120 so as to minimize or eliminate the chance of an electrical spark which could cause an explosion in the presence of the sterilization gas or an explosive gas during the sterilization process when supported in the packaging element or elements. Additionally, where there are a plurality of batteries, the batteries can be spaced apart or otherwise separated in the packaging to prevent any power loss or sparking of the batteries during the sterilization process or otherwise before usage.

Any pump embodiments disclosed herein can be as light as approximately 8 grams or less, or approximately 10 grams, or between approximately 6 grams and 15 grams, or between any values within the foregoing range. The pump can have a pump capacity of approximately 500 mL per minute, or between approximately 100 mL per minute or less and approximately 600 mL per minute or more, or between approximately 300 mL per minute and approximately 500 mL per minute, or between any values within the foregoing ranges. In any embodiments disclosed herein, the pump assembly 800 could comprise two or more pumps, including two or more voice coil actuated pumps. For example, the pump assembly 800 could have a first pump having a high flow rate, configured to provide a rapid drawdown of the space between the wound overlay and the wound, and a second, smaller capacity pump configured to maintain the level of reduced pressure of the space between the wound overlay and the wound after the initial draw down. In any embodiments disclosed herein, the pump flow rate can be approximately 20 times the leak alarm flow rate, which can be set at approximately 15 milliliters per minute.

As mentioned, any pump assembly embodiment disclosed herein can have a pressure monitor. The pressure monitor can be supported by the control board and can be configured to monitor a level of pressure in the fluid flow passageway. The pressure monitor can be configured to protect the motor from exceeding a predefined threshold pressure. In any embodiments disclosed herein, the pressure monitor can be calibrated to not exceed 175+/−50 mmHg. In any embodiments disclosed herein, the pressure monitor can be calibrated to not exceed 235 mmHg. The pressure monitor can be configured to cut power to the motor if the pressure reading reaches a predetermined value, and be configured to resume when the pressure level drops below the predetermined value or a second predetermined value that can be higher or lower than the first predetermined value. Additionally, the pump assembly 800 can be programmed to prevent such over-pressurization. The pump assembly 800 can be configured such that the software provides the primary mechanism for preventing over-pressurization, and the pressure monitor can provide backup over-pressurization protection.

The pump device can have a layer of open foam or other material wrapped at least partially around an outside surface of the pump to reduce the noise and vibration produced by the pump. One or more labels can be affixed to an outside surface of the housing 802. In any embodiments disclosed herein, the label can be used to seal one side or more than one side an air conduit that is part of the pump assembly. Additionally, In any embodiments disclosed herein, the pump can have one or more weights, cushions, foam (such as a viscoelastic foam), plastic (such as ABS, polyurethane, urethane, or otherwise), or other pads, panels, sheets, or segments supported by the pump or positioned adjacent to one or more outside surfaces of the pump. Any embodiments can have mass based or compliant damping materials. Such components or materials (not illustrated) can damp vibration and/or attenuate noise produced by the pump.

For example, one or more weights (made from steel, metal, or any other suitable material) can be supported or attached to an outside surface of the pump device or any other pump embodiment disclosed herein. The steel weights can weigh approximately 1.8 grams, 3.8 grams, or 5.8 grams, or between 1 gram and 10 grams or more, or between 1.5 grams and 6 grams. Two or more weights can be supported or attached to an outside surface of the pump or any other pump embodiment disclosed herein. Two steel weights each weighing approximately 1.8 grams, 3.8 grams, or 5.8 grams, or between 1 gram and 10 grams or more, or between 1.5 grams and 6 grams, can be attached to an outside surface of the pump. Each of the two plates can be positioned on opposite sides of the motor, or otherwise. In any embodiments disclosed herein, four steel weights each weighing approximately 1.8 grams, 3.8 grams, or 5.8 grams, or between 1 gram and 10 grams or more, or between 1.5 grams and 6 grams, can be attached to an outside surface of the pump. The plates can be arranged such that two plates are positioned on each of two opposite sides of the motor, or otherwise. In any embodiments disclosed herein, weights can be positioned adjacent to three or more sides of the pump including, for example and without limitation, the sides and top surfaces of the pump.

FIGS. 40A-40G are an isometric view, a top view, a bottom view, a top end view, a bottom end view, a first side view, and a second side view, respectively, of another embodiment of a pump assembly 900. Any embodiments of the pump assembly 900 can have any of the same features, components, weights, dimensions, shapes, or other details of any other pump assembly embodiment disclosed herein, including without limitation the pump assembly embodiment 800 disclosed above. Additionally, the pump assembly embodiment 900 can be used with any of the dressing embodiments disclosed herein or otherwise. However, In any embodiments disclosed herein, the pump assembly 900 can have a number of differences as compared to other pump assemblies disclosed herein.

For example, a control button or switch 912 can be supported on a side wall surface of the second housing portion 902b. Additionally, pump assembly can have any number of indicator lights, such as indicator lights 916, positioned on an outside, front surface of the housing.

Figure 40A:
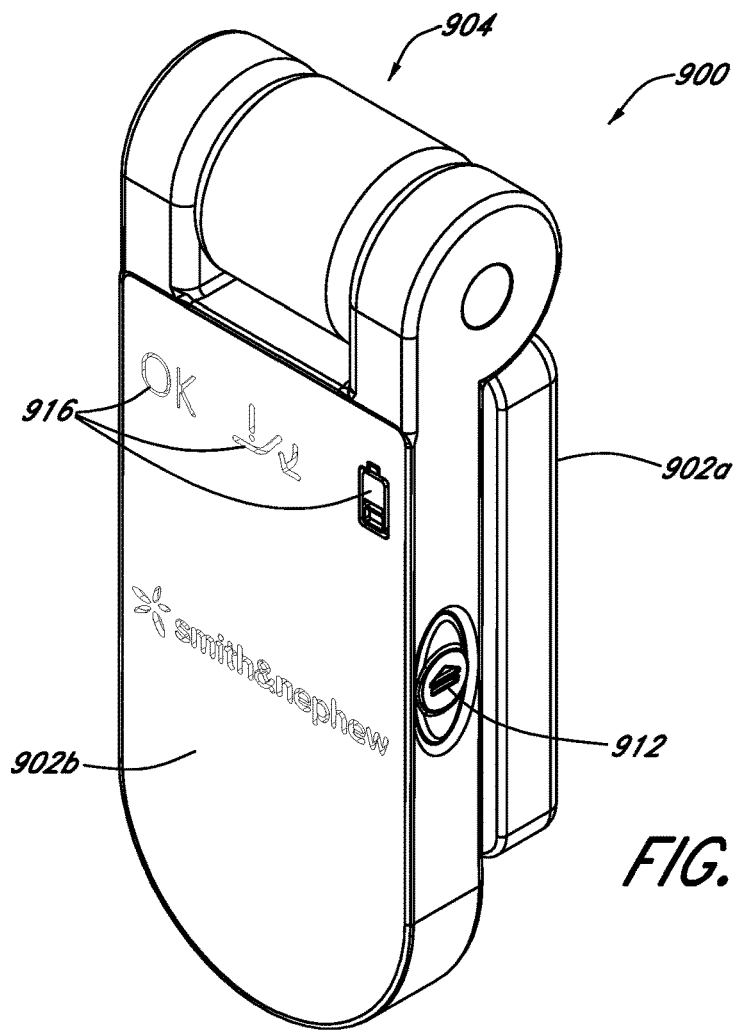
FIGS. 40A-40G are an isometric view, a top view, a bottom view, a top end view, a bottom end view, a first side view, and a second side view, respectively, of another embodiment of a pump assembly.
Figure 40H:
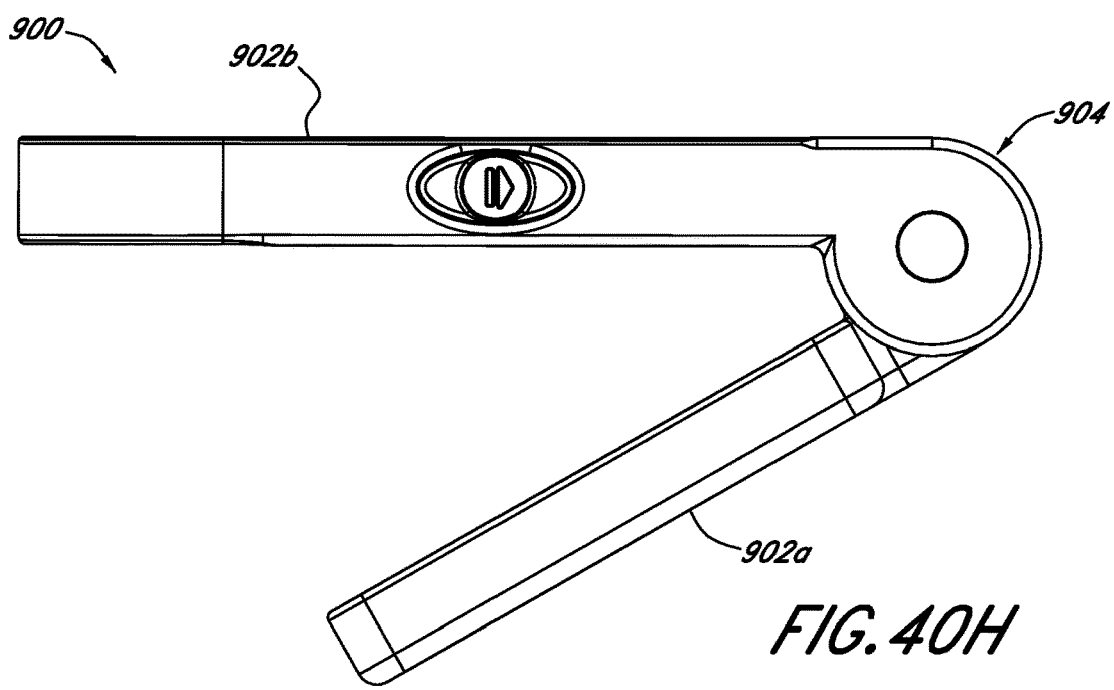
FIG. 40H is a side view of the pump assembly embodiment shown in FIG. 40A, showing the pump assembly in a partially open position.
Figure 40B:
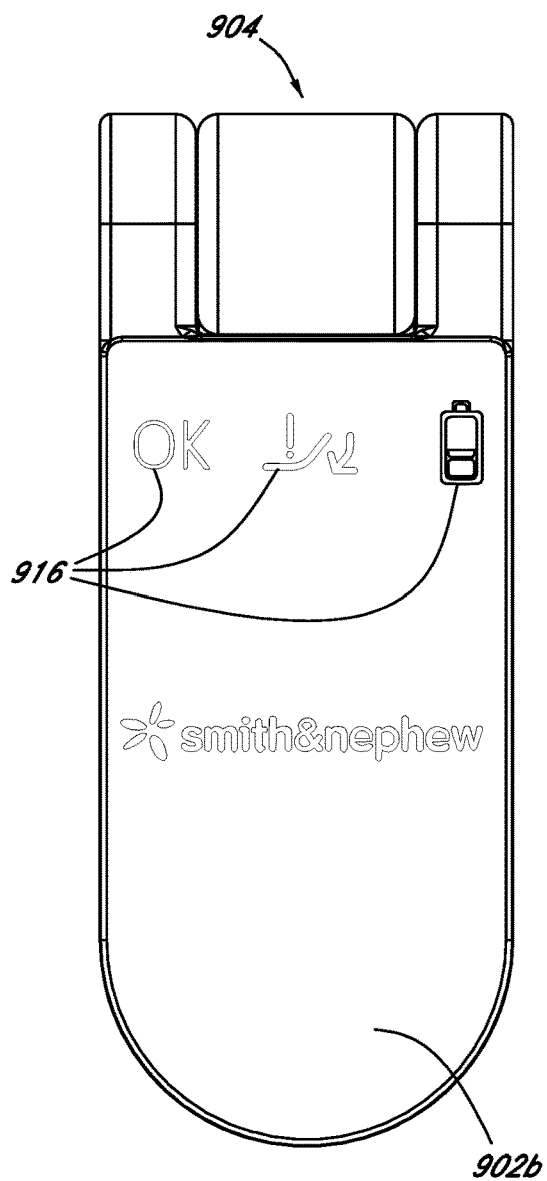
Figure 40C:
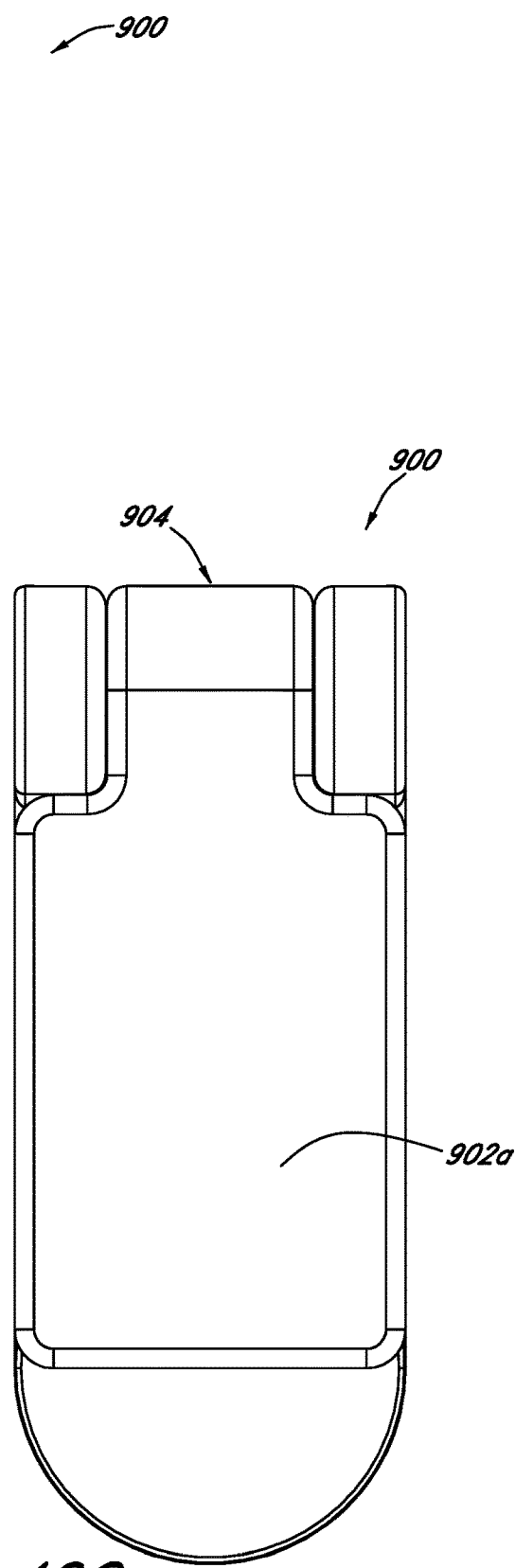
Figure 40D:
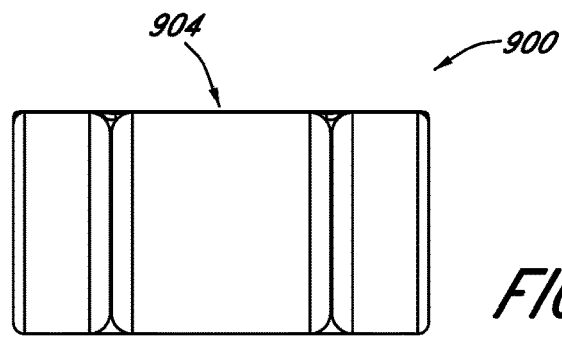
Figure 40E:
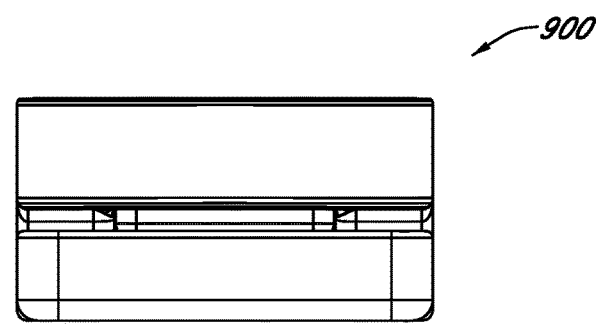
Figure 40F:
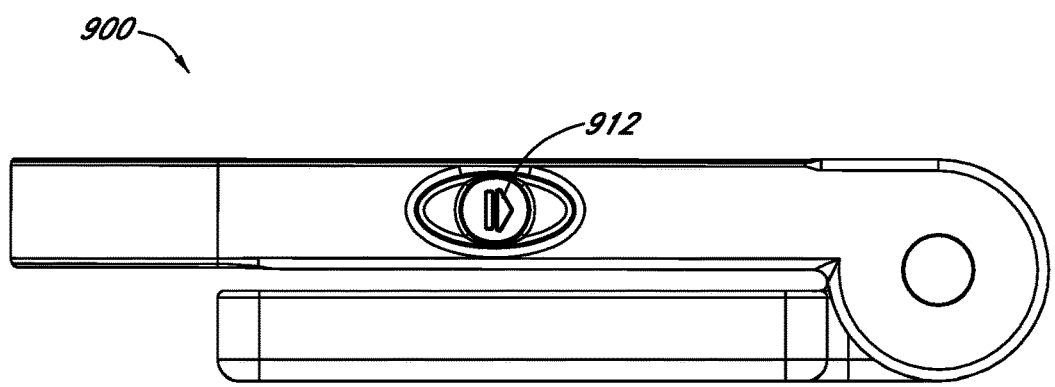
Figure 40G:
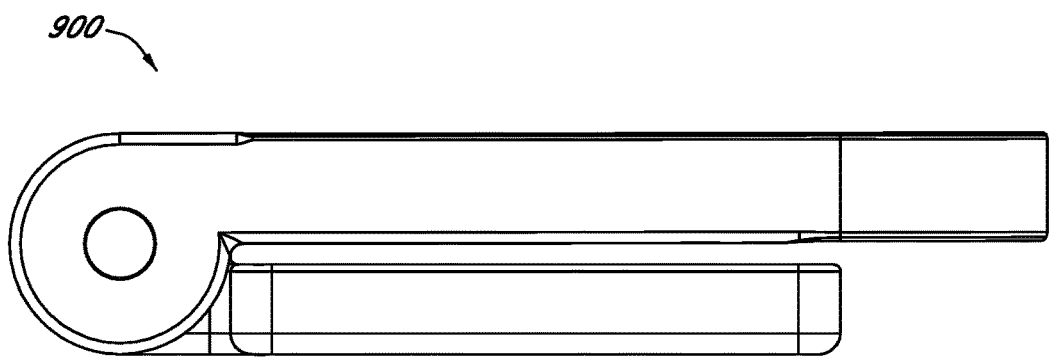
Figure 41A:
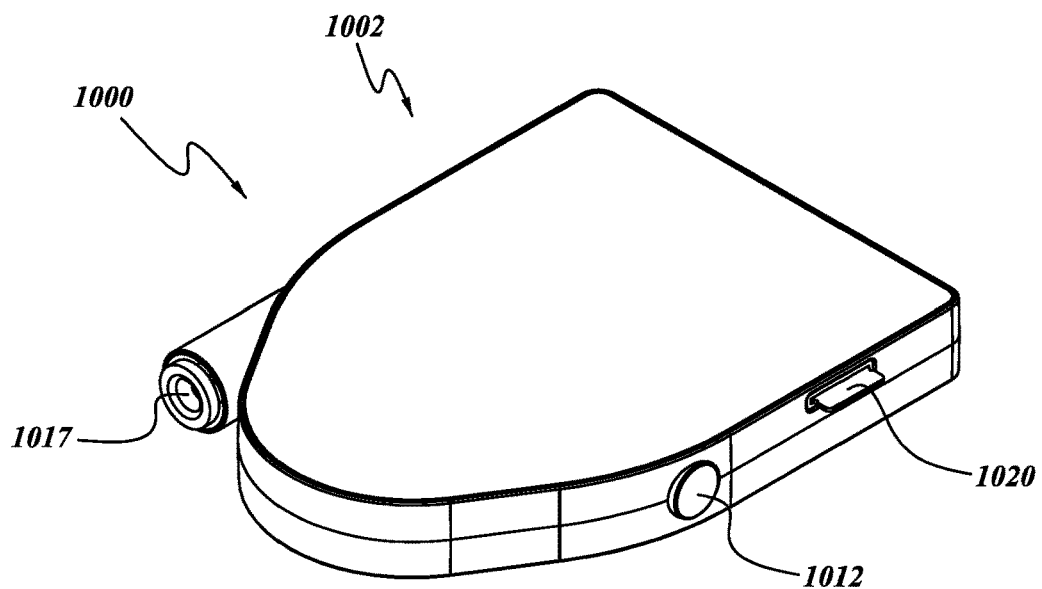
FIGS. 41A-41G are an isometric view, a top view, a bottom view, a top end view, a bottom end view, a first side view, and a second side view, respectively, of an embodiment of a pump assembly.
Figure 41B:
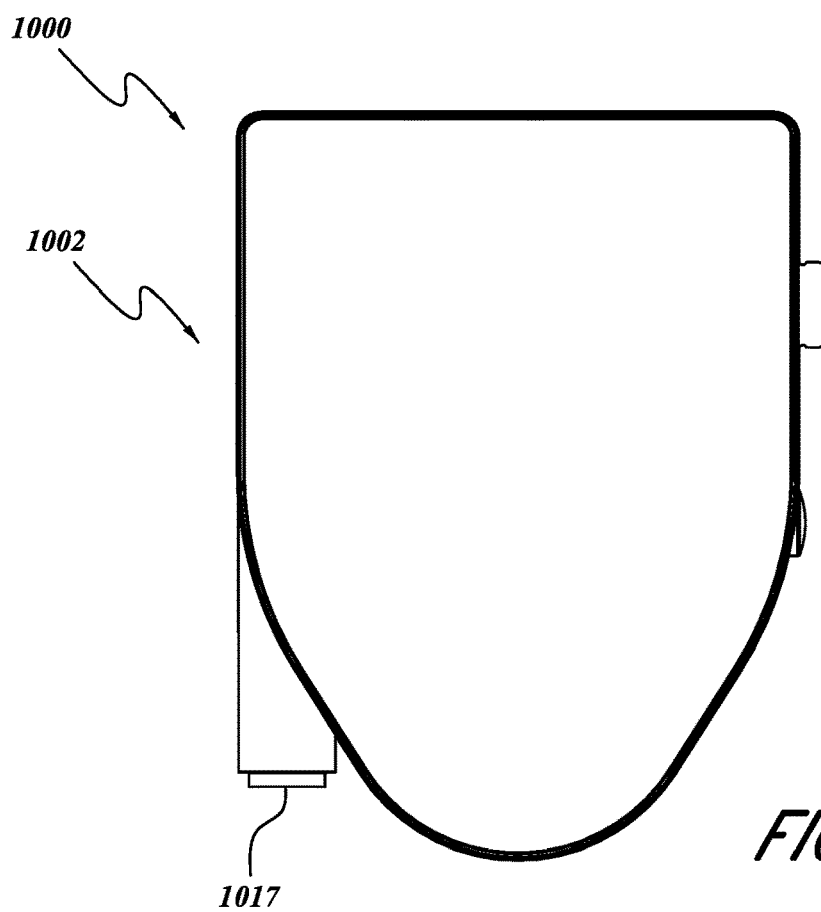
Figure 41C:
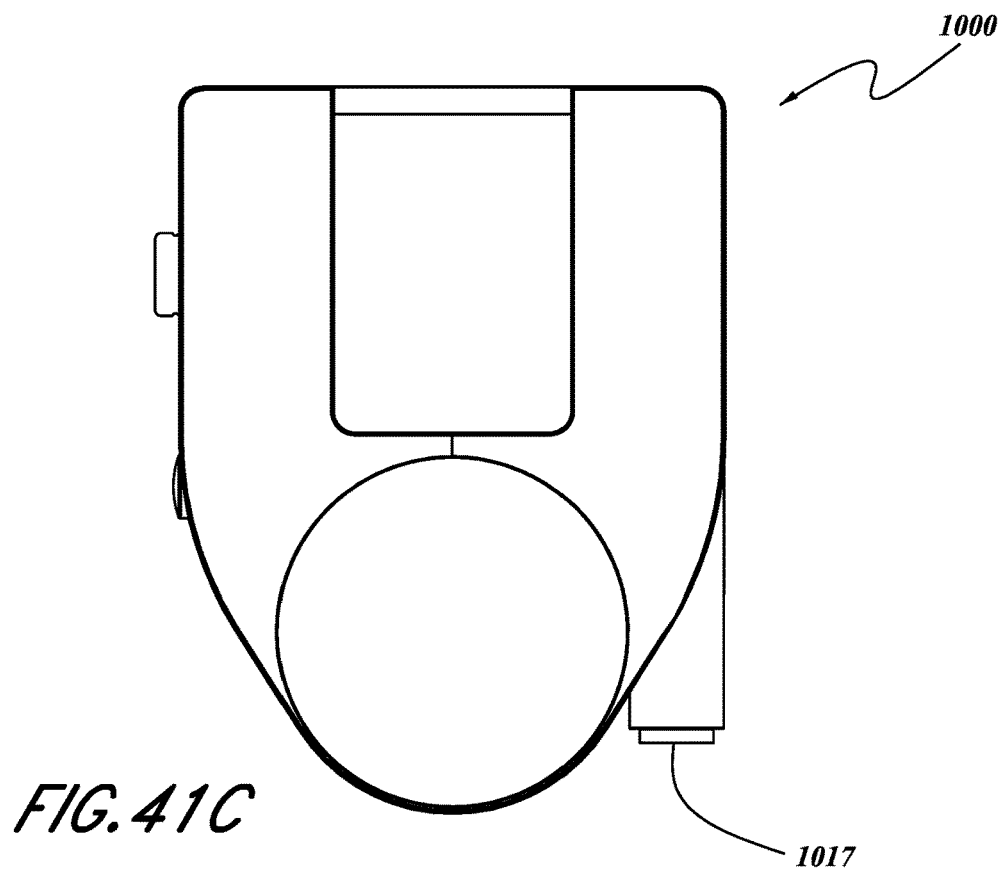
Figure 41D:
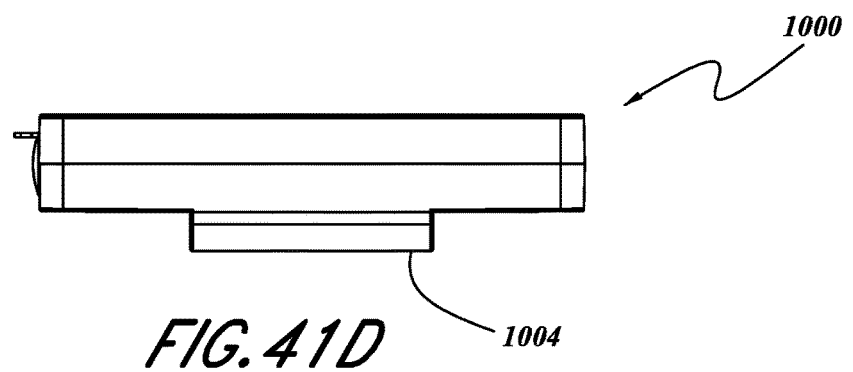
Figure 41E:
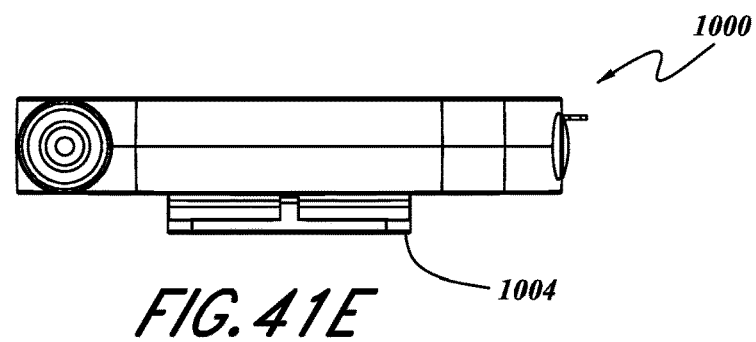
Figure 41F:
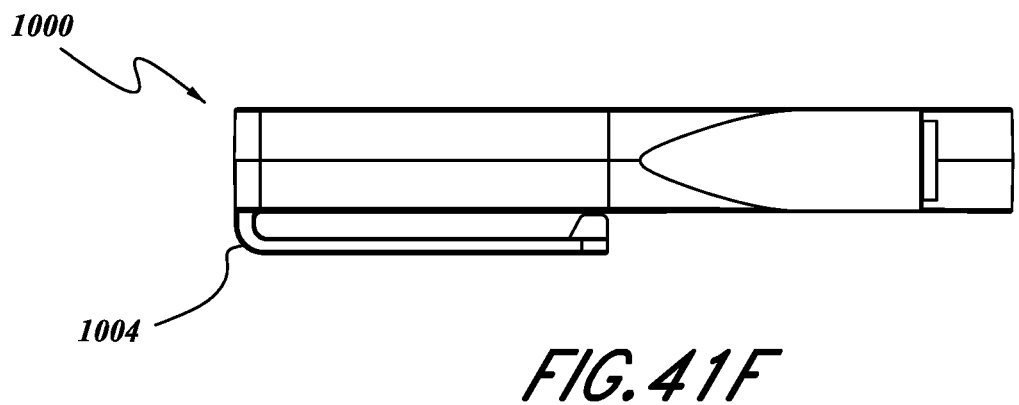
Figure 41G:
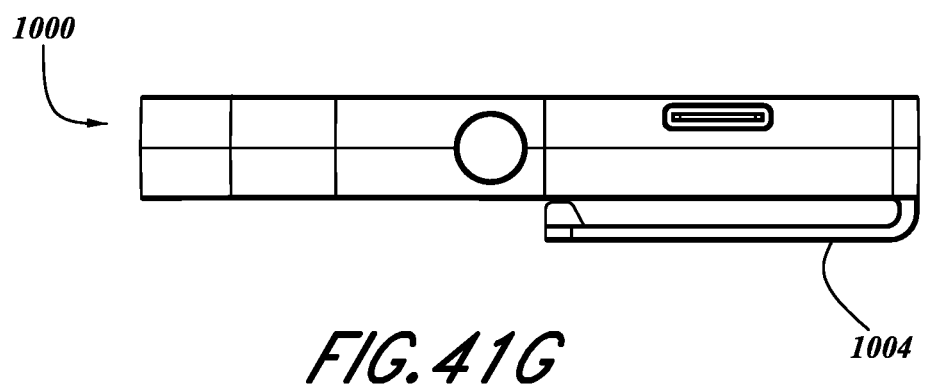
Figure 42D:
Figure 42E:
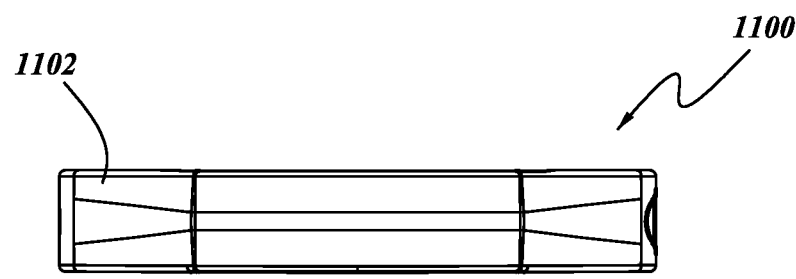
Figure 42F:
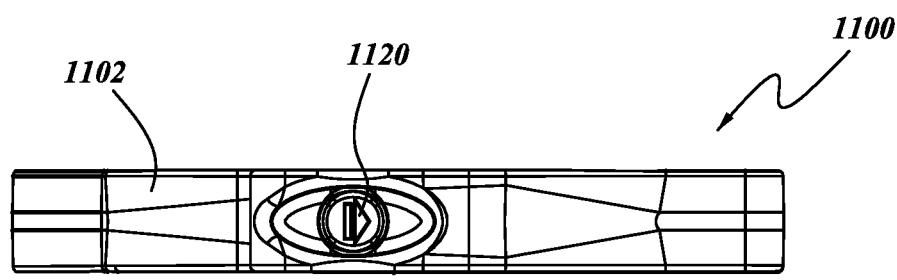
Figure 42G:
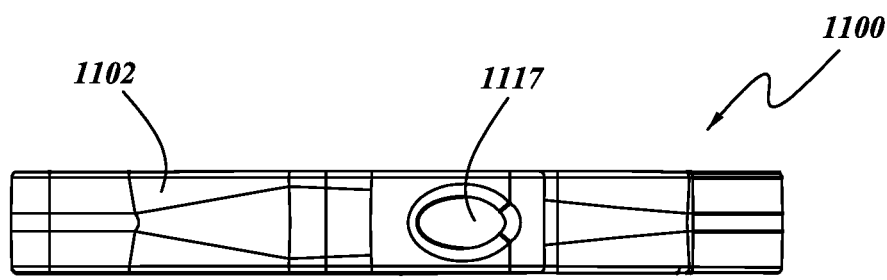
Figure 43A:
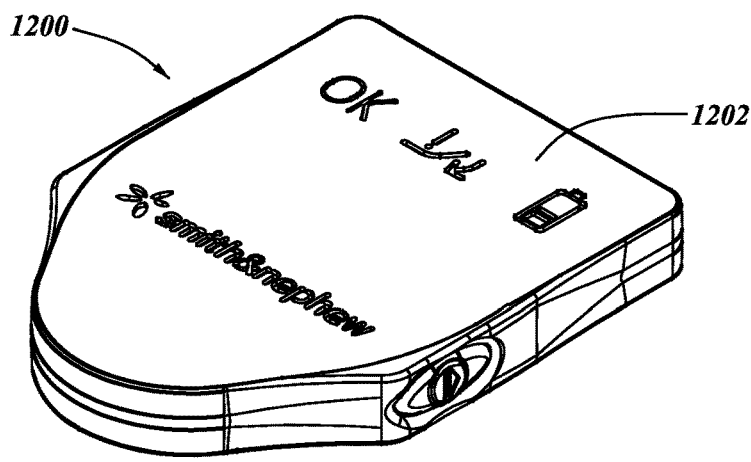
FIGS. 43A-43G are an isometric view, a top view, a bottom view, a top end view, a bottom end view, a first side view, and a second side view, respectively, of another embodiment of a pump assembly.
Figure 43B:
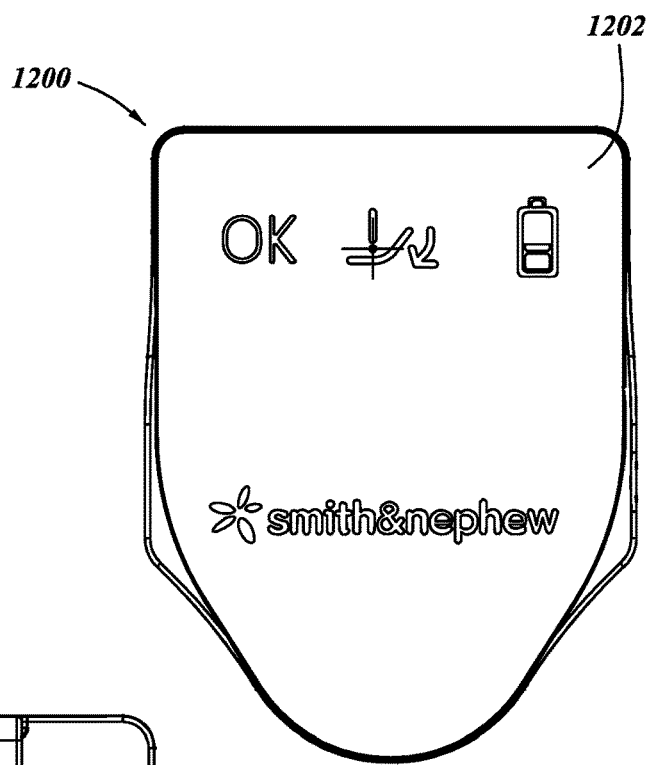
Figure 43C:
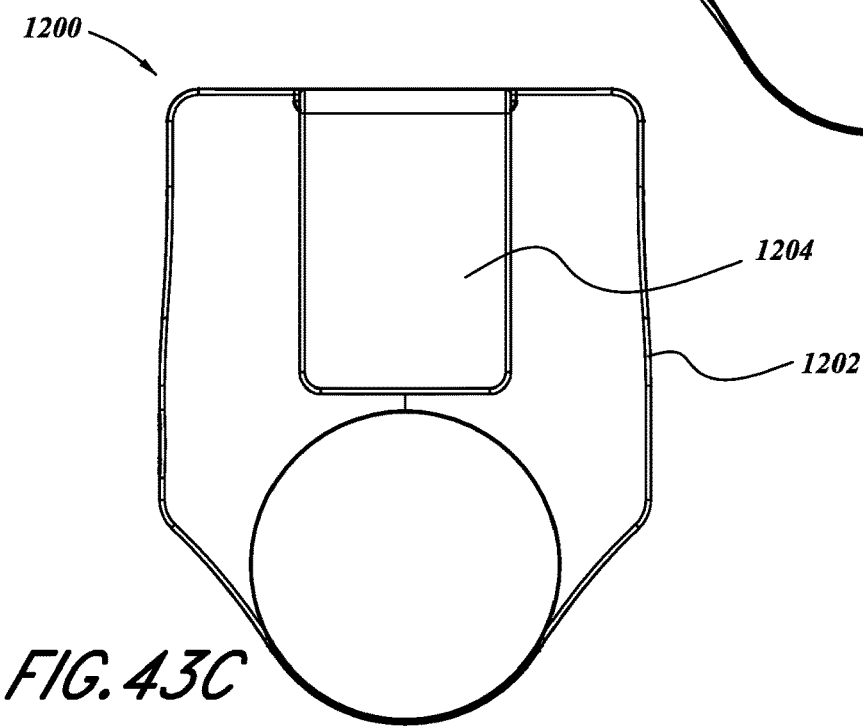
Figure 43D:
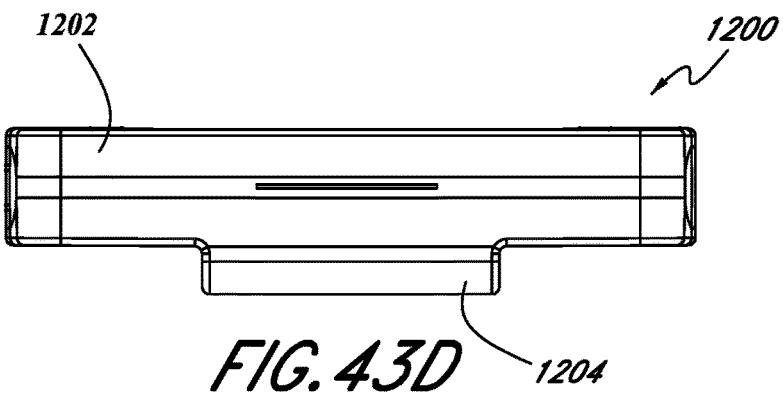
Figure 43E:
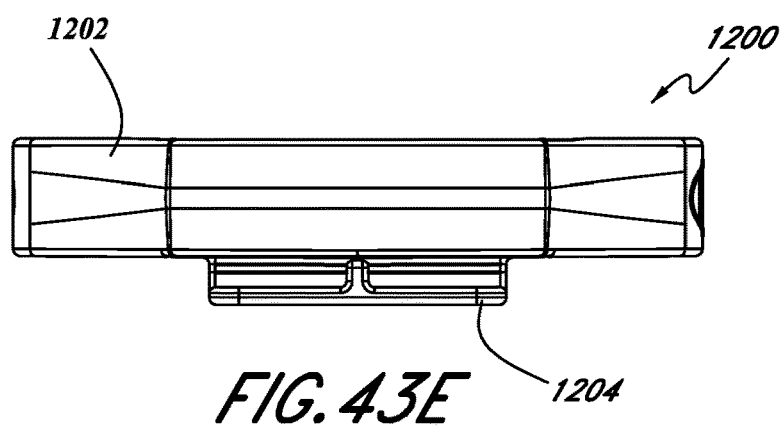
Figure 43F:
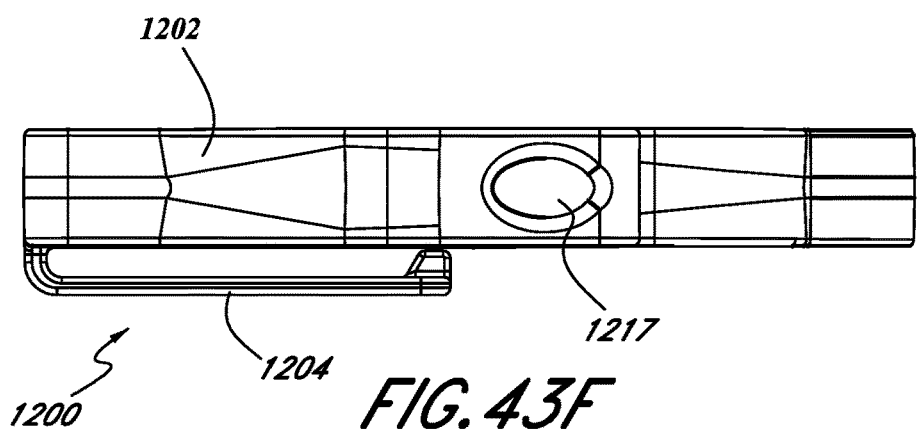
Figure 43G:
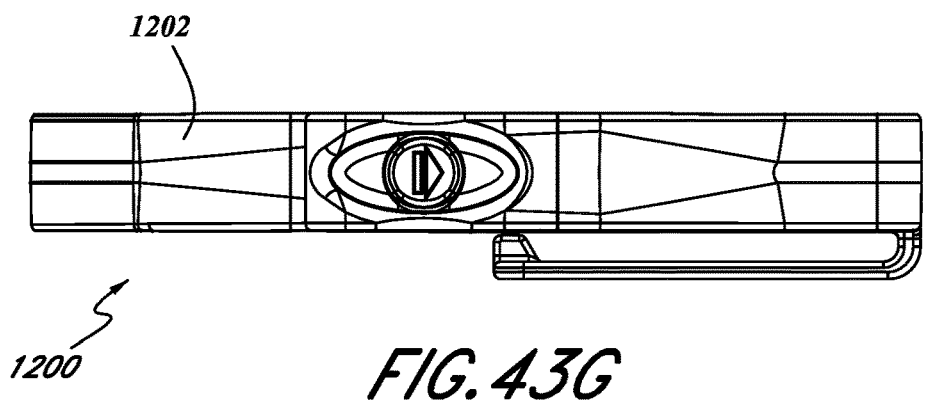
Figure 44A:
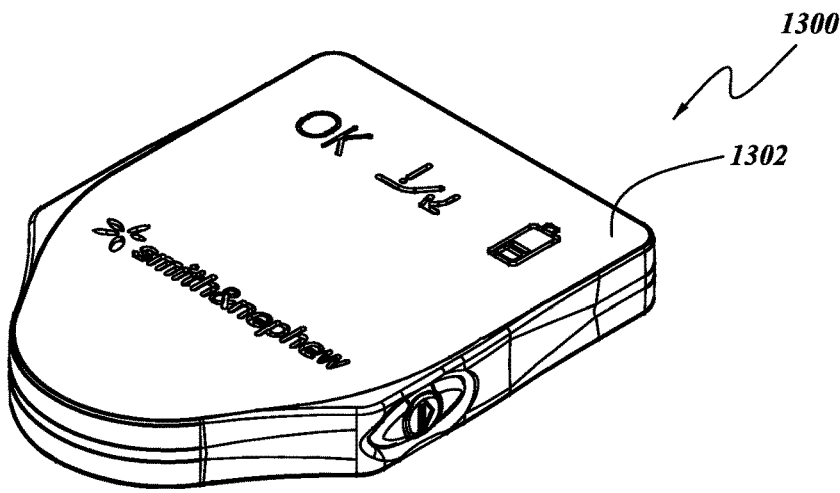
FIGS. 44A-44G are an isometric view, a top view, a bottom view, a top end view, a bottom end view, a first side view, and a second side view, respectively, of another embodiment of a pump assembly.
Figure 44B:
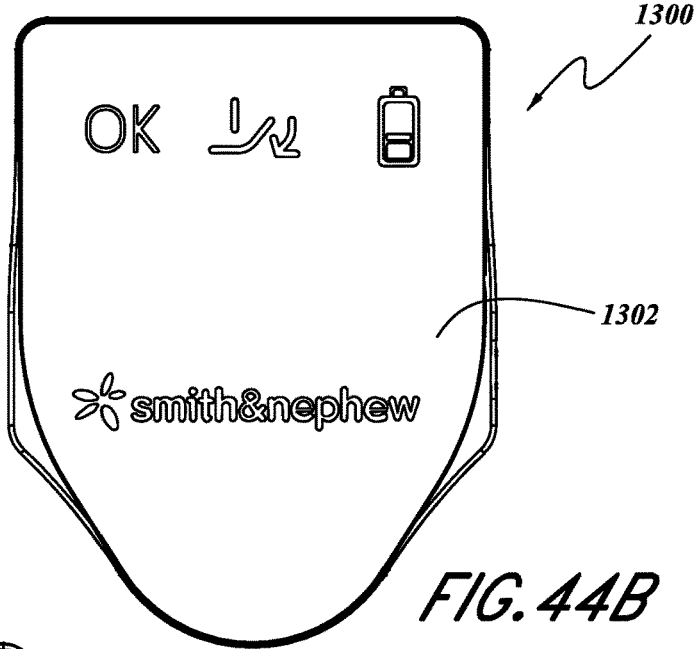
Figure 44C:
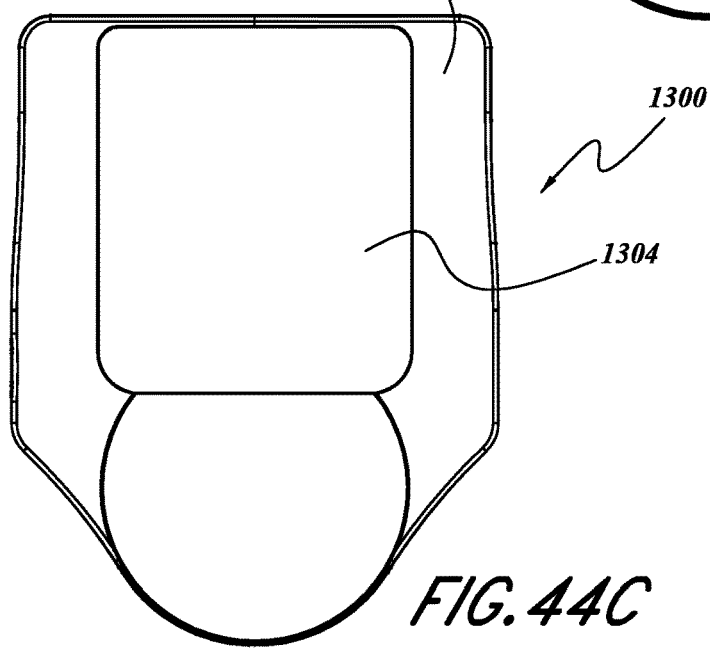
Figure 44D:
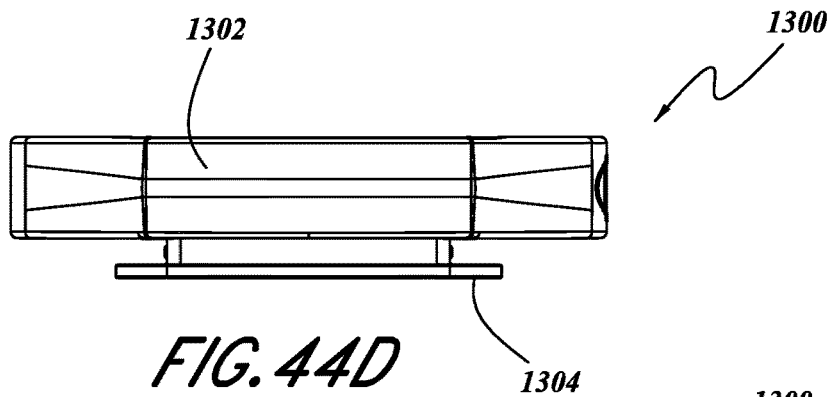
Figure 44E:
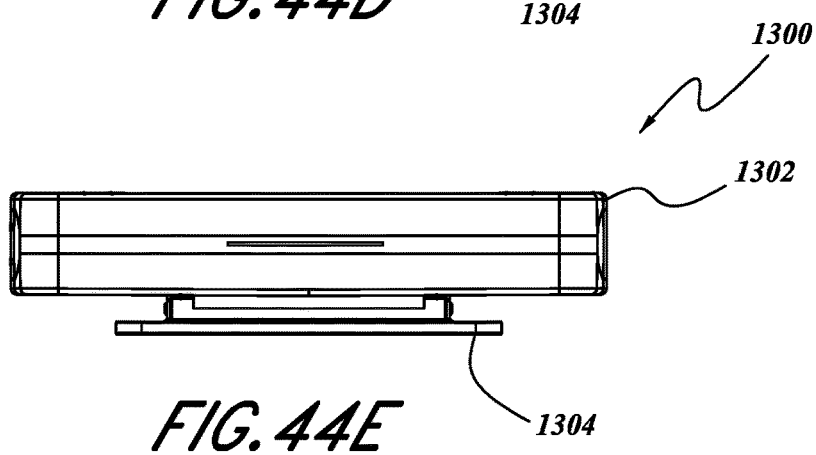
Figure 44F:
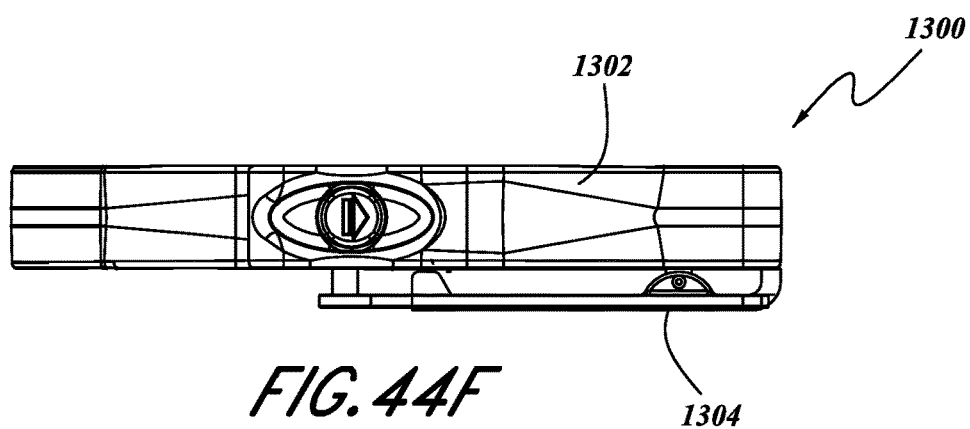
Figure 44G:
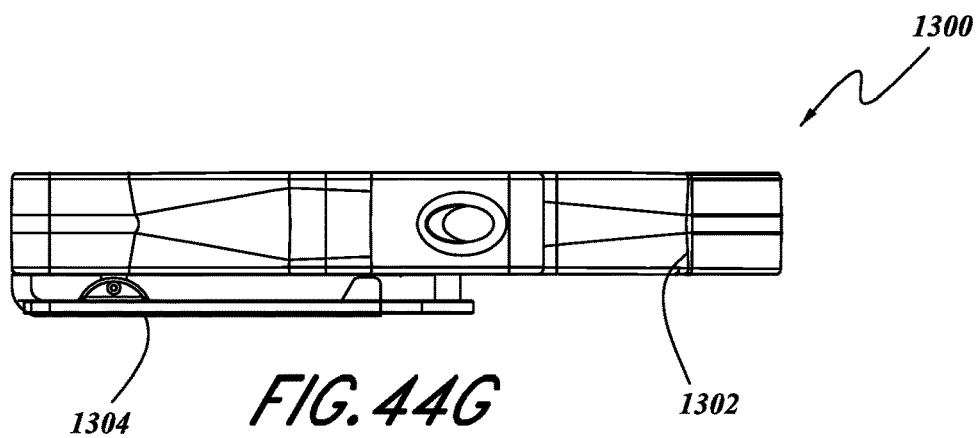
Figure 45A:
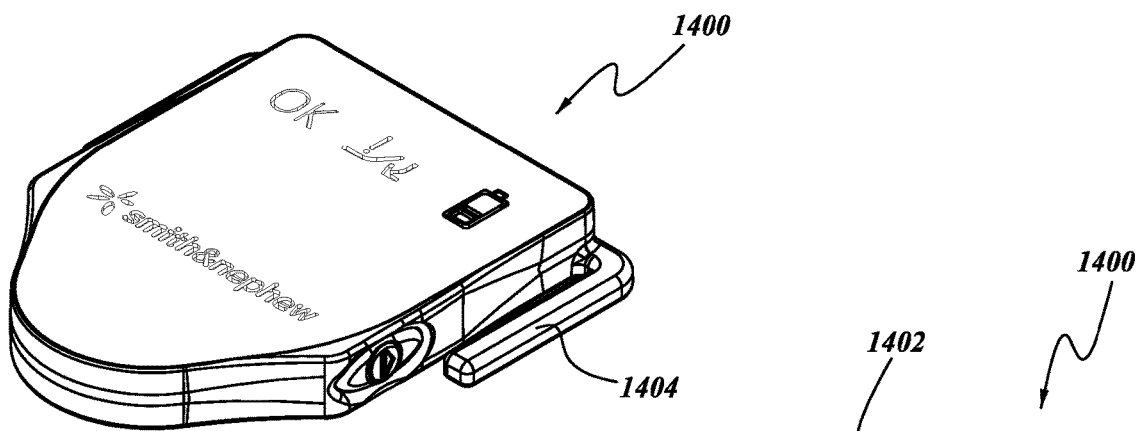
FIGS. 45A-45G are an isometric view, a top view, a bottom view, a top end view, a bottom end view, a first side view, and a second side view, respectively, of another embodiment of a pump assembly.
Figure 45B:
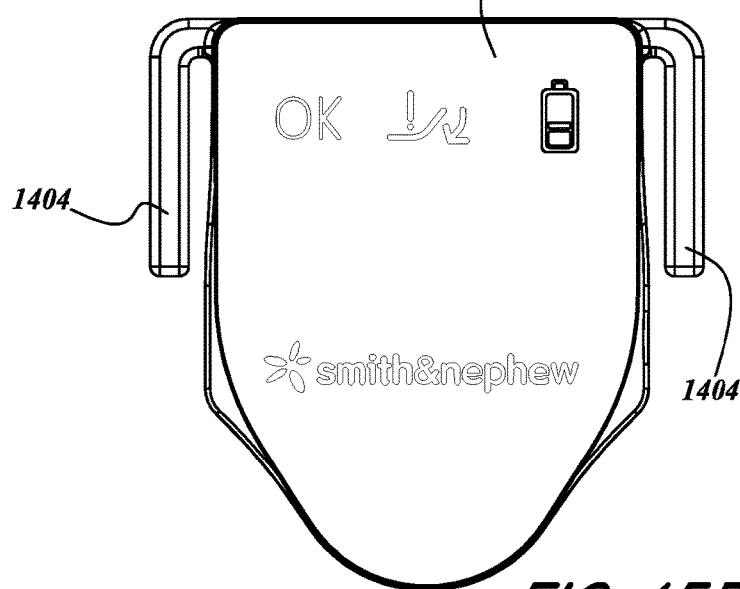
Figure 45C:
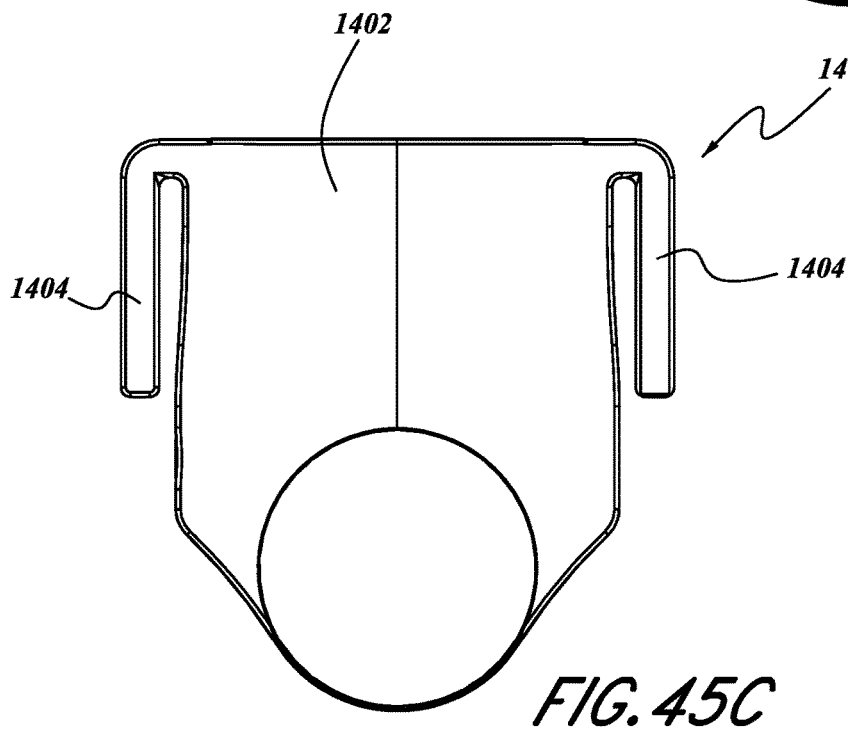
Figure 45D:
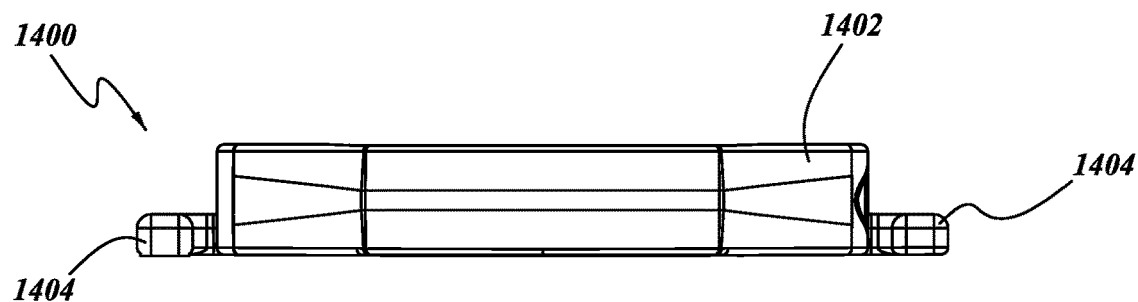
Figure 45E:
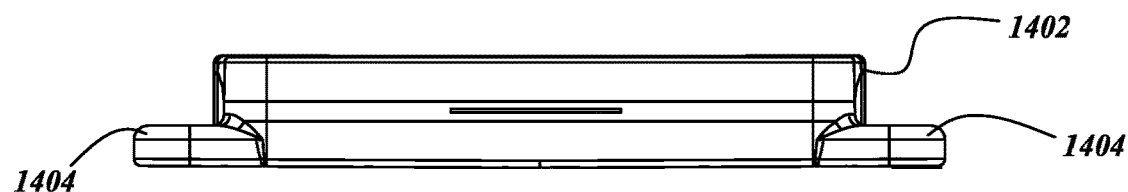
Figure 45F:
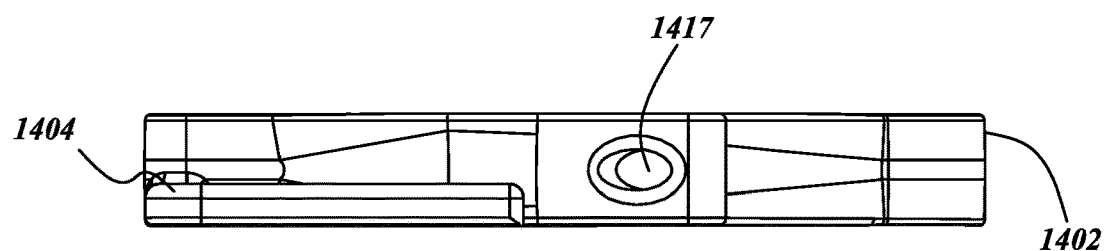
Figure 45G:
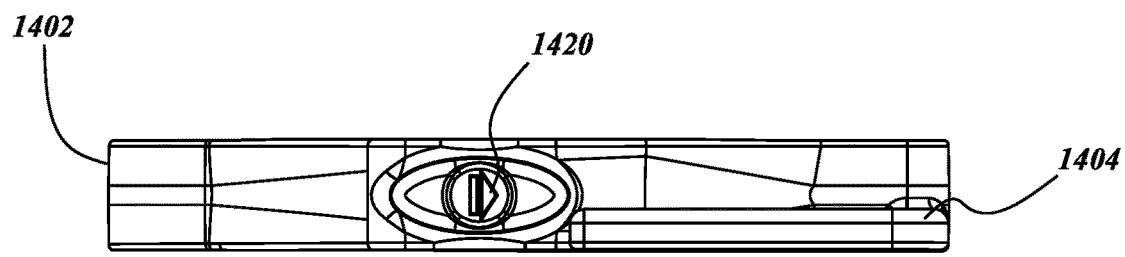
Figure 46D:
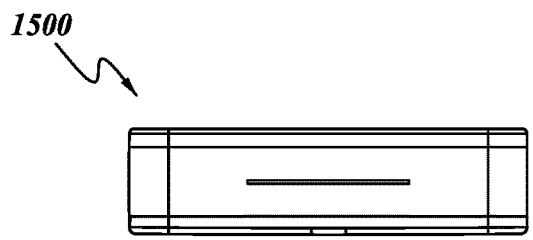
Figure 46E:
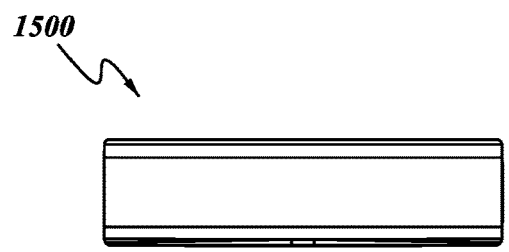
Figure 46F:
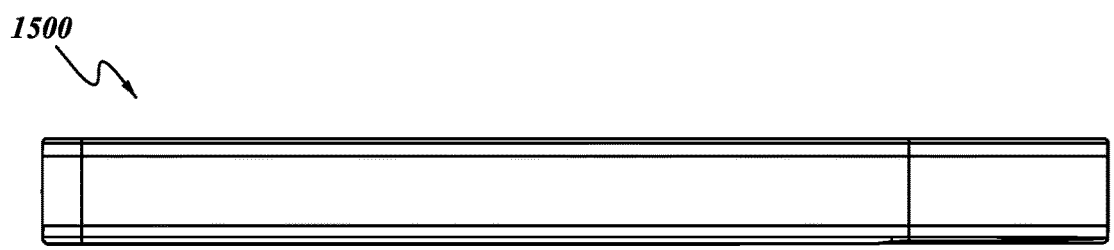
Figure 46G:
Figure 47A:
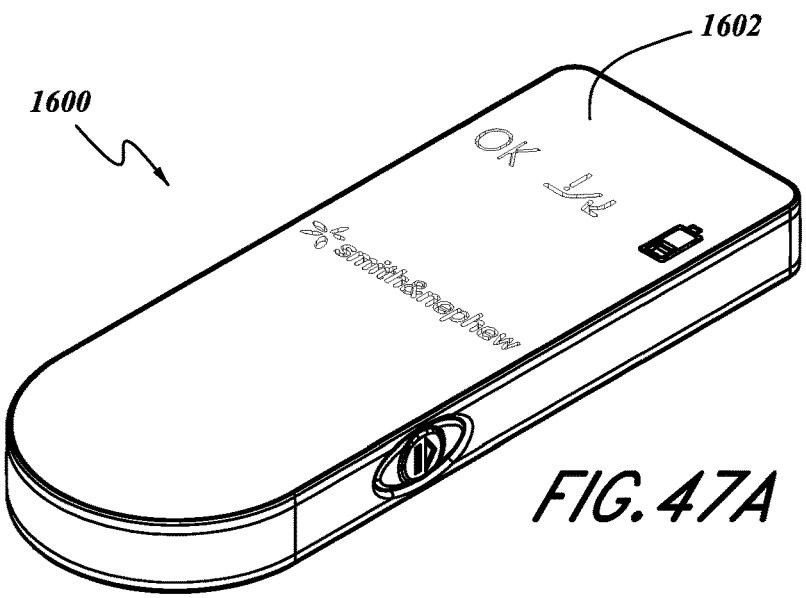
FIGS. 47A-47G are an isometric view, a top view, a bottom view, a top end view, a bottom end view, a first side view, and a second side view, respectively, of another embodiment of a pump assembly.
Figure 47B:
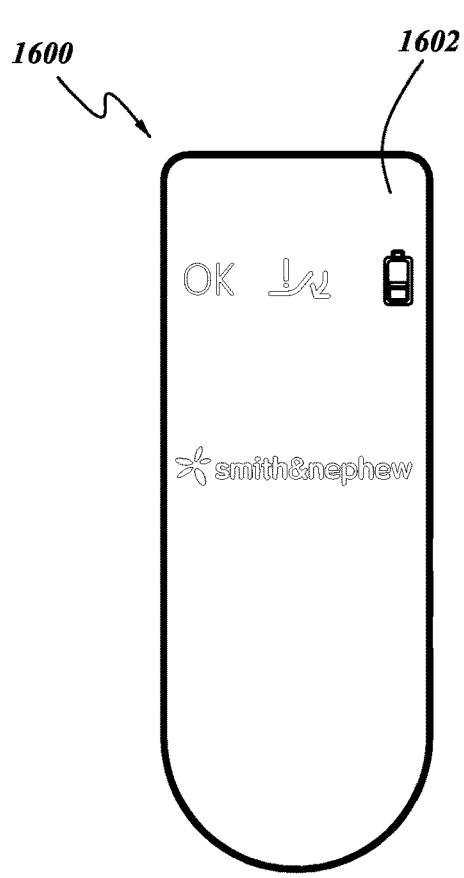
Figure 47C:
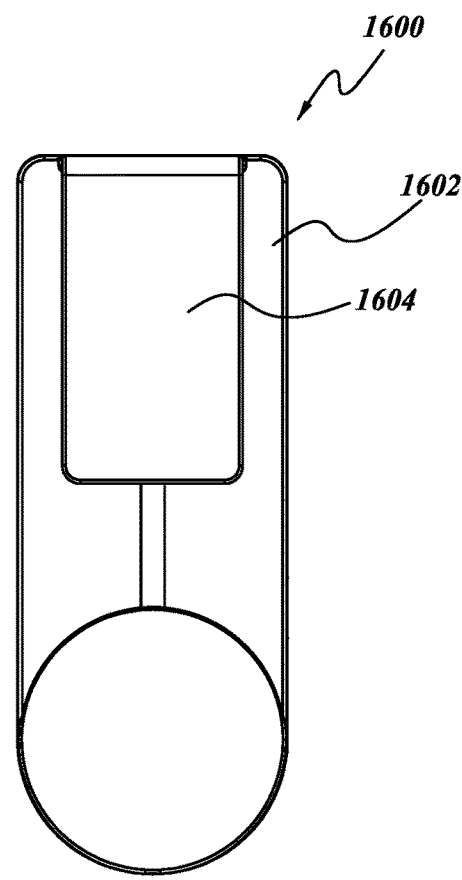
Figure 47D:
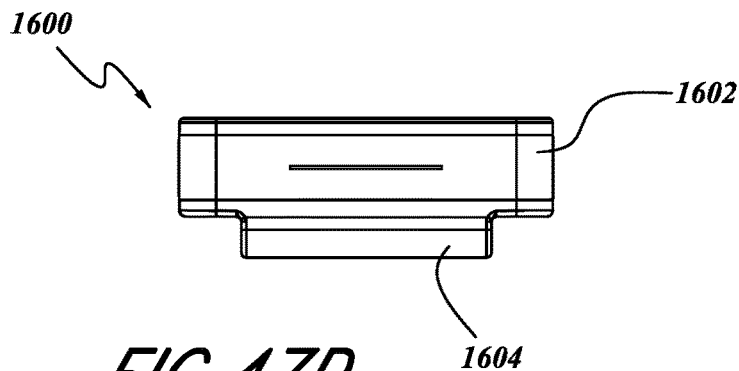
Figure 47E:
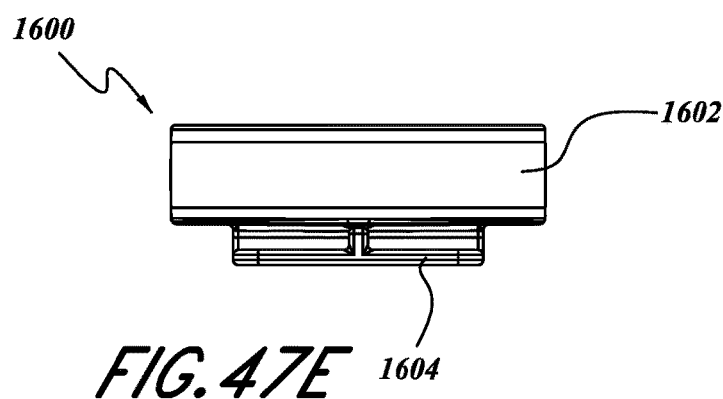
Figure 47F:
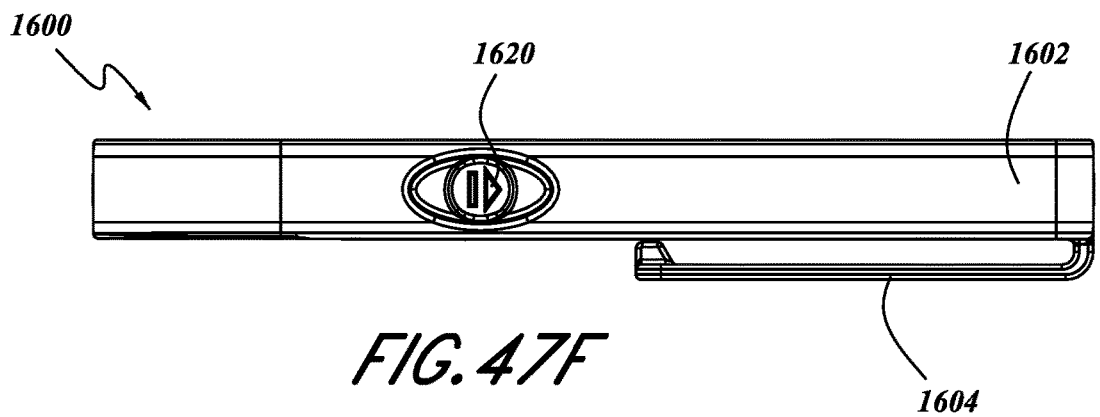
Figure 47G:
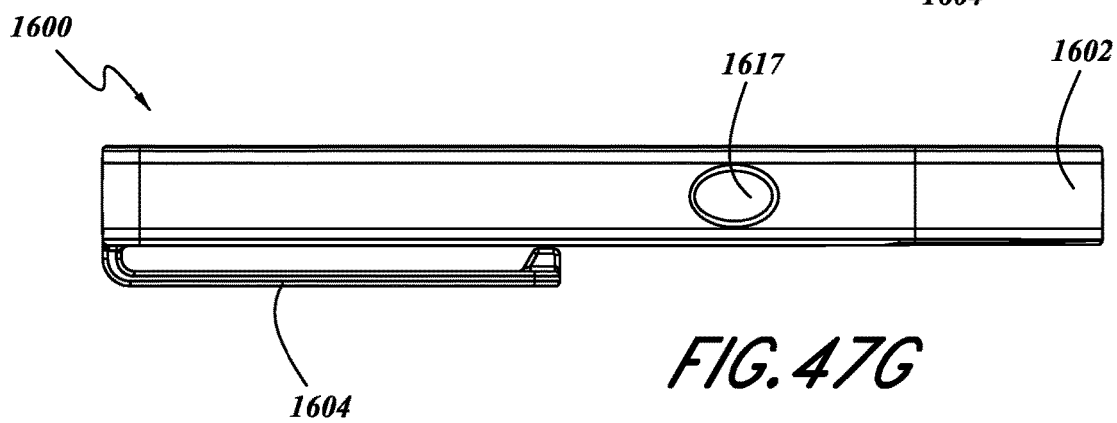
Figure 48A:
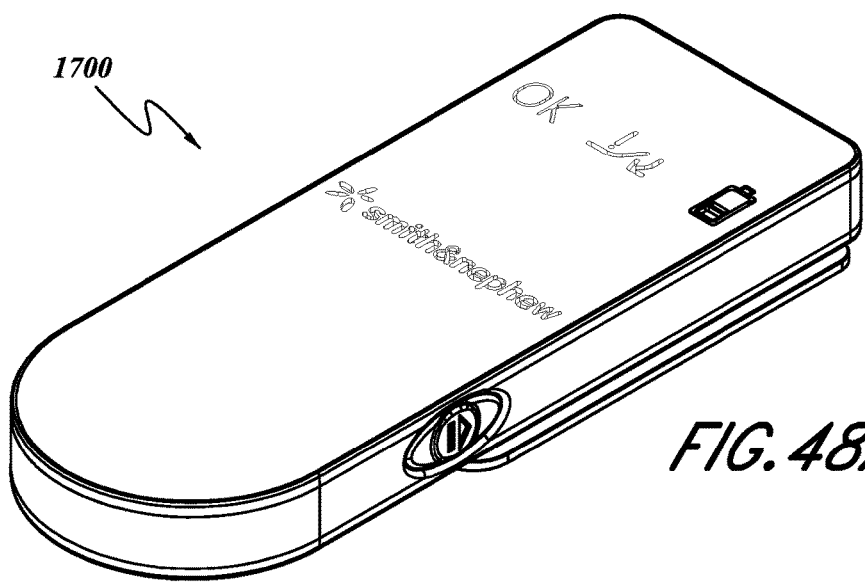
FIGS. 48A-48G are an isometric view, a top view, a bottom view, a top end view, a bottom end view, a first side view, and a second side view, respectively, of another embodiment of a pump assembly.
Figures 48B, 48C:
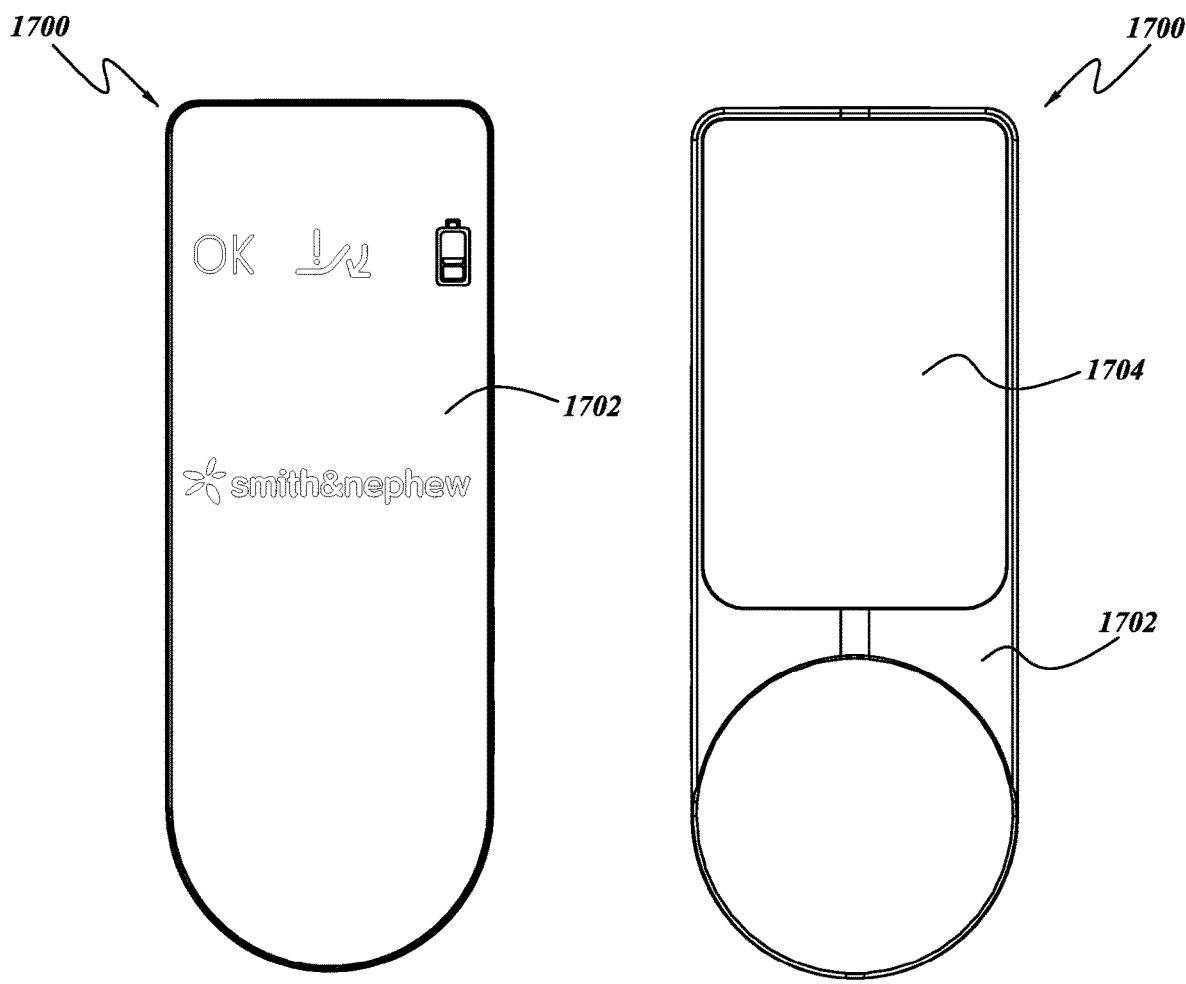
Figure 48D:
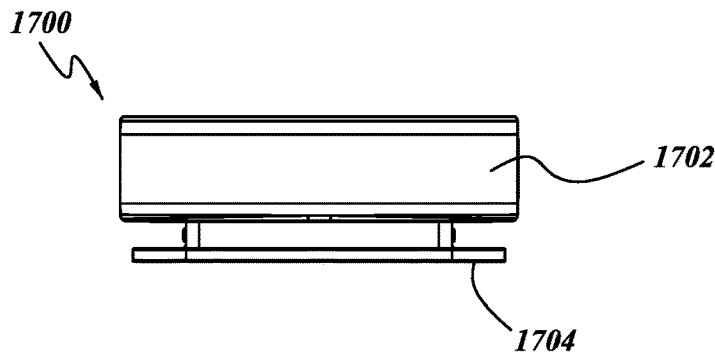
Figure 48E:
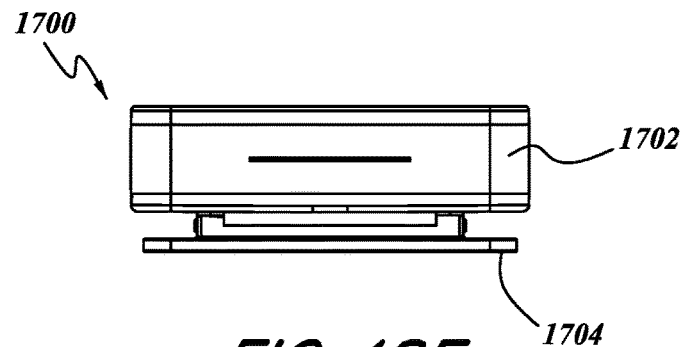
Figure 48F:
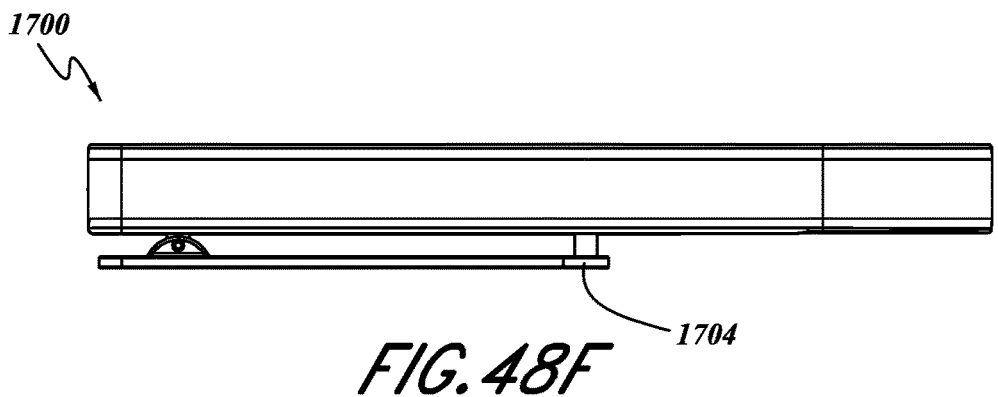
Figure 48G:
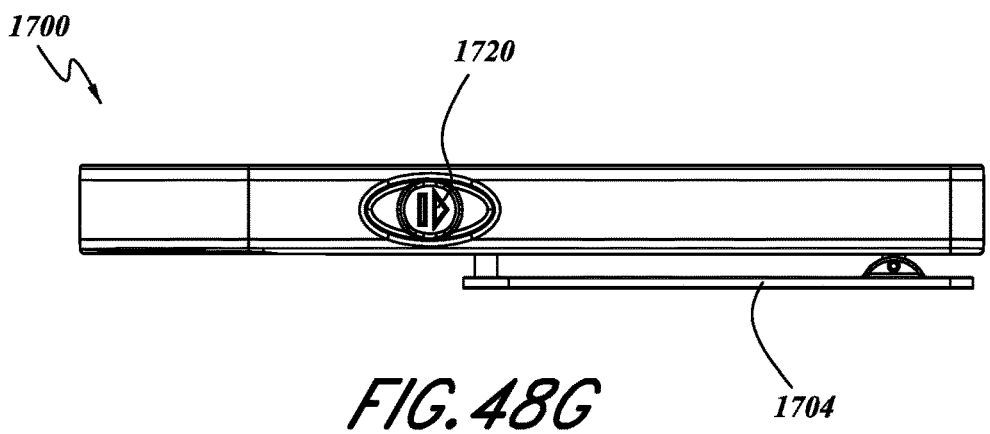

With reference to FIG. 40H, the first portion 902a and the second portion 902b of the housing 902 can be rotatably connected to one another by a hinge 904. The hinge 904 can permit the first portion 902a to rotate about an axis A within a particular angular range relative to the second portion 902b. The hinge 904 can be biased toward a closed position, as illustrated in FIG. 29A, such that the two portions 902a, 902b form a clip or a clamp. In this configuration, the housing 902 can be clipped to a person's clothing, such as in a pocket, over a belt, to a flap or in a pouch or a pocket on the dressing, or otherwise. For example, the first portion 902a can be positioned on the inside of a pouch, pocket, or otherwise, and the second portion 902b can be positioned outside of the pouch, pocket, or otherwise. The bias can be created with a coil spring, a bent spring, or otherwise, and can cause the housing 902 to grip the flap or pocket. The clamping force can be low enough that a user can open the housing from the clamped position, but strong enough so that it will remain clamped about the pocket, flap, or other material.

FIGS. 41A-41G are an isometric view, a top view, a bottom view, a top end view, a bottom end view, a first side view, and a second side view, respectively, of another embodiment of a pump assembly 1000. Any embodiments of the pump assembly 1000 can have any of the same features, components, weights, dimensions, shapes, or other details of any other pump assembly embodiment disclosed herein, including without limitation the pump assembly embodiment 800 disclosed above. Additionally, the pump assembly embodiment 1000 can be used with any of the dressing embodiments disclosed herein either directly, by incorporation by reference, as part of the Appendix A from Application No. 61/791,984 included below, or otherwise. Therefore, any use of the term "disclosed herein" in this disclosure is meant to refer to any embodiments described or illustrated in this application, incorporated by reference herein, and/or attached as an appendix to Application No. 61/791,984. However, In any embodiments disclosed herein, the pump assembly 1000 can have a number of differences as compared to other pump assemblies disclosed herein.

With reference to FIGS. 41A-41G, the pump assembly 1000 can have a housing 1002 that only has one portion. In this configuration, control button, the pump device, battery power, and control board will be supported within one housing portion. As with the pump assembly 800, an actuation tab (i.e., pull tab) 0 can be used to prevent inadvertent operation of the pump device before the pump assembly 1000 is ready for treatment. In any embodiments disclosed herein, the housing 1002 can have an opening 1017 configured to receive a conduit for communication of reduced pressure to a dressing. A clip 1004 can be supported by the housing 1002, the clip 1004 being configured to enable a user to removably clip the pump assembly to a pocket, pouch, or other flap.

FIGS. 42A-42G are an isometric view, a top view, a bottom view, a top end view, a bottom end view, a first side view, and a second side view, respectively, of another embodiment of a pump assembly 1100. Any embodiments of the pump assembly 1100 can have any of the same features, components, weights, dimensions, shapes, or other details of any other pump assembly embodiment disclosed herein, including without limitation the pump assembly embodiment 800 disclosed above. Additionally, the pump assembly embodiment 1100 can be used with any of the dressing embodiments disclosed herein or otherwise. However, In any embodiments disclosed herein, the pump assembly 1100 can have a number of differences as compared to other pump assemblies disclosed herein.

With reference to FIGS. 42A-42G, the pump assembly 1100 can have a housing 1102 that only has one portion. In this configuration, control button, the pump device, battery power, and control board will be supported within one housing portion. In any embodiments disclosed herein, an actuation tab (not shown) can be used to prevent inadvertent operation of the pump device before the pump assembly 1100 is ready for treatment. In any embodiments disclosed herein, the housing 1102 can have an opening 1117 configured to receive a conduit for communication of reduced pressure to a dressing. A single operation button 1120 can be supported by the housing 1002, the clip 1004 being configured to enable a user to removably clip the pump assembly to a pocket, pouch, or other flap.

FIGS. 43A-43G are an isometric view, a top view, a bottom view, a top end view, a bottom end view, a first side view, and a second side view, respectively, of another embodiment of a pump assembly 1200. FIGS. 44A-44G are an isometric view, a top view, a bottom view, a top end view, a bottom end view, a first side view, and a second side view, respectively, of another embodiment of a pump assembly 1300. FIGS. 45A-45G are an isometric view, a top view, a bottom view, a top end view, a bottom end view, a first side view, and a second side view, respectively, of another embodiment of a pump assembly 1400.

Any embodiments of the pump assembly 1200, 1300, or 1400 can have any of the same features, components, weights, dimensions, shapes, or other details of any other pump assembly embodiment disclosed herein, including without limitation the pump assembly embodiment 1100 disclosed above. Additionally, any embodiments of the pump assembly 1200, 1300, or 1400 can be used with any of the dressing embodiments disclosed herein or otherwise.

However, In any embodiments disclosed herein, the pump assembly 1200, the pump assembly 1300, or the pump assembly 1400 can have a number of differences as compared to other pump assemblies disclosed herein. For example, without limitation, the pump assembly 1200 can have a clip 1204 supported by the housing 1202, the clip 1204 being configured to clip the pump assembly to a pocket, pouch, belt, flap, or otherwise. Similarly, without limitation, the pump assembly 1300 can have a clip 1304 supported by the housing 1302, the clip 1304 being configured to clip the pump assembly to a pocket, pouch, belt, flap, or otherwise. The clip 1304 can have a rotatable hinge having a spring or other biasing mechanism to bias the clip 1304 to a closed position. Further, without limitation, the pump assembly 1400 can have a pair of tabs 1404 (also referred to herein as clips or arms) configured to clip the pump assembly to a pocket, pouch, belt, flap, or otherwise. The pump assembly 1400 can also have an opening 1417 for connecting a tube or conduit to the pump assembly 1400 as well as a single button 1420 for control of the pump assembly.

FIGS. 46A-46G are an isometric view, a top view, a bottom view, a top end view, a bottom end view, a first side view, and a second side view, respectively, of another embodiment of a pump assembly 1500. Any embodiments of the pump assembly 1500 can have any of the same features, components, weights, dimensions, shapes, or other details of any other pump assembly embodiment disclosed herein, including without limitation the pump assembly embodiments 800 or 1100 disclosed above. Additionally, the pump assembly embodiment 1500 can be used with any of the dressing embodiments disclosed herein or otherwise. However, In any embodiments disclosed herein, the pump assembly 1500 can have a number of differences as compared to other pump assemblies disclosed herein.

FIGS. 47A-47G are an isometric view, a top view, a bottom view, a top end view, a bottom end view, a first side view, and a second side view, respectively, of another embodiment of a pump assembly 1600. FIGS. 48A-48G are an isometric view, a top view, a bottom view, a top end view, a bottom end view, a first side view, and a second side view, respectively, of another embodiment of a pump assembly 1700.

Any embodiments of the pump assembly 1600 or 1700, or any other pump assembly embodiments disclosed herein, can have any of the same features, components, weights, dimensions, shapes, or other details of any other pump assembly embodiment disclosed herein, including without limitation the pump assembly embodiments 1100 or 1500 disclosed above. Additionally, any embodiments of the pump assembly 1600 or 1700 can be used with any of the dressing embodiments disclosed herein or otherwise.

However, in any embodiments disclosed herein, the pump assembly 1600 and the pump assembly 1700 can have a number of differences as compared to other pump assemblies disclosed herein. For example, without limitation, the pump assembly 1600 can have a clip 1604 supported by the housing 1602, the clip 1604 being configured to clip the pump assembly to a pocket, pouch, belt, flap, or otherwise. Additionally, any embodiments of the pump assembly 1600 can have an opening or tubing connector 1617 supported by the housing 1602 and a single button 1620 for operation of the pump assembly. The housing of any pump assembly embodiments can disclosed herein can support any of the pump motors disclosed in this application or incorporated by reference, including without limitation any embodiments of the voice coil pump apparatuses disclosed herein, in addition to one or more batteries.

Similarly, without limitation, the pump assembly 1700 can have a clip 1704 supported by the housing 1702, the clip 1704 being configured to clip the pump assembly to a pocket, pouch, belt, flap, or otherwise. The clip 1704 can have a rotatable hinge having a spring or other biasing mechanism to bias the clip 1704 to a closed position. Additionally, any embodiments of the pump assembly 1700 can have an opening or tubing connector (not illustrated) supported by the housing 1702 and a single button 1720 for operation of the pump assembly. The housing of any pump assembly embodiments disclosed herein can support a removable activation switch or tab, configured to prevent electrical conductivity from the batteries to the pump controller and motor in a first, close position, and to permit such electrical conductivity in a second, open (or removed) position.

Additionally, any of the pump assembly or pump device embodiments disclosed herein can be configured to have one or more of the indicator lights illustrated in any of FIGS. 38-58. For example and without limitation, the housing of any of the pump assemblies disclosed herein can support one or more indicator lights of the type and design illustrated in any of such figures.

Figure 49:
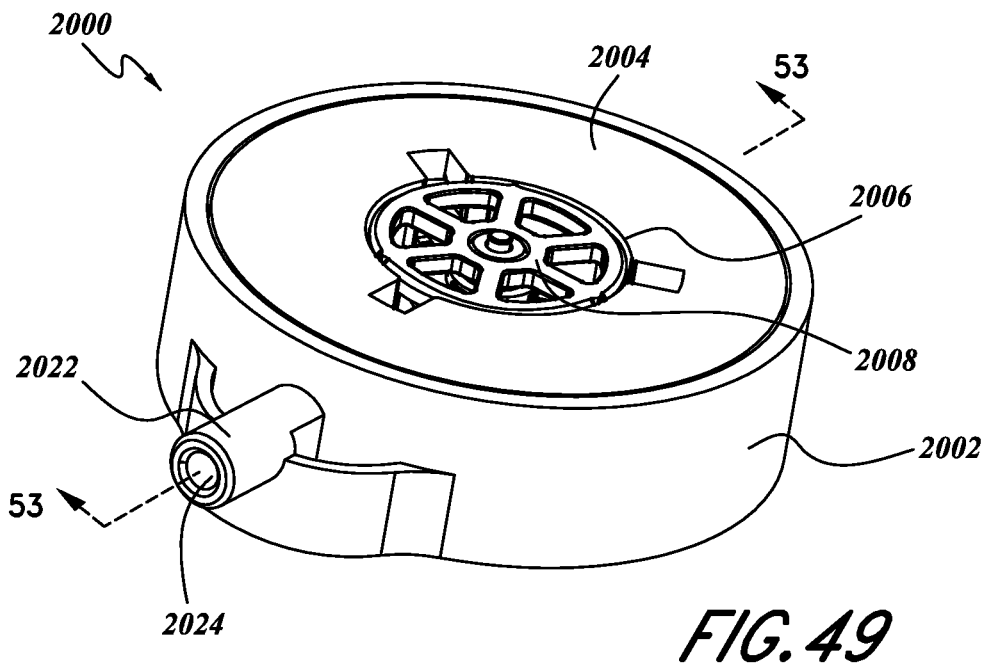
FIG. 49 is an isometric view of another embodiment of a pump assembly, showing a top surface of the pump assembly.
Figure 50:
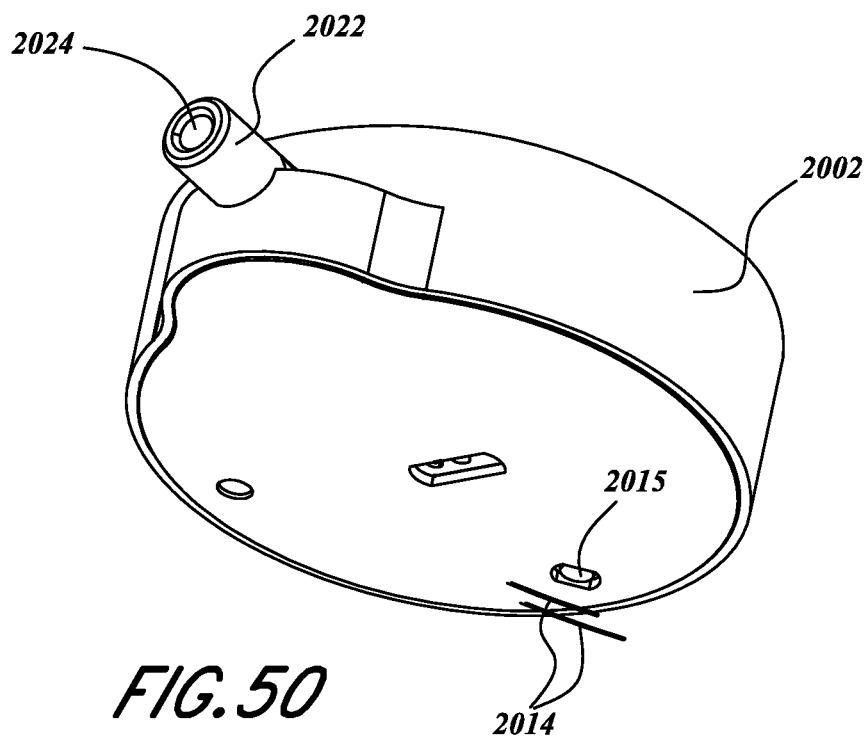
FIG. 50 is an isometric view of the pump assembly embodiment illustrated in FIG. 49, showing a bottom surface of the pump assembly.
Figure 51:
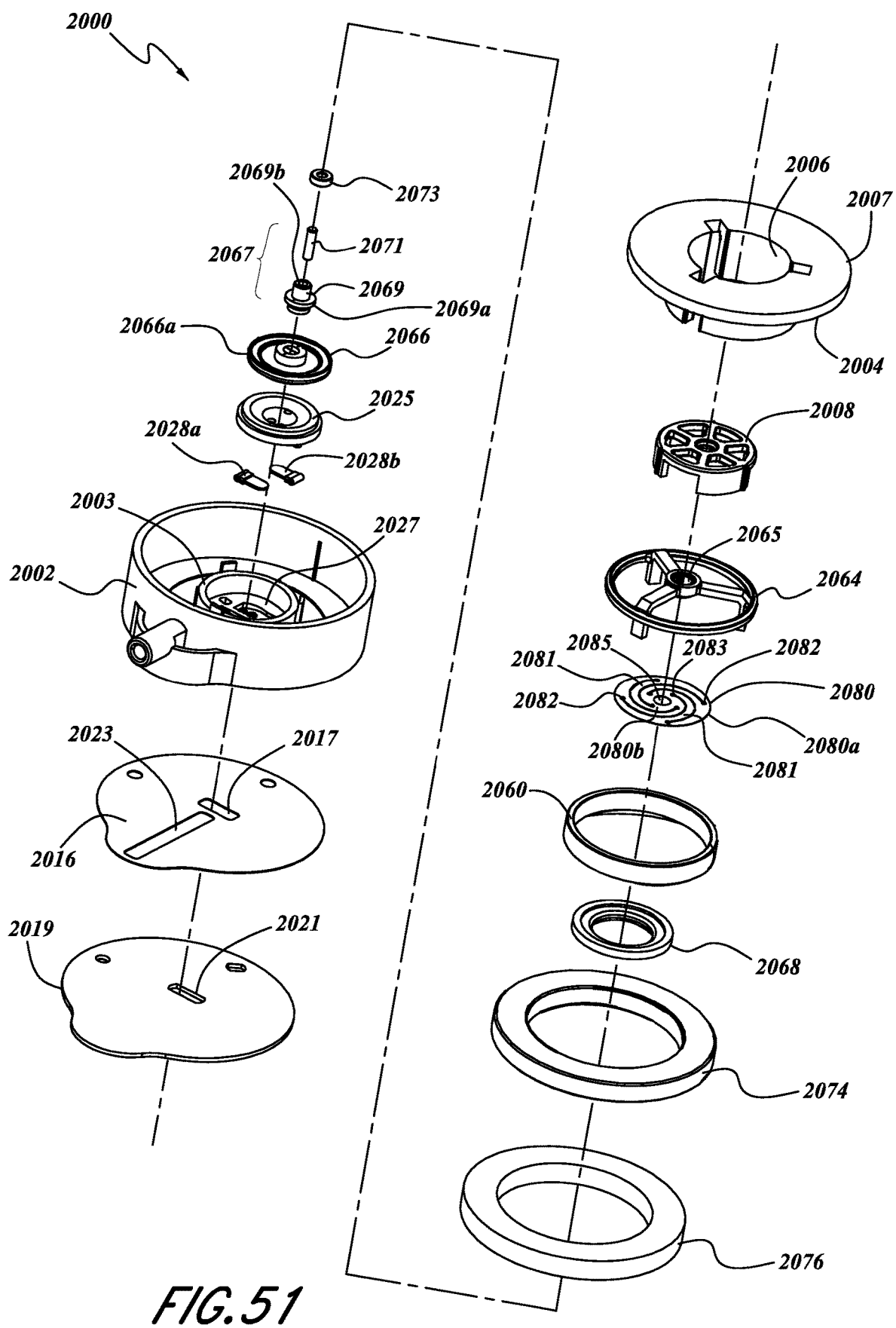
FIG. 51 is an exploded view of the pump assembly embodiment illustrated in FIG. 49, showing the top of the pump assembly.
Figure 52:
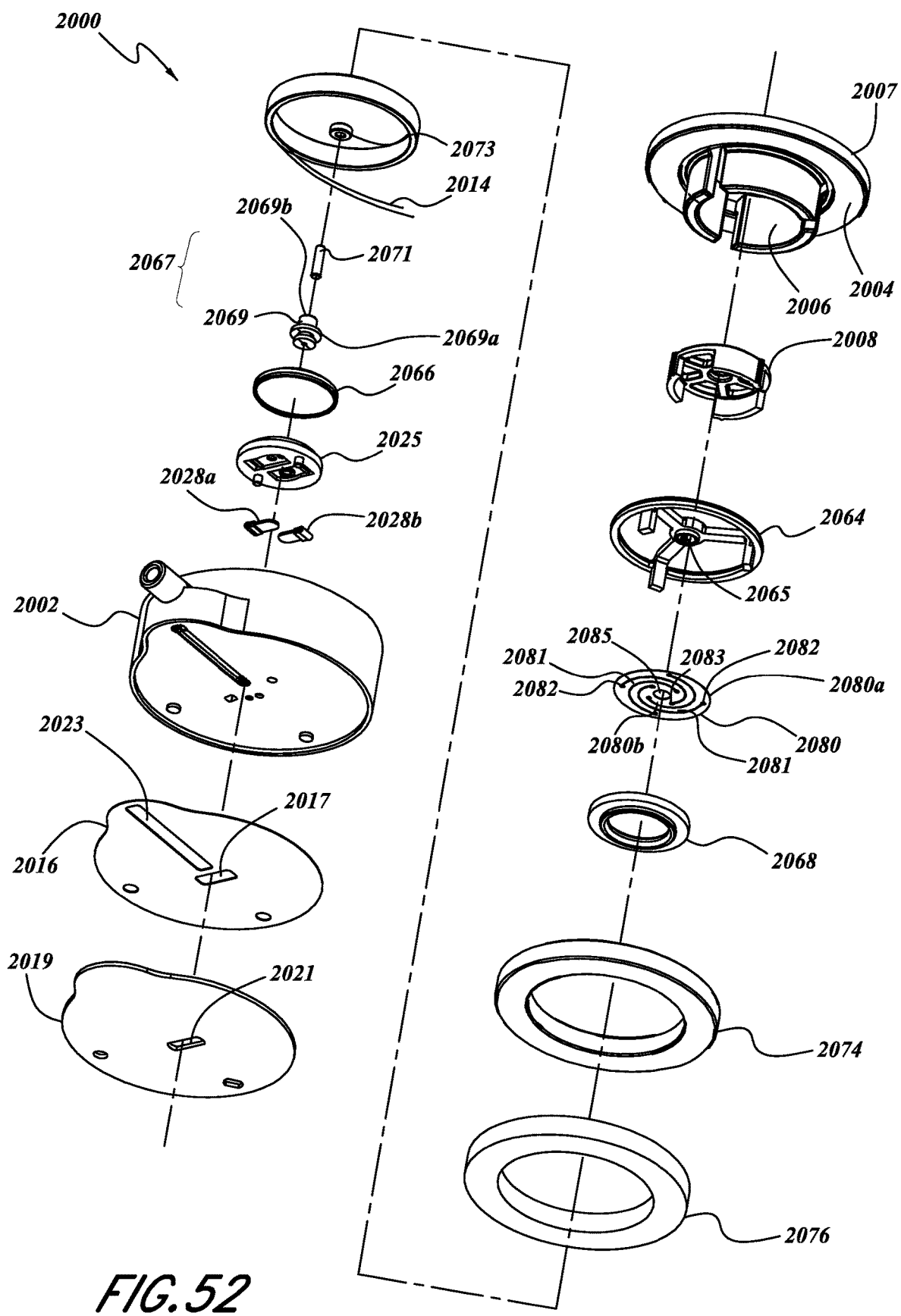
FIG. 52 is an exploded view of the pump assembly embodiment illustrated in FIG. 49, showing the bottom of the pump assembly.
Figure 53:
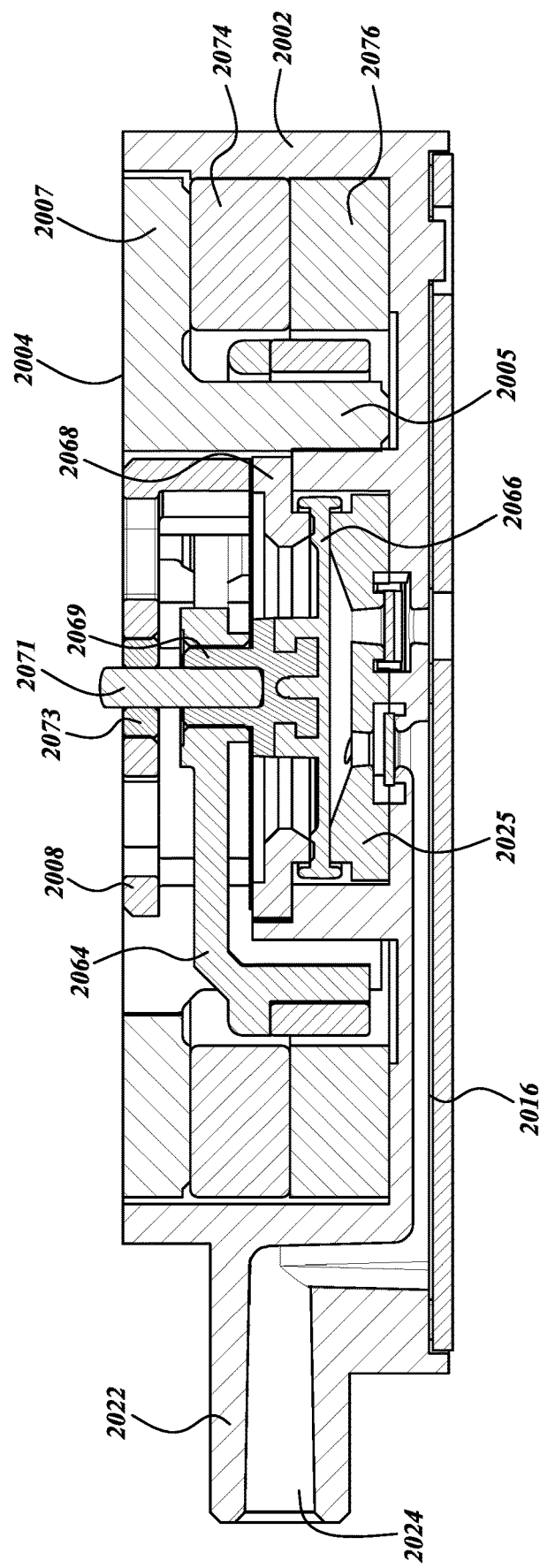
FIG. 53 is a section view of the pump assembly embodiment illustrated in FIG. 49, the section being taken through the center of the pump assembly embodiment.

FIGS. 49 and 50 are isometric views of another embodiment of a pump assembly 2000, showing a top surface of the pump assembly and the bottom surface of the pump assembly, respectively. FIGS. 51 and 52 are exploded views of the pump assembly embodiment illustrated in FIG. 49, showing the top of the pump assembly and the bottom of the pump assembly, respectively. FIG. 53 is a section view of the pump assembly embodiment illustrated in FIG. 49, the section being taken through the center of the pump assembly embodiment. The pump assembly embodiment 2000 can have a compact, small size and can have any of the same features, sizes, components, materials, or other details of the pump assembly embodiment 200 described above, or any of the other pump assembly embodiments disclosed herein.

In any embodiments disclosed herein, the pump assembly 2000 can have a diameter or lateral size in the range of approximately 26-29 mm, or between approximately 25 and approximately 28 mm. In any embodiments disclosed herein, the pump assembly embodiment 2000 can have a thickness or height of approximately 8 mm, or between approximately 6 mm and approximately 10 mm.

The pump assembly embodiment 2000 can be produced for a low cost and can operate at high efficiencies, making it beneficial for portable, disposable, and/or single use applications. In any embodiments disclosed herein, the pump assembly embodiment 2000 can run for a week on a small primary cell without the need for battery replacement or recharging. This pump can be used in an ultra-portable single-use negative-pressure wound therapy (NPWT) device, but is not so limited. In any embodiments disclosed herein, as mentioned, the pump assembly embodiment 2000 can be used for negative pressure wound therapy. However, the pump assembly embodiment 2000 is not limited to use in negative pressure wound therapy systems. The pump assembly embodiment can be adapted and configured for use in any reduced pressure system or in any system or application in which the movement of gaseous and liquid fluids is desired.

The pump assembly embodiment 2000 can be designed to work at pressures of 60-80 mm Hg or more, and can be configured to produce a flow rate of approximately 200 ml min-1, with a minimum efficiency of 15%, in order for the NPWT device to run for a week on a specified battery capacity. In any embodiments disclosed herein, the pump assembly embodiment 2000 can be adapted to operate at efficiency levels in excess of 25%.

The pump assembly embodiment 2000 can have a housing 2002 adapted to support and protect many of the components of the pump assembly embodiment 2000. An upper pole 2004, which can be made from any suitable materials such as mild steel or sintered steel, can be supported at one end (for example, a first end) 2002a of the housing 2002. In any embodiments disclosed herein, the upper pole 2004 can have an opening 2006 formed through an axial centerline of the upper pole 2004. A bearing 2008 can be supported by the upper pole 2004, within the opening 2006. Two or more electrical wires 2014 can be connected to the pump assembly embodiment 2000, configured to provide power to the pump assembly embodiment 2000. In particular, the wires 2014 can be used to provide electrical current to the coil 2060 of the pump assembly. The electrical wires 2014 can be routed through one or more openings or channels formed in the housing 2002, such as channels 2015 shown in FIG. 50 or in any other opening formed in the housing.

A cover 2016 (also referred to herein as a first cover) can be positioned over the electrical wires 2014 after the electrical wires have been advanced through the channels 2015. The cover 2016 can be an adhesive backed foil, film, paper, plastic sheet or label, or other similar object. The cover 2016 can have adhesive on both planar surfaces thereof. An opening 2017 can be formed in the cover 2016 to permit air, gas, or other fluid to be exhausted from the pump through the outlet manifold or opening. Additionally, in any embodiments, a second channel or opening 2023 can be formed in the cover 2016 to form an inlet conduit for the pump. A second cover 2019 can be positioned over the first cover 2016, the second cover 2019 having an opening 2021 therein for exhaust gas. The second cover 2019 can be used to close or substantially seal one or more openings, such as the opening 2023 for an inlet conduit, formed in the cover 2016.

Additionally, in any embodiments disclosed herein, the first cover 2016 and/or the second cover 2019 can be configured to complete the inlet vacuum channel. In other words, the cover 2016 can be configured to separate or seal the vacuum created by the pump from atmosphere. Using a thin label, such as the cover 2016, in place of a thicker plastic molded part or otherwise can decrease the height or thickness of the pump as much as possible. Alternatively, any embodiments of the pump assembly can have a thicker cover that can be molded, cast, machined, or formed by any other suitable method.

The housing 2002 can support a valve assembly 2020 at an end (for example, a second end 2002b) of the housing 2002. The housing 2002 can support a boss member 2022 that can receive a conduit therein or thereover, the boss member 2022 having an opening 2024 therethrough. The opening 2024 can be in fluid communication with one or more passageways inside the pump assembly embodiment 2000, such as air passageway 2003 formed (that can be covered by the cover 2016) in the housing 2002 that communicates with the air passageway 2029 formed in the valve assembly 2020.

With reference to FIGS. 51 and 52, the valve assembly 2020 can have a first valve member 2025, and a second valve member 2027 (that can be formed into the housing 2002). The valve plate 2026 (also referred to herein as a valve support) can support two flexible valve flaps 2028, a first valve flap 2028a for the inlet valve chamber and a second valve flap 2028b for the outlet valve chamber. The first flap 2028a and the second flap 2028b can be configured to deflect away from the relaxed position of the flaps 2028 shown to block passage of air through the valve assembly 2020 during operation of the pump, or possibly even during sterilization of the pump.

As with the other valve supports or valve assembly embodiments disclosed herein, a first inlet valve chamber of the second valve member 2027 can have a cavity or depression and one or more openings, such as an opening in communication with the depression to permit the passage of air from the channel into the pump assembly embodiment 2000 when the flap valve 2028a is in an open position. In any pump assembly embodiments disclosed herein, the first valve support can provide a sealing surface for the valve flap 2028 to selectively seal against to seal the opening 2024. In any embodiments disclosed herein, the sealing surface for any of the valves can have an angled or curved surface configured to substantially match the profile of the valve flap 2028a as the valve flap 2028a is deflected from the relaxed position against the sealing surface. This arrangement can improve the seal between the valve flap 2028a and the sealing surface to increase the efficiency of the pump assembly embodiment 2000. In some embodiments, the sealing surface can be straight and not angled or curved.

In use, for any of the embodiments disclosed herein, as the voltage supplied to the coil oscillates between a positive voltage and a negative voltage, the coil (which can be fixed to the support member and the diaphragm) can oscillate up and down in the pump between the two poles 2004 and 2076. The oscillation of the diaphragm 2066 can cause the volume within the pump to increase or decrease and, hence, cause the pressure within the pump to decrease or increase. A pressure decrease within the pump chamber can draw air into the pump chamber and open the inlet manifold (or flap), while the flap on the outlet manifold can seal the outlet manifold closed. Then, as the diaphragm 2066 returns toward the valve support, the volume of airspace decreases, causing the air pressure to increase. This forces air out of the chamber through the outlet valve, while the inlet valve is sealed closed.

The first outlet valve chamber of the second valve member 2027 can have a cavity or depression and one or more openings configured to allow the passage or exit of air from the inside of the depression and the pump assembly embodiment 2000 when the valve flap 2028b is in an open position. In any embodiments, the valve assembly 2020 can have one, two, three, or more openings formed in either of the inlet and outlet valve chambers. The housing 2002 can have a similar arrangement of inlet and outlet valve chambers as compared to the first inlet and outlet valve chambers.

A second inlet valve chamber supported by the first valve member 2025 can have a cavity or depression and one or more openings in communication with the depression to permit the passage of air from the first inlet valve chamber into the second inlet valve chamber when the valve flap is in an open position (e.g., not sealingly covering the opening 2024). One or more openings can be formed in the second inlet valve chamber to permit air to pass from the second inlet valve chamber into the inside of the pump assembly embodiment 2000. In any of the pump embodiments disclosed herein, the inlet valve chamber and/or the outlet valve chamber, on either side of the flap valve, can have one, two, three, ore more openings configured to permit air to pass therethrough.

Similarly, a second outlet valve chamber can be supported by first valve member 2025. The second outlet valve chamber can have a depression formed therein and an opening in communication with the second outlet valve chamber. In any embodiments disclosed herein, similar to the boss 2031, the boss 2052 can have an angled or curved surface configured to substantially match the profile of the valve flap as the valve flap is deflected from the relaxed position against the surface of the boss. This arrangement can improve the seal between the valve flap and the boss or sealing surface to increase the efficiency of the pump assembly embodiment 2000. When the valve flap 2028b is in an open position, air or other fluid within the pump assembly embodiment 2000 can pass through the opening into the first outlet valve chamber and exit the pump assembly embodiment 2000 through the one or more openings.

In any embodiments disclosed herein, valve flaps 2028a, 2028b can be configured to be unstressed in a neutral position, neither fully open nor fully closed. Therefore, rather than there being a 'cracking pressure' required to open them, In any embodiments disclosed herein, a small back-pressure (for example, approx. 30 mbar or more) can be used to hold valve flaps 2028a, 2028b closed. This improves efficiency by reducing the pressure force that must be generated by the VCA during the suction stroke.

The pump assembly embodiment 2000 can have a coil 2060 comprising electrical wires 2014, and a support member 2064. The coil 2060 can be formed from a length of wound conductive wire, such as without limitation copper wire. In operation, the coil 2060 can be configured to move within a magnetic circuit, and can be supported via a support member to a pump diaphragm assembly 2066. In any embodiments disclosed herein, an opening 2065 formed in the support member 2064 can be configured to receive a shaft assembly or protrusion 2067 (which can comprise a base portion 2069 and a shaft portion 2071) of the diaphragm assembly 2066 so the pump diaphragm assembly 2066 can be coupled with the support member 2064. The diaphragm 2066 can be supported and fixed at its peripheral portion 2066a, wherein an interior portion 2066b of the diaphragm assembly 2066 is permitted to flex and deflect in either direction away from the relaxed position of the diaphragm assembly 2066. The diaphragm assembly 2066 is configured to elastically return the coil 2060 to its relaxed position.

The housing 2002 can have a generally cylindrical protrusion or wall 2003 that can engage the peripheral portion 2066a of the diaphragm. A bearing or bushing 2008 that can have extending cylindrical walls can support the peripheral portion 2066a from the opposite side as compared to the wall 2003 of the housing.

The diaphragm 2066 can be supported and/or fixed along all or a portion of its peripheral portion 2066a, wherein an interior portion 2066b of the diaphragm assembly 2066 is permitted to flex and deflect in either direction away from the relaxed position of the diaphragm assembly 2066. In any embodiments disclosed herein, the diaphragm can be clamped and compressed between two rigid surfaces to provide such support. The rigid surfaces can define an annular shape. For example, any embodiments of the diaphragm 2066 (or any other diaphragm disclosed herein) can have a moulding and a separate compression ring (made from a rigid plastic, aluminium or other metal, or any other suitable material or composite material). Additionally, any embodiments of the diaphragm 2066 (or any other diaphragm disclosed herein) can have one plastic or other frame or moulding on each side of the flexible diaphragm membrane. The mouldings and the flexible diaphragm membrane can be held together with adhesive, mechanical connections between the mouldings, ultrasonically welding, or by any other suitable method. In any embodiments disclosed herein, the diaphragm can have a single frame or moulding having a channel therein configured to receive and support a peripheral edge of the flexible diaphragm membrane. Additionally, In any embodiments disclosed herein, the diaphragm 2066 can be sealed at its outer perimeter 2066a. The diaphragm assembly 2066 is configured to elastically return the coil 160 to its relaxed position. Any of the pump embodiments disclosed herein (i.e., in this application) can be formed from cast or molded silicone, polyurethane, thermoplastic polyurethane, EPDM, and/or other suitable materials, having a hardness value of approximately 20 A, 30 A, 40 A, 50 A, 55 A, or more.

Any embodiments disclosed herein can also have a flat spring member 2080 positioned adjacent to the diaphragm. In any embodiments, the spring member 2080 can be positioned against a flange portion 2069a of the base portion 2069 of the diaphragm assembly 2066. In any embodiments, the spring member 2080 can be positioned at a top portion 2069b of the base portion 2069 of the diaphragm assembly 2066, or can be positioned in any desired locations. In any embodiments, the spring member 2080 can be sized and configured to provide frequency tuning or adjustment to the resonance frequency of the diaphragm and/or the components of the oscillating coil assembly. In any embodiments, the spring member 2080 can be configured to maintain the radial alignment of the diaphragm assembly 2066 with the remainder of the pump assembly (to inhibit wobble of the diaphragm member or otherwise), or both to maintain alignment and to provide resonance frequency adjustment. The spring member 2080 can be made from stainless steel, spring steel, or any other suitable material.

In any embodiments disclosed herein, the spring member 2080 can have a thickness of approximately 0.08 mm, or from approximately 0.06 mm to approximately 0.2 mm, or between any two values in the foregoing range. In any embodiments, an outside diameter of the spring member 2080 can be approximately 9.75 mm, or from approximately 6.0 mm or less to approximately 11.0 mm. In any embodiments, the gap between the arms can be approximately 0.2 mm wide.

Additionally, in any pump embodiments disclosed herein, the spring member 2080 can have a plurality of arms 2081. The arms 2081 in any embodiment can be straight, can be radially oriented, or can be curved or helically shaped, as in the illustrated embodiment. To reduce stress concentrations and to improve the flexibility of the arms 2081, openings 2083 can be formed in the spring member 2081 adjacent to the ends of the arms. In any embodiments, as in the illustrated embodiment, the spring member 2080 can have four arms. In other embodiments, as in other embodiments disclosed herein, the spring member can have three arms, or five or more arms. The arms can be flexible and can be configured to provide the spring-like displacement between an outer portion 2080a of the spring member 2080 and an inner portion 2080b of the spring member 2080. An opening 2085 can be positioned at a center of the spring member 2081 for receiving the shaft portion 2071.

The pump assembly embodiment 2000 can have a magnet 2074 positioned between a lower pole 2076 and the upper pole 2004. In any embodiments disclosed herein, the magnet 2074 can be made from sintered Neodymium-Iron-Boron (NdFeB), from Neodymium N33, or any other suitable material. Any of the pole pieces disclosed herein can be formed from soft iron or any suitable material. This material can be used to maximize field strength and minimize losses, thereby increasing the efficiency of the pump assembly embodiment 2000. However, In any embodiments disclosed herein, the magnet 2074 can be formed from any suitable magnetic material. In any embodiments disclosed herein, the lower pole can be approximately 1.5-2.0 mm thick and can be made from any suitable material, such as mild steel.

The arrangement of the pump assembly embodiment 2000 can be configured to differ from a typical low fidelity loudspeaker. For example, some embodiments of the pump assembly 2000 can differ in the following ways. In the pump assembly embodiment 2000, the coil 2060 can be configured to underhang below the end of the magnetic circuit. For example, the coil 2060 can be configured such that it does not extend above the magnetic circuit. This can improve the efficiency and reduce the overall height of the pea 2000, but can result in the degradation of the linearity of response of the pump assembly embodiment 2000.

The coil 2060 can have a relatively high number of turns. Having a relatively high number of turns can give the coil 2060 greater structural rigidity and can maximize the efficiency of the pump assembly embodiment 2000. Additionally, the pump assembly embodiment 2000 will not have a speaker cone that is typically in a low fidelity speaker, which normally serves to control coil motion. In the pump assembly embodiment 2000, the diaphragm can be used to center the coil 2060, and a linear bearing 2008 can be used to limit any wobble of the coil 2060 by engaging the protrusion 2067 and controlling the movement of the support member 2064.

The housing 2002, support 2014, valve assembly 2020, retainer 2062, and/or support member 2064 can be made of a plastic or hard rubber material, metal, or any other suitable material or combination of materials. Such components can be formed by any suitable methods such as casting, any molding process such as injection molding, forging, sintering, machining, or any other suitable process.

Figure 54:
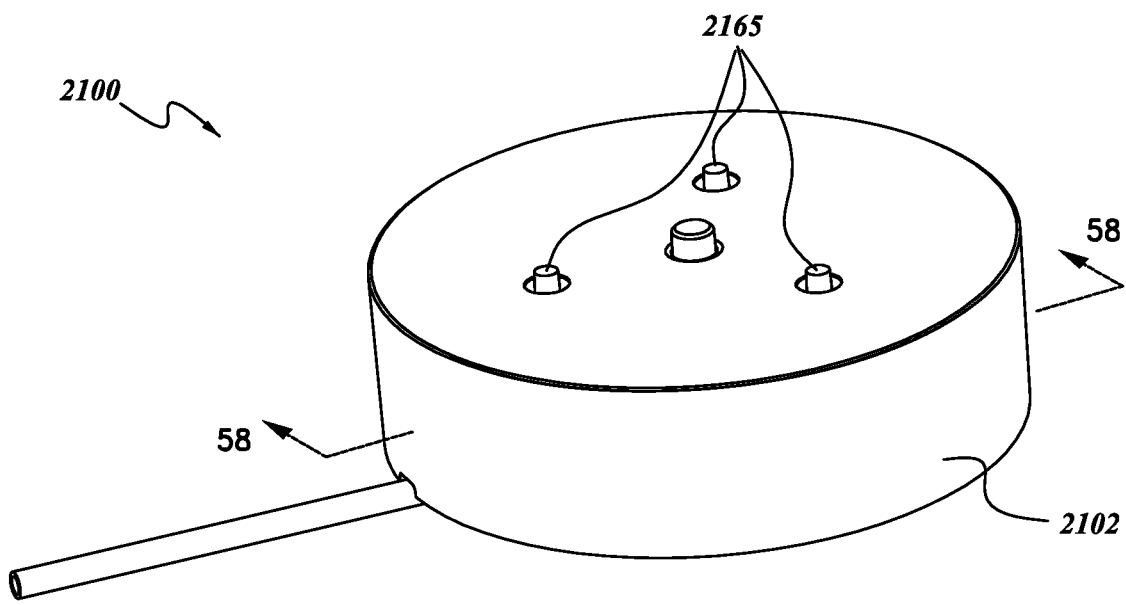
FIGS. 54 and 55 are isometric views of another embodiment of a pump assembly, showing a top surface of the pump assembly and the bottom surface of the pump assembly, respectively.
Figure 55:
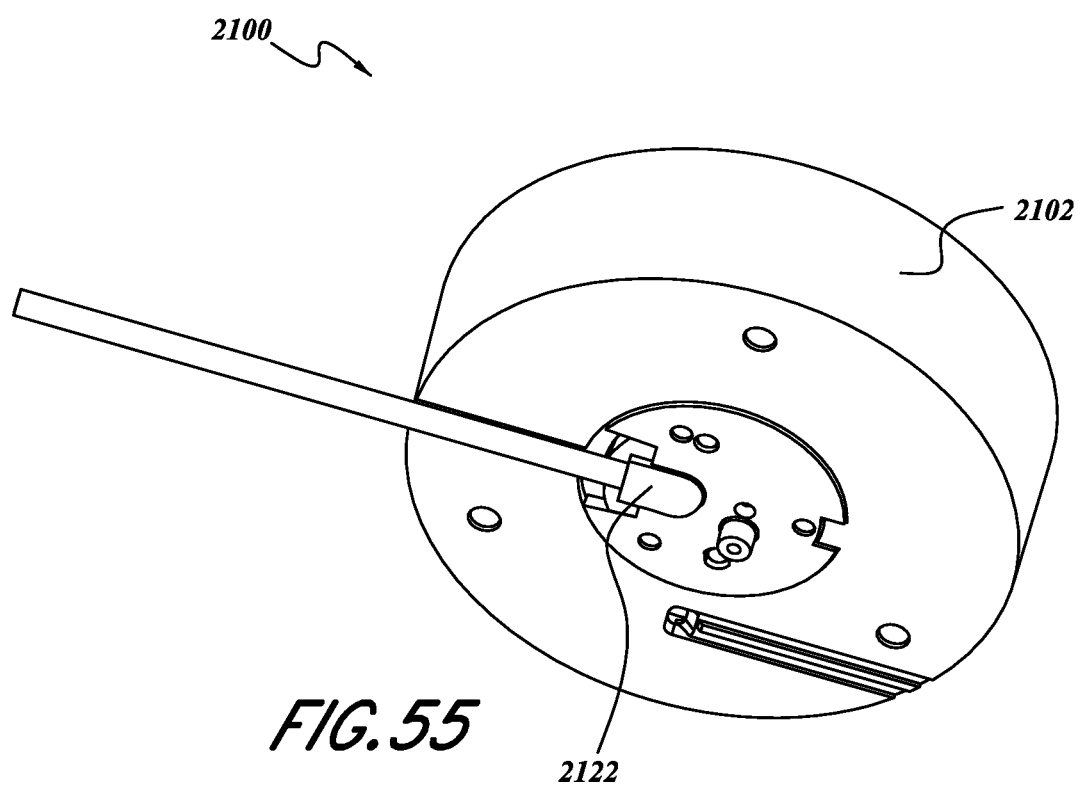
Figure 56:
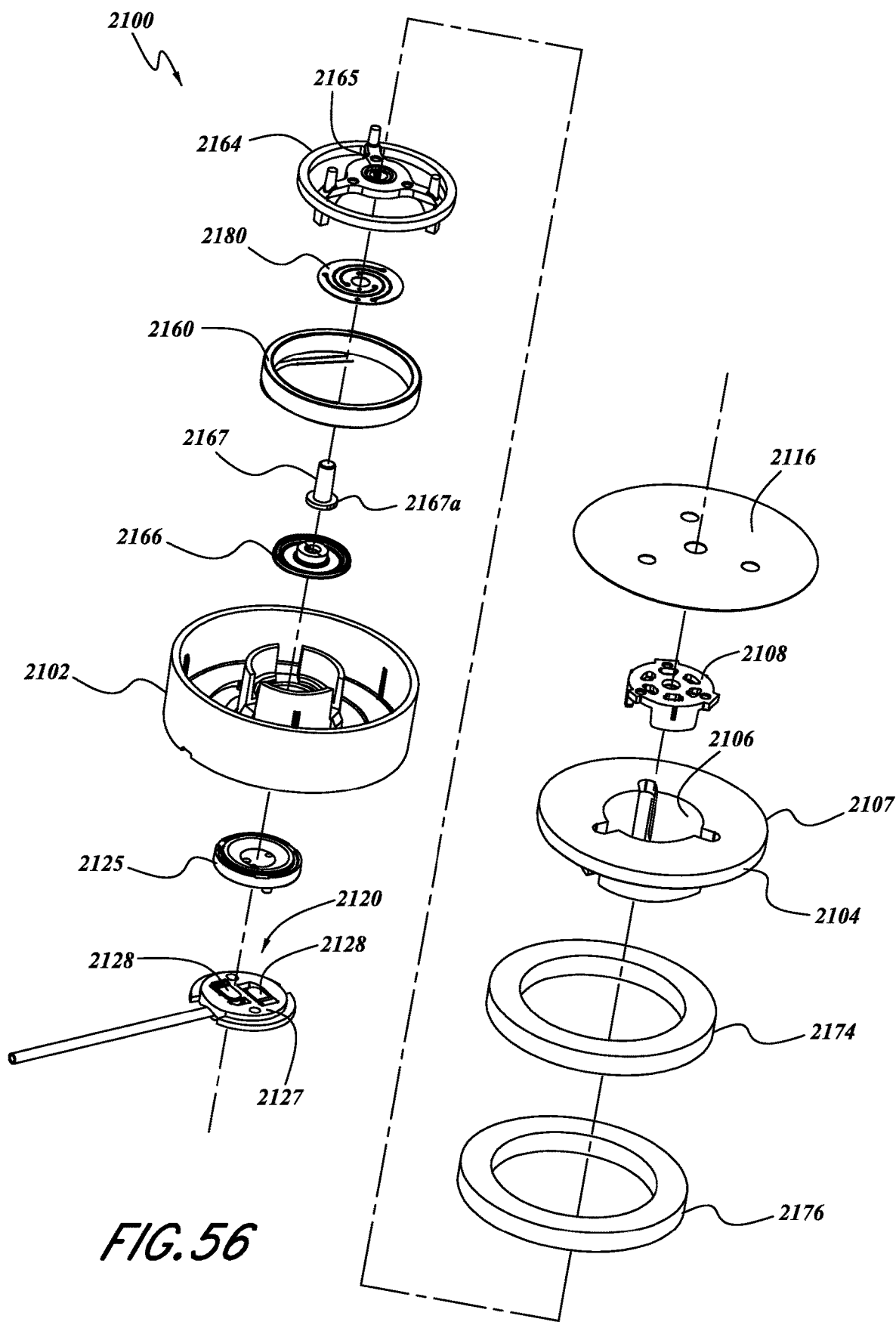
FIGS. 56 and 57 are exploded views of the pump assembly embodiment illustrated in FIG. 54, showing the top and the bottom of the pump assembly, respectively.
Figure 57:
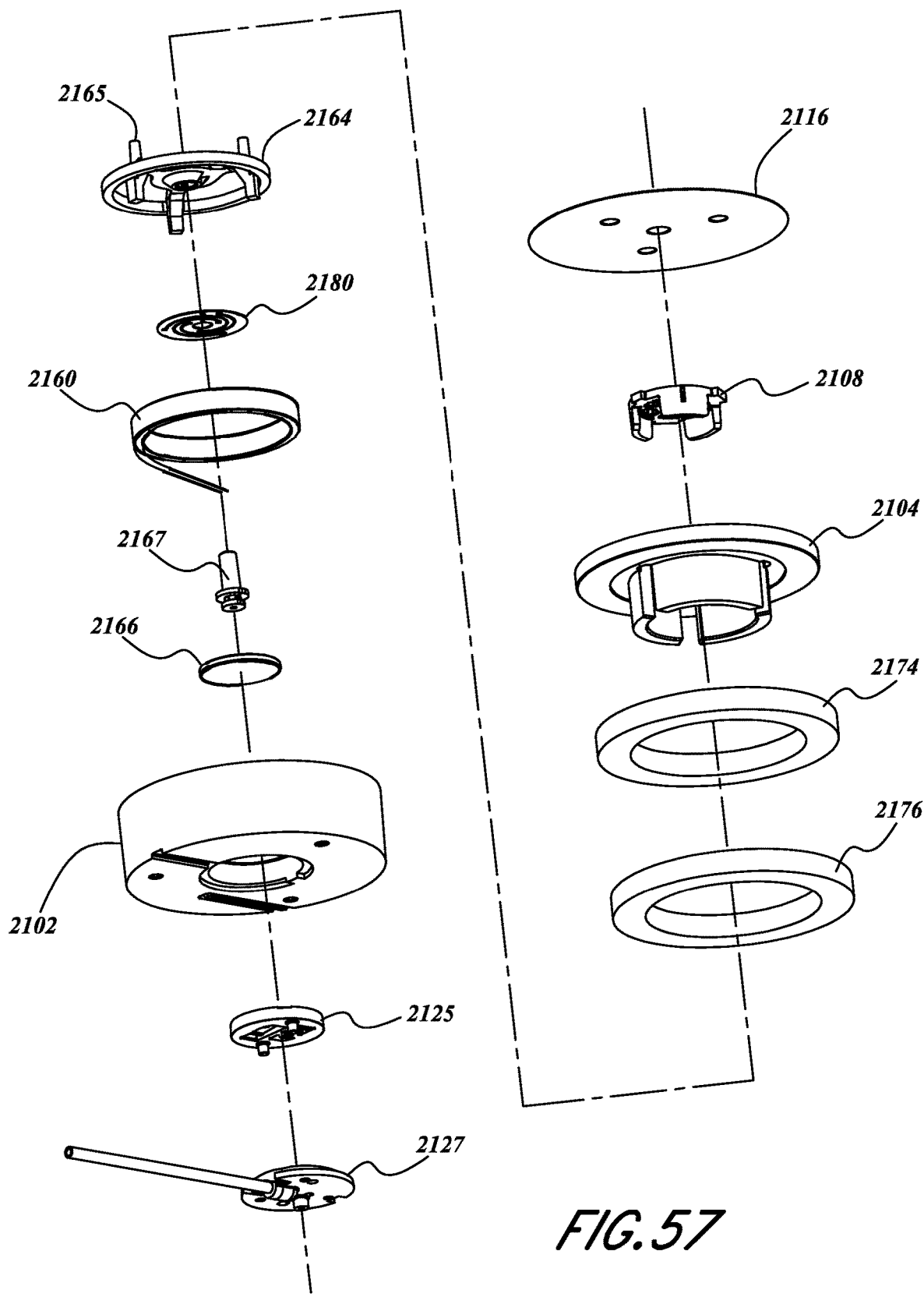
Figure 58:
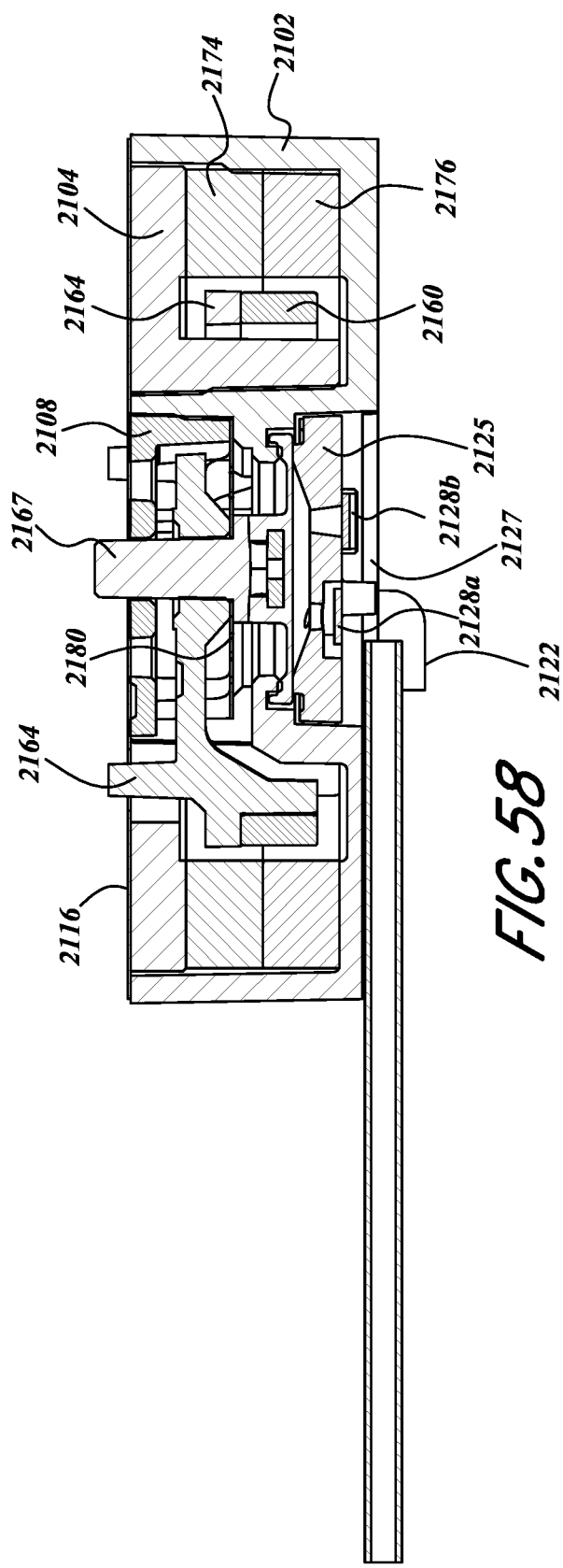
FIG. 58 is a section view of the pump assembly embodiment illustrated in FIG. 54, the section being taken through the center of the pump assembly embodiment.

FIGS. 54 and 55 are isometric views of another embodiment of a pump assembly 2100, showing a top surface of the pump assembly and the bottom surface of the pump assembly, respectively. FIGS. 56 and 57 are exploded views of the pump assembly embodiment illustrated in FIG. 54, showing the top of the pump assembly and the bottom of the pump assembly, respectively. FIG. 58 is a section view of the pump assembly embodiment illustrated in FIG. 54, the section being taken through the center of the pump assembly embodiment. The pump assembly embodiment 2100 can have a compact, small size and can have any of the same features, sizes, components, materials, or other details of the pump assembly embodiment 210 described above, or any of the other pump assembly embodiments disclosed herein.

In any embodiments disclosed herein, the pump assembly 2100 can have a diameter or lateral size in the range of approximately 26-29 mm, or between approximately 25 and approximately 28 mm. In any embodiments disclosed herein, the pump assembly embodiment 2100 can have a thickness or height of approximately 8 mm, or between approximately 6 mm and approximately 10 mm.

The pump assembly embodiment 2100 can be produced for a low cost and can operate at high efficiencies, making it beneficial for portable, disposable, and/or single use applications. In any embodiments disclosed herein, the pump assembly embodiment 2100 can run for a week on a small primary cell such as a 1200 mAh battery without the need for battery replacement or recharging. This pump can be used in an ultra-portable single-use NPWT device, but is not so limited. In any embodiments disclosed herein, as mentioned, the pump assembly embodiment 2100 can be used for negative pressure wound therapy. However, the pump assembly embodiment 2100 is not limited to use in negative pressure wound therapy systems. The pump assembly embodiment can be adapted and configured for use in any reduced pressure system or in any system or application in which the movement of gaseous and liquid fluids is desired.

The pump assembly embodiment 2100 can be designed to work at pressures of 60-80 mm Hg or more, and can be configured to produce a flow rate of approximately 200 ml min-1, with a minimum efficiency of 15%, in order for the NPWT device to run for a week on a specified battery capacity. In any embodiments disclosed herein, the pump assembly embodiment 2100 can be adapted to operate at efficiency levels in excess of 25%.

The pump assembly embodiment 2100 can have a housing 2102 adapted to support and protect many of the components of the pump assembly embodiment 2100. An upper pole 2104, which can be made from any suitable materials such as mild steel or sintered steel, can be supported at one end (for example, a first end) 2102a of the housing 2102. In any embodiments disclosed herein, the upper pole 2104 can have an opening 2106 formed through an axial centerline of the upper pole 2104. A bearing 2108 can be supported by the upper pole 2104, within the opening 2106. In any embodiments disclosed herein, one or more channels can be formed in the housing for routing wires or conduit, or to create an air passageway.

A cover 2116 (also referred to herein as a first cover) can be positioned over an end portion of the housing 2102. The cover 2116 can be an adhesive backed foil, film, paper, plastic sheet or label, or other similar object. An opening 2117 can be formed in the cover 2116 to permit air, gas, or other fluid to be exhausted from the pump through the outlet manifold.

The valve assembly 2120 can have a first valve member 2125 and a second valve member 2127 that can also have a conduit connection thereon, such as the port or conduit connection 2122 (also referred to herein as a boss). The conduit connection 2122 can engage the conduit at a 90 degree angle relative to the axial centerline of the housing. Any other pump assembly embodiments disclosed herein, including without limitation the pump assembly embodiments 2500, 2600, and 2700 disclosed below, can have one or more conduit connections similar to conduit connection 2122, wherein the conduit connection engages the conduit at a 90 degree angle relative to the axial centerline of the housing. The first valve support 2127 can support two flexible valve flaps 2128, a first valve flap 2128a for the inlet valve chamber and a second valve flap 2128b for the outlet valve chamber. The first flap 2128a and the second flap 2128b can be configured to deflect away from the relaxed position of the flaps 2128 shown to block passage of air through the valve assembly 2120 during operation of the pump, or possibly even during sterilization of the pump.

The first outlet valve chamber of the second valve member 2127 can have a cavity or depression and one or more openings configured to allow the passage or exit of air from the inside of the depression and the pump assembly embodiment 2100 when the valve flap 2128b is in an open position. In any embodiments, the valve assembly 2120 can have one, two, three, or more openings formed in either of the inlet and outlet valve chambers. The housing 2102 can have a similar arrangement of inlet and outlet valve chambers as compared to the first inlet and outlet valve chambers.

A second inlet valve chamber supported by the first valve member 2125 can have a cavity or depression and one or more openings in communication with the depression to permit the passage of air from the first inlet valve chamber into the second inlet valve chamber when the valve flap is in an open position (e.g., not sealingly covering the opening 2124). One or more openings can be formed in the second inlet valve chamber to permit air to pass from the second inlet valve chamber into the inside of the pump assembly embodiment 2100. In any of the pump embodiments disclosed herein, the inlet valve chamber and/or the outlet valve chamber, on either side of the flap valve, can have one, two, three, ore more openings configured to permit air to pass therethrough.

Similarly, a second outlet valve chamber can be supported by first valve member 2125. The second outlet valve chamber can have a depression formed therein and an opening in communication with the second outlet valve chamber. In any embodiments disclosed herein, similar to the boss 2131, the boss 2152 can have an angled or curved surface configured to substantially match the profile of the valve flap as the valve flap is deflected from the relaxed position against the surface of the boss. This arrangement can improve the seal between the valve flap and the boss or sealing surface to increase the efficiency of the pump assembly embodiment 2100. When the valve flap 2128*b* is in an open position, air or other fluid within the pump assembly embodiment 2100 can pass through the opening into the first outlet valve chamber and exit the pump assembly embodiment 2100 through the one or more openings.

The pump assembly embodiment 2100 can have a coil 2160 comprising electrical wires 2114, and a support member 2164. The support member 2164 can have legs 2165 extending through openings in the housing 2102. The coil 2160 can be formed from a length of wound conductive wire, such as without limitation copper wire. In operation, the coil 2160 can be configured to move within a magnetic circuit, and can be supported via a support member to a pump diaphragm assembly 2166.

The diaphragm 2166 can be supported and/or fixed along all or a portion of its peripheral portion 2166*a*, wherein an interior portion 2166*b* of the diaphragm assembly 2166 is permitted to flex and deflect in either direction away from the relaxed position of the diaphragm assembly 2166. In any embodiments disclosed herein, the diaphragm can be clamped and compressed between two rigid surfaces to provide such support. The rigid surfaces can define an annular shape. For example, any embodiments of the diaphragm 2166 (or any other diaphragm disclosed herein) can have a moulding and a separate compression ring (made from a rigid plastic, aluminium or other metal, or any other suitable material or composite material). Additionally, any embodiments of the diaphragm 2166 (or any other diaphragm disclosed herein) can have one plastic or other frame or moulding on each side of the flexible diaphragm membrane. The diaphragm assembly 2166 is configured to elastically return the coil 160 to its relaxed position. Any of the pump embodiments disclosed herein (i.e., in this application) can be formed from cast or molded silicone, polyurethane, thermoplastic polyurethane, EPDM, and/or other suitable materials, having a hardness value of approximately 20 A, 30 A, 40 A, 50 A, 55 A, or more.

Any embodiments disclosed herein can also have a flat spring member 2180 positioned adjacent to the diaphragm. In any embodiments, the spring member 2180 can be positioned against a flange portion 2167*a* of the shaft portion 2167 of the diaphragm assembly 2166. In any embodiments, the spring member 2180 can be positioned at a top portion 2167*b* of the shaft portion 2167 of the diaphragm assembly 2166, or can be positioned in any desired locations. In any embodiments, the spring member 2180 can be sized and configured to provide frequency tuning or adjustment to the resonance frequency of the diaphragm and/or the components of the oscillating coil assembly. In any embodiments, the spring member 2180 can be configured to maintain the axial alignment of the diaphragm assembly 2166 with the remainder of the pump assembly, or both to maintain alignment and to provide resonance frequency adjustment. The spring member 2180 can be made from stainless steel, spring steel, or any other suitable material.

The pump assembly embodiment 2100 can have a magnet 2174 positioned between a lower pole 2176 and the upper pole 2104, any of which components can be made from any of the materials disclosed herein.

Figure 61:
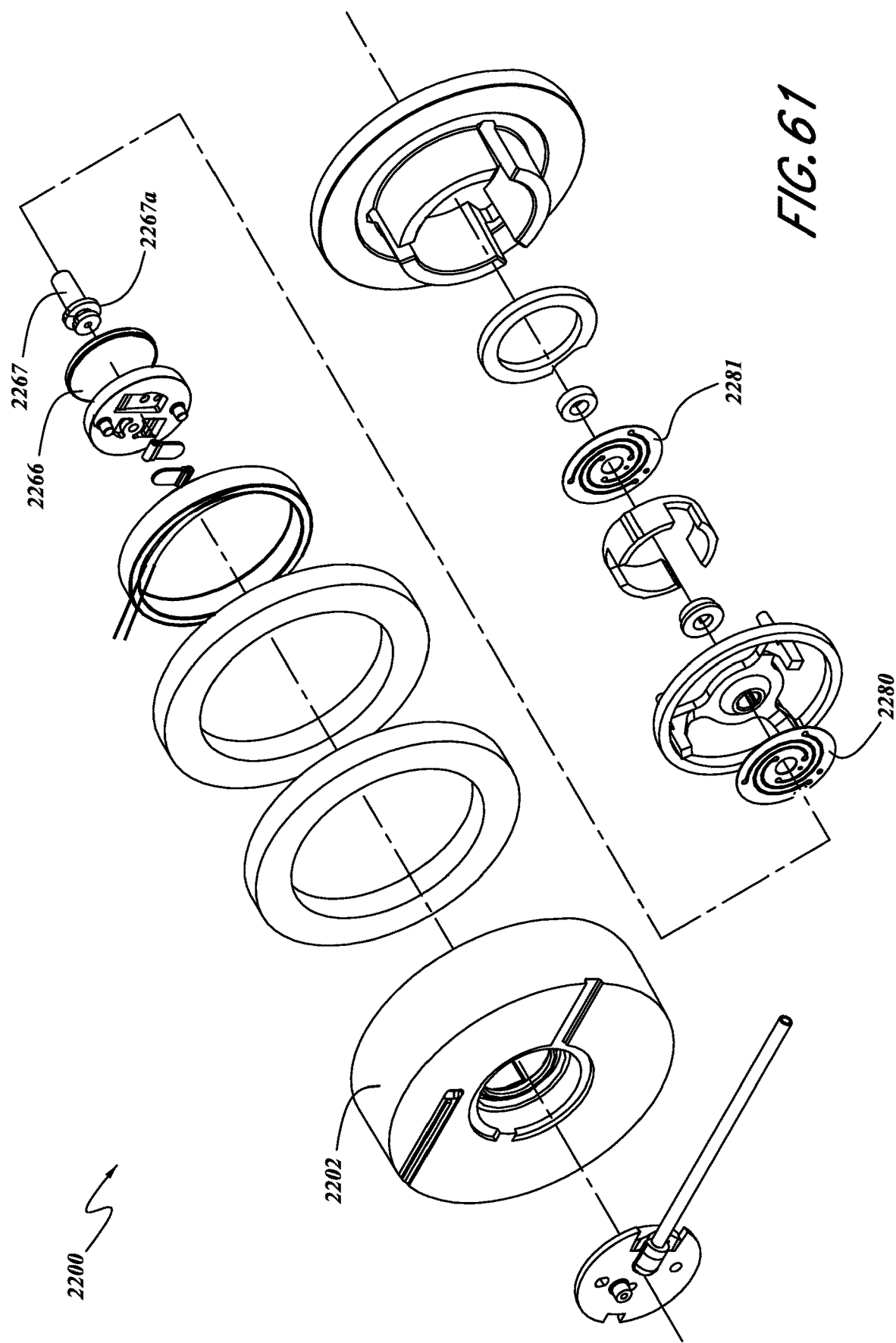
FIG. 61 is an exploded view of the pump assembly embodiment illustrated in FIG. 59.

FIGS. 59 and 60 are a top view and a section view of another embodiment of a pump assembly 2200. FIG. 61 is an exploded view of the pump assembly embodiment 2200 illustrated in FIG. 59. The pump assembly embodiment 2200 can have a compact, small size and can have any of the same features, sizes, components, materials, or other details of the pump assembly embodiment 2100 described above, or any of the other pump assembly embodiments disclosed herein.

Additionally, with reference to FIGS. 60 and 61, the pump assembly embodiment 2200 can have two flat springs 2280 and 2281 supported by the housing 2202 along the length of the shaft 2267 for the diaphragm 2266. A first flat spring 2280 can be positioned at a base 2267*a* of the shaft 2267 and can be configured to provide alignment (via radial support or otherwise) and resonance frequency adjustment for the diaphragm shaft 2267 and the diaphragm 2266. A second spring member 2281 can be positioned closer to a distal end of the shaft 2267 and can be configured to provide radial support to the diaphragm shaft 2267.

Figure 62:
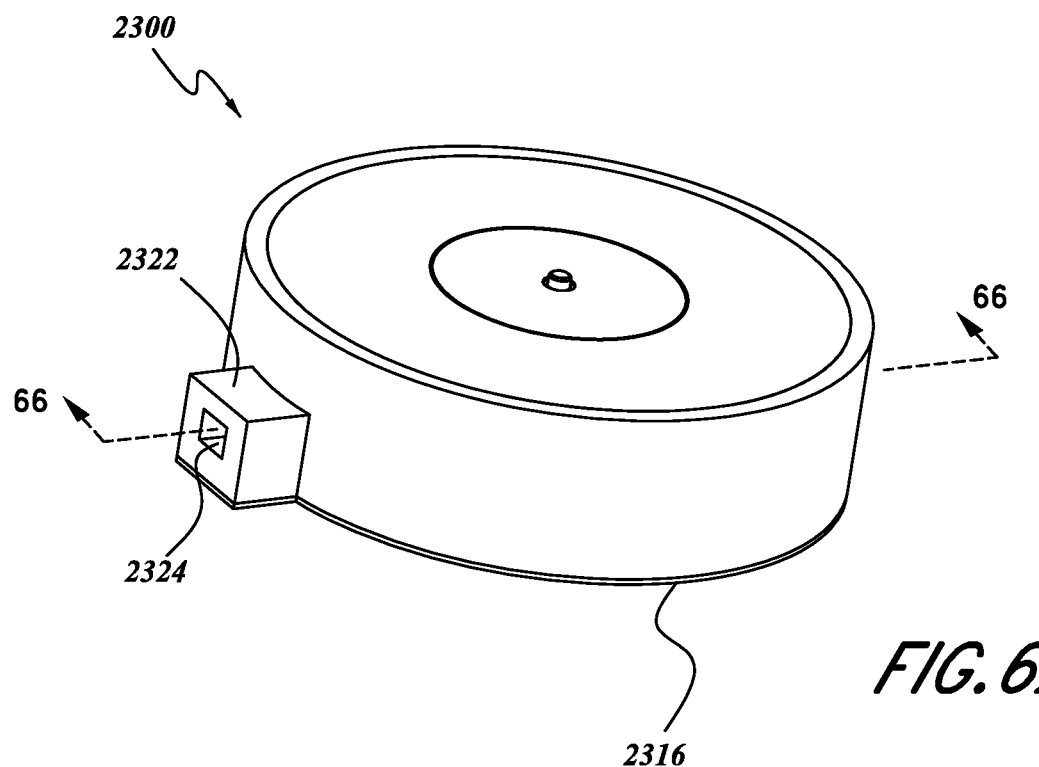
FIGS. 62 and 63 are isometric views, showing the top and the bottom sides of another embodiment of a pump assembly.
Figure 63:
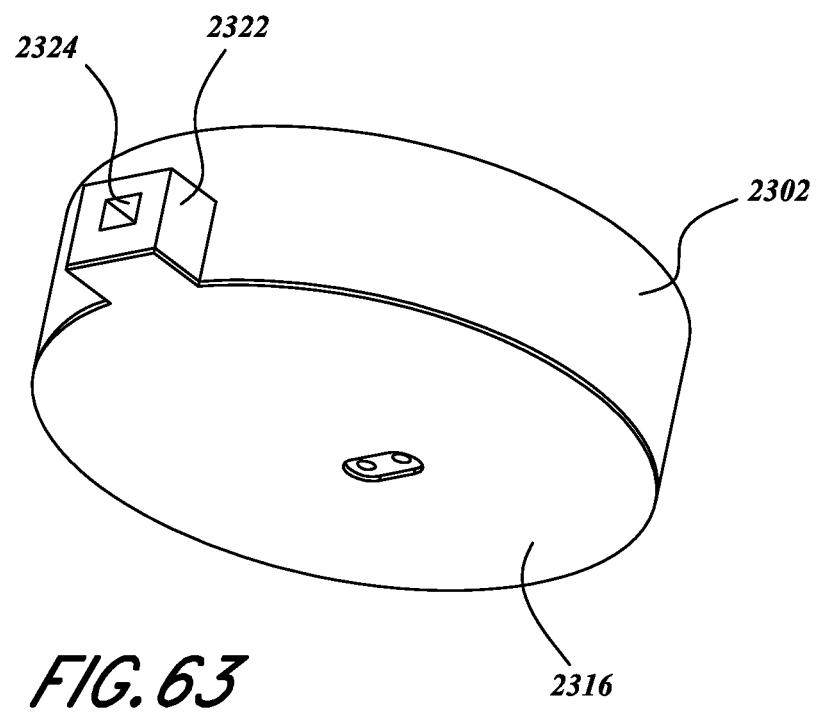
Figure 64:
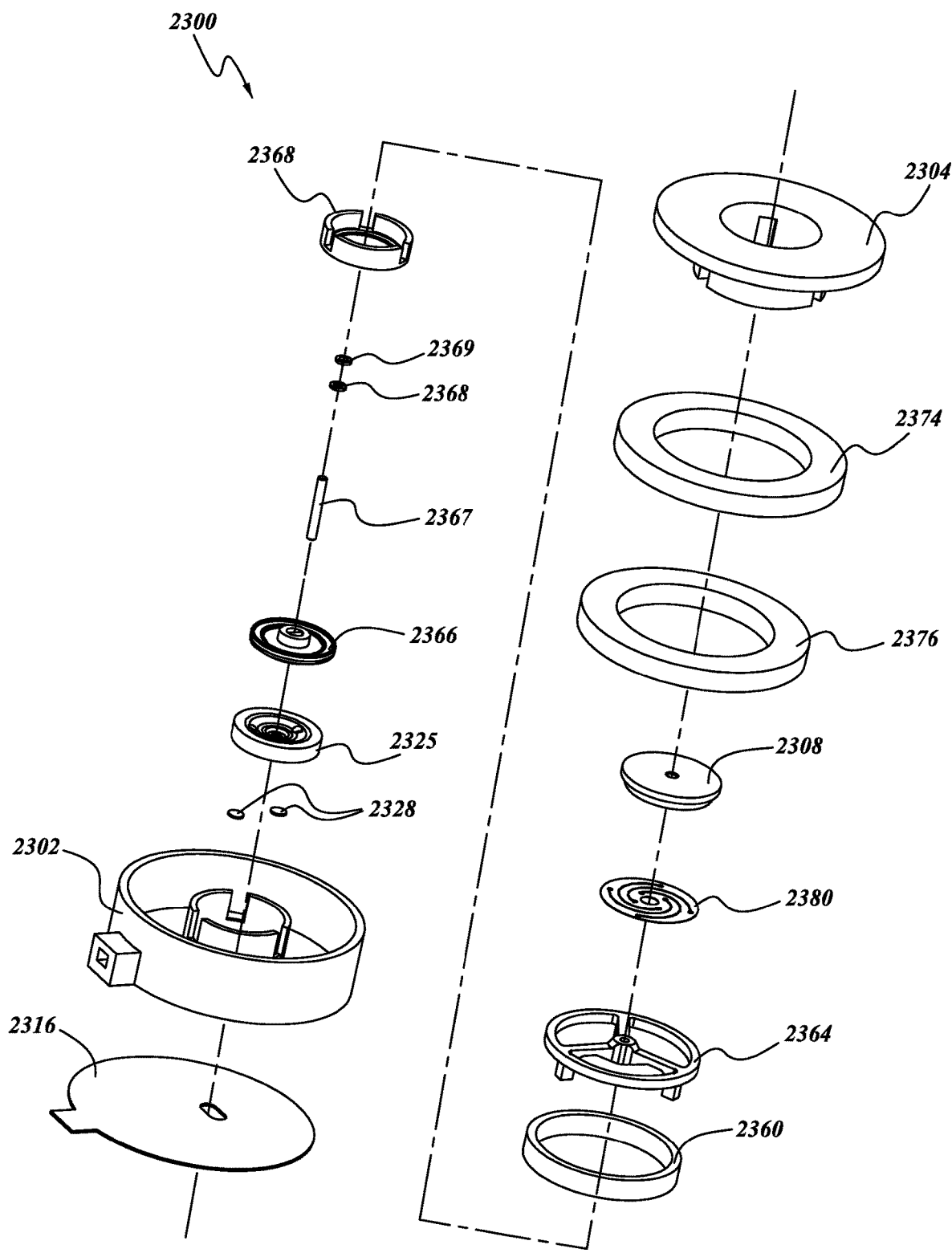
FIGS. 64 and 65 are exploded views of the pump assembly embodiment illustrated in FIG. 62.
Figure 65:
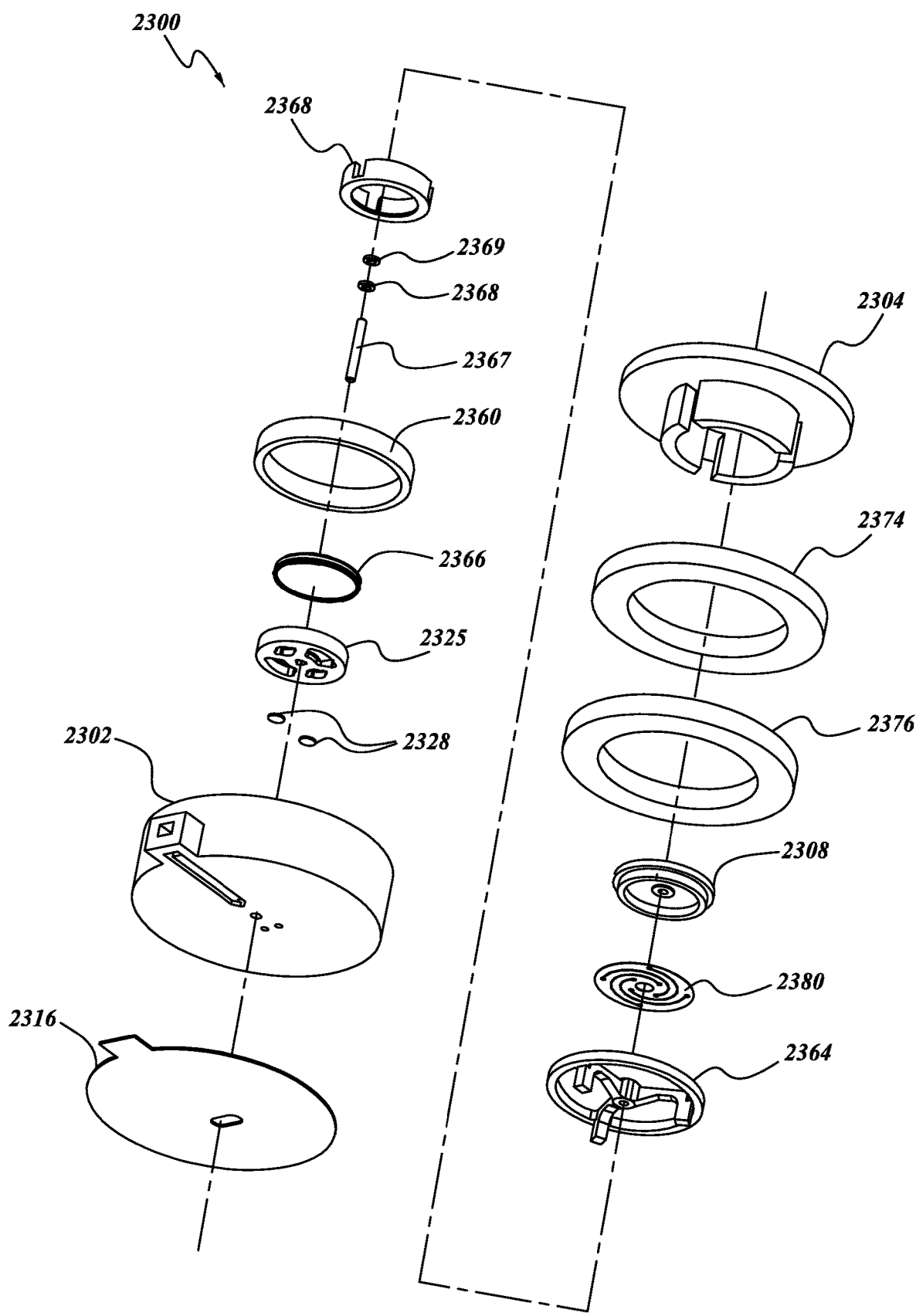
Figure 66:
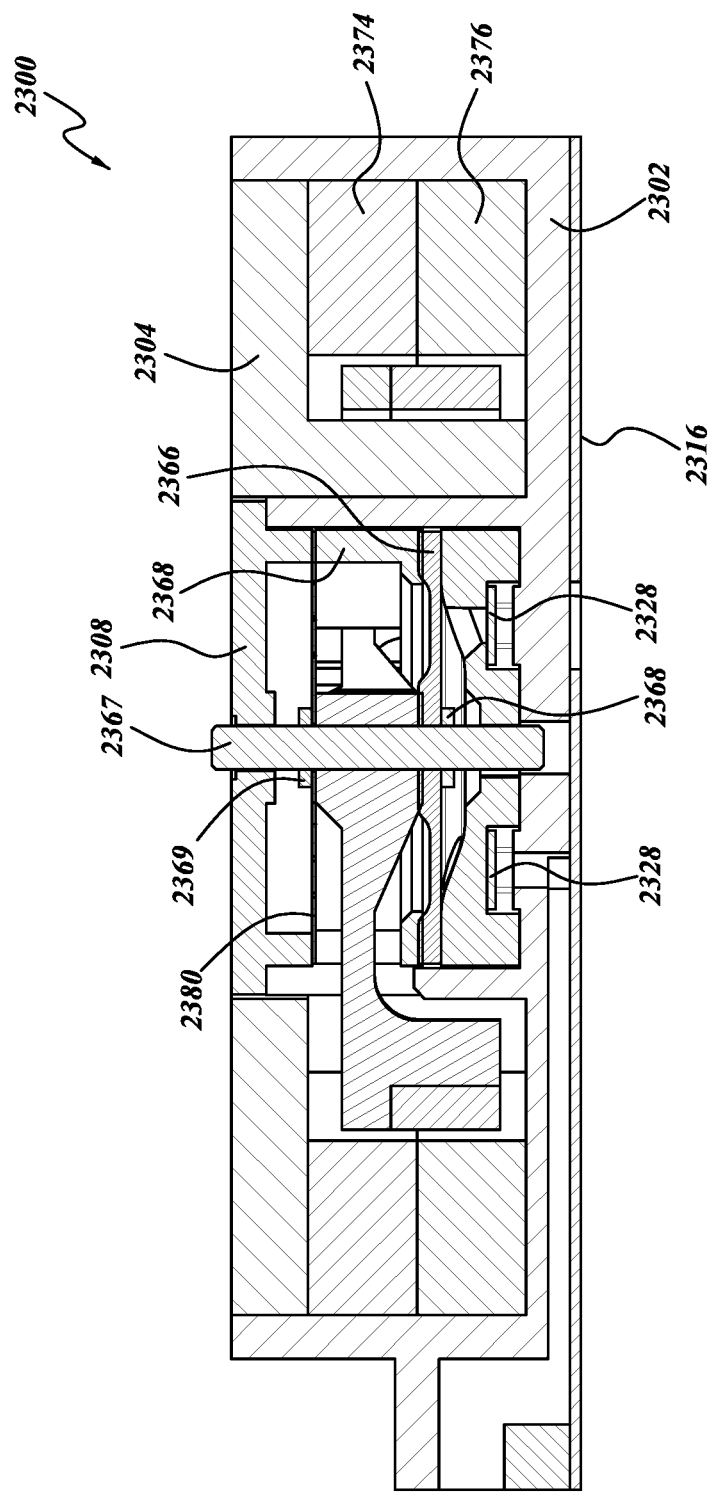
FIG. 66 is a section view of the pump assembly embodiment illustrated in FIG. 62.

FIGS. 62 and 63 are isometric views, showing the top and the bottom sides of another embodiment of a pump assembly 2300. FIGS. 64 and 65 are exploded views of the pump assembly embodiment illustrated in FIG. 62, and FIG. 66 is a section view. The pump assembly embodiment 2300 can have a compact, small size and can have any of the same features, sizes, components, materials, or other details of the pump assembly embodiment 2100 and/or 2200 described above, or any of the other pump assembly embodiments disclosed herein.

Additionally, the pump assembly embodiment 2300 can have a flat spring 2380 positioned above the support member 2364 for alignment of the diaphragm member 2366 and the shaft 2367 that is coupled with the diaphragm member 2366 using one or more rings 2368 and 2369.

Additionally, in any embodiments herein, the valve flaps 2328 can have a round, disc-like shape and can be supported within the first valve member 2325 between the housing 2302 and the first valve member 2325. A bushing 2368 can be positioned between the diaphragm 2366 and the upper busing 2308. The bushing 2368 can be configured to support a perimeter of the diaphragm 2366 against a perimeter of the first valve support 2325 within the housing 2302. In any pump embodiments disclosed herein, the housing can support a square or rectangular shaped tubing connector.

Figure 67:
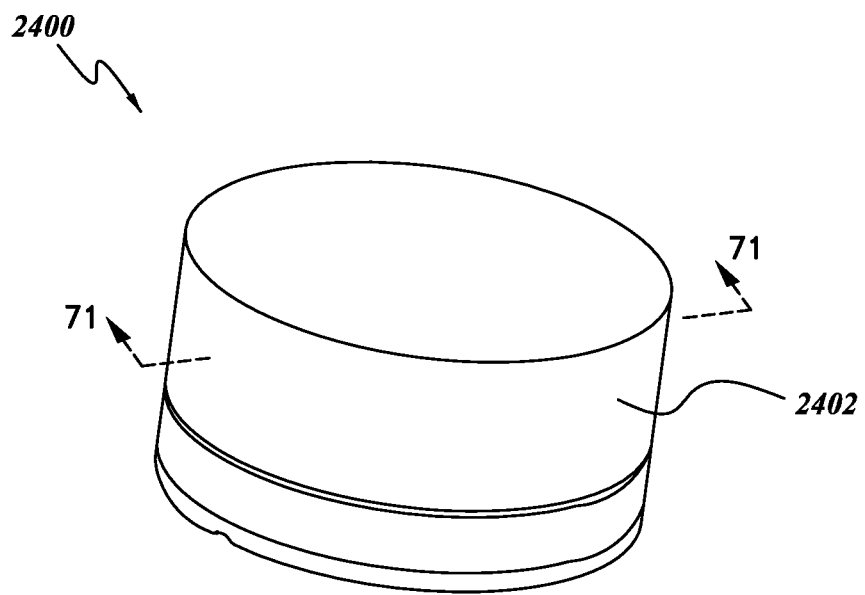
FIGS. 67 and 68 are isometric views of another embodiment of a pump assembly, showing a top surface of the pump assembly and the bottom surface of the pump assembly, respectively.
Figure 68:
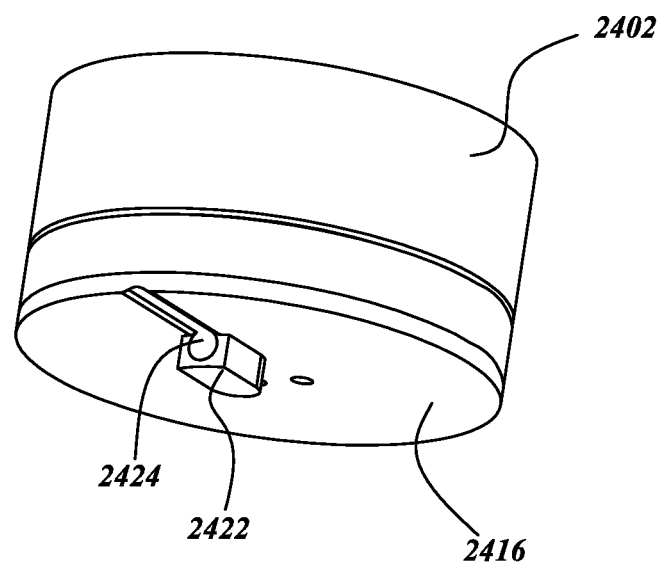
Figure 69:
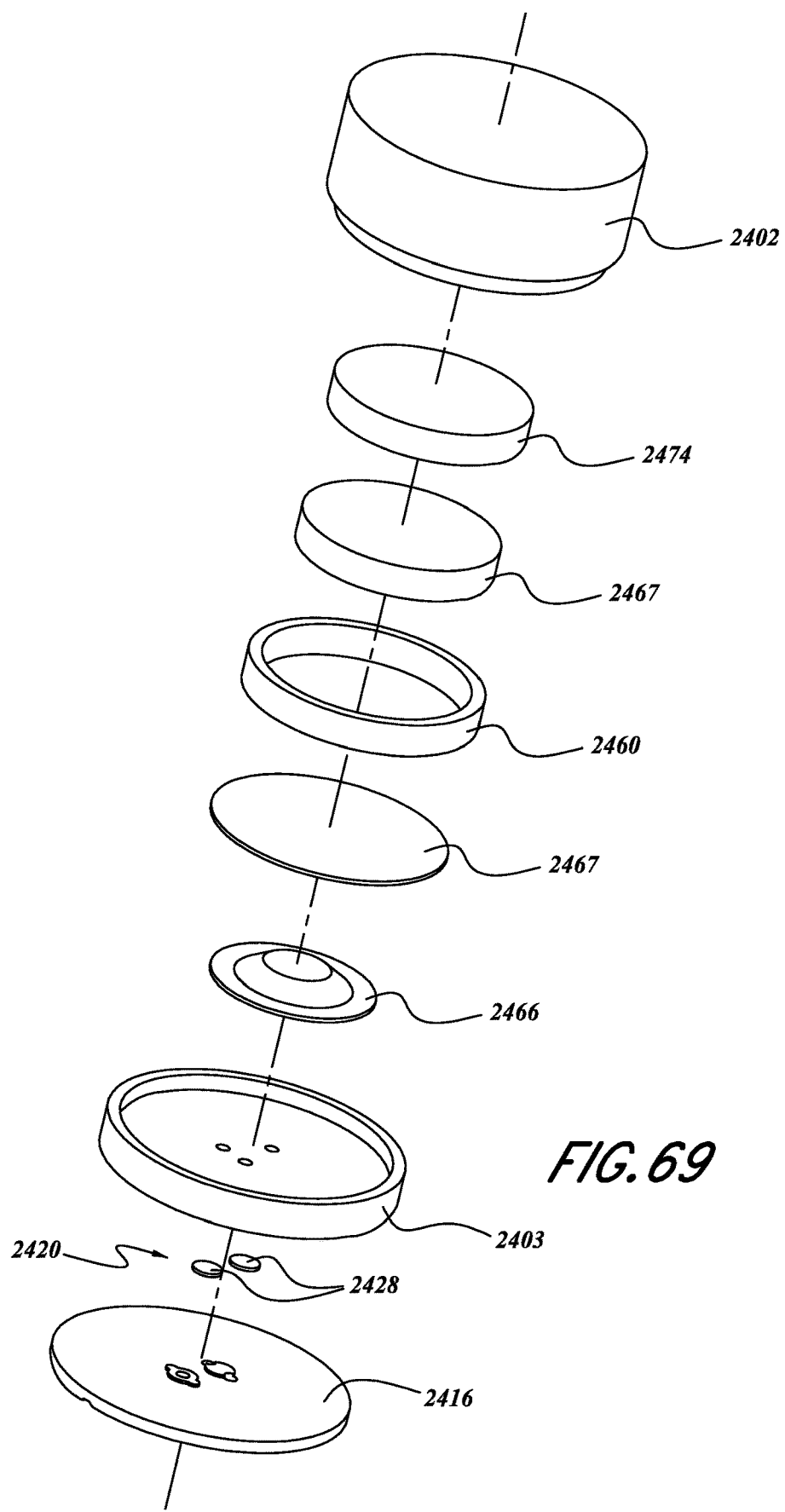
FIGS. 69 and 70 are exploded views of the pump assembly embodiment illustrated in FIG. 67, showing the top and the bottom of the pump assembly, respectively.
Figure 70:
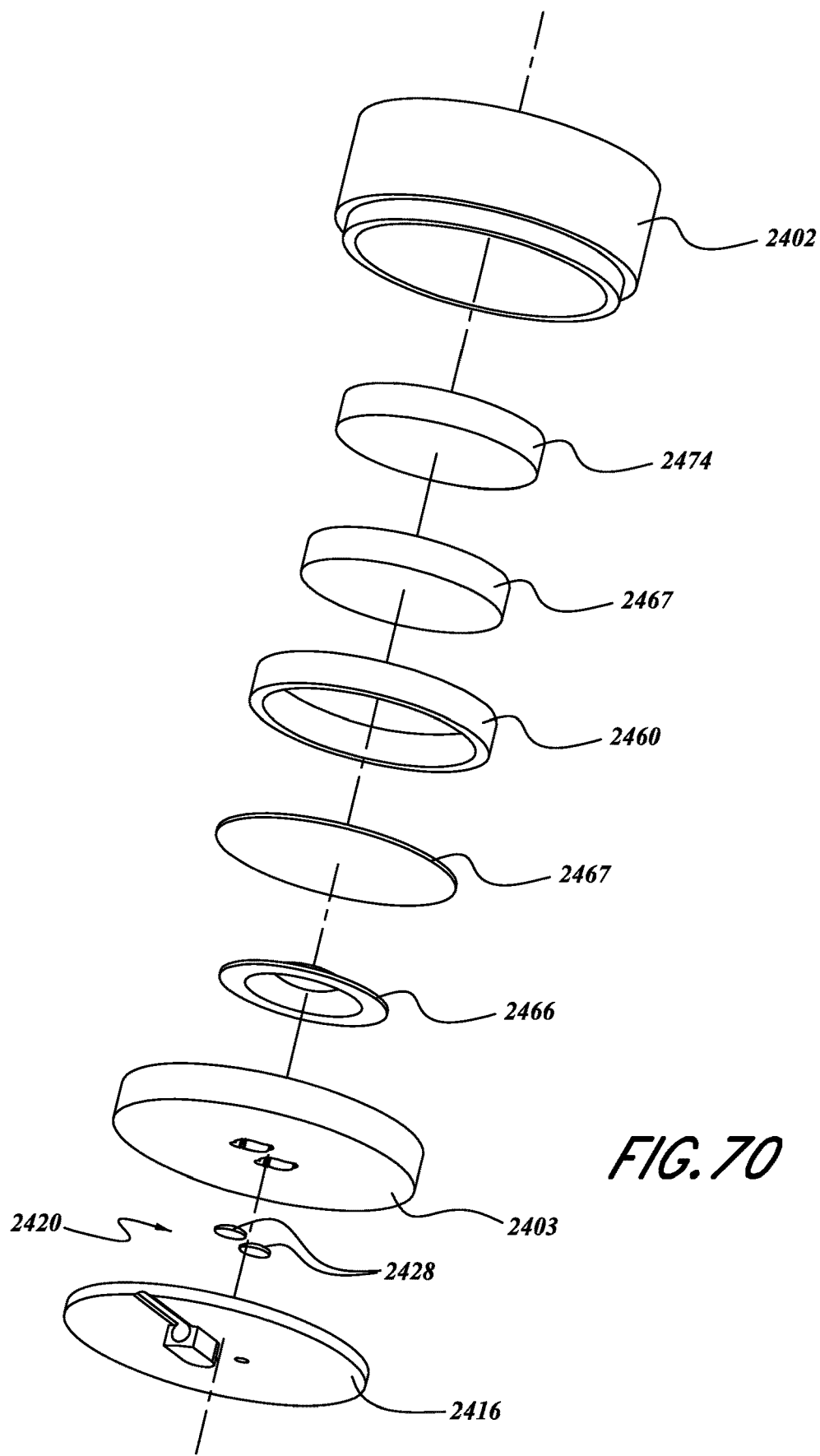
Figure 71:
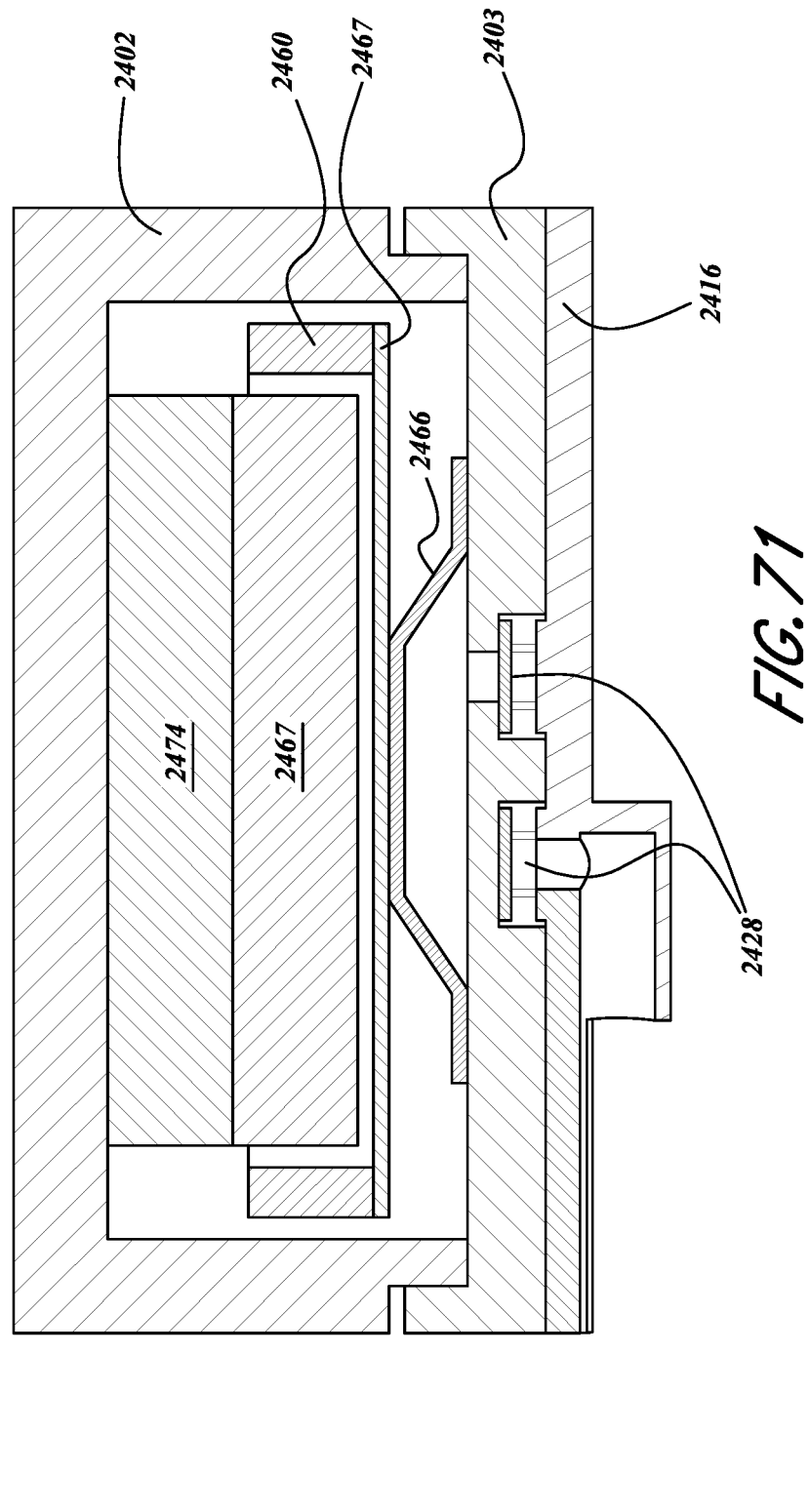
FIG. 71 is a section view of the pump assembly embodiment illustrated in FIG. 67, the section being taken through the center of the pump assembly embodiment.

FIGS. 67 and 68 are isometric views of another embodiment of a pump assembly 2400, showing a top surface of the pump assembly and the bottom surface of the pump assembly, respectively. FIGS. 69 and 70 are exploded views of the pump assembly embodiment illustrated in FIG. 67, showing the top of the pump assembly and the bottom of the pump assembly, respectively. FIG. 71 is a section view of the pump assembly embodiment illustrated in FIG. 67, the section being taken through the center of the pump assembly embodiment. The pump assembly embodiment 2400 can have a compact, small size and can have any of the same features, sizes, components, materials, or other details of the pump assembly embodiment 240 described above, or any of the other pump assembly embodiments disclosed herein.

In any embodiments disclosed herein, the pump assembly 2400 can have a diameter or lateral size in the range of approximately 26-29 mm, or between approximately 25 and approximately 28 mm. In any embodiments disclosed herein, the pump assembly embodiment 2400 can have a thickness or height of approximately 15 mm, or between approximately 10 mm and approximately 18 mm.

The pump assembly embodiment 2400 can be produced for a low cost and can operate at high efficiencies, making it beneficial for portable, disposable, and/or single use applications. In any embodiments disclosed herein, the pump assembly embodiment 2400 can run for a week on a small primary cell such as a 1200 mAh battery without the need for battery replacement or recharging. This pump can be used in an ultra-portable single-use NPWT device, but is not so limited. In any embodiments disclosed herein, as mentioned, the pump assembly embodiment 2400 can be used for negative pressure wound therapy. However, the pump assembly embodiment 2400 is not limited to use in negative pressure wound therapy systems. The pump assembly embodiment can be adapted and configured for use in any reduced pressure system or in any system or application in which the movement of gaseous and liquid fluids is desired.

The pump assembly embodiment 2400 can be designed to work at pressures of 60-80 mm Hg or more, and can be configured to produce a flow rate of approximately 200 ml min-1, with a minimum efficiency of 15%, in order for the NPWT device to run for a week on a specified battery capacity. In any embodiments disclosed herein, the pump assembly embodiment 2400 can be adapted to operate at efficiency levels in excess of 25%.

The pump assembly embodiment 2400 can have a housing 2402 adapted to support and protect many of the components of the pump assembly embodiment 2400. An upper pole (which can be the upper casing for the housing), which can be made from any suitable materials such as mild steel or sintered steel. A cover 2416 (also referred to herein as a first cover) can be positioned over an end portion of the housing 2402. The cover 2416 can be an adhesive backed foil, film, paper, plastic sheet or label, or other similar object. An opening can be formed in the cover in communication with a port member 2422 having an opening 2424 therein to permit air, gas, or other fluid to be exhausted from the pump through the outlet manifold.

The valve assembly 2420 can have a first valve member or plate that can be formed into a bottom portion 2403 of the housing 2402. The pump can have two round or disc shaped valve flaps 2428, a first valve flap 2428 for the inlet valve chamber and a second valve flap 2428 for the outlet valve chamber. The first flap 2428 and the second flap 2428 can be configured to translate away from the openings in the first valve supports to block passage of air through the valve assembly 2420 during operation of the pump, or possibly even during sterilization of the pump.

The diaphragm 2466 can be supported and/or fixed along all or a portion of its peripheral portion 2466a, wherein an interior portion 2466b of the diaphragm assembly 2466 is permitted to flex and deflect in either direction away from the relaxed position of the diaphragm assembly 2466. In any embodiments, the diaphragm can simply rest against the planar surface of the housing portion 2466. In any embodiments disclosed herein, the diaphragm can be clamped and compressed between two rigid surfaces to provide such support.

The pump assembly embodiment 2400 can have a magnet 2474 positioned between a lower pole 2476 and the upper pole 2404, any of which components can be made from any of the materials disclosed herein. In use, for any of the embodiments disclosed herein, as the voltage supplied to the coil oscillates between a positive voltage and a negative voltage, the coil can oscillate up and down in the pump between the two poles 2004 and 2076. The coil can be in contact with plate 2467, which can in turn contact the diaphragm, so that the diaphragm can cyclically compress and extend as the coil oscillates.

Thus, the oscillation of the diaphragm 2066 can cause the volume within the pump to increase or decrease and, hence, cause the pressure within the pump to decrease or increase. A pressure decrease within the pump chamber can draw air into the pump chamber and open the inlet manifold (or flap), while the flap on the outlet manifold can seal the outlet manifold closed. Then, as the diaphragm 2466 returns toward the valve support, the volume of airspace decreases, causing the air pressure to increase. This forces air out of the chamber through the outlet valve, while the inlet valve is sealed closed.

Figure 72:
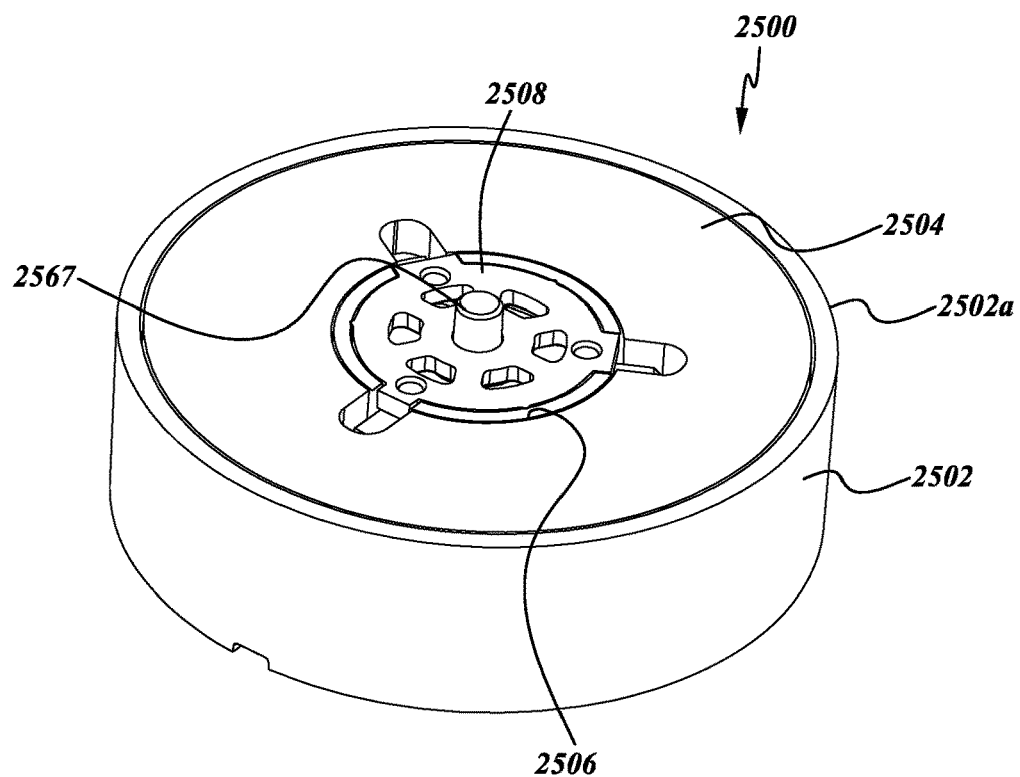
FIGS. 72 and 73 are isometric views of another embodiment of a pump assembly that can be used to provide reduced pressure to a wound dressing.
Figure 73:
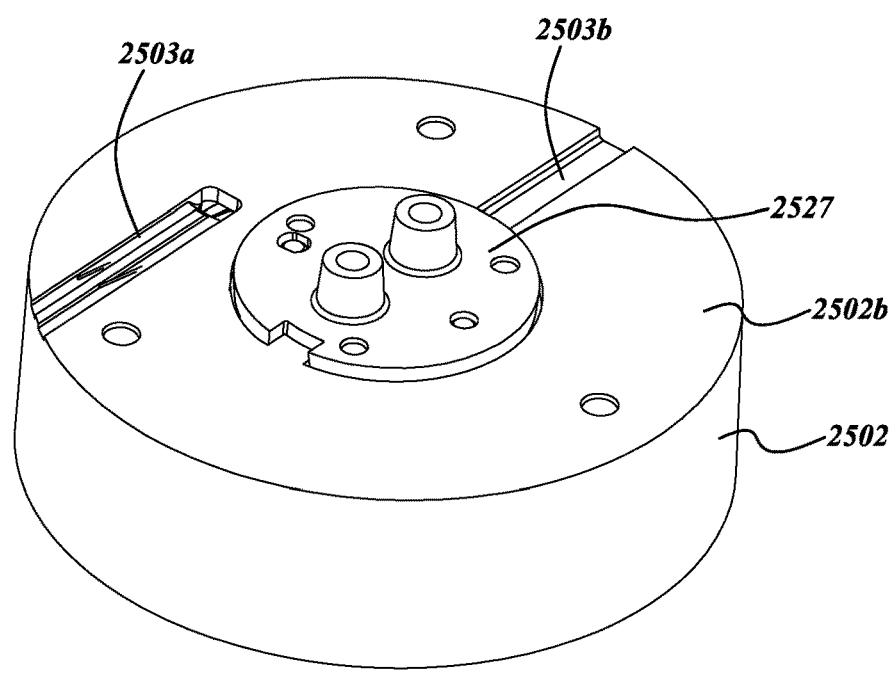
Figure 74:
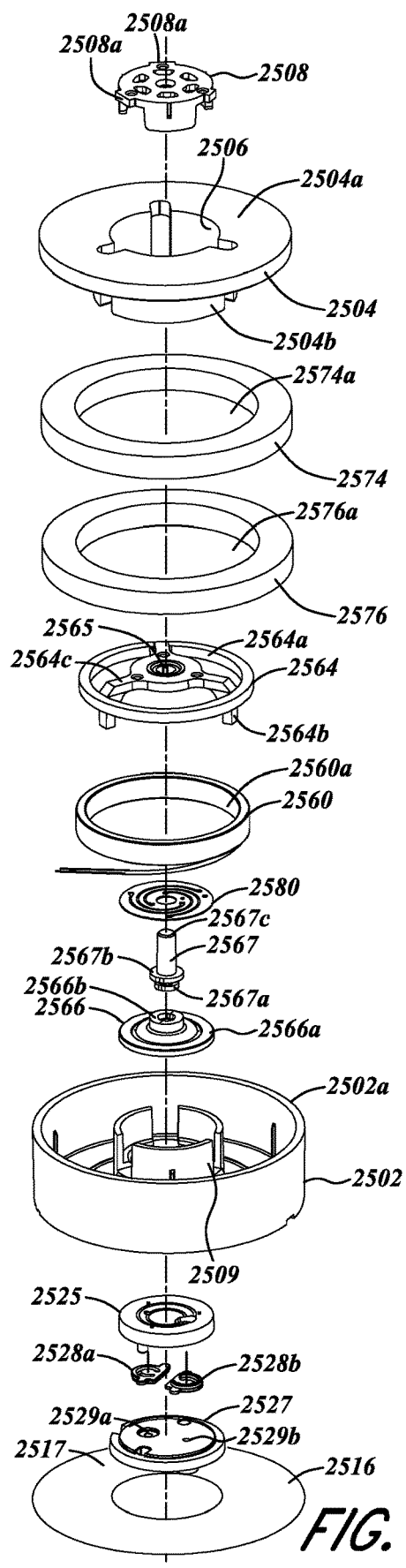
FIGS. 74 and 75 are exploded views of the pump assembly embodiment illustrated in FIG. 72, showing the top and the bottom of the pump assembly, respectively.
Figure 75:
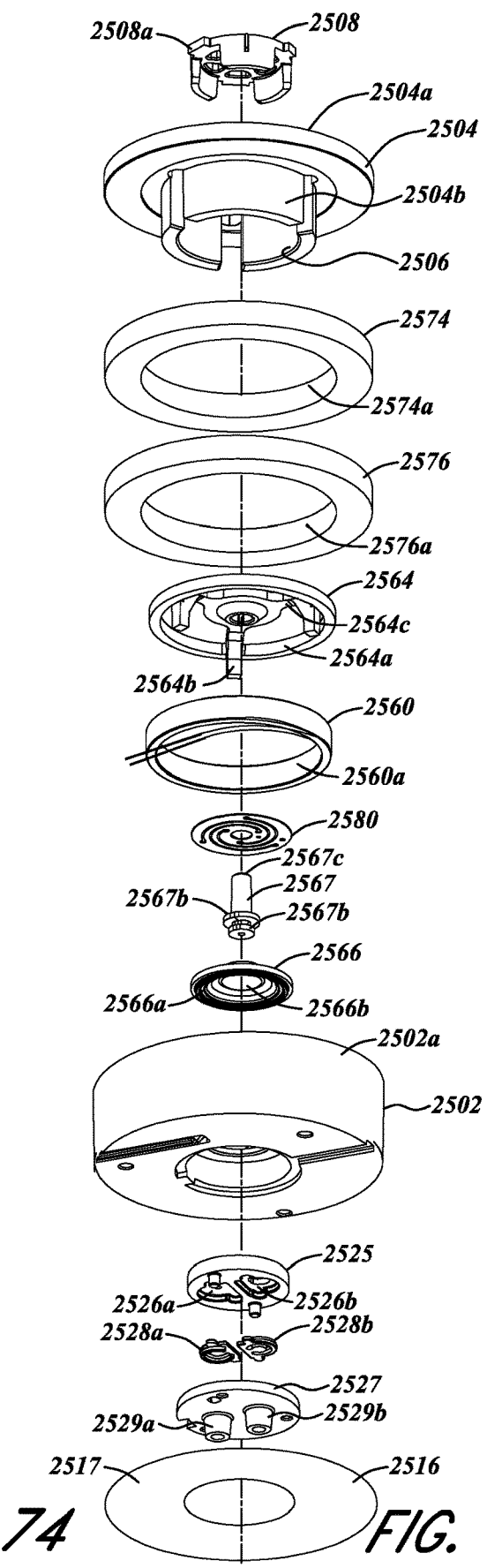
Figure 76:
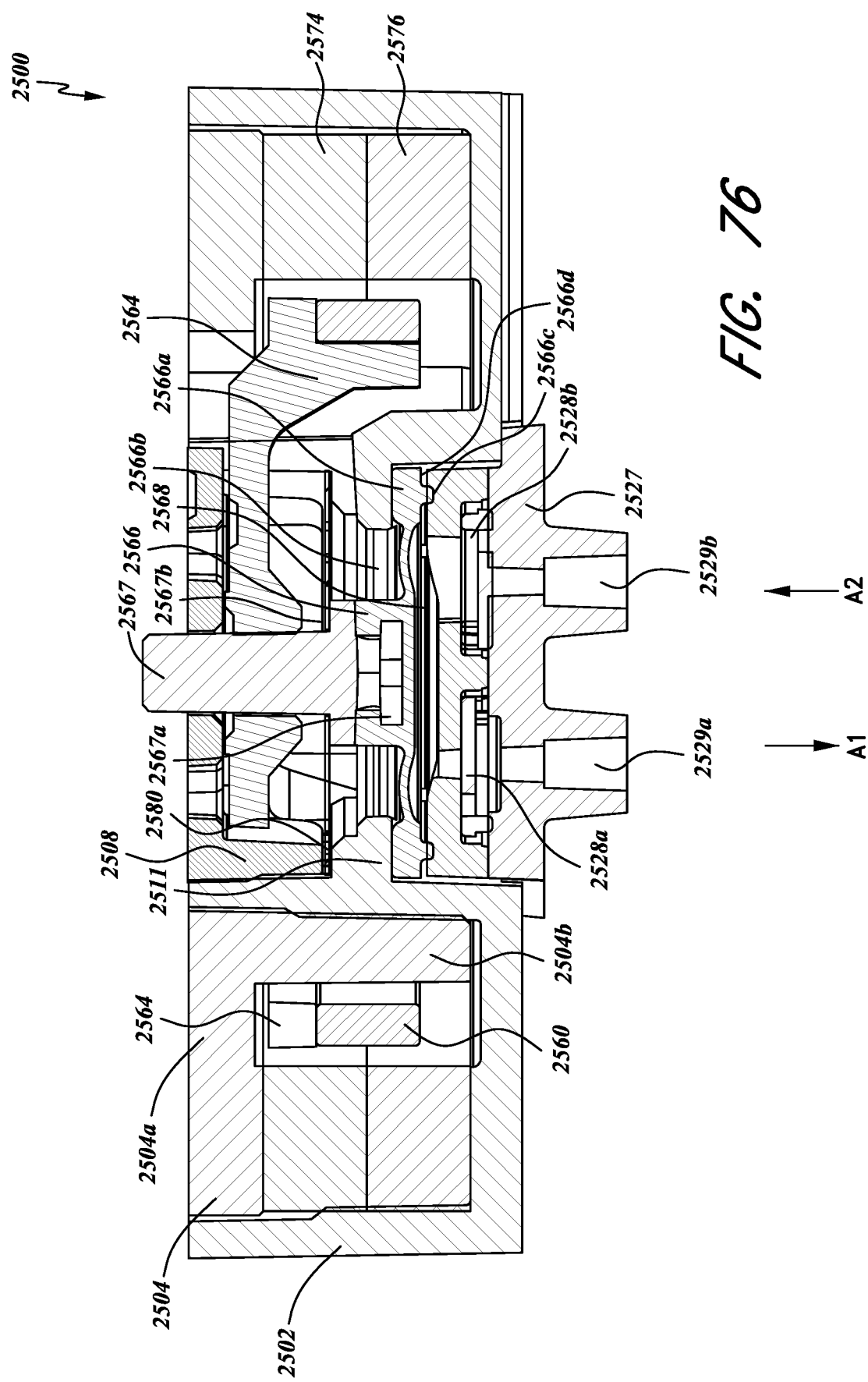
FIG. 76 is a sectional view of the embodiment of the pump assembly of the pump assembly embodiment shown in FIG. 72.

FIGS. 72 and 73 are isometric views of another embodiment of a pump assembly 2500, showing a top surface of the pump assembly and the bottom surface of the pump assembly 2500, respectively. FIGS. 74 and 75 are exploded views of the pump assembly embodiment illustrated in FIG. 72, showing the top of the pump assembly and the bottom of the pump assembly, respectively. FIG. 76 is a section view of the pump assembly embodiment illustrated in FIG. 72, the section being taken through the center of the pump assembly embodiment. The pump assembly embodiment 2500 can have a compact, small size and can have any of the same features, sizes, components, materials, operating methods or parameters, or other details of any of the pump assembly embodiments described herein, or any components thereof.

In any pump embodiments disclosed herein, the pump can have a small volume. For example and without limitation, any embodiments of the pump assembly disclosed herein can have a volume of approximately 6.26 cubic centimeters, or from approximately 5.0 cubic centimeters or less to approximately 7.0 cubic centimeters. The housing of any embodiment disclosed herein can have a diameter of approximately 28.2 mm, or from approximately 25.0 mm or less to approximately 30.0 mm, and a height of approximately 10.0 mm, or from approximately 8.0 mm to approximately 12.0 mm.

In any pump embodiments disclosed herein, including without limitation the pump assembly 2500, the pump housing can have a diameter or lateral size in the range of approximately 26-29 mm, or between approximately 25 or less and approximately 28 mm or more. In any embodiments disclosed herein, the pump assembly embodiment 2500 can have a thickness or height of approximately 8 mm, or between approximately 6 mm and approximately 10 mm.

The pump assembly embodiment 2500 can be produced for a low cost and can operate at high efficiencies, making it beneficial for portable, disposable, and/or single use applications. In any embodiments disclosed herein, the pump assembly embodiment 2500 can run for a week on a small primary cell such as one or more batteries having a total capacity of 3000 mAh without the need for battery replacement or recharging. This pump can be used in an ultra-portable single-use NPWT device, but is not so limited. In any embodiments disclosed herein, as mentioned, the pump assembly embodiment 2500 can be used for negative pressure wound therapy. However, the pump assembly embodiment 2500 is not limited to use in negative pressure wound therapy systems. The pump assembly embodiment can be adapted and configured for use in any reduced pressure system or in any system or application in which the movement of gaseous and liquid fluids is desired.

Any pump assembly disclosed herein, including without limitation the pump assembly embodiment 2500, can be designed to work at pressures of approximately 60 to approximately 80 mm Hg or more, or from approximately 60 to approximately 120 mm Hg or more, and can be configured to produce a flow rate of approximately 200 ml/min, or from approximately 100 ml/min or less to approximately 250 ml/min or more, with an efficiency of from approximately 15% to approximately 29% or more, or from approximately 20% to approximately 25% or 26%, in order for the NPWT device to run for a week on a specified battery capacity. In any embodiments disclosed herein, the pump assembly embodiment 2500 can be adapted to operate at efficiency levels in excess of 27%. In any embodiments disclosed herein, the pump efficiency can be approximately 20%-25%.

The pump assembly embodiment 2500 can have a housing 2502 adapted to support and protect many of the components of the pump assembly embodiment 2500. An upper pole 2504, which can be made from any suitable materials such as mild steel or sintered steel (or any suitable magnetic or ferromagnetic material), can be supported at one end (for example, a first end) 2502a of the housing 2502. In any embodiments disclosed herein, the upper pole 2504 can have an opening 2506 formed through an axial centerline of the upper pole 2504. A bearing 2508 can be supported by the upper pole 2504, within the opening 2506. Any bearing embodiment disclosed herein, including without limitation the bearing 2508, can be formed from a low friction material (polymeric or otherwise) or any other suitable material. For example and without limitation, any bearing embodiments disclosed herein can be made from phosphor bronze, oilite, PTFE, acetal, nylon, PTFE, or a roller race construction. In any embodiments disclosed herein, one or more channels 2503 can be located at or formed in a second end or second surface 2502b the housing 2502 for routing wires or conduit, or to create an air passageway, such as but without limitation channel 2503a for routing electrical wires into the housing 2502 and/or for supporting conduit adjacent to the housing, such as with channel 2503b. Channel 2503b can be configured such that a conduit in communication with the opening 2529b can be partially recessed within the channel 2503b to secure the conduit and also to make the conduit lower profile. The conduit can connect to the opening 2529b at an angle that is perpendicular to the axial centerline of the pump.

Though not required, a cover 2516 (also referred to herein as a first cover) can be positioned over either end portion of the housing 2502, including without limitation the second end portion 2502b of the housing 2502. The cover 2516 can be an adhesive backed foil, film, paper, plastic sheet or label, or other similar object. An opening 2517 can be formed in the cover 2516 to permit air, gas, or other fluid to be exhausted from the pump through the outlet manifold. Any embodiments of the cover 2516 can have an opening 2517 that is large enough to surround a second valve support 2527, but configured to sealingly cover the second end or second surface 2502b and any channels 2503 formed therein. Additionally, any embodiments of the cover 2516 can also have any suitable or desired printing thereon regarding the pump or operation thereof. Additionally, in any embodiments disclosed herein, a flat battery (such as but not limited to a low profile printed battery) could be adhered directly to one or both end surfaces, or the side or perimeter surfaces, of the pump housing 2502.

The valve assembly 2520 can have a first valve member 2525 (also referred to herein as a first valve support) and a second valve support 2527 (also referred to herein as a second valve support) that can also have a first port 2529a (also referred to herein as an exhaust port or exhaust outlet) for exhausting gas or air within the pump assembly and a second port 2529b (also referred to herein as an inlet port or just an inlet) thereon. In any embodiments, the inlet port can be configured to sealingly receive a conduit for communicating the negative pressure produced by the pump assembly to a wound dressing.

In any embodiments of the pump assembly disclosed herein, the first valve support 2525 can support two flexible flap valves 2528, a first flap valve 2528a for the outlet valve chamber or the outlet port or opening 2529a and a second flap valve 2528b for the inlet valve chamber or the inlet port or opening 2529b. For example and without limitation, the first flap valve 2528a can be supported within a first recess 2526a formed in the first valve support 2525. Similarly, for example and without limitation, the second flap valve 2528b can be supported within a second recess 2526b formed in the first valve support 2525. The first flap 2528a and the second flap 2528b can be configured such that a flap 2530 deflects away from the relaxed position of the flaps 2530 shown to block passage of air through the valve assembly 2520 during operation of the pump, or possibly even during sterilization of the pump. In any embodiments disclosed herein, though not required, the flap portions 2530 can be surrounded by or supported by a frame portion. The flap portion can deflect away from the relaxed position of the flap portion in response to a pressure differential between a first main surface and a second main surface of the flap portion. Some additional details of the valves 2528 and the valve supports 2525, 2527 will be described in greater detail below.

In any embodiments herein, the valves or flap valves can be positioned against the sealing surface of the adjacent valve support so as to improve the seal of the flap valve against the valve support surface. For example, the first flap valve 2528a can be preloaded against or relative to the planar surface of recess 2526a formed in the first valve support 2525. The second flap valve 2528b can be preloaded against or relative to the planar surface of the second valve support 2527.

For example, with reference to FIG. 76, which is a section view of the pump assembly 2500, when the diaphragm deflects in the direction A1 shown in FIG. 76, the air or gas within the chamber 2568 between an inside surface of the diaphragm and the flap valves 2528 will compress and increase in pressure, causing the first flap valve 2528a to deflect away from the first valve support 2525 and causing air to flow around the first flap valve and exit through the outlet port 2529a. Additionally, the second flap valve 2528b will be deflected against or further sealed against the second valve support 2527, sealing the second flap valve 2528b against the second valve support 2527 and substantially preventing air from going around the second flap valve 2528b and out through the inlet port 2529b. This is referred to as an outtake or exhaust cycle.

Again with reference to FIG. 76, when the diaphragm deflects in the direction A2 shown in FIG. 76, the air or gas within the chamber 2568 between an inside surface of the diaphragm and the flap valves 2528 will decrease in pressure, causing the first flap valve 2528a to sealingly deflect or further press against the first valve support 2525, substantially preventing air from going around the first flap valve 2528a and in through the outlet port 2529a. Additionally, the second flap valve 2528b will be deflected toward the diaphragm and away from the second valve support 2527, allowing air to flow through the inlet port 2529b, around the second flap valve 2528b and into the air chamber. This is referred to as an intake cycle.

The pump assembly embodiment 2500 can have a coil 2560 comprising electrical wires 2514, and a support member 2564. In any embodiments, the coil 2560 can have an opening 2564a extending therethrough. Additionally, in any embodiments, the support member 2564 can have an opening 2564a extending therethrough. The support member 2564 can have legs 2565 extending through openings in the housing 2502. The coil 2560 can be formed from a length of wound conductive wire, such as without limitation copper wire. In operation, the coil 2560 can be configured to move within a magnetic circuit, and can be supported via a support member to a pump diaphragm assembly 2566.

Any embodiments of the diaphragm disclosed herein, including without limitation the diaphragm 2566, can have any of the following features or details. The diaphragm 2566 can be supported and/or fixed along all or a portion of the peripheral portion 2566a of the diaphragm, wherein an interior portion 2566b of the diaphragm assembly 2566 is permitted to flex and deflect in either direction away from the relaxed position of the diaphragm assembly 2566. In any embodiments disclosed herein, the diaphragm can be clamped and compressed between two rigid surfaces to provide such support. The rigid surfaces can define an annular shape. For example, any embodiments of the diaphragm 2566 (or any other diaphragm disclosed herein) can have a moulding and a separate compression ring (made from a rigid plastic, aluminium or other metal, or any other suitable material or composite material). Additionally, any embodiments of the diaphragm disclosed herein can have a peripheral portion 2566a made from the same material as is used to make the interior portion 2566b of the diaphragm. As show, the peripheral portion 2566a can have a greater thickness than the interior portion 2566b of the diaphragm. For example and without limitation, the peripheral portion 2566a can have a thickness that is approximately two or more times greater than, or from approximately two times greater than to approximately three or more times greater than a thickness of the interior portion 2566b of the diaphragm.

Additionally, in any embodiments of the diaphragm, an annular protrusion 2566c can extend away from a first main surface 2566d of the peripheral portion 2566c of the diaphragm 2566. The annular protrusion 2566c can be formed integrally with the peripheral portion and/or the interior portion of the diaphragm. The increased thickness that results from the annular protrusion 2566c can improve the sealability of the peripheral portion of the diaphragm and hence improve the sealability of the diaphragm.

Additionally, with reference to FIGS. 77A-77D, in any embodiments of the diaphragm disclosed herein, including without limitation diaphragm 2566, the interior portion of the diaphragm can have excess material (e.g., length) along a path length of the interior portion 2566b of the diaphragm 2566, the interior portion 2566b configured to extend as the interior portion of the diaphragm displaces away from the peripheral portion of the diaphragm or to bend more easily when the interior portion of the diaphragm moves toward the peripheral portion of the diaphragm. For example, in any embodiments, the interior portion 2566b of the diaphragm 2566 can have approximately 20%, or from approximately 10% to approximately 35% or more, more material along a length along a path length of the interior portion 2566b as compared a design not having the articulation or excess material.

In this arrangement, the interior portion of the diaphragm can be more flexible when the interior portion moves relative to the peripheral portion of the diaphragm as compared to a diaphragm that must stretch as the interior portion is displaced away from the peripheral portions. In other words, the extra material or articulation(s) in the interior portion can reduce tensile forces acting on the interior portion of the diaphragm as the interior portion displaces away from the peripheral portion, and can reduce the compressive forces acting on the interior portion of the diaphragm as the interior portion moves toward the peripheral portion of the diaphragm to reduce the amount of force required to displace the interior portion of the diaphragm relative to the peripheral portion of the diaphragm. In any embodiments, the interior portion 2566b can be arcuately curved and can have a radius of approximately 0.45 mm to an inside surface thereof, or from approximately 0.40 mm to approximately 0.6 mm or more.

For example, in any embodiments disclosed herein, the interior portion of the diaphragm can have one or more annular articulations or curved portions 2566e configured to extend or decrease in curvature as the interior portion of the diaphragm displaces away from the peripheral portion of the diaphragm or to bend more easily when the interior portion of the diaphragm moves toward the peripheral portion of the diaphragm such that the interior portion of the diaphragm is more flexible when the interior portion moves relative to the peripheral portion of the diaphragm. This can result in a more axially flexible and, hence, more efficient (in terms or power consumption) diaphragm to improve the power efficiency of the pump assembly, yet maintaining the rigidity of the diaphragm in terms of resisting against the collapse of the interior surface of the diaphragm as the pressure within the space bound by the diaphragm decreases, such that the volume of space bound by the diaphragm is maximized. Any embodiments of the diaphragm 2566 (or any other diaphragm disclosed herein, i.e., in this application) can be formed from cast or molded silicone, polyurethane, thermoplastic polyurethane, EPDM, and/or other suitable materials, having a hardness value of approximately 20 A, 30 A, 40 A, 50 A, 55 A, or more.

A shaft portion 2567 (also referred to herein as a shaft member) can be engaged with the interior portion 2566b of the diaphragm member 2566. For example and without limitations, in any embodiments of the pump assembly disclosed herein, an end portion 2567a of the shaft member 2567 can be received within an opening 2569 formed in the diaphragm member 2566. The opening can be configured to engage with the end portion 2567a of the shaft member such that the end portion of the shaft member is axially engaged by the opening of the diaphragm. For example, a flange portion 2566f of the diaphragm member can be configured to engage or interfere with a flange portion on the end portion of the shaft member. In this arrangement, as the shaft member displaces axially relative to the peripheral portion of the diaphragm, the shaft member will cause the interior portion 2566b of the diaphragm member 2566 to displace relative to the peripheral portion of the diaphragm. In any embodiments, the support member 2564 can be axially fastened to the shaft member such that, as the coil and, hence, the support member are moved axially within the pump assembly as a result of the drive signal and magnetic field, the shaft member 2567 will cause the interior portion 2566b of the diaphragm member to displace relative to the peripheral portion 2566a of the diaphragm, thereby changing the volume of space bounded by the diaphragm.

In any embodiments disclosed herein, the diaphragm member can have a total outside diameter of approximately 9.9 mm, or from approximately 8 mm or less to approximately 11.0 mm or more. Though not required, a thickness of the middle portion 2566b of the diaphragm can be approximately 0.25 mm, or from approximately 0.20 mm or less to approximately 0.30 mm or more. Additionally, though not required, a thickness of a peripheral portion 2566a of the diaphragm 2566 can be approximately 1.0 mm, or from approximately 0.75 mm or less to approximately 1.5 mm or more.

In any pump embodiments disclosed herein, the shaft member 2567 or any shaft member disclosed herein can be axially fixed to the support member 2564 such that any axial motion of support member 2564 results in the equal and simultaneous movement of the shaft member 2567. Hence, in any embodiments herein, any movement of the coil can cause the equivalent and simultaneous movement of the support member and the shaft member, which can cause the simultaneous and equal movement of the middle portion of the diaphragm.

Any pump embodiments disclosed herein can also have a flat spring member 2580 positioned adjacent to the diaphragm. In any embodiments, the spring member 2580 can be positioned against a flange portion 2567b of the shaft portion 2567 (also referred to herein as a shaft member) of the diaphragm assembly. Alternatively or additionally, in any embodiments, the spring member 2580 can be positioned at a top portion 2567c of the shaft portion 2567 of the diaphragm assembly 2566, or can be positioned in any desired locations. The spring member 2580 can be sized and configured to provide frequency tuning or adjustment to the resonance frequency of the diaphragm and/or the components of the oscillating coil assembly.

Additionally, in any embodiments disclosed herein, the spring member 2580 or any number of spring members can be configured to maintain the axial alignment of the diaphragm assembly 2566 with the remainder of the pump assembly, or both to maintain alignment and to provide a mechanism for adjusting the resonance frequency of the pump. The spring member 2580 can be made from stainless steel, spring steel, or any other suitable material. In any embodiments disclosed herein, the spring member (such as, but not limited to, spring member 2580) can be positioned in contact with the diaphragm member (such as, but not limited to, the diaphragm member 2566) or the shaft portion (such as, but not limited to, the shaft portion 2567) such that the spring member exerts an axial force on at least a middle portion of the diaphragm member that causes the middle portion of the diaphragm member to deflect away from a relaxed position of the middle portion of the diaphragm member in an assembled state, but before power has been provided to the pump assembly.

The pump assembly embodiment 2500 can have a magnet 2574 having an opening 2574a extending axially therethrough positioned between a lower pole 2576 having an opening 2576a extending axially therethrough and the upper pole 2504, any of which components can be made from any of the materials disclosed herein. Additionally, with reference to the figures, the upper pole of any pump embodiments disclosed herein, including without limitation pump embodiment 2500, can have a first portion 2504a and a second portion 2504b. In any embodiments, the first portion can extend in a generally planar direction, and the second portion 2504b can extend away from the first portion 2504a in an axial direction parallel to the centerline axis of the pump assembly. In any embodiments, the second portion 2504b of the upper pole 2504 can extend through the opening 2574a of the magnet 2754 and the opening 2576a of the lower pole 2576 in the assembled configuration. Additionally, the second portion 2504b of the upper pole 2504 can extend through the opening 2560a of the coil 2560 and the opening 2564a of the 2564. This can shift the magnetic field away from the first portion 2504a of the upper pole, closer to the center of the coil 2560.

Figure 78A:
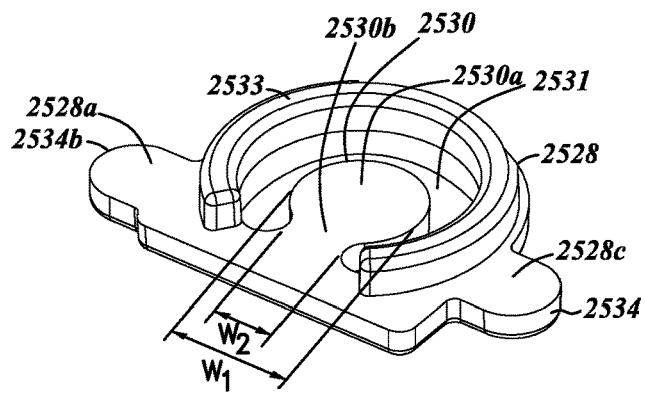
FIGS. 78A-78B are a first and a second isometric view of an embodiment of a valve member of the pump assembly embodiment shown in FIG. 72.
Figure 78B:
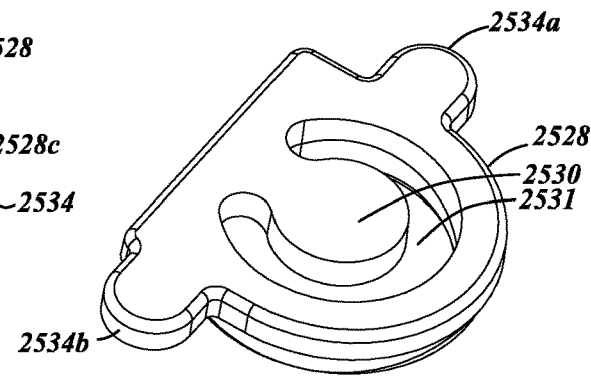

With reference to FIGS. 78A and 78B, any embodiments of the pump assembly disclosed herein can have a valve member with the following features, components, or other details. Embodiments of the valve member 2528 can have a flexible and/or deflectable tab portion or member 2530 supported in a middle portion of the valve 2528. The deflectable tab 2530 can be supported in cantilever, such that the deflectable tab 2530 can bend or deflect away from the relaxed position, the relaxed position being shown in FIGS. 78A and 78B. An opening 2531 surrounding a portion of the deflectable tab 2530 can be permitted to allow air to pass around the deflectable tab 2530 when the pump is being operated, during sterilization, or otherwise. In any embodiments, the opening or gap 2531 can have a width of approximately 0.4 mm, or from approximately 0.3 mm to approximately 0.5 mm, and can surround approximately 80% of a perimeter of the flap 2530.

In any embodiments disclosed herein, the valve member 2528 can have a raised surface or protrusion 2533 extending away from a first main surface 2528c of the valve member 2528. Additionally, the valve member 2528 can have one or more alignment tabs 2534a, 2534b configured to facilitate the placement, securement, and alignment of the valve 2528, two being shown. However, the valve member 2528 can have just one alignment tab 2534. In any embodiments disclosed herein, the flap valve 2528 can have one or more hinges, joints, articulations, or curves therein at or adjacent to the base portion of the deflectable tab portion 2530 to improve the ability of the tab portion 2530 to bend and deflect, thereby potentially improving the efficiency of the valves. In any pump embodiments disclosed herein, the valves and valve supports can be configured such that the valves are preloaded against the intake side of the valve or valve supports for improved seal and pump efficiency.

Figure 79A:
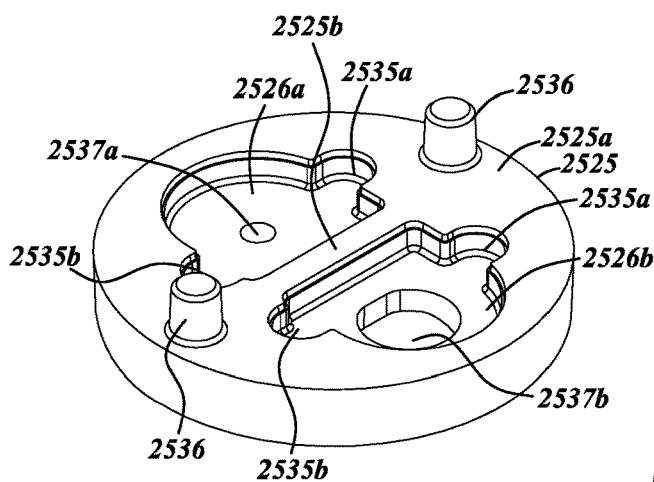
FIGS. 79A-79B are a first and a second isometric view of an embodiment of a first valve support of the pump assembly embodiment shown in FIG. 72.
Figure 79B:
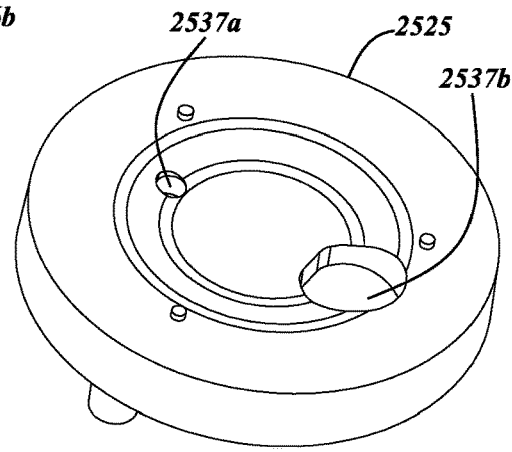

Additionally, with reference to FIGS. 79A-79C, the first valve member 2525 can have a first recess 2526a and a second recess 2526b formed in a first main surface 2525a of the first valve support 2525. In any embodiments, the recesses 2526 can have indexing cutouts or features, such as the cutouts 2535a, 2535b sized and configured to receive the alignment tabs 2534a, 2534b of the valve members 2528. The positioning of the alignment tabs 2534a, 2534b and the cutouts 2535a, 2535b can ensure that the valve members 2528 will be in the proper orientation when positioned in the recesses 2526. For example and without limitation, a first valve member 2528a can be positioned in a first recess 2526a such that the first alignment tab 2534a is positioned in the first cutout 2535a. The position of the alignment tabs 2534 and cutouts 2535 ensure that the raised surface 2533 will be facing in a desired direction. For example, for a first valve member positioned in the first recess 2526a, the position of the alignment tabs 2534 and cutouts 2535 ensure that the raised surface 2533 of the first valve 2528a will be facing in the same direction that the one or more alignment pins or protrusions 2536 extend.

Thus, in this configuration, the flap 2530 will lie flush against the first opening 2537a when the flap 2530 is in a relaxed state. To allow air to pass through the first opening 2537a, the flap will deflect away from the bottom planar surface of the first recess 2526a so that air can pass around the flap 2530 and through the first opening 2537a. Similarly, for a second valve member positioned in the second recess 2526b, the position of the alignment tabs 2534 and cutouts 2535 ensure that the raised surface 2533 of the second valve 2528b will be facing in the opposite direction as compared to the direction that the one or more alignment pins or protrusions 2536 extend. In this arrangement, the second opening 2537b can be sized and configured to be large enough such that the flap 2530, when deflected away from the relaxed position of the flap, can deflect into the opening 2537b thereby allowing air to pass through the opening 2537b. The raised portion 2533 would be positioned against the bottom planar surface of the second recess 2526b to improve the airflow around the second valve member 2528 positioned in the second recess 2526b. The raised portion 2533 can extend around all or a portion of a perimeter of the flap valve 2528.

Figure 80A:
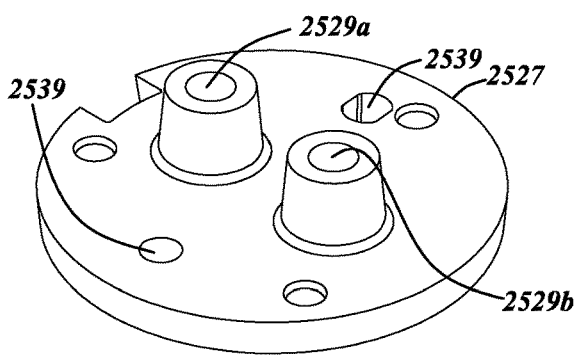
FIGS. 80A-80B are a first and a second isometric view of a second valve support embodiment of the pump assembly embodiment shown in FIG. 72.
Figure 80B:
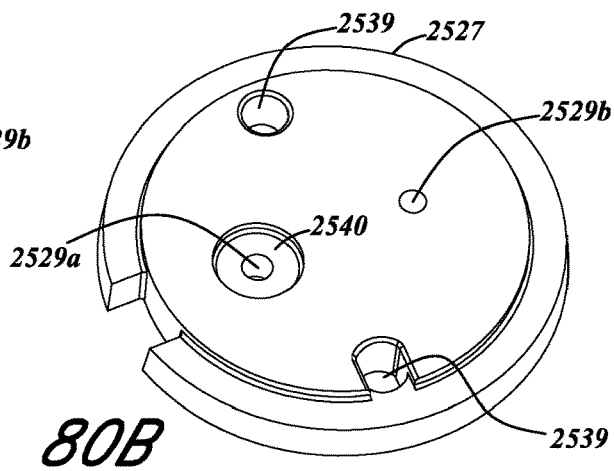

Additionally, with reference to FIGS. 80A-80B, the second valve support 2527 can have a first opening or recess 2539 and a second opening or recess 2539 configured to receive the alignment tabs or protrusions 2536 therein to ensure the appropriate alignment of the second valve support 2527. In any embodiments, the first and second recesses 2539 can have a different shape, as illustrated in FIG. 80 and the alignment protrusions 2536 can each have the unique shape matching or complementary to the shapes of the recesses 2539 such that the first and second valve supports 2525 and 2527 can only be engaged in one orientation. Additionally, with reference to FIG. 80B, a recess 2540 can be formed coaxial with the first opening 2529a to permit the flap 2530 of the valve to displace away from the first valve support 2525 and into the recess 2540 formed in the second valve support 2527 to enable air to flow around the valve flap 2530 and through the opening 2529a.

Figure 81A:
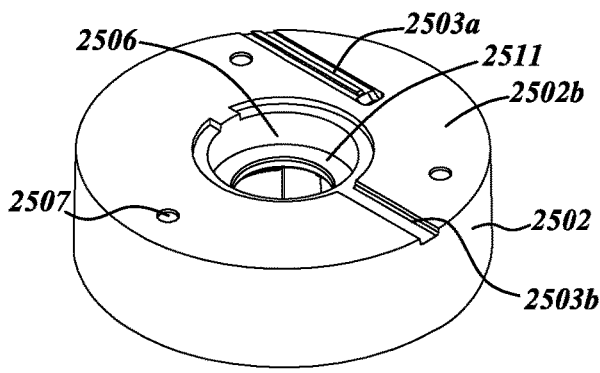
FIGS. 81A-81B are a first and a second isometric view of an embodiment of a housing of the pump assembly embodiment shown in FIG. 72.
Figure 81B:
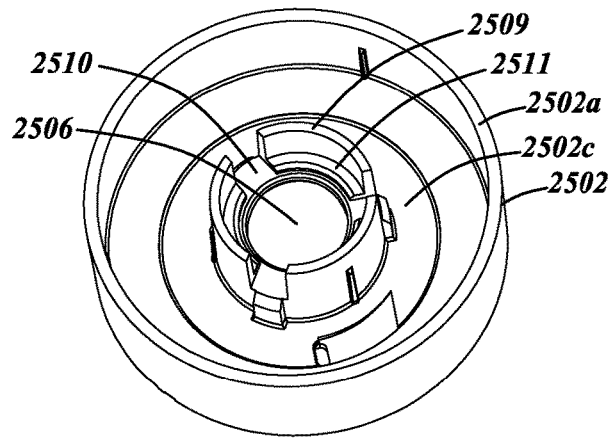

FIGS. 81A-81B illustrate the housing 2502. In addition to the features described above, any embodiments of the housing disclosed herein can have any of the features of any other housing embodiments disclosed herein. Any embodiments of the housing disclosed herein, including without limitation the housing 2502, can have any of the features, components, or other details as described as follows. In addition to the opening 2506 formed in approximated the axial center of the housing 2502, the housing can have one or more alignment features configured to ensure the alignment of one or more components supported within the housing. For example and without limitation, though not required, the housing 2502 can have one or more (three being shown) openings or recesses 2507 extending partially or completely through the second surface 2502b of the housing for fabrication purposes. For example, the recesses 2507 can be configured to accommodate a residual gate vestige due to the injection moulding process.

Additionally, in any embodiments disclosed herein, the housing 2502 can have a middle portion 2509 defining a wall extending away from an inside surface 2502c of the housing 2502. The middle portion 2509 (also referred to herein as wall or wall portion) can be approximately coaxially aligned with the opening 2506 and can have one or more cutouts or openings 2510 (three being shown) formed therein, the openings 2510 extending all or a portion of the length of the wall 2509. The openings 2510 can be used to index and/or rotationally secure one or more of the components supported within the housing 2502, including without limitation the support member 2564. For example, the support member 2564 can have one or more radially extending arms 2564c (three being shown) configured to be positioned within the openings 2510 in an assembled state. Additionally, in any embodiments, the bearing 2508 can define one or more radially extending tabs or protrusions 2508a (three being shown) configured to be positioned within the openings 2510 in an assembled state. As mentioned, the openings 2510 can be configured to prevent the rotation or twisting of the support member 2564, the bearing 2508, and/or any other components supported within or by the housing. The middle portion or wall 2509 can extend through the opening 2506 formed in the upper pole 2504.

Additionally, in any embodiments disclosed herein, the middle portion 2509 of the housing 2502 can define a flange or step portion 2511 configured to provide a support surface for one or more components supported within or by the housing 2502. For example, with reference to FIG. 76, the step portion 2511 can be configured to support the peripheral portion 2566a of the diaphragm 2566 against or adjacent to a first side of the step portion 2511, with the peripheral portion 2566a of the diaphragm 2566 being positioned between the step portion 2511 and the first valve support 2525. Additionally, the step portion 2511 can form a support surface against which a peripheral portion of the flat spring 2580 can be supported. In any embodiments, the peripheral portion of the flat spring 2580 can be supported against a second side of the step portion 2511, the peripheral portion of the flat spring 2580 being positioned between one or more legs of the bearing 2508 and the step portion 2511.

Figure 82:
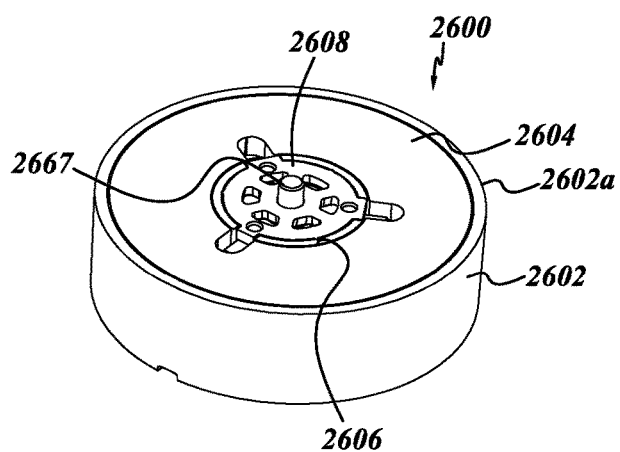
FIGS. 82 and 83 are isometric views of another embodiment of a pump assembly that can be used to provide reduced pressure to a wound dressing.
Figure 83:
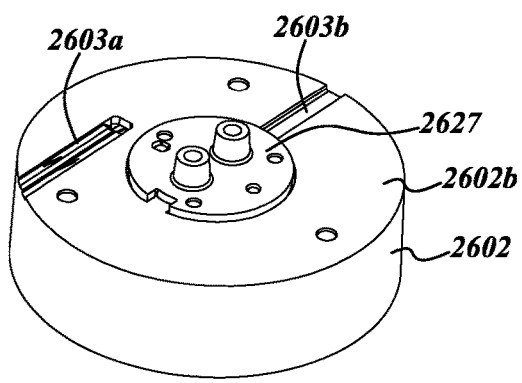
Figure 84:
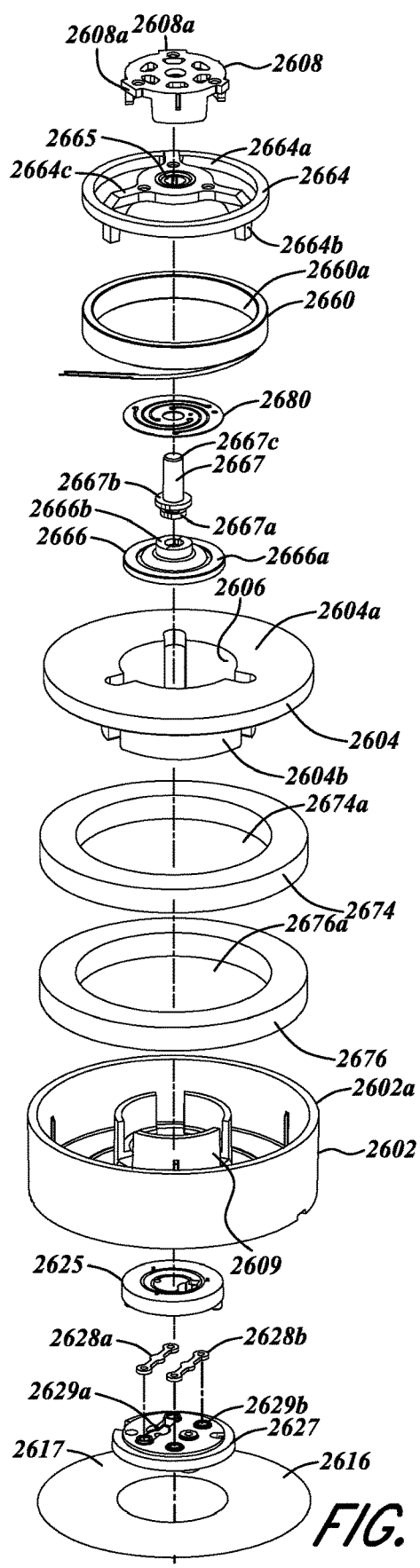
FIGS. 84 and 85 are exploded views of the pump assembly embodiment illustrated in FIG. 82, showing the top and the bottom of the pump assembly, respectively.
Figure 85:
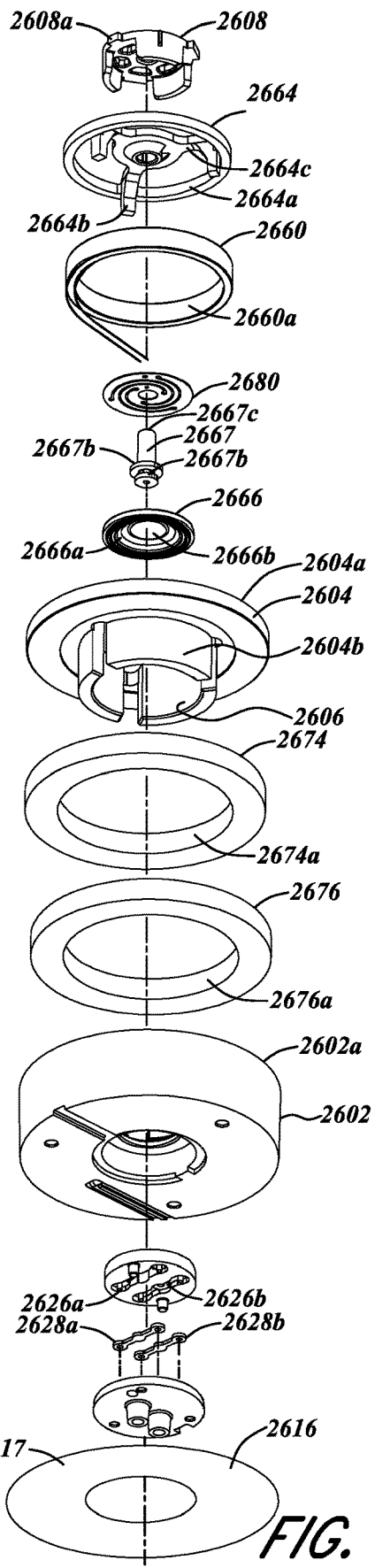
Figure 86:
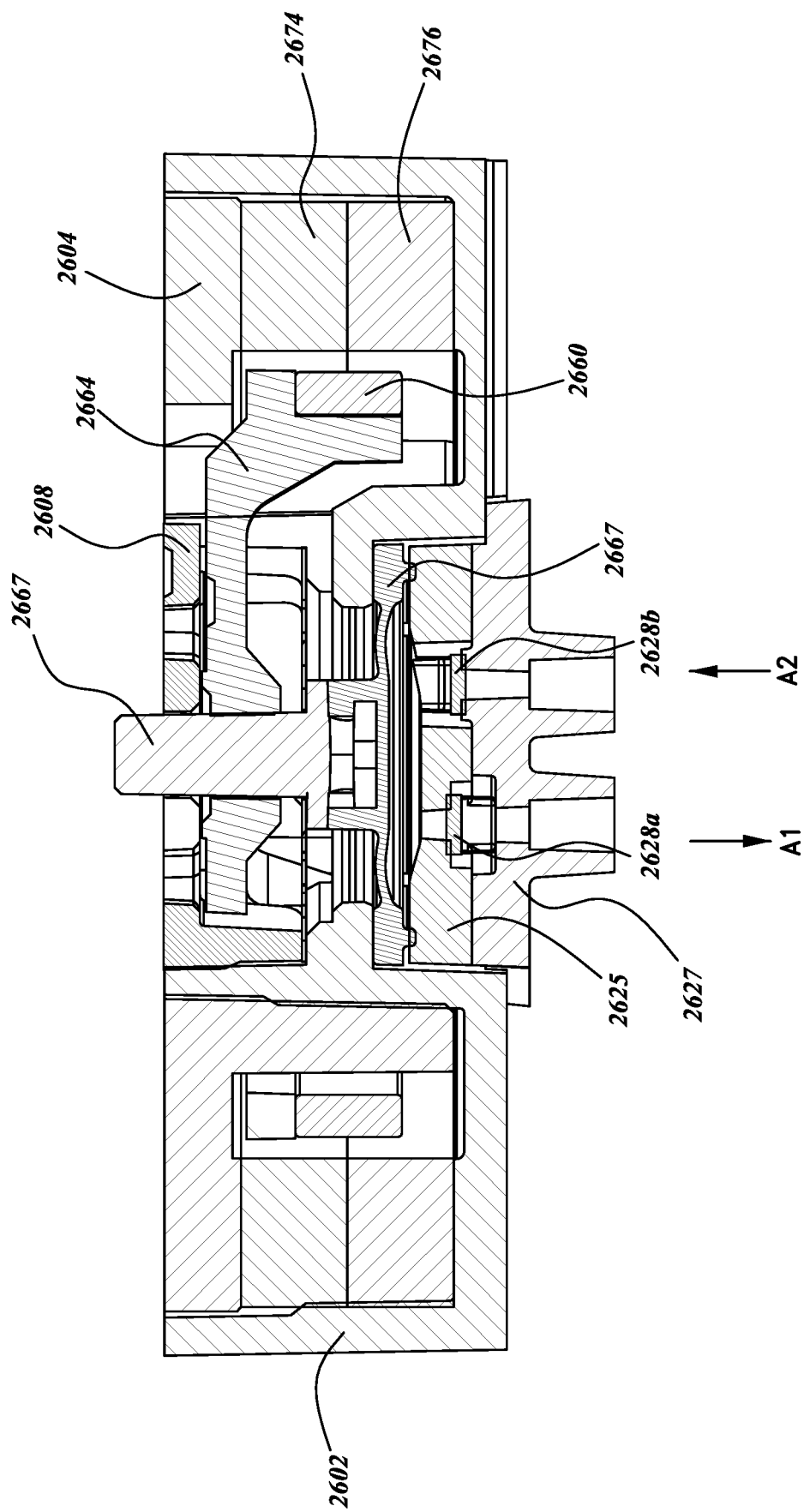
FIG. 86 is a sectional view of the embodiment of the pump assembly of the pump assembly embodiment shown in FIG. 82.

FIGS. 82 and 83 are isometric views of another embodiment of a pump assembly 2600, showing a top surface of the pump assembly and the bottom surface of the pump assembly 2600, respectively. FIGS. 84 and 85 are exploded views of the pump assembly embodiment illustrated in FIG. 82, showing the top of the pump assembly and the bottom of the pump assembly, respectively. FIG. 86 is a section view of the pump assembly embodiment illustrated in FIG. 82, the section being taken through the center of the pump assembly embodiment. The pump assembly embodiment 2600 can have a compact, small size and can have any of the same features, sizes, components, materials, operating methods or parameters, or other details of any of the pump assembly embodiments described herein, or any components thereof, including without limitation the pump assembly 2500 described above. In any embodiments disclosed herein, the pump assembly 2600 can be the same as the pump assembly 2500 except for the configuration and details of the valve assembly, as described below. Additionally, any of the other pump assembly embodiments disclosed herein can have any of the same features, sizes, components, materials, operating methods or parameters, or other details of the pump assembly 2600 or any component thereof.

The pump assembly embodiment 2600 can have a housing 2602 adapted to support and protect many of the components of the pump assembly embodiment 2600. The housing 2602 can have any of the same features, materials, or other details of any of the other housing embodiments disclosed herein, including without limitation the housing embodiment 2502. An upper pole 2604 can be supported at one end (for example, a first end) 2602a of the housing 2602. A bearing 2608 can be supported by the upper pole 2604, within the opening 2606. A cover 2616 (also referred to herein as a first cover) can be positioned over either end portion of the housing 2602, including without limitation the second end portion 2602b of the housing 2602. The cover can have an adhesive surface to adhere to the housing or upper pole surface.

The valve assembly 2620 can have a first valve support or plate 2625 and a second valve support or support 2627 that can also have a first port 2629*a* (also referred to herein as an exhaust port or exhaust outlet) for exhausting gas or air within the pump assembly and a second port 2629*b* (also referred to herein as an inlet port or just an inlet) thereon. In any embodiments, the inlet port can be configured to sealingly receive a conduit for communicating the negative pressure produced by the pump assembly to a wound dressing.

In any embodiments of the pump assembly disclosed herein, the first valve support 2625 can support two flexible valve members 2628, a first valve member 2628*a* for the outlet valve chamber or the outlet port or opening 2629*a* and a second valve member 2628*b* for the inlet valve chamber or the inlet port or opening 2629*b*. For example and without limitation, the first valve member 2628*a* can be supported within a first recess 2626*a* formed in the first valve support 2625. In any embodiments, the first recess 2626*a* can define a raised portion surrounding the opening 2637*a*, configured to increase the contact force and pressure between the first valve member 2628*a* and the surface of the first recess 2626*a* around the first opening 2637*a*, thereby improving the seal between the first valve member 2628*a* and the first valve support 2625.

The second valve member 2628*b* can be supported within a second recess 2626*b* formed in the first valve support 2625. The first valve member 2628*a* and the second valve member 2628*b* (or at least a middle portion of each of the valve members) can be configured to deflect away from the relaxed position of the flaps 2628 shown to respectively block passage of air through the valve assembly 2620 during operation of the pump, or possibly even during sterilization of the pump. Some additional details of the valves 2628 and the valve supports 2625, 2627 will be described in greater detail below. Similar to the first valve support 2625, in any embodiments, the second valve support 2627 can define a raised portion surrounding the opening 2629*b*, configured to increase the contact force and pressure between the second valve member 2628*b* and the surface of the second valve support 2627 around the opening 2629*b*, thereby improving the seal between the second valve member 2628*b* and the second valve support 2627. In any embodiments herein, the raised surface can be formed on either the first or second valve member itself.

For example, with reference to FIG. 86, which is a section view of the pump assembly 2600, when the diaphragm 2666 deflects in the direction A1 shown in FIG. 86, the air or gas within the chamber 2668 between an inside surface of the diaphragm and the valve members 2628 will compress and increase in pressure, causing the first valve member 2628*a* to deflect away from the first valve support 2625 and causing air to flow around the first valve member and exit through the outlet port 2629*a*. Additionally, the second valve member 2628*b* will be deflected against or further sealed against the second valve support 2627, sealing the second valve member 2628*b* against the second valve support 2627 and substantially preventing air from going around the second valve member 2628*b* and out through the inlet port 2629*b*. This is referred to as an outtake or exhaust cycle.

In any embodiments disclosed herein, the spring member 2580 can be configured to offset the diaphragm member relative to the relaxed position of the diaphragm member in the direction represented by arrow A1 shown in FIG. 76. In some arrangements, this offset can alter the force required to deflect the diaphragm in both the A1 and A2 directions to be more similar or equalized during the operation of the pump, so that the current draw of the pump during operation is more even during intake and exhaust cycles. In any embodiments disclosed herein, the total stroke of the diaphragm can be approximately 1.2 mm, or between approximately 1.0 mm and approximately 2.0 mm. The offset of the diaphragm from the spring member 2580 in any embodiments disclosed herein can be approximately 0.5 mm, or from approximately 0.4 mm or less to approximately 0.7 mm or more.

Again with reference to FIG. 86, when the diaphragm deflects in the direction A2 shown in FIG. 86, the air or gas within the chamber 2668 between an inside surface of the diaphragm and the valve members 2628 will decrease in pressure, causing the first valve member 2628*a* to sealingly deflect or press against the first valve support 2625, substantially preventing air from going around the first valve member 2628*a* and in through the outlet port 2629*a*. Additionally, the second valve member 2628*b* will be deflected toward the diaphragm and away from the second valve support 2627, allowing air to flow through the inlet port 2629*b*, around the second valve member 2628*b* and into the air chamber. This is referred to as an intake cycle, during which air can be drawn through a conduit attached at one end to a dressing for negative pressure wound therapy and at the other end to the inlet port on the pump assembly.

Figure 88A:
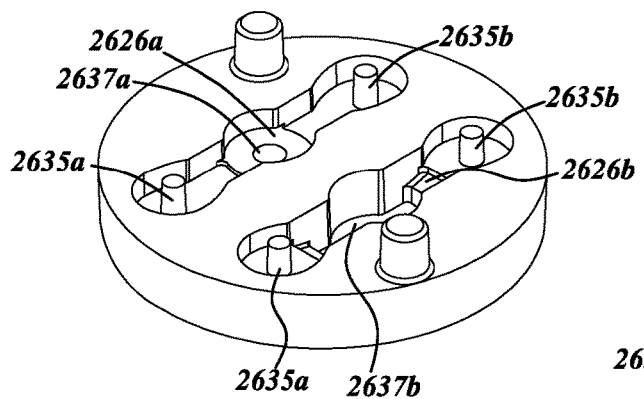
FIGS. 88A-88B are a first and a second isometric view of an embodiment of a first valve support of the pump assembly embodiment shown in FIG. 82.
Figure 88B:
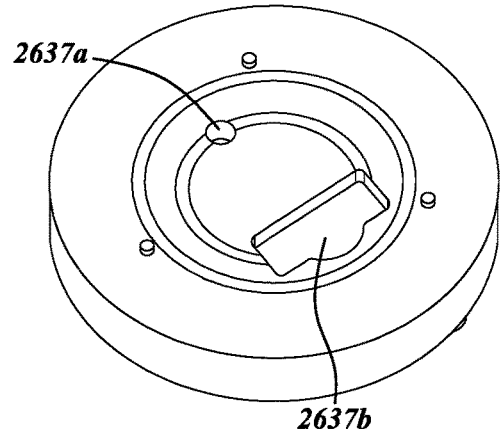

With reference to FIGS. 88A and 88B, any embodiments of the pump assembly disclosed herein can have a valve member with the following features, components, or other details. Embodiments of the valve member 2628 can have a flexible and/or deflectable middle portion 2630 spanning between a first end portion 2628*c* and a second end portion 2628*d* of the valve 2628. The deflectable middle portion 2630 can be unrestrained such that the middle portion 2630 can bend or deflect away from the relaxed position, the relaxed position being shown in FIGS. 88A and 88B. In any embodiments disclosed herein, though not illustrated, the valve member 2628 can have a raised surface or protrusion extending away from a first main surface 2628*e* of the valve member 2628. Additionally, the valve member 2628 can have one or more openings 2634*a*, 2634*b* in the end portions thereof or otherwise. The openings can facilitate the placement, securement, and alignment of the valve 2628 in or by the first and second valve supports.

With reference to FIGS. 88A-88C, the first valve support 2625 can have a first recess 2626*a* and a second recess 2626*b* formed in a first main surface 2625*a* of the first valve support 2625. In any embodiments, the recesses 2626 can have indexing cutouts or features or protrusions, such as protrusions 2635*a*, 2635*b* (also referred to herein as posts), sized and configured to secure the position of the valve members relative to the valve supports and recesses. For example, the protrusions 2635*a*, 2635*b* can be configured to pass through the openings 2634*a*, 2634*b* of the valve members 2628. The positioning of the openings 2634*a*, 2634*b* and the protrusions 2635*a*, 2635*b* can ensure that the valve members 2628 will be in the proper position and secured in the recesses 2626. The protrusions 2635*a*, 2635*b* can be received within the openings 2641 formed in the second valve support 2627 to provide additional support and alignment between the first and second valve supports and the valve members 2628. Additionally, in any embodiments disclosed herein, the distance from a center of the first protrusion 2635*a* to a center of the second protrusion 2635*b* can be greater than, equal to, or smaller than the distance from a center of the first opening 2634*a* to a center of the second opening 2634*b*. For example, in any embodiments disclosed herein, the distance from the center of the first protrusion 2635*a* to the center of the second protrusion 2635*b* of the first valve support 2625 can be greater than the distance from the center of the first opening 2634*a* to the center of the second opening 2634b of at least one of the valves 2628 so that the valve 2634 is placed under tension when assembled to the first valve support 2625. Pre-stretching the valve 2628 can improve the structural stability of the valve and reduce the likelihood that the valve will buckle in operation.

Figure 89A:
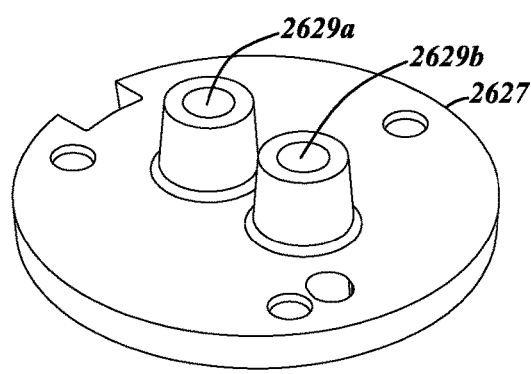
FIGS. 89A-89B are a first and a second isometric view of a second valve support embodiment of the pump assembly embodiment shown in FIG. 82.
Figure 89B:
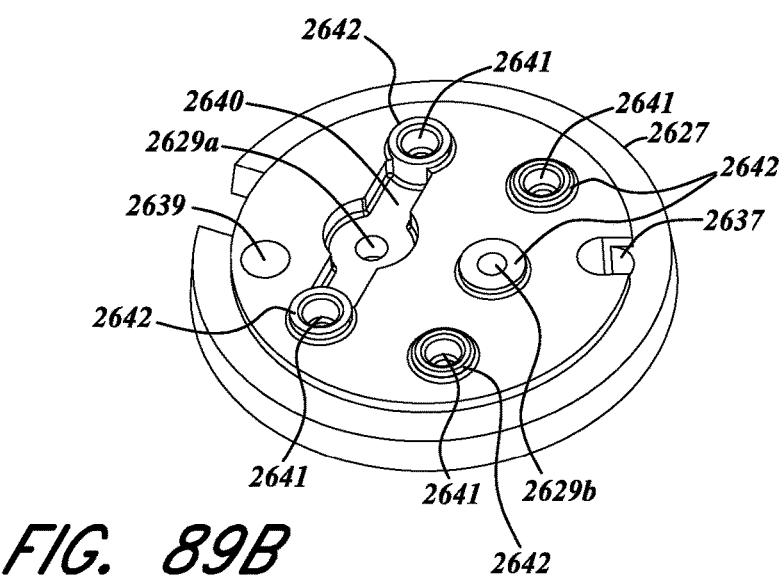

Additionally, with reference to FIG. 89B, in any embodiments, the second valve support 2627 can have a raised portion 2642 (also referred to herein as a boss, or protrusion) surrounding each of the openings 2641. When the second valve support 2627 is joined with the first valve support 2625 with the valves 2628 therebetween, the raised portions 2642 can exert a compressive force on the portions of the valves 2628 surrounding the openings 2634, as the valves 2628 are supported against the first valve support 2625. This configuration or arrangement can result in better securement of the end portions of the valves 2628 around the protrusions 2635. In any embodiments, a height of the bosses 2642 can be approximately 20% of a thickness of the valve 2628, or from approximately 10% to approximately 40% of the thickness of the valve 2628.

In this configuration, the mid portion 2630 can lie flush against the surface of the first valve support 2625 (or any raised surfaces thereon) surrounding the first opening 2637a when the mid portion 2630 is in a relaxed state. To allow air to pass through the first opening 2637a, the valve or mid portion thereof can deflect away from the bottom planar surface of the first recess 2626a so that air can pass around the mid portion 2630 and through the first opening 2637a. As mentioned, in any embodiments herein, the valves or valve members can be positioned against the sealing surface of the adjacent valve support so as to improve the seal of the valve member against the valve support surface. For example, the first valve member 2528a can be preloaded against or relative to the planar surface of recess 2526a formed in the first valve support 2525. The second flap valve 2528b can be preloaded against or relative to the planar surface of the second valve support 2527.

In any embodiments disclosed herein, the valve (including the valve 2528) can have a total thickness (which includes the thickness of the raised portion 2533) of approximately 0.75 mm, or from approximately 0.6 mm to approximately 1.0 mm or more, or from approximately 0.7 mm to approximately 0.85 mm. Additionally, in any embodiments disclosed herein, the valve flap 2530 can have a thickness of approximately 0.35 mm, or from approximately 0.25 mm to approximately 0.45 mm or more, or from approximately 0.30 mm to approximately 0.40 mm. As mentioned, a depression, channel, or notch can be formed in a base portion of the flap portion 2530 to permit greater flexibility in bending.

A width of the valve 2528, not including the one or more alignment tabs 2534, can be approximately 3.5 mm, or from approximately 3.0 mm or less to approximately 4.0 mm or more. A width of a main portion 2530a of the flap 2530 (or diameter of the flap, if generally circular shaped, for example, the width W1 shown in FIG. 78A) can be approximately 1.4 mm, or from approximately 1.0 mm or less to approximately 2.0 mm or more. Further, a base portion 2530b of the flap 2530 can have a width of approximately 0.75 mm, or from approximately 0.6 mm to approximately 1.0 mm. Reducing the width of the flap 2530 relative to the main portion of the flap can improve the flexibility of the flap 2530. In any embodiments disclosed herein, the base portion 2530b of the flap 2530 can have a width that is approximately 50% of the width of the body portion 2530a of the flap, or from approximately 40% to approximately 60% of the width of the body portion 2530a of the flap. In any embodiments, the width of the base portion 2530b can be from approximately 80% to approximately 100% of the width of the main portion 2530a of the flap. The valve can be made from any suitable material, such as silicone or any resilient rubber or plastic.

In any pump embodiments disclosed herein, any of the two or more valve supports (such as, without limitation, the first and second valve supports 2525, 2527 or first and second valve supports 2625, 2627) can be sealed, adhered, clamped, ultrasonic welded, laser welded or welded by any other suitable method, screwed, riveted, or otherwise fastened together. For example and without limitation, the valve supports can be sealed, adhered, laser welded, or otherwise fastened together after the valves have been assembled therewith. In the laser welding process, a portion of the material of the two respective valve supports will be melted so as to form a molecular joint between the two parts. In any embodiments, the valve supports can be configured to create a substantially air-tight seal between the valve supports, using the laser welding process, adhesive, one or more gaskets, or otherwise. Creating a seal between the two valve supports can reduce or eliminate the intake or exhaust of air between the valve supports during operation of the pump. Additionally, the first and/or second valve support can have a barrier between the intake air passageway and the exhaust air passageway that can reduce or eliminate the cross-passage of air between the intake and exhaust air passageways. For example, in any embodiments, the air flowing through the recess 2526a (or through the intake valve) can be substantially isolated from the air flowing through the recess 2526b (or through the exhaust valve). For example, in any embodiments, the first and/or second recesses that support the first and second flap valves, respectively, can be separated by a raised portion or barrier 2525b of the first and/or second valve supports. An adhesive seal, a laser or other weld, gasket, or other sealing element positioned adjacent to the barrier 2525b can reduce or eliminate the air flowing through the recess 2526a (or through the intake valve) from the air flowing through the recess 2526b (or through the exhaust valve).

FIGS. 87D and 87E are a side view and top view, respectively, of another embodiment of a valve member 2628'. In any embodiments disclosed herein, the valve member 2628' can have any of the features, elements, materials, or other details of any other valve member disclosed herein, including without limitation valve member 2628, and can work with any of the valve support components or embodiments, or other pump contains or embodiments, disclosed herein. Additionally or alternatively, the valve member 2628' can have any of the features, elements, materials, or other details described below.

Though not required, the valve member 2628' can be supported between a first valve support 2625 and a second valve support 2627, or between any two valve components or elements. For example and without limitation, a first valve member 2628' can be supported within a first recess and/or a second recess formed in a first valve support, such as the first valve support 2625 modified in accordance with the changes to the valve 2628' described herein. The first valve member 2628' and a second valve member 2628' (or at least a middle portion of each of the valve members) can be configured to deflect away from the relaxed position of the valve members 2628' shown to respectively block passage of air through the valve assembly during operation of the pump, or possibly even during sterilization of the pump.

For example, with reference to FIG. 86, which is a section view of the pump assembly 2600, when the diaphragm 2666 deflects in the direction A1 shown in FIG. 86, the air or gas within the chamber 2668 between an inside surface of the diaphragm and the valve members 2628' will compress and increase in pressure, causing the first valve member 2628a' to deflect away from the first valve support and causing air to flow around the first valve member and exit through the outlet port. Additionally, the second valve member 2628b' will be deflected against or further sealed against the second valve support, sealing the second valve member 2628b' against the second valve support and substantially preventing air from going around the second valve member 2628b' and out through the inlet port. This is referred to as an outtake or exhaust cycle.

Again with reference to FIG. 86, when the diaphragm deflects in the direction A2 shown in FIG. 86, the air or gas within the chamber 2668 between an inside surface of the diaphragm and the valve members 2628' will decrease in pressure, causing the first valve member 2628a' to sealingly deflect or press against the first valve support, substantially preventing air from going around the first valve member 2628a' and in through the outlet port. Additionally, the second valve member 2628b' or at least a middle portion thereof will be deflected toward the diaphragm and away from the second valve support, allowing air to flow through the inlet port, around the second valve member 2628b' and into the air chamber. This is referred to as an intake cycle, during which air can be drawn through a conduit attached at one end to a dressing for negative pressure wound therapy and at the other end to the inlet port on the pump assembly.

Embodiments of the valve member 2628' can have a flexible and/or deflectable middle portion 2630' spanning between a first end portion 2628a' and a second end portion 2628b' of the valve 2628'. The first and second end portions 2628a', 2628b' can have a greater thickness as compared to the spanning portions 2631'. The increased thickness of the end portions can provide more material for an improved connection between the two valve supports and the valve member. In any embodiments, the end portions 2628' can have a thickness that is twice as thick as the spanning portions 2631', or from approximately 90% greater than to approximately 120% or more greater than a thickness of the spanning portions 2631'. Additionally, in any embodiments, the middle portion 2630' can have a thickness that is greater than a thickness of the spanning portions 2631'. The spanning portions 2631' can have a decreased thickness to provide greater flexibility to the valve 2628'. The increased thickness of the middle portion 2630' can provide a greater contact force in a static state against the valve support contact surface to improve the seal between the valve and the contact plate.

In any embodiments disclosed herein, the end portions 2628a' and 2628b' can have a thickness that is approximately 0.6 mm, or from approximately 0.4 mm to approximately 0.8 mm, a middle portion that has a thickness of approximately 0.4 mm, or from approximately 0.3 mm to approximately 0.6 mm, and a spanning portion having a thickness of approximately 0.25 mm, or from approximately 0.15 mm to approximately 0.4 mm. The overall length of any embodiments of the valve member 2628' can be approximately 7.06 mm, or from approximately 5.0 mm or less to approximately 9.0 mm or more. A width of the end portions can be approximately 1.8 mm, or from approximately 1.0 mm or less to approximately 3.0 mm or more. In any embodiments disclosed herein, the end portions 2628' can have an inside edge 2628c' having a flat surface along substantially the entire width of the end portion 2628'. In any embodiments disclosed herein, an outer edge 2628d' of the end portions 2628a' can have a curved profile, and can have a diameter of approximately 2.06 mm, or from approximately 1.5 mm to approximately 2.5 mm. In any embodiments disclosed herein, the middle portion 2630' can have a circular profile (from an aerial or top view such that the shape of the surface contacting the valve support is circular), and can have a diameter of approximately 1.4 mm, or from approximately 1.0 mm or less to approximately 2.0 mm or more. The spanning portions 2631' can define a width of approximately 0.6 mm, or from approximately 0.4 mm or less to approximately 0.8 mm or more.

In any embodiments, the width of the spanning portions 2631' can be approximately 50% or less as compared to the width of the middle portion 2630'. Additionally, in any embodiments, a cross-sectional area of the spanning portion 2631' can be approximately 15%, or from approximately 10% or less to approximately 25% or more of the cross-sectional area of the end portions 2628'. Additionally, in any embodiments, the cross-sectional area of the spanning portion 2631' can be approximately 27%, or from approximately 20% or less to approximately 40% or more of the cross-sectional area of the middle portion 2630'.

Figure 90:
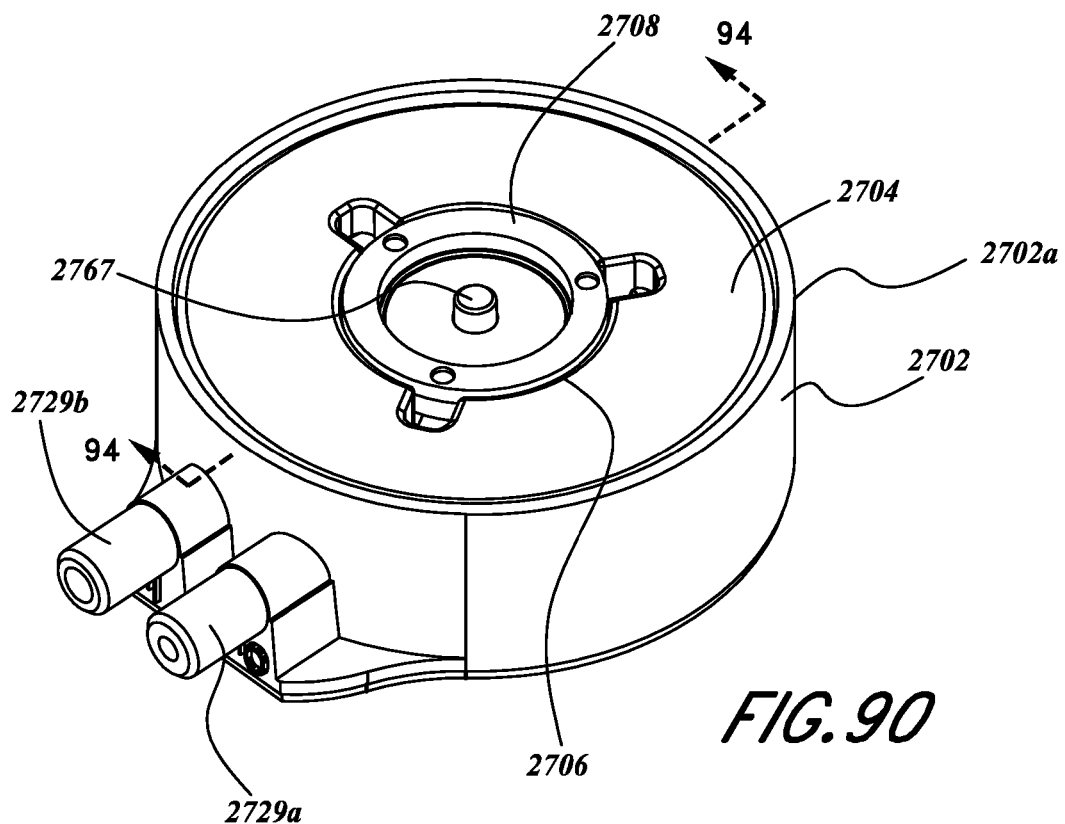
FIGS. 90 and 91 are isometric views of another embodiment of a pump assembly that can be used to provide reduced pressure to a wound dressing.
Figure 91:
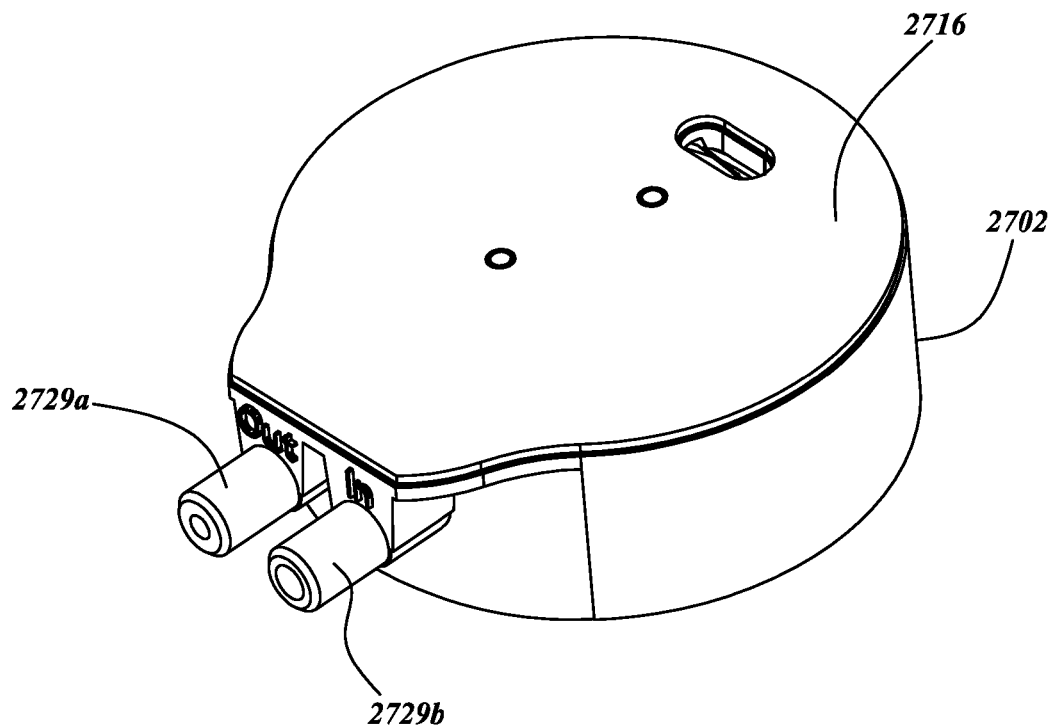
Figure 94:
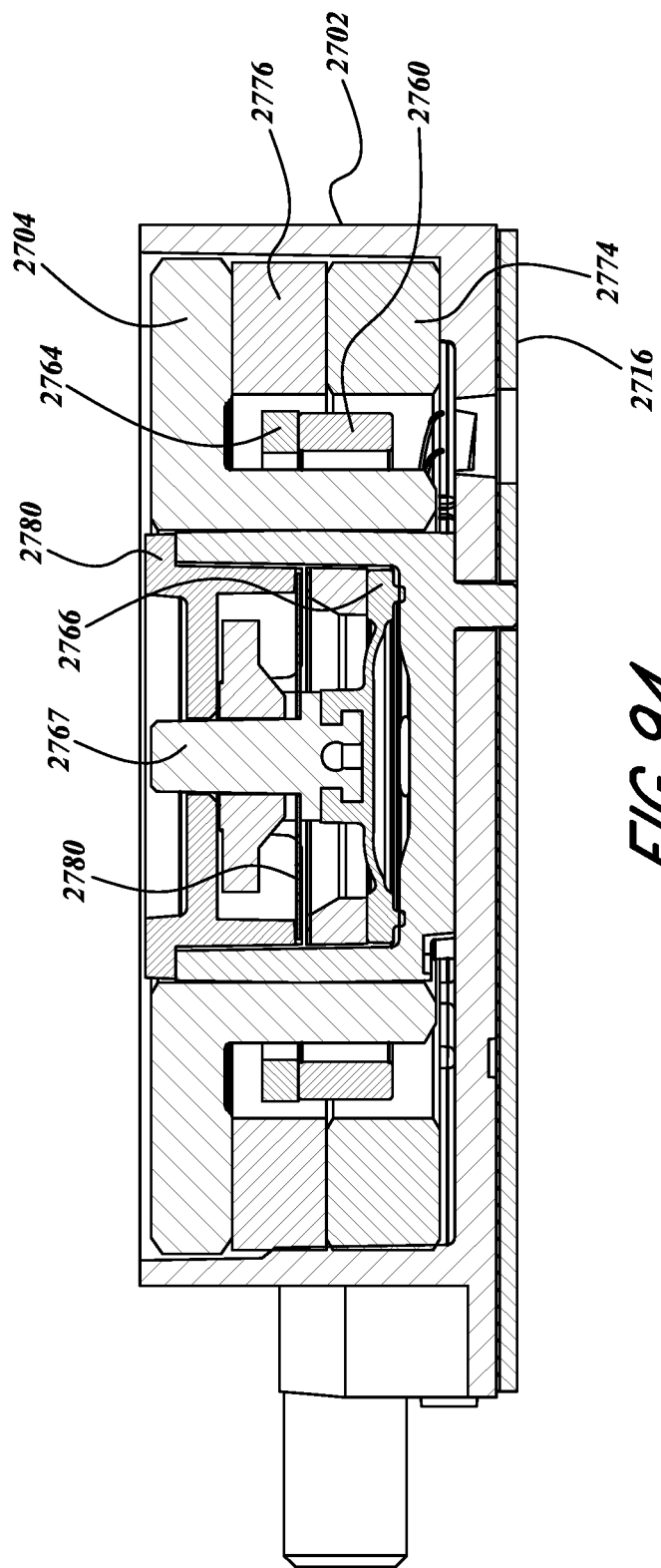
FIG. 94 is a sectional view of the embodiment of the pump assembly of the pump assembly embodiment shown in FIG. 90.

FIGS. 90 and 91 are isometric views of another embodiment of a pump assembly 2700, showing a top surface of the pump assembly and the bottom surface of the pump assembly 2700, respectively. FIGS. 92 and 93 are exploded views of the pump assembly embodiment illustrated in FIG. 90, showing the top of the pump assembly and the bottom of the pump assembly, respectively. FIG. 94 is a section view of the pump assembly embodiment illustrated in FIG. 90, the section being taken through the center of the pump assembly embodiment. The pump assembly embodiment 2700 can have a compact, small size and can have any of the same features, sizes, components, materials, operating methods or parameters, or other details of any of the pump assembly embodiments described herein, or any components thereof.

In any pump embodiments disclosed herein, the pump can have a small volume. For example and without limitation, any embodiments of the pump assembly disclosed herein can have a volume of approximately 6.26 cubic centimeters, or from approximately 5.0 cubic centimeters or less to approximately 7.0 cubic centimeters. The housing of any embodiment disclosed herein can have a diameter of approximately 28.2 mm, or from approximately 27.0 mm or less to approximately 30.0 mm, and a height of approximately 10.0 mm, or from approximately 8.0 mm to approximately 12.0 mm.

In any pump embodiments disclosed herein, including without limitation the pump assembly 2700, the pump housing can have a diameter or lateral size in the range of approximately 26-29 mm, or between approximately 27 or less and approximately 28 mm or more. In any embodiments disclosed herein, the pump assembly embodiment 2700 can have a thickness or height of approximately 8 mm, or between approximately 6 mm and approximately 10 mm.

The pump assembly embodiment 2700 can be produced for a low cost and can operate at high efficiencies, making it beneficial for portable, disposable, and/or single use applications. In any embodiments disclosed herein, the pump assembly embodiment 2700 can run for a week on a small primary cell such as one or more batteries having a total capacity of 3000 mAh without the need for battery replacement or recharging. This pump can be used in an ultra-portable single-use NPWT device, but is not so limited. In any embodiments disclosed herein, as mentioned, the pump assembly embodiment 2700 can be used for negative pressure wound therapy. However, the pump assembly embodiment 2700 is not limited to use in negative pressure wound therapy systems. The pump assembly embodiment can be adapted and configured for use in any reduced pressure system or in any system or application in which the movement of gaseous and liquid fluids is desired.

Any pump assembly disclosed herein, including without limitation the pump assembly embodiment 2700, can be designed to work at pressures of approximately 60 to approximately 80 mm Hg or more, or from approximately 60 to approximately 120 mm Hg or more, and can be configured to produce a flow rate of approximately 200 ml/min, or from approximately 100 ml/min or less to approximately 250 ml/min or more, with an efficiency of from approximately 15% to approximately 29% or more, or from approximately 20% to approximately 25% or 26%, in order for the NPWT device to run for a week on a specified battery capacity. In any embodiments disclosed herein, the pump assembly embodiment 2700 can be adapted to operate at efficiency levels in excess of 27%. In any embodiments disclosed herein, the pump efficiency can be approximately 20%-25%.

The pump assembly embodiment 2700 can have a housing 2702 adapted to support and protect many of the components of the pump assembly embodiment 2700. The housing 2702 can have one or more air passageways or channels 2703 formed in a bottom surface 2702b thereof. The air passageways 2703 can be used to channel or communicate air from the outlet port 2729a or inlet port 2729b (either ports also referred to herein as a tube connector) to the respective valve chambers and into the diaphragm chamber. The ports 2729 can be formed integrally with the housing. An upper pole 2704 can be supported at one end (for example, a first end) 2702a of the housing 2702. In any embodiments disclosed herein, the upper pole 2704 can have an opening 2706 formed through an axial centerline of the upper pole 2704. A bearing 2708 can be supported by the upper pole 2704, within the opening 2706.

A cover 2716 (also referred to herein as a first cover) can be positioned over either end portion of the housing 2702, including without limitation the second end portion 2702b of the housing 2702. The cover 2716 can be an adhesive backed foil, film, paper, plastic sheet or label, or other similar object. Additionally, any embodiments of the cover 2716 can also have any suitable or desired printing thereon regarding the pump or operation thereof. Additionally, in any embodiments disclosed herein, a flat battery (such as but not limited to a low profile printed battery) could be adhered directly to one or both end surfaces, or the side or perimeter surfaces, of the pump housing 2702. An intermediate layer 2717 can be positioned between the cover layer 2716 and the housing 2702. The intermediate layer 2717 can be adhered to the housing 2702 and the cover layer 2716 can be adhered to the gasket layer 2717. In any embodiments, the intermediate layer can be a gasket or can provide sealing benefits. In any embodiments, the intermediate layer can comprise adhesive on both a first main surface and a second main surface thereof, the second main surface being opposite the first main surface.

The pump assembly 2700 can have a first valve member 2725 (also referred to herein as a first valve support) and a pair of flap valves 2728, or any other suitable valves. The valves 2728 can be positioned between the first valve member 2725 and an inside surface of the housing 2702. One or more recesses capable of supporting the valve members 2728 can be formed inside the housing.

In any embodiments herein, the valves or flap valves can be positioned against the sealing surface of the adjacent valve support and/or housing surface so as to improve the seal of the flap valve against the valve support or housing surface. For example, the first flap valve 2728a can be preloaded against or relative to the planar surface of recess 2726a formed in the first valve support 2725. The second flap valve 2728b can be preloaded against or relative to the planar surface of recess 2726b formed in the first valve support 2725.

The pump assembly embodiment 2700 can have a coil 2760 comprising electrical wires 2714, and a support member 2764. In any embodiments, the coil 2760 can have an opening 2764a extending therethrough. Additionally, in any embodiments, the support member 2764 can have an opening 2764a extending therethrough. The support member 2764 can have legs 2765 extending through openings in the housing 2702. The coil 2760 can be formed from a length of wound conductive wire, such as without limitation copper wire. In operation, the coil 2760 can be configured to move within a magnetic circuit, and can be supported via a support member to a pump diaphragm assembly 2766. The diaphragm 2766 can have any of the same features, configurations, materials, sizes, or other details of any other diaphragm embodiment disclosed herein, including without limitation the diaphragm embodiment 2566 described above.

Additionally, any embodiments can have a diaphragm support ring 2768 which can be positioned adjacent to or against a peripheral portion of the diaphragm to better secure the peripheral portion of the diaphragm in a fixed position relative to the housing 2702. In other words, the support ring 2768 can serve as a spacer in contact with a periphery of the diaphragm. Though not required, in any embodiments, the pump can have an adhesive layer or ring 2770 positioned adjacent to an upper surface of the support ring 2768, which can facilitate the assembly of the various components. For example, the adhesive ring 2770 can provide a bond between a bottom surface of the spring 2780 and the upper surface of the support ring 2768.

A shaft portion 2767 (also referred to herein as a shaft member) can be engaged with the interior portion 2766b of the diaphragm member 2766. For example and without limitations, in any embodiments of the pump assembly disclosed herein, an end portion 2767a of the shaft member 2767 can be received within an opening 2769 formed in the diaphragm member 2766. The opening can be configured to engage with the end portion 2767a of the shaft member such that the end portion of the shaft member is axially engaged by the opening of the diaphragm.

In any pump embodiments disclosed herein, the shaft member 2767 or any shaft member disclosed herein can be axially fixed to the support member 2764 such that any axial motion of support member 2764 results in the equal and simultaneous movement of the shaft member 2767. Hence, in any embodiments herein, any movement of the coil can cause the equivalent and simultaneous movement of the support member and the shaft member, which can cause the simultaneous and equal movement of the middle portion of the diaphragm.

Any pump embodiments disclosed herein can also have a flat spring member 2780 positioned adjacent to the diaphragm. In any embodiments, the spring member 2780 can be positioned against a flange portion 2767b of the shaft portion 2767 (also referred to herein as a shaft member) of the diaphragm assembly. Alternatively or additionally, in any embodiments, the spring member 2780 can be positioned at a top portion 2767c of the shaft portion 2767 of the diaphragm assembly 2766, or can be positioned in any desired locations. The spring member 2780 can be sized and configured to provide frequency tuning or adjustment to the resonance frequency of the diaphragm and/or the components of the oscillating coil assembly.

Additionally, in any embodiments disclosed herein, the spring member 2780 or any number of spring members can be configured to maintain the axial alignment of the diaphragm assembly 2766 with the remainder of the pump assembly, or both to maintain alignment and to provide a mechanism for adjusting the resonance frequency of the pump. The spring member 2780 can be made from stainless steel, spring steel, or any other suitable material. In any embodiments disclosed herein, the spring member (such as, but not limited to, spring member 2780) can be positioned in contact with the diaphragm member (such as, but not limited to, the diaphragm member 2766) or the shaft portion (such as, but not limited to, the shaft portion 2767) such that the spring member exerts an axial force on at least a middle portion of the diaphragm member that causes the middle portion of the diaphragm member to deflect away from a relaxed position of the middle portion of the diaphragm member in an assembled state, but before power has been provided to the pump assembly.

The pump assembly embodiment 2700 can have a magnet 2774 having an opening 2774a extending axially therethrough positioned between a lower pole 2776 having an opening 2776a extending axially therethrough and the upper pole 2704, any of which components can be made from any of the materials disclosed herein. Additionally, with reference to the figures, the upper pole of any pump embodiments disclosed herein, including without limitation pump embodiment 2700, can have a first portion 2704a and a second portion 2704b. In any embodiments, the first portion can extend in a generally planar direction, and the second portion 2704b can extend away from the first portion 2704a in an axial direction parallel to the centerline axis of the pump assembly. In any embodiments, the second portion 2704b of the upper pole 2704 can extend through the opening 2774a of the magnet 2774 and the opening 2776a of the lower pole 2776 in the assembled configuration. Additionally, the second portion 2704b of the upper pole 2704 can extend through the opening 2760a of the coil 2760 and the opening 2764a of the 2764. This can shift the magnetic field away from the first portion 2704a of the upper pole, closer to the center of the coil 2760.

Any embodiments of the pump assembly disclosed herein can have a valve member with the following features, components, or other details. Embodiments of the valve member 2728 can have a flexible and/or deflectable tab portion or member 2730 supported in a middle portion of the valve 2728. The deflectable tab 2730 can be supported in cantilever, such that the deflectable tab 2730 can bend or deflect away from the relaxed position, the relaxed position being shown in FIGS. 78A and 78B. An opening 2731 surrounding a portion of the deflectable tab 2730 can be permitted to allow air to pass around the deflectable tab 2730 when the pump is being operated, during sterilization, or otherwise. In any embodiments, the opening or gap 2731 can have a width of approximately 0.4 mm, or from approximately 0.3 mm to approximately 0.5 mm, and can surround approximately 80% of a perimeter of the flap 2730.

In any embodiments disclosed herein, the valve member 2728 can have a raised surface or protrusion 2733 extending away from a first main surface 2728c of the valve member 2728. Additionally, the valve member 2728 can have one or more alignment tabs 2734a, 2734b configured to facilitate the placement, securement, and alignment of the valve 2728, two being shown. However, the valve member 2728 can have just one alignment tab 2734. In any embodiments disclosed herein, the flap valve 2728 can have one or more hinges, joints, articulations, or curves therein at or adjacent to the base portion of the deflectable tab portion 2730 to improve the ability of the tab portion 2730 to bend and deflect, thereby potentially improving the efficiency of the valves. In any pump embodiments disclosed herein, the valves and valve supports can be configured such that the valves are preloaded against the intake side of the valve or valve supports for improved seal and pump efficiency.

The first valve member 2725 can have a first recess 2726a and a second recess 2726b formed in a first main surface 2725a of the first valve support 2725. In any embodiments, the recesses 2726 can have one or more indexing cutouts or features, such as the cutout 2735 sized and configured to receive the alignment tab 2734 of the valve members 2728. The positioning of the alignment tab 2734 and the cutouts 2735 can ensure that the valve members 2728 will be in the proper orientation when positioned in the recesses 2726. Additionally, in any embodiments, the first valve member 2725 can have a wall or protrusions extending away from a first main surface of the valve member 2725. The wall can have a cylindrical shape and can have one or more cutouts therein (three being shown) configured to receive one or more arms or cross-members of the support member.

FIGS. 97A and 97B illustrate another embodiment of a valve assembly 2820 that can be used in any of the pump embodiments disclosed herein, or any portion or components of the valve assembly 2820 can be used in any of the valve assemblies or pump embodiments disclosed herein. With reference to FIGS. 97A and 97B, the valve assembly can have a first valve support or plate 2825, a second valve support or plate 2827, and a valve member 2828. For example, any embodiments of the pump assembly 2500 can be configured to use the valve member 2828 in place of the valve member(s) 2528, with any necessary modifications to the first and/or second valve supports 2525, 2527.

In the valve assembly 2820 embodiment illustrated in FIGS. 97A, 97B, the second valve plate 2827 (also referred to herein as a second valve support) can have a first port 2829a (also referred to herein as an exhaust port or exhaust outlet) for exhausting gas or air within the pump assembly and a second port 2829b (also referred to herein as an inlet port or just an inlet) thereon. In any embodiments, the inlet port can be configured to sealingly receive a conduit for communicating the negative pressure produced by the pump assembly to a wound dressing, and can be angled transverse to the axial centerline of the pump assembly.

In any embodiments of the pump assembly disclosed herein, the first valve support 2825 can support the valve member 2828. The valve member 2828 can have a first flap valve 2828a for the outlet valve chamber or the outlet port or opening 2829a and a second flap valve 2828b for the inlet valve chamber or the inlet port or opening 2829b. The valve member 2828 can be supported within a recess 2826 formed in the first valve support 2825. The first flap 2828a and the second flap 2828b can be configured to deflect away from the relaxed position of the flaps 2830 shown to block passage of air through the valve assembly 2820 during operation of the pump, or possibly even during sterilization of the pump. Some additional details of the valves 2828 and the valve supports 2825, 2827 will be described in greater detail below.

In any embodiments herein, the valves or flap valves can be positioned against the sealing surface of the adjacent valve support so as to improve the seal of the flap valve against the valve support surface. For example, the flap 2830 of the first valve 2828a can be preloaded or positioned against or relative to the planar surface of recess 2826 formed in the first valve support 2825. The flap 2830 of the second valve 2828b can be preloaded or positioned against or relative to the planar surface 2827a of the second valve support 2827.

When the diaphragm deflects so as to cause air or gas within the chamber between an inside surface of the diaphragm and the flap valves 2828 to compress and increase in pressure, this will cause the first flap valve 2828a to deflect away from the first valve support 2825 and cause air to flow around the first flap valve and exit through the outlet port 2829a. Additionally, the second flap valve 2828b will be deflected against or further sealed against the second valve support 2827, sealing the second flap valve 2828b against the second valve support 2827 and substantially preventing air from going around the second flap valve 2828b and out through the inlet port 2829b. This is referred to as an outtake or exhaust cycle.

When the diaphragm deflects so as to cause the air or gas within the chamber between an inside surface of the diaphragm and the flap valves 2828 to decrease in pressure, this can cause the first flap valve 2828a to sealingly deflect or further press against the first valve support 2825, substantially preventing air from going around the first flap valve 2828a and in through the outlet port 2829a. Additionally, the second flap valve 2828b will be deflected toward the diaphragm and away from the second valve support 2827, allowing air to flow through the inlet port 2829b, around the second flap valve 2828b and into the air chamber. This is referred to as an intake cycle.

With reference to FIGS. 98A and 98B, any embodiments of the pump assembly disclosed herein can have a valve member with the following features, components, or other details. Embodiments of the valve member 2828 can have a flexible and/or deflectable tab portion or member 2830 supported in a middle portion of the valve 2828. The deflectable tab 2830 can be supported in cantilever, such that the deflectable tab 2830 can bend or deflect away from the relaxed position. An opening 2831 surrounding a portion of the deflectable tab 2830 can be permitted to allow air to pass around the deflectable tab 2830 when the pump is being operated, during sterilization, or otherwise. In any embodiments, the opening or gap 2831 can have a width of approximately 0.4 mm, or from approximately 0.3 mm to approximately 0.5 mm, and can surround approximately 80% of a perimeter of the flap 2830.

In any embodiments disclosed herein, the valve member 2828 can have a raised surface or protrusion 2833a extending away from a first main surface 2828c of the valve member 2828 (shown in FIG. 98A) and a raised surface or protrusion 2833b extending away from a second main surface 2828d of the valve member 2828 (shown in FIG. 98B). Additionally, the valve member 2828 can have one or more openings or cutouts 2838a, 2838b configured to facilitate the placement, securement, and alignment of the valve 2828, two being shown. However, the valve member 2828 can have just one cutout or opening 2838. The cutouts or openings 2838 can be configured to receive or engage with one or more protrusions or posts 2836 extending from the first valve plate 2825 and can ensure that the valve member 2828 is in the proper orientation relative to the first and second valve plates.

In any embodiments disclosed herein, the flap valve 2828 can have one or more hinges, joints, articulations, or curves therein at or adjacent to the base portion of the deflectable tab portion 2830 to improve the ability of the tab portion 2830 to bend and deflect, thereby potentially improving the efficiency of the valves. In any pump embodiments disclosed herein, the valves and valve supports can be configured such that the valves are preloaded against the intake side of the valve or valve supports for improved seal and pump efficiency.

In any embodiments disclosed herein, as in any of the illustrated embodiments, the pump assembly can be of a sufficiently small and portable size to be supported on a user's body or in a user's clothing. For example, any of the pump assemblies disclosed herein can be sized to be attached using adhesive medical tape or otherwise to a person's skin or to a dressing in a comfortable location, adjacent to or on the dressing or otherwise. Further, any of the pump assembly embodiments disclosed herein can be sized to fit within a person's pants or shirt pocket, or can be tethered to a person's body using a lanyard, pouch, or other suitable device or article.

FIGS. 99-105 are isometric, front, sectional, and exploded views of another embodiment of a pump assembly 3000 that can be used to provide reduced pressure to a wound dressing. The pump assembly 3000 can be referred to as a crank pump assembly. In any embodiments disclosed herein, the pump assembly can have a housing 3002 to support the pump components. The housing can have a first housing portion 3004 couplable with a second housing portion 3006. The first housing portion 3006 can support an electric motor 3010 having electrical wires 3012 for connection to a power source, the control board, or otherwise. The motor shaft 3014 can projects from the motor along the axial centerline of the motor 3010. Any suitable control board, including any control board of any of the other pump embodiments disclosed herein, can be used to control the operation of the pump motor. Additionally, any embodiments of the pump assembly 3000 can be configured to have any of the components, features, power sources, sizes, materials, or other details of any of the other pump embodiments disclosed herein.

In any embodiments disclosed herein, including without limitation the embodiment of the pump 3000, the pump can have a mass of approximately 5 grams, and an efficiency of approximately 12%. As mentioned above, efficiency can be defined as (fluid power out)/(electrical power in). The pump motor 3010 can be a DC electric motor, having a diameter of 6 mm, 7 mm, 8 mm, or 10 mm, or any suitable size. In any embodiments disclosed herein, the motor can be a DC electric micro-motor such as any of the following manufactured by Precision Microdrives: PMD 107-001, PMD 108-105, or PMD 110-002.

In any embodiments disclosed herein, the end of the motor shaft 3014 can be coupled with a shaft connector 3018. A bushing or bearing 3019 can be supported on the connector 3018. The bushing 3019 can be used to couple the connector 3018 with a pump shaft 3020. In particular, the bushing 3019 can be received within a recess formed within a first portion 3022 of the pump shaft 3020.

To enable the reciprocating motion for the pump shaft 3020, the shaft connector 3018 can have an opening 3026 that is configured to receive the shaft 3014 therein. The opening 3026 can be positioned eccentrically relative to the axial centerline C1 of the motor shaft 3014. In this configuration, with the connector 3018 having the eccentric opening 3026, the bushing 3019 and the head portion 3022 of the pump shaft will be eccentrically positioned relative to the motor shaft 3014 such that, as the motor shaft 3014 rotates the connector 3018 and the bushing 3019, the pump shaft 3020 will experience reciprocating motion in an axial direction (represented by arrow A1 in FIG. 101).

Any embodiments of the pump assembly 3000 can be configured such that the pump shaft 3020 reciprocates (i.e., travels) approximately 0.6 mm in either direction. In any embodiments disclosed herein, the pump assembly 3000 can be configured such that the pump shaft 3020 reciprocates approximately 1.0 mm in either direction, or approximately 1.4 mm in either direction, or within a range between 0.6 mm and 1.4 mm or to or from any values within this range.

In any embodiments disclosed herein, the connector 3018 can support one or more weights at an eccentric position to balance the pump and/or offset and attenuate vibration produced by the eccentrically supported pump shaft 3020. For example, the connector 3018 can have a first tab 3018*a* and/or a second tab 3018*b* used to support weights thereby. The weights can be formed from steel or any other suitable material suitable for reducing the vibration produced by the pop during operation. In the illustrated embodiment, the weights are spherically shaped, such a small steel BBs or shot.

In any embodiments disclosed herein, the pump assembly 3000 can have a flexible diaphragm 3030 supported within the housing 3002. With reference to the illustrated embodiment, the diaphragm 3030 can be coupled with a second end portion 3023 of the pump shaft 3020. In this configuration, as the pump shaft 3020 reciprocates in the axial direction, the movement of the pump shaft 3020 will cause corresponding and simultaneous displacement or deflection of the flexible diaphragm 3030. The displacement of the diaphragm 3030 within the sealed space 3032 defined by the diaphragm 3030, the gasket seal or ring 3034, and the first valve support 3035 (also referred to herein as a valve nozzle or first valve nozzle) will cause the pressure within such sealed space 3032 (that is to say, with the exception of the ports and valves that will be discussed in greater detail below) to cyclically increase and decrease in response to the position of the diaphragm. For example, as one of ordinary skill in the art would understand, moving the shaft 3020 and hence diaphragm 3030 in a first direction (defined by arrow A2 in FIG. 101) will compress the air within the space 3032 to increase the pressure within such space 3032. Similarly, moving the shaft 3020 and hence diaphragm 3030 in a second direction (defined by arrow A3 in FIG. 101) will increase the volume and temporally decrease the pressure within the space 3032.

In any embodiments disclosed herein, the valve and valve support arrangement of the pump embodiment 3000 illustrated in FIGS. 99-105 can have any of the same features, components, or other details of any other pump embodiments disclosed herein. In any embodiments disclosed herein, the valve assembly 3033 can have a first valve support 3035 that can have a first side 3035*a* and a second side 3035*b*, and a plurality of openings or apertures therethrough. For example, in the illustrated embodiment, an first inflow opening 3042 (also referred to as a first inflow opening) can be used to permit the passage of air into the space 3032. Two or more openings 3044 (which can be outflow or exhaust openings) can be used to permit the flow of air out of the space 3032.

Similarly, the valve assembly 3033 can have a second valve support 3050 (also referred to herein as a valve nozzle or second valve nozzle) having a first side 3050*a*, a second side 3050*b*, and a plurality of apertures or openings therethrough. For example, in the illustrated embodiment, the second valve support 3050 can have a first inflow opening 3056 and one or more outflow or exhaust openings 3058. The first inflow opening 3056 can be configured to permit the passage of air into the space 3032, while the outflow or exhaust openings 3058 can be configured to permit the passage of air out of the space 3032. Either of the valve nozzles can be machined from aluminium wrought or cast material. In any embodiments disclosed herein, the first valve support 3035 can be positioned in an opposite orientation relative to how it is illustrated in FIG. 104 such that the openings 3044 can be in fluid communication with the inflow opening 3056 and such that the opening 3042 can be in fluid communication with the openings 3058.

A boss or protrusion 3060 can be used to sealingly receive an end portion of a conduit or tubing used to communicate the reduced pressure produced by the pump 3000 to a negative pressure wound therapy dressing. A lumen or opening 3061 within the protrusion 3060 can form a flow passageway through the first inlet opening 3056, in communication with one or more openings in the flexible valve support 3070, through the opening 3042 and into the space 3032, when the tab 3072 is not obstructing the flow of fluid through the openings. Similarly, the openings 3044 in the first valve support 3035 will be in communication with the opening or slit around the flexible tab 3074 of the flexible valve support 3070 and the openings 3058 of the second valve support 3050 to permit air within the space 3032 to exit the pump embodiment 3000.

In any embodiments disclosed herein, one or more of the valve supports or the features on the valve supports can be integrated into the housing of the pump assembly. For example, In any embodiments disclosed herein, not illustrated, the second valve support 3035 or 3050 and/or the protrusion 3060 can be integrated into the housing In use, when the diaphragm 3030 retracts and enlarges the volume of the space 3032, thereby drawing air through the lumen or opening 3061 of the boss 3060 into the space 3032 (and thereby reducing the pressure within a wound dressing in fluid communication with the pump 3000), the tab 3072 of the flexible valve support 3070 will permit the passage of air into the space 3032 and the outflow tab 3074 of the flexible valve support 3070 will substantially prevent or restrict the flow of air through the openings 3044 in the first valve support 3035 and/or the openings 3058 in the second valve support 3050 into the space 3032. In any embodiments disclosed herein, this can be achieved by sealing the openings 3044 with the flexible tab 3074.

Similarly, when the diaphragm 3030 extends and reduces the volume of the space 3032, thereby increasing the pressure within the space 3032, the valve assembly 3033 can be configured such that air will be substantially prevented from flowing through the openings 3042 of the first valve support 3035 and the one or more openings 3056 of the second valve support 3050, thereby preventing air from flowing back into the dressing in fluid communication with the pump. In any embodiments disclosed herein, this can be achieved by configuring the valve tab 3072 to seal the opening 3056 of the second valve support, so that air is prevented from flowing through the opening 3056.

Additionally, In any embodiments disclosed herein, the pump can be configured such that the openings 3044, 3058 are never sealed by the valve assembly. Rather, a one-way flow valve can be attached external to the valve assembly 3033 which can be configured to only permit the flow of air out of the pump assembly 3000.

In any embodiments disclosed herein, the surface (which can be a raised protrusion around the one or more openings formed in the plates 3035, 3050) against which the flaps or tabs 3072, 3074 contact to seal the opening therethrough can be angled between 2° and 8°, or In any embodiments disclosed herein between 4° and 8°, to improve the surface contact between the tabs 3072, 3074 and the raised portion around the openings in each of the first and second plates 3035, 3050. Additionally, ridges or raised portions around the valve taps 3072, 3074 can be configured to mate with corresponding or complementary groups in the first and second valve supports 3035, 3050 to provide a substantially leak free connection between the components of the valve assembly. The valve assembly 3033 can be coupled with the housing 3002 using one or more screws or other fasteners 3062. Any other suitable attachment method or mechanism, such as with screws, welds, clips, or otherwise, can be used to attach the valve assembly 3033 to the housing or to attach the various portions of the housing together.

Many of the components of the pump embodiment 3000 can be formed from the rigid plastic, metal, alloy, or any other composite or suitable material. For example, In any embodiments disclosed herein, the housing 3002, the connector 3018, bushing 3019, the first valve support 3035, the second valve support 3050, the pump shaft 3020 and other portions or components of the pump embodiment 3020 can be made from an injection molded plastic. Where needed or desired, the plastic can be reinforced with a fibrous material, such as glass or graphite. Other components can be formed from of more flexible material, such as a suitable silicone or other rubber. For example, In any embodiments disclosed herein, the diaphragm 3030 and the flap valve support 3070 can be formed from such a flexible material.

Any of the pump assembly embodiments or pump device embodiments disclosed herein can be configured to work with any of the dressing embodiments disclosed herein. The dressing can be provided as a single article with all wound dressing elements (including a port) pre-attached and integrated into a single unit. The wound dressing can then be connected, via a conduit, to any of the pump assemblies or pump devices disclosed herein. Additionally, In any embodiments disclosed herein, any of the pump assemblies or pump devices disclosed herein can be configured to be supported by any of the dressing embodiments disclosed herein. In any embodiments disclosed herein, though not required, the pump assembly embodiments disclosed herein can be miniaturized and portable.

The wound dressing can be located over a wound site to be treated. The dressing can form a substantially sealed cavity or enclosure over the wound site. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, sub-acute and dehisced wounds, traumatic wounds, flaps and skin grafts, lacerations, abrasions, contusions, burns, diabetic ulcers, pressure ulcers, stoma, surgical wounds, trauma and venous ulcers or the like. In any embodiments disclosed herein, the components of the TNP system described herein can be particularly suited for incisional wounds that exude a small amount of wound exudate.

As described in U.S. patent application Ser. No. 13/092,042, which disclosure is hereby incorporated by reference as if fully set forth herein, a lower surface of any of the wound dressing embodiments disclosed herein can have an optional wound contact layer. Any of the dressing embodiments disclosed herein can be made without the wound contact layer. The wound contact layer can be a polyurethane layer or polyethylene layer or other flexible layer which can be made porous or perforated, for example via a hot pin process, laser ablation process, ultrasound process or in some other way or otherwise made permeable to liquid and gas. The perforations can enable fluid and/or gas to flow through the layer. The wound contact layer can help prevent tissue ingrowth into the other material of the wound dressing.

The perforations can be sized small enough to meet this requirement but still allow fluid through. For example, perforations formed as slits or holes having a size ranging from 0.025 mm to 1.2 mm are considered small enough to help prevent tissue ingrowth into the wound dressing while allowing wound exudate to flow into the dressing. The wound contact layer helps hold the whole wound dressing together and helps to create an air tight seal around the absorbent pad in order to maintain negative pressure at the wound. The wound contact layer also acts as a carrier for an optional lower and upper adhesive layer (not shown). For example, a lower pressure sensitive adhesive can be provided on the underside surface of the wound dressing whilst an upper pressure sensitive adhesive layer can be provided on the upper surface of the wound contact layer. The pressure sensitive adhesive, which can be a silicone, hot melt, hydrocolloid or acrylic based adhesive or other such adhesives, can be formed on both sides or optionally on a selected one or none of the sides of the wound contact layer. When a lower pressure sensitive adhesive layer is utilized this helps adhere the wound dressing to the skin around a wound site.

As mentioned, any dressing embodiments for use in the dressing kits disclosed or incorporated by reference herein can have an adhesive covered bottom (e.g., wound contacting) surface. In any embodiments disclosed herein, as mentioned, the adhesive can be a silicone adhesive including, for example, polysiloxanes or polyorganosiloxanes or other polymeric pressure sensitive silicone adhesives. For example, polydimethylsiloxane or the like can be used. The adhesive formulation may be a mixture of alkyl pendant siloxanes, which can be spread and cast as a two part mix with a catalyst such that a final polymerisation step takes place following casting or spreading. In any embodiments disclosed herein, a dressing layer can have a non-perforated silicone adhesive coating (coat weight 130 gsm nominal) and full spread acrylic adhesive (27 to 37 gsm) coated onto opposite sides of an extruded EU30 polyurethane clear film (27 to 37 gsm). Moisture vapour permeability of any embodiments of such an arrangement can be between approximately 367 $gm^{-2}/24$ hrs to approximately 405 $gm^{-2}/24$ hrs, or a mean moisture vapour permeability of 382 $gm^{-2}/24$ hrs.

Any embodiments or arrangements of a silicone adhesive layer suitable for dressing embodiments disclosed herein can have a moisture vapour transmission rate between approximately 350 $gm^{-2}/24$ hrs and approximately 410 $gm^{-2}/24$ hrs. Aptly, the average moisture vapour permeability of any embodiments or arrangements of a silicone adhesive layer suitable for dressing embodiments disclosed herein can be approximately 380 gm$^{-2}$/24 hrs. Some of the dressing embodiments disclosed herein can have a Wacker silres PSA 45 pressure sensitive adhesive coated thereon.

Additionally, any of the dressing embodiments disclosed herein can have an anti-microbial agent or substance incorporated into the dressing or coated on one or more surfaces of the dressing. For example, without limitation, a wound contact layer of any dressing embodiments disclosed herein can have nanocrystalline silver agents, silver salts, copper salts, or gold salts such as, without limitation, those disclosed in U.S. patent application Ser. No. 11/922,894 (titled ANTIMICROBIAL BIGUANIDE METAL COMPLEXES), filed May 21, 3008, which application is incorporated by reference herein as if made part of this disclosure, PHMB, chlorohexadine, peroxide, hypochloride, or other bleaches therein or thereon. Further, an absorbent layer of any dressing embodiments disclosed herein can have silver sulphur diazine or any of the previously mentioned substances or active agents therein or thereon. These may be used separately or together. These respectively can eliminate microorganisms in the wound and micro-organisms in the absorption matrix. As a still further option, other active components, for example, pain suppressants such as ibuprofen or healing agents can be incorporated into the dressing. Also agents which enhance cell activity, such as growth factors or that inhibit enzymes, such as matrix metalloproteinase inhibitors, such as tissue inhibitors of metalloproteinase (TIMPS) or zinc chelators, can be incorporated into the dressing. Odor trapping elements such as activated carbon, cyclodextrine, zeolite or the like can also be included in the absorbent layer or other portions or components of the dressing, or above the filter layer.

A layer of porous material can be located above the wound contact layer. This porous layer, or transmission layer, allows transmission of fluid including liquid and gas away from a wound site into upper layers of the wound dressing. In particular, the transmission layer can ensure that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalized negative pressure. The layer can be formed of a material having a three dimensional structure. For example, a knitted or woven spacer fabric (for example Baltex 7970 weft knitted polyester) or a non-woven fabric can be used. Other materials can be utilized, and examples of such materials are described in U.S. patent application Ser. No. 13/092,042, which are hereby incorporated by reference and made part of this disclosure.

In any embodiments disclosed herein, the transmission layer can have a 3D polyester spacer fabric layer. This layer can have a top layer (that is to say, a layer distal from the wound-bed in use) which is a 84/144 textured polyester, and a bottom layer (that is to say, a layer which lies proximate to the wound bed in use) which can be a 100 denier flat polyester and a third layer formed sandwiched between these two layers which is a region defined by a knitted polyester viscose, cellulose or the like monofilament fiber. Other suitable materials and other linear mass densities of fiber can be used.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Preferably, to improve the liquid flow across the transmission layer (that is to say perpendicular to the channel region formed between the top and bottom spacer layers, the 3D fabric is treated with a dry cleaning agent (such as, but not limited to, Perchloro Ethylene) to help remove any manufacturing products such as mineral oils, fats and/or waxes used previously which might interfere with the hydrophilic capabilities of the transmission layer. In any embodiments disclosed herein, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Again, as described in greater detail in U.S. patent application Ser. No. 13/092,042, a layer of absorbent material can be provided above the transmission layer. The absorbent material which can be a foam or non-woven natural or synthetic material and which can optionally include or be super-absorbent material forms a reservoir for fluid, particularly liquid, removed from the wound site and draws those fluids towards a cover layer. The material of the absorbent layer can prevent liquid collected in the wound dressing from flowing in a sloshing manner. The absorbent layer can also help distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer can be manufactured from ALLEVYN™ foam, Freudenberg 114-224-4 and/or Chem-Posite™11C-450, or any other suitable material.

In any embodiments disclosed herein, the absorbent layer can be a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing. The wicking action also assists in delivering liquid downwards towards the wound bed when exudation slows or halts. This delivery process helps maintain the transmission layer and lower wound bed region in a moist state which helps prevent crusting within the dressing (which could lead to blockage) and helps maintain an environment optimized for wound healing.

In any embodiments disclosed herein, the absorbent layer can be an air-laid material. Heat fusible fibers can optionally be used to assist in holding the structure of the pad together. It will be appreciated that rather than using super-absorbing particles or in addition to such use, super-absorbing fibers can be utilized according to any embodiments of the present disclosure. An example of a suitable material is the Product Chem-Posite™ 11 C available from Emerging Technologies Inc (ETi) in the USA.

Optionally, the absorbent layer can include synthetic stable fibers and/or bi-component stable fibers and/or natural stable fibers and/or super-absorbent fibers. Fibers in the absorbent layer can be secured together by latex bonding or thermal bonding or hydrogen bonding or a combination of any bonding technique or other securing mechanism. In any embodiments disclosed herein, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer can comprise a layer of multiple fibers. Preferably, the fibers are strand-like and made from cellulose, polyester, viscose or the like. Preferably, dry absorbent particles are distributed throughout the absorbent layer ready for use. In any embodiments disclosed herein, the absorbent layer comprises a pad of cellulose fibers and a plurality of super absorbent particles. In additional embodiments, the absorbent layer is a non-woven layer of randomly orientated cellulose fibers.

Super-absorber particles/fibers can be, for example, sodium polyacrylate or carbomethoxycellulose materials or the like or any material capable of absorbing many times its own weight in liquid. In any embodiments disclosed herein, the material can absorb more than five times its own weight of 0.9% W/W saline, etc. In any embodiments disclosed herein, the material can absorb more than 15 times its own weight of 0.9% W/W saline, etc. In any embodiments disclosed herein, the material is capable of absorbing more than 30 times its own weight of 0.9% W/W saline, etc. Preferably, the material is capable of absorbing more than 30 times its own weight of 0.9% W/W saline, etc. The absorbent layer can have one or more through holes located so as to underlie the suction port.

The dressing can have a gas impermeable, but moisture vapor permeable, cover layer extending across the width of the wound dressing. The cover layer, which can for example be a polyurethane film (for example, Elastollan SP9109) or any other suitable material having a pressure sensitive adhesive on one side, is substantially gas impermeable, thereby creating a substantially sealed enclosure over the wound. In this way an effective chamber is made between the cover layer and a wound site where a negative pressure can be established. The cover layer can be sealed to the wound contact layer in a border region around the circumference of the dressing, ensuring that no air is drawn in through the border area, for example via adhesive or welding techniques. The cover layer can protect the wound from external bacterial contamination (bacterial barrier) and allows liquid from wound exudates to be transferred through the layer and evaporated from the film outer surface. The cover layer can have a polyurethane film and an adhesive pattern spread onto the film. The polyurethane film is moisture vapor permeable and may be manufactured from a material that has an increased water transmission rate when wet.

An orifice can be provided in the cover film to allow a negative pressure to be applied to the dressing. As mentioned, In any embodiments disclosed herein, a suction port 108 can be sealed to the top of the cover film over the orifice, which can communicate negative pressure through the orifice. The port may be adhered and sealed to the cover film using an adhesive such as an acrylic, cyanoacrylate, epoxy, UV curable or hot melt adhesive. The port 108 can be formed from a soft polymer, for example a polyethylene, a polyvinyl chloride, a silicone or polyurethane having a hardness of 30 to 90 on the Shore A scale.

The dressing can have a filter element that is impermeable to liquids, but permeable to gases. The filter element can act as a liquid barrier, to substantially prevent or inhibit liquids from escaping from the wound dressing, as well as an odor barrier. The filter element may also function as a bacterial barrier. In any embodiments disclosed herein, the pore size of the filter element can be approximately 0.2 μm. Suitable materials for the filter material of the filter element include 0.2 micron Gore™ expanded PTFE from the MMT range, PALL Versapore™ 300R, and Donaldson™ TX6628. The filter element thus enables gas to be exhausted through the orifice. Liquid, particulates and pathogens however are contained in the dressing. Other details regarding the filter are disclosed in U.S. patent application Ser. No. 13/092,042 and incorporated by reference herein.

The wound dressing and its methods of manufacture and use as described herein may also incorporate features, configurations and materials described in the following patents and patent applications, each of which is incorporated by reference in their entireties herein as if made part of this disclosure: U.S. Pat. Nos. 7,524,315, 7,708,724, and 7,909,805; U.S. Patent Application Publication Nos. 2005/0261642, 2007/0167926, 2009/0012483, 2009/0254054, 2010/0160879, 2010/0160880, 2010/0174251, 2010/0274207, 2010/0298793, 2011/0009838, 2011/0028918, 2011/0054421, and 2011/0054423; as well as U.S. application Ser. No. 12/941,390, filed Nov. 8, 2010, Ser. No. 29/389,782, filed Apr. 15, 2011, and Ser. No. 29/389,783, filed Apr. 15, 2011. From these incorporated by reference patents and patent applications, features, configurations, materials and methods of manufacture or use for similar components to those described in the present disclosure may be substituted, added or implemented into embodiments of the present application.

In operation, the wound dressing is sealed over a wound site forming a wound cavity. The pump assembly provides a source of a negative pressure to the dressing. Fluid is drawn towards the orifice through the wound dressing from a wound site below the wound contact layer. The fluid moves towards the orifice through the transmission layer. As the fluid is drawn through the transmission layer, wound exudate is absorbed into the absorbent layer.

The general shape of the wound dressing can be square, ovular, rectangular, or otherwise. The dressing can have rounded corner regions. It will be appreciated that wound dressings according to other embodiments of the present disclosure can be shaped differently such as square, circular or elliptical dressings, or the like.

The desired size of the wound dressing can be selected based on the size and type of wound it will be used in. In any embodiments disclosed herein, the wound dressing can measure between 30 and 40 cm on its long axis, and between 10 to 25 cm on its short axis. For example, dressings can be provided in sizes of approximately 10×30 cm, 10×30 cm, 10×40 cm, 15×30 cm, and 15×30 cm, as described above.

In any embodiments disclosed herein, the wound dressing can be a square-shaped dressing with sides measuring between 15 and 25 cm (e.g., 15×15 cm, 30×30 cm and 25×25 cm). The absorbent layer can have a smaller area than the overall dressing, and In any embodiments disclosed herein may have a length and width that are both about 3 to 10 cm shorter, more preferably about 5 cm shorter, than that of the overall dressing. In some rectangular-shape embodiments, the absorbent layer may measure between approximately 10 and 35 cm on its long axis, and between 5 and 10 cm on its short axis. For example, absorbent layers can be provided in sizes of 5.6×15 cm or 5×10 cm (for 10×30 cm dressings), 5.6×25 cm or 5×30 cm (for 10×30 cm dressings), 5.6×35 cm or 5×30 cm (for 10×40 cm dressings), 10×15 cm (for 15×30 cm dressings), and 10×25 cm (for 15×30 cm dressings). In some square-shape embodiments, the absorbent layer may have sides that are between 10 and 30 cm in length (e.g., 10×10 cm for a 15×15 cm dressing, 15×15 cm for a 30×30 cm dressing, or 30×30 cm for a 25×25 cm dressing). The transmission layer can be of a smaller size than the absorbent layer, and In any embodiments disclosed herein can have a length and width that are both about 0.5 to 2 cm shorter, more preferably about 1 cm shorter, than that of the absorbent layer. In some rectangular-shape embodiments, the transmission layer may measure between 9 and 34 cm on its long axis and between 3 and 5 cm on its short axis. For example, transmission layers may be provided in sizes of 4.6×14 cm or 4×9 cm (for 10×30 cm dressings), 4.6×24 cm or 4×19 cm (for 10×30 cm dressings), 4.6×34 cm or 4×29 cm (for 10×40 cm dressings), 9×14 cm (for 15×30 cm dressings), and 9×24 cm (for 15×30 cm dressings). In some square-shape embodiments, the transmission layer may have sides that are between 9 and 19 cm in length (e.g., 9×9 cm for a 15×15 cm dressing, 14×14 cm for a 30×30 cm dressing, or 19×19 cm for a 25×25 cm dressing).

The dressing can contain anti-microbial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilized. As a still further option odor trapping elements such as activated carbon, cyclodextrine, zeolite or the like may be included in the absorbent layer or as a still further layer above the filter layer.

Whilst any embodiments of the present disclosure have so far been described in which the transmission layer is formed as a 3D knit layer, e.g., two layers spaced apart by a monofilament layer, it will be appreciated that any embodiments of the present disclosure are not restricted to the use of such a material. In any embodiments disclosed herein, as an alternative to such a 3D knit material, one or more layers of a wide variety of materials could be utilized. In each case, according to embodiments of the present disclosure, the openings presented by layers of the transmission layer are wider and wider as one moves away from the side of the dressing which, in use will be located proximate to the wound. In any embodiments disclosed herein, the transmission layer may be provided by multiple layers of open celled foam. In any embodiments disclosed herein, the foam is reticulated open cell foam. The foam can be hydrophilic or able to wick aqueous based fluids. The pore size in each layer is selected so that in the foam layer most proximate to the wound side in use the pores have a smallest size. If only one further foam layer is utilized that includes pore sizes which are greater than the pore sizes of the first layer. This helps avoid solid particulate being trapped in the lower layer which thus helps maintain the lower layer in an open configuration in which it is thus able to transmit air throughout the dressing. In any embodiments disclosed herein, two, three, four or more foam layers may be included. The foam layers may be integrally formed, for example, by selecting a foam having a large pore size and then repeatedly dipping this to a lesser and lesser extent into material which will clog the pores or alternatively, the transmission layer formed by the multiple foam layers may be provided by laminating different types of foam in a layered arrangement or by securing such layers of foam in place in a known manner.

As mentioned, any of the features, components, or details of any of the arrangements or embodiments disclosed in this application, including those disclosed below, are interchangeably combinable with any other features, components, or details of any of the dressing kit, dressing member, pump assembly, or pump housing arrangements or embodiments disclosed herein to form new arrangements and embodiments.

Additional embodiments disclosed herein relate to methods and apparatuses for dressing and treating a wound with topical negative pressure (TNP) therapy, any parts, features, or components of which can be used with any of the pump assembly or housing embodiments disclosed or incorporated by reference herein, any of the pump components, features, or any of the indicator lights and alarms disclosed herein. For example but without limitation, some additional embodiments disclosed herein relate to treating a wound with reduced pressure provided from a pump kit. Although not required, any embodiments of the pump kit disclosed herein can be integral to, supported by, or coupled with any of the dressing kit or dressing member embodiments disclosed here, wherein the pump is mounted to or otherwise supported by or adjacent to the dressing. Any reference to a pump in any of the dressing embodiments disclosed herein is meant to refer to any of the pump embodiments disclosed herein, including without limitation any of the voice coil actuated pumps, crank pumps, or any of the other pump embodiments disclosed or incorporated by reference herein. Any reference to objects disclosed herein is meant to refer also to any objects incorporated by reference herein, as such objects are meant to form a part of this disclosure.

Other Negative Pressure Therapy Apparatuses, Dressings and Methods Incorporated from International Application No. PCT/IB2013/000847 (Included as Appendix A in U.S. Provisional Application No. 61/791,984)

Embodiments disclosed herein relate to methods and apparatuses for dressing and treating a wound with topical negative pressure (TNP) therapy. For example but without limitation, the embodiments disclosed herein relate to treating a wound with reduced pressure provided from a pump kit. Although not required, any embodiments of the pump kit can be integral, wherein the pump is mounted to or otherwise supported by or adjacent to the dressing. Additionally, although not required, any embodiments of the pump kit can be sterile. As another non-limiting example, some embodiments disclosed herein relate to apparatuses, features, and methods for controlling the operation of a TNP system and/or apparatuses, features, and methods for detecting one or more conditions or parameters of the dressing, such as pressure, temperature, or saturation level, and, although not required, controlling the operation of the pump or other components of the dressing kit accordingly. As another non-limiting example, any embodiments disclosed herein can be configured to provide a visual indication one or more conditions or parameters of the dressing, such as pressure, temperature, or saturation level.

Any of the features, components, or details of any of the arrangements or embodiments disclosed in this application, including those disclosed below, are interchangeably combinable with any other features, components, or details of any of the dressing kit, dressing member, pump assembly, or pump housing arrangements or embodiments disclosed herein to form new arrangements and embodiments. With that, the following arrangements are disclosed herein, inter alia.

1. A wound dressing kit for reduced pressure wound therapy, comprising:
  a pump assembly;
  a power source; and
  a dressing member having one or more absorptive layers and a fluid impermeable backing layer, and defining a first dressing portion and a second dressing portion;
  a score along at least a portion of the dressing member between the first and the second dressing portions, the score being configured to increase the tearability of the dressing member between the first and second dressing portions;
  wherein:
    the first dressing portion is configured to support the one or more absorptive layers; and
    the second dressing portion is configured to support at least one of the pump assembly and the power source.

2. The wound dressing kit of Arrangement 1, comprising a conduit in fluid communication with the pump assembly and the dressing member.

3. The wound dressing kit of any one of the previous arrangements, comprising a conduit in fluid communication with the pump assembly and the dressing member, the conduit being selectively removable from the dressing member.

4. The wound dressing kit of any one of the previous arrangements, comprising a conduit positioned on a third dressing portion of the dressing member, the dressing member having a score along at least a portion of the dressing member between the first and the third dressing portions and/or the second and the third dressing portions, the score being configured to increase the tearability of the dressing member between the first and the third dressing portions and/or the second and the third dressing portions.

5. The wound dressing kit of any one of the previous arrangements, comprising a conduit having perforated edges therealong and being configured to extend about a perimeter of the first portion of the dressing member, the conduit being selectively detachable from the first portion of the dressing member by tearing the conduit along at least one perforated edge thereof.

6. The wound dressing kit of any one of the previous arrangements, comprising a conduit in fluid communication with the pump assembly and the dressing member, the conduit being coiled about the pump assembly in a helical arrangement.

7. The wound dressing kit of any one of the previous arrangements, comprising a conduit in fluid communication with the pump assembly and the dressing member having a connector on an end portion thereof, the connector being configured to activate the pump assembly when engaged with a second connector supported by the first dressing portion.

8. The wound dressing kit of any one of the previous arrangements, wherein the pump assembly comprises a voice coil actuated pump.

9. The wound dressing kit of any one of the previous arrangements, wherein the score comprises a plurality of perforations, channels, partial thickness cuts, and notches configured to increase the tearability of the dressing along the score.

10. The wound dressing kit of any one of the previous arrangements, wherein the power source is removable from the pump assembly by tearing the dressing along a score in the second dressing portion between the power source and the pump assembly.

11. The wound dressing kit of any one of the previous arrangements, wherein the pump is powered by a single 1200 mAh lithium battery.

12. The wound dressing kit of any one of the previous arrangements, wherein the pump is powered by one or more printed batteries.

13. The wound dressing kit of any one of the previous arrangements, wherein the pump is powered by one or more flexible batteries having a thickness of from approximately 450 microns to approximately 770 microns.

14. The wound dressing kit of any one of the previous arrangements, wherein the pump is powered by one or more flexible batteries having a thickness of from approximately 450 microns to approximately 500 microns.

15. The wound dressing kit of any one of the previous arrangements, wherein the pump is powered by 10 or more interconnected batteries.

16. The wound dressing kit of any one of the previous arrangements, wherein the pump is powered by one or more flexible batteries having a thickness of less than approximately 500 microns.

17. The wound dressing kit of any one of the previous arrangements, wherein the pump assembly is powered by one or more flexible batteries positioned about at least one of the first dressing portion and a conduit configured to communicate a source of negative pressure from the pump assembly to the one or more absorptive layers.

18. The wound dressing kit of any one of the previous arrangements, wherein the pump assembly is powered by one or more flexible batteries supported by the first dressing portion beneath the backing layer.

19. The wound dressing kit of any one of the previous arrangements, wherein the pump assembly is powered by one or more flexible batteries supported by the first dressing portion, the one or more flexible batteries being embedded within the one or more absorptive layers.

20. The wound dressing kit of any one of the previous arrangements, wherein the pump assembly is powered by one or more flexible batteries supported by the first dressing portion outside of the backing layer.

21. The wound dressing kit of any one of the previous arrangements, wherein the pump assembly is powered by one or more air activatable batteries.

22. The wound dressing kit of any one of the previous arrangements, wherein the dressing member has a wound contact layer and a transmission layer positioned between the wound contact layer and the backing layer.

23. The wound dressing kit of any one of the previous arrangements, wherein the pump is at least partially powered by one or more photovoltaic cells.

24. The wound dressing kit of any one of the previous arrangements, wherein the pump is at least partially powered by one or more photovoltaic cells positioned about at least one of the dressing backing layer, a housing for the pump assembly, and a conduit configured to communicate a negative pressure provided by the pump assembly to the one or more absorptive layers.

25. The wound dressing kit of any one of the previous arrangements, wherein the pump is at least partially powered by one or more batteries attachable to the dressing member using using snap connectors, adhesive, Velcro, a housing having a closeable opening, or a pouch supported by the dressing member.

26. The wound dressing kit of any one of the previous arrangements, further comprising a flexible hinge positioned between the power source and the pump assembly to improve the flexibility and conformability of the portion of the dressing kit supporting the pump and the power source.

27. The wound dressing kit of any one of the previous arrangements, comprising a V-shaped cut out in the dressing layer between the pump assembly and the power source.

28. The wound dressing kit of any one of the previous arrangements, comprising a OLED display.

29. The wound dressing kit of any one of the previous arrangements, comprising a one or more indicator lights configured to indicate a condition of the dressing kit.

30. The wound dressing kit of any one of the previous arrangements, comprising a pull tab, button, conductive label, or switch configured to activate the power source.

31. The wound dressing kit of any one of the previous arrangements, comprising a first packaging member configured prevent an electrical connection between the power source and the pump assembly while the power source is supported by the first packaging member.

32. The wound dressing kit of any one of the previous arrangements, comprising a pressure indicator supported by the first dressing portion configured to provide a visual indication of a level of pressure beneath the backing layer.

33. The wound dressing kit of any one of the previous arrangements, comprising a saturation indicator supported by the first dressing portion configured to provide a visual indication of a level of liquid saturation beneath the backing layer.

34. The wound dressing kit of any one of the previous arrangements, wherein the first portion of the dressing member has one or more features or colored regions detectable only when the backing layer is drawn against the one or more features or colored regions, the dressing kit being configured such that the backing layer is drawn against the one or more features or colored regions when a threshold level of negative pressure is achieved under the backing layer.

35. The wound dressing kit of any one of the previous arrangements, comprising n activation switch or button configured to move between a first on position and a second off position, the switch or button being configured to remain in the first position when a threshold level of negative pressure is maintained beneath the backing layer.

36. The wound dressing kit of Arrangement 36, wherein the switch or button is configured to move to the second position when the level of negative pressure under the backing layer is less than a threshold level of negative pressure and the pump assembly exceeds a threshold flow rate or has been operating continuously for a threshold period of time.

37. The wound dressing kit of Arrangement 36, wherein the switch or button is configured to move to the second position when the level of negative pressure under the backing layer is less than 60 mmHg and the pump assembly has been operating continuously for 4 minutes.

38. The wound dressing kit of Arrangement 36, wherein the switch or button comprises a depressible dome and a tact switch.

39. A wound dressing kit for reduced pressure wound therapy, comprising:
a pump assembly;
a dressing member; and
a power source;
wherein the pump assembly and the power source are supported by the dressing member.

40. The wound dressing kit of Arrangement 39, wherein:
the power source comprises a plurality of batteries positioned about the dressing member;
the plurality of batteries are configured to provide a source of power to at least the pump assembly; and
each of the plurality of batteries has a thickness of from approximately 450 microns to approximately 700 microns.

41. The wound dressing kit of Arrangement 40, wherein the plurality of batteries each have a thickness of from approximately 450 microns to approximately 500 microns.

42. The wound dressing kit of any one of Arrangements 39-41, wherein:
the dressing member comprises one or more absorptive layers and a fluid impermeable backing layer, and defines a first dressing portion and a second dressing portion;
the dressing member comprises a score along at least a portion of the dressing member between the first and the second dressing portions, the score being configured to increase the tearability of the dressing member between the first and second dressing portions;
wherein:
the first dressing portion is configured to support the one or more absorptive layers; and
the second dressing portion is configured to support the pump assembly.

43. The wound dressing kit of any one of Arrangements 39-42, comprising a conduit having perforated edges therealong and being configured to extend about a perimeter of the first portion of the dressing member, the conduit being selectively detachable from the first portion of the dressing member by tearing the conduit along at least one perforated edge thereof.

44. The wound dressing kit of any one of Arrangements 39-42, comprising a conduit in fluid communication with the pump assembly and the dressing member, the conduit being coiled about the pump assembly in a helical arrangement.

45. The wound dressing kit of any one of Arrangements 39-44, wherein the pump assembly comprises a voice coil actuated pump.

46. The wound dressing kit of any one of Arrangements 39-45, comprising a pull tab, button, conductive label, or switch configured to activate the power source.

47. The wound dressing kit of any one of Arrangements 39-46, comprising a pressure indicator supported by the dressing member configured to provide a visual indication of a level of pressure beneath the backing layer.

48. The wound dressing kit of any one of Arrangements 39-46, comprising a saturation indicator supported by the dressing member configured to provide a visual indication of a level of liquid saturation beneath the backing layer.

49. A wound dressing kit for reduced pressure wound therapy, comprising:

a pump assembly;
a power source configured to provide a source of power to at least the pump assembly; and
a dressing member having a fluid impermeable backing layer;
wherein:
the pump assembly is supported by the dressing member; and
the power source is supported by a separate support member and is positionable in a remote position spaced apart from the dressing member.

50. The wound dressing kit of Arrangement 49, wherein the dressing member comprises one or more absorptive layers and a fluid impermeable backing layer over the one or more absorptive layers, wherein the pump assembly is supported adjacent to one or more of the absorptive layers.

51. The wound dressing kit of any one of Arrangements 49-50, wherein the pump assembly comprises a voice coil actuated pump.

52. The wound dressing kit of any one of Arrangements 49-51, comprising a pull tab, button, conductive label, or switch configured to activate the power source.

53. The wound dressing kit of any one of Arrangements 49-52, comprising a pressure indicator supported by the dressing member configured to provide a visual indication of a level of pressure beneath the backing layer.

54. The wound dressing kit of any one of Arrangements 49-53, comprising a saturation indicator supported by the dressing member configured to provide a visual indication of a level of liquid saturation beneath the backing layer.

55. The wound dressing kit of Arrangements 49-54 or any one of the previous arrangements, comprising a viewing window in an opaque backing layer, the viewing window being configured to permit a user to determine a level of saturation within the dressing member.

56. A wound dressing kit for reduced pressure wound therapy, comprising:
a dressing member having a fluid impermeable backing layer, a transmission layer, and an absorption layer between the transmission layer and the backing layer; and
a pump assembly positioned within an opening formed in the absorption layer sized and configured such that the pump assembly is positioned in direct contact with the transmission layer.

57. The wound dressing kit of Arrangement 56, wherein the pump has a port that is in direct fluid communication with the transmission layer, such that negative pressure is applied by the pump assembly directly to the transmission layer.

58. The wound dressing kit of any one of Arrangements 56-57, further comprising a liquid barrier or liquid filter in communication with the pump assembly and configured to prevent the passage of liquid into the pump.

59. The wound dressing kit of any one of Arrangements 56-58, wherein the opening does not extend into the transmission layer.

60. The wound dressing kit of any one of Arrangements 56-59, wherein the opening extends through the transmission layer.

61. The wound dressing kit of any one of Arrangements 56-60, further comprising an impermeable film between the absorption layer and the transmission layer, the impermeable film having an opening therein in communication with a port in the pump assembly configured to permit the passage of negative pressure from the pump assembly into the transmission layer.

62. The wound dressing kit of any one of Arrangements 56-61, wherein the pump assembly is configured to transfer liquid from the transmission layer through the pump into the absorption layer.

63. The wound dressing kit of any one of Arrangements 56-62, wherein the pump assembly is covered by the backing layer.

64. The wound dressing kit of Arrangements 63, further comprising a vent hole in the backing layer configured to permit exhaust air from the pump assembly to pass through the backing layer.

65. The wound dressing kit of any one of Arrangements 56-64, wherein the pump assembly comprises a voice coil actuated pump.

66. The wound dressing kit of any one of Arrangements 56-64, comprising a pull tab, button, conductive label, or switch configured to activate the power source.

67. The wound dressing kit of any one of Arrangements 56-66, comprising a pressure indicator supported by the dressing member configured to provide a visual indication of a level of pressure beneath the backing layer.

68. The wound dressing kit of any one of Arrangements 56-67, comprising a saturation indicator or sensor supported by the dressing member configured to provide a visual indication of a level of liquid saturation beneath the backing layer.

69. The wound dressing kit of Arrangement 68, wherein the saturation indicator or sensor is positioned adjacent to the pump assembly.

70. The wound dressing kit of any one of Arrangements 56-69, further comprising a power source configured to provide a source of power to at least the pump assembly.

71. The wound dressing kit of any one of Arrangements 56-70, wherein the backing layer is opaque, and comprising one or more viewing windows in the backing layer configured to permit a user to determine a level of saturation within the dressing member.

72. A method of treating a wound, comprising;
placing a wound dressing kit of any one of the previous arrangements over a wound;
applying negative pressure to the wound from the pump assembly.

In any of the apparatus embodiments disclosed herein, as in the embodiments illustrated in FIGS. 134A-134B, the pump assembly can be a canisterless pump assembly (meaning that the pump assembly does not have an exudate or liquid collection canister). However, any of the pump embodiments disclosed herein can be configured to include or support a canister. Additionally, in any of the apparatus embodiments disclosed herein, any of the pump assembly embodiments can be mounted to or supported by the dressing, or adjacent to the dressing. Additionally, in any of the apparatus embodiments disclosed herein, the pump assembly can have two or more pumps and one, two, or more power sources. In any of the embodiments disclosed herein, the pump assembly, power source, and or any support member or film supporting or covering the pump assembly or power source can have any of a variety of colors used to match a person's skin including any tone or coloring thereof. Further, in any embodiments disclosed herein, the pump assembly can have any of the components, features, or other details of any of the pump assembly embodiments disclosed in U.S. patent application Ser. No. 13/287,897 (titled "REDUCED PRESSURE THERAPY APPARATUSES AND METHODS OF USING SAME), filed on Nov. 2, 2011, which disclosure is hereby incorporated by reference as if fully set forth herein.

Any of the wound dressing embodiments disclosed herein can be arranged or configured to operate without the use of an exudate canister. Any dressing embodiments can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. Some embodiments of the pump are designed for an operation period of up to fourteen days, and some for up to twenty days. The pump can be programmed to automatically terminate therapy after a desired number of days, e.g., after seven days, further operation of the pump will not be possible. Some embodiments are designed for longer or repeated usage, and can be configured to support an exudate canister.

In any dressing kit embodiments, including without limitation the illustrated embodiments, the pump assembly can be of a sufficiently small and portable size to be supported on or adjacent to the dressing, or on another location of a user's body or in a user's clothing. For example and without limitation, as will be described in greater detail below, in any of the embodiments disclosed herein, the pump assembly can be attached to a specially formed depression or space on the dressing, can be embedded within, supported on top of or adjacent to one or more absorbent or other dressing layers, or can be otherwise supported by the dressing. Additionally, in any embodiments disclosed or incorporated by reference herein (collectively referred to as "disclosed herein"), the pump assembly can be sized to be attached using adhesive medical tape or otherwise to a person's skin in a comfortable location, adjacent to or on the dressing or otherwise, or can be sized to fit within a person's pants or shirt pocket or tethered to a person's body using a lanyard, pouch, or other suitable device or article.

Any of the dressing kit embodiments disclosed herein can be manufactured in a wide variety of different models or versions, wherein the size of the dressing can be varied to accommodate a wide range of wound sizes. For example, any of the dressing kits can be made having the following sizes of dressings and wound pads or other absorbent elements. In any embodiments disclosed herein, the size of the dressing or the wound pad can be defined by the area of the dressing or the wound pad, wherein the specific length and width (if rectangular) can be varied to accommodate a wider range of wound sizes. For example, the dressings and/or wound pads can be rectangular, circular, ovular, triangular, pentagonal, hexagonal, trapezoidal, or otherwise. The shape and dimensions of the various dressings and wound pads can fall within any of the area ranges listed below, otherwise disclosed in this application, or otherwise. Thus, the dressing dimensions and shapes are not limited to those specified in this disclosure but can be any suitable size and shape.

| Approximate Dressing Size (Dimensions) | Approximate Dressing Size (Area) | Approximate Wound Pad Size (Dimensions) | Approximate Wound Pad Size (Area) |
|---|---|---|---|
| 10 cm × 30 cm | 300 cm² | 5 cm × 20 cm | 100 cm² |
| (4 in × 11.75 in) | (47 in²) | (2 in × 8 in) | (16 in²) |
| 15 cm × 15 cm | 225 cm² | 10 cm × 10 cm | 100 cm² |
| (6 in × 6 in) | (36 in²) | (4 in × 4 in) | (16 in²) |
| 15 cm × 20 cm | 300 cm² | 10 cm × 15 cm | 150 cm² |
| (6 in × 8 in) | (48 in²) | (4 in × 6 in) | (24 in²) |
| 10 cm × 20 cm | 200 cm² | 5 cm × 10 cm | 50 cm² |
| (4 in × 8 in) | (32 in²) | (2 in × 4 in) | (8 in²) |
| 20 cm × 20 cm | 400 cm² | 15 cm × 15 cm | 225 cm² |
| (8 in × 8 in) | (64 in²) | (6 in × 6 in) | (36 in²) |

In any embodiments disclosed herein, the dressing can be sized such that the pad or absorptive portion of the dressing is approximately 50×100 mm, 100×150 mm, 100×250 mm, or any size within these ranges. Some embodiments of the dressing can be configured to be universal, so that one dressing size, shape, and configuration can be adhered to the hips, arms, thighs, torso, back, and/or other body parts.

Some embodiments of the overlay or dressing can be substantially impervious to air flow and the flow of bacteria or other contaminants through the overlay layer, while being pervious to vapor transmission.

As described in greater detail in U.S. patent application Ser. No. 13/092,042, which is hereby incorporated by reference in its entirety as if fully set forth herein, in any of the dressing embodiments disclosed herein, a layer of absorbent material can be provided above the transmission layer. The absorbent material which can be a foam or non-woven natural or synthetic material and can optionally include or be super-absorbent material that can form a reservoir for fluid, particularly liquid, removed from the wound site and draws those fluids towards a cover layer. The material of the absorbent layer can prevent liquid collected in the wound dressing from flowing in a sloshing manner. The absorbent layer can also help distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressure, the material of the absorbent layer can be selected to absorb liquid. A number of materials exist that are able to absorb liquid when under negative pressure, for example superabsorber material. For example and without limitation, any embodiments of the absorbent layer can be manufactured using ALLEVYN™ foam, Freudenberg 114-224-4 and/or Chem-Posite™11C-450, or any other suitable material. Other materials may be more appropriate for and can be used in and of the dressing embodiments disclosed herein. Suitable superabsorbers can have polyacrylate or carbomethoxycellulose based materials in the form of granules or fibers or combinations thereof.

In any embodiments disclosed herein, the absorbent layer can be a layer of non-woven cellulose fibers having super-absorbent material in the form of dry particles dispersed throughout. In some arrangements, the use of natural and/or synthetic fibres such as cotton, cellulose and viscose fibres can introduce fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action can also assist in bringing liquid into contact with the upper cover layer to aid increase transpiration rates of the dressing. The wicking action can also assist in delivering liquid downward towards the wound bed when exudation slows or halts. This delivery process helps maintain the transmission layer and lower wound bed region in a moist state which helps prevent crusting within the dressing. Crusting could lead to blockage both within the dressing layers or components beneath the cover or backing layer, and also within the port and/or conduit which can inhibit the flow of wound fluids in the dressing and also inhibit a flow of reduced pressure to the wound or portions of the wound. Thus, the delivery process can help maintain an environment optimized for wound healing.

A layer of porous material can be located above the wound contact layer. This porous layer, or transmission layer, allows transmission of fluid including liquid and gas away from a wound site into upper layers of the wound dressing. In particular, the transmission layer can ensure that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalized negative pressure. The layer can be formed of a material having a three dimensional structure. For example, a knitted or woven spacer fabric (for example Baltex 7970 weft knitted polyester) or a non-woven fabric can be used. Other materials can be utilized, and examples of such materials are described in U.S. patent application Ser. No. 13/092,042, which are hereby incorporated by reference and made part of this disclosure.

In any embodiments disclosed herein, the transmission layer can have a 3D polyester spacer fabric layer, such as with any embodiments of the dressing disclosed in U.S. Patent Application Publication No. 2011/0282309 (Ser. No. 13/092,042), (titled WOUND DRESSING AND METHOD OF USE), filed Apr. 21, 2011, which application is hereby incorporated by reference as if fully set forth herein. Some embodiments of the transmission layer can have a top layer (that is to say, a layer distal from the wound-bed in use) which is a 84/144 textured polyester (which can be approximately 24.5%, or from approximately 22% to approximately 27% in terms of material composition), and a bottom layer (i.e., a layer which lies proximate to the wound bed in use) which can be a 100 denier flat polyester (which can be approximately 31.4%, or from approximately 28% to approximately 34% in terms of material composition), and a third layer formed sandwiched between these two layers which is a region defined by a knitted polyester viscose, cellulose or the like monofilament fiber (which can be approximately 44.1%, or from approximately 40% to approximately 48% in terms of material composition). Other suitable materials and other linear mass densities of fiber can be used.

Additionally, any embodiments of the transmission layer can be formed using any of the following needle arrangement parameters.

Needle Arrangement
Dial Set Out

| F1 | F2 | F3 | F4 | F5 | F6 | F7 | F8 | F9 | F10 | F11 | F12 |
|----|----|----|----|----|----|----|----|----|-----|-----|-----|
| TA WB | AW | KA TB | WA TB | AW | TA KB | | | | | | |

Pattern area: 4 wales×12 courses

| F12 | K | K | K | K |
|-----|---|---|---|---|
| F11 | W | W | W | W |
| F10 | W | T | W | T |
| F9  | K | K | K | K |
| F8  | W | W | W | W |
| F7  | T | W | K | W |
| F6  | K | K | K | K |
| F5  | W | W | W | W |
| F4  | W | T | W | T |
| F3  | K | K | K | K |
| F2  | W | W | W | W |
| F1  | T | W | T | W |

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Material Layer Composition

Preferably, to improve the liquid flow across the transmission layer (that is to say perpendicular to the channel region formed between the top and bottom spacer layers, the 3D fabric is treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

In some embodiments, the absorbent layer can be an air-laid material. Heat fusible fibers can optionally be used to assist in holding the structure of the pad together. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Optionally, the absorbent layer can include synthetic stable fibers and/or bi-component stable fibers and/or natural stable fibers and/or super-absorbent fibers. Fibers in the absorbent layer can be secured together by latex bonding or thermal bonding or hydrogen bonding or a combination of any bonding technique or other securing mechanism. In any embodiments disclosed herein, the absorbent layer can be formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer can comprise a layer of multiple fibers. Preferably, the fibers are strand-like and made from cellulose, polyester, viscose or the like. Preferably, dry absorbent particles are distributed throughout the absorbent layer ready for use. In any embodiments disclosed herein, the absorbent layer can have a pad of cellulose fibers and a plurality of super absorbent particles. In additional embodiments, the absorbent layer is a non-woven layer of randomly orientated cellulose fibers.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc., or more than 15 times its own weight of 0.9% W/W saline, etc., or, in some embodiments, more than 20 times its own weight of 0.9% W/W saline, etc. Preferably, the material is capable of absorbing more than 30 times its own weight of 0.9% W/W saline, etc. The absorbent layer can have one or more through holes located so as to underlie a suction port. In any embodiments disclosed herein, a hydrophobic filter or other filter or object configured to permit the flow of air or gas through the port or openings in the dressing and prevent the flow of liquid or solids through the port or openings in the dressing can be positioned upstream of the pump to prevent any liquids or solids from entering the pump.

In some embodiments, the wound site can be filled partially or completely with a wound packing material. Deeper wounds can benefit from such packing material. The wound packing material can be used in addition to the wound dressing, or can be integral to the wound dressing. The wound packing material generally can comprise a porous and conformable material, for example foam (including reticulated foams), and gauze. Preferably, the wound packing material is sized or shaped to fit within the wound site so as to fill any empty spaces. The wound dressing can then be placed over the wound site and wound packing material overlying the wound site. When a wound packing material is used, once the wound dressing is sealed over the wound site, TNP is transmitted from a pump through the wound dressing, through the wound packing material, and to the wound site. This negative pressure draws wound exudate and other fluids or secretions away from the wound site.

The dressing of any dressing kit embodiments disclosed herein can have a gas impermeable, but moisture vapor permeable, cover layer extending across the width of the wound dressing. The cover layer, which can for example be a polyurethane film (for example, Elastollan SP9109) or any other suitable material having a pressure sensitive adhesive on one side, is substantially gas impermeable, thereby creating a substantially sealed enclosure over the wound. In this way an effective chamber is made between the cover layer and a wound site where a negative pressure can be established. The cover layer can be sealed to the wound contact layer in a border region around the circumference of the dressing, ensuring that no air is drawn in through the border area, for example via adhesive or welding techniques. The cover layer can protect the wound from external bacterial contamination (bacterial barrier) and allows liquid from wound exudates to be transferred through the layer and evaporated from the film outer surface. The cover layer can have a polyurethane film and an adhesive pattern spread onto the film. The polyurethane film is moisture vapor permeable and can be manufactured from a material that has an increased water transmission rate when wet.

An orifice can be provided in the cover film to allow a negative pressure to be applied to the dressing. As mentioned, in some embodiments, a suction port can be sealed to the top of the cover film over the orifice, which can communicate negative pressure through the orifice, or the pump assembly can be mounted directly over the orifice. The port or pump assembly can be adhered and sealed to the cover film using an adhesive such as an acrylic, cyanoacrylate, epoxy, UV curable or hot melt adhesive. If used, the port can be formed from a soft polymer, for example a polyethylene, a polyvinyl chloride, a silicone or polyurethane having a hardness of 30 to 90 on the Shore A scale.

The dressing can have a filter element that is impermeable to liquids, but permeable to gases. The filter element can act as a liquid barrier, to substantially prevent or inhibit liquids from escaping from the wound dressing, as well as an odor barrier. The filter element can also function as a bacterial barrier. In some embodiments, the pore size of the filter element can be approximately 0.2 µm. Suitable materials for the filter material of the filter element include 0.2 micron Gore™ expanded PTFE from the MMT range, PALL Versapore™ 200R, and Donaldson™ TX6628. The filter element thus enables gas to be exhausted through the orifice. Liquid, particulates and pathogens however are contained in the dressing. Other details regarding the filter are disclosed in U.S. patent application Ser. No. 13/092,042 (2011/0282309) and incorporated by reference herein.

The wound dressing and its methods of manufacture and use as described herein may also incorporate features, configurations and materials described in the following patents and patent applications, each of which is incorporated by reference in their entireties herein as if made part of this disclosure: U.S. Pat. Nos. 7,524,315, 7,708,724, 7,909,805; 7,964,766; 8,062,272; 8,080,702, 8,105,295, 8,282,611, and 8,303,552; U.S. Patent Application Publication Nos. 2009/0254054, 2010/0160880, 2010/0274207, 2011/0009838, 2011/0028918, 2011/0054421, 2011/0054423, and 2011/0118683, as well as U.S. application Ser. No. 29/389,782, filed Apr. 15, 2011, and Ser. No. 29/389,783, filed Apr. 15, 2011. From these incorporated by reference patents and patent applications, features, configurations, materials and methods of manufacture or use for similar components to those described in the present disclosure can be substituted, added or implemented into embodiments of the present application.

In operation, the wound dressing can be sealed over a wound site forming a wound cavity. The pump assembly can provide a source of a negative pressure to the dressing. Fluid can be drawn toward the orifice through the wound dressing from a wound site below the wound contact layer. The fluid can move towards the orifice through the transmission layer. As the fluid is drawn through the transmission layer, wound exudate can be absorbed into the absorbent layer.

The general shape of the wound dressing can be square, ovular, rectangular, or otherwise. The dressing can have rounded corner regions. It will be appreciated that wound dressings according to other embodiments of the present invention can be shaped differently such as square, circular or elliptical dressings, or the like.

The desired size of the wound dressing can be selected based on the size and type of wound it will be used in. In any embodiments, though not required, the wound dressing can measure between 20 and 40 cm on its long axis, and between 10 to 25 cm on its short axis. For example, dressings can be provided in sizes of approximately 10×20 cm, 10×30 cm, 10×40 cm, 15×20 cm, and 15×30 cm, or any other sizes within these ranges or otherwise.

Whilst some embodiments of the present invention have so far been described in which the transmission layer is formed as a 3D knit layer, e.g., two layers spaced apart by a monofilament layer, it will be appreciated that some embodiments of the present invention are not restricted to the use of such a material. In some embodiments, as an alternative to such a 3D knit material, one or more layers of a wide variety of materials could be utilized. In each case, according to embodiments of the present invention, the openings presented by layers of the transmission layer are wider and wider as one moves away from the side of the dressing which, in use will be located proximate to the wound. In any embodiments disclosed herein, the transmission layer can be provided by multiple layers of open celled foam. Though note required, the foam can be reticulated open cell foam. The foam can be hydrophilic or able to wick aqueous based fluids. The pore size in each layer is selected so that in the foam layer most proximate to the wound side in use the pores have a smallest size. If only one further foam layer is utilized that includes pore sizes which are greater than the pore sizes of the first layer. This helps avoid solid particulate being trapped in the lower layer which thus helps maintain the lower layer in an open configuration in which it is thus able to transmit air throughout the dressing. In any embodiments disclosed herein, two, three, four or more foam layers can be included. The foam layers can be integrally formed, for example, by selecting a foam having a large pore size and then repeatedly dipping this to a lesser and lesser extent into material which will clog the pores or alternatively, the transmission layer formed by the multiple foam layers can be provided by laminating different types of foam in a layered arrangement or by securing such layers of foam in place in a known manner.

Some embodiments of the dressing can be configured to permit the repositionability of the dressing. In any embodiments disclosed herein, the dressing can have a wound contact surface that is covered with an adhesive, such as a silicone based adhesive. As described in U.S. patent application Ser. No. 13/092,042, which disclosure is hereby incorporated by reference as if fully set forth herein, though not required, a lower surface of any of the wound dressing embodiments disclosed herein can have an optional wound contact layer. Any of the dressing embodiments disclosed herein can be made without the wound contact layer. The wound contact layer can be a polyurethane layer or polyethylene layer or other flexible layer which can be made porous or perforated, for example via a hot pin process, laser ablation process, ultrasound process or in some other way or otherwise made permeable to liquid and gas. The perforations can enable fluid and/or gas to flow through the layer. The wound contact layer can help prevent tissue ingrowth into the other material of the wound dressing.

The perforations of the contact layer can be sized small enough to meet this requirement but still allow fluid through. For example, the contact layer can have perforations formed as slits or holes having a size ranging from approximately 0.025 mm to approximately 1.8 mm, or from approximately 1.2 mm to approximately 1.8 mm, which are considered small enough to help prevent tissue ingrowth into the wound dressing while allowing wound exudate to flow into the dressing. In any embodiments, therefore, the perforations can be formed as holes ranging in diameter from approximately 1.2 mm to approximately 2.8 mm, or from approximately 1.2 mm to approximately 1.8 mm. The hole spacing or density in any embodiments can be approximately 8 holes/cm$^2$, or from approximately 6 holes/cm$^2$ to approximately 10 holes/cm$^2$. As used throughout this disclosure, unless otherwise defined, the term approximately can be used to describe a range of +/−10% of the stated value. Additionally, in any embodiments of the contact layer, the holes can be formed at approximately a 3.655 mm triangular pitch. Any of the wound contact layer embodiments disclosed herein can be formed from silicone.

The wound contact layer can help hold the whole wound dressing together and help to create an air tight seal around the absorbent pad in order to maintain negative pressure at the wound. The wound contact layer also acts as a carrier for an optional lower and upper adhesive layer (not shown). For example, a lower pressure sensitive adhesive can be provided on the underside surface of the wound dressing whilst an upper pressure sensitive adhesive layer can be provided on the upper surface of the wound contact layer. The pressure sensitive adhesive, which can be a silicone, hot melt, hydrocolloid or acrylic based adhesive or other such adhesives, can be formed on both sides or optionally on a selected one or none of the sides of the wound contact layer. When a lower pressure sensitive adhesive layer is utilized, this helps adhere the wound dressing to the skin around a wound site.

As mentioned, any dressing embodiments for use in the dressing kits disclosed or incorporated by reference herein can have an adhesive covered bottom (e.g., wound contacting) surface. In any embodiments disclosed herein, as mentioned, the adhesive can be a silicone adhesive including, for example, polysiloxanes or polyorganosiloxanes or other polymeric pressure sensitive silicone adhesives. For example, polydimethylsiloxane or the like can be used. The adhesive formulation can be a mixture of alkyl pendant siloxanes, which can be spread and cast as a two part mix with a catalyst such that a final polymerisation step takes place following casting or spreading. In any embodiments disclosed herein, a dressing layer can have a non-perforated silicone adhesive coating (coat weight 130 gsm nominal) and full spread acrylic adhesive (27 to 37 gsm) coated onto opposite sides of an extruded EU30 polyurethane clear film (27 to 37 gsm). Moisture vapour permeability of such an arrangement can be between approximately 367 gm$^{-2}$/24 hrs to approximately 405 gm$^{-2}$/24 hrs, or a mean moisture vapour permeability of 382 gm$^{-2}$/24 hrs.

Some embodiments or arrangements of a silicone adhesive layer suitable for dressing embodiments disclosed herein can have a moisture vapour transmission rate between approximately 350 gm$^{-2}$/24 hrs and approximately 410 gm$^{-2}$/24 hrs. Aptly, the average moisture vapour permeability of some embodiments or arrangements of a silicone adhesive layer suitable for dressing embodiments disclosed herein can be approximately 380 gm$^{-2}$/24 hrs. Some of the dressing embodiments disclosed herein can have a Wacker silres PSA 45 pressure sensitive adhesive coated thereon.

Additionally, any of the dressing embodiments disclosed herein can have an anti-microbial agent or substance incorporated into the dressing or coated on one or more surfaces of the dressing. For example, without limitation, the dressing can contain anti-microbial e.g. nanocrystalline silver agents on the wound contact layer, or otherwise, and/or silver sulphur diazine in the absorbent layer, or otherwise. These respectively can eliminate micro-organisms in the wound and micro-organisms in the absorption matrix. A wound contact layer of any dressing embodiments disclosed herein can have nanocrystalline silver agents, silver salts, copper salts, or gold salts such as, without limitation, those disclosed in U.S. patent application Ser. No. 11/922,894 (titled ANTIMICROBIAL BIGUANIDE METAL COMPLEXES), filed May 21, 2008, which application is incorporated by reference herein as if made part of this disclosure, PHMB, chlorohexadine, peroxide, hypochloride, or other bleaches therein or thereon.

One or more of such agents can be used separately or together. These can reduce or eliminate micro-organisms in the wound and micro-organisms in the absorption matrix. As a still further option other active components, for example, pain suppressants, such as ibuprofen, can be included. Also agents which enhance cell activity, such as growth factors or that inhibit enzymes, such as matrix metalloproteinase inhibitors, such as tissue inhibitors of metalloproteinase (TIMPS) or zinc chelators could be utilized. As a still further option odor trapping elements such as activated carbon, cyclodextrine, zeolite or the like can be included in the absorbent layer or as a still further layer above the filter layer.

Additionally, adhesive fixation strips can be positioned around the peripheral edges of the any of the dressing embodiments disclosed herein to provide additional support to the dressing. Such fixation strips can be advantageous in some situations so as to provide additional sealing against the skin of the patient surrounding the wound site. For example, the sealing or fixation strips can provide additional sealing for when a patient is more mobile. In some cases, the fixation strips can be used prior to activation of the pump assembly, particularly if the dressing is placed over a difficult to reach or contoured area. In any embodiments disclosed herein, the dressing kit can be provided with up to five sealing strips.

Moreover, some embodiments disclosed herein are directed to systems that include negative pressure therapy apparatuses and dressings, and methods and algorithms for operating such negative pressure therapy apparatuses for use with negative pressure therapy dressings. In some embodiments, a negative pressure therapy apparatus comprises a pump assembly configured to, inter alia, provide negative pressure to a wound. Some embodiments of pump assemblies disclosed herein comprise novel and inventive control logic configured to control the operation of the pump assembly. For example, some embodiments comprise novel and inventive control logic configured to control the operation of a pump assembly in response to monitoring and detecting various operating conditions, such as presence and/or severity of a leak or leaks in the system, rate of flow of fluid (e.g., air, liquid and/or solid exudate, etc.) aspirated from a wound, and the like. In some embodiments, the control logic can be configured to detect a leak or leaks in a system (e.g., leak or leaks in the dressing that is in fluid communication with the pump, leak or leaks in the seal created by the dressing over the wound, etc.) as well as to control the operation of the pump assembly when such leak or leaks are detected. In some embodiments, the pump assembly can be configured to distinguish between at least a normal or low leak (e.g., a leak that has a relatively low flow rate), a high leak (e.g., a leak that has a relatively high flow rate), and a very high leak (e.g., a leak that has a relatively very high flow rate). Some embodiments can further be configured to also distinguish between the aforementioned leaks and an extremely high leak.

The operation of the pump can be controlled by the use of one or more buttons, pull tabs, sliding switches, or other similar features.

In some embodiments, the dressing kit can comprise a source of negative pressure, such as a miniature, disposable pump, powered by a power source. The pump assembly can be configured to provide therapy for a predetermined period of time, such as approximately 1 day, 1 or 2 to 10 days, 1 or 2 to 14 days, etc. In some embodiments, the pump assembly can be required to provide uninterrupted therapy for such period of time. In some embodiments, the pump assembly can be configured to deactivate itself a predetermined period of time (e.g., 7 days) after an initial activation. The algorithms or logic disclosed herein can help the pump assembly operate more efficiently and conserve power, for example but without limitation, battery power.

In any embodiments disclosed herein, the pump, circuit board or other controller, indicator lights, audible or visual alarms, and/or any other electronic components (collectively referred to herein as "pump electronics") of the dressing embodiments disclosed herein can be powered by one or more batteries (for example, two batteries) and can weigh approximately 84 grams, or less than 90 grams, including the weight of the batteries. In some embodiments, the pump assembly can weigh less than 84 grams, including the weight of the batteries, or can weigh from approximately 80 grams to approximately 90 grams, from approximately 75 grams or less to approximately 100 grams, or between any values within the foregoing ranges. The weight and/or size of the pump assembly can be reduced by reducing the battery size and/or weight to, for example, AAA sized batteries, or smaller, or to one or more flat lithium batteries, or by using an array of batteries.

For example, in some embodiments, the pump can be powered by a single 1200 mAh lithium battery. A non-limiting example of a battery that would be suitable is a JAUCH LiMnO$_2$ battery having a nominal voltage of 3.0 volts, a nominal capacity of 1200 mAh, a maximum continuous discharge current of 150 mA, a max pulse discharge current of 300 mA, a length of 40.0 mm, a width of 25.0 mm, a thickness of 5.0 mm, and a weight approximately 9.5 grams or less. The dimensions and/or weight of the battery can be reduced if a smaller capacity, voltage, and/or current is desired. For example, in any of the dressing embodiments disclosed herein, a plurality of lithium batteries can be used, each having a reduced size and weight as compared to the single battery described above. In any embodiments disclosed herein, any number of batteries (including any of the battery types disclosed herein) and/or capacitors can be positioned about the dressing cover layer and/or any of the dressing layers beneath the cover layer, the pump housing, and/or the conduit providing reduced pressure from the pump to the dressing, if such conduit is used. In any dressing embodiments, as described herein, the pump can be positioned directly on the dressing an configured such that no conduit is needed.

Any embodiments of the pump assembly and dressings disclosed herein can have a plurality of small capacitors, flexible batteries, and/or printed batteries supported by the dressing, the pump, and/or the conduit between the pump and the dressing, or otherwise. For example, an array of flat batteries can be distributed across the dressing cover layer, within the dressing layers under the cover layer (including being positioned across a plurality of the dressing layers), and/or across any conduit positioned on the dressing or between the pump and the dressing. Additionally, the weight and/or size of the pump assembly can be reduced by reducing the pump size and/or weight.

The batteries of any of the embodiments disclosed herein can be lithium chloride, lithium ion disulfide, lithium manganese dioxide or any other suitable batteries that are suitable for exposure to ethylene dioxide and/or other sterilization gases. Lithium air or zinc air batteries can also be used with any embodiment disclosed herein. Coin shaped or button shaped batteries of any composition can also be used with any embodiment disclosed herein. The batteries can be supported outside of the pump housing so as to minimize or eliminate the chance of an electrical spark which could cause an explosion in the presence of the sterilization gas or an explosive gas during the sterilization process when supported in the packaging element or elements. Additionally, where there are a plurality of batteries, the batteries can be spaced apart or otherwise separated in the packaging to prevent any power loss or sparking of the batteries during the sterilization process or otherwise before usage.

Additionally, in any embodiments disclosed herein, the power source for the pump can be provided by one or more flexible batteries. For example, one or more flexible printed batteries based on the technology developed by Imprint Energy and/or Solicore. For example, in any embodiments disclosed herein, the power source can comprise one or more lithium polymer batteries manufactured by Solicore, Inc. Solicore Flexion lithium polymer batteries are ultra-thin, flexible, and have a high energy density. For example, in some embodiments, the power source can have a plurality of thin, flexible lithium polymer batteries. In any embodiments disclosed herein, the power source can comprise a plurality of thin, flexible lithium polymer batteries each having a nominal capacity of approximately 10 to approximately 14 mAh or greater, and a voltage of approximately 3.0 V. In some embodiments, the batteries can each have a size of approximately 26 mm by approximately 29 mm, or approximately 49 mm by approximately 23 mm, and a thickness of approximately 0.45 mm.

In any embodiments disclosed herein, the power source can have from approximately 6 to approximately 10 flexible batteries, or from approximately 10 to approximately 50 or more flexible batteries, depending on the spatial area of the battery, having a thickness of approximately 0.5 mm or less. In any embodiments disclosed herein, the power source can have one or more batteries having a thickness of approximately 0.5 mm or less, or approximately 0.45 mm or less, and can be configured to have a total nominal capacity of from approximately 1000 mAh or less to approximately 1200 mAh.

Additionally, in any embodiments disclosed herein, the power can be provided by one or more carbon zinc flexible batteries manufactured by Blue Spark Technologies, built on 1.5V carbon-zinc battery chemistry. Voltages above 1.5V can be provided to the pump embodiments by providing multiple battery cells in series. Providing one or more flexible batteries in parallel can increase the total capacity of the power provided by the plurality of batteries. The Blue Spark Technologies ST series printed batteries can provide peak drain currents of approximately at least 1 mA. Such batteries can have a thickness of less than 500 micron (0.020 in). For example, the Blue Spark Technologies 110-ST1 battery provides 1.5V, has a capacity of 30 mAh, a peak drain current of 1-2 mA, a height of 55 mm (2.17 in), a length of 47 mm (1.87 in), and a thickness of 750 microns (0.029 in). The Blue Spark Technologies 111-ST1 battery provides 1.5V, has a capacity of 54 mAh, a peak drain current of 1-2 mA, a height of 78.7 mm (3.10 in), a length of 47.6 mm (1.87 in), and a thickness of 750 microns (0.029 in). The Blue Spark Technologies 111-ST1 battery provides 1.5V, has a capacity of 37 mAh, a peak drain current of 1-2 mA, a height of 79 mm (3.10 in), a length of 47 mm (1.87 in), and a thickness of 500 microns (0.020 in).

Any of the foregoing printed batteries, or similar printed batteries, can be used to provide a power source to any of the pump electronics of any of the dressing embodiments disclosed herein. Additionally, any of the batteries, including the flexible batteries, disclosed herein can be formed in a flat, planar relaxed shape, curved relaxed shape, or any other desired shape. Though not required, in any embodiments disclosed herein, the power source (including the thin, flexible batteries) can be positioned or distributed over or within the dressing absorption, transmission, and/or backing layers, positioned about the housing for the pump assembly, and/or positioned about the one or more layers comprising the conduit (if any) between the pump assembly and the dressing absorption, transmission, and/or backing layers.

Further, as in any of the dressing kit embodiments disclosed herein, the dressing kits can be configured such that the conductive connections between the power source and the pump assembly can be separated by a pull tab, isolation tab, activation switch, or other isolation mechanism to prevent any power supply from being provided to the pump assembly during sterilization, shipment, or handling prior to initiation of the negative pressure therapy.

In some embodiments, the pump assembly can be configured such that the battery connections or terminals have polarity protection. For example and without limitation, one or more of the battery contacts can be configured to have plastic or other non-conductive protrusions adjacent to the battery terminal contacts to inhibit the contact between the battery contact and the incorrect side of a battery that is inserted into the battery compartment in the incorrect orientation. In some embodiments, the one or more protrusions can be sized and configured to prevent the negative side of a standard cylindrical battery from contacting the battery contact adjacent to the one or more protrusions, while permitting a positive side of such battery to contact the battery contact. Generally, with this configuration, the battery can generally only make contact with the contact if the battery is inserted in the battery compartment in the correct orientation, thereby providing polarity protection to the pump assembly. Alternatively or additionally, a control board of the pump assembly can be configured to have polarity protective features or components. Additionally, a control board of the pump assembly can have one or more fuses to protect against overpower conditions or surge power conditions.

Additionally, any of the dressing embodiments disclosed herein can have one or more photovoltaic cells configured to provide energy to the pump electronics. Though not required, the embodiments having one or more photovoltaic cells can additionally have one or more batteries or capacitors configured to provide energy to the pump electronics. The photovoltaic cells, batteries, capacitors, and/or other suitable power sources of any of the dressing kit embodiments disclosed herein can be positioned about at least one of the dressing cover layer, the pump housing, and the conduit between the pump housing and the dressing cover layer.

In any embodiments disclosed herein, the conduit can have a plurality of articulations in along the length thereof, configured to bias the conduit to a shorter length state. The conduit can be extended if increased length is needed.

Additionally, in some embodiments, a connector (or first connector) can be positioned at an end portion of the conduit to connect the conduit to a mating connector (or second connector) on the dressing. In some embodiments, the connector can be configured to activate the pump once the connector is attached to a mating connector fixed to the dressing.

For example and without limitation, in some embodiments, the dressing kit can have a pair of wires or electrical conductors extending from the pump assembly to the first connector. The two conductive wires or electrical conductors can form an open circuit along the length of the conduit. A low voltage can be provided through one of the two conductive wires, sufficient to activate the pump when the two conductive wires are in communication with one another. The two electrical conductors can terminate in a first set of electrical contact points. A second connector supported by the dressing can be configured to engage the first connector and can have a second set of electrical contact points. The second contact points can be electrically connected such that, when the first connector is fully engaged with the second connector supported by the dressing, the first set of contact points will be in contact with the second set of contact points, and close the circuit between the two conductive wires in the conduit to activate the pump.

Some embodiments of the pump assembly can be configured to abate noise and/or vibration of the pump during operation. Noise canceling chips can be used in some embodiments to reduce noise. In some embodiments, the pump output can be configured to ramp in and ramp out or gradually increase and decrease to eliminate sudden changes in the operation of the pump, thereby minimizing or eliminating any sudden transitions. Additionally, in any of the embodiments disclosed herein, the pump assembly or pump motor can be supported within a silicone or foam envelop or layer to attenuate vibration and noise.

Additionally, in any of the embodiments disclosed herein, the pump assembly or dressing member can be configured to support an organic light emitting diode ("OLED") display or other suitable interface display.

Some of the embodiments comprise a pump and/or a pump and dressing kit. Some embodiments are directed to a pump and/or pump and dressing kit that have been sterilized before delivery to the hospital, operating room or theatre, or to the medical practitioner using such devices such that the sterile pump and/or a sterile pump/dressing kit can be applied immediately following the surgical or operating procedures. One advantage of this is that the surgeon can release the patient from the operating room knowing that the reduced pressure pump is operating and that the reduced pressure therapy has been started at the earliest point in time possible. A further advantage of applying the dressing kit immediately following the surgical or other procedure is that doing so can reduce the chance of infection by eliminating a subsequent dressing change that may otherwise be required in the ward. In other words, for those patients where a dressing (but not a pump) is applied in the operating theatre and then a problem is found thereafter, such as a leak or other issue with the dressing, if the dressing is required to be removed to be repositioned, replaced, or otherwise after the patient is released from the operating theater, the patient's wound can be exposed to infection risk when the dressing is repositioned, replaced, or otherwise outside of the operating theater. However, with the embodiments disclosed herein, if the pump is applied and tested while the patient is in the operating theater, any issues with the dressing that may require the dressing to be removed, repositioned, or otherwise, can be handled in the sterile operating room environment, thereby significantly reducing or eliminating the risk of exposure to pathogens, bacteria, or other contaminants. Further, it is generally not possible for a hospital to sterilize a traditional pump once it has been received by the hospital, and therefore the hospital may resort to bagging the pumps in sterile bags but risk compromising the operating room sterile field with this approach, particularly once the device is turned on and pathogens, bacteria, or other contaminants that may be inside the pump are release due to the operation of the pump.

In some embodiments, the pump can be configured to be amenable to gas sterilization, having features, components, and other characteristics that make the pump amenable to full sterilization gas exposure and penetration throughout the components of the pump. For example, without limitation, one or more pump valves have been selected or configured to permit a sufficient flow of sterilization gas therethrough such that the entire fluid pathway within the pump can be exposed to the sterilization gas. As will be explained in greater detail below, in some embodiments, the pump can have other components, such as without limitation, strategically positioned one way flow valves, to complement the other valves within the pump, which can improve the efficiency of the pump by reducing leakage through the flow pathway within the pump assembly.

Additionally, where provided, the sterile pump/dressing kit can also be designed and configured to be amenable to gas sterilization. As described below, the sterile pump/dressing kit can be configured such that all of the components comprising the sterile pump/dressing kit, including the pump assembly, are packaged together in at least a first packaging element before sterilization, permitting all of the components to be sterilized together. Furthermore, as will be described, the components comprising the sterile pump/dressing kit can be arranged in the packaging such that at least some of the components can be removed in a predefined order, making it easier for the surgeon or medical practitioner to assemble and apply the dressing to the patient.

There are a number of benefits to being able to begin treatment of a wound in the operating theater, including without limitation providing a substantially sealed barrier over the wound while the wound is in a sterile condition and environment that will inhibit or prevent bacteria or other contaminants from getting into the wound. Additionally, initiating the reduced pressure treatment at the earliest stage possible is also advantageous to healing of the wound.

The housing of any of the pump assembly embodiments can be configured such that a sterilization gas, such as ethylene dioxide, can penetrate into the housing such that the internal components of the pump assembly are exposed to the sterilization gas during normal sterilization processes. Typically, the pump will be exposed to the sterilization gas in a chamber that has been substantially evacuated of air or any other gas, so that the sterilization gas is drawn into the pump housing and into the other spaces and chambers within the pump assembly. For example, some embodiments of the pump housing can have an unsealed gap surrounding the connector through which the sterilization gas can pass. Also, in some embodiments, the first housing member can be joined to the second housing member without the use of a seal therebetween, and the pump assembly can have one or more valves that permit a sufficient amount of sterilization gas therein to effectively sterilize all of the internal components of the pump.

In some embodiments, the pump assembly can be mounted to any of the dressing embodiments disclosed herein and can have any suitable pump components (including, without limitation, a standard off-the-shelf vacuum pump such as the Koge Electronics KPV8A-3A pump). Some embodiments of the pump can be approximately 37 mm (length)×20 mm (width)×8 mm (depth). In any of the embodiments disclosed herein, one or more of the pumps can be a piezoelectric pump or a diaphragm pump or any other suitable pump. Additionally, in some embodiments, the pump can be a voice coil actuated pump.

The batteries can be lithium or zinc air activatable batteries, though not so required. If the dressing kit is to be sterilized, the batteries can be separated during the sterilization process by positioning a non-conductive barrier between the batteries. Additionally, to accommodate current legislation regarding battery disposal, some embodiments of the pump assembly can be configured such that the batteries are easily removable or separable from the dressing, for example before the dressing is removed from the body, for disposal after the dressing kit and pump assembly have been used.

In some embodiments, the pump can be configured such that the pump needs to be powered on at the start of the treatment cycle. Additionally, the pump can be configured such that the pump needs to be re-started when a leak is detected and dressing has been assessed. Regarding leaks, the pump assembly and dressing kit can be configured such that the device provides the following operation indications, without limitation: communication of device operating correctly; communication of leak being found; communication indicating that the dressing is full; and/or communication of a low or dead battery. The pump can be configured to communicate in multiple different languages. Any embodiments of the pump disclosed herein can be configured to communicate in 19 or more different languages. Any embodiments of the pump disclosed herein can be configured to maintain reduced pressure in the wound site between approximately 60 and approximately 80 mmHg, or between approximately 60 and approximately 130 mmHg.

FIGS. 134A-138B illustrate five dressing embodiments, the dressing being configured to support the pump and power source such that the pump and power source is on-board the dressing. In any of the embodiments herein, the power source used to provide power to the pump electronics can have one or more batteries, one or more capacitors, one or more photovoltaic cells, one or more fuel cells, or any combination of the foregoing. Such power sources are collectively referred to herein as "power source."

Any of the embodiments illustrated in FIGS. 134A-138B or elsewhere in this disclosure can comprise any feature, component, material, and/or details of any or all of the other embodiments described herein. FIGS. 134A-B illustrate one embodiment of a dressing kit A50 having a pump assembly A52 supported by the dressing A54 at a corner A54a of a dressing A54. The power source A52 of this embodiment or any dressing kit embodiment disclosed herein can have any of the types of batteries disclosed herein or otherwise, including printed and/or flexible batteries, lithium batteries, and/or air activatable batteries A56, or can have one or more capacitors, photovoltaic cells, fuel cells, or otherwise. Having the pump assembly A52 on the corner A54a of the dressing A54 can improve the handleability of the dressing A50.

In some embodiments, the power source A52 can be positioned along the short edge of the dressing A54 and the pump assembly A52 can be positioned along the long edge of the dressing A54, or vice versa. In any of the dressing embodiments disclosed herein, a control board and/or user interface, which can include operation buttons, visual displays, alarms, indicator lights, or otherwise, can be positioned in any desired position on the dressing, including above or below the backing layer (the backing layer being the outermost dressing layer), integrated within the dressing layers positioned beneath the backing layer, or otherwise.

As further illustrated by FIG. 134A, some embodiments of the invention can include a removable label A58. The removable label A58 can be made of an airtight polymer material or any other suitable material. The removable label can be removably fixed to the batteries A56 via an adhesive or any other suitable mechanism. Removing the label A58 can expose the batteries A56 to air, thereby activating the batteries A56.

FIG. 134B illustrates the dressing A50 with the label A58 removed. When the dressing A50 is applied to a wound, the corner placement of the pump assembly A52 and batteries A56 can frame the wound. For example, the pump assembly A52 and the batteries A56 can lay outside the periphery of the wound and attach to healthy skin. Further, the pump assembly A52 and batteries A56 can be raised from the surface of the skin, such that if the patient bumps into an object, the raised surface prevents damage to the wound.

Though not required, in some embodiments, the pump assembly can be positioned on one end of the dressing and the batteries or other power source can be positioned on another side or end of the dressing, such as the opposite side. This arrangement can result in a more balanced dressing in terms of weight, rigidity, and/or size.

In some embodiments, as with the dressing kit A70 embodiment illustrated in FIG. 135B, the pump A72 and power source A76 can be positioned at opposite ends of the dressing A74. With reference to FIGS. 135A-135C, the pump assembly A72, printed circuit board (PCB) or other pump controller, and battery assembly A76 can be positioned in recesses or openings formed in the dressing material or foam A78, or can be embedded within the foam or dressing material A78. The foam or dressing material A78, with the pump A72 and/or power source therein, can be flexible and conformable to curved or contoured body surfaces. An elastomeric carriage A84 can line the dressing material or foam A78 close to the pump A72, PCB, and battery A76. The elastomeric carriage A84 can provide flexibility to the dressing A70. The pump assembly A72, PCB, and battery assembly A76 can be configured such that the components are flexible to permit the wound dressing A70 to bend about the body or flex with the movement of the body. For example, a hinge can be provided between the pump assembly A72, PCB, and/or the battery A76 to permit flexibility. Additionally, the portion of the dressing A74 supporting the pump A72 and/or battery A76 can be configured to provide a handle, to improve the handleability of the dressing during placement of the dressing on the body. Separating the battery A76 on the dressing A70 also has the benefit of permitting the battery or batteries A76 to be easily removed after use for separate disposal.

In any of the dressing kit embodiments disclosed herein (which includes the pump embodiments supported remote to the dressing, such as adjacent to the dressing), the PCB or pump controller can be a flexible circuit board and/or can have one or more flexible components. A flexible circuit board is generally a patterned arrangement of printed circuitry and components that utilizes flexible based material with or without flexible overlay. These flexible electronic assemblies can be fabricated using the same components used for rigid printed circuit boards, but allowing the board to conform to a desired shape (flex) during its application. In their simplest form, flexible circuits are PCBs made of materials that allow for a non-planar positioning within the end product. Typical materials a polyimide-based, and can go under trade names such as Kapton (DuPont). Additionally, any of the control boards or controllers disclosed herein can have a combination of flexible and rigid substrates laminated into a single package.

Additionally, in any embodiments, the circuit boards can be printed on any desired substrate, including printing the circuits on one or more surfaces of the pump housing, on one or more dressing layers or surfaces, on one or more conduit and/or port layers or surfaces, or any combination of the foregoing.

In any of the dressing embodiments disclosed herein, with reference to FIG. 135A, malleable metal or other materials (such as metal wires or strips) A84 can be added to the dressing A70 to maintain the shape of the dressing A70 after it has been molded to the body surface. The malleable material A84 can be under, within, or above the gauze. Additionally, the malleable material A84 can be positioned under, within, or above the cover layer. The malleable material A84 can be positioned in a parallel arrangement, as illustrated by FIG. 135A, or in any other suitable arrangement.

Additionally, in any embodiments disclosed herein, a hinge (such as a living hinge) can be positioned between the various components comprising the pump assembly, such as between a control board and the pump motor A72, or between an power source A76 and the pump A72, to improve the flexibility of the pump assembly and/or dressing kit. Printed connectors could be used to provide electrical connections between the PCB and the pump motor A72 and/or between the batteries A76 and the PCB or pump motor A72. Additionally, in any embodiments disclosed herein, if both the pump assembly A72 and the batteries A80 are positioned at one end of the dressing A70, a foam handle could be positioned at the other end to improve the handleability of the dressing A70.

As illustrated in FIGS. 136A-136C, the dressing kit A90 can be configured such that both the pump assembly A92 and the power source A94 can be positioned on one end A96a of the dressing A96. As shown in FIG. 136B, a cover A98 can be positioned over the pump A92 and power source A94 to contain those components. The cover A98 can be supported by the dressing A92 with a living hinge A100 or by any other suitable mechanism. The dressing contact layer A102, the packing layer A104, and the cover A106 can have rounded corners. The dressing can come in a variety of lengths and sizes, as illustrated by FIG. 136C. Additionally, a pull tab, as further described herein, can be used for activation and deactivation of the pump. Additionally, in this and any other dressing embodiments disclosed herein, the border around the dressing can be baggy or have additional slack or material therein to for increased user movement.

With reference to FIGS. 137A-137C, in some embodiments of the dressing A110, the power source A112 (which can comprise one or more batteries) and pump assembly A114 can be positioned along the lengthwise side A116a of the dressing A116. Referring to FIGS. 137A-137C, the dimensions of the dressing A110 according to some embodiments of the invention can be approximately 50 mm×100 mm, 100 mm×150 mm, or 100 mm×250 mm, respectively. In these embodiments, the power source A112 and pump assembly A114 can be placed along the side of the dressing measuring 100 mm, 150 mm, and 250 mm, respectively.

Although FIG. 137A illustrates various dimensions of the dressing A116, it will be appreciated that the dimensions can be of any suitable length and width.

The power source A112 (which can have one or more batteries) and pump assembly A114 can be separated, as shown in FIG. 137C, or can be positioned adjacent to one another, as illustrated in FIGS. 137A and 137B. This arrangement can result in the pump assembly A114 being more flush to the user's body, to prevent or reduce the risk of dislodgement and discomfort. Additionally, positioning the pump A114 at one end and the batteries A112 at the other end can result in greater conformability of the dressing kit A110 to the body, and increased comfort and performance of the dressing kit A110. Referring to FIG. 137C, separating the power source A112 and the pump assembly A114 can increase the flexibility of the dressing A110. Both enhance flexibility and enhanced conformability can improve the dressing's seal to the body, to reduce leakage pathways to the space between the dressing and the wound.

With reference to FIGS. 138A-138B, any embodiments disclosed herein of the dressing kit A130 can have one or more zinc air activated batteries A136 that can activate the pump A132 with air that is introduced to the batteries A136. The batteries A136 and pump assembly A132 can be positioned along an end portion A138a of the dressing A138. The batteries A136 can be low profile to reduce the profile of the dressing A130. As illustrated by FIGS. 138A-138B, the batteries A136 and pump assembly A132 can be placed on an end portion A138 of the dressing A130 according to some embodiments of the invention. The batteries A136 and pump assembly A132 can be placed along the shorter side (as illustrated in FIG. 138A) or the longer side (as illustrated in FIG. 138B) of the dressing A138. Therefore, in any embodiments disclosed herein, the pump and power source can be positioned adjacent to one or more packing layers of the dressing, and can be positioned adjacent to an edge of a cover layer to reduce the likelihood that the power source and/or pump will be positioned over the wound.

As shown in FIG. 139A, in any embodiments disclosed herein, the dressing film or cover layer A152 can extend beyond the dressing borders and form a loop A154 at one end to improve the handleability of the dressing A150 and prevent the dressing from flopping around or becoming limp and unhandleable during application of the dressing to the body. The looped over support layer could be removable, to permit the support layer to be removed after positioning the dressing on the body. Additionally, in some embodiments, the pump A156 and/or battery source A158 can be positioned in a corner of the dressing A152 or in any other suitable location. In this or any other embodiment disclosed herein, the dressing A152 and/or pump assembly A156 can have one or more press studs to provide mechanical attachment between the dressing and the pump assembly, and/or to loop and removably hold the dressing layer in the desired looped configuration.

Figure 140B:
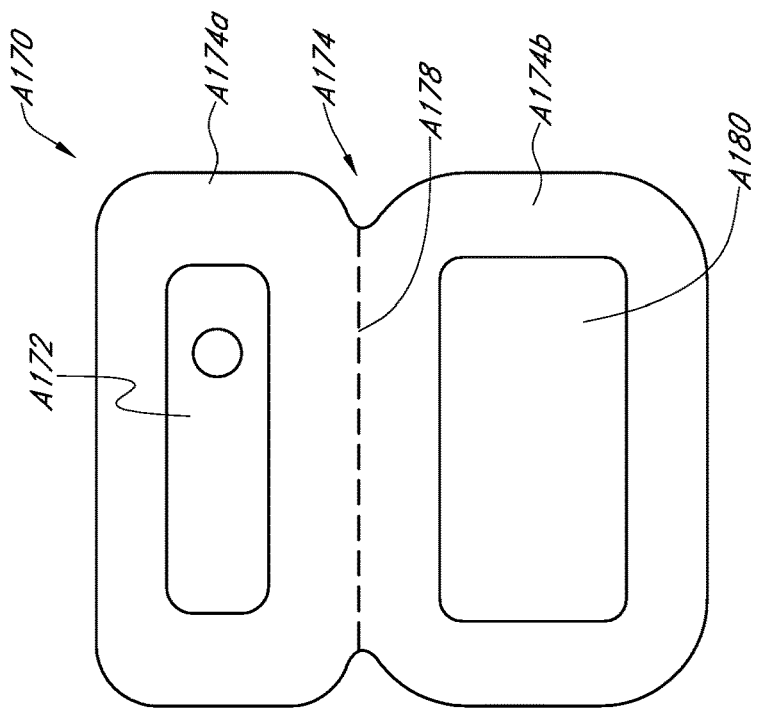
FIGS. 140A-140B illustrate additional embodiments of a dressing kit for negative pressure wound therapy, showing two different exemplifying sizes of such embodiment.
Figure 140A:
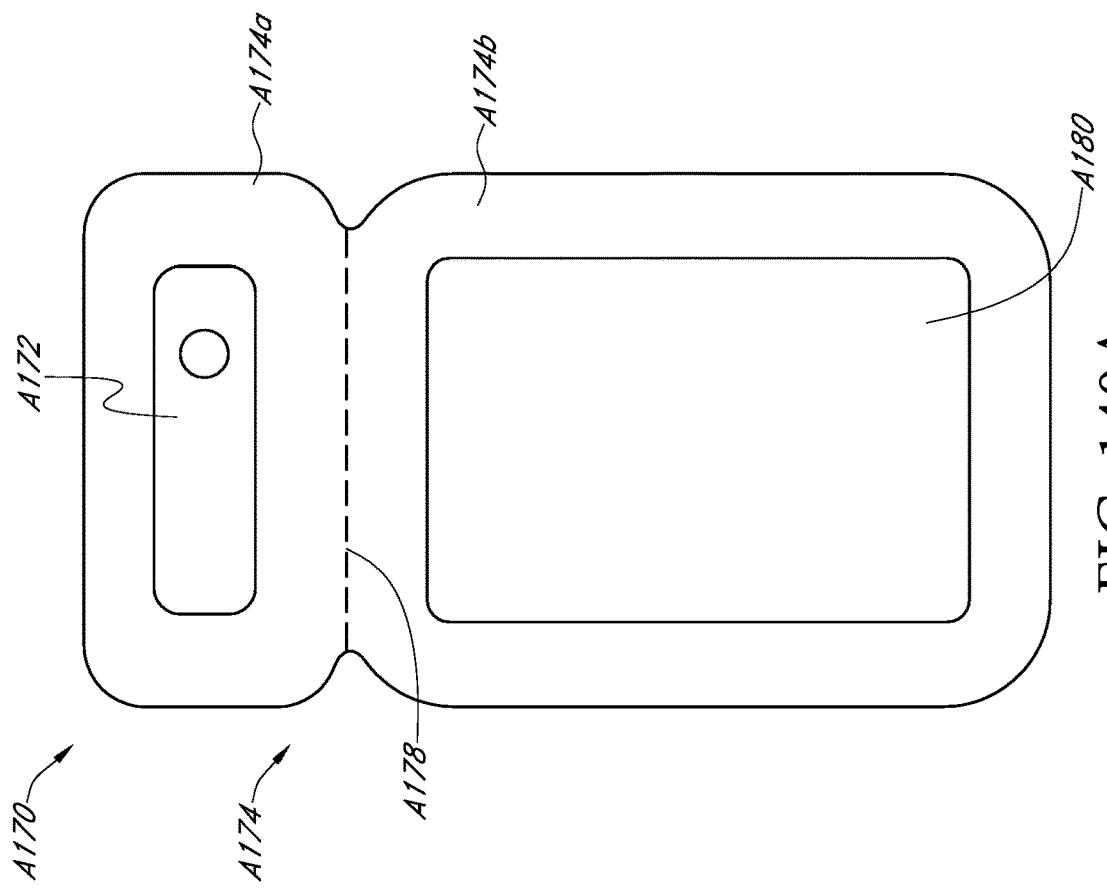

With reference to FIGS. 140A-140B, the dressing kit A170 can be arranged such that the pump assembly A172 can be supported by the dressing A174 in an offset position so that the pump assembly A172 is not positioned over any portion of the dressing A174. A conduit can be used to communicate the reduced pressure produced by the pump assembly A172 to the dressing A174 and wound. The dressing kit A170 can be configured such that the pump portion A172 can be easily removed for disposal of the pump assembly separate from the dressing. In any embodiments disclosed herein, the dressing can have a one or more cuts, channels, scores, reduced thickness portions, partial thickness cuts, or perforations A178 between a first portion A174a of the dressing A174 supporting the pump assembly and a second portion A174b of the dressing A174 having one or more absorbing layers A180 to be positioned over the wound.

As such, any dressing member disclosed herein can be configured to have at least a first portion and a second portion configured to be separable from the first portion by hand and without the use of tools. The dressing member can be configured to be torn by hand to separate the first portion from the second portion. Additionally, positioning the pump A172 and power source (e.g., batteries) adjacent to the wound site instead of over the wound site can improve the comfort to the user by preventing the pump assembly and/or power source from contacting the sensitive wound bed. The dressing A174 can have at least one continuous layer that covers the entire dressing A174. The dressing member A174 can be approximately air-tight adjacent to the perforations or boundary between the first and second portions so that, upon separation of the second portion from the first portion of the dressing, no air leaks result.

Figure 141B:
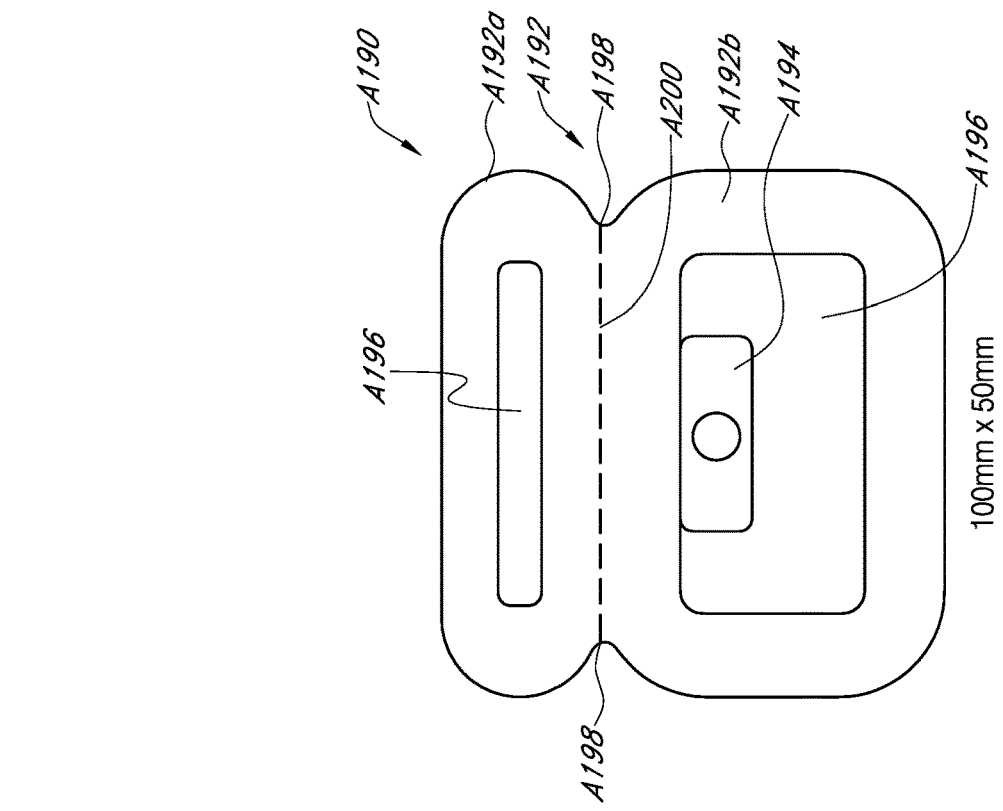
FIGS. 141A-141B illustrate additional embodiments of a dressing kit for negative pressure wound therapy, showing two different exemplifying sizes of such embodiment.
Figure 141A:
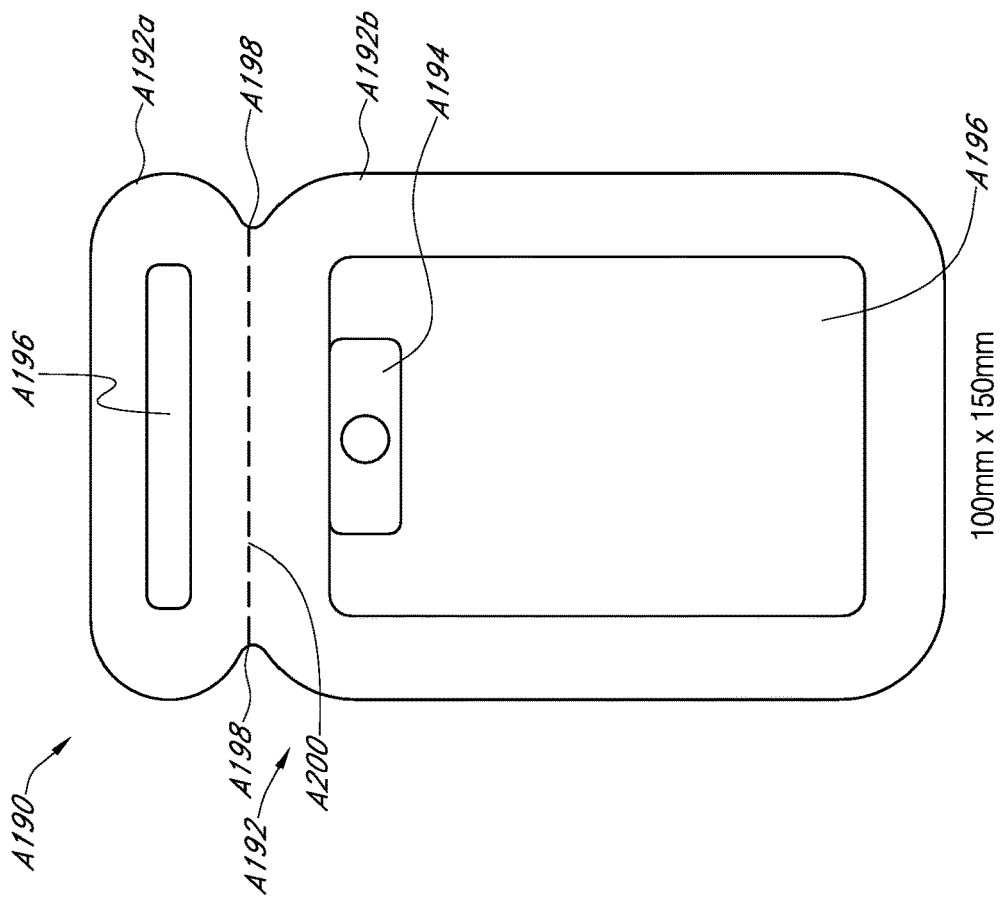

FIGS. 141A-141B are illustrations is an illustration of another embodiment of a dressing kit A190 having a dressing A192, a pump A194, and an power source A196. As illustrated in FIGS. 141A-141B, the pump assembly A194 can be positioned over or within the wound packing material A196 over the wound, while the power source A196, which can have one or more batteries, can be positioned in an offset position on the dressing. For example, in some embodiments, the power source A196 can be positioned on a first portion A192a of the dressing A192, which the pump assembly A194 can be positioned on a second portion A192b of the dressing A192. The absorbing or packing layers A196 can be positioned on the second portion A192b of the dressing A192.

In some embodiments, one or more cutouts A198 can be formed in the dressing between the first portion A192a and the second portion A192b to improve the flexibility of the dressing and to permit better articulation of the dressing. In this configuration, the dressing can have a narrowed or necked portion between the first and second portions. In some embodiments, a perforation A200 can be formed in the dressing A192 to permit separation of the first portion from the second portion of the dressing A192. This can facilitate the separation of the power source A196 from the rest of the dressing upon termination of the treatment for disposal of the two portions.

Figure 142B:
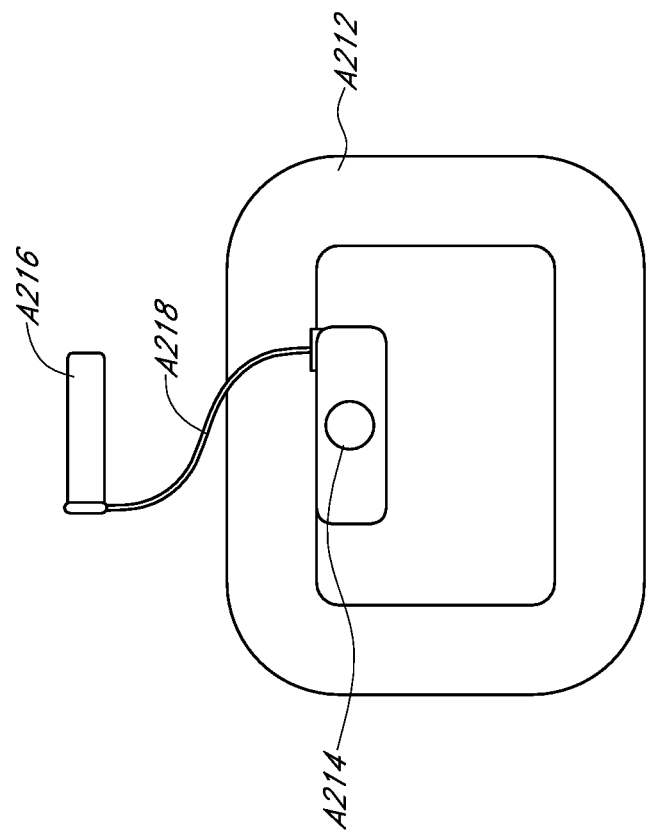
FIGS. 142A-142B illustrate additional embodiments of a dressing kit for negative pressure wound therapy, showing two different exemplifying sizes of such embodiment.
Figure 142A:
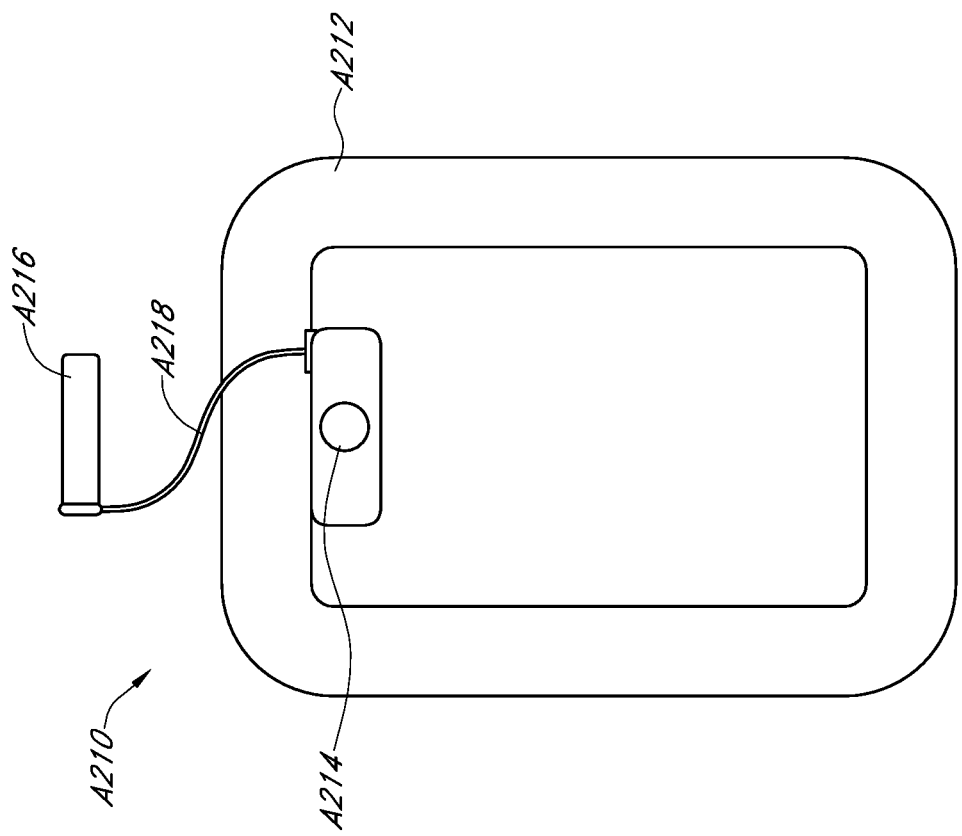

FIGS. 142A-142B illustrate an additional embodiment of a dressing kit A210, having a dressing A212, a pump assembly A214, and an power source A216. As with any of the embodiments disclosed herein, the power source A216 can have one or more flexible or rigid batteries of any of the configurations disclosed herein. In any embodiments disclosed herein, as illustrated in FIGS. 142A-142B, the power source A216 can be freely positionable relative to the dressing A212, either on or adjacent to the dressing A212. A printed ribbon or wiring A218 can provide an electrical connection between the power source A216 and the pump assembly A214. This arrangement can improve the ability of the user or medical practitioner to change the batteries during operation of the dressing kit, can improve the flexibility of the dressing A212, and can move heavy and/or semi-rigid objects away from the wound surface. Additionally, detaching and reattaching the batteries can be used for deactivating and activating the pump.

Figure 143A:
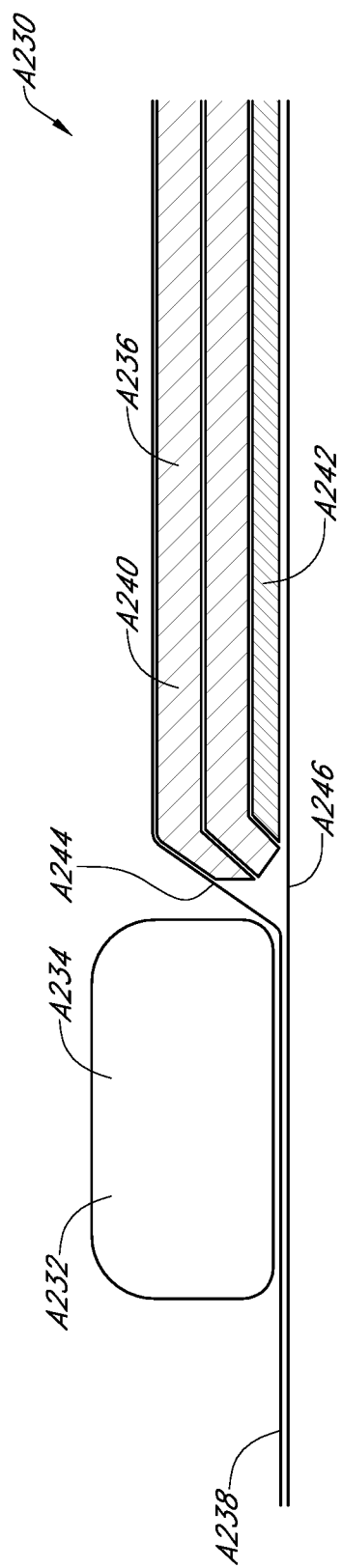
FIGS. 143A-143C illustrate additional embodiments of a dressing kit for negative pressure wound therapy, showing such dressing kit schematically in section, isometrically, and in a top view, respectively.
Figure 143B:
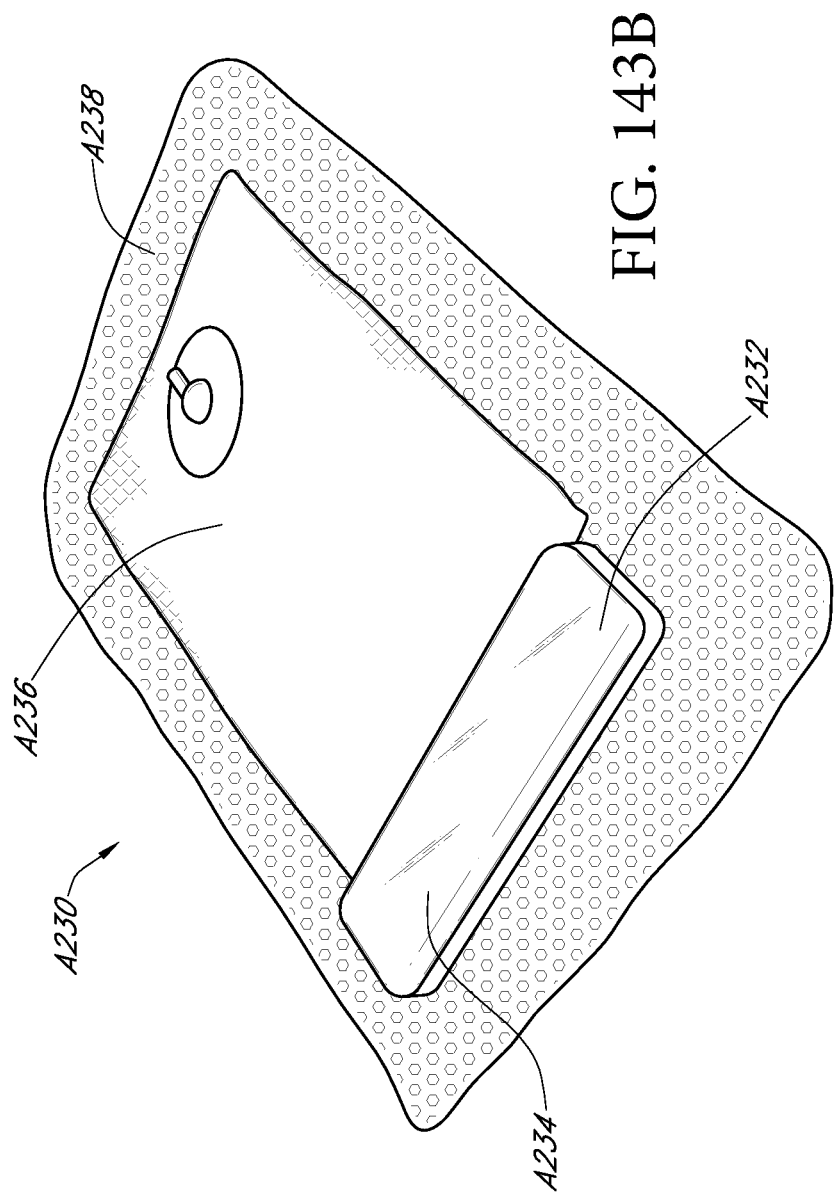
Figure 143C:
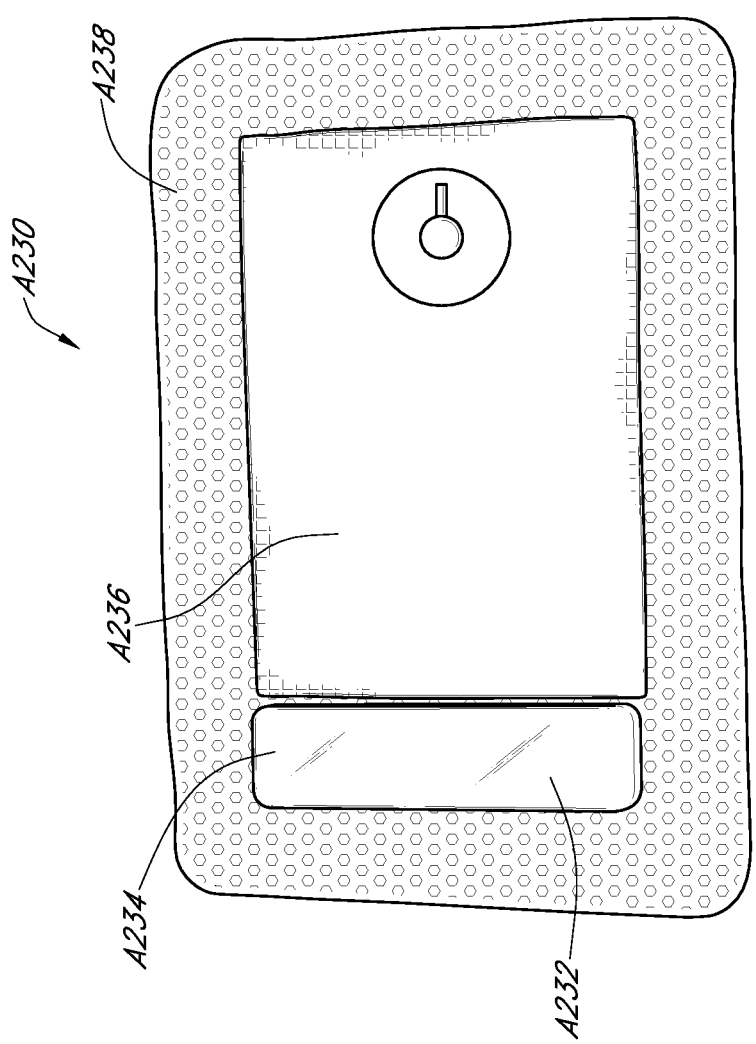

FIGS. 143A-143C illustrate an embodiment of a dressing kit A230 wherein the pump assembly A232 and batteries A234 are positioned adjacent to the dressing packing or absorption layers A236 of the dressing A238. In some embodiments, the dressing member A240 and the transmission layer A242 can terminate adjacent to the pump assembly A232 and the batteries A234 such that the pump A232 and batteries A234 can be positioned on an outside surface of the backing layer A240, with no dressing absorbing layers A240 or transmission layer A242 beneath the pump A232. Only the backing layer A244 and the wound contact layer A246 are positioned under the pump assembly A232 and batteries A234.

Figure 144A:
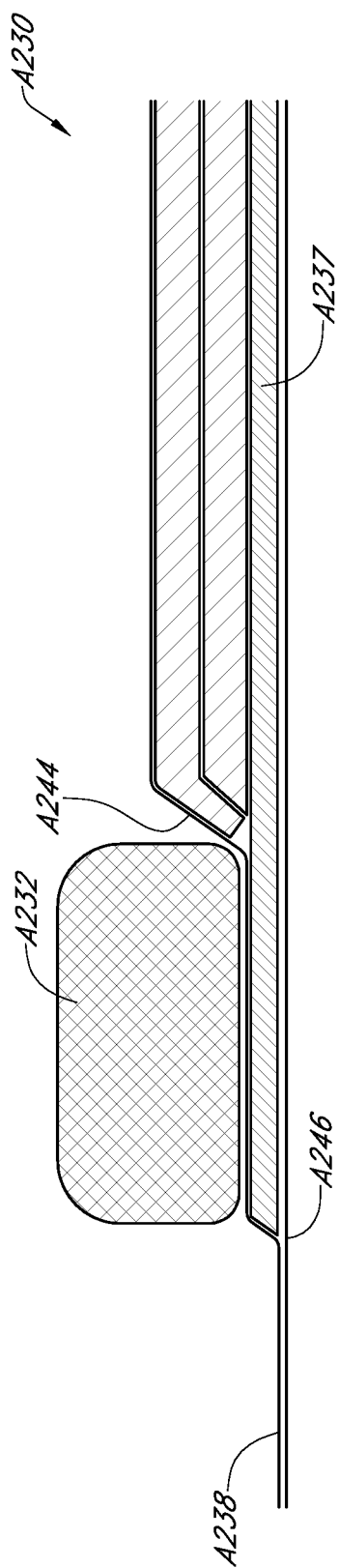
FIGS. 144A-144C illustrate additional embodiments of a dressing kit for negative pressure wound therapy, showing such dressing kit schematically in section, isometrically, and in a top view, respectively.
Figure 144B:
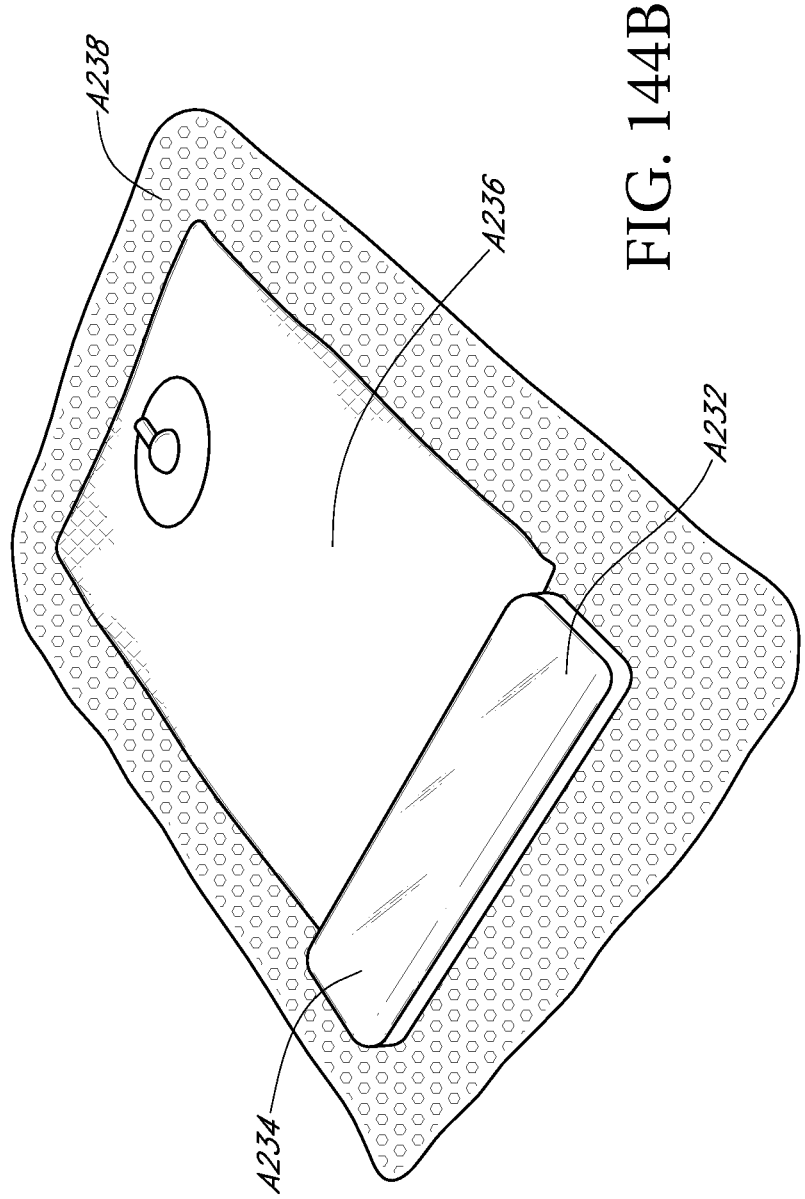
Figure 144C:
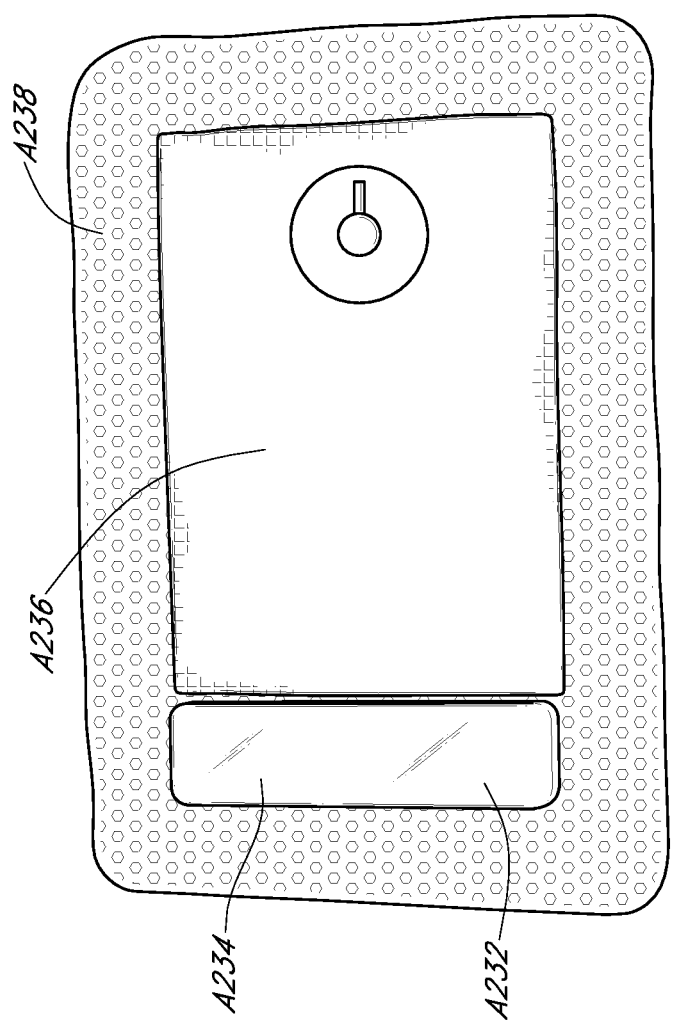

Alternatively, with reference to FIGS. 144A-144C, in some embodiments, an additional layer (which can be a transmission layer, spacer layer, absorption layer, and/or a 3D knitted or 3D fabric layer) can be positioned under the pump A232, between the backing layer and the wound contact layer A246. For example, in any embodiments, the pump can be positioned over a 3D knitted and/or fabric layer (such as the 3D knitted and/or fabric layer A237 shown in FIG. 144A) of any of the compositions disclosed herein, either with or without a liquid filter being positioned between the pump and the 3D knitted and/or fabric layer. A port in the pump A232 can be in fluid communication with the 3D knitted and/or fabric layer. In any embodiments, the backing layer A244 can be positioned over the pump A232, with an exhaust valve and/or filter to prevent pathogens, bacteria, odors, or other contaminants from leaving the pump. Positioning the pump over the transmission of 3D knitted and/or fabric layer can reduce the risk of maceration of the skin beneath the pump assembly and batteries that can result from the buildup of moisture against the skin, and can improve the comfort of the dressing by providing additional cushion between the pump assembly A232 and/or batteries A234 and the skin. This arrangement can also reduce the profile height of the dressing kit.

In the embodiment illustrated in FIGS. 144A-144C, or in any other embodiments disclosed herein, the dressing kit A230 can have one or more filters or valves upstream of the pump assembly A232 configured to prevent liquids and solids from entering the pump A232, but permitting the flow of air or gas through the filter or valve. In the case of a filter, the filter can be a hydrophobic filter, a hydrophilic filter, an occlusive filter, for example a membrane having a hydrogel and/or superabsorber material, or any other suitable type of filter or valve configured to prevent the passage of liquids or solids therethrough. In some embodiments, the filter or valve can be positioned adjacent to a port member, beneath the pump assembly, or otherwise positioned upstream of the pump assembly. For example, for the embodiment illustrated in FIGS. 144A-144C, the filter can be positioned between the pump assembly A232 and the backing layer A244, between the backing layer A244 and the wound packing layer A246 beneath or adjacent to the pump assembly A232, or in any other suitable location. In the embodiment illustrated in FIGS. 144A-144C, the backing layer A244 can have a puncture, opening, or other port feature adjacent to the filter to provide the passage of air through the backing layer A244 to the pump assembly A232.

Additionally, in some embodiments, the pump can be directly positioned on top of the wound contact layer, but have a port in communication with the 3D knitted and/or fabric layer so as to provide a source of negative pressure directly to the 3D knitted and/or fabric layer. As mentioned above, a liquid filter or liquid barrier can be positioned between the pump A232 and the 3D knitted and/or fabric layer to prevent liquid from entering the pump. In any of these embodiments, an absorption layer (which can be a superabsorbing layer) can be positioned above the 3D knitted and/or fabric layer or other transmission layer and can be configured to wick fluid out of the 3D knitted and/or fabric layer or other transmission layer.

The pump assembly A232 and/or batteries A234 can be positioned at an edge portion of the dressing A238, as illustrated in FIGS. 144A-144C, or can be positioned inside of an edge portion of the dressing, as illustrated in FIGS. 145A-145B. A double layer of absorptive material A238 can surround the pump assembly A232. Some embodiments only have a single layer of absorptive material A238. Additionally, with reference to FIGS. 146A-146B, in any dressing kit embodiment disclosed herein, the pump assembly A232 and/or batteries A234 can be positioned inside an edge portion of the dressing A238 and beneath the backing layer of the dressing in a depression or cutout that passes through the entire thickness of the absorptive layers so as to be positioned on top of the transmission layer A237. A port from the pump can be in communication with the transmission layer A237 so as to provide negative pressure to the transmission layer A237. A liquid filter to prevent liquid from passing through the pump can be positioned between the pump and the 3D knitted and/or fabric layer or other transmission layer, such as the 3D knitted and/or fabric layer A237 shown in FIG. 145A.

Additionally, in any embodiments, the pump can be positioned in a depression formed in the absorption layer so as to be positioned directly on top of the transmission layer. A port in the pump can be positioned so as to be in communication with the absorption layer so that negative pressure is applied directly to the absorption layer. Some embodiments can have a perforated or permeable polymeric film between the absorption layer and the transmission layer, such as a polyurethane or polyethylene layer.

Further, in any embodiments disclosed herein, the pump can be positioned directly over the transmission layer (which can be a 3D knitted and/or fabric layer, or any other suitable transmissive material), either embedded within one or more absorption layers or positioned adjacent to one or more absorption layers. In such arrangements, an impermeable film can be positioned between the transmission layer and the absorption layer, surrounding the pump. The pump can be configured to apply negative pressure directly to the transmission layer and to draw liquid from the transmission layer through the pump and exhaust such liquid into the absorption layer. An impermeable backing layer can be, but is not required to be, positioned over the pump assembly. In any arrangements wherein the pump is located under the backing layer, a filtered or unfiltered exhaust port can be formed in the backing layer to ensure that gas can be exhausted from the dressing. In some embodiments, a bacteria, pathogen, or other contaminant filter can be positioned within the pump assembly.

In any dressing kit embodiments disclosed herein, the 3D knitted and/or fabric layer can have any of the properties of any of the dressing layers disclosed in U.S. Patent Application Publication No. 2011/0282309 (Ser. No. 13/092,042), (titled WOUND DRESSING AND METHOD OF USE), filed Apr. 21, 2011, and/or PCT Patent Application Publication No. WO 2011/087871 (International Patent Application No. PCT/US2010/061938), (titled APPARATUS AND METHODS FOR NEGATIVE PRESSURE WOUND THERAPY), filed internationally on Dec. 22, 2010, which applications are hereby incorporated by reference as if fully set forth herein.

Figure 146A:
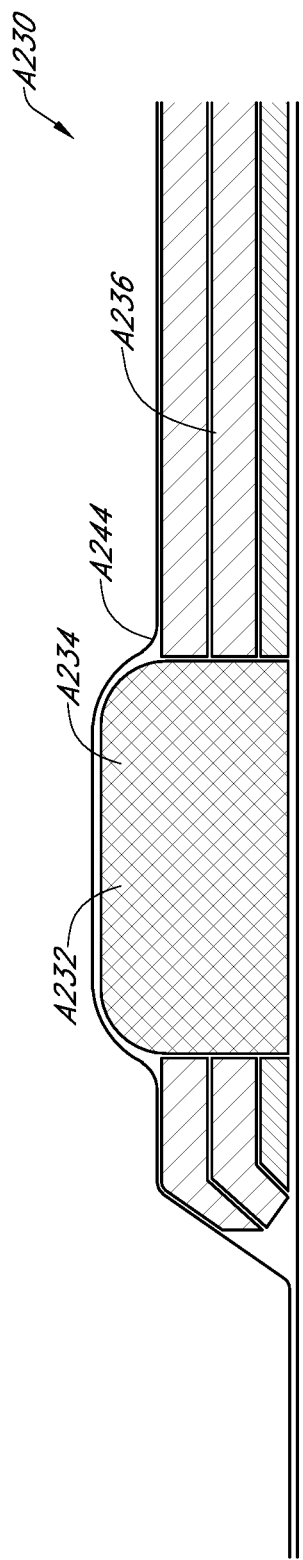
FIGS. 146A-146B illustrate additional embodiments of a dressing kit for negative pressure wound therapy, showing such dressing kit schematically in section and isometrically.
Figure 146B:
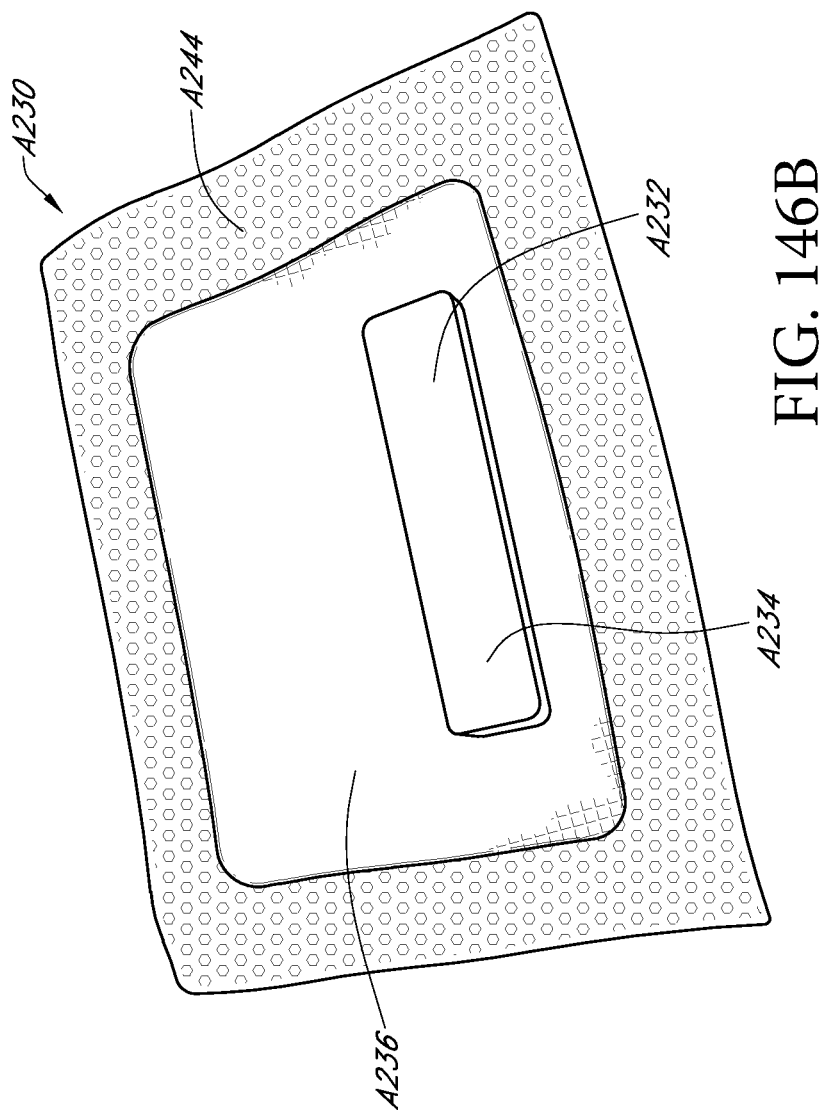

The power source for any of these embodiments can be positioned within the pump assembly housing, can be positioned adjacent to the pump assembly housing and supported by the dressing, either within or above the absorptive layers adjacent to or apart from the absorptive layers, can be positioned on top of the absorptive layers, or can be positioned in a remote position apart from the pump assembly. With reference to FIGS. 146A-146B, in any embodiments, the pump assembly A232 and/or batteries A234 can be positioned inside an edge portion of the dressing A238 and beneath the backing layer of the dressing in a depression or cutout that passes through the entire thickness of the absorptive or transmission layers so as to be positioned on top of the wound contact layer A246.

Further, any of the dressing kit embodiments disclosed herein can have an exhaust filter downstream of the pump assembly. The exhaust filter can be configured to prevent the spread of any bacteria, pathogens, or other harmful constituents from leaving the dressing through the exhaust port in the dressing kit. The exhaust filter can be supported by the pump assembly, or supported by any other layer or component of the dressing kit. For example, with reference the embodiment illustrated in FIGS. 145A-145B or in any other embodiment wherein the pump assembly is positioned beneath the backing layer, the exhaust filter can be supported by the backing layer or within or adjacent to an opening or port in or on the backing layer.

In any of the embodiments disclosed herein, including without limitation the embodiments illustrated in FIGS. 145A-145B and 146A-146B, the pump assembly A232 and/or batteries A234 can be positioned under the backing layer A244. Additionally, in some embodiments, the pump assembly A232 and/or batteries A234 can be embedded within one or more of the absorption layers A236 of the dressing A238. This configuration can reduce the profile of the dressing kit A230, improve the ability of the pump assembly and/or batteries to withstand impact, and provide a more aesthetic design. In some embodiments, the backing layer A244 can be perforated or gas permeable to permit gas exhausted by the pump assembly to pass through the backing layer A244. Additionally, in any of the embodiments disclosed herein, the backing layer A244 can be water vapor permeable to permit vapor from the liquid within the dressing to pass through the cover layer A244.

Figure 147A:
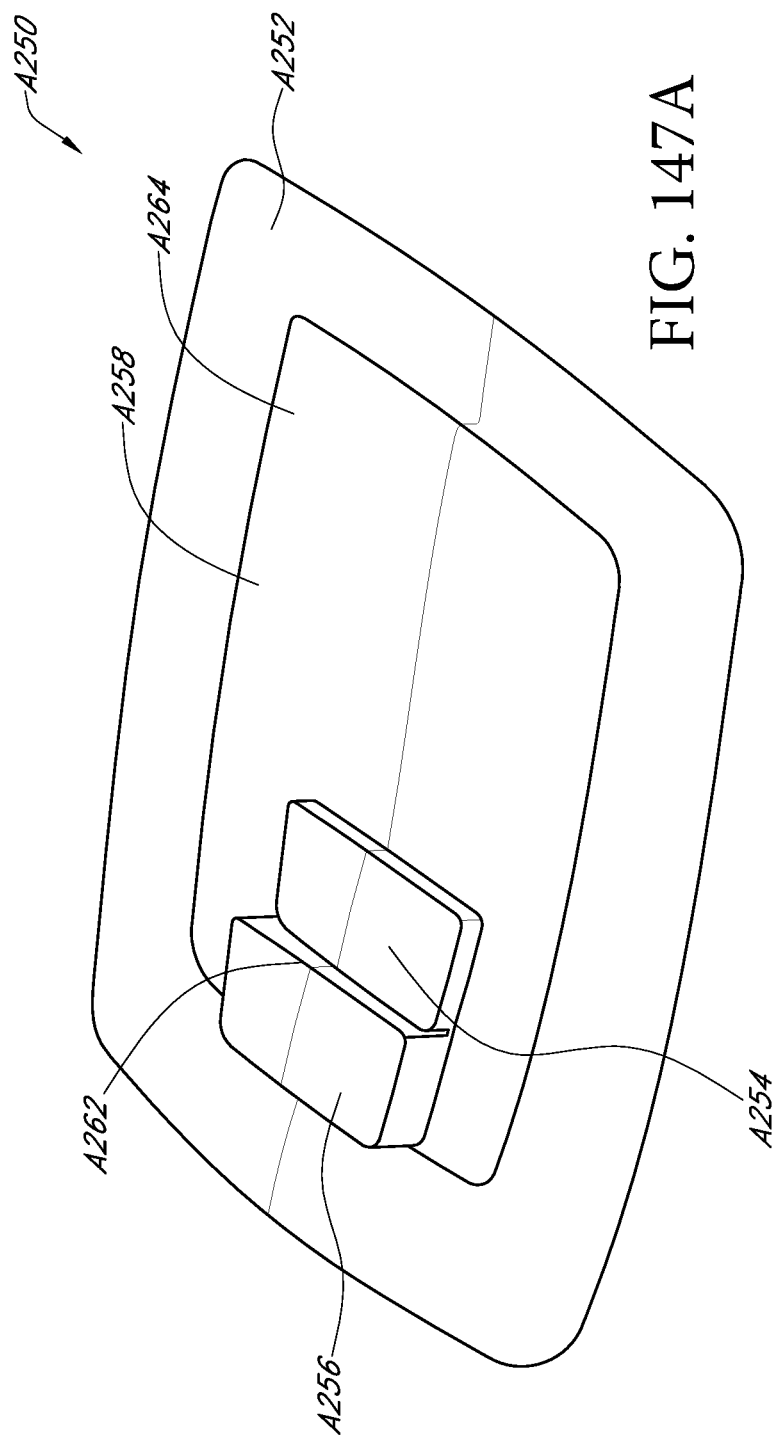
FIG. 147A illustrates additional embodiments of a dressing kit for negative pressure wound therapy.

FIG. 147A illustrates another embodiment of a dressing kit A250 having a dressing A252, a pump A254, and a power source A256. In some embodiments, as with any of the embodiments of the dressing kits disclosed herein, the pump A254 and or power source A256 can be positioned above, within, partially within, adjacent, or remote to the absorptive and transmission layers A258 of the dressing A252. Additionally, in any of the embodiments disclosed herein, as illustrated in FIG. 147A, a hinge A262 such as a living hinge can be positioned between the pump assembly A254 and the power source A256, which can have one or more batteries. The hinge A262 can improve the flexibility and conformability of the dressing A250 between the pump assembly A254 and the power source A256. In any embodiments disclosed herein, the pump assembly A254 and/or the power source A256 can be configured to be positioned in a casing that does not have a bottom surface, such that the batteries and/or pump assembly are more compact. For example, the pump assembly A254 and/or the power source A256 can be positioned above one or more of the transmission and/or absorptive layers A258 of the dressing A252 or a backing layer A264 of the dressing A252 without having any additional layers or materials beneath the pump assembly A254 and/or the power source A256.

Figure 148:
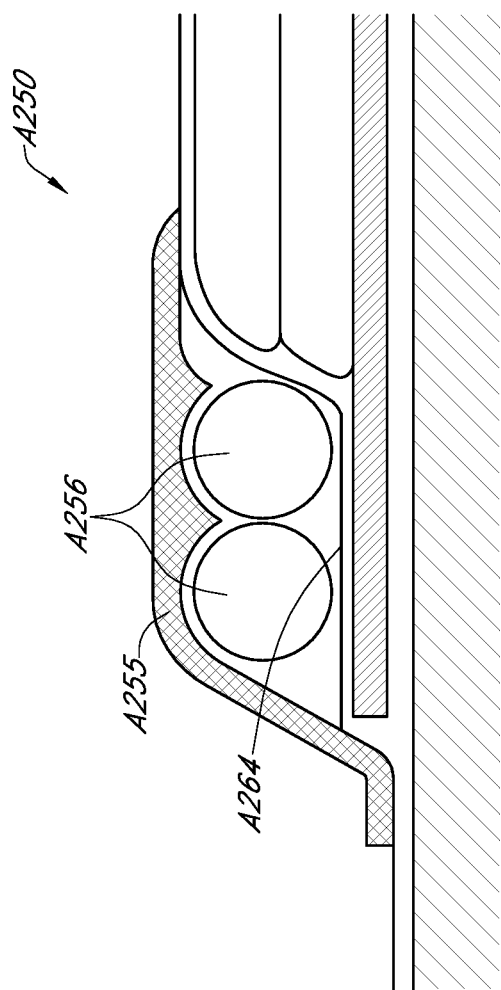
FIG. 148 illustrates an additional embodiment of a dressing kit for negative pressure wound therapy.

For example, with reference to FIG. 148, the power source A256 (which, in this illustration, consists of two batteries) is positioned directly on top of the backing layer A264 so as to minimize the profile of the dressing kit A250 in the region of the power source A256. Additionally, as illustrated, any embodiments disclosed herein can have a molding A255 configured to cover and support the power source A256 and/or the pump assembly A254.

This arrangement can reduce the profile of the pump assembly and/or the one or more batteries and improve the flexibility of the pump assembly and the one or more batteries. This can be produced in a single molding with internal components held captive between the one or more dressing layers and the upper casing of the pump assembly and/or the one or more batteries or between very thin layers within the pump assembly and the one or more batteries. The dressing kit illustrated in FIG. 147 can have any suitable pump type, including without limitation a diaphragm pump, a voice coil pump, a crank pump, or any other suitable pump.

Figure 149:
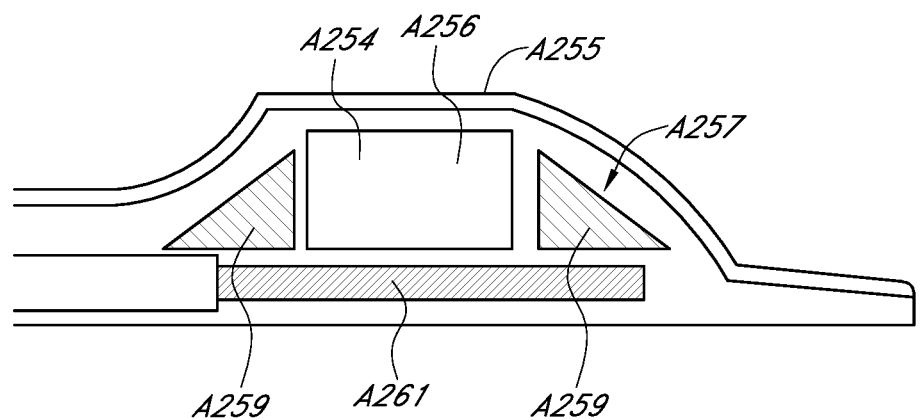

Additionally, in some embodiments, as illustrated in FIG. 149, one or more transitional members A257 can be positioned adjacent to the pump assembly A254 and/or the power source A256 to provide a smooth transition to the height or profile of the pump assembly A254 and/or the power source A256, underneath the component cover A255. The transitional members A257 can be formed from foam, silicone or other rubber, or other soft or malleable materials to provide flexibility and comfort to the dressing and the user. Additionally, though not required, a thin spacer A261 can be positioned beneath the pump assembly A254 and/or the power source A256.

Figure 147B:
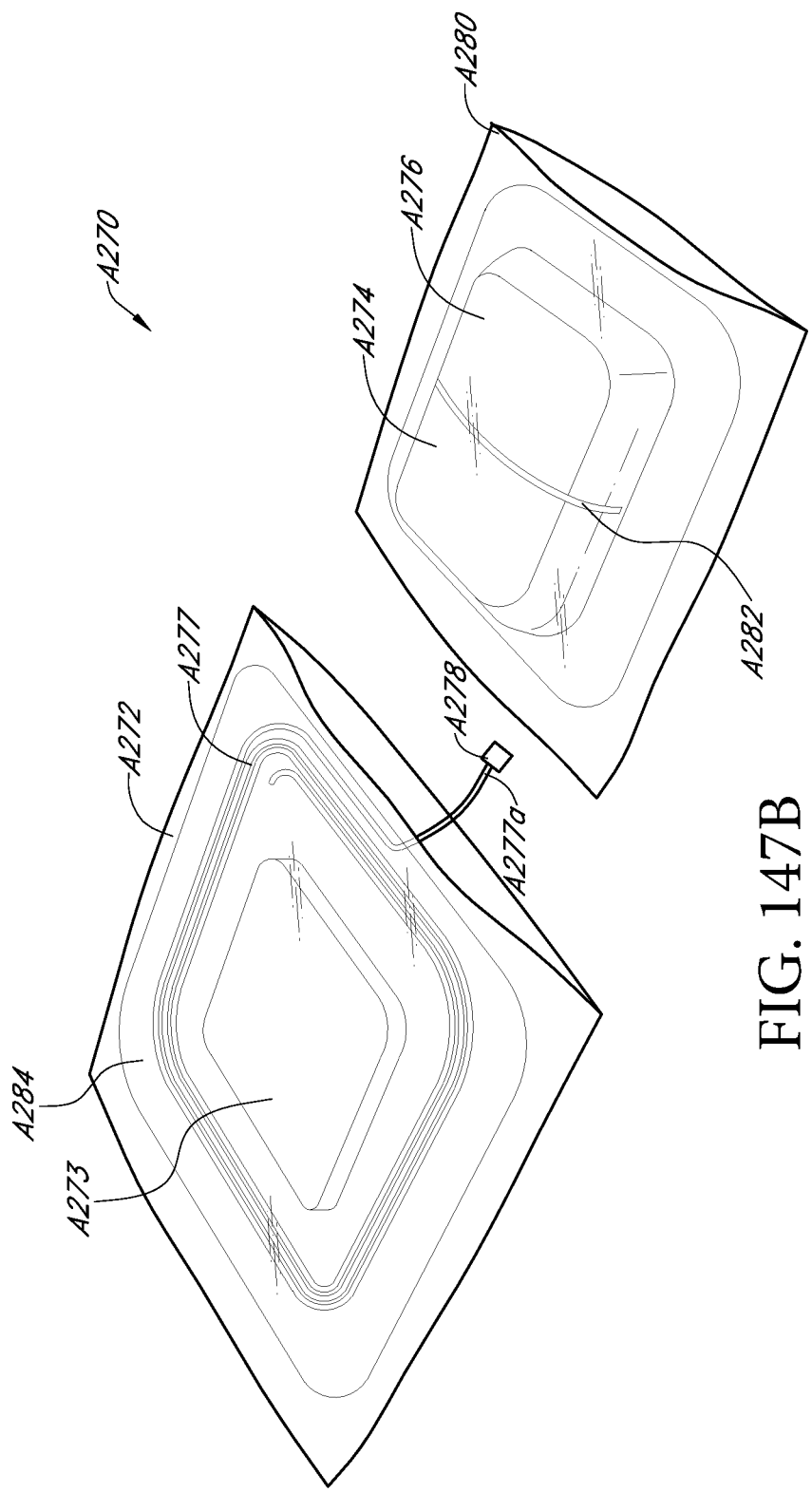
FIGS. 147B-147D illustrate additional embodiments of a dressing kit for negative pressure wound therapy.
Figure 147C:
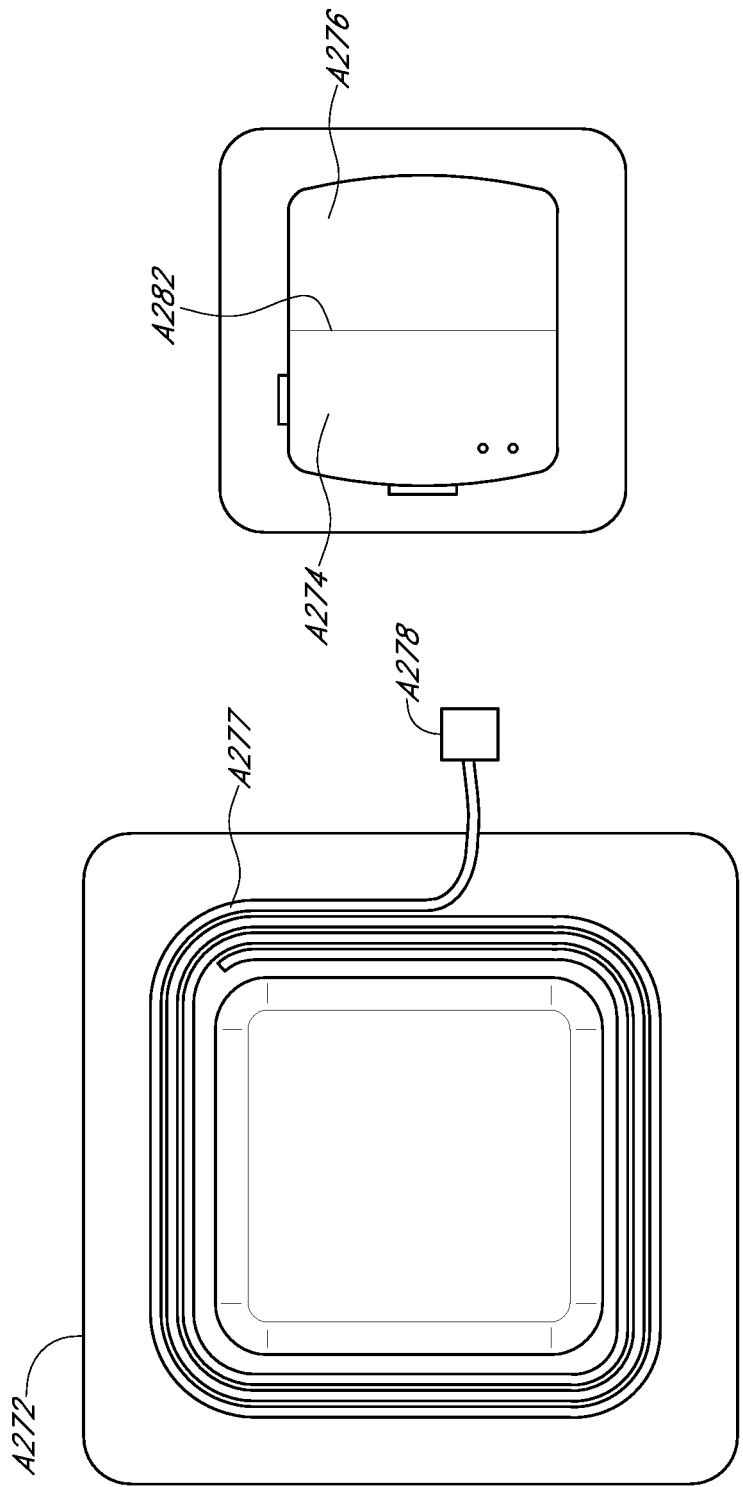
Figure 147D:
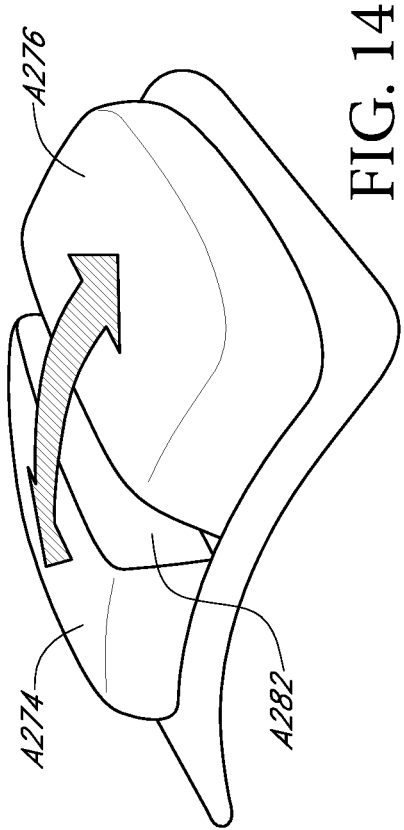

FIGS. 147B-147D illustrates another embodiment of a dressing kit A270 having a wound dressing A272, a pump assembly A274, a power source A276, and a conduit A277 configured to communicate the negative pressure produced by the pump assembly A274 to the space between the dressing A272 in the wound. In some embodiments, the conduit A277 can have a connector A278 fixed to a distal end A277a of the conduit A277 configured to connect with the pump assembly A274. A complementary coupling or mating feature can be supported by the pump assembly A274 to receive the connector A278 and provide a substantially sealed connection therewith. In some arrangements, the conduit A277 can be supported on the dressing A272 in a helical or winding arrangement around the absorptive layers A273 of the dressing A272. Additionally, the conduit A277 can be held in place with a supplemental backing layer A284 configured to adhere to the top of the conduit A277 and the dressing A272 and to hold the conduit A277 in the desired position. The supplemental backing layer A284 can be configured to permit a medical practitioner or user to remove a desired length of conduit A277 from the coil conduit so as to position the pump assembly A274 at any desired position either on the dressing A272 or remote to the dressing A272. Additionally, in some embodiments, the supplemental backing layer A284 can have a cut out or opening in the middle thereof over the portion that covers the dressing and/or absorptive layers A273 so as to not inhibit vapor transmission from within the dressing. Additionally or alternatively, the supplemental backing layer A284 can have a plurality of perforations therein configured to permit vapor transmission through the dressing layers.

Alternatively, the conduit A277 can be adhered to the top of the dressing A272 around a perimeter of the dressing and/or transmission layers A273 using adhesive or any other suitable mechanism that will removably secure the conduit A277 in the desired location, but permit a medical practitioner or user to remove a desired length of conduit A277 from the coil so as to position the pump assembly A274 at any desired position either on the dressing A272 or remote to the dressing A272. In any embodiments disclosed herein, the pump assembly A274 and power source A276 can be supported on a separate support member A280 so that the pump assembly A274 and the power source A276 can be positioned at any desired location either remotely relative to the dressing A272, adjacent to the dressing A272, or even on board the dressing A272. The support member A280 can have adhesive on a bottom surface thereof for each into any desired surface, or any other desired fastening mechanism such as hook and loop connectors, snaps, wires, or otherwise. Additionally, as described above, a flexible hinge A282 can be positioned between the pump assembly A274 and the power source A276 to increase the flexibility and conformability of the support member A280. Any of the dressing kit embodiments disclosed herein can have a similar arrangement of conduit as disclosed for the dressing kit A270, or any of the other features, details, or configurations disclosed were shown for dressing kit embodiment A270.

Figure 150:
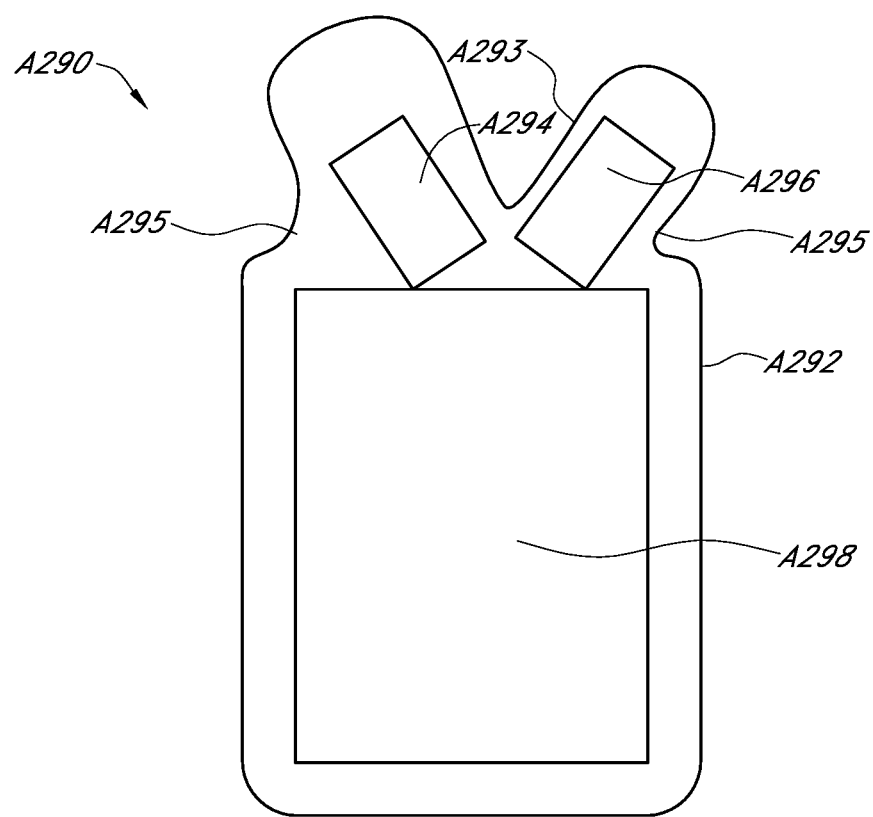

FIG. 150 illustrates another embodiment of a dressing kit A290 having a dressing A292, a pump assembly A294, and a power source A296 supported by the dressing A292 in some embodiments, the pump assembly A294 and the power source A296 can be positioned adjacent to the one or more absorptive and/or transmission layers A298 of the dressing kit A290. As illustrated therein, the pump assembly A294 and the power source A296 can be supported on portions of the dressing A292 extending in a V-shaped pattern away from the dressing pad A298. In other words, a cut out A293 can be formed in the dressing A292 to permit greater flexibility and conformability of the dressing in the region of the pump assembly A294 and the power source A296. In some embodiments, the cut out can have a V-shape. In some embodiments, the cut out A293 can have a U-shaped, or a smooth cutout shape.

Additionally or alternatively, any of the embodiments disclosed herein of the dressing A292 can also have additional cutouts A295 formed in the dressing A292 to the outside of the pump assembly A294 and/or the power source A296 to also increase the flexibility and conformability of the dressing. As mentioned, this arrangement can improve the conformability and flexibility of the dressing and enable the pump assembly A294 and/or the power source A296 to better mold around a curved body surface. Additionally, in some embodiments, this arrangement can have a pinpoint hinge rather than a lengthwise hinge to permit the components to better mold over curved or complex surface contours. Any of the dressing kit embodiments disclosed herein can have the pump assembly and the power source arranged on the dressing in this configuration, and can have a dressing of this shape.

FIGS. 151A-151C illustrate another embodiment of a dressing kit A310 wherein the pump assembly A314 and the power source A316 are supported by the dressing A312 and can have a hinge A322 therebetween. In some embodiments, the hinge A322 can be a living hinge. The hinge A322 can improve the flexibility of the dressing and the components supported thereby. Additionally, in some embodiments, the edges of the pump assembly A312 and/or the power source can be tapered and can be flexible.

Additionally, in any embodiments disclosed herein, for example, FIGS. 152A-152C illustrate an embodiment of the dressing kit A330 that can have a dressing member A332, a pump assembly A334, a power source A336, and a pressure indicator A342 supported by the dressing A332. Additionally, in some embodiments, a flexible hinge A344 can be molded into, formed on, or positioned on the support layer or support material used to house or support the pump assembly A334 and the power source A336, the hinge A344 being positioned between the pump assembly A334 and the power source A336. The pressure bubble or pressure indicator can be positioned A342 were supported by the dressing A332 in any desired location on the dressing A332.

Additionally, as with any other embodiments disclosed herein, one or more press studs A346 can be supported on an outside surface of the cover layer of the dressing A332, the press studs being configured to receive complementary fastening features on the power source A346 and/or the pump assembly A334. In some embodiments, as is illustrated in FIGS. 152A-152C, a filter layer can be positioned beneath the pressure indicator A342.

FIG. 153 illustrates another embodiment of a dressing kit having a dressing A352, a pump assembly A354, and a power source A356. In some embodiments, the pump assembly A354 and/or the power source A356 can be removably attached to the dressing member A352 using one or more stud connectors A362 fixed to the dressing member A352. The use of stud connectors A362 (also referred to herein as metal connectors or snap connectors) to support the battery and/or pump assembly on the dressing can enable the removability of the pump and/or power source from the dressing for replacement or for disposal. Additionally, the snap connectors can be used to not only removably support the battery and/or pump assembly on the dressing, but also to provide an electrical connection between the one or more batteries and the pump assembly.

In some embodiments, a first snap connector A362a can engage a first female receiver A364a positioned on a housing for the pump assembly A354. Similarly, a second snap connector A362a can engage a second female receiver A364a positioned on housing for the power source A356. The first snap connector A362a can be electrically connected or in communication with the second snap connector A362b so that a current supplied from the power source connected to the second snap connector A362b can be communicated to the pump assembly through such electrical connection or wiring between the two snap connectors. Additionally, in any embodiments disclosed herein, the pump and battery module could have a hinge therebetween for added conformability and flexibility. A hinge could also be used to connect the pump and battery module to the dressing kit. Further, in any embodiments disclosed herein, the battery and the pump assembly can be separate modules that can be independently removed and/or replaced.

In any of the embodiments disclosed herein, the batteries can be positioned and supported apart from the dressing. The batteries can be secured to the body or to the dressing using tape, a local pad, snaps, a clip supported by the dressing, Velcro, and/or any other desired fastening member. The batteries can be inserted and removed to facilitate activation and deactivation of the pump, and to permit replacement and/or disposal of the batteries.

Additionally, in any embodiments disclosed herein, one or more press studs can be supported by the dressing. The one or more press studs can be configured to engage complementary connectors supported by the pump assembly and/or the one or more batteries to permit the pump assembly and/or the one or more batteries to be removably snap supported by the dressing. The stud connectors can also be used to create an electrical connection between one or more batteries and the pump assembly and, accordingly, can be used to activate the pump.

The press studs or snap connectors can allow the one or more batteries to be electrically disconnected from the pump assembly until one or both of the components is snapped into the snap connectors. Additionally, if there are two or more batteries, such batteries can also have stud type electrically conductive connectors that permit the batteries to be separately supportable by the dressing so that the power circuit can be completed by snapping each of the one or more batteries into the dressing. In this configuration, the batteries and/or pump assembly can be snapped into position following sterilization of the dressing kit. Such assembly can also serve to activate the pump.

Additionally, any of the dressing embodiments disclosed herein can be configured to support one or more power source modules or pump assemblies on or adjacent to the dressing. For example, having a multiple number of power sources (e.g., a plurality of batteries, or any combination of batteries, fuel cells, capacitors, and photovoltaic cells) can improve the flexibly and conformability of the dressing and can reduce the profile of the dressing. The dressing can be configured such that the batteries are replaceable or interchangeable with similar or different batteries, selectable depending on the duration of time the dressing is to be on the patient. In configurations wherein the power source is preferably removable, the power source can be snapped into the dock or otherwise removably attachable and detachable from the dressing and configured to be lifted out of the dock or otherwise removed from the dressing when it is time to either disposed of or replace the batteries or power source.

The batteries can be positioned within or supported by the docks prior to positioning the dressing on the patient's body. In embodiments using conductive connectors fixed to the dressing and or the pump assembly, starting or restarting the pump can be achieved by inserting or re-inserting the one or more batteries in the docks, so as to permit a user to control an operation of the pump by inserting or re-inserting the batteries.

FIGS. 154A-154C illustrate another dressing kit embodiment A370 having a pump assembly A374 and a power source A376 supported on either of a dressing member A372 or a separate support member. In some embodiments, the dressing member A372 can have a depression A373 therein configured to receive the pump assembly A374 and/or power source A376. With reference to FIGS. 154A-154C, in any embodiments disclosed herein, one or more batteries can be supported in a removable cartridge configured to be removably engageable with a housing A377 surrounding at least a portion of the power source A376. In some embodiments, the housing A377 can also support or surround the pump assembly A374. With reference to FIG. 154B, in some embodiments, the housing A377 used to support the power source A376 can have a lid, cover, or hatch A379 that can be opened to access the power source A376, which can be batteries.

In some embodiments, the hatch A379 can have one or more battery terminals or electrical connections thereon configured such that, during sterilization or before the pump is to be activated, the battery terminals are out of contact with the power source A376. After sterilization or before therapy is to be initiated, the hatch can be closed to create an electrical connection between the power source A376 and the pump assembly A374, thereby initiating the negative pressure wound therapy.

FIGS. 155A-155C illustrate another dressing kit embodiment A390 having a pump assembly A394 and a power source A396 supported on either of a dressing member A392 or a separate support member. With reference to FIGS.

155A-155C, similar to the dressing kit embodiment A370, in any embodiments disclosed herein, one or more batteries can be supported in a removable cartridge configured to be removably engageable with a housing A397 supported by the dressing member A392. In some embodiments, the housing A397 can also support or surround the pump assembly A394 if desired. However, in some embodiments, as in the illustrated embodiment, the pump assembly A394 can be separately supported by the dressing member A392. The dressing kit A390 can be configured such that the power source can be removable and disposed of and/or replaceable with a replacement power source when desired. For example, any of the dressing kits disclosed herein can come with a first power source and a second power source that can be used sequentially.

Figure 156A:
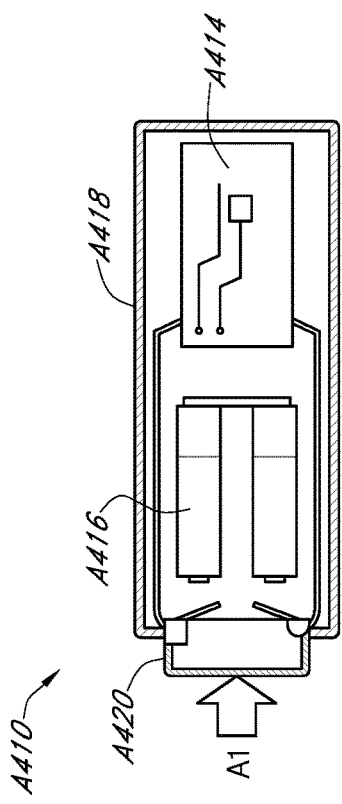
Figure 156B:
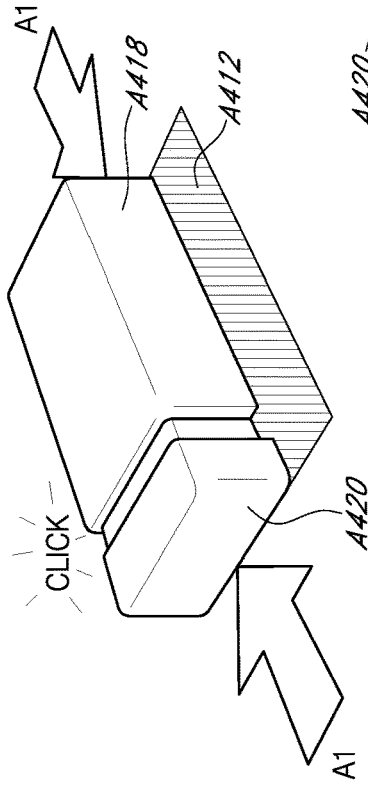
Figure 156C:
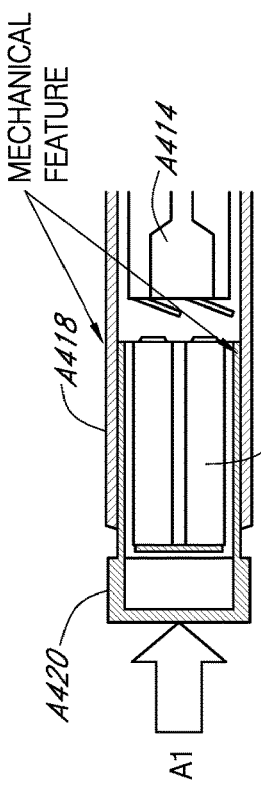
Figure 157B:
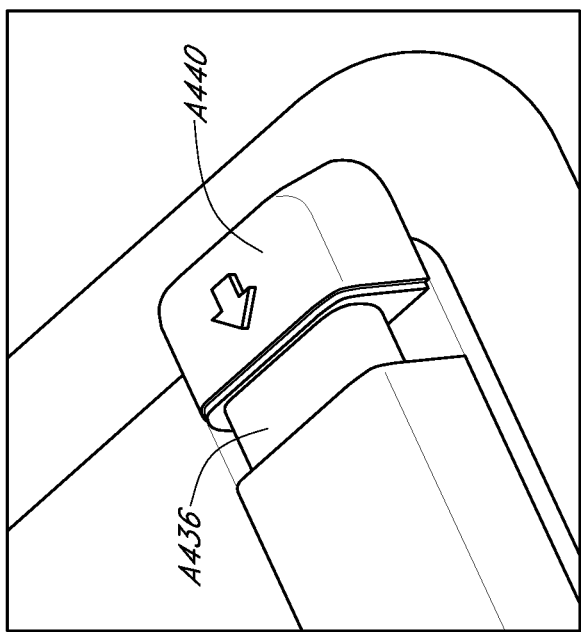
Figure 157C:
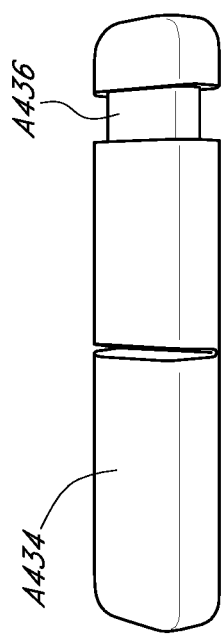
Figure 157A:
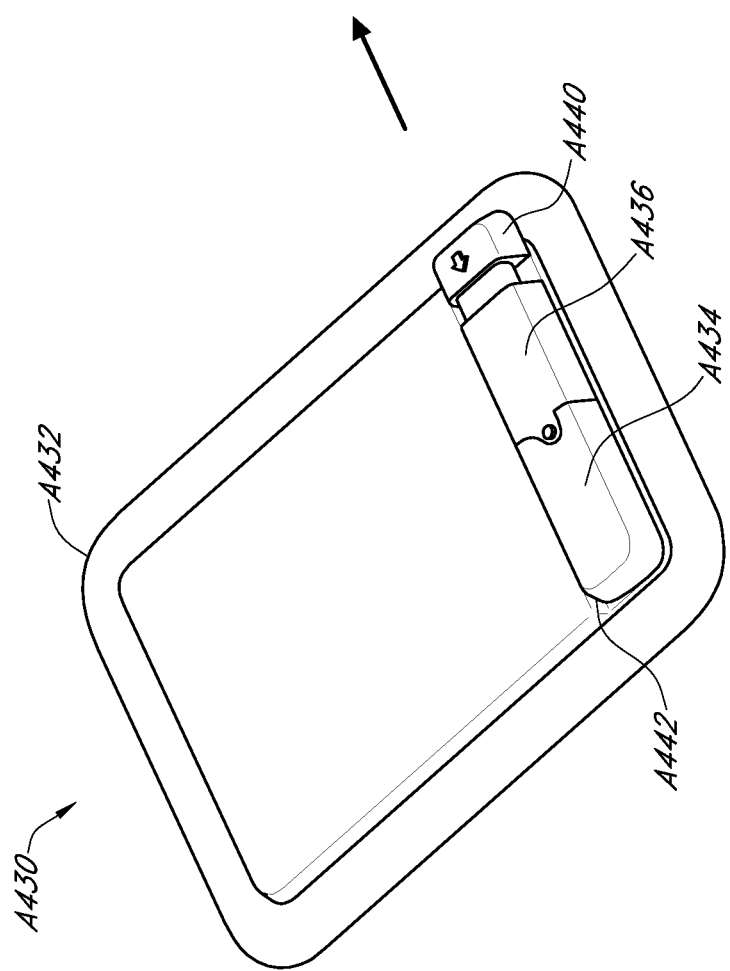
Figure 157D:
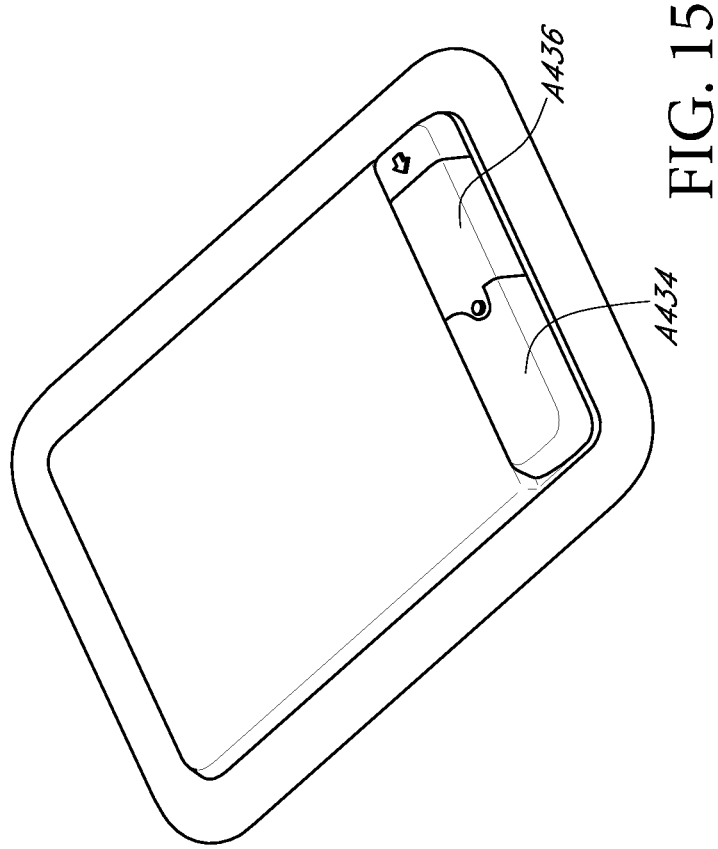
Figure 157E:
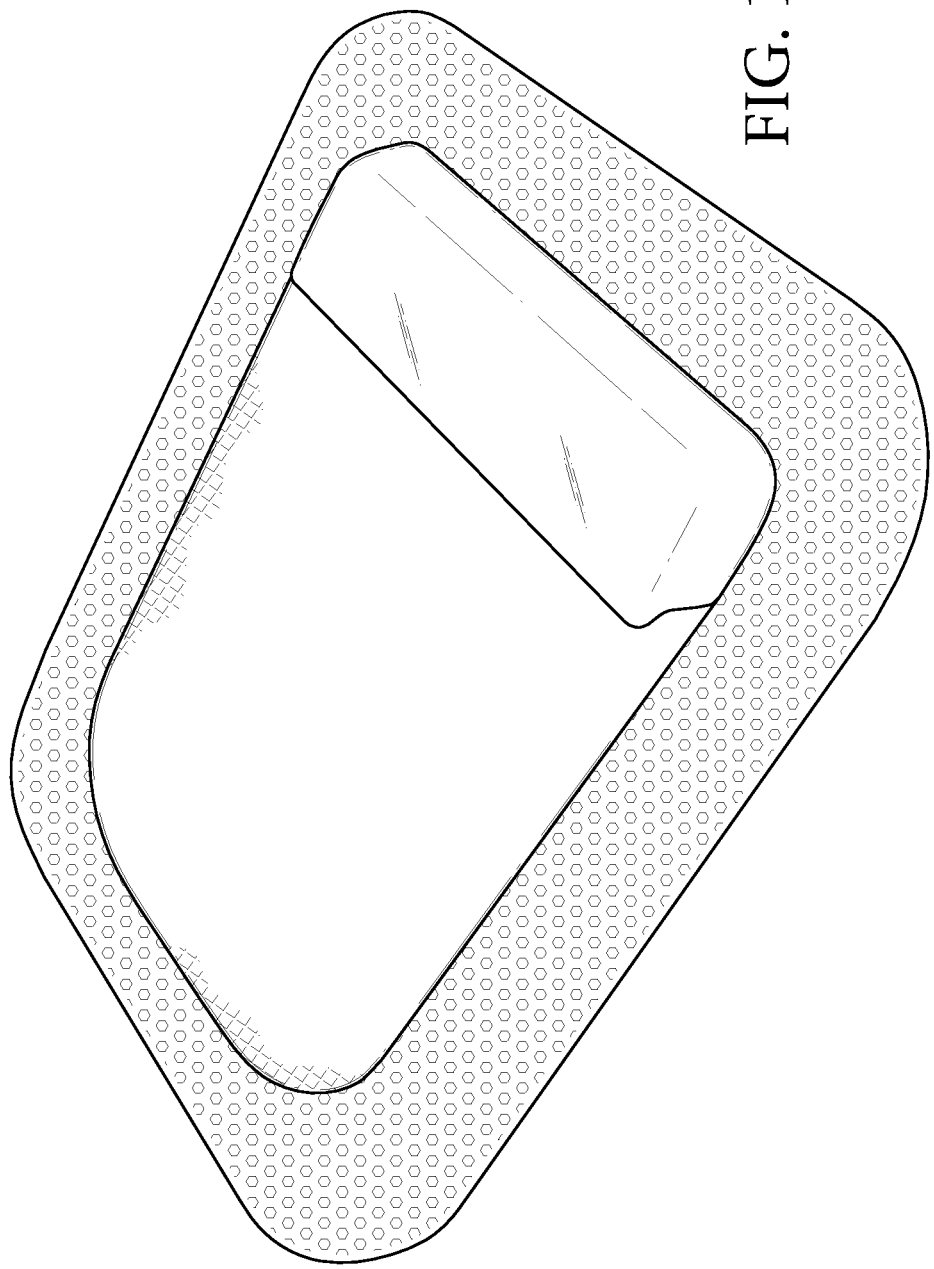
Figure 157F:
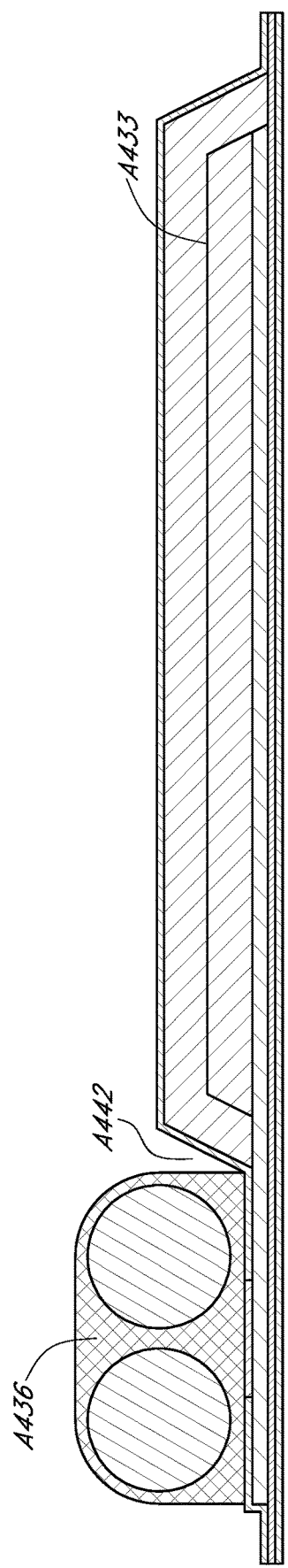

FIGS. 156A-156C illustrate an embodiment of a dressing kit A410 having a support layer A412, a pump assembly A414, a power source A416, and a housing or support member A418 configured to support the power source A416 and/or a pump assembly A414. In some embodiments, the power source A416 can be removably attachable to or engageable with the support member A418. The support member A418 can be configured to have conductive terminals such that, when the power source A416 is engaged therewith, power is automatically provided to the pump assembly A414 to either provide the power to the pump assembly A414 (but requiring a switch or button to activate the pump assembly) or to power and activate the pump assembly A414 to initiate negative pressure. Additionally, in some embodiments, multiple batteries or sources of power can be provided with the dressing kit A410. For example, a first battery pack A416 and a second battery pack A416 can be provided with the dressing kit A410 to provide interchangeable power sources. In some embodiments, the support member A418 can be attached directly to a dressing backing layer, or can be attached to a separate support layer, such as support layer A412, to enable the pump assembly and the power source to be attached adjacent to the wound and the dressing member positioned over the wound.

As an example, as illustrated in FIGS. 156A-156C, one or more batteries can be supported in a removable cartridge or carrier A420 configured to be removably engageable with a housing A418 supported by the support layer A412. In some embodiments, the housing A418 can also support or surround the pump assembly A414 if desired. However, in some embodiments, as in the illustrated embodiment, the pump assembly A414 can be separately supported by the support layer A412. The dressing kit A410 can be configured such that the power source can be removable and disposed of and/or replaceable with a replacement power source when desired. Any of the dressing kits disclosed herein can come with a first power source and a second power source that can be used sequentially.

With reference to FIG. 156C, the dressing can be configured such that sliding the batteries into engagement with the battery terminals (in the direction indicated by arrow A1 in the figures) will result in an audible click, to alert a user regarding the position of the components of the battery enclosure that the battery circuit is closed. Any of the dressing kit embodiments disclosed herein can be supported in packaging configured such that, while the dressing kit is supported in the packaging, the components of the battery pack or pump assembly are held in a first or non-operational position and prevented from moving to a second operational position. In this configuration, when the components are in the first position, the pump is non-operational due to the fact that the battery terminals are not in contact with the one or more batteries. For example, the packaging supporting the dressing kit can prevent a lid of the battery housing from moving to the second position by holding the housing lid or cap in the first position. The packaging can have protrusions that are positioned between the housing lid or cap and the body of the battery housing that separate the battery housing lid from the body of the battery housing. Once the dressing kit is removed from the packaging, the battery housing lid or cartridge can be slid inward, permitting the terminals to contact the batteries so that the pump can be activated. In this configuration, the battery housing can serve as an activation button. Sliding the lid out of contact from the batteries can stop the operation of the pump.

The dressing kit A430 embodiment of FIGS. 157A-157F is similar to the dressing kit A410 embodiment of FIGS. 156A-156C, having a slideable carriage A420 configured to move the power source A436 in contact with the pump assembly A434. Additionally, the dressing kit A430 can have a flexible hinge A442 positioned between the housing used to support the power source and pump assembly, and the absorption and/or transmission layers A433 of the dressing A432 to permit greater flexibility and conformability of the dressing A432.

Figure 158B:
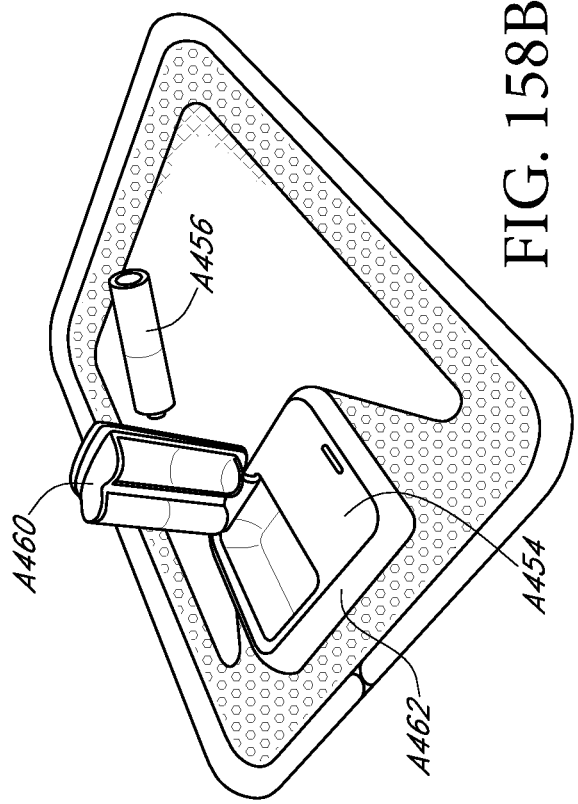
Figure 158A:
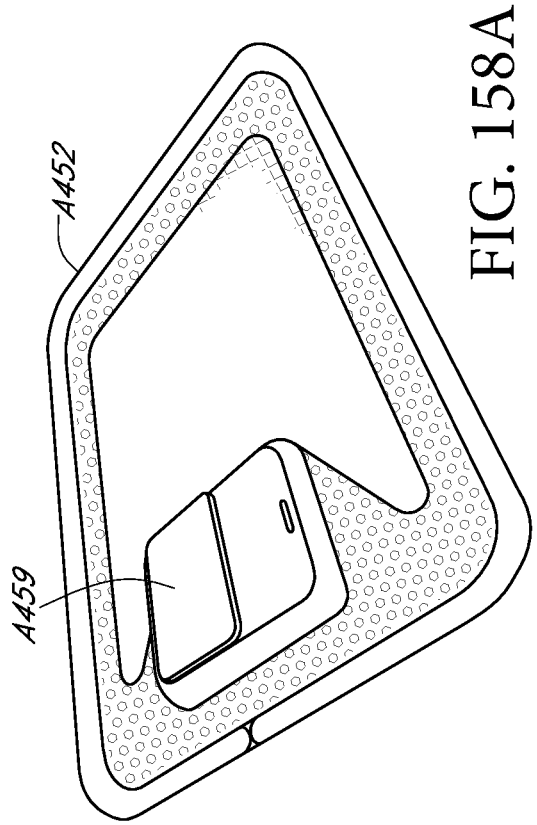

Additionally, with reference to FIGS. 158A-158B, in some embodiments, the dressing kit A450 can have a dressing A452, a pump assembly A454, a power supply A456, and a support member A462 configured to support the pump assembly A454 and the power supply A456. The support member A462 can be supported by the dressing member A452 and can enable the power supply A456 to be removably supported by the dressing member A452. In some embodiments, the power supply A456 can be supported in a carriage A460 hingeably supported by the support member A462 or having an adhesive cover that can hold the power supply in the desired position within the support member A462.

Figure 159A:
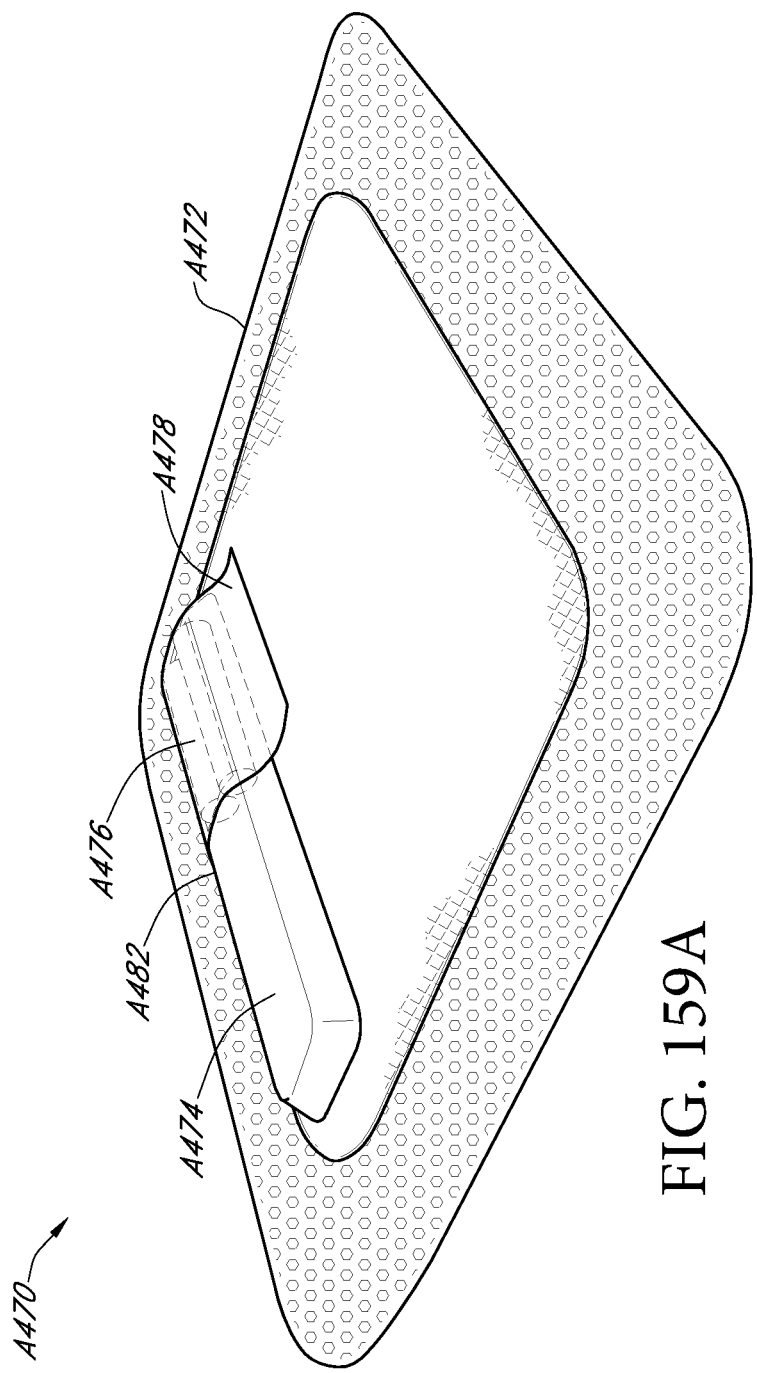
Figure 159B:
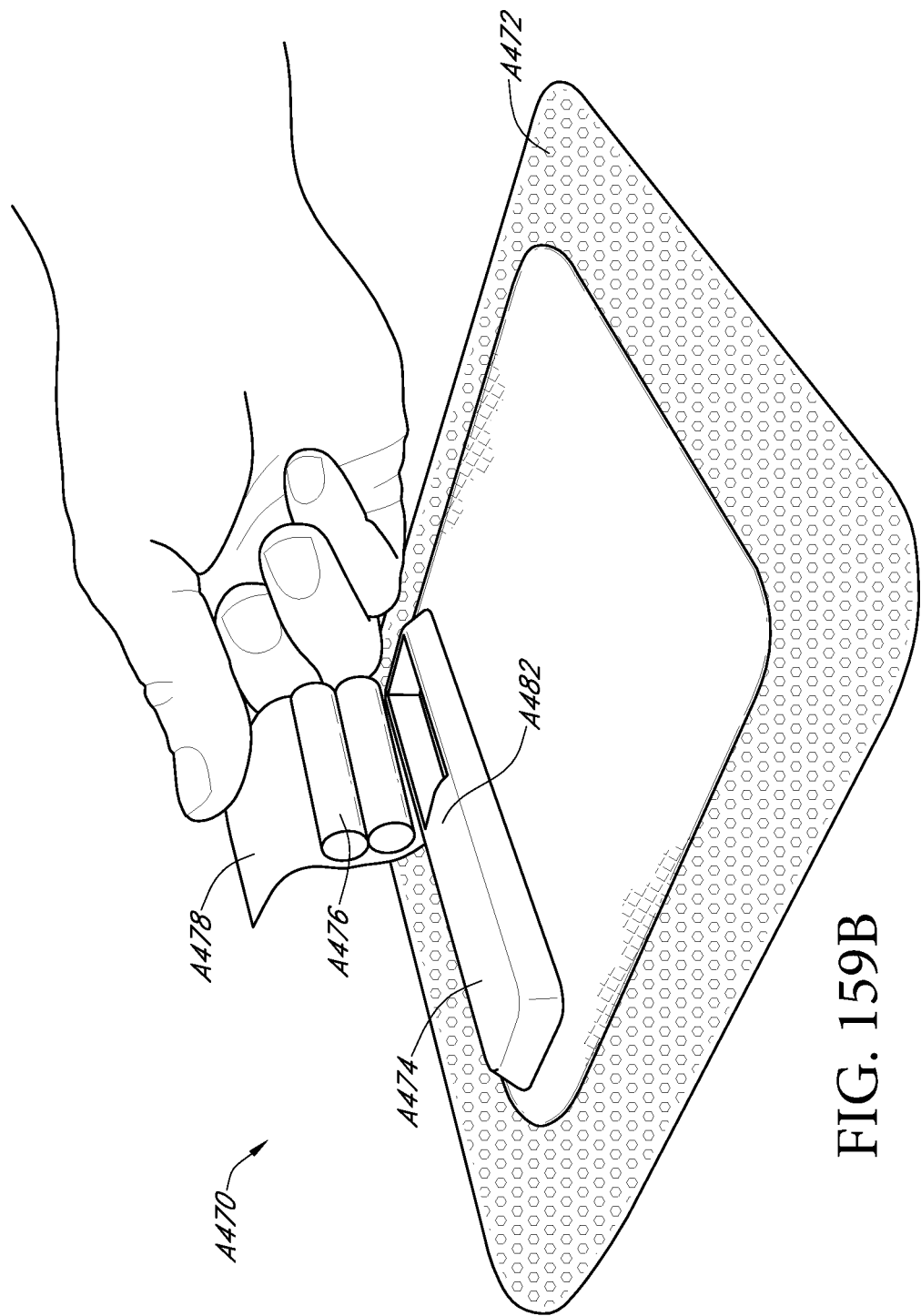
Figure 159C:
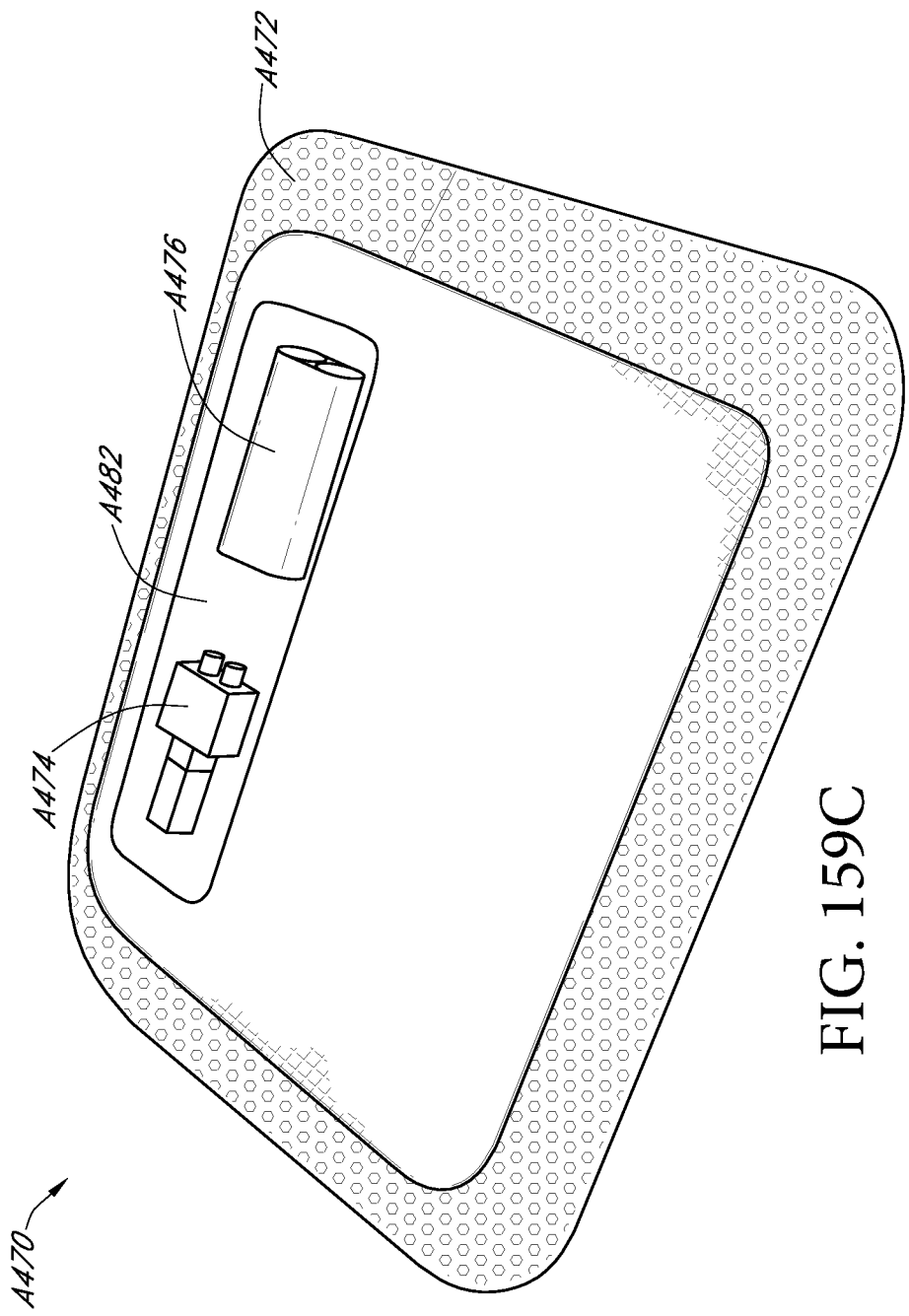
Figure 159D:
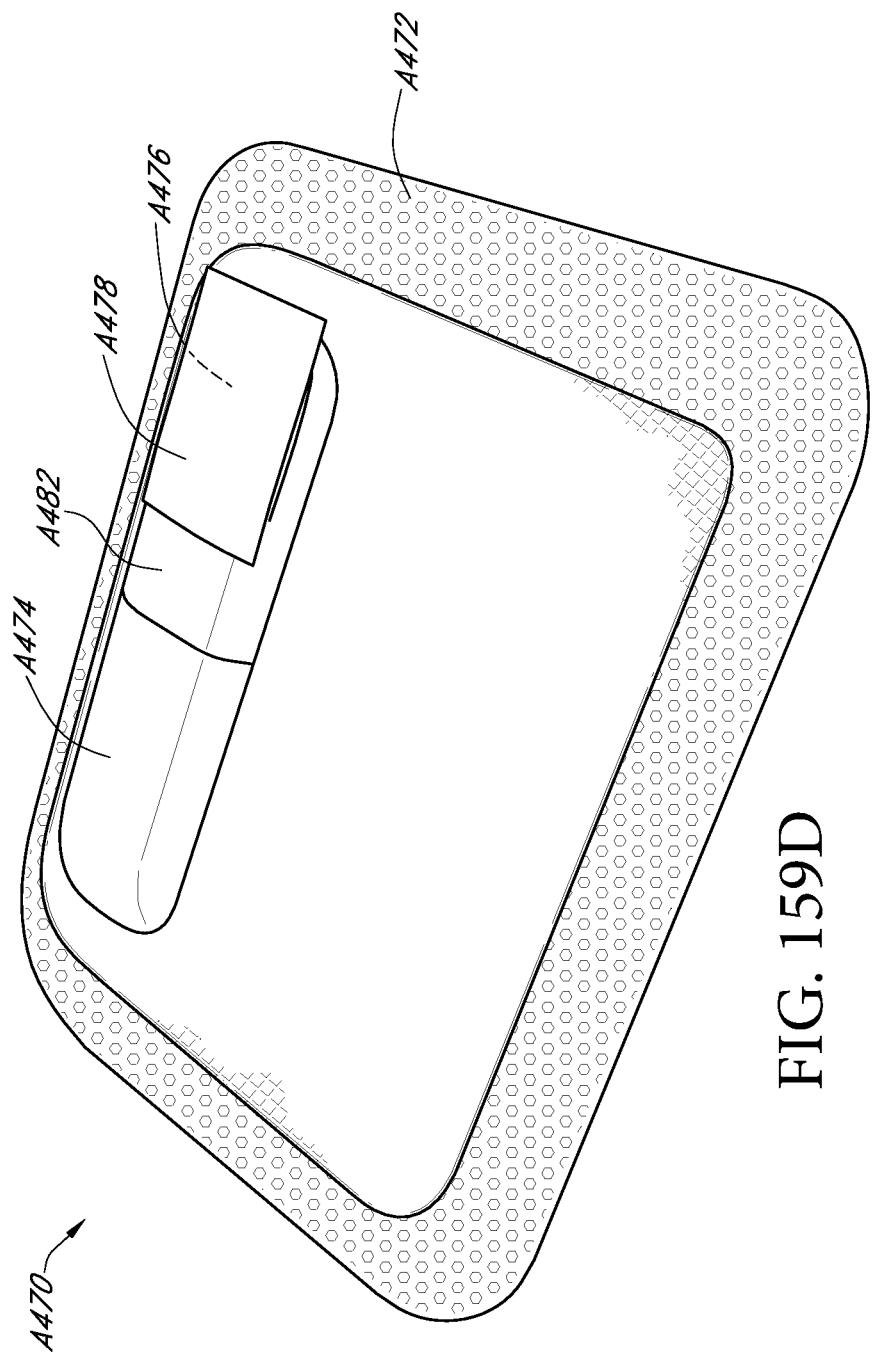
Figure 159E:
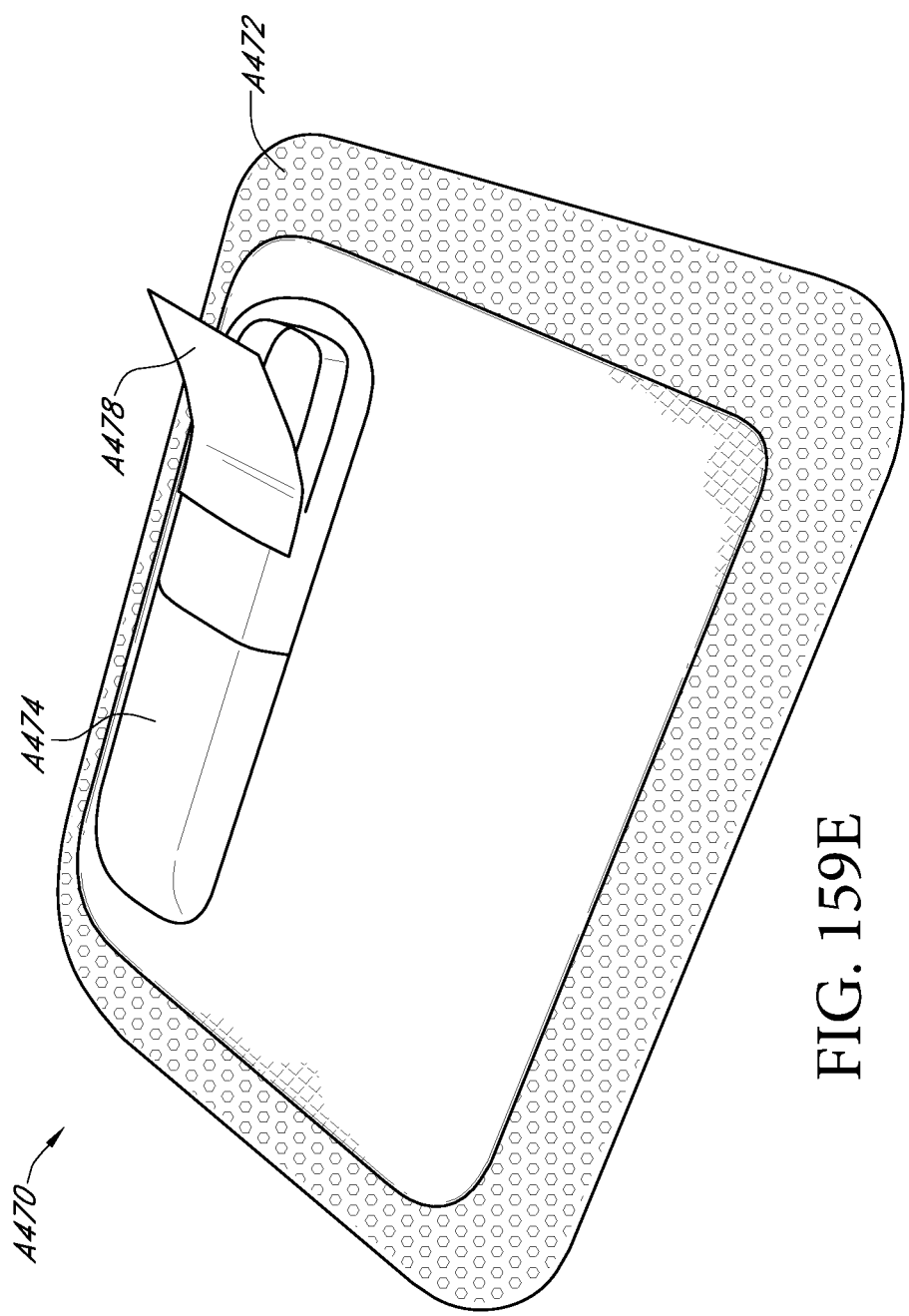
Figure 159F:
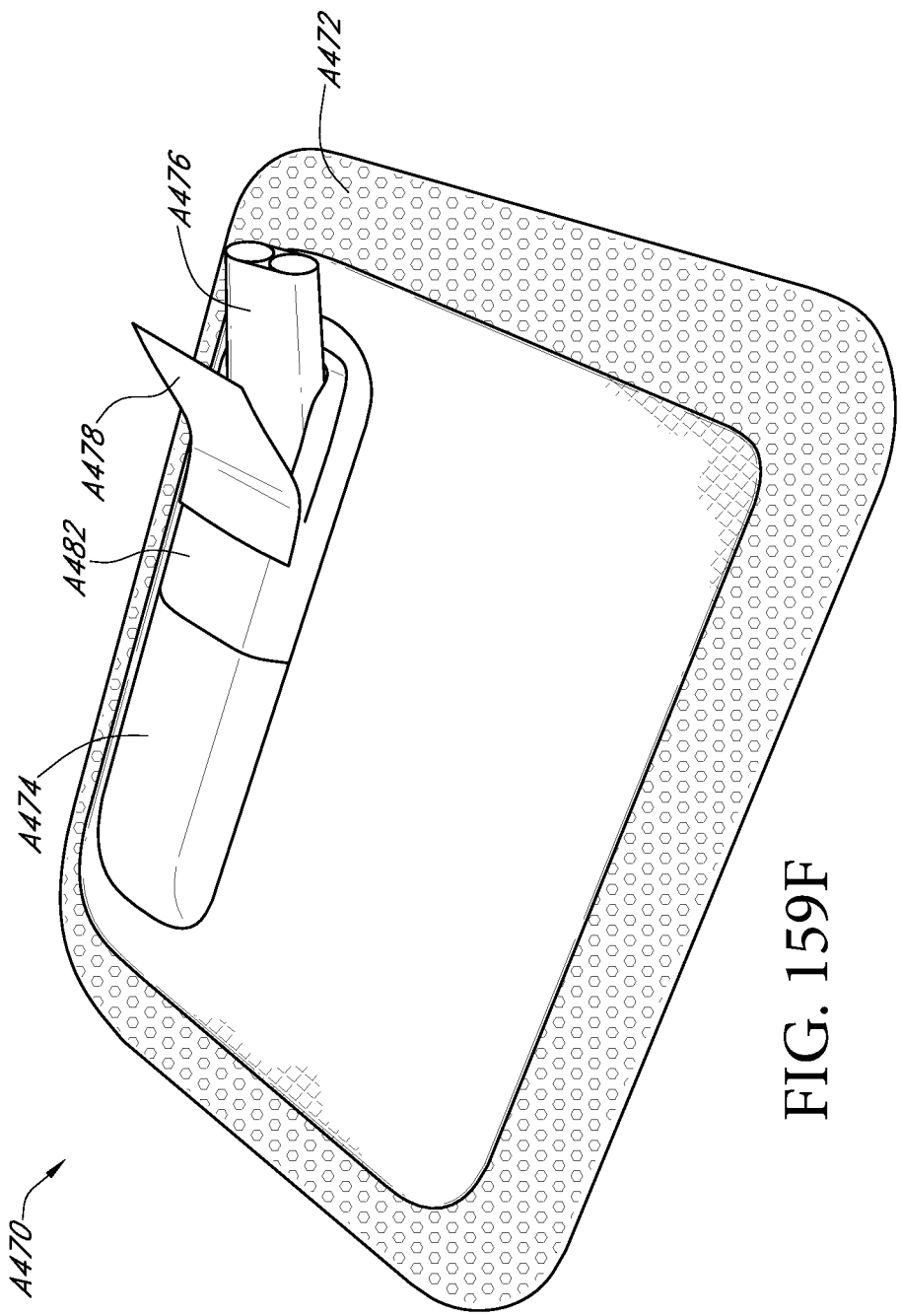
Figure 159G:
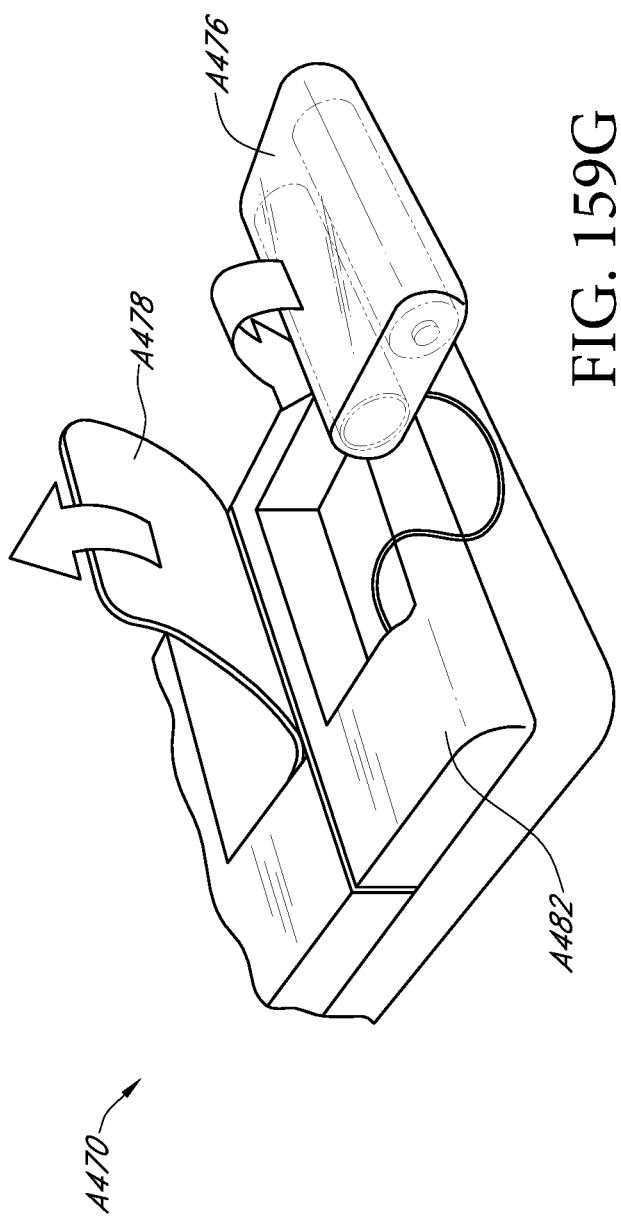

FIGS. 159A-159G illustrate another embodiment of a dressing kit A470 having a dressing A472, a pump assembly A474, a power supply A476, and a support member A482 configured to support the pump assembly A474 and/or the power supply A476. The support member A482 can be supported by the dressing member A472 and can enable the power supply A476 to be removably supported by the dressing member A472. In some embodiments, the power supply A476 can be supported by an adhesive strap A476 having one end thereof fastened or secured to the support member A482. The adhesive strap A476 can be sealingly closed over the support member A482 to provide a mechanism for holding the power source A476 in the support member A482. The strap can have a tabbed portion for grasping, and can be flexible enough to deflect away from the dressing when the user wishes to withdraw the battery. The adhesive strap can be colored and/or labeled to alert a user that the batter should be removed before the medical device is incinerated or otherwise disposed of. In some embodiments, as illustrated in FIG. 159C, the power source can be positionable in a compartment in the support member A482 and not attached to the strap A476.

Figure 160C:
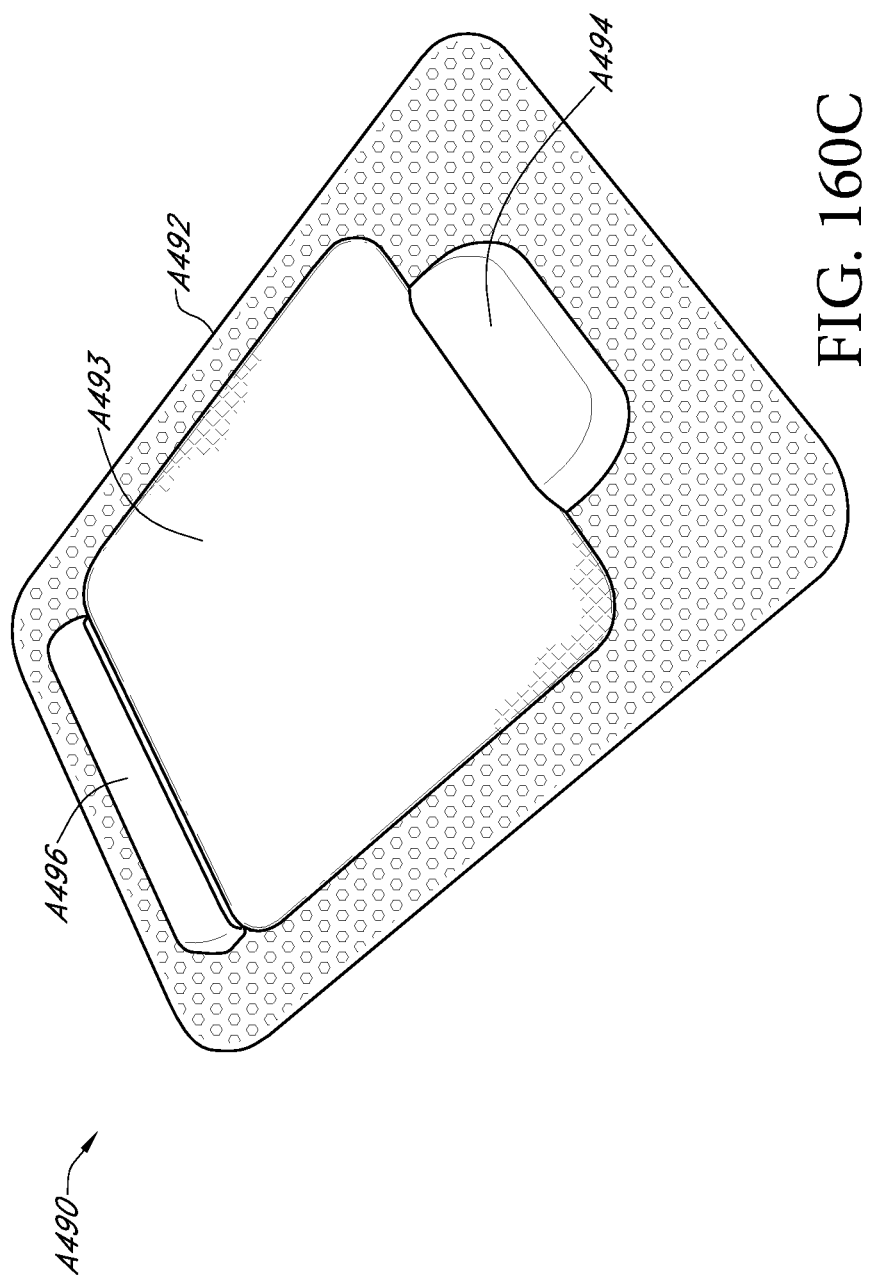
Figure 160D:
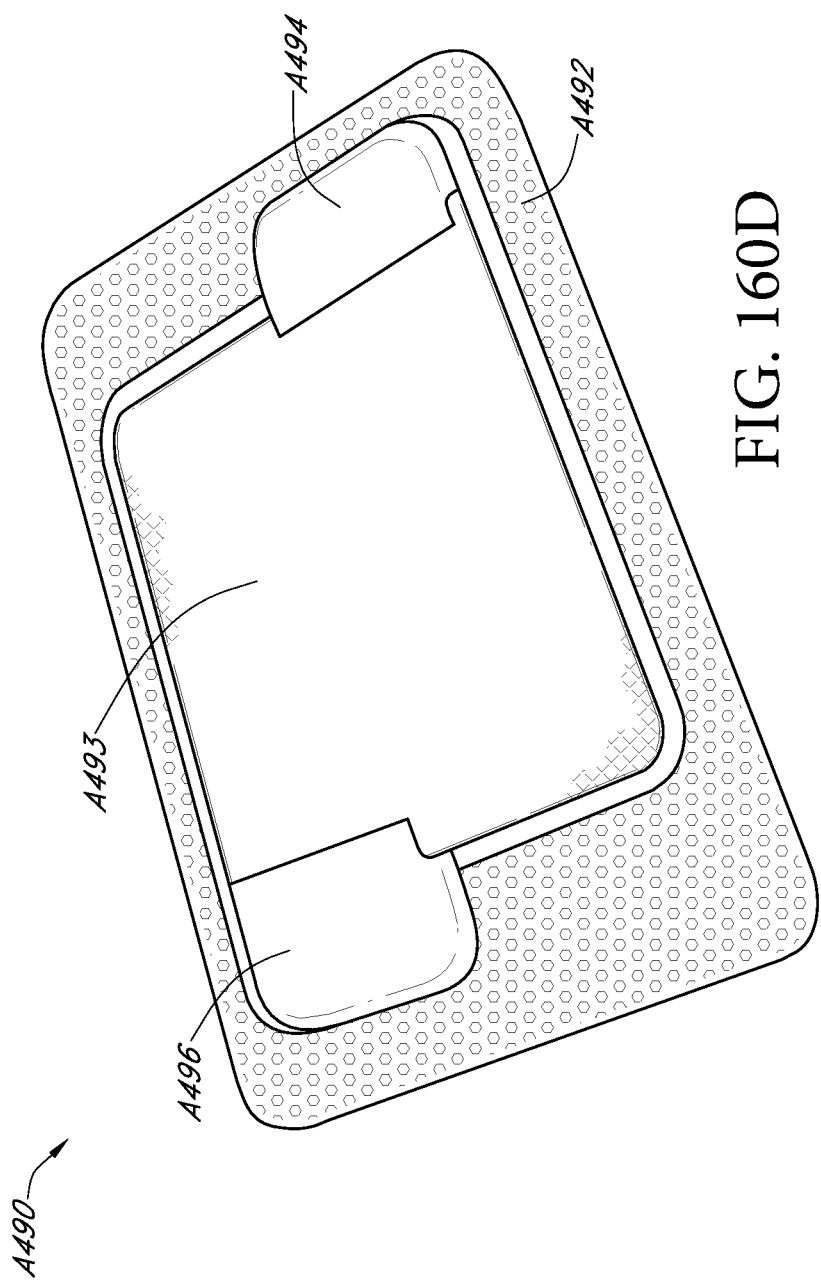
Figure 161A:
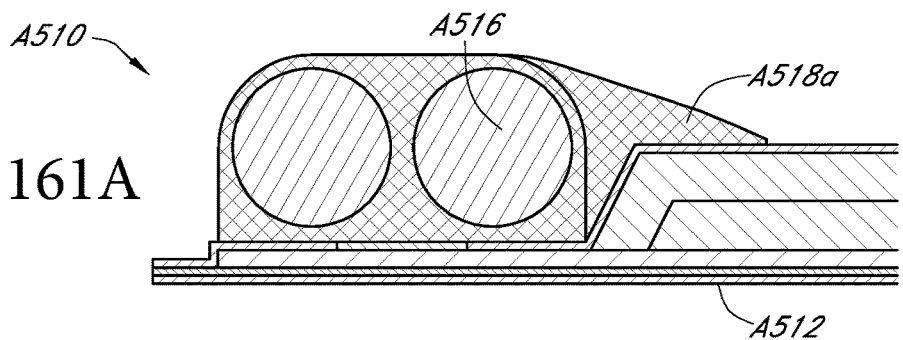
Figure 161B:
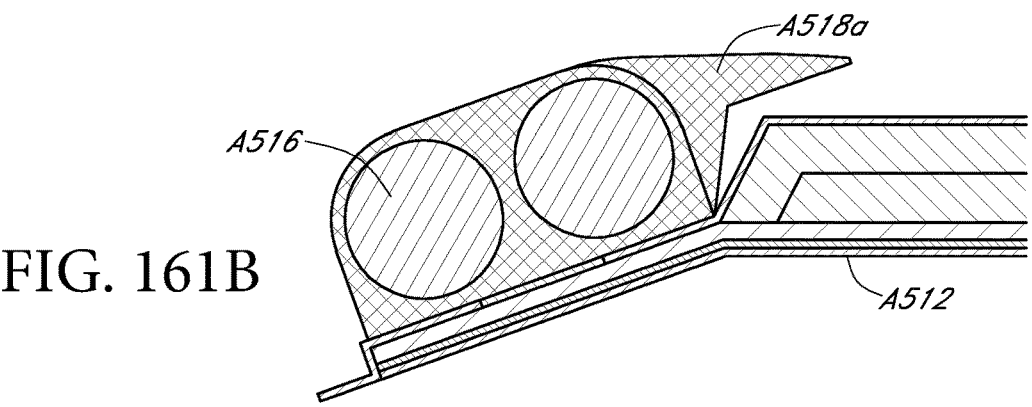
Figure 161C:
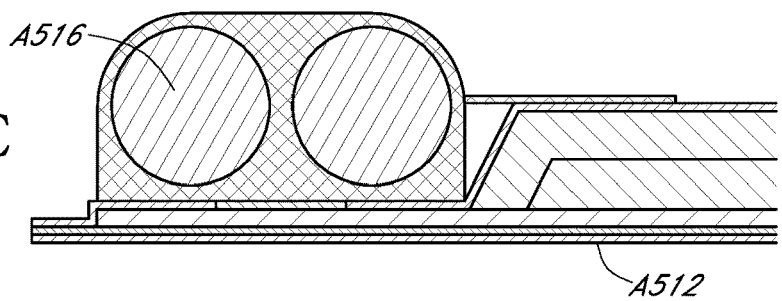
Figure 161D:
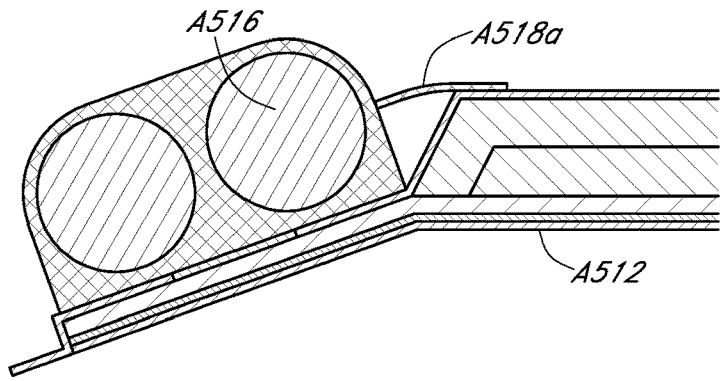
Figure 161E:
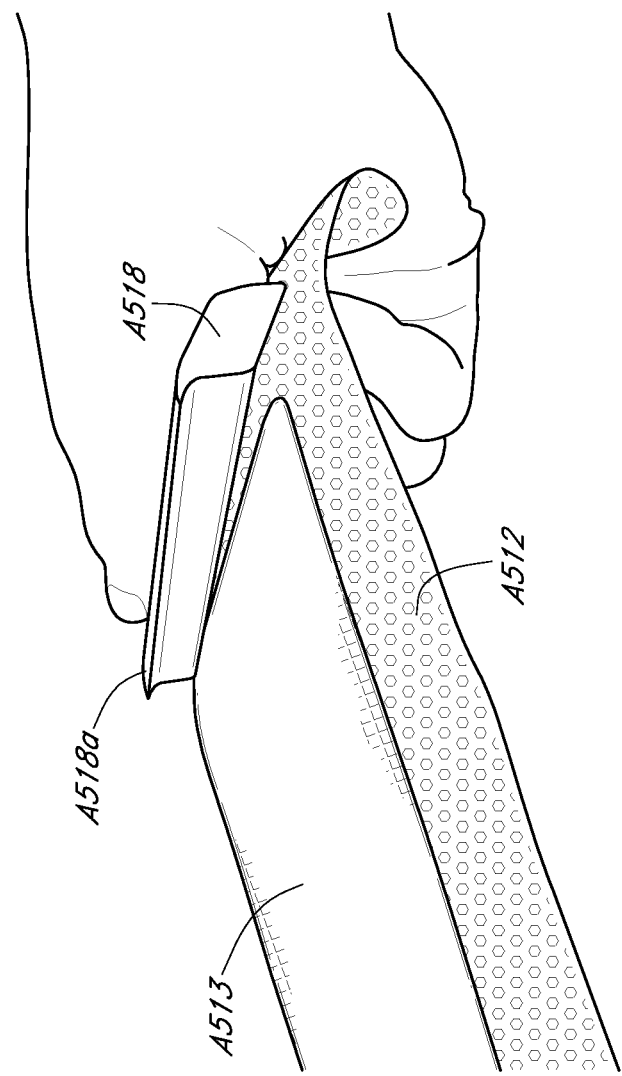
Figure 161F:
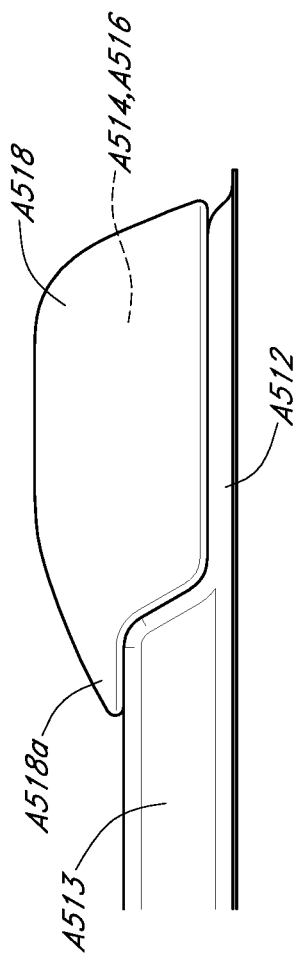
Figure 161G:
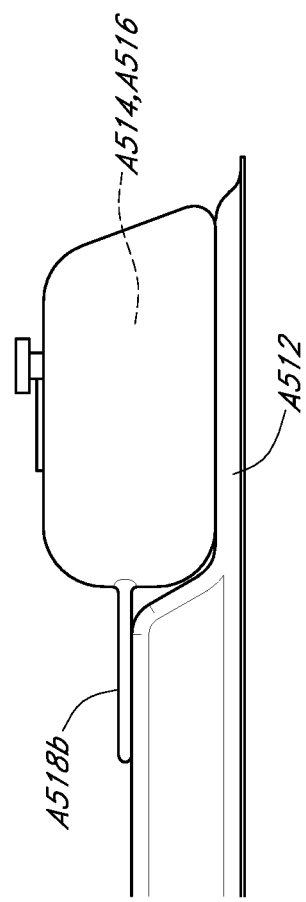

In the embodiment of the dressing A490 illustrated in FIGS. 160A-160D, the pump assembly A494 and the power source A496 can be positioned at opposite ends or on different portions of the dressing A492. For example, the pump assembly A494 and the power source A496 can be adjacent to opposite edges of the absorption and/or transmission layers A493. As shown in FIG. 160A, the pump A494 and power source A496 modules can be positioned at opposite corners of the dressing A492. The circuitry used for this arrangement or any other dressing kit embodiments disclosed herein can be flexible so that the dressing A492 is conformable and flexible to the user.

With reference to the dressing kit A510 embodiment illustrated in FIGS. 161A-161G, the pump assembly A514 can be supported on an edge portion of the dressing A512. A support member A518 can be used to support either or both of the pump assembly A514 and the power source A516. An overhang or extended portion A518a can extend over or overlap an adjacent portion of the dressing A512 having the absorptive and or transmission layers A513. In some embodiments, as in FIG. 161A, the overhang A518a can have a curved and smooth profile. In some embodiments, as in FIG. 161C, the overhang A518b can have a straight and flexible profile. The overhang or extended portion A518a can extend over the adjacent edge portion of the dressing to provide a more integrated look and feel.

Figure 162B:
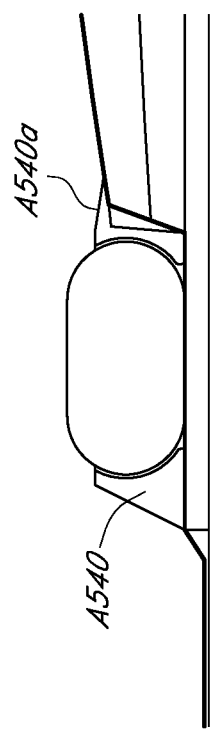
Figure 162A:
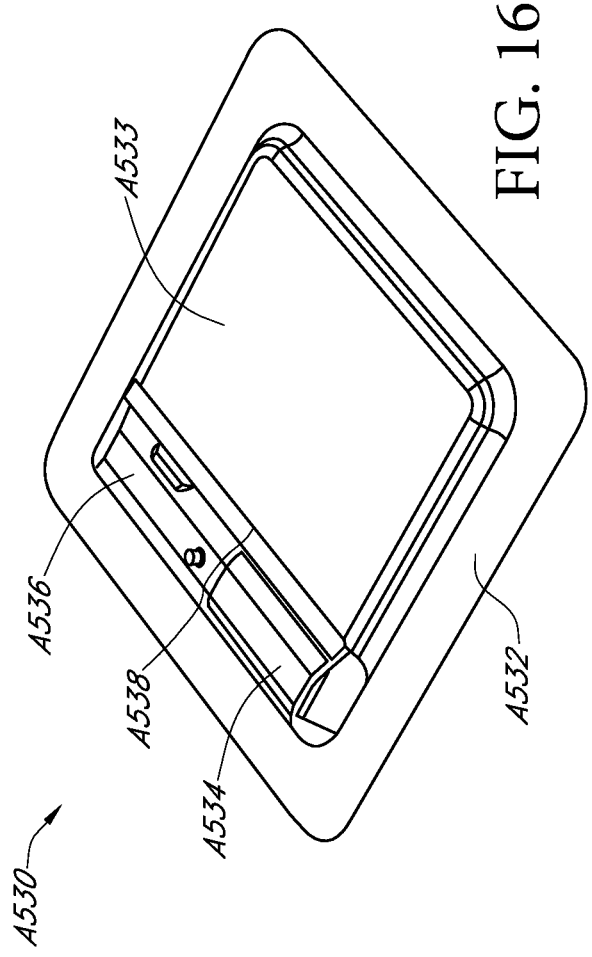

With reference to the dressing kit A530 embodiment illustrated in FIGS. 162A-162B, the pump assembly A534 can be supported on an edge portion of the dressing A532. A support member A540 can be used to support either or both of the pump assembly A534 and the power source A536. An overhang or extended portion A540a can extend over or overlap an adjacent portion of the dressing A532 having the absorptive and or transmission layers A533. In some embodiments, as in FIG. 161A, the overhang A538a can have a curved and smooth profile. Additionally, in some embodiments, a joint or flexible hinge A538 can be positioned between the pump assembly A534 and the power source A536. The overhang or extended portion A540a can extend over the adjacent edge portion of the dressing to provide a more integrated look and feel.

Figure 163:
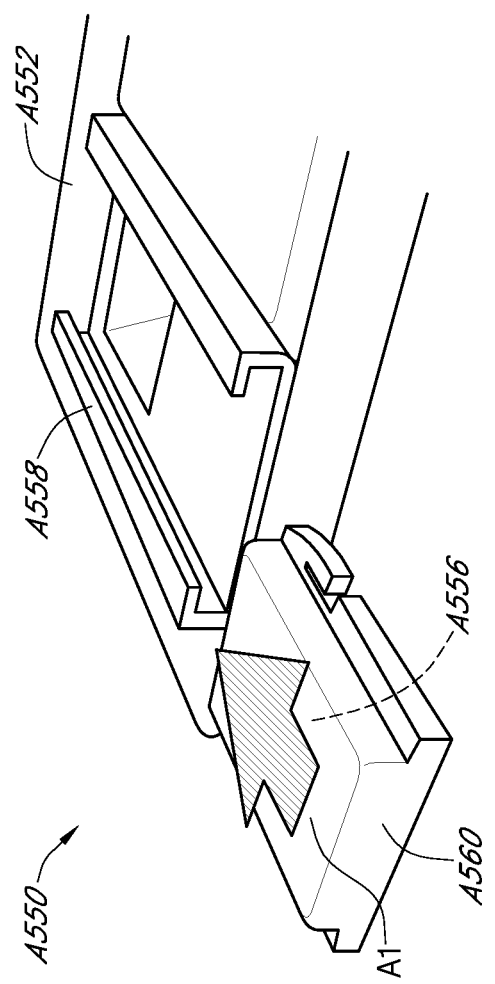

FIG. 163 illustrates an embodiment of a dressing kit A550 having a support layer A552, a pump assembly (not illustrated), a power source A556, and a housing or support member A558 configured to support the power source A556 and/or a pump assembly A554. In some embodiments, the power source A556 can be removably attachable to or engageable with the support member A558. The support member A558 can be configured to have conductive terminals such that, when the power source A556 is engaged therewith, power is automatically provided to the pump assembly A554 to either provide the power to the pump assembly A554 (but requiring a switch or button to activate the pump assembly) or to power and activate the pump assembly A554 to initiate negative pressure. Additionally, in some embodiments, multiple batteries or sources of power can be provided with the dressing kit A550. For example, a first battery pack A556 and a second battery pack A556 can be provided with the dressing kit A550 to provide interchangeable power sources. In some embodiments, the support member A558 can be attached directly to a dressing backing layer, or can be attached to a separate support layer, such as support layer A552, to enable the pump assembly and the power source to be attached adjacent to the wound and the dressing member positioned over the wound.

Further, one or more batteries A556 can be supported in a removable cartridge or carrier A560 configured to be removably engageable with a housing A558 supported by the support layer A552. In some embodiments, the housing A558 can also support or surround the pump assembly A554 if desired. However, the pump assembly A554 can be separately supported by the support layer A552. The dressing kit A550 can be configured such that the power source can be removable and disposed of and/or replaceable with a replacement power source when desired. Any of the dressing kits disclosed herein can come with a first power source and a second power source that can be used sequentially.

With reference to FIG. 163, the dressing can be configured such that sliding the batteries into engagement with the battery terminals (in the direction indicated by arrow A1 in the figures) will result in an audible click, to alert a user regarding the position of the components of the battery enclosure that the battery circuit is closed. Any of the dressing kit embodiments disclosed herein can be supported in packaging configured such that, while the dressing kit is supported in the packaging, the components of the battery pack or pump assembly are held in a first or non-operational position and prevented from moving to a second operational position and prevented from moving to a second operational position. In this configuration, when the components are in the first position, the pump is non-operational due to the fact that the battery terminals are not in contact with the one or more batteries. For example, the packaging supporting the dressing kit can prevent a lid of the battery housing from moving to the second position by holding the housing lid or cap in the first position. The packaging can have protrusions that are positioned between the housing lid or cap and the body of the battery housing that separate the battery housing lid from the body of the battery housing. Once the dressing kit is removed from the packaging, the battery housing lid or cartridge can be slid inward, permitting the terminals to contact the batteries so that the pump can be activated. In this configuration, the battery housing can serve as an activation button. Sliding the lid out of contact from the batteries can stop the operation of the pump.

Figure 164:
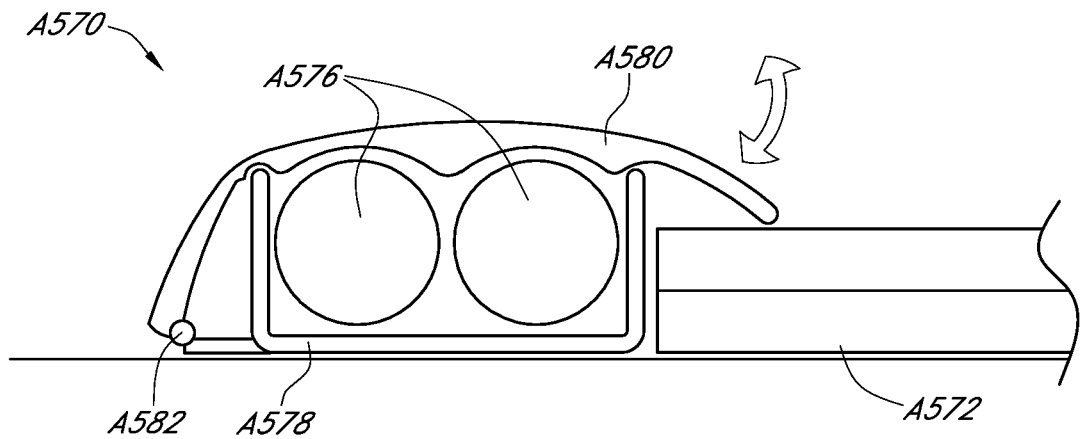

FIG. 164 illustrates a dressing kit A570 having a dressing member A572, a power source A576 positioned within a support member A578, and a hinged lid A580 hingably positioned over an opening in the support member A578. The lid A580 can rotate about an axis or joint A582. In some embodiments, the hinge can be configured such that, when the hinge is moved to a closed position, the power source A576 will be secured within the support member A578 and an electrical connection will be created between the power source A576 and a pump assembly (not illustrated) so that the pump can be changed to an operational state. The hinged door can have a living hinge, soft pivot, an axle, or other suitable mechanism.

Figure 165A:
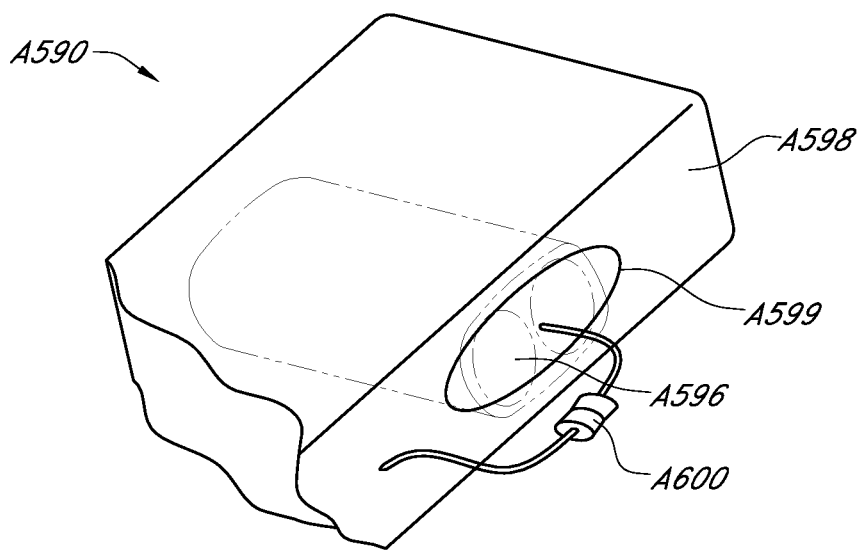
Figure 165B:
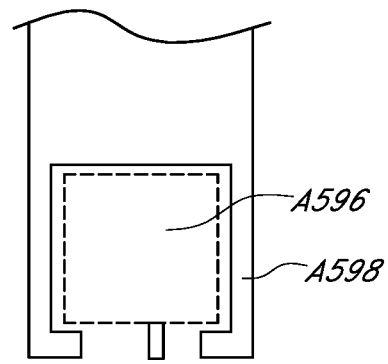
Figure 166A:
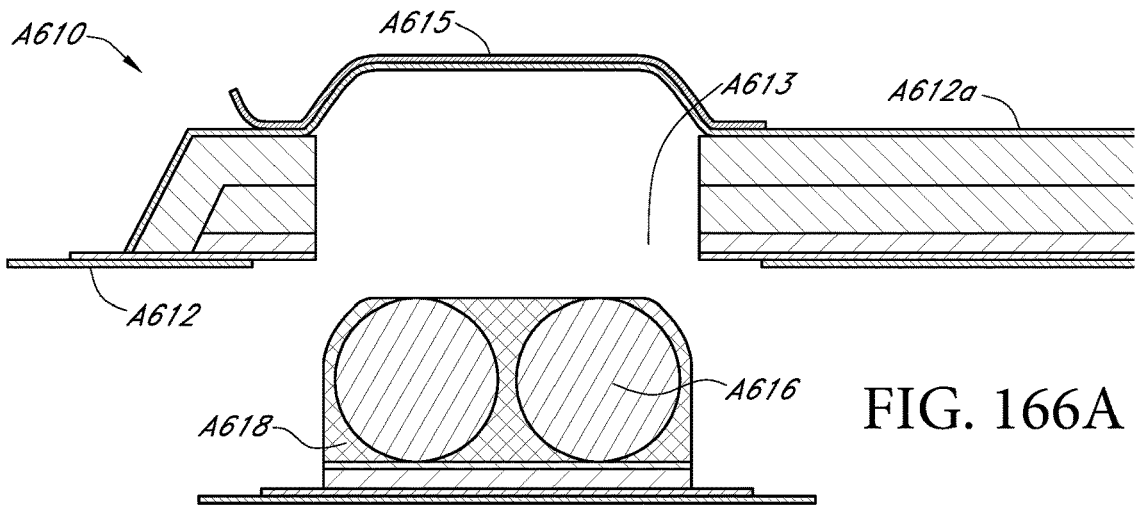
Figure 166B:
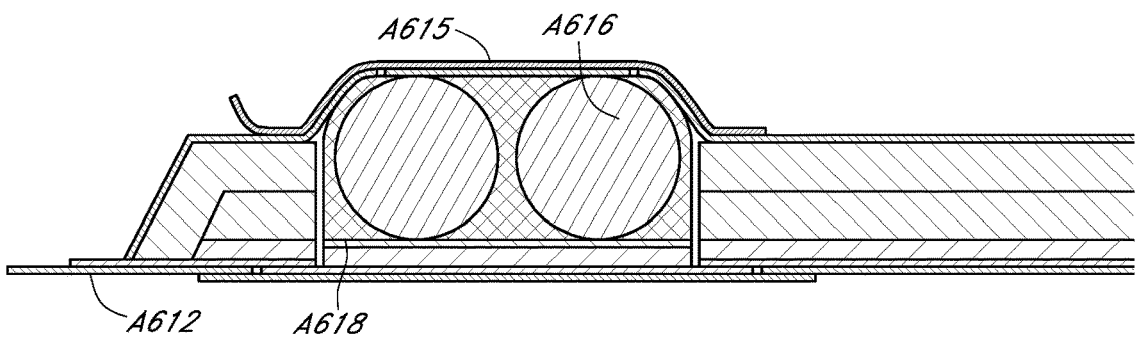
Figure 166C:
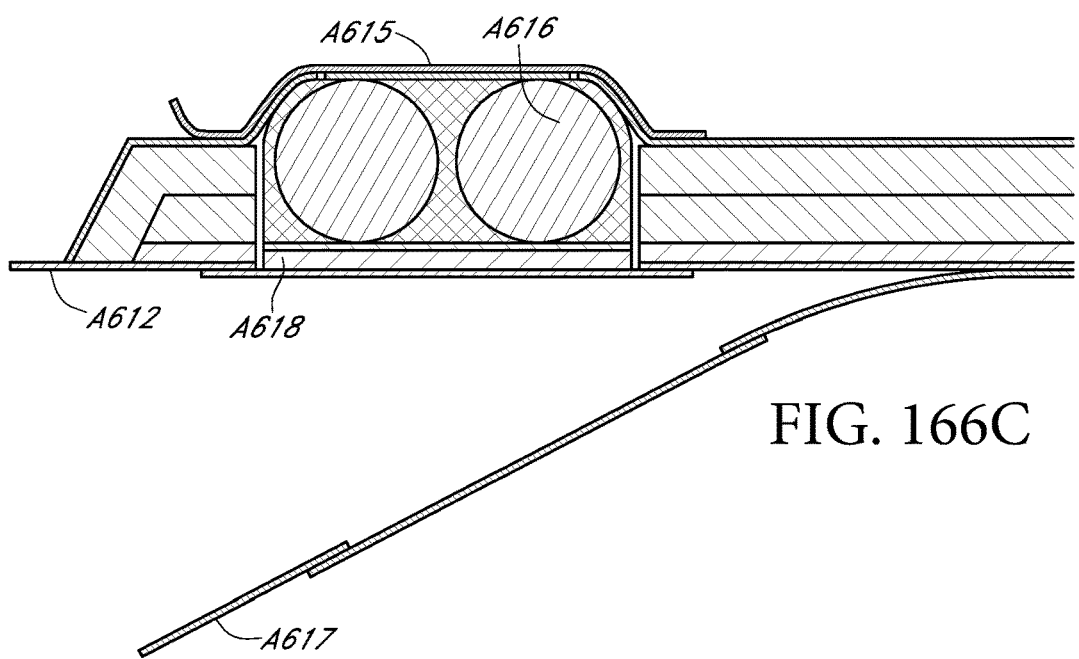
Figure 166D:
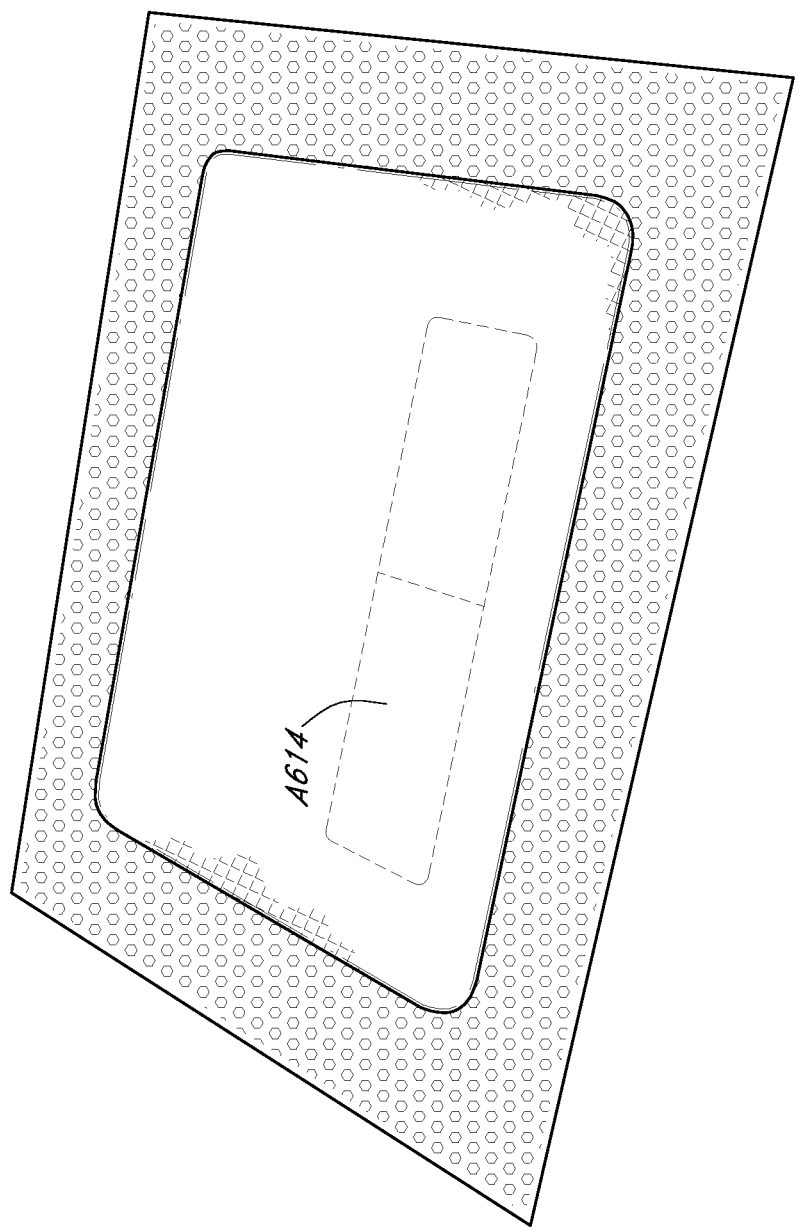
Figure 166E:
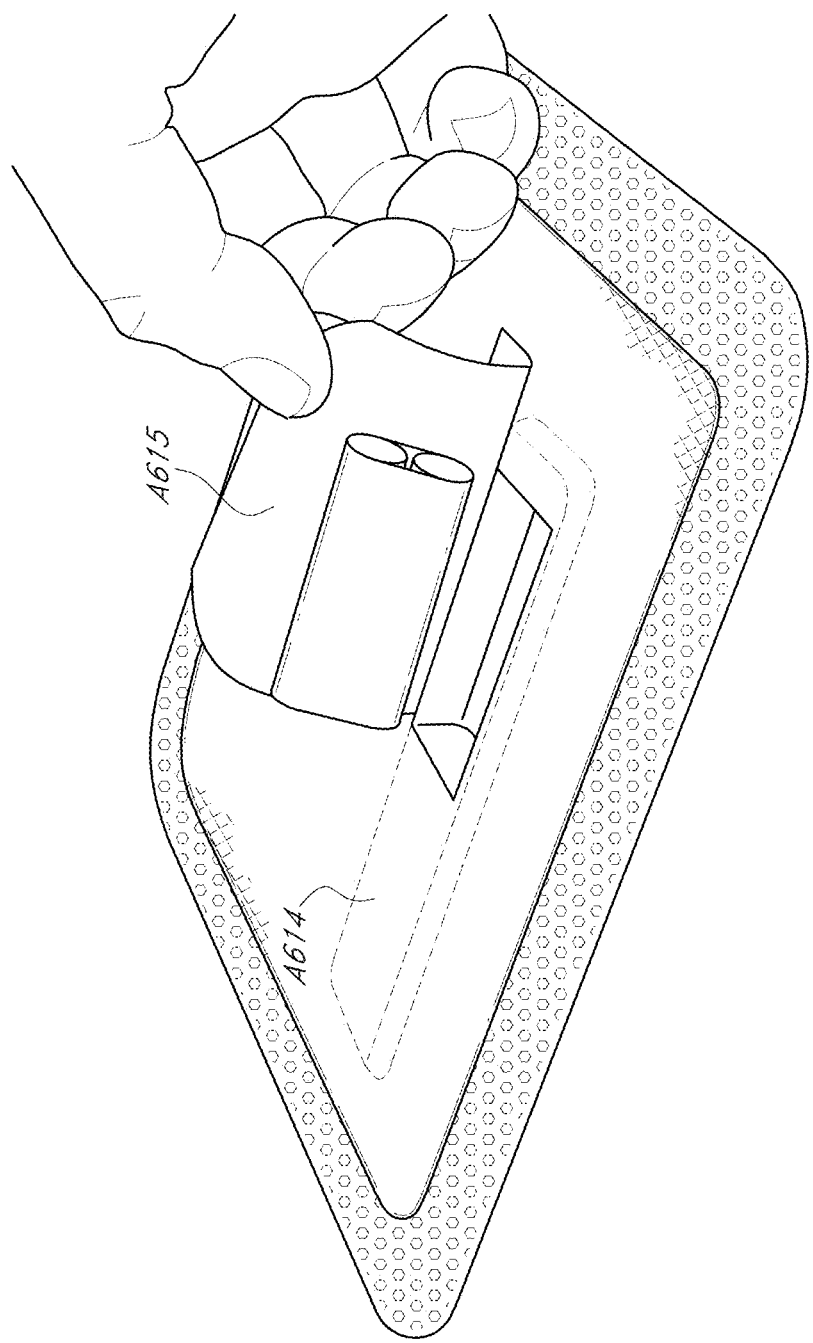

In some embodiments, as illustrated in FIGS. 165A-165B, the dressing kit A590 can have a housing A598 made from a resilient, thin-walled material having an opening A599 therein can be used to hold the power source A596 within the housing A598. The power source A596 can be squeezed through the opening A599 with sufficient force to cause the opening A599 to widen sufficiently to permit the passage of the power source therethrough. Thereafter, being formed of a resilient material, the opening in the housing can reduce in size, thereby securely holding the power source A596 within the housing A598. A plug connection A600 can be used to electrically connect the power source to the pump assembly.

FIGS. 166A-166E illustrate an embodiment of a dressing kit A610 having a dressing member A612, a pump assembly A614, a power source A616, and a housing or support member A618 configured to support the power source A616 and/or a pump assembly A614. In some embodiments, the support member A618 can be configured to pass through an opening A613 in a bottom or base portion of the dressing member A612 so that the power source A616 and/or the pump assembly A614 are positioned within the opening A613. A cover layer A615, which can be removable or hingably attached to the dressing member A612, can be positioned over a top surface of the power supply A616, pump assembly A614, and/or the support member A618. In some embodiments, the power source A616 and the pump assembly A614 can be positioned within the dressing member A612 so as to be flush or beneath a top surface A612a of the dressing member A612.

The battery and/or pump module can be loaded from the bottom to give the dressing a more integrated look and feel. Further, the device could be positioned beneath the backing layer (i.e., outermost layer away from the wound).

In some embodiments, the dressing kit A610 can be configured to have conductive terminals such that, when the power source A616 is engaged therewith or positioned within the opening A613, power is automatically provided to the pump assembly A614 from the power source A616 to either provide the power to the pump assembly A614 (but requiring a switch or button to activate the pump assembly) or to power and activate the pump assembly A614 to initiate negative pressure. A bottom layer A617 can be used to secure the housing and/or power source in the opening A613 on a bottom or base surface of the dressing member A612.

Multiple batteries or sources of power can be provided with the dressing kit A610. For example, a first battery pack A616 and a second battery pack A616 can be provided with the dressing kit A610 to provide interchangeable power sources. In some embodiments, the support member A618 can be attached directly to a dressing backing layer, or can be attached to a separate support layer, such as support layer A612, to enable the pump assembly and the power source to be attached adjacent to the wound and the dressing member positioned over the wound.

In some embodiments, the housing A618 can also support or surround the pump assembly A614 if desired. However, the pump assembly A614 can be separately supported by the support layer A612. The dressing kit A610 can be configured such that the power source can be removable and disposed of and/or replaceable with a replacement power source when desired. Any of the dressing kits disclosed herein can come with a first power source and a second power source that can be used sequentially. In some embodiments, the cover layer over the top of the dressing member A612 can form a continuous layer over the opening A613 such that a separate cover tab or layer A615 is not required. The cover layer over the top of the opening can be perforated or porous to permit air exhausted from the pump to exit the dressing.

Figure 167A:
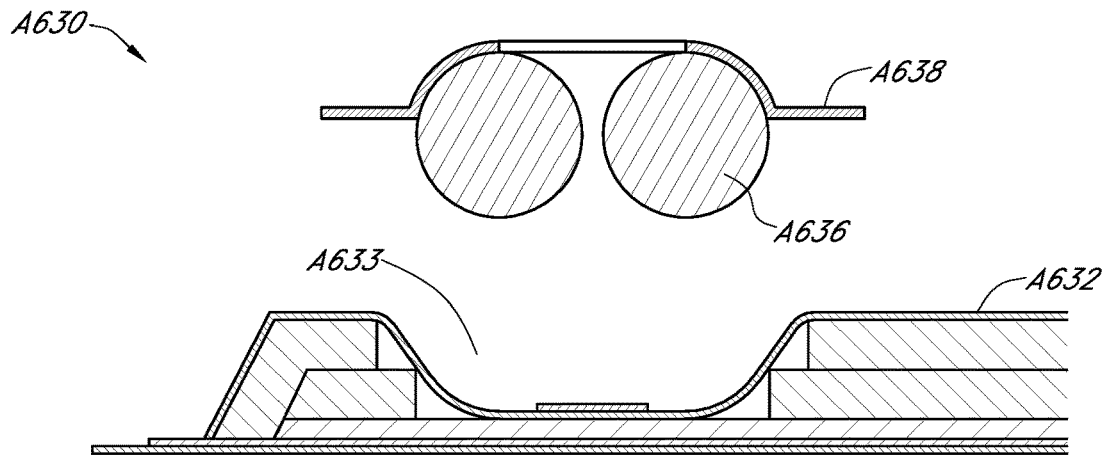
Figure 167B:
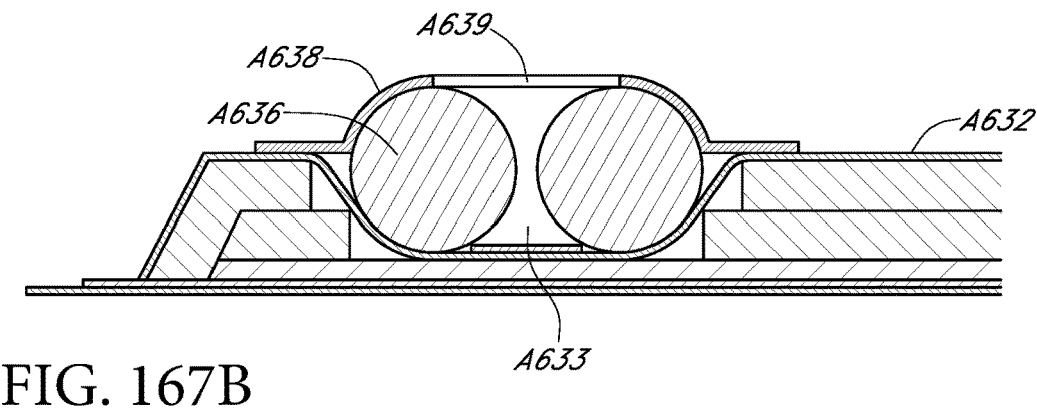
Figure 167C:
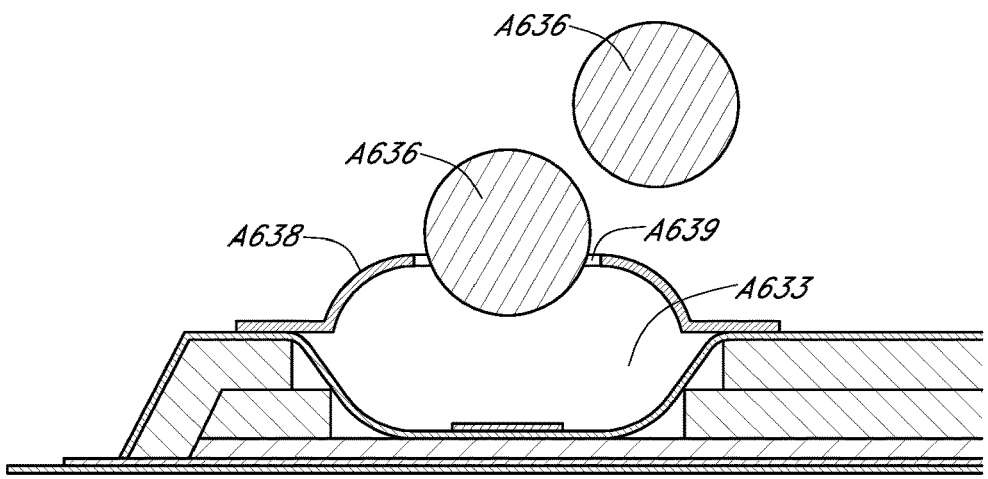

FIGS. 167A-167C illustrate an embodiment of a dressing kit A630 having a dressing member A632, a pump assembly (not illustrated), a power source A636, and a support layer A638 configured to support the power source A636 and/or a pump assembly A634. In some embodiments, the support layer A638 can be configured to cover an opening A633 in the dressing member A632 so that the power source A636 and/or the pump assembly A634 are positioned within the opening A633. In some embodiments, the power source A636 and the pump assembly A634 can be positioned within the dressing member A632 so as to be flush or beneath a top surface A632a of the dressing member A632.

In some embodiments, the dressing kit A630 can be configured to have conductive terminals such that, when the power source A636 is engaged therewith or positioned within the opening A633, power is automatically provided to the pump assembly A634 from the power source A636 to either provide the power to the pump assembly A634 (but requiring a switch or button to activate the pump assembly) or to power and activate the pump assembly A634 to initiate negative pressure.

Additionally, in some embodiments, multiple batteries or sources of power can be provided with the dressing kit A630. For example, a first battery pack A636 and a second battery pack A636 can be provided with the dressing kit A630 to provide interchangeable power sources. In some embodiments, as shown in FIG. 167C, the cover layer A638 can have an opening A639 therein, the opening being configured to permit the removal of the power supply A636 from the opening or compartment A633 when disposal or replacement of the power supply is desired.

The pump assembly can also be supported within the opening A633 and can be covered by the cover layer A638. The cover layer A638 can be perforated to permit exhaust gas to exit the opening or compartment A633. In some embodiments, the cover layer over the top of the dressing member A632 can form a continuous layer over the opening A633 such that a separate cover tab or layer A638 is not required. The cover layer over the top of the opening can be perforated or porous to permit air exhausted from the pump to exit the dressing.

Figure 168A:
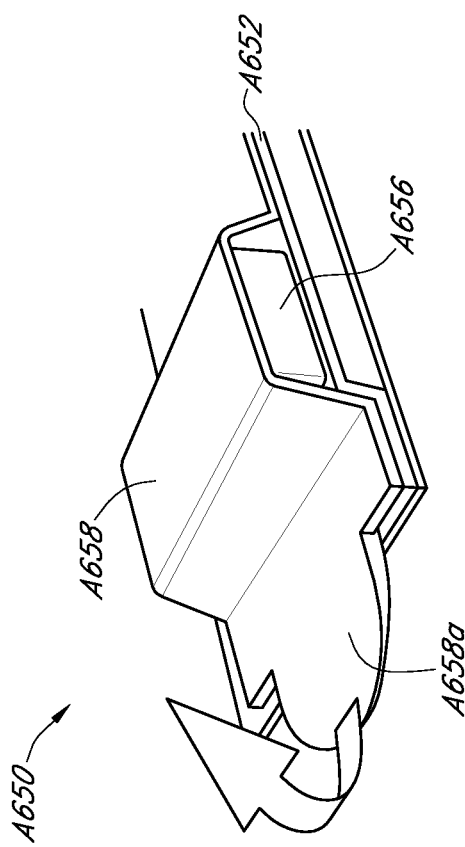
Figure 168B:
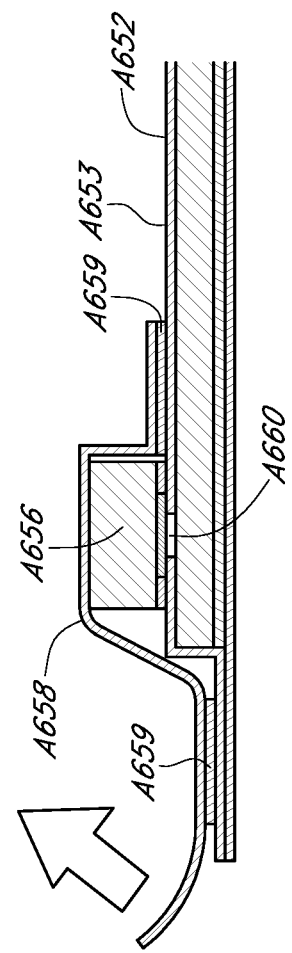

FIGS. 168A-168B illustrates another embodiment of a dressing kit A650 having a dressing member A652, a pump assembly (not illustrated), a power source A656, and a support layer A658 configured to support the power source A656 and/or a pump assembly A654 over the cover layer A653 of the dressing. In some embodiments, the support layer A658 can be configured to cover the power source A656 and/or the pump assembly A654. The support layer A658 can have a tabbed portion A658a configured to permit a user to grasp the support layer A658 for removal thereof. The support layer A658 can be fastened to the top layer A653 of the dressing member A652 using adhesive A659. When the power source A656 is desired to be removed for replacement or disposal, a user can grasp the support layer A658 by the tabbed portion A658a and lift the support layer A658 off of the power source A656. In some embodiments, where a pump assembly A654 can be supported under the support layer A658, an opening A660 formed in the upper layer A653 of the dressing member A652 can permit the passage of gas from within the dressing member or between the dressing member and the wound to pass through the pump assembly A654 and out of the dressing kit A650.

In some embodiments, the dressing kit A650 can be configured to have conductive terminals such that, when the support layer A658 is closed against the upper layer A653 of the dressing A652 on both sides of the power source A656, power is then provided to the pump assembly A654 from the power source A656 to either provide the power to the pump assembly A654 (but requiring a switch or button to activate the pump assembly) or to power and activate the pump assembly A654 to initiate negative pressure.

Additionally, in some embodiments, multiple batteries or sources of power can be provided with the dressing kit A650. For example, a first battery pack A656 and a second battery pack A656 can be provided with the dressing kit A650 to provide interchangeable power sources. The cover layer A658 can be perforated to permit exhaust gas to exit through the cover layer A658. In some embodiments, the cover layer over the top of the dressing member A652 can form a continuous layer over the opening A653 such that a separate cover tab or layer A658 is not required.

Figure 169B:
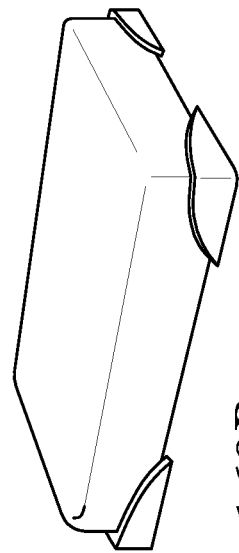
Figure 169A:
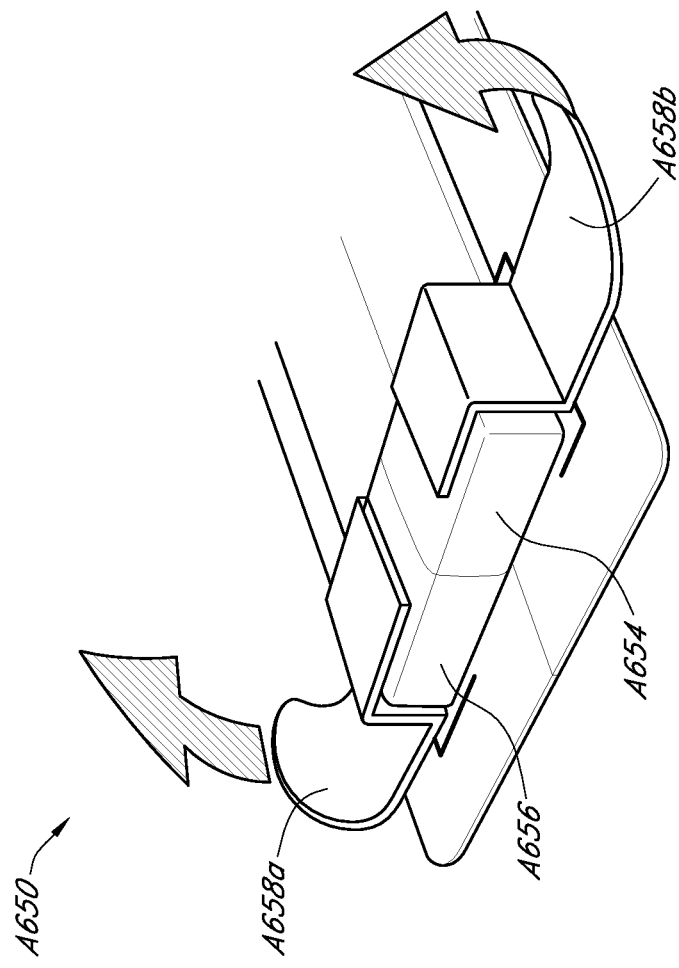

As illustrated in FIGS. 169A-169B, some embodiments of the dressing kit A650 can have multiple support layers were release tabs A658 used to releasably fasten the pump assembly A654 and/or the power source A656 to the dressing. For example, as illustrated in FIG. 169A, a first tab A658a and the second tab A658b can be positioned on mutually opposing ends of a housing used to support the pump assembly A654 and the power supply A656.

Furthermore, in some embodiments, the dressing kit can have a tearable strap covering at least one of a pump assembly and a power source that can be perforated or slit to facilitate the tearing of the strap. Additionally, the strap could be non-tearable but could be adhered to the supporting surface using Velcro or other similar adhesive materials. With some embodiments of the pull-tab arrangement, the batteries can be removed by pulling on a label or pull tab. This can be achieved with either side or end ejection. As illustrated in FIGS. 170A-170B, the cover layer A658 of some embodiments of the dressing kit A650 or any other dressing kit disclosed herein can have one or more perforated or tearable portions A661 configured to tear open to permit the removal of the pump assembly A654 and/or the power source A656. A tab A663 can be grasped to initiate the tear.

Figure 171:
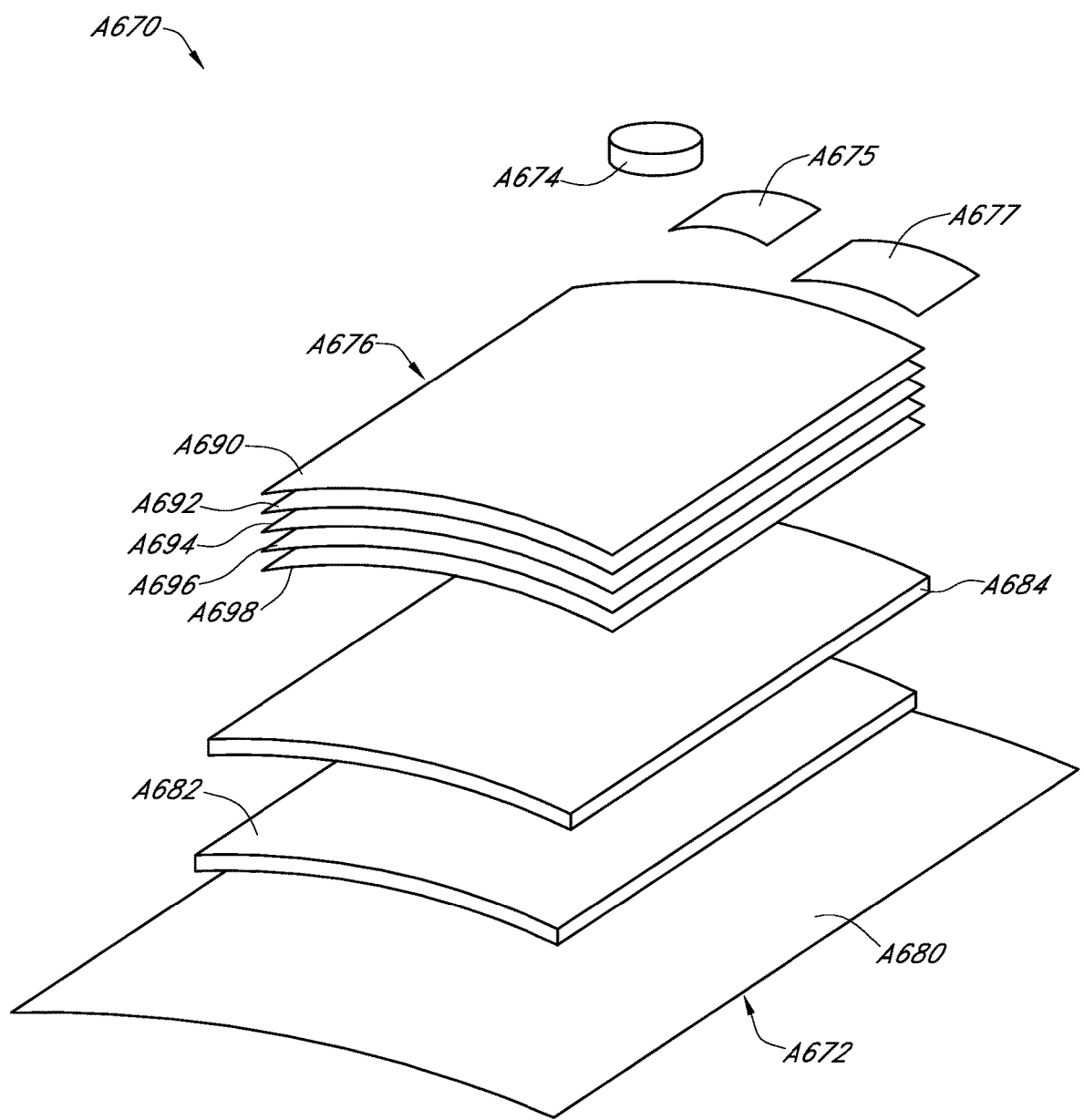

FIG. 171 illustrates another embodiment of a dressing kit A670 having a dressing member A672, a pump assembly A674, and a power source A676. In any of the dressing kit embodiments disclosed herein, the dressing member A672 can but is not required to have a wound contact layer A680, one or more layers of spacer material A682 (also referred to herein as a transmission layer or layers), one or more layers of absorbent material A684, and a cover layer (not illustrated) configured to cover at least the layer of spacer material A682 and the layer of absorbent material A682. Additionally, in any of the embodiments disclosed herein, the power source can have a flexible battery A676 configured to cover a portion of the absorption and transmission layers.

In some embodiments, the flexible battery A676 can have a plurality of different material layers coupled with one another. For example, in some embodiments, the flexible battery A676 can have a current collector layer A690, above an anode layer A692, followed by a separator layer A694, the cathode layer A696, and finally a current collector layer A698 on the bottom thereof. Additionally, any embodiments of the dressing kit disclosed herein can be powered by one or more flexible printed batteries based on the technology developed by Imprint Energy, or by one or more carbon zinc flexible batteries manufactured by Blue Spark Technologies, built, such as any of those described above. The size of the flexible battery A676 can depend on the power requirements of the pump assembly and duration desired for the negative pressure wound therapy. In some embodiments, however, the flexible battery A676 can be approximately the same size as the absorption layers in the dressing and can be configured to cover the absorption layers in the dressing.

Further, in any of the dressing kit embodiments disclosed herein, such as dressing kit A670, the pump assembly A674 can be controlled by a flexible control board. Further, any dressing kit embodiments disclosed herein can further have an organic light emitting diode ("OLED") display or other suitable interface display.

Figure 172:
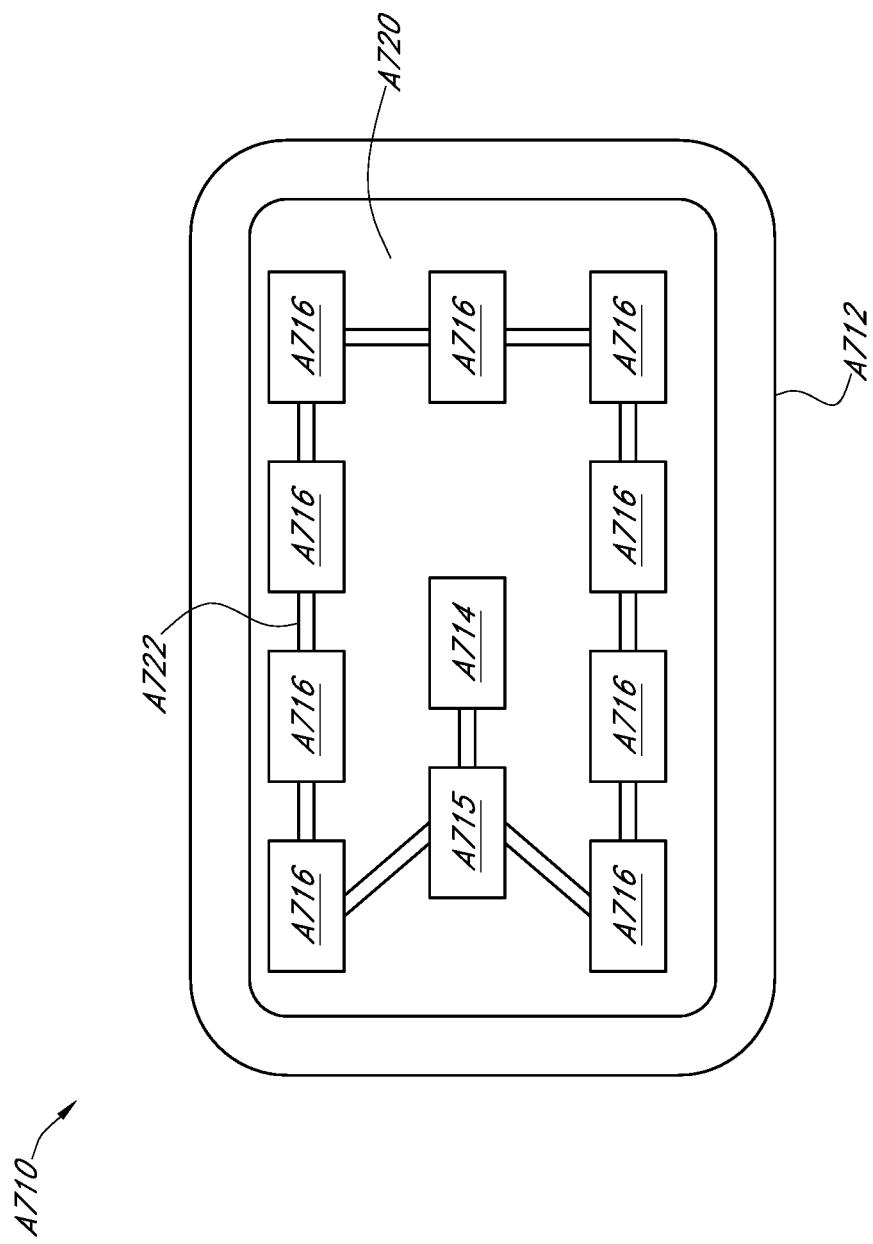

FIG. 172 is an illustration of another embodiment of a dressing kit A710 configured to be positioned over a wound. The dressing kit A710 can have any of the features of any other dressing kits disclosed herein. In some embodiments, the dressing kit A710 can have a dressing member A712 a pump assembly A714 powered by a flexible PCB A715, and plurality of power sources A716 position about the dressing member A712. For example, in some embodiments, each of the power sources A716 can be a flexible battery such as a flexible printed battery, a thin lithium battery, a photovoltaic cell, and/or any other suitable power source. The plurality of power sources A716 can be interconnected by electrical wiring A722 in any suitable configuration or arrangement to permit the optimal level of current flow and voltage to the pump assembly. The electrical wiring A722 can be connected to the control board A715 configured to control an operation of the pump assembly A714.

Figure 173:
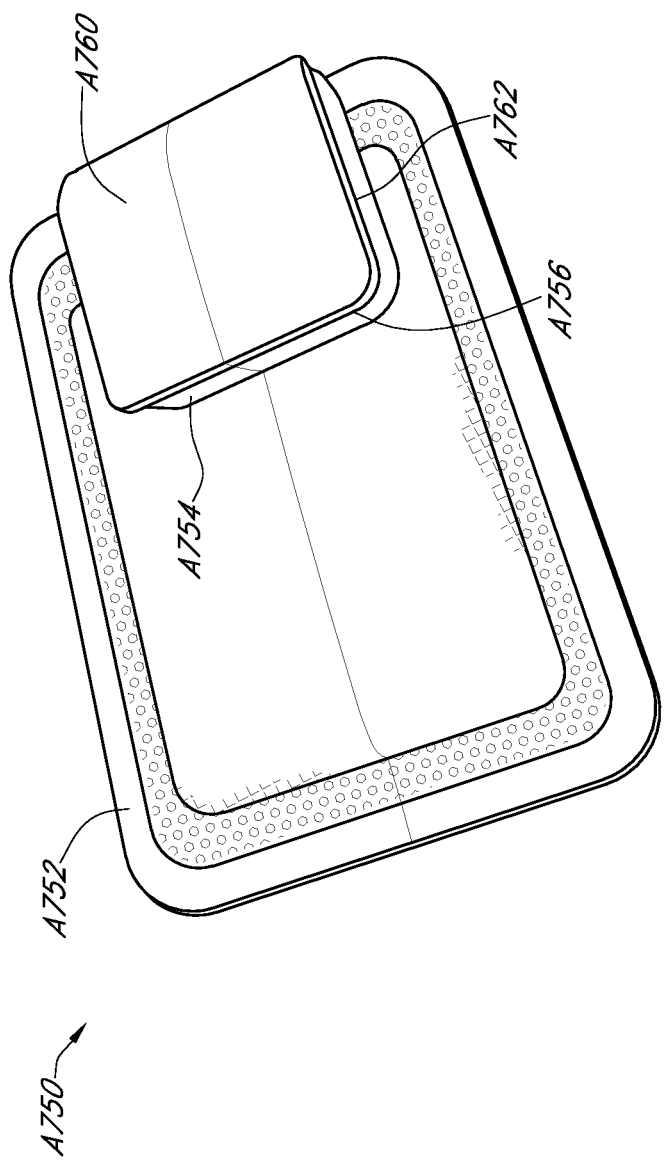

FIG. 173 illustrates another embodiment of a dressing kit A750 having a dressing member A752, a pump assembly A754, and a power source A756. The dressing kit can be packaged with the pump assembly A754 and the power source A756 positioned on top of the dressing member A752. The dressing kit A750 is configured such that the pump assembly A754 and the power source A756 can remain positioned above the dressing member during treatment. Or, alternatively and at the user's preference, releasable backing layer A760 can be removed from the pump assembly A754 and the power source A756 so that the pump assembly A754 and the power source A756 can be flipped or folded out and adhere to the skin adjacent to the wound dressing member A752. A conduit can communicate the negative pressure generated by the pump assembly A754 to the dressing member A772 and/or to the space between the dressing member A772 and the wound.

Figure 174B:
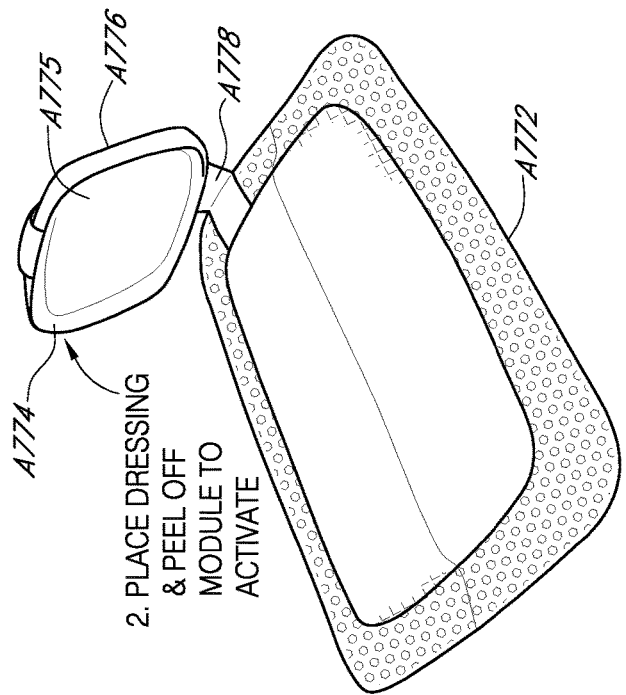
Figure 174A:
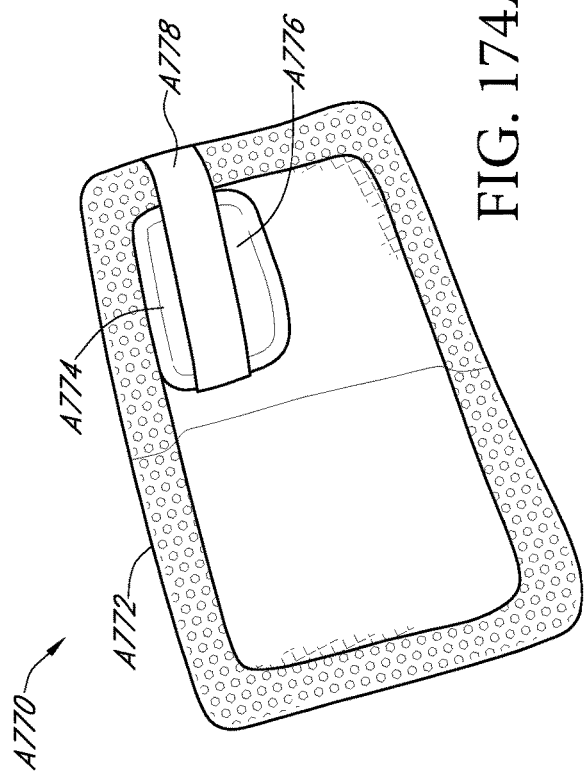
Figure 174C:
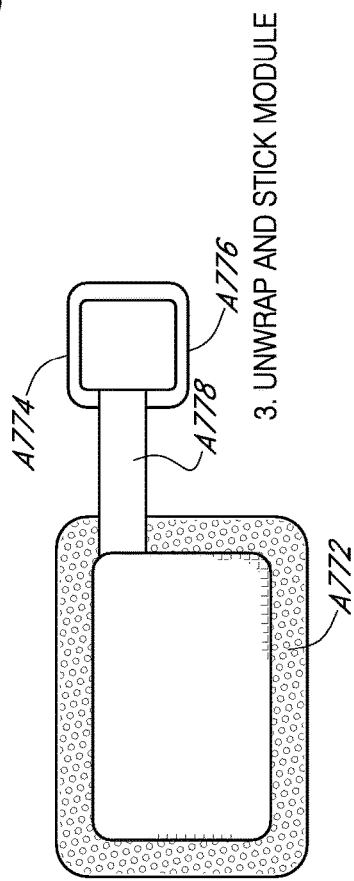

FIGS. 174A-174C illustrates another embodiment of a dressing kit A770 having a dressing member A772, a pump assembly A774, and a power source A776. The dressing kit can be packaged with the pump assembly A774 and the power source A776 positioned on top of the dressing member A772. The dressing kit A770 is configured such that the pump assembly A774 and the power source A776 can remain positioned above the dressing member during treatment. Or, alternatively and at the user's preference, releasable backing layer A780 can be removed from the pump assembly A774 and the power source A776 so that the pump assembly A774 and the power source A776 can be flipped or folded out and adhere to the skin adjacent to the wound dressing member A772. A flexible conduit A778 can communicate the negative pressure generated by the pump assembly A774 to the dressing member A772 and/or to the space between the dressing member A772 and the wound. A film layer A775 adhered to a surface of the power source or the pump assembly, or a non-conductive material separating electrical connections between the power source and the pump assembly can be removed to activate the pump assembly.

In any embodiments disclosed herein, including the embodiment illustrated in FIGS. 174A-174C, the conduit A778 can have a foam, a transmission layer or 3d knit fabric, and/or other porous material therein to prevent or significantly prevent the collapse of the conduit during operation from kinking, crushing, etc., while permitting the passage of fluids therethrough. For example and without limitation, in any embodiments disclosed herein, the conduit can have a top and a bottom layer constructed from a liquid impermeable material, a 3D knitted or 3D fabric material located between the top and bottom layers, an opening in fluid communication with the 3D knitted or 3D fabric material, and an elongate channel extending between the top and bottom layers containing the 3D knitted or 3D fabric material. The opening can be in fluid communication with any of the transmission and/or absorption layers within the dressing member. In any embodiments disclosed herein, the conduit can be integrally formed with the remainder of the dressing member. Additionally, in any embodiments disclosed herein, the conduit can have a width from approximately 0.5 inches or less to approximately 0.75 inches or more, from approximately 0.75 inch to approximately 1.5 inches or more, having a low profile height of from approximately 0.1 or less to approximately 0.25 or more inches.

Figure 175:
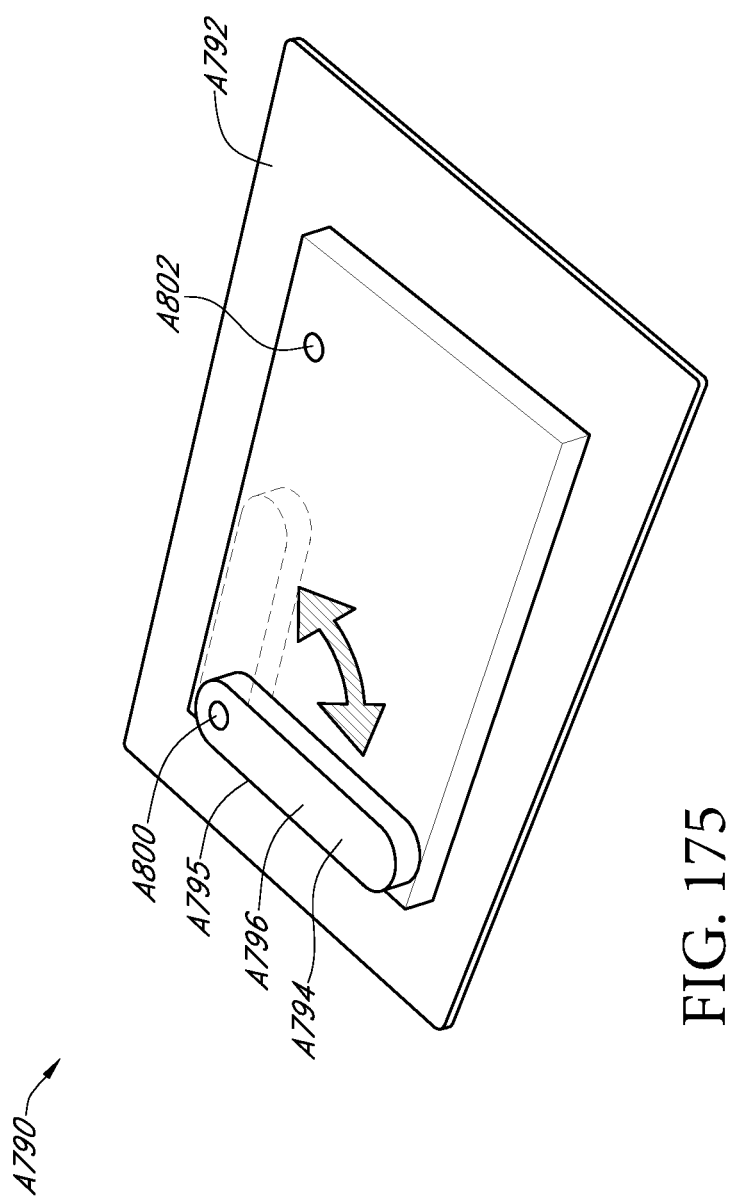
Figure 176B:
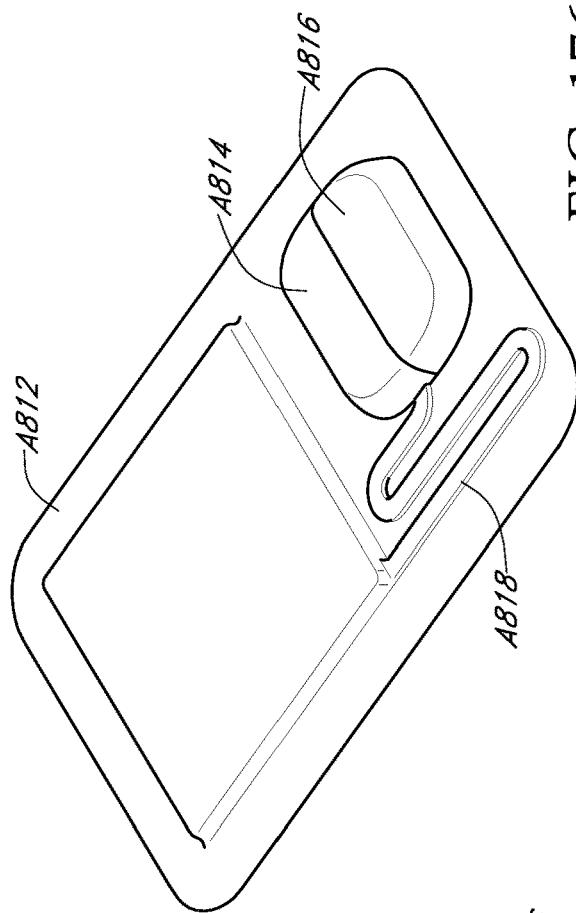
Figure 176A:
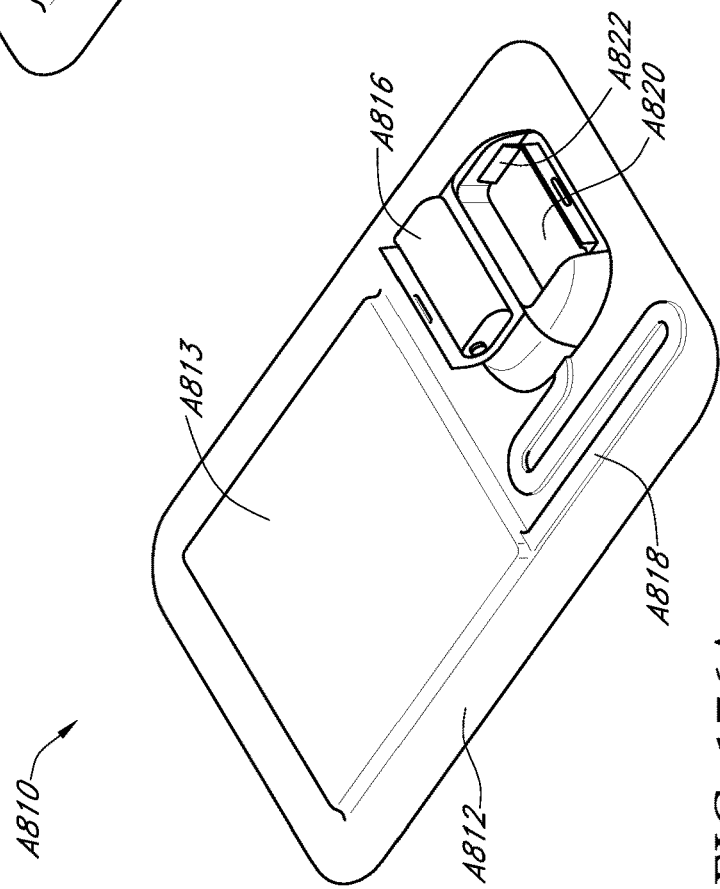
Figure 176C:
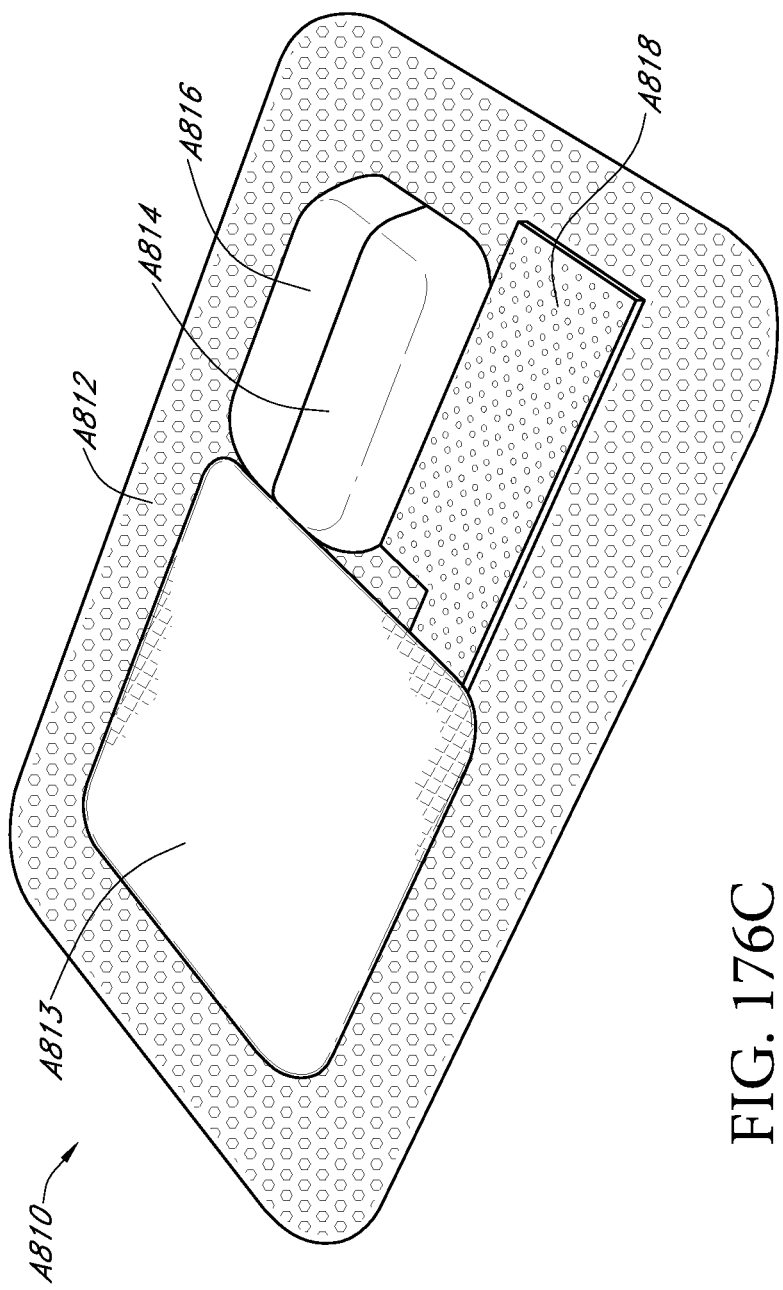
Figure 176D:
Figure 176E:
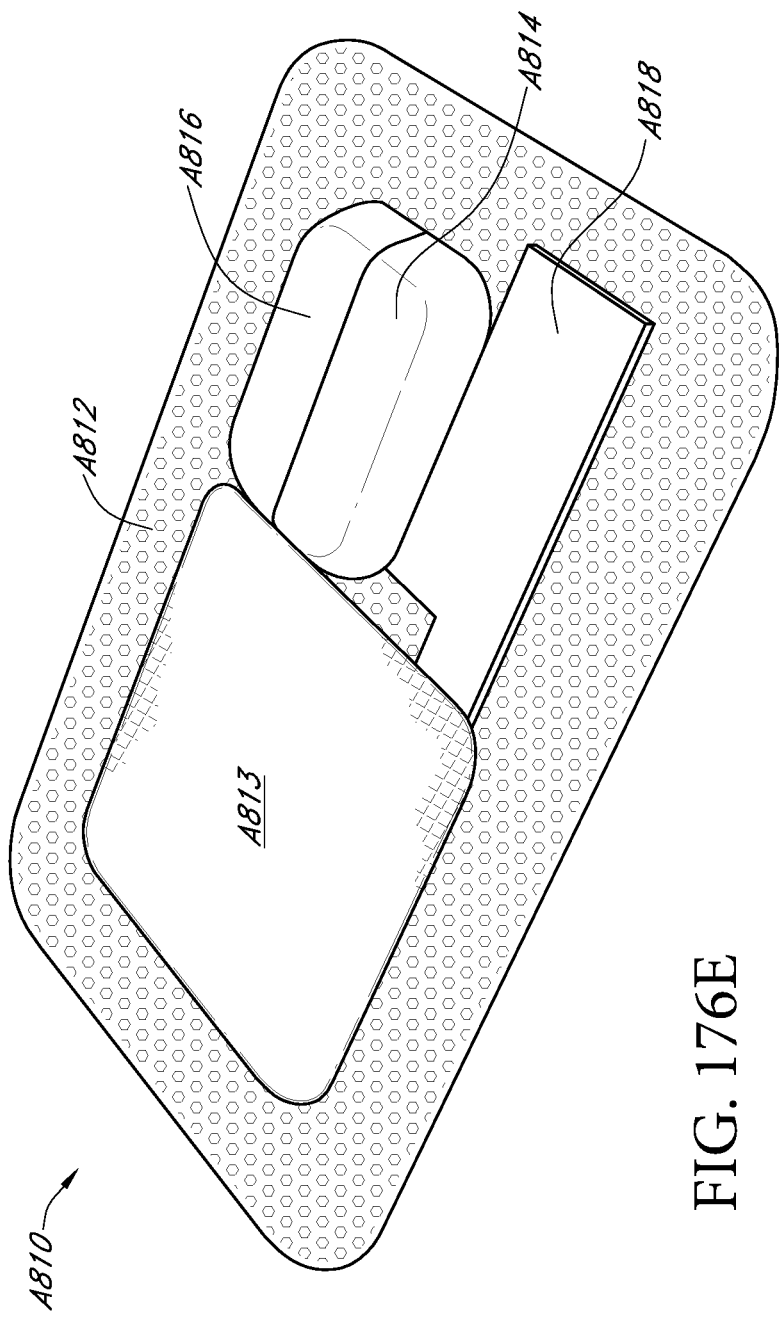

FIG. 175 illustrates another embodiment of a dressing kit A790 having a dressing member A792, a pump assembly A794, and a power source A796. The dressing kit can be configured such that the pump assembly A794 and the power source A796 are supported within a module A795 that is rotatable an axis. In some embodiments, the axis of rotation can be coincident with a port member A800 configured to communicate the negative pressure generated by the pump assembly to the dressing. Thus, in some embodiments, the dressing kit A790 can be configured such that the battery A796 and/or pump assembly A794 are pivotably positionable on the dressing so that the position and/or orientation of the battery module and/or pump assembly can be adjusted or adjustable depending on the contour of the body. Additionally, a second sealable port A802 can be formed in the top layer of the dressing member A792 to permit the user to select which port to use for the pump assembly A794. An angular orientation of the module A795 can be adjusted in position from a first orientation to a second orientation. In the first orientation, the module A795 can be positioned along a lengthwise edge or a first edge of the dressing member A792. In a second orientation, the module A795 can be positioned along a short edge or a second edge of the dressing member A792. Additionally, the module A795 can be positioned at any desired orientation between the first and second positions or orientations.

FIGS. 176A-176E illustrates another embodiment of a dressing kit A810 having a dressing member A812 having one or more absorption and/or transmission layers A813, a pump assembly A814, and a power source A816. The embodiment illustrated in FIGS. 176A-176E can have a length of conduit A818 between the pump and the dressing that permits the dressing to be mounted adjacent to or on top of the dressing. The dressing kit can be packaged with the pump assembly A814 and the power source A816 positioned on top of the dressing member A812 or adjacent to the dressing member. The dressing kit A810 is configured such that the pump assembly A814 and the power source A816 can remain positioned above the dressing member during treatment, being adhered or removably fastened to the top of the dressing using a Velcro, adhesive, one or more clips, a pouch, or otherwise. Or, alternatively and at the user's preference, the pump assembly A814 and/or the power source A816 can be moved away from the wound so that the pump assembly A814 and the power source A816 can be positioned remote to the dressing A812. For example, the pump assembly A814 and/or the power source A816 can be adhered to the skin adjacent to the wound dressing member A812.

A flexible conduit A818 can communicate the negative pressure generated by the pump assembly A814 to the dressing member A812 and/or to the space between the dressing member A812 and the wound. In any embodiments disclosed herein, including the embodiment illustrated in FIGS. 176A-176E, the conduit A818 can have a foam, a transmission layer or 3d knit fabric, and/or other porous material therein to prevent or significantly prevent the collapse of the conduit during operation from kinking, crushing, etc., while permitting the passage of fluids therethrough. In some embodiments, with reference to FIGS. 175C-175E, the conduit A818 can comprise a small sheet of a transmission material forming a conduit between the pump assembly A814 and the absorption material A812. In this arrangement, the transmission material can have a foam, a transmission layer or 3d knit fabric, and/or other porous material therein to prevent or significantly prevent the collapse of the conduit during operation from kinking, crushing, etc., and can have a cross-sectional area transverse to the flow direction that is approximately one-third the width of the absorption and/or transmission layers A813, or from approximately one-quarter to approximate one-half the width of the absorption and/or transmission layers A812. This extra width of the conduit A818 can help prevent blockage of the conduit that may affect the transmission of reduced pressure to the dressing layers A813.

In any embodiments, the dressing layers A813, pump assembly A814, the power source A816, and the conduit A818 can be supported by the dressing member A812. Additionally, the conduit A818 can have any of the materials, features, or other details of any of the other conduit arrangements disclosed herein.

Figure 177B:
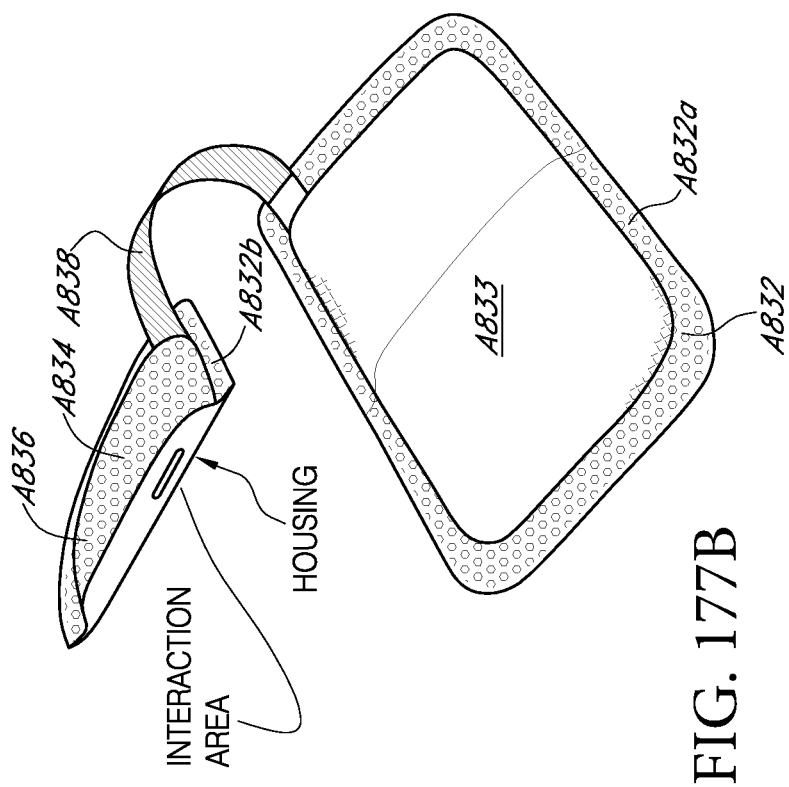
Figure 177A:
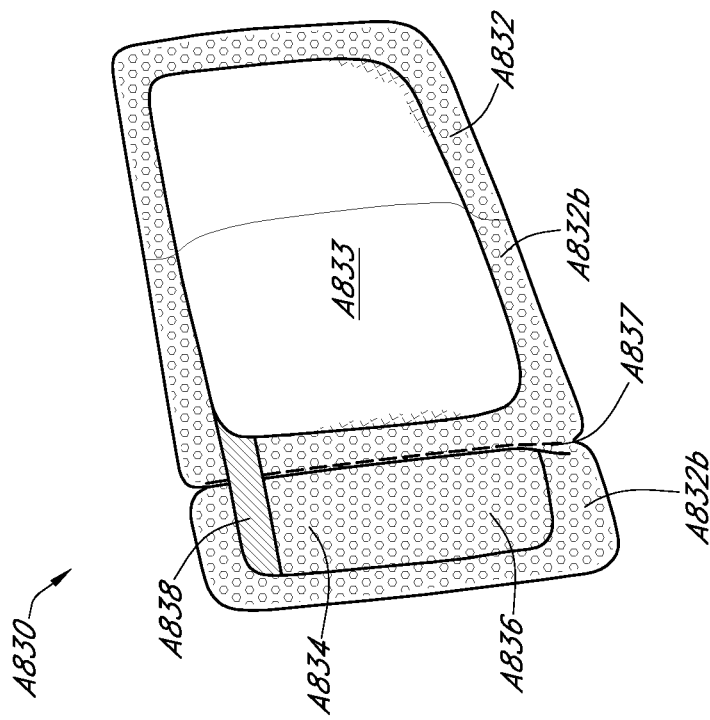

FIGS. 177A-177B illustrate another embodiment of a dressing kit A830 having a dressing member A832 having one or more absorption and/or transmission layers A833, a pump assembly A834, and a power source A836. The dressing kit can be packaged with the pump assembly A834 and the power source A836 positioned adjacent to one or more absorption and/or transmission layers A833 but being removably attached to the dressing member A832 supporting the one or more absorption and/or transmission layers A833.

The dressing kit A830 can be configured such that the pump assembly A834 and the power source A836 can remain positioned adjacent to the dressing member A832 during treatment. Or, alternatively and at the user's preference, the pump assembly A834 and the power source A836 can be positioned on a portion of the dressing member A832 that can be detached from the portion of the dressing member A832 supporting the one or more absorption and/or transmission layers A833. For example, in some embodiments, the one or more absorption and/or transmission layers A833 can be positioned on a first portion A832a of the dressing member A812, and the pump assembly A834 and the power source A836 can be positioned on a second portion A832b of the dressing member A832 that can be detached from the first portion A832a of the dressing member A832. In some embodiments, the dressing member A832 can have a perforation, indentations, reduced thickness, or one or more cutouts between the first portion A832a and the second portion A832b of the dressing member A832 to facilitate the detachability of the first portion A832a from the second portion A832b of the dressing. This can facilitate the detachment of the second portion A832b of the dressing A832 from the first portion A832a of the dressing for placement of the second portion A832b of the dressing A832 in a desired location spaced apart from the first portion A832a of the dressing, and hence, spaced apart from the wound. The second portion A832b of the dressing member A832 can have a different adhesive thereon as compared to the adhesive on the first portion A832a of the dressing member A832 for adhesion to the skin or otherwise.

A flexible conduit A838 can communicate the negative pressure generated by the pump assembly A834 to the dressing member A832 and/or to the space between the dressing member A832 and the wound. A film layer adhered to a surface of the power source or the pump assembly, or a non-conductive material separating electrical connections between the power source and the pump assembly can be removed to activate the pump assembly.

In any embodiments disclosed herein, including the embodiment illustrated in FIGS. 177A-177B, the conduit A838 can have a foam, a transmission layer or 3d knit fabric, and/or other porous material therein to prevent or significantly prevent the collapse of the conduit during operation from kinking, crushing, etc., while permitting the passage of fluids therethrough, and can have a width from approximately 0.5 inches or less to approximately 0.75 inches or more, from approximately 0.75 inch to approximately 1.5 inches or more, having a low profile height of from approximately 0.1 or less to approximately 0.25 or more inches.

FIGS. 178A-178C illustrate another embodiment of a dressing kit A850 having a dressing member A852, a pump assembly A854, and a power source A856. In some embodiments, the dressing kit A850 can have any of the features, details, or components of any of the other dressing kit embodiments disclosed herein. In any dressing kit or pump assembly embodiments herein, including the embodiment of the dressing kit A850 shown in FIGS. 178A-178C, the pump assembly can have one or more indicator lights (such as LED indicator lights), and one or more control buttons or switches. The dressing kit can be packaged with the pump assembly A854 and the power source A856 positioned adjacent to the dressing layers A853. The dressing kit A850 can be configured such that the pump assembly A854 and the power source A856 can remain positioned adjacent to the absorption and/or transmission layers A853 (collectively referred to as the dressing layers) during treatment. Or, alternatively and at the user's preference, the pump assembly A854 and the power source A856 can be positioned on a portion of the dressing member A852 that can be detached from the portion of the dressing member A852 supporting the one or more absorption and/or transmission layers A853.

For example, in any dressing kit embodiments disclosed herein, the one or more absorption and/or transmission layers A853 can be positioned on a first portion A852a of the dressing member A812, and the pump assembly A854 and the power source A856 can be positioned on a second portion A852b of the dressing member A852 that can be detached from the first portion A852a of the dressing member A852. Additionally, in any embodiments disclosed herein, the conduit A858 can be positioned on a third portion A852c of the dressing member A852 that can be detached from the first portion A852a of the dressing member A852 and/or the second portion A852b of the dressing member A852.

In any embodiments, the dressing member A852 can have one or more intermittent or continuous scores, perforation, indentations, notches, cuts, cutouts, partial thickness cuts, or reduced thickness A855 between the first portion A852a and the second portion A852b of the dressing member A852, between the second portion A852b and the third portion A852c of the dressing member A852, and/or between the first portion A852a and the third portion A852c of the dressing member A852 to facilitate the detachability of the first portion A852a from the second portion A852b of the dressing member A852. This can facilitate the detachment of the second portion A852b of the dressing member A852 from the first portion A852a of the dressing member for placement of the second portion A852b of the dressing A852 in a desired location spaced apart from the first portion A852a of the dressing, and hence, spaced apart from the wound. The second portion A852b of the dressing member A852 can have a different adhesive thereon as compared to the adhesive on the first portion A852a of the dressing member A852 for adhesion to the skin or otherwise. Further, as with any embodiments disclosed herein, the pump assembly A854 can have pull tabs or strips configured to activate the pump or permit the conduction of current from the power source to the pump assembly.

Additionally, as illustrated in FIGS. 178A-178C, a conduit A858 can communicate the negative pressure produced by the pump assembly A858 to the dressing layers A853. The conduit can be attached to or formed as part of the dressing cover layer used to cover the dressing layers A813. In some embodiments, at least one of an outer or top layer used to form the conduit in any embodiments disclosed herein can be vapor permeable. In this configuration, the conduit A858 can be sealed along a length thereof and can have perforations along the length thereof so that any desired length of conduit A858 can be detached from the dressing member A852, with the remaining portion of the conduit A858 remaining attached to the dressing member A852, as illustrated in FIG. 178B.

For example, in some embodiments, as illustrated in FIG. 178A, the dressing member A852 have a plurality of perforations, including without limitation first perforation A855a, second perforation A855b, third perforation A855c, and so on. A user can tear and detach the conduit A858 along any desired number of the perforations to permit any desired length of conduit A858, while the remaining portion of the conduit remains removably attached to the dressing member A852. In any embodiments, the perforations A855 can be arranged in a parallel orientation, as illustrated in FIGS. 178A and 178B. Alternatively or additionally, one or more perforations A855 can be arranged about a perimeter of the dressing member A852, which can surround the dressing layers A853, as illustrated in FIG. 178C.

Additionally, with reference to FIG. 178C, the dressing member A852 can support a plurality of power sources (which can be any of the flexible battery or any other power source embodiments disclosed herein) A856 distributed about a first portion A852a of the dressing member A852, either under, within or on top of any of the layers, materials, or members comprising the dressing layers A853 or dressing member A852. The power sources A856 can be interconnected in any desired fashion using one or more electrical connectors or wires A857. In some embodiments, the wire connectors A857 can extend along or within the conduit A858 to provide power to the pump assembly A854 located on the second portion A852b of the dressing member A852. The pump assembly A854 in any embodiments disclosed herein, including dressing kit embodiment A850, can be a miniature pump have a voice coil, a diaphragm, or otherwise.

In any embodiments disclosed herein, including the embodiment illustrated in FIGS. 178A-178C, the conduit A858 can have a foam, a transmission layer or 3d knit fabric, and/or other porous material therein to prevent or significantly prevent the collapse of the conduit during operation from kinking, crushing, etc., while permitting the passage of fluids therethrough, and can have a width from approximately 0.5 inches or less to approximately 0.75 inches or more, from approximately 0.75 inch to approximately 1.5 inches or more, having a low profile height of from approximately 0.1 or less to approximately 0.25 or more inches.

In any embodiments disclosed herein, the conduit can be formed of two layers of liquid and air impervious material (such as a thin polymer film) and have one or more layers of foam or other porous material to prevent the conduit from collapsing, formed in a circular, square, or other shaped length of material having foam or other porous material therein. As such, the dressing can be configured such that a user can adjust the length of the conduit by the amount of the conduit removed from the dressing.

Additionally, with reference to the dressing kit embodiment A870 illustrated in FIG. 179, in any of the embodiments disclosed herein, the dressing kit can have a conduit A878 that is arranged in a spiral or helical arrangement adjacent to the one of more dressing layers A873 of the dressing member A872. The conduit can be spirally wound about the pump assembly and/or power source. In some embodiments, the dressing kit A870 can have any of the features, details, or components of any of the other dressing kit embodiments disclosed herein, including without limitation those of dressing kit A850, including without limitation any of the details regarding the power source, pump assembly, dressing member, or conduit described with respect to any of the other embodiments, such as for dressing kit A850. For example, in some embodiments, the conduit can be perforated along a length thereof for selective detachment from the dressing member A872.

In any of these arrangements, the conduit A878 can be unwound or extended to permit the user to select the appropriate length of the conduit A878. The dressing can be used in the completely wound up arrangement illustrated in FIGS. 178A-178C, or can be partially unwound and used with the conduit partially wound up around the pump assembly A878, or the conduit A878 can be fully extended such that the pump assembly is positioned apart from the dressing. A bottom surface of the pump assembly can be coated with an acrylic or other suitable adhesive or fastener (such as any of the other fasteners disclosed herein) for attaching the pump and/or conduit to the body or even to the dressing member A872, as desired.

FIGS. 180A-180B illustrate another embodiment of a dressing kit A890 having a dressing member A892, a pump assembly A894, and a power source A896. In some embodiments, the dressing kit A890 can have any of the features, details, or components of any of the other dressing kit embodiments disclosed herein. The dressing kit can be packaged with the pump assembly A894 and/or the power source A896 positioned adjacent to the dressing layers A893. In some embodiments, the power source can be separable from the dressing member A892 and positionable in any desired position on the dressing member A892 and/or on the body adjacent to the dressing member or wound or otherwise. The power source A896 can be connected to the pump assembly A894 using a wired connection A897 that can have a connector for easy removal of the power source A896 for disposal or replacement.

Additionally, the dressing can be configured such that a perforated or weakened band of material is routed around the portion of the dressing that supports the battery. This can form a detachable portion of the dressing that supports the battery. Such configurations can facilitate battery removal, replacement, and/or proper disposal. Additionally, the battery module can be supported on a removable or separate portion of the dressing that tape or otherwise adhered to the main portion of the dressing and is easily removed therefrom for easy disposal of the battery module. The portion of the dressing that can support the battery module can be connected to the remaining portion of the dressing by tape, a local pad, or otherwise. The pump can be supported by the main dressing area. This could have a benefit for sterilization or sterilization of particular parts of the dressing, and could permit frequent (e.g., daily) battery changes. Additionally, in some embodiments, the batteries can be supported in a battery tray that can be easily supported by the dressing. The battery tray can be configured to be snapped into and out of the receiving portion of the dressing or pump assembly. This can reduce the wall thickness of the battery module and battery compartment.

Figure 181B:
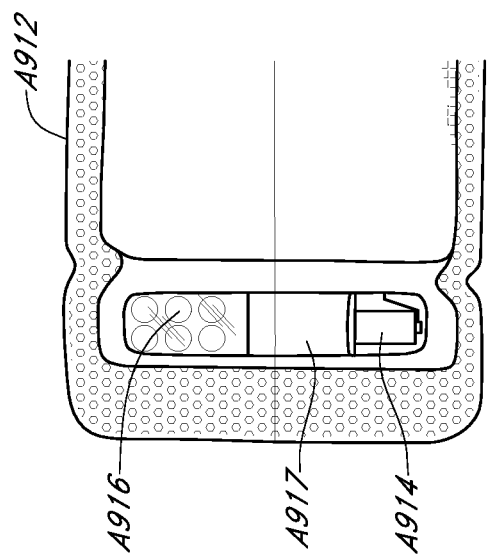
Figure 181A:
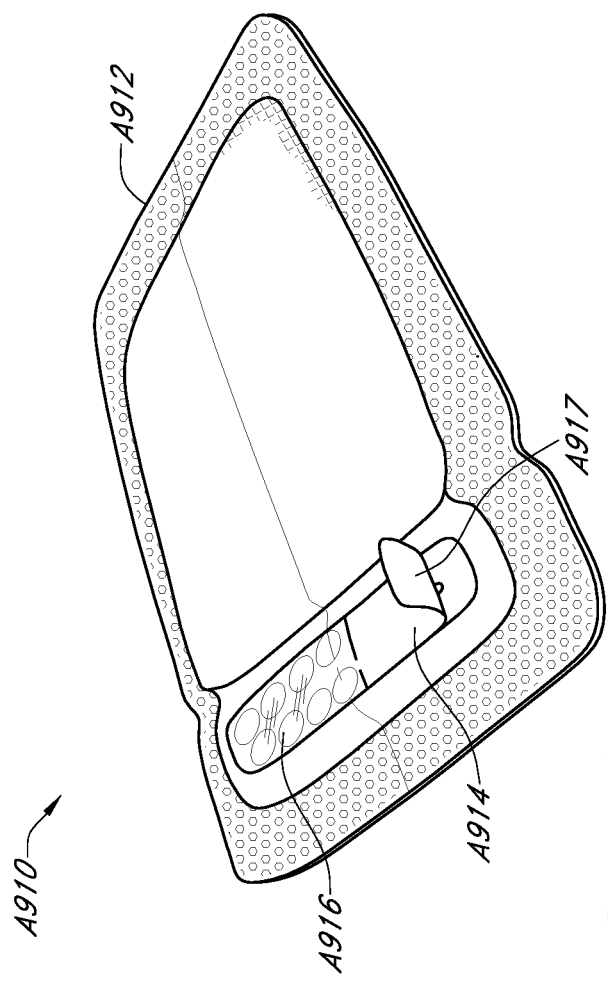

In the embodiment of the dressing kit A910 illustrated in FIGS. 181A-181B, the battery module can have one or more zinc air activated batteries A916 as the power source for the pump assembly A914. In this arrangement, removing a pull-tab A917 so as to expose the batteries A916 to air will activate the batteries A916 and start the operation of the pump A914. The pull-tab or label A917 can cover the openings or air passageways in communication with the batteries A916 and can be peeled back or removed to activate or re-activate the batteries A916. The pull-tab A917 can be configured to cover only a portion of the dressing member A912 or the battery module A916, or can be integral to larger dressing support for added stiffness during application of the dressing to the body. Any of the dressing kit embodiments disclosed herein can use any of the features, details, or components of the dressing kit A910 therein, including without limitation the air activated batteries.

With reference to FIG. 182, which illustrates a dressing kit A930 having a dressing member A932, and a pump assembly having a PCB A933, the power source or pump assembly can have one or more conductive labels A937 that, when in a first position, do not provide an electrical connection between a first terminal A938a and a second terminal A938b supported by the dressing member A932 or the PCB A933. When the conductive label or tab A937 is moved to a second position, the conductive tab A937 can provide an electrical connection between the first terminal A938a and the second terminal A938b, so as to activate the pump assembly. The packaging supporting the dressing can be configured such that such conductive label is held fixed in the first position to ensure that the batteries are not electrically connected to the pump assembly or other components during sterilization or prior to application to a patient or user. The conductive label A937 could be used as a pause button, or to terminate the operation of the pump.

In any dressing kit embodiments disclosed herein, the dressing kit can have one or more pull tabs (such as pull tab A957 illustrated in FIGS. 183A-183D) configured to activate and deactivate the pump assembly. In this arrangement, each pull tab A957 can be configured to be positioned between a first terminal A958a and a second terminal A958b to selectively control an activation of the pump assembly A954. With the pull tab A957 is positioned between the first terminal A958a and the second terminal A958b, thereby separating the first and second terminals A958a, A958b, no power will be provided to the pump assembly A954. By retracting the pull tab A957, the first and second terminals A958a, A958b can be placed in contact with one another such that power can be provided to the pump assembly.

Figure 183B:
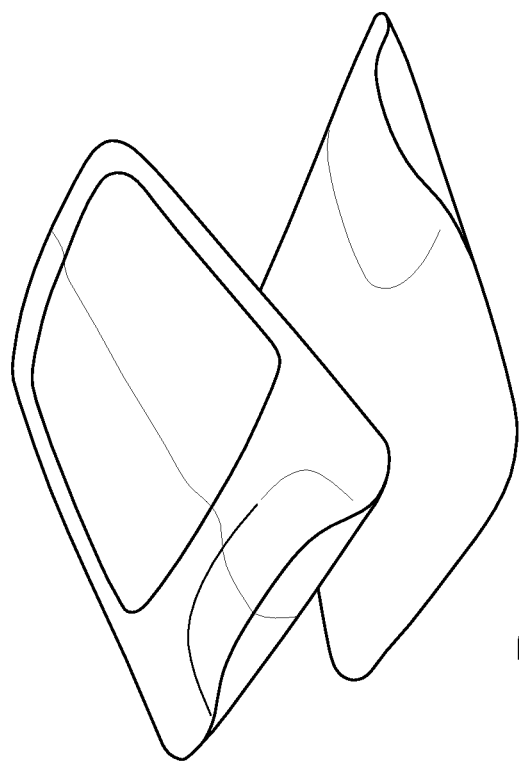
Figure 183A:
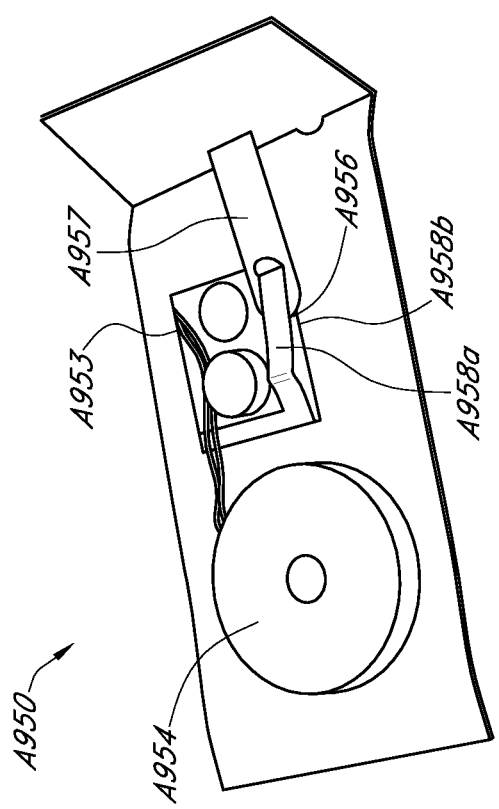
Figure 183C:
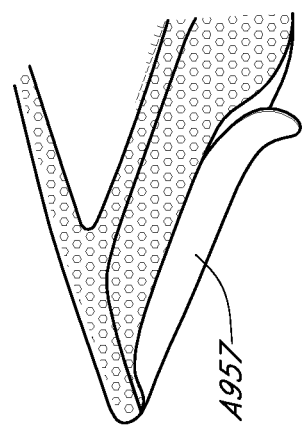
Figure 183D:
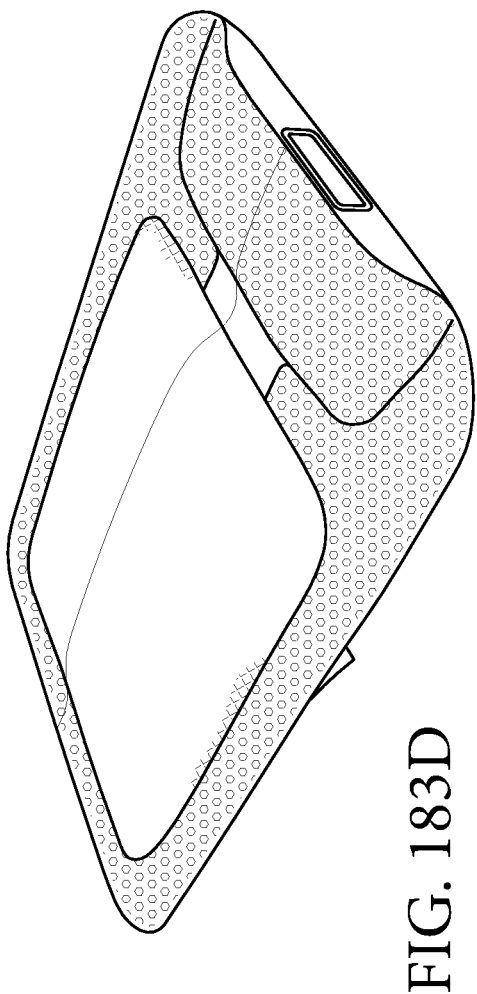

Additionally, in any embodiments, the packaging supporting the dressing kit can be configured such that such tab or isolator is fixedly positioned between the components in the electrical circuit to ensure that the batteries are not electrically connected to the pump assembly or other components during sterilization (if used) or prior to activation. For example, as illustrated in FIGS. 183B-183D, a pull tab can be positioned over any desired surface of the dressing, power supply, or pump assembly, of any of the dressing or pump assembly embodiments disclosed herein. As is disclosed in other embodiments, the label or tab can be conductive such that the first and second terminals are in communication with one another when the label is connected to both terminals.

As shown in FIGS. 184A-184B, in any embodiments disclosed herein, the dressing kit (such as dressing kit A970 disclosed in FIGS. 184A-184B) can have one or more buttons A979 supported by the dressing member A972. The buttons A979 can be fixed to the backing layer A975 of the dressing member A972 and can be positioned near an edge portion of the dressing (such as outside of the perimeter of the dressing layers A973) where operation of the buttons will not irritate or cause discomfort or damage to the wound. The controls can comprise one or more keypad buttons that can be positioned anywhere on the wound. The dressing can have one or more printed cables A981 to provide electrical connections between the batteries, activation buttons, LED or other lights A986 for indicating a condition under the dressing or with regard to the pump assembly A974, and/or power source A976.

With reference to the dressing kit A990 shown in FIGS. 185A-185C, in any embodiments disclosed herein, the pump assembly A994 can be activated using one or more pop buttons A997. Each pop button A997 can be configured such that, when the pump is activated and the conditions under the overlay are within threshold parameters, the pop button will remain depressed and the pump will continue to operate. The circuitry of the pump assembly A994 can be configured to maintain the button A997 in the depressed position during optimal or threshold conditions, for example when a sufficient vacuum has been achieved. The button can be configured to pop up when a sufficient vacuum has not been achieved, or when other operating conditions under the overly are not within the threshold parameters. As such, the button can be used to provide a visual indication of the operating conditions of the dressing. The button can be depressed to initially activate operation of the pump.

Figure 186A:
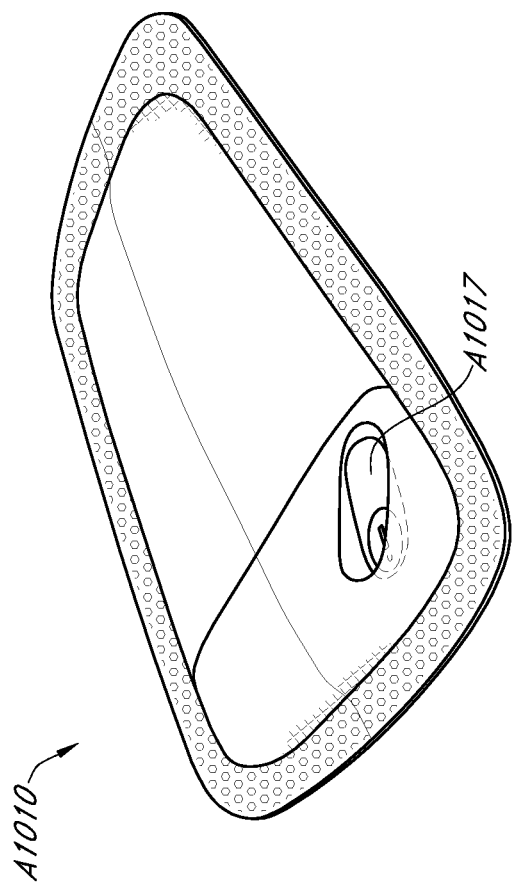
Figure 186B:
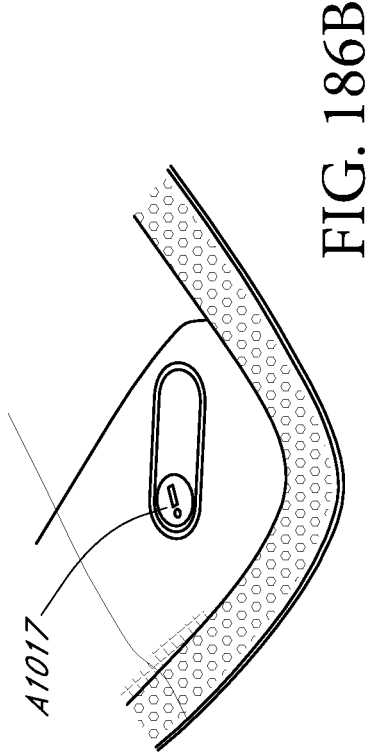

The switch A1017 (which can be a trip switch) illustrated in FIGS. 186A-186B can also be used to activate or control any of the pump assembly or dressing kit embodiments disclosed herein, and can also provide a visual indication of the operating conditions of the dressing. Depressing the switch A1017 can activate a pump. The switch A1017 can move between a first, relaxed position to a second, depressed position.

In some embodiments, the circuitry of the pump can be used to maintain the switch in the depressed state when the operating conditions under the backing layer are within threshold parameters. In some embodiments, the switch A1017 can have one or more components made from a shape memory material, or have a memory bistable dome or diaphragm therein that can hold the switch A1017 in a depressed position for a predetermined period of time during initial pump down until the level of reduced pressure under the overlay is sufficient to maintain the switch in the depressed (or second) position. In some embodiments, a pressure sensor within the dressing or pump assembly can be configured to provide a current of electricity to a shape memory, piezoelectric material sufficient to hold the switch in the depressed or second position.

The switch can be configured to pop up if there is a leak in the dressing (detected based flow rate through the pump or on duty cycle feedback or other parameters), or if one or more other parameters or conditions are not met, such as but not limited to insufficient battery power or insufficient negative pressure within the dressing after a predetermined period of time. For example, the switch of this or any other embodiment disclosed herein can be configured to move between a first on position and a second off position, and to remain in the first position when a threshold level of negative pressure is maintained beneath the backing layer. The switch of this or any other embodiment disclosed herein can be configured to move to the second position when the level of negative pressure under the backing layer is less than a threshold level of negative pressure and the pump assembly exceeds a threshold flow rate for a threshold period of time, which can be caused by the presence of a leak in the system. For example, any of the embodiments disclosed herein can be configured to trigger an alarm or change the switch or button from a first operational position to a second non-operational position when the pressure beneath the dressing is less than 60 mmHg (i.e., less meaning 59 mmHg or lower) and the pump assembly has been operating for a threshold period of time, such as for approximately 5 minutes, from approximately 5 minutes to approximately 8 minutes, or from approximately 2 minutes to approximately 5 minutes, or any values within any of the foregoing ranges. Additionally, depressing the switch can produce an audible click to alert the user that the switch has been activated.

The embodiment of the dressing kit A1030 illustrated in FIGS. 187A-187C can have a pump assembly A1034 supported on the dressing member A1032. The pump assembly A1034 can have a flexible activation switch A1037 that can activate or control any of the pump assembly or dressing kit embodiments disclosed herein. The activation switch can be configured to be a flexible tab A1041 having one or more buttons A1039 supported there. The flexible tab A1041 can be rotated upward away from the pump assembly to a first position to permit a user to grasp and activate the button or buttons A1039. In any embodiments disclosed herein, the button A1039 can be activated by squeezing the button A1039, so that no force or very little force is imparted on the wound dressing or wound bed. When in the stowed or second position, the activation switch or tab A1037 can have a low profile and lie substantially flat against the pump assembly.

Alternatively, in any embodiments, the activation switch can be a slide activation switch (such as slide activation switch A1057 illustrated in FIG. 188 or slide activation switch A1077 illustrated in FIGS. 189A-189B) or a squeeze activation button or switch (such as switch A1097 illustrated in FIG. 190) to reduce the forces imparted on the wound. Though not required, the slide switches of the embodiments shown in FIGS. 188 and 189A-189B can be a reed switch with a sliding magnet. The slide switches can be configured to provide an illustration or indication of the position of the switch, for example, to alert a user that the switch is in a particular position, such as in the on or active position. The switch mechanism can be used for battery isolation prior to operation of the pump or during sterilization, if sterilization is used. The switches in any of these embodiments can move the batteries into and out of contact with the pump assembly such that, prior to operation, the battery can be out of contact with the battery terminals or other electrical connections between the batteries and the pump assembly.

Any of the embodiments disclosed herein wherein the activation mechanism has a sliding mechanism, a sliding switch, or other moving activation mechanism, including without limitation the embodiments illustrated in FIGS. 188-190, can have any of the features configured to prevent the premature activation of the pump in the packaging supporting the dressing kit and pump assembly or otherwise. Additionally, any such embodiments can be configured such that the packaging can be configured to securely hold the pump assembly and/or battery module in a disconnected state.

For example, the dressing kit embodiments can be supported in the packaging such that, while the dressing kit is supported in the packaging, the components of the battery pack or pump assembly are held in a first or non-operational position and prevented from moving to a second operational position. In this configuration, when the components are in the first position, the pump is non-operational due to the fact that the battery terminals are not in contact with the one or more batteries. For example, the packaging supporting the dressing kit can prevent a lid of the battery housing from moving to the second position by holding the housing lid or cap in the first position. The packaging can have protrusions that are positioned between the housing lid or cap and the body of the battery housing that separate the battery housing lid from the body of the battery housing. Once the dressing kit is removed from the packaging, the battery housing lid or cartridge can be slid inward, permitting the terminals to contact the batteries so that the pump can be activated. In this configuration, the battery housing can serve as an activation button. Sliding the lid out of contact from the batteries can stop the operation of the pump. Further, the dressing kit can be configured such that sliding the batteries into engagement with the battery terminals will result in an audible click, to alert a user regarding the position of the components of the battery enclosure or regarding whether the battery circuit is open or closed.

Any of the dressing kit embodiments disclosed herein can have a rotating or wheel activation switch (such as the rotating switch A1117 illustrated in FIGS. 191A-191C) or an axial sliding tab or reed (such as the sliding tab switch A1137 illustrated as shown in FIG. 192) having two or more positions corresponding to two or more pump operation positions. For example, the wheel switch A1117 can define an off position, as shown in FIG. 191B and an on position shown in FIG. 191C. A protrusion or bump A1117a on the wheel A1117 can be used to limit the rotational range of the switch A1117, and one or more detents can be used to give tactile feedback regarding the switch position and/or bias the switch to remain in the positions associated with the detents.

Similarly, the pull tab A1137 in FIG. 192 can trigger an operational state if moved to a first position (such as by pulling the tab in the direction indicated by arrow A1) and a non-operational state if moved to an opposite, second position (such as by pushing or pulling the tab in the direction indicated by arrow A2). In some embodiments, though not required, the pull tab A1137 can have two end portions that can be grasped, such as first end portion A1137a and second end portion A1137b. Though not required, any of the switches or buttons of any of the dressing kit embodiments disclosed herein can have one or more intermediary positions corresponding to different operation states, such as different operational programs or otherwise. Detents or tabs on any of the switches can be used to define the two or more operational states or positions.

Additionally, as mentioned, for any of the switches or buttons of any of the dressing kits disclosed herein, the pump assemblies and/or battery modules can be configured such that the position of the switch or button dictates the position of the batteries relative to the battery terminals or other electrical connections with the pump assembly. Further, as with any other embodiment disclosed herein, the packaging surrounding the dressing kit having the pull tab arrangement illustrated in FIG. 192 can be configured such that the dressing kit with the pull tab fits in the packing only when the pull tab is in the non-operational position.

In any of the pull tab arrangements disclosed herein, with reference to FIG. 193, the receiver or support A1159 for the pull tab A1157 can be configured such that the receiver or support A1159 must be squeezed inwardly to permit the pull tab A1157 to be slideable relative to the receiver or support A1159. This can prevent or reduce the likelihood that the pull tab A1157 will be inadvertently moved to a different position. In use, a user can squeeze the receiver or support A1159 while simultaneously moving the switch A1157 to the desired position.

FIGS. 194A-194B illustrate an embodiment of a dressing kit A1170 having an arrangement of an isolator switch A1177 that can be used with any of the dressing kit embodiments disclosed herein, including the sliding switch embodiments. For example, the rotating or sliding switch A1177 can be formed from a non-conductive material and can be configured to open a switch or spread a pair of contact terminals, such as first contact terminal A1179a and A1179b apart to prevent the flow of electricity between the two terminals A1179a, A1179b, when the switch A1177 is in a first position (as illustrated in FIG. 194A). In some embodiments, the isolator can be a plastic tab or switch that rotates about a living hinge. When moved to a second position (as illustrated in FIG. 194B), the contact terminals A1179a, A1179b can in contact such that the electrical connection can be closed and permit a flow of electricity through the electrical connection. The batteries can be electrically isolated from each other and/or from the rest of the circuitry in this arrangement.

In any embodiments disclosed herein, as illustrated in FIG. 195, the pump can be activated by passing a key fob or activator A1217 over an RF ID receiver A1219 positioned on the pump assembly A1214. This can eliminate the force that would otherwise be imparted on the wound dressing during activation of the wound dressing. In some arrangements, as illustrated in FIG. 196, the activation button A1237 can be activated by infrared radiation, light, or by touch. This can reduce or eliminate the pressure exerted on the wound when switching the pump assembly between an on and an off state.

FIGS. 197A-197B illustrate a push button arrangement A1257 that can be used to activate any of the pump assemblies disclosed herein. The push button can have a flexible dome switch A1259 over a surface mount tact switch A1261. A threshold level of reduced pressure can hold the flexible dome A1259 in place as visual indicator that a sufficient level of reduced pressure is being exerted on the wound bed. In this arrangement, the button can serve as an activation switch and a tactile or visual indicator. The indicator can be used to alert the user to any or any combination of the following conditions: user device is operating correctly; leak detected; battery dead; and/or dressing saturated or full.

As mentioned, any of the dressing kit embodiments disclosed herein can have a visual pressure indicator configured to provide a visual indication of the pressure beneath the backing layer. The visual pressure indicator can be configured to change position in response to a differential in pressure between the space beneath the backing layer and atmospheric pressure. In some embodiments, the pressure indicator or bubble can be configured to retract or collapse toward the wound surface in response to increasing levels of reduced pressure beneath the backing layer.

In some embodiments, the pressure indicator can have a different color as compared to the remainder of the dressing, or can be configured to change color in response to threshold pressure differentials between the space beneath the backing layer and atmospheric pressure. The pressure indicator can be positioned in an opening or depression formed in the dressing to shield the pressure indicator from impact and to protect the pressure indicator. For example, as described above, the dressing kit A330 of FIGS. 152A-152C can have one or more pressure indicators thereon.

The one or more pressure indicators can be supported in any desired location on the dressing. With reference to FIGS. 198A-198B, the pressure indicator A1270 can have a pressure bubble A1272 configured to be in an expanded position (as shown in FIG. 198A) when the dressing is in a first, low or no reduced pressure state and in a collapsed position (as shown in FIG. 198B) when the dressing is in a second, increased reduced pressure state. In any embodiments disclosed herein, the dressing can have a pressure bubble (such as pressure bubble A1272) positioned over a membrane (such as membrane A1274), which can be stretchable or substantially stretchable. The membrane A1274 can be formed from a material that is gas permeable, but liquid impermeable in some embodiments. The membrane A1274 can be configured to be substantially or completely opaque in a first, relaxed state and less opaque (i.e., more translucent) in a second, more depressed state. Alternatively, the membrane material can be somewhat translucent in the first, unstretched state and more translucent in a second, stretched state. Reduced pressure imparted on the dressing can cause the membrane to depress or move from the first toward the second state.

In some embodiments, the membrane can be substantially opaque except when in contact with the colored material or liquid A1276 beneath the membrane A1274. When the membrane A1274 contacts the liquid or solid material A1276 beneath the membrane A1274, the color of such liquid or solid material A1276 can become more visible such that the color becomes apparent when a threshold level of reduced pressure is exerted on the membrane A1274, causing it to more toward the colored material.

As mentioned, a colored material such as ink or other material can be positioned under the membrane. The dressing can be configured such that the membrane layer between the pressure bubble and the colored material is substantially more visible in the second state than in the first state, permitting the user to visually inspect the level of reduced pressure in the overlay by visually monitoring the color under the pressure bubble. In some arrangements, the pressure bubble can be visually observed after depressing the button.

Other pressure indicators can be supported by the wound dressing. For example, as illustrated in FIGS. 199A-199C, a wound dressing can have a plurality of pressure indicators A1270 (of any suitable configuration or configuration disclosed with respect to any embodiments disclosed herein) positioned about a top surface of the dressing to provide a visual and/or a tactile indication of a level of negative pressure beneath the dressing overlay A1272. The plurality of indicators A1270 can have a plurality of pressure bubbles activated by reduced pressure. In some embodiments, the pressure bubbles or indicators can have a colored substance or material beneath the dome of the indicator, or a light beneath the indicator to enhance the visual appearance of the indicator. In some embodiments, the pressure indicators A1270 can be configured to define two states or positions—a depressed or collapsed position when a threshold level of reduced pressure is present under the overlay and an extended or inflated position when no pressure or less than the threshold pressure is present under the overlay. In some embodiments, the pressure indicators A1270 can also define intermediate positions.

The pressure indicators or bubbles can be mounted on a panel or formed in a panel arrangement and can have any suitable shape or size. The pressure indicators can be integrally formed with the overlay material, or can be integrally formed in a panel arrangement that can be attached to or mounted on the overlay. Additionally, the pressure indicators can be individually formed. In any embodiments disclosed herein, a pressure indicator can be positioned in each of four corners on the overlay.

With reference to FIGS. 200-203, any dressing kit embodiments disclosed herein can have an indicator light A1290 supported by or embedded within the dressing to provide a visual indication of one or more of the operating parameters of the dressing, pump assembly, or battery modules. In some embodiments, the light A1290 can be positioned such that it is visible from two or more planes or directions. Additionally, the light can be supported on a protrusion projecting from an outside surface of the dressing so that the light A1290 is more visible from a greater number of angles. The light A1290 can be an incandescent light, and LED light, or any other suitable light and can be constant or pulsating, or programmable. Additionally, the light A1290 can be configured to change intensity of the light output and can be programmed to gradually increase and decrease the light output.

Figure 201:
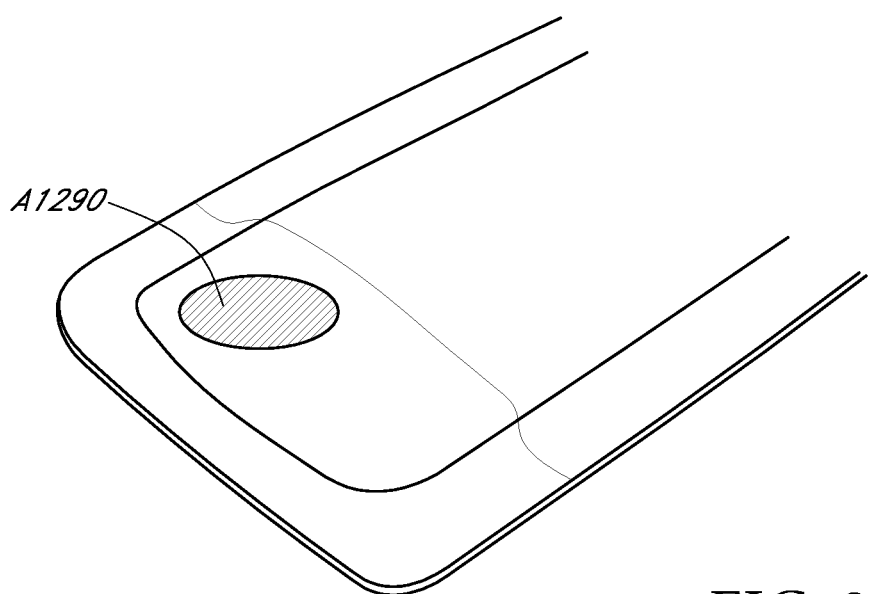
Figure 202:
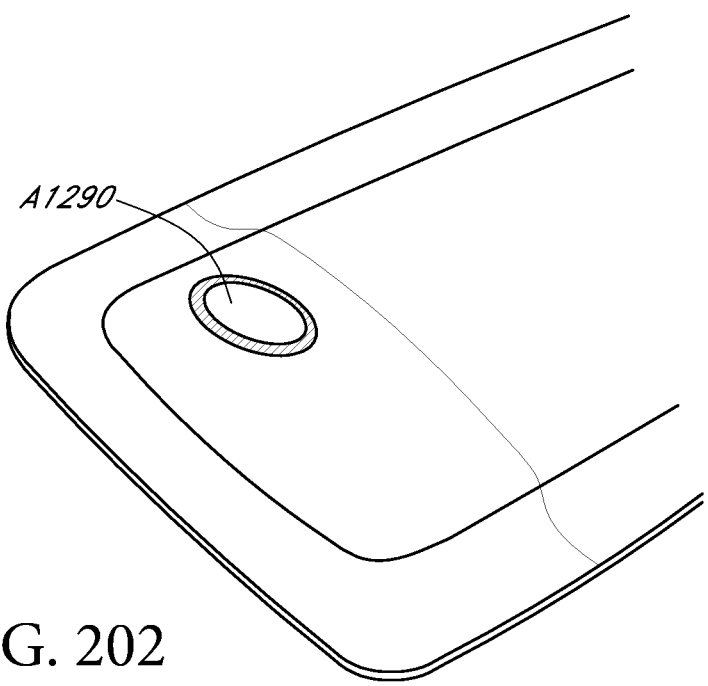
Figure 203:
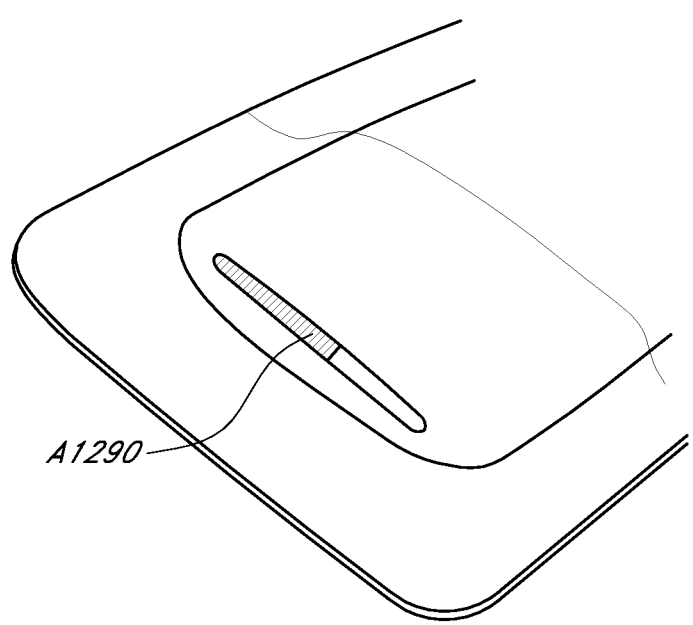

With reference to FIGS. 201, 202, and 203, in some embodiments, the dressing can have a soft or diffused light (as in FIG. 201), a light ring (as in FIG. 202), or an array of lights (as in FIG. 203). As shown in FIG. 201, the dressing can have a discrete diffused light area. The light area can be a continuously lit area, providing reassurance that the dressing and pump assembly is operating correctly.

As shown in FIG. 203, the dressing can support a panel of lights A1290 that is configured to provide an indication of a magnitude of a reading or level within the overlay, or a level of power in the power source. For example, in any embodiments disclosed herein, for light based pressure sensors, temperature sensors, or saturation sensors or indicators, the number of lights illuminated in an array of lights can increase as a level of reduced pressure, level of temperature, or saturation level under the overlay increases. The lights can also be used to indicate a duration of therapy, or a remaining duration of therapy. Multiple light arrays can be used to indicate multiple indications. Additionally, any of the lights disclosed herein can be configured to pulse or flash to provide a variety of signals regarding a variety of conditions to a user. Any of the lights disclosed herein can be LED lights.

Further, as shown in FIG. 202, any of the user buttons on the dressing can have lights integrated into the button design. In any embodiments disclosed herein, the light can surround the button so that a user can easily locate the button.

In any embodiments disclosed herein, as is shown for the embodiment of the dressing kit A1310 shown in FIGS. 204A-204B, the dressing can have shaped features A1312 positioned on a surface of the dressing A1314 that are fully revealed and identifiable by touch only when a threshold level of reduced pressure is achieved in the dressing. FIG. 204A shows the dressing A1310 in first state, where less than a threshold level of reduced pressure exists under the overlay A1316. The dressing can be in a first state when the pump is not operational or when less than the optimal level of reduced pressure is present under the overlay A1316. Dressing components or the strength of the overlay layer A1316 can hold the overlay layer A1316 in a raised position so that the overlay layer A1316 (i.e., the outermost layer) does not collapse under gravity against the foam or other materials below the overlay layer A1316. The dressing A1310 can be configured such that, when a sufficient or threshold level of reduced pressure exists under the overlay A1316, the overlay layer A1316 collapses against a top surface or a top layer A1314 of the packing material or materials, as shown in FIG. 204B. When this occurs, in some embodiments, a color of the packing material layer A1314 can be revealed through the overlay A1316.

Additionally, with reference to FIGS. 205A-205D, in any embodiments disclosed herein, the dressing can have a one or more discrete openings or depressions A1332 for detecting a level or a threshold level of reduced pressure under the backing layer A1333. In any embodiments disclosed herein, the top surface or top layer A1334 of the packing material can define one or more raised, depressed, and/or colored features A1336 that have a shape that departs from the surface of the packing material. For example, though not required, the packing material A1334 can have one or more protrusions or tactile bubbles A1336 projecting away from the surface of the packing material A1334. Further, in some embodiments, the features can be depressions or even holes or openings formed through or into the top surface A1334 of the packing material. The features can be sized, positioned, and configured such that a user can see and/or feel the features more when the dressing backing layer is in the second state than in the first state.

In any embodiments disclosed herein, at least the top layer or top surface of the packing material can be a different color than the other materials comprising the dressing. The dressing can be configured such that the color of the packing material is substantially only visible, or is visibly darker or different, when the dressing is in the second reduced pressure state than when it is in the first state.

With reference to FIGS. 205A-205D, the dressing A1333 can be configured such that the deflecting membrane A1332 changes color in the presence of moisture and/or pressure. In some embodiments, the dressing can be configured such that the dressing reveals a different color substrate under the backing layer A1333 when the backing layer A1333 is collapsed against the packing material. Any of the dressing kit or dressing embodiments disclosed herein can have any or any combination of the features disclosed in the embodiment of the dressing illustrated in FIG. 204A-204B or 205A-205D, or otherwise.

Any of the dressing kit embodiments disclosed herein can have a vibration buzzer A1352 that can be tethered to the dressing A1354 (as shown in FIG. 206), or can have an audible alarm or alert function A1362 (as shown in FIG. 207). The vibration alarm or buzzer A1352 or audible alarm or buzzer A1362 can be configured to alarm or alert a user to a particular condition regarding the wound dressing, pump, batteries, or any other component of the dressing kit. This can provide the user with feedback regarding the performance of the pump without requiring the user to see the pump, which can be particularly beneficial when the pump is worn under clothing or in any other fashion or manner that conceals the dressing or pump. The vibration buzzer can be mounted directly to a patient's skin, to the dressing, or otherwise. The vibration buzzer can have combination of any of the other features disclosed herein. In some embodiments, the vibration buzzer use the pump assembly to provide the vibration. On/off patterns of the pump can be used to provide the desired vibration or alert. Additionally, the audible alarm or buzzer can be positioned or supported apart from the dressing.

In any embodiments disclosed herein, the dressing can have one or more sensors therein that can trigger an alarm when a threshold level or when one or more predetermined levels of saturation within the dressing has been reached. For example, the dressing can be configured to trigger a first alarm when a first level of saturation has been reached, to trigger a second alarm when a second level of saturation has been reached, to trigger a third alarm when a third level of saturation has been reached, and so on, wherein the level of saturation is the level of fullness of the dressing. In some embodiments, the sensors can be positioned within the absorption layers of the dressing and can be configured to generate a signal based on exposure to liquid within the dressing. For example, one or more hygroscopic sensors could be positioned under the backing layer of the overlay. The sensors can be positioned within the dressing layers, and discrete locations about the dressing layers to monitor the amount of liquid throughout the dressing layers. For example, in any embodiments disclosed herein, between 2 and 4 sensors can be positioned symmetrically about the dressing layers, or between 4 and 6 sensors can be positioned symmetrically about the dressing layers. Some embodiments of the dressing kit can have one sensor positioned under the backing layer. In any embodiments disclosed herein, one or more sensors can be positioned adjacent to the port to the pump assembly. Without limitation, the first level can be at approximately 60% saturation, the second level can be at approximately 75% saturation, and the third level can be at approximately 90% saturation. In some embodiments, the first level can be from approximately 60% saturation to approximately 70% saturation, the second level can be from approximately 70% saturation to approximately 80% saturation, and the third level can be from approximately 80% saturation to approximately 90% saturation. In some embodiments, the saturation level can be detected using one or more resistance or capacitance sensors (such as a humidity or moisture sensor based on resistivity or capacitance) positioned within the dressing. In any embodiments disclosed herein, the moisture sensor can be positioned close to or adjacent the wound facing side of the filter or otherwise adjacent to the pump assembly or port to indicate the dressing is saturated or the fluid level is close to the level that will result in blockage to the filter, which could inhibit further negative pressure transmission from the pump assembly.

In any of the embodiments disclosed herein, with reference to FIG. 208, the dressing A1370 can have one or more saturation indicators A1372. For example, without limitation, any of the dressings can have one or more markings or indicators A1372 on the backing layer to indicate or reveal a level of exudate in the dressing when the exudate reaches a threshold level. The indicator can be a clear or transparent window in an otherwise opaque dressing. The dressing can have instructional text around or adjacent to the window to provide a user with instructions regarding how to use the saturation indicator. Additionally, such saturation indicators could be positioned at a variety of different locations on the dressing. Any of the dressing embodiments disclosed herein can have this feature.

Similarly, with reference to FIG. 209, any dressing embodiments disclosed herein can have one or more fill line indicators A1382 to help a user or medical practitioner assess a level of exudate within a dressing. The fill line indicators A1382 could be lines of substantially transparent appearance across a surface of the dressing, or could be printed lines or markings on the overlay. The fill line indicator can be used to assess when a dressing is ready for changing. With reference to FIG. 210, any embodiments disclosed herein can have a plurality of viewing windows A1392 supported by the backing layer or can have one or more openings or depressions formed in the packing material to permit a user to detect a level of exudate or saturation of the dressing.

As illustrated in FIG. 211, any dressing kit embodiments disclosed herein can be configured to produce a motor pulse or sound to indicate in a controlled manner that the device is working correctly. For example, the dressing kit A1400 can have a pump motor A1402 that can be configured to produce a sound and/or vibration that repeats at regular intervals or following regular patterns.

With reference to FIG. 212A, any embodiments disclosed herein can be configured to have a bubble indicator A1410 that serves as a pressure indicator, but which also activates the device, similar to one or more of the other embodiments described above. The bubble indicator will be in communication with the space between the cover layer A1412 and the wound, and can be configured to depress a switch A1413 when depressed. This establishes a clear communication between a working device and the interaction to restart it. As with other embodiments disclosed herein, with a color change material positioned under the bubble, as shown in FIG. 212B, the collapse of the pressure bubble under reduced pressure can reveal a colored bottom to the indicator A1412.

With reference to FIGS. 213A-213B, any of the pressure indicators disclosed herein can have two or more different colors to help a user better visualize the position of the indicator and, hence, the condition under the overlay. For example, a first colored ring A1432 could be positioned around the protrusion A1433, and the protrusion A1433 can have a similarly colored top surface such that, when the protrusion is collapsed, the color of the top A1434 of the protrusion A1433 matches the color surrounding the protrusion so that it is clear that the protrusion is collapsed. When less than a sufficient amount of reduced pressure is exerted on the overlay such that the protrusion A1433 extends away from the cover of the overlay, a different colored portion of the protrusion can contrast with the color surrounding the overlay to provide a clear indication to a user that the protrusion A1433 is extended and that a less than optimal amount of reduced pressure is present under the overlay. In some embodiments, the color separation or differentiation on the protrusion or indicator can add an extra visual indication that the device requires re-activation. A red side wall can indicate that the device has lost the vacuum or that less than the threshold vacuum level is present.

With reference to the embodiment depicted in FIGS. 214A-214B, any of the dressing kit embodiments disclosed herein can have a plurality of discrete depressions, openings, or other features A1452 formed in a top surface of the packing layers A1454 that can be used to provide a visual and/or tactile indication of the level of reduced pressure beneath a backing layer. In some embodiments, openings A1456 can pass through to a lower layer A1458 of the dressing A1450. In this configuration, when the dressing A1450 is in an operational state, the backing layer to be drawn into or toward the depressions, but relaxed when the dressing is not in an operational state.

FIGS. 215A-215B illustrate another embodiment of a dressing kit A1470 having a dressing member A1472, a pump assembly A1474, and a power source A1476 (which can be housed within a housing A1477 that also houses the pump assembly, or can be distributed across the dressing member A1472, or otherwise). A conduit A1478 can be used to transfer the negative pressure from within the pump assembly A1474 to the dressing member A1472. The dressing member A1472 can have a pocket member A1480 positioned adjacent to the dressing layers A1473 or positioned above the dressing layers A1473 and can be used to removably support the housing A1477 for the pump assembly A1474 and/or the power source A1476. With reference to FIG. 215B, the housing A1477 can be removed from the pocket member A1480 for servicing, battery replacement, or to position the housing A1477 in a different location apart from the dressing for comfort, etc.

FIGS. 216A-216C illustrate a carrier A1490 for a pump assembly A1494 that can be used with any of the pump assemblies or dressing kits disclosed herein. The carrier A1490 can be worn on a person's belt or otherwise clipped onto a person's clothing.

In some embodiments, such as the embodiment of the noise attenuating system A1510 illustrated in FIGS. 217A-217B, a special pouch or overmold A1512 can be formed to surround any of the pump assemblies disclosed herein. The overmold A1512 can be formed from silicone, rubber, foam, and/or any other material available configured to attenuate the noise and/or vibration of the pump assembly. Additionally, a special pouch or overmold A1514 can be formed to surround any of the pump motor embodiments disclosed herein. The overmold A1514 can be formed from silicone, rubber, foam, and/or any other material available configured to attenuate the noise and/or vibration of the pump motor. In some embodiments, an overmold A1516 for a pump motor can have a slot A1518 therein along a length of the wall portion of the overmold A1516.

With reference to FIGS. 218A-218D, any of the dressing kit embodiments disclosed herein can have one or more support handle member A1551 removably positioned around a periphery of the dressing A1552 to provide support to the dressing A1552 during application of the dressing A1552 to the body. The support handle member A1551 can increase the stiffness and, hence, reduce the floppiness, of the dressing A1552 to facilitate handleability of the dressing A1552. Providing the additional support on the dressing can be very important to the application of the dressing A1552 to the body, in light of the weight of the pump assembly and batteries on the dressing A1552. The support can be formed from paper, and plastic film, or any other suitable material. Additionally, instructions or other information can be printed on the support material.

In some embodiments, the support handle member A1551 can have a first lengthwise portion A1551a and a second lengthwise portion A1551a positioned between the dressing layers A1553 and an outer perimeter A1552a of the dressing member A1552. In some embodiments, the first and second lengthwise portions A1551a can be interconnected. Additionally, the support handle member A1551 can have a first end portion A1551b and a second end portion A1551b positioned between the dressing layers A1553 and an outer perimeter A1552a of the dressing member A1552. In some embodiments, the first and second end portions A1551b can be interconnected. Additionally, in some embodiments, the support handle member A1551 can have a housing or third portion A1557 configured to cover an end portion of the dressing member A1552. For example, one or more buttons, switches, a pump assembly, a power source, and/or other features can be protectably supported under the third portion A1557 of the support handle member A1551. The support handle member A1551 can be configured to activate the pump upon removal. In some embodiments, the support handle member can be continuous such that each portion is interconnected.

Other Negative Pressure Therapy Apparatuses, Dressings and Methods (Including Description from Appendix B of U.S. Provisional Application No. 61/791,984)

Moreover, some embodiments disclosed herein are directed to systems that include negative pressure therapy apparatuses and dressings, and methods for operating such negative pressure therapy apparatuses for use with negative pressure therapy dressings. In one embodiment, a wound treatment apparatus for treatment of a wound site comprises: a wound dressing comprising: an absorbent layer configured to retain fluid, a backing layer above the absorbent layer, and an obscuring layer configured to at least partly visually obscure fluid within the absorbent layer; and a fluidic connector configured to transmit negative pressure from a negative pressure source to the wound dressing for the application of topical negative pressure at the wound site.

In some embodiments, the obscuring layer is above or below the backing layer. The obscuring layer may configured to at least partially visually obscure fluid contained within the absorbent layer. The obscuring layer may comprise at least one viewing window configured to allow a visual determination of the saturation level of the absorbent layer. The at least one viewing window may comprise at least one aperture made through the obscuring layer. The at least one viewing window may comprise at least one uncolored region of the obscuring layer. The viewing window may comprise an array of dots. The array of dots may be distributed in a straight line of dots, the straight line of dots being positioned on a center line along a length of the absorbent layer. The straight line of dots may comprise an array of three dots. The straight line of dots may comprise an array of five dots. The straight line of dots may comprise an array of eight dots. The array of dots may be distributed in two straight lines of dots, the two straight lines of dots positioned to be an equal distance from a center line along a length of the absorbent layer, the two straight lines of dots having an equal number of dots. The two straight lines of dots may comprise an array of three dots. The two straight lines of dots may comprise an array of five dots. The array of dots may be distributed regularly over the obscuring layer to enable assessment of wound exudate spread. The viewing window may be selected from the group consisting of a graphical element or a typographical element. The obscuring layer may comprise an auxiliary compound, wherein the auxiliary compound may comprise activated charcoal configured to absorb odors and configured to color or tint the obscuring layer. The fluidic connector may comprise an obscuring element configured to substantially visually obscure wound exudate.

Some embodiments may further comprise an acquisition distribution layer between the wound contact layer and the absorbent material. The absorbent layer may comprise cellulose fibers and between 40% and 80% (or between about 40% and about 80%) superabsorbent particles. The obscuring layer, in a dry state, may be configured to yield a CIE y value of 0.4 or less and a CIE x value of 0.5 or less on a CIE x, y chromacity diagram. The obscuring layer, in a dry state, may have a color of Bg, gB, B, pB, bP, P, rP, pPk, RP, O, rO, or yO on a CIE x, y chromacity diagram.

In some embodiments, the wound dressing further comprises an orifice in the backing layer, the orifice configured to communicate negative pressure to the wound site. The orifice may comprise at least one orifice viewing window configured to be positioned adjacent to the orifice in the backing layer, the orifice viewing window configured to allow a visual determination of the saturation level of the absorbent layer adjacent to the orifice. The orifice viewing window may be cross-shaped. The wound dressing may comprise a first length corresponding to a first edge of a wound dressing and a first width corresponding to a second edge of the wound dressing, a first x axis runs along the first width and a first y axis runs along the first length, wherein the first x axis and the first y axis are in a perpendicular alignment. The viewing window may comprise a first arm and a second arm, the first arm of the viewing window define a second length and the second arm defines a second width, a second x axis runs along the second width and a second y axis runs along the second length, wherein the second x axis and the second y axis are in a perpendicular alignment. The second x axis and second y axis of the viewing window is offset from the first x axis and the first y axis of the absorbent layer. The second x axis and second y axis of the viewing window may be aligned with the first x axis and the first y axis of the absorbent layer. The cross-shaped transparent layer may comprise flared ends. The fluidic connector may be configured to transmit air. The fluidic connector may comprise a filter, the filter configured to block fluid transport past itself. The fluidic connector may comprise a secondary air leak channel, the secondary air leak channel configured to allow a flow of ambient air to the wound site. The secondary air leak channel may comprise a filter. The fluidic connector may comprise a soft fluidic connector. The soft fluidic connector may comprise a three dimensional fabric. In some embodiments, the three dimensional fabric is configured to transmit therapeutic levels of negative pressure while an external pressure up to 2 kg/cm$^2$ is applied thereto. The soft fluidic connector may be configured to be connected to a tube in fluid communication with the vacuum source. The soft fluidic connector may be configured to be connected directly to the vacuum source. The soft fluidic connector may comprise an enlarged distal end, the enlarged distal end configured to be connected to the wound dressing. The apparatus may further comprise a tube connected to the fluidic connector. The apparatus may further comprise a pump in fluid communication with the fluidic connector. In some embodiments, the absorbent layer comprises two or more lobes. The absorbent layer may further comprise a tissue dispersant layer.

In another embodiment, a wound treatment apparatus for treatment of a wound site comprises: a wound dressing configured to be positioned over a wound site, the wound dressing comprising: a backing layer having an upper surface and a lower surface and defining a perimeter configured to be positioned over skin surrounding the wound site, the backing layer including an opening; a wound contact layer adhered to the lower surface of the backing layer, the wound contact layer comprising an adhesive on a lower surface thereof; an absorbent material positioned between the backing layer and the wound contact layer, wherein the absorbent material comprises a vertical hole positioned below the opening in the backing layer; an obscuring layer positioned at least partially over the absorbent material, wherein the obscuring layer comprises a vertical hole positioned between the opening in the backing layer and the vertical hole in the absorbent material; one or more viewing windows extending through the obscuring layer configured to allow visualization of wound exudate in the absorbent material; and a port positioned over the opening in the backing layer configured to transmit negative pressure through the port for the application of topical negative pressure at the wound site.

In some embodiments, the backing layer is transparent or translucent. The backing layer may define a perimeter with a rectangular or a square shape. The wound contact layer may be adhered to the lower surface of the backing layer along the perimeter of the backing layer. The hole in the obscuring layer may have a different diameter than the hole in the absorbent material or the opening in the backing layer. The one or more viewing windows may be arranged in a repeating pattern across the obscuring layer. The one or more viewing windows may have a circular shape.

Some embodiments may further comprise an acquisition distribution layer between the wound contact layer and the absorbent material. The absorbent layer may comprise cellulose fibers and between 40% and 80% (or between about 40% and about 80%) superabsorbent particles. The obscuring layer, in a dry state, may be configured to yield a color of Bg, gB, B, pB, bP, P, rP, pPk, RP, O, rO, or yO on the CIE x, y chromacity diagram.

Some embodiments further comprise a transmission layer between the absorbent material and the wound contact layer. In some embodiments, the apparatus further comprises a hydrophobic filter positioned in or below the port. The absorbent material may have a longitudinal length and a transverse width, wherein the length is greater than the width, and wherein the width of the absorbent material narrows in a central portion along the longitudinal length of the absorbent material. The obscuring layer may have substantially the same perimeter shape as the absorbent material. The apparatus may further comprise a pump In another embodiment, a wound treatment apparatus for treatment of a wound site comprises: a wound dressing configured to be conformable to a nonplanar wound comprising: an absorbent layer comprising a contoured shape, the contoured shape comprising a substantially rectangular body with a waisted portion, and a backing layer above the absorbent layer; and a fluidic connector configured to transmit negative pressure from a negative pressure source to the wound dressing for the application of topical negative pressure at a wound site.

Some embodiments may further comprise a wound contact layer. The backing layer may be rectangular. In some embodiments, the negative pressure source is a pump.

In some embodiments, the wound dressing has a longer axis and a shorter axis, and wherein the waisted portion configured to be on the longer axis. The apparatus may further comprise an obscuring layer configured to at least partly visually obscure fluid within the absorbent layer. The obscuring layer may comprise at least one viewing window configured to allow a visual determination of the saturation level of the absorbent layer. The viewing window may comprise an array of dots. The fluidic connector may be located along a side or corner of the rectangular body.

Some embodiments may further comprise an acquisition distribution layer between the wound contact layer and the absorbent material. The absorbent layer may comprise cellulose fibers and 40%-80% (or about 40% to about 80%) superabsorbent particles. The obscuring layer, in a dry state, may be configured to yield a color of Bg, gB, B, pB, bP, P, rP, pPk, RP, O, rO, or yO on the CIE x, y chromacity diagram. The absorbent layer may further comprise a tissue dispersant layer.

In yet another embodiment, an apparatus for dressing a wound for the application of topical negative pressure at a wound site, comprises: an absorbent layer having one or more slits extending at least partially across the width of the absorbent layer; and a backing layer above the absorbent layer, the backing layer having an orifice for communicating negative pressure to the wound site, wherein the orifice is positioned over a portion of the absorbent layer having no slits.

In some embodiments, the one or more slits comprise one or more concentric arcs.

In another embodiment, a wound treatment apparatus comprises: a wound dressing configured to be conformable to a nonplanar wound comprising: an absorbent layer above the contact layer, the absorbent layer comprising a contoured shape, the contoured shape comprising two or more lobes, and a backing layer above the absorbent layer.

In some embodiments, the wound treatment apparatus comprises a pump. The wound dressing may comprise a fluidic connector configured to transmit negative pressure from a pump to the wound dressing for the application of topical negative pressure at a wound site. The wound dressing may also comprise a wound-facing contact layer. The contoured shape may comprise three lobes. The contoured shape may comprise four lobes. The two or more lobes may comprise rounded projections. The apparatus may comprise two or more lobes flared lobes. The contoured shape may be oval-shaped. The contoured shape may comprise six lobes. The apparatus may further comprise an obscuring layer disposed so as to obscure the absorbent layer. The apparatus may further comprise an obscuring layer configured to at least partly visually obscure fluid within the absorbent layer. The obscuring layer may comprise at least one viewing window configured to allow a visual determination of the saturation level of the absorbent layer. The viewing window may comprise an array of dots.

In yet another embodiment, an apparatus for dressing a wound for the application of topical negative pressure at a wound site, comprises: a wound contact layer; an acquisition distribution layer above the transmission layer; an absorbent layer over the acquisition and distribution layer, the absorbent layer comprising a matrix and superabsorbing particles within the matrix; and a backing layer above the absorbent layer.

Some embodiments of the apparatus may further comprise a transmission layer between the wound contact layer and the acquisition distribution layer. The acquisition distribution layer may comprise viscose, polyester, polypropylene, cellulose, polyethylene or a combination of some or all of these materials. The absorbent layer may comprise between 30% and 40% (or between about 30% and about 40%) cellulose matrix and between 60% and 70% (or between about 60% and about 70%) superabsorbing polymers. The backing layer may be transparent or translucent.

Some embodiments may further comprise an obscuring layer between the absorbent layer and the backing layer. There may be one or more viewing windows in the obscuring layer. At least the obscuring layer may be shaped with a narrowed central portion along its length. The obscuring layer may comprise two rows of three viewing windows, one row of three viewing windows, one row of eight viewing windows, two rows of five viewing windows, or one row of five viewing windows. At least the obscuring layer may be shaped with a narrowed central portion along both its width and its length. The obscuring layer may comprise a 3×3 array of viewing window or a quincunx array of viewing windows. In some embodiments, at least the obscuring layer may comprise a six-lobed shape. The absorbent layer and acquisition distribution layer may be substantially the same shape as the obscuring layer. The obscuring layer may further comprise a cross or maltese cross shaped hole over which a fluidic connector for transmitting negative pressure may be connected. The apparatus may further comprise a fluidic connector configured to connect the backing layer to a source of negative pressure. The absorbent layer may further comprise a tissue dispersant layer.

In yet another embodiment, an apparatus for dressing a wound for the application of topical negative pressure at a wound site, comprises: an absorbent layer configured to retain fluid, a backing layer above the absorbent layer, and an obscuring layer configured to at least partly visually obscure fluid within the absorbent layer, wherein the obscuring layer, in a dry state, is configured to yield a color of Bg, gB, B, pB, bP, P, rP, pPk, RP, O, rO, or yO on the CIE x, y chromacity diagram.

Some embodiments may further comprise one or more viewing windows in the backing layer. At least the obscuring layer may be shaped with a narrowed central portion along its length. The obscuring layer may comprise a 3×3 array of viewing window or a quincunx array of viewing windows. In some embodiments, at least the obscuring layer may comprise a six-lobed shape. The absorbent layer and acquisition distribution layer may be substantially the same shape as the obscuring layer. The obscuring layer may further comprise a cross or maltese cross shaped hole over which a fluidic connector for transmitting negative pressure may be connected. The apparatus may further comprise a fluidic connector configured to connect the backing layer to a source of negative pressure. The absorbent layer may further comprise a tissue dispersant layer.

FIG. 219 illustrates an embodiment of a TNP wound treatment system B100 comprising a wound dressing B110 in combination with a pump B150. As stated above, the wound dressing B110 can be any wound dressing embodiment disclosed herein including without limitation dressing embodiment or have any combination of features of any number of wound dressing embodiments disclosed herein. Here, the dressing B110 may be placed over a wound as described previously, and a conduit B130 may then be connected to the port B120, although in some embodiments the dressing B101 may be provided with at least a portion of the conduit B130 preattached to the port B120. Preferably, the dressing B110 is provided as a single article with all wound dressing elements (including the port B120) pre-attached and integrated into a single unit. The wound dressing B110 may then be connected, via the conduit B130, to a source of negative pressure such as the pump B150. The pump B150 can be miniaturized and portable, although larger conventional pumps may also be used with the dressing B110. In some embodiments, the pump B150 may be attached or mounted onto or adjacent the dressing B110. A connector B140 may also be provided so as to permit the conduit B130 leading to the wound dressing B110 to be disconnected from the pump, which may be useful for example during dressing changes.

Figure 220A:
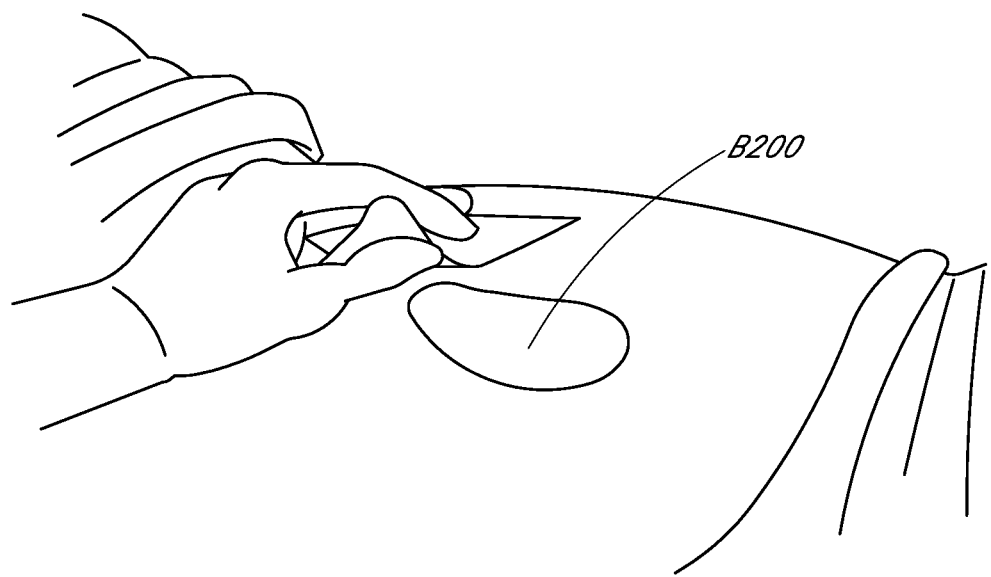

FIGS. 220A-D illustrate the use of an embodiment of a TNP wound treatment system being used to treat a wound site on a patient. FIG. 220A shows a wound site B200 being cleaned and prepared for treatment. Here, the healthy skin surrounding the wound site B200 is preferably cleaned and excess hair removed or shaved. The wound site B200 may also be irrigated with sterile saline solution if necessary. Optionally, a skin protectant may be applied to the skin surrounding the wound site B200. If necessary, a wound packing material, such as foam or gauze, may be placed in the wound site B200. This may be preferable if the wound site B200 is a deeper wound.

Figure 220B:
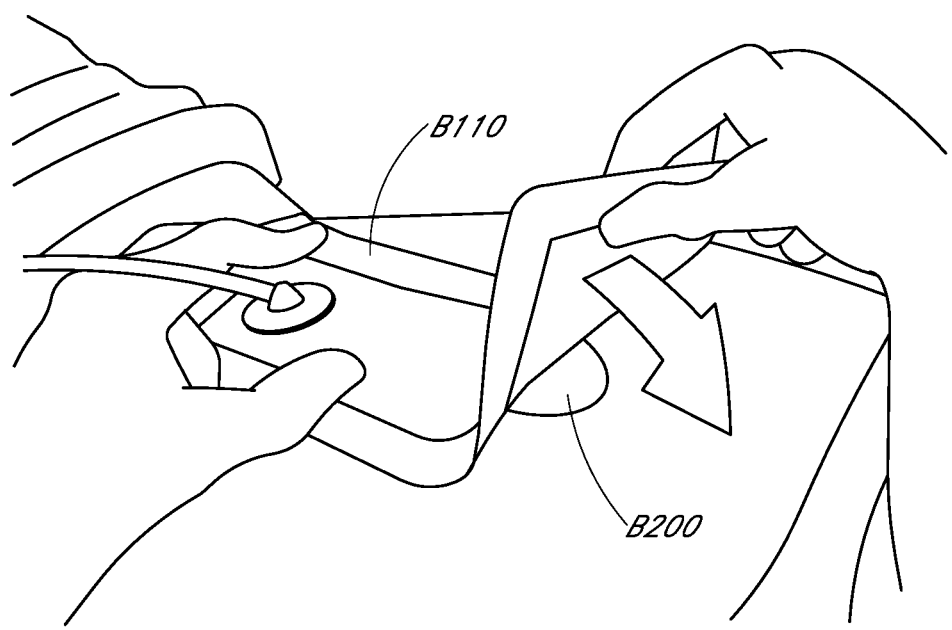

After the skin surrounding the wound site B200 is dry, and with reference now to FIG. 220B, the wound dressing B110 may be positioned and placed over the wound site B200. Preferably, the wound dressing B110 is placed with the wound contact layer B2102 over and/or in contact with the wound site B200. In some embodiments, an adhesive layer is provided on the lower surface B2101 of the wound contact layer B2102, which may in some cases be protected by an optional release layer to be removed prior to placement of the wound dressing B110 over the wound site B200. Preferably, the dressing B110 is positioned such that the port B2150 is in a raised position with respect to the remainder of the dressing B110 so as to avoid fluid pooling around the port. In some embodiments, the dressing B110 is positioned so that the port B2150 is not directly overlying the wound, and is level with or at a higher point than the wound. To help ensure adequate sealing for TNP, the edges of the dressing B110 are preferably smoothed over to avoid creases or folds.

Figure 220C:
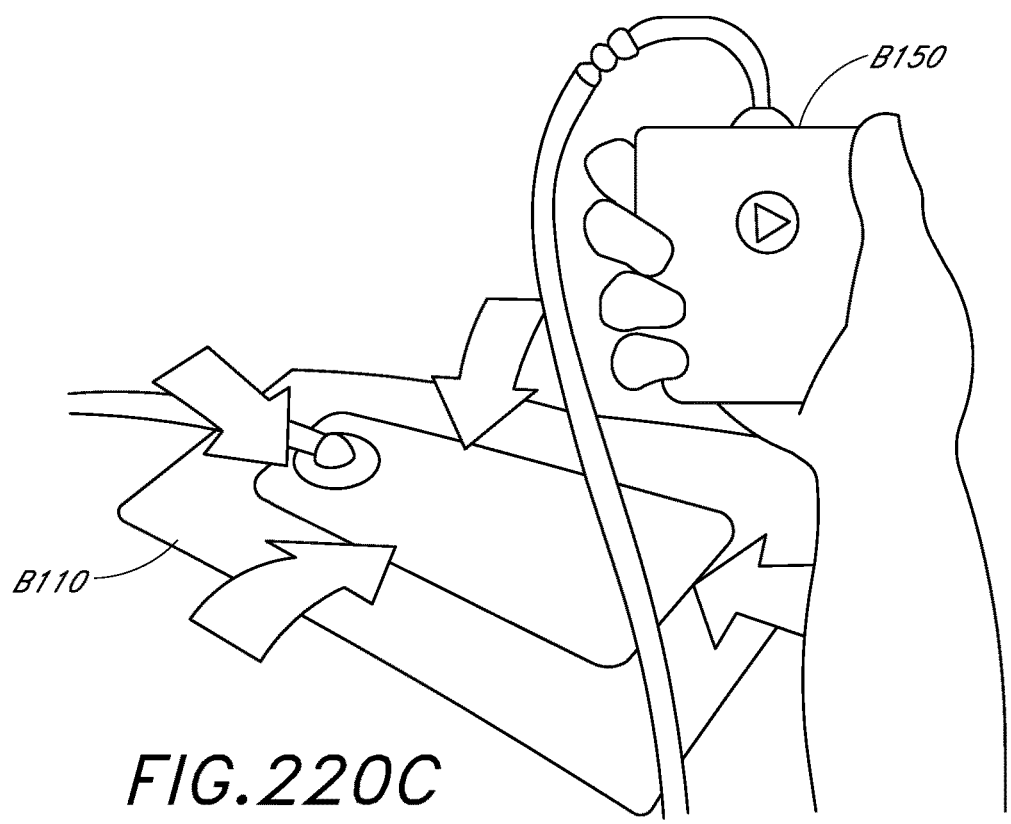

With reference now to FIG. 220C, the dressing B110 is connected to the pump B150. The pump B150 is configured to apply negative pressure to the wound site via the dressing B110, and typically through a conduit. In some embodiments, and as described above in FIG. 219, a connector may be used to join the conduit from the dressing B110 to the pump B150. Upon the application of negative pressure with the pump B150, the dressing B110 may, in some embodiments, partially collapse and present a wrinkled appearance as a result of the evacuation of some or all of the air underneath the dressing B110. In some embodiments, the pump B150 may be configured to detect if any leaks are present in the dressing B110, such as at the interface between the dressing B110 and the skin surrounding the wound site B200. Should a leak be found, such leak is preferably remedied prior to continuing treatment.

Figure 220D:
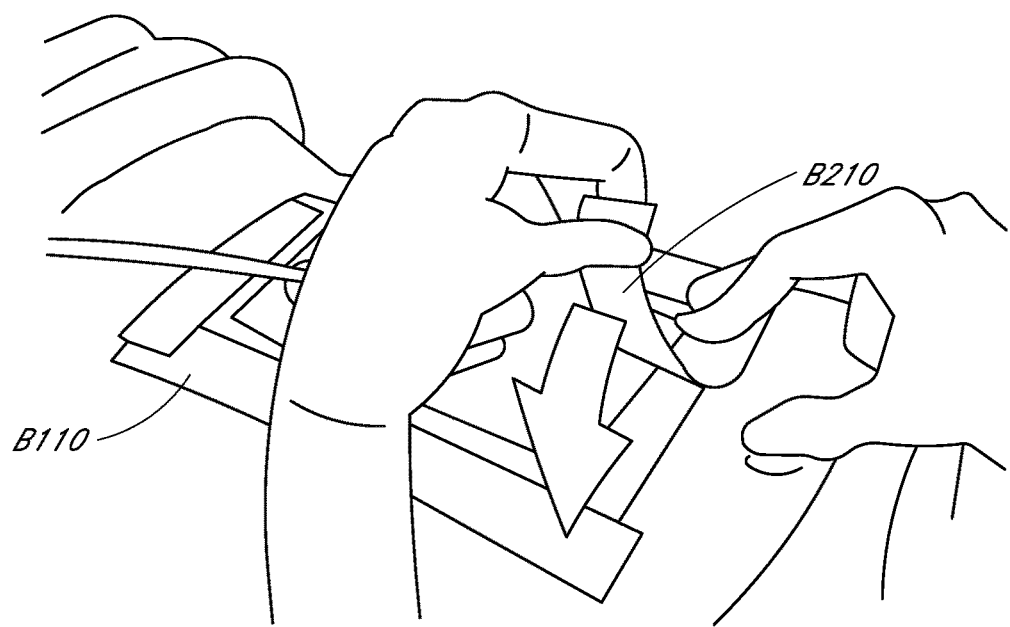

Turning to FIG. 220D, additional fixation strips B210 may also be attached around the edges of the dressing B110. Such fixation strips B210 may be advantageous in some situations so as to provide additional sealing against the skin of the patient surrounding the wound site B200. For example, the fixation strips B210 may provide additional sealing for when a patient is more mobile. In some cases, the fixation strips B210 may be used prior to activation of the pump B150, particularly if the dressing B110 is placed over a difficult to reach or contoured area.

Treatment of the wound site B200 preferably continues until the wound has reached a desired level of healing. In some embodiments, it may be desirable to replace the dressing B110 after a certain time period has elapsed, or if the dressing is full of wound fluids. During such changes, the pump B150 may be kept, with just the dressing B110 being changed.

FIGS. 221A-C illustrate cross-sections through a wound dressing B2100 similar to the wound dressing of FIG. 219 according to an embodiment of the disclosure. A view from above the wound dressing B2100 is illustrated in FIG. 219 with the line A-A indicating the location of the cross-section shown in FIGS. 221A and 221B. The wound dressing B2100, which can alternatively be any wound dressing embodiment disclosed herein including without limitation wound dressing B110 or any combination of features of any number of wound dressing embodiments disclosed herein, can be located over a wound site to be treated. The dressing B2100 may be placed to as to form a sealed cavity over the wound site. In a preferred embodiment, the dressing B2100 comprises a backing layer B2140 attached to a wound contact layer B2102, both of which are described in greater detail below. These two layers B2140, B2102 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer B2105 and an absorbent layer B2110.

As illustrated in FIGS. 221A-C, a lower surface B2101 of the wound dressing B2100 may be provided with an optional wound contact layer B2102. The wound contact layer B2102 can be a polyurethane layer or polyethylene layer or other flexible layer which is perforated, for example via a hot pin process, laser ablation process, ultrasound process or in some other way or otherwise made permeable to liquid and gas. The wound contact layer B2102 has a lower surface B2101 and an upper surface B2103. The perforations B2104 preferably comprise through holes in the wound contact layer B2102 which enable fluid to flow through the layer B2102. The wound contact layer B2102 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer B2102 may help maintain the integrity of the entire dressing B2100 while also creating an air tight seal around the absorbent pad in order to maintain negative pressure at the wound.

Some embodiments of the wound contact layer B2102 may also act as a carrier for an optional lower and upper adhesive layer (not shown). For example, a lower pressure sensitive adhesive may be provided on the lower surface B2101 of the wound dressing B2100 whilst an upper pressure sensitive adhesive layer may be provided on the upper surface B2103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing B2100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer B2105 of porous material can be located above the wound contact layer B2102. This porous layer, or transmission layer, B2105 allows transmission of fluid including liquid and gas away from a wound site into upper layers of the wound dressing. In particular, the transmission layer B2105 preferably ensures that an open air channel can be maintained to communicate negative pressure over the wound area even when the absorbent layer has absorbed substantial amounts of exudates. The layer B2105 should preferably remain open under the typical pressures that will be applied during negative pressure wound therapy as described above, so that the whole wound site sees an equalized negative pressure. The layer B2105 may be formed of a material having a three dimensional structure. For example, a knitted or woven spacer fabric (for example Baltex 7970 weft knitted polyester) or a non-woven fabric could be used.

A layer B2110 of absorbent material is provided above the transmission layer B2105. The absorbent material, which comprise a foam or non-woven natural or synthetic material, and which may optionally comprise a super-absorbent material, forms a reservoir for fluid, particularly liquid, removed from the wound site. In some embodiments, the layer B2100 may also aid in drawing fluids towards the backing layer B2140.

With reference to FIGS. 221A-C, a masking or obscuring layer B2107 can be positioned beneath at least a portion of the backing layer B2140. In some embodiments, the obscuring layer B2107 can have any of the same features, materials, or other details of any of the other embodiments of the obscuring layers disclosed herein, including but not limited to having any viewing windows or holes. Additionally, the obscuring layer B2107 can be positioned adjacent to the backing layer, or can be positioned adjacent to any other dressing layer desired. In some embodiments, the obscuring layer B2107 can be adhered to or integrally formed with the backing layer. Preferably, the obscuring layer B2107 is configured to have approximately the same size and shape as the absorbent layer B2110 so as to overlay it. As such, in these embodiments the obscuring layer B2107 will be of a smaller area than the backing layer B2140.

The material of the absorbent layer B2110 may also prevent liquid collected in the wound dressing B2100 from flowing freely within the dressing, and preferably acts so as to contain any liquid collected within the absorbent layer B2110. The absorbent layer B2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer B2110 may typically be manufactured from ALLEVYN™ foam, Freudenberg 114-224-4 and/or Chem-Posite™11C-450. In some embodiments, the absorbent layer B2110 may comprise a composite comprising superabsorbent powder, fibrous material such as cellulose, and bonding fibers. In a preferred embodiment, the composite is an airlaid, thermally-bonded composite.

An orifice B2145 is preferably provided in the backing layer B2140 to allow a negative pressure to be applied to the dressing B2100. A suction port B2150 is preferably attached or sealed to the top of the backing layer B2140 over an orifice B2145 made into the dressing B2100, and communicates negative pressure through the orifice B2145. A length of tubing B2220 may be coupled at a first end to the suction port B2150 and at a second end to a pump unit (not shown) to allow fluids to be pumped out of the dressing. The port may be adhered and sealed to the backing layer B2140 using an adhesive such as an acrylic, cyanoacrylate, epoxy, UV curable or hot melt adhesive. The port B2150 is formed from a soft polymer, for example a polyethylene, a polyvinyl chloride, a silicone or polyurethane having a hardness of 30 to 90 on the Shore A scale. In some embodiments, the port B2150 may be made from a soft or conformable material, for example using the embodiments described below in FIGS. 241A-B.

Preferably the absorbent layer B2110 and the obscuring layer B2107 include at least one through hole B2146 located so as to underlie the port B2150. The through hole B2146, while illustrated here as being larger than the hole through the obscuring layer B2107 and backing layer B2140, may in some embodiments be bigger or smaller than either. Of course, the respective holes through these various layers B2107, B2140, and B2110 may be of different sizes with respect to each other. As illustrated in FIGS. 221A-C a single through hole can be used to produce an opening underlying the port B2150. It will be appreciated that multiple openings could alternatively be utilized. Additionally should more than one port be utilized according to certain embodiments of the present disclosure one or multiple openings may be made in the absorbent layer and the obscuring layer in registration with each respective port. Although not essential to certain embodiments of the present disclosure the use of through holes in the super-absorbent layer may provide a fluid flow pathway which remains unblocked in particular when the absorbent layer B2100 is near saturation.

The aperture or through-hole B2146 is preferably provided in the absorbent layer B2110 and the obscuring layer B2107 beneath the orifice B2145 such that the orifice is connected directly to the transmission layer B2105. This allows the negative pressure applied to the port B2150 to be communicated to the transmission layer B2105 without passing through the absorbent layer B2110. This ensures that the negative pressure applied to the wound site is not inhibited by the absorbent layer as it absorbs wound exudates. In other embodiments, no aperture may be provided in the absorbent layer B2110 and/or the obscuring layer B2107, or alternatively a plurality of apertures underlying the orifice B2145 may be provided.

The backing layer B2140 is preferably gas impermeable, but moisture vapor permeable, and can extend across the width of the wound dressing B2100. The backing layer B2140, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer B2140 and a wound site where a negative pressure can be established. The backing layer B2140 is preferably sealed to the wound contact layer B2102 in a border region 2200 around the circumference of the dressing, ensuring that no air is drawn in through the border area, for example via adhesive or welding techniques. The backing layer B2140 protects the wound from external bacterial contamination (bacterial barrier) and allows liquid from wound exudates to be transferred through the layer and evaporated from the film outer surface. The backing layer B2140 preferably comprises two layers; a polyurethane film and an adhesive pattern spread onto the film. The polyurethane film is preferably moisture vapor permeable and may be manufactured from a material that has an increased water transmission rate when wet.

The absorbent layer B2110 may be of a greater area than the transmission layer B2105, such that the absorbent layer overlaps the edges of the transmission layer B2105, thereby ensuring that the transmission layer does not contact the backing layer B2140. This provides an outer channel B2115 of the absorbent layer B2110 that is in direct contact with the wound contact layer B2102, which aids more rapid absorption of exudates to the absorbent layer. Furthermore, this outer channel B2115 ensures that no liquid is able to pool around the circumference of the wound cavity, which may otherwise seep through the seal around the perimeter of the dressing leading to the formation of leaks.

As shown in FIG. 221A, one embodiment of the wound dressing B2100 comprises an aperture B2146 in the absorbent layer B2110 situated underneath the port B2150. In use, for example when negative pressure is applied to the dressing B2100, a wound facing portion of the port B150 may thus come into contact with the transmission layer B2105, which can thus aid in transmitting negative pressure to the wound site even when the absorbent layer B2110 is filled with wound fluids. Some embodiments may have the backing layer B2140 be at least partly adhered to the transmission layer B2105. In some embodiments, the aperture B2146 is at least 1-2 mm larger than the diameter of the wound facing portion of the port B2150, or the orifice B2145.

A filter element B2130 that is impermeable to liquids, but permeable to gases is provided to act as a liquid barrier, and to ensure that no liquids are able to escape from the wound dressing. The filter element may also function as a bacterial barrier. Typically the pore size is 0.2 µm. Suitable materials for the filter material of the filter element B2130 include 0.2 micron Gore™ expanded PTFE from the MMT range, PALL Versapore™ B200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the backing layer B2140 over the orifice B2145. For example, the filter element B2130 may be molded into the port B2150, or may be adhered to both the top of the backing layer B2140 and bottom of the port B2150 using an adhesive such as, but not limited to, a UV cured adhesive.

In FIG. 221B, an embodiment of the wound dressing B2100 is illustrated which comprises spacer elements B2152, B2153 in conjunction with the port B2150 and the filter B2130. With the addition of such spacer elements B2152, B2153, the port B2150 and filter B2130 may be supported out of direct contact with the absorbent layer B2110 and/or the transmission layer B2105. The absorbent layer B2110 may also act as an additional spacer element to keep the filter B2130 from contacting the transmission layer B2105. Accordingly, with such a configuration contact of the filter B2130 with the transmission layer B2105 and wound fluids during use may thus be minimized. As contrasted with the embodiment illustrated in FIG. 221A, the aperture B2146 through the absorbent layer B2110 and the obscuring layer B2107 may not necessarily need to be as large or larger than the port B2150, and would thus only need to be large enough such that an air path can be maintained from the port to the transmission layer B2105 when the absorbent layer B2110 is saturated with wound fluids.

With reference now to FIG. 221C, which shares many of the elements illustrated in FIGS. 221A-C, the embodiment illustrated here comprises the backing layer B2140, masking layer B2107, and absorbent layer B2110, all of which have a cut or opening made therethrough which communicate directly to the transmission layer B2105 so as to form the orifice B2145. The suction port B2150 is preferably situated above it and communicates with the orifice B2145.

In particular for embodiments with a single port B2150 and through hole, it may be preferable for the port B2150 and through hole to be located in an off-center position as illustrated in FIGS. 221A-C and in FIG. 219. Such a location may permit the dressing B2100 to be positioned onto a patient such that the port B2150 is raised in relation to the remainder of the dressing B2100. So positioned, the port B2150 and the filter B2130 may be less likely to come into contact with wound fluids that could prematurely occlude the filter B2130 so as to impair the transmission of negative pressure to the wound site.

FIGS. 222A-C illustrate embodiments of wound dressings B300 similar to the embodiments described above and provided with a narrowed central portion in various lengths and widths. FIG. 222A illustrates an embodiment of a wound dressing B300 with a narrowed central portion or a waisted middle portion. The wound dressing B300 has a backing layer B301. The backing layer B301 can have a rectangular or square shaped perimeter and can be a transparent or translucent material. The backing layer B301 can have a lower surface B305 and an upper surface B306. The lower surface of the backing layer B301 can be configured to be placed on the skin surface surrounding the wound site as discussed previously with reference to FIGS. 221A-C. Additionally, the lower surface B305 can have a wound contact layer. The wound contact layer can have all the features and embodiments described herein, including without limitation wound dressing embodiments described in reference to FIGS. 221A-C. The wound contact layer can be adhered to the perimeter of the lower surface B305 of the backing layer B301. The wound contact layer can comprise an adhesive or any other method of attachment that allows attachment of the wound dressing to the skin surface as previously described.

In some embodiments, the wound dressing B300 can have a port B304 offset from the center of the dressing as described previously. The port B304 can be a domed port or a soft fluidic connector (described in detail below). Although the port B304 can be placed in a central location on the dressing, it is preferably offset from the center of the dressing to a particular side or edge. As such, the orientation of the port B304, when placed on the body, may thus permit the port B304 to be situated in an elevated position, thereby increasing the amount of time that the dressing B300 may be used before coming into contact with fluids. Although other orientations may be used, and may occur in practice (e.g., when the patient shifts positions), placing the port B304 at a lower position may cause the filter proximate the port (not illustrated here) to become saturated, which may cause the dressing to need changing even though there may still remain some absorptive capacity within the absorbent layer. Preferably, the port B304 has an orifice for the connection of a tube or conduit thereto; this orifice may be angled away from the center of the dressing B300 so as to permit the tube or conduit to extend away from the dressing B300. In some preferred embodiments, the port B304 comprises an orifice that permits the tube or conduit inserted therein to be approximately parallel to the top surface of the backing layer B301.

In various embodiments, the wound dressing B300 can have an absorbent material B302. The absorbent material B302 can be accompanied by the additional components within the wound dressing as described with reference to the wound dressing cross-section in FIG. 221A-B, such as a transmission layer and a masking or obscuring layer (not shown).

In some embodiments, the wound dressing B300 can have an absorbent material B302 with a central portion B308. The absorbent material B302 can have a longitudinal length and a transverse width. In some embodiments, the longitudinal length is greater than the transverse width. In some embodiments, the longitudinal length and the transverse width are of equal size. In various embodiments, the absorbent material B302 can have a contoured shape with a substantially rectangular body.

The central portion B308 of the absorbent material B302 may comprise a waisted portion B303. The waisted portion B303 can be defined by the transverse width of the absorbent material B302 narrowing at the central portion B308 of the longitudinal length. For example, in some embodiments, the waisted portion B303 can be a narrow width at the central portion B308 of the absorbent material B302, as illustrated in FIGS. 222A-C. Additional embodiments of the waisted portion B303 are possible including those described herein. Further, the shape of the accompanying components within the wound dressing as described with reference to FIGS. 221A-C can be formed to the same contoured shape of the absorbent material including the waisted portion.

The waisted portion B303 can increase the flexibility of the wound dressing and can allow enhanced compatibility of the wound dressing to the patient's body. For example, the narrow central region may allow for improved contact and adhesion of the wound dressing to the skin surface when the wound dressing is used on non-planar surfaces and/or wrapped around an arm or leg. Further, the narrow central portion provides increased compatibility with the patient's body and patient movement.

As in FIGS. 233A-B, embodiments of wound dressings may comprise various configurations of slits (described in detail below) so as to further enhance conformability of the dressing in non-planar wounds. Also, as described below, the absorbent layers may be colored or obscured with an obscuring layer, and optionally provided with one or more viewing windows. The domed ports may also be replaced with one or more fluidic connectors of the type described below in FIGS. 241A-B. Further, the wound dressing B300 can comprise all designs or embodiments herein described or have any combination of features of any number of wound dressing embodiments disclosed herein.

FIG. 222B illustrates an embodiment of a wound dressing B300 with a waisted portion. A wound dressing B300 as illustrated in FIG. 222B can have the features and embodiments as described above with reference to FIG. 222A. However, FIG. 222B illustrates an embodiment with a shorter longitudinal length with respect to the transverse width. FIG. 222C illustrates an additional embodiment of a wound dressing B300 with a waisted portion. As illustrated in FIG. 222C, the wound dressing can have a longitudinal length and a transverse width that are not substantially different in size, as opposed to a longitudinal length that is substantially longer than the transverse width of the wound dressing as shown in the embodiments illustrated in FIGS. 222A and 222B. The embodiments of a wound dressing illustrated in FIGS. 222B and 222C can include all features and embodiments described herein for wound dressings including those embodiments of the waisted portion B303 described with reference to FIG. 222A.

FIGS. 223A-F, 224A-F, 225A-F, 226A-F, 227A-F, 228A-F, 229A-F, 230A-F, and 242 illustrate additional embodiments of wound dressings. In these embodiments, a waisted portion B408 is located inwardly with reference to an edge B409 of the absorbent layer B402. Preferably, the contour of the absorbent layer B402 is curved from the edge B409 to the waisted portion B408, so as to form a smooth countour.

Figure 223A:
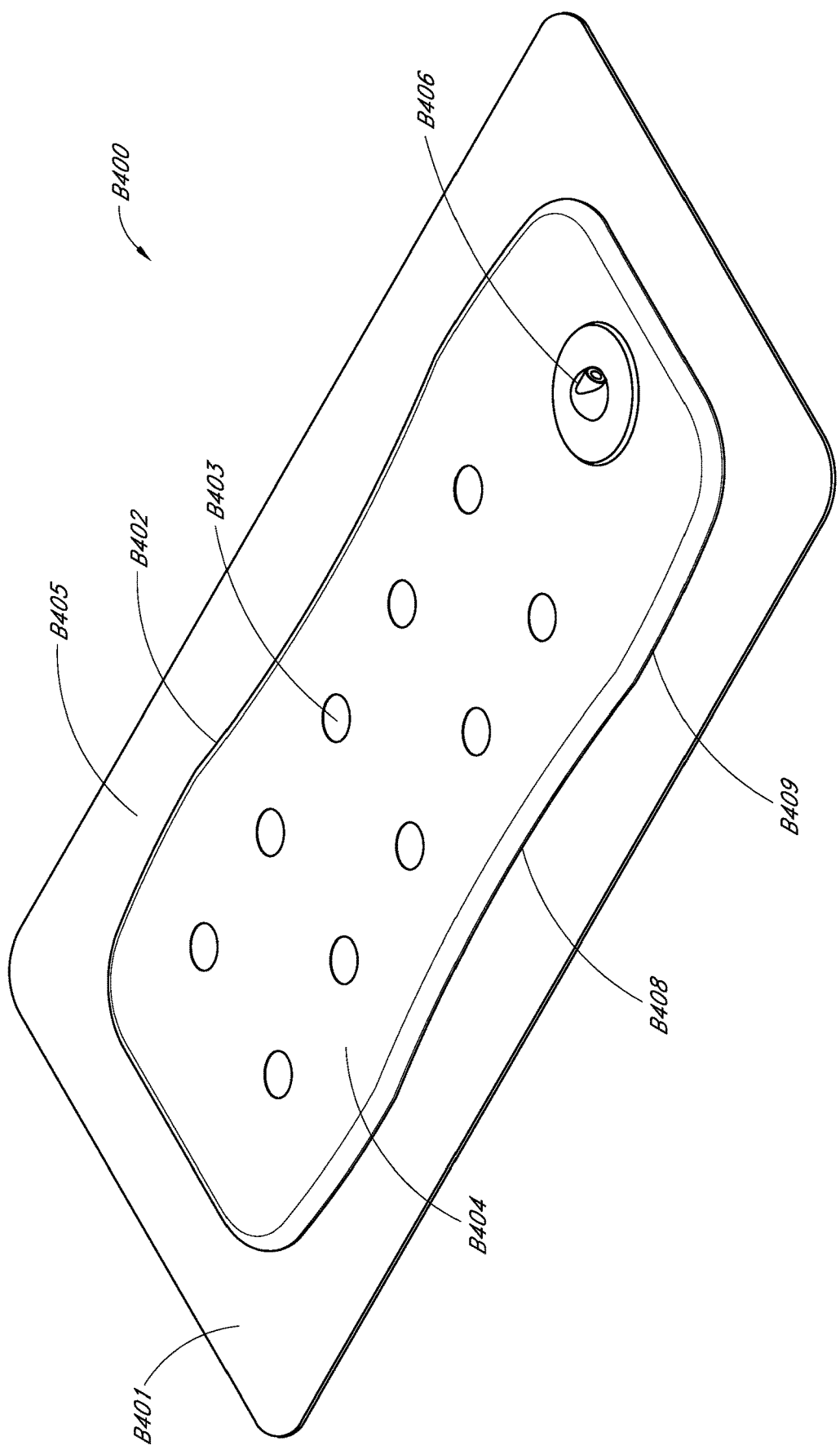

FIGS. 223A-F illustrate multiple views of an embodiment of a wound dressing with a waisted portion, obscuring layer, and viewing windows. FIG. 223A illustrates a perspective view of an embodiment of a wound dressing B400. The wound dressing B400 preferably comprises a port B406. The port B406 is preferably configured to be in fluid communication with a pump as described with reference to FIG. 219, and may include a tube or conduit pre-attached to the port. Alternatively, negative pressure can be supplied to the wound dressing through other suitable fluidic connectors, including but not limited to the fluidic connectors of the type described below in FIGS. 241A-B.

The wound dressing B400 can be constructed similar to the embodiments of FIGS. 221A and 221B above, and may comprise an absorbent material B402 underneath or within a backing layer B405. Optionally, a wound contact layer and a transmission layer may also be provided as part of the wound dressing B400 as described above. The absorbent material B402 can contain a narrowed central or waisted portion B408, as described previously to increase flexibility and conformability of the wound dressing to the skin surface. The backing layer B405 may have a border region B401 that extends beyond the periphery of the absorbent material B402. The backing layer B405 may be a translucent or transparent backing layer, such that the border region B401 created from the backing layer B405 can be translucent or transparent. The area of the border region B401 of the backing layer B405 can be approximately equal around the perimeter of the entire dressing with the exception of the narrowed central portion, where the area of the border region is larger. One will recognize that the size of the border region B401 will depend on the full dimensions of the dressing and any other design choices.

As illustrated in FIG. 223A, provided at least at the top of or over the absorbent layer B402 and under the backing layer B405 may be an obscuring layer B404 that optionally has one or more viewing windows B403. The obscuring layer B404 may partially or completely obscure contents (such as fluids) contained within the wound dressing B400 and/or the absorbent material (i.e., within the absorbent material B402 or under the backing layer B405). The obscuring layer may be a colored portion of the absorbent material, or may be a separate layer that covers the absorbent material. In some embodiments, the absorbent material B402 may be hidden (partially or completely), colored, or tinted, via the obscuring layer B404, so as to provide cosmetic and/or aesthetic enhancements, in a similar manner to what is described above. The obscuring layer is preferably provided between the topmost backing layer B405 and the absorbent material B402, although other configurations are possible. The cross-sectional view in FIGS. 221A and 221B illustrates this arrangement with respect to the masking or obscuring layer B2107. Other layers and other wound dressing components can be incorporated into the dressing as herein described.

The obscuring layer B404 can be positioned at least partially over the absorbent material B402. In some embodiments, the obscuring layer B404 can be positioned adjacent to the backing layer, or can be positioned adjacent to any other dressing layer desired. In some embodiments, the obscuring layer B404 can be adhered to or integrally formed with the backing layer and/or the absorbent material.

As illustrated in FIG. 223A, the obscuring layer B404 can have substantially the same perimeter shape and size as the absorbent material B402. The obscuring layer B404 and absorbent material B402 can be of equal size so that the entirety of the absorbent material B402 can be obscured by the obscuring layer B404. The obscuring layer B404 may allow for obscuring of wound exudate, blood, or other matter released from a wound. Further, the obscuring layer B404 can be completely or partially opaque having cut-out viewing windows or perforations.

In some embodiments, the obscuring layer B404 can help to reduce the unsightly appearance of a dressing during use, by using materials that impart partial obscuring or masking of the dressing surface. The obscuring layer B404 in one embodiment only partially obscures the dressing, to allow clinicians to access the information they require by observing the spread of exudate across the dressing surface. The partial masking nature of this embodiment of the obscuring layer enables a skilled clinician to perceive a different color caused by exudate, blood, by-products etc. in the dressing allowing for a visual assessment and monitoring of the extent of spread across the dressing. However, since the change in color of the dressing from its clean state to a state containing exudate is only a slight change, the patient is unlikely to notice any aesthetic difference. Reducing or eliminating a visual indicator of wound exudate from a patient's wound is likely to have a positive effect on their health, reducing stress for example.

In some embodiments, the obscuring layer can be formed from a non-woven fabric (for example, polypropylene), and may be thermally bonded using a diamond pattern with 19% bond area. In various embodiments, the obscuring layer can be hydrophobic or hydrophilic. Depending on the application, in some embodiments, a hydrophilic obscuring layer may provide added moisture vapor permeability. In some embodiments, however, hydrophobic obscuring layers may still provide sufficient moisture vapor permeability (i.e., through appropriate material selection, thickness of the obscuring layer), while also permitting better retention of dye or color in the obscuring layer. As such, dye or color may be trapped beneath the obscuring layer. In some embodiments, this may permit the obscuring layer to be colored in lighter colors or in white. In the preferred embodiment, the obscuring layer is hydrophobic. In some embodiments, the obscuring layer material can be sterilizable using ethylene oxide. Other embodiments may be sterilized using gamma irradiation, an electron beam, steam or other alternative sterilization methods. Additionally, in various embodiments the obscuring layer can colored or pigmented, e.g., in medical blue. The obscuring layer may also be constructed from multiple layers, including a colored layer laminated or fused to a stronger uncolored layer. Preferably, the obscuring layer is odorless and exhibits minimal shedding of fibers.

The absorbent layer B402, itself may be colored or tinted in some embodiments, however, so that an obscuring layer is not necessary. The dressing may optionally include a means of partially obscuring the top surface. This could also be achieved using a textile (knitted, woven, or non-woven) layer without openings, provided it still enables fluid evaporation from the absorbent structure. It could also be achieved by printing an obscuring pattern on the top film, or on the top surface of the uppermost pad component, using an appropriate ink or colored pad component (yarn, thread, coating) respectively. Another way of achieving this would be to have a completely opaque top surface, which could be temporarily opened by the clinician for inspection of the dressing state (for example through a window), and closed again without compromising the environment of the wound.

Additionally, FIG. 223A illustrates an embodiment of the wound dressing including one or more viewing windows B403. The one or more viewing windows B403 preferably extend through the obscuring layer B404. These viewing windows B403 may allow visualization by a clinician or patient of the wound exudate in the absorbent material below the obscuring layer. FIG. 223A illustrates an array of dots (e.g., in one or more parallel rows) that can serve as viewing windows B403 in the obscuring layer B404 of the wound dressing. In a preferred embodiment, two or more viewing windows B403 may be parallel with one or more sides of the dressing B400. In some embodiments, the one or more viewing windows may measure between 0.1 mm and 20 mm, preferably 0.4 mm to 10 mm, and even more preferably, 1 mm to 4 mm.

The viewing windows B403 may be cut through the obscuring layer B404 or may be part of an uncolored area of the obscuring layer B404 and therefore may allow visualization of the absorbent material B402. The one or more viewing windows B403 can be arranged in a repeating pattern across the obscuring layer B404 or can be arranged at random across the obscuring layer. Additionally, the one or more viewing windows can be a circular shape or dots. Preferably, the one or more viewing windows B403 are configured so as to permit not only the degree of saturation, but also the progression or spread of fluid toward the fluid port B406, as in some embodiments, dressing performance may be adversely affected when the level of fluid has saturated the fluid proximate the port B406. In some embodiments, a "starburst" array of viewing windows B403 emanating around the port B406 may be suitable to show this progression, although of course other configurations are possible.

In FIG. 223A, the viewing windows B403 correspond to the area of the absorbent material B402 that is not covered by the obscuring layer B404. As such, the absorbent material B402 is directly adjacent the backing layer B405 in this area. Since the obscuring layer B404 acts as a partial obscuring layer, the viewing windows B403 may be used by a clinician or other trained user to assess the spread of wound exudate throughout the dressing. In some embodiments, the viewing windows B403 can comprise an array of dots or crescent shaped cut-outs. For example, an array of dots as viewing windows B403 are illustrated in Figures FIGS. 223A-F, 224A-F, 225A-F, 226A-F, 227A-F, 228A-F, 229A-F, and 230A-F in which the array of dots are arranged in an 5×2, 3×2, 8×1, 5×1, 3×1, 3×3, 3×3, and quincunx array respectively. Additionally, in some embodiments, the dot pattern can be distributed evenly throughout the obscuring layer and across the entire or substantially the entire surface of the obscuring layer. In some embodiments, the viewing windows B403 may be distributed randomly throughout the obscuring layer. Preferably, the area of the obscuring layer B404 uncovered by the one or more viewing windows B403 is balanced to as to minimize the appearance of exudate while permitting the inspection of the dressing B400 and/or absorbent material B402. In some embodiments, the area exposed by the one or more viewing windows B403 does not exceed 20% of the area of the obscuring layer B404, preferably 10%, and even more preferably 5%.

The viewing windows B403 may take several configurations, as will be discussed in relation to FIGS. 234-236. In FIG. 235, the viewing windows B403 may comprise an array of regularly spaced uncolored dots (holes) made into the obscuring layer B404. While the dots illustrated here are in a particular pattern, the dots may be arranged in different configurations, or at random. The viewing windows B403 are preferably configured so as to permit a patient or caregiver to ascertain the status of the absorbent layer, in particular to determine its saturation level, as well as the color of the exudate (e.g., whether excessive blood is present). By having one or more viewing windows, the status of the absorbent layer can be determined in an unobtrusive manner that is not aesthetically unpleasing to a patient. Because a large portion of the absorbent layer may be obscured, the total amount of exudate may therefore be hidden. As such, the status and saturation level of the absorbent layer B402 may therefore present a more discreet external appearance so as to reduce patient embarrassment and visibility and thereby enhance patient comfort. In some configurations, the one or more viewing windows B403 may be used to provide a numerical assessment of the degree of saturation of the dressing B400. This may be done electronically (e.g., via a digital photograph assessment), or manually. For example, the degree of saturation may be monitored by counting the number of viewing windows B403 which may be obscured or tinted by exudate or other wound fluids.

In some embodiments, the absorbent layer B402 or the obscuring layer B404, in particular the colored portion of the absorbent layer, may comprise (or be colored because of) the presence of an auxiliary compound. The auxiliary compound may in some embodiments be activated charcoal, which can act to absorb odors. The use of antimicrobial, antifungal, anti-inflammatory, and other such therapeutic compounds is also possible. In some embodiments, the color may change as a function of time (e.g., to indicate when the dressing needs to be changed), if the dressing is saturated, or if the dressing has absorbed a certain amount of a harmful substance (e.g., to indicate the presence of infectious agents). In some embodiments, the one or more viewing windows B403 may be monitored electronically, and may be used in conjunction with a computer program or system to alert a patient or physician to the saturation level of the dressing B400.

FIG. 234 illustrates an embodiment of a dressing containing a viewing window in the shape of a trademarked brand name ("PICO"). FIG. 236 illustrates an embodiment of a dressing comprising a viewing window in the shape of a logo, here, the Smith & Nephew logo. Of course, many other configurations are possible, including other graphics, texts, or designs. The graphical or textual elements present in the viewing window may also be, for example, instructional in nature.

In other alternatives, instructions may be given to change the wound dressing when the exudate reaches a predetermined distance from the edge of the wound dressing, such as 5 mm from the wound dressing edge or 7 mm from the wound dressing edge, etc. Alternatively a 'traffic light' system may be implemented whereby an electronic indicator shows green, amber or red light to indicate the spread of exudate in the wound dressing. Alternatively or additionally, another suitable indicator may be used for indicating the spread of exudate over the dressing.

Figure 223B:
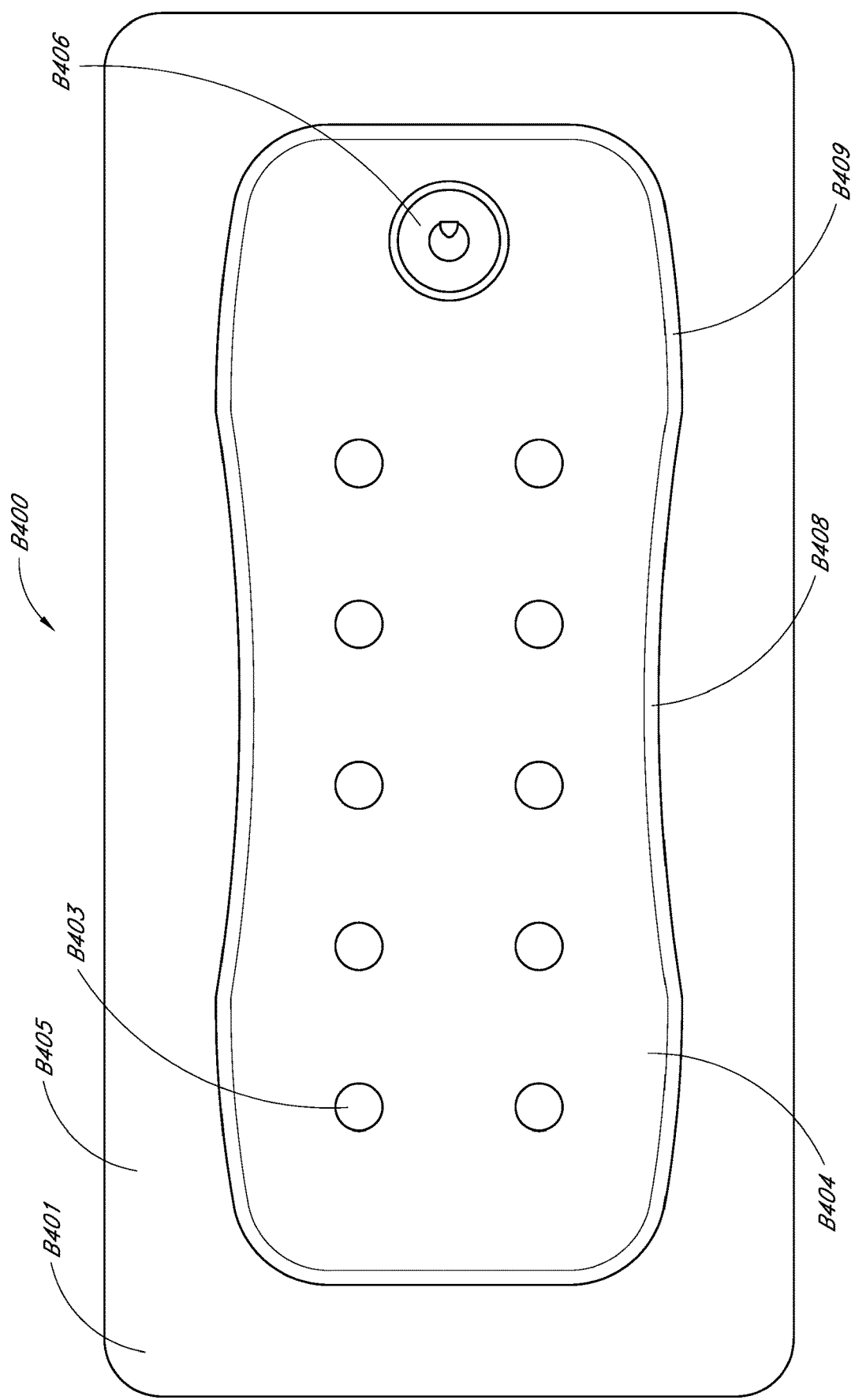
Figure 223C:
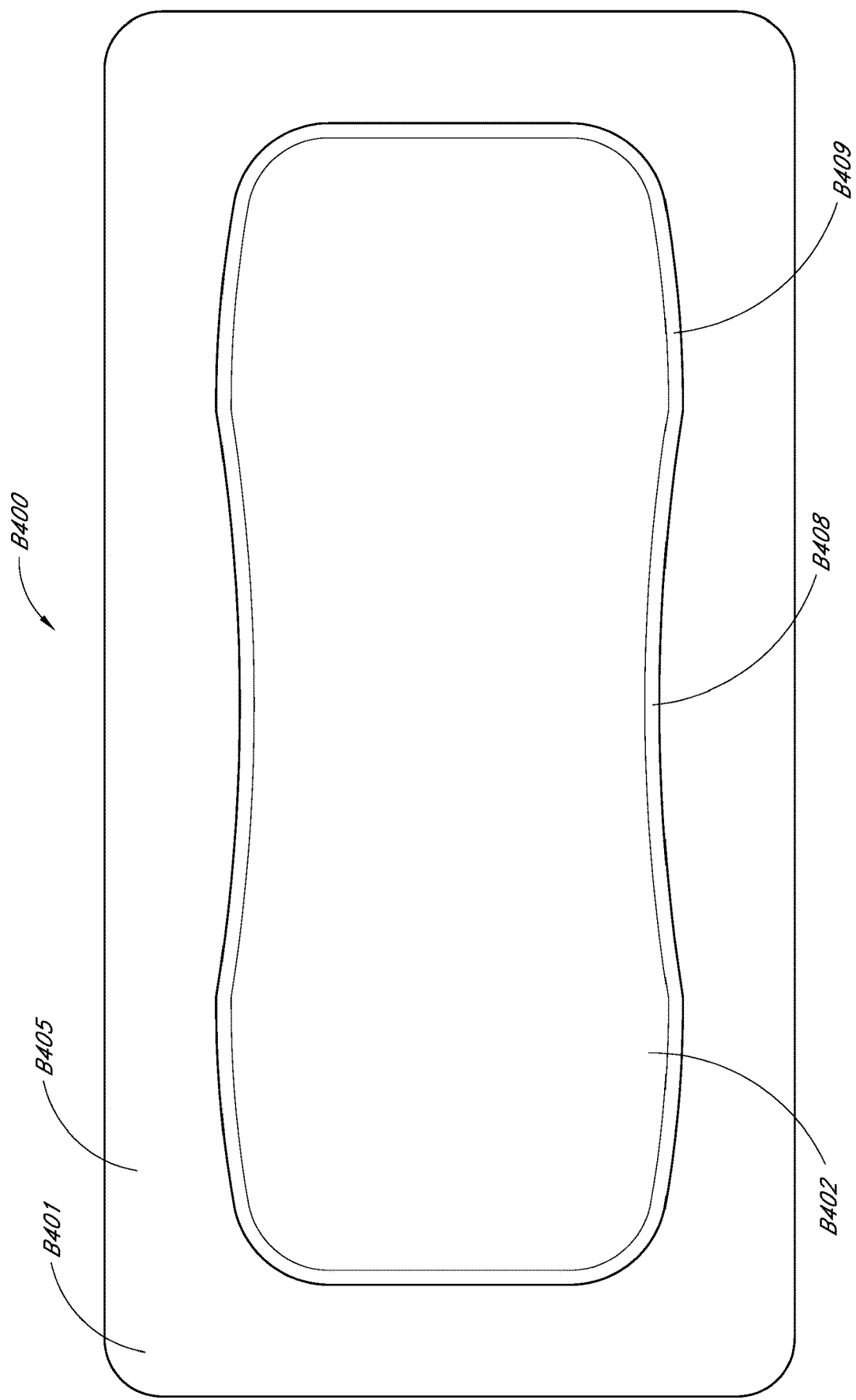
Figure 223D:
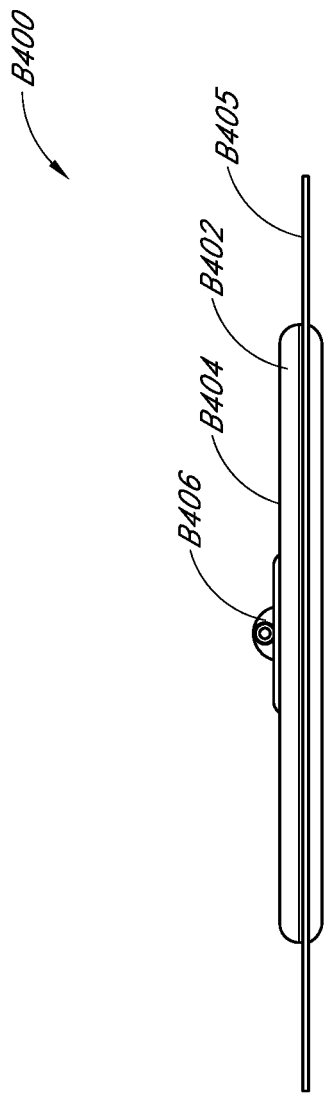
Figure 223E:
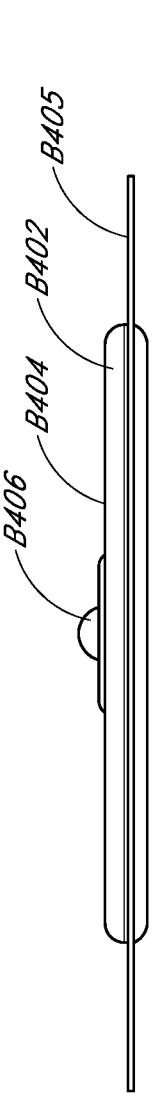
Figure 224A:
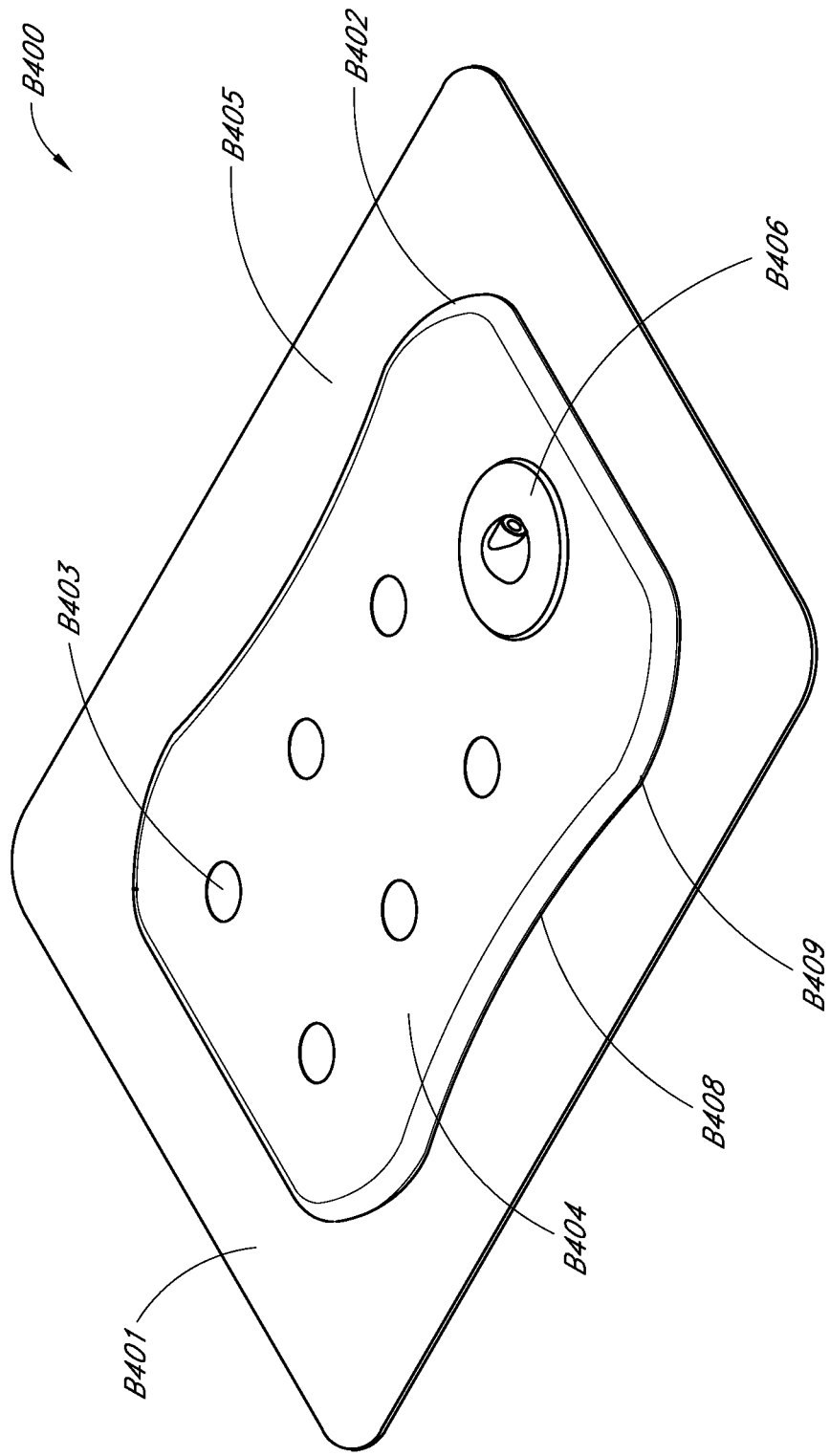
Figure 224B:
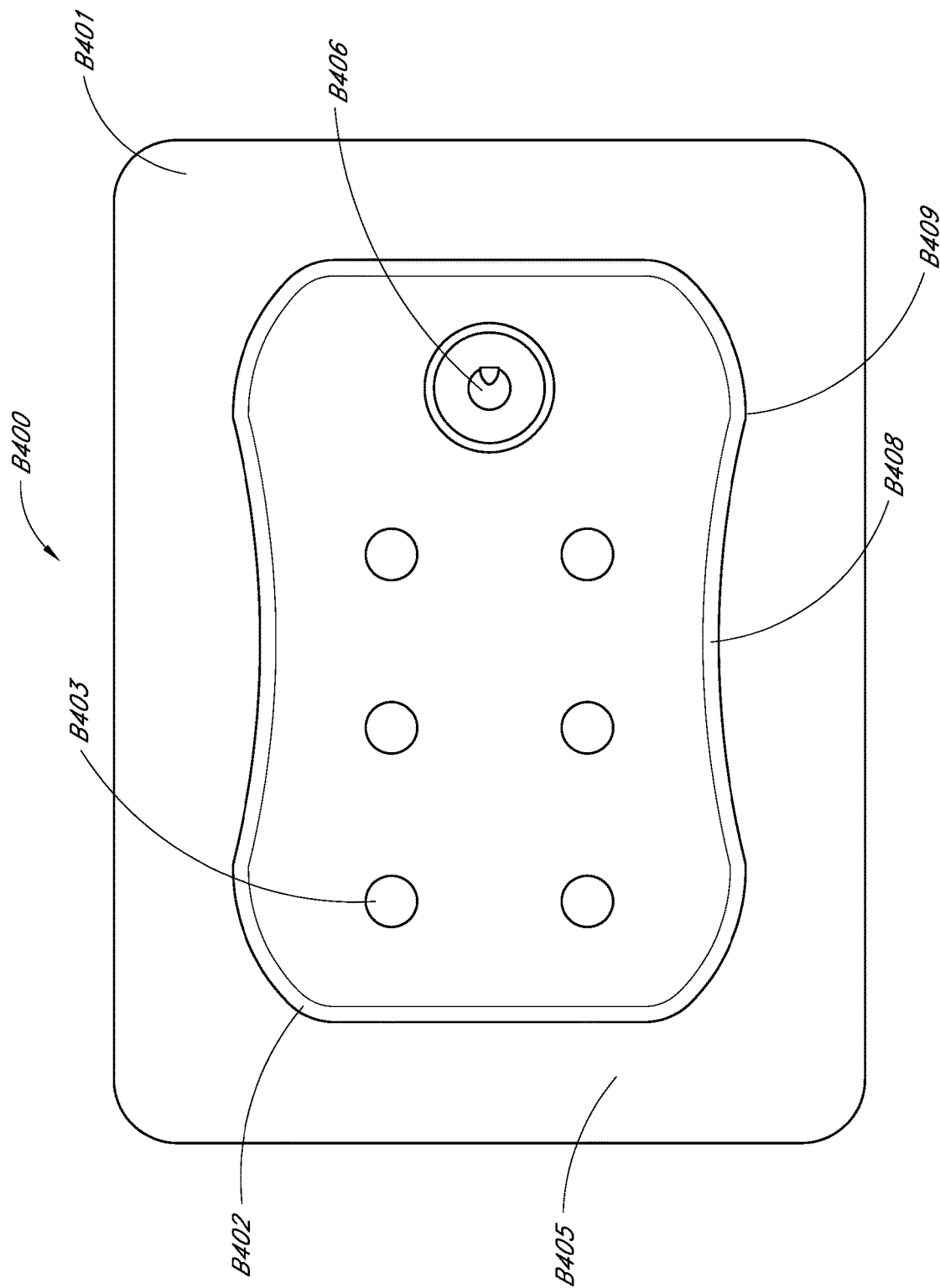
Figure 224D:
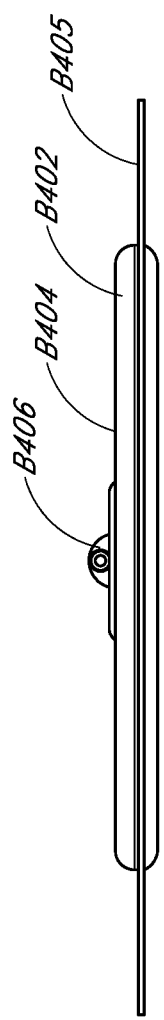
Figure 224E:
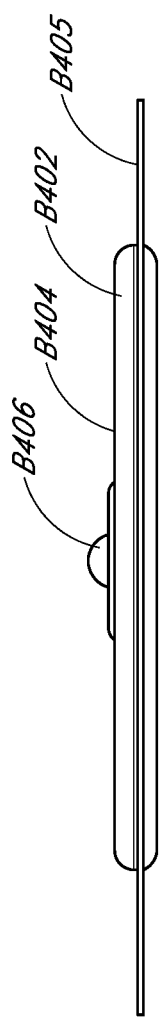
Figure 224F:
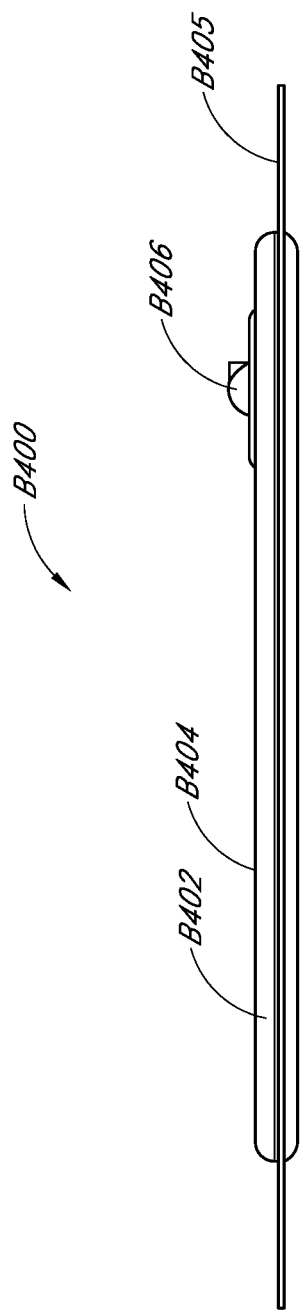
Figure 225A:
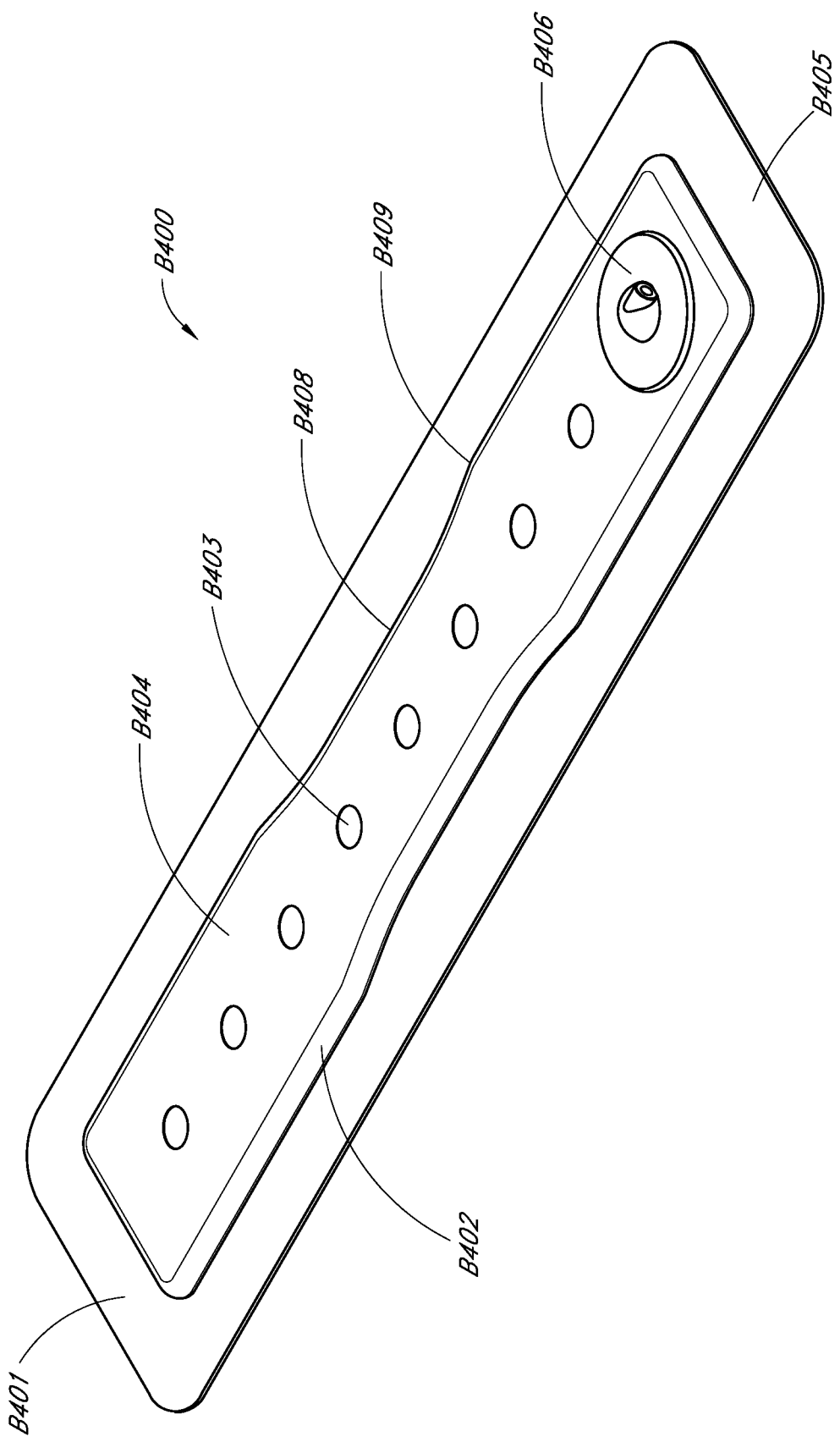
Figure 225B:
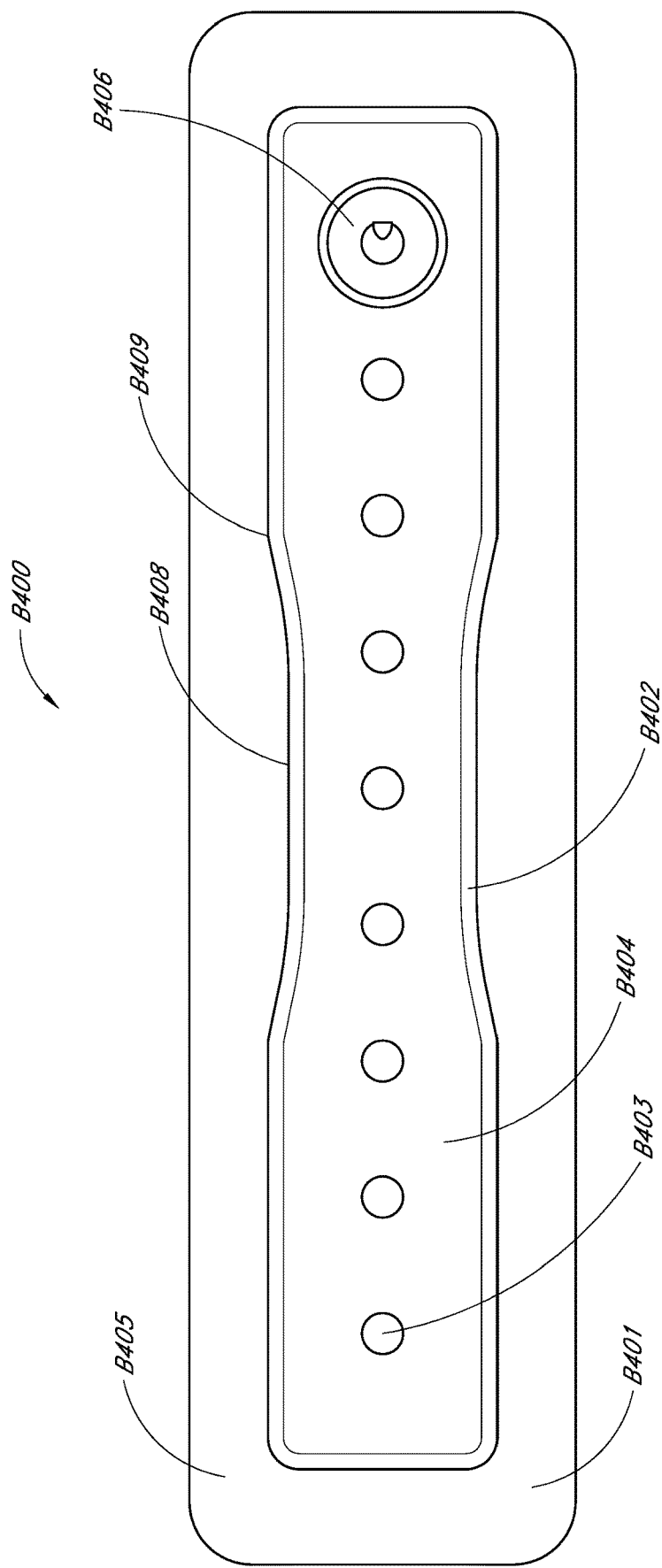
Figure 225C:
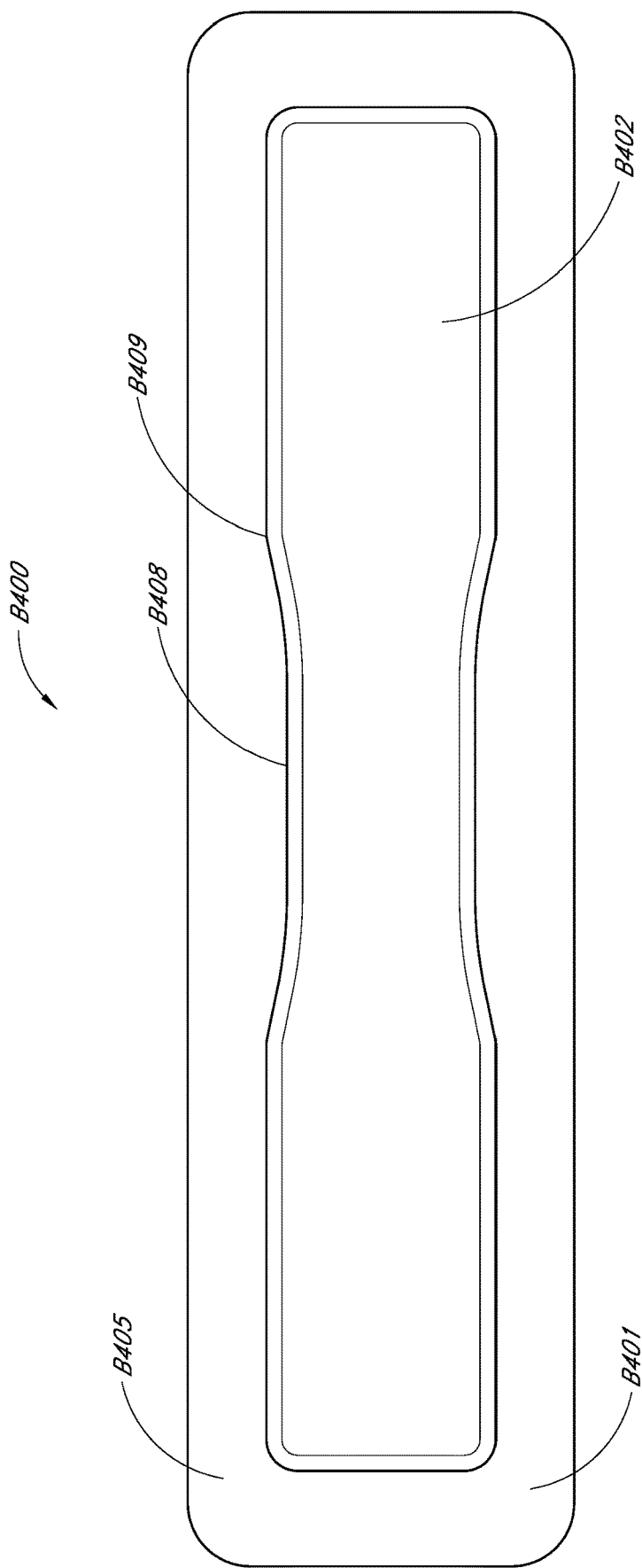
Figure 225D:
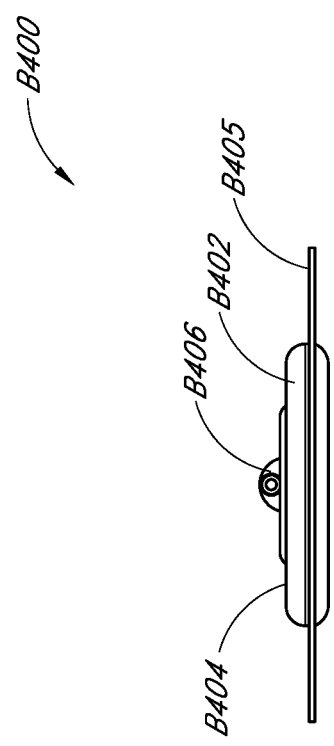
Figure 225E:
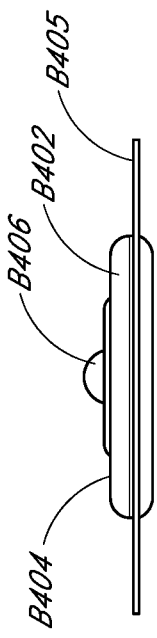
Figure 225F:
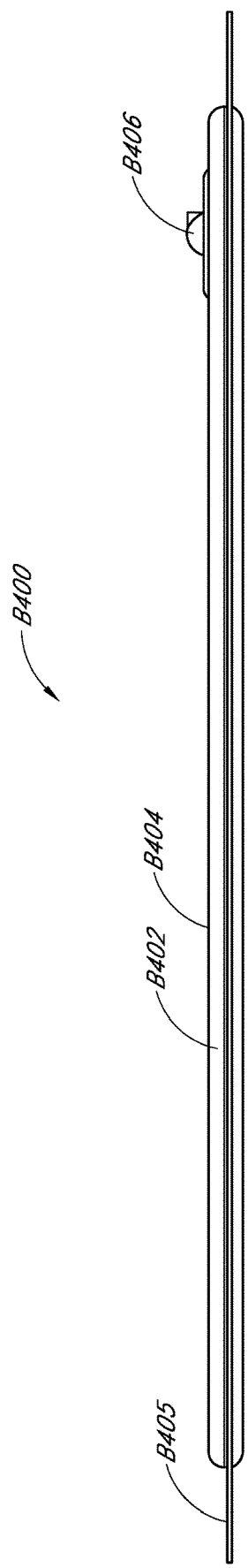
Figure 226A:
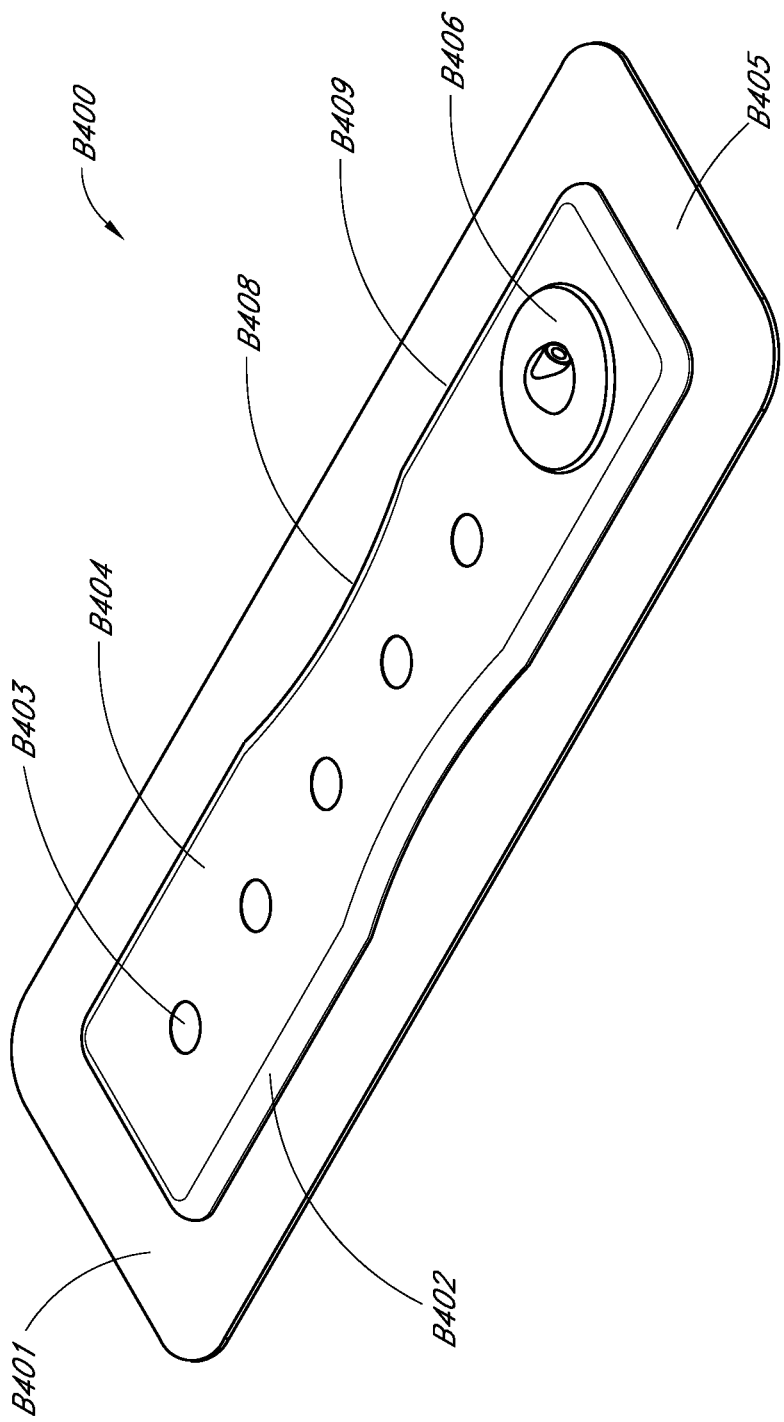
Figure 226B:
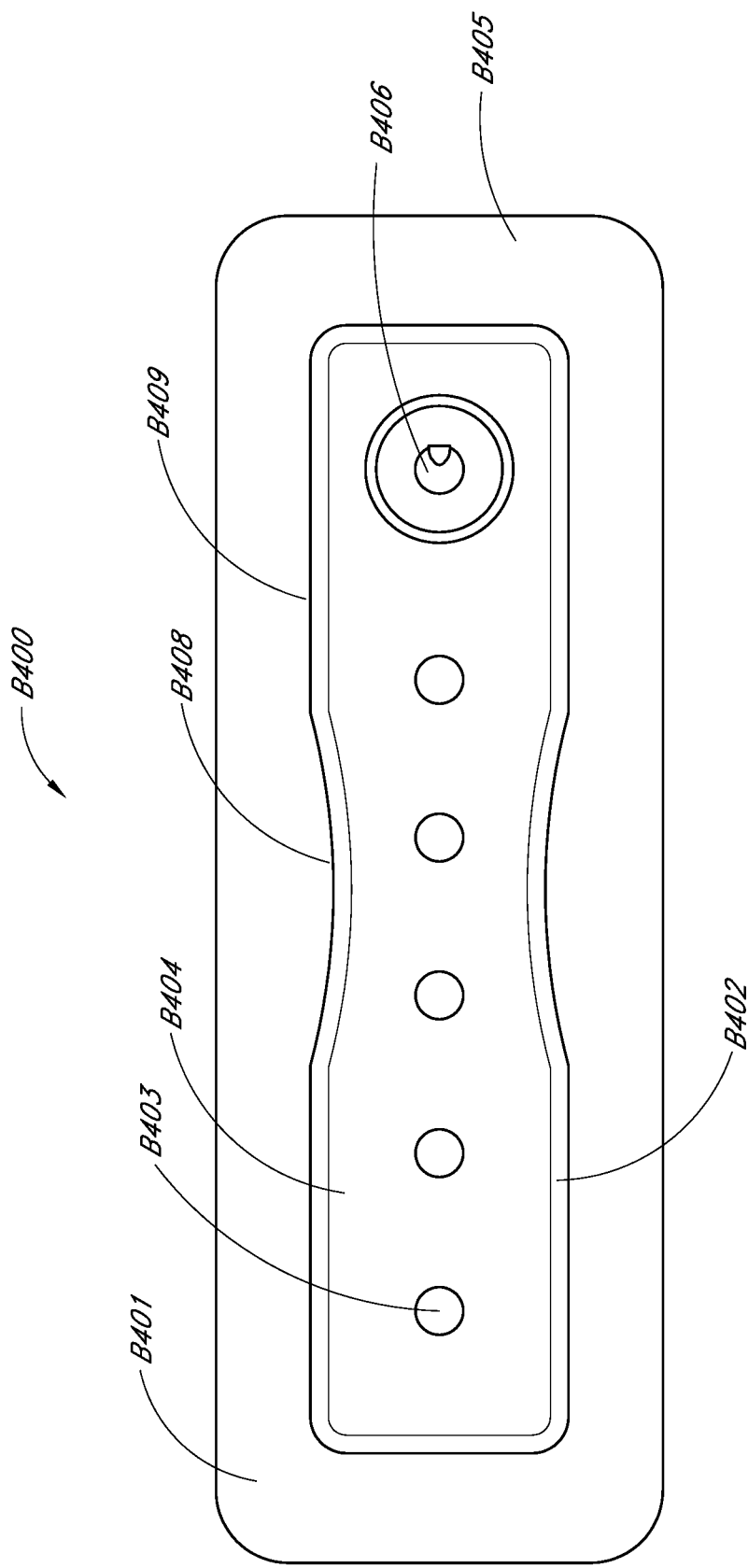
Figure 226C:
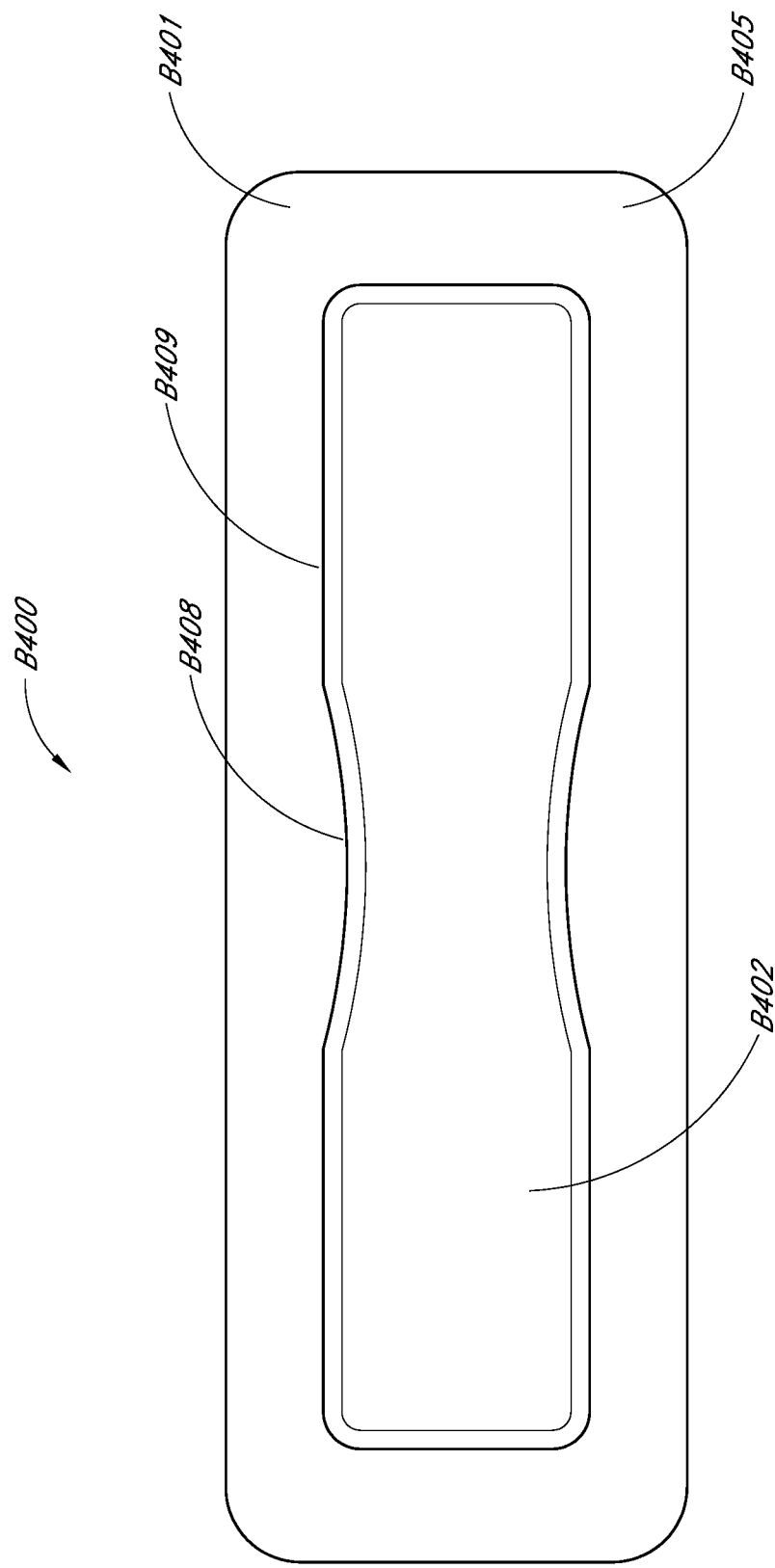
Figure 226D:
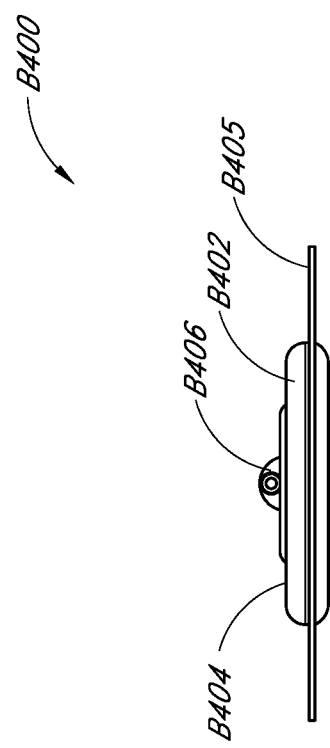
Figure 226E:
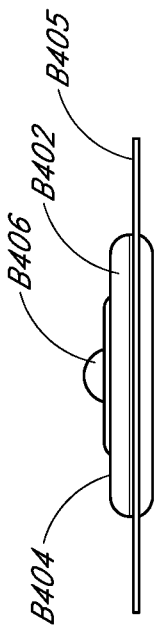
Figure 226F:
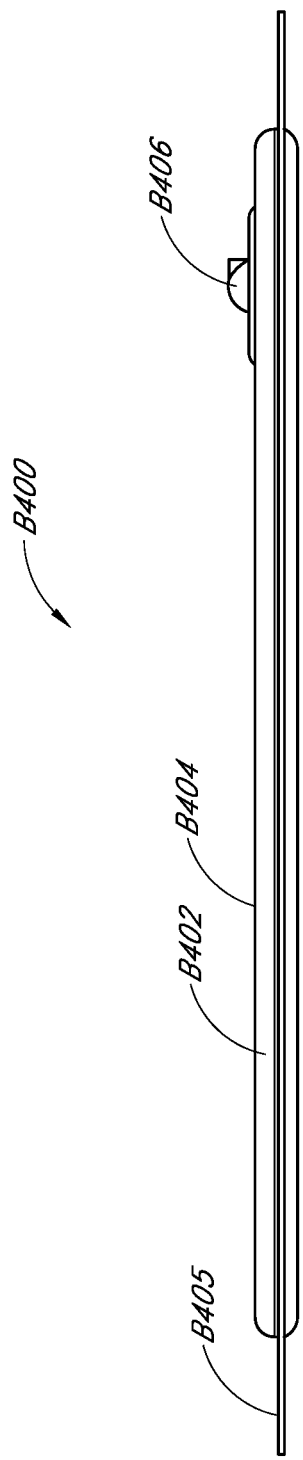
Figure 227A:
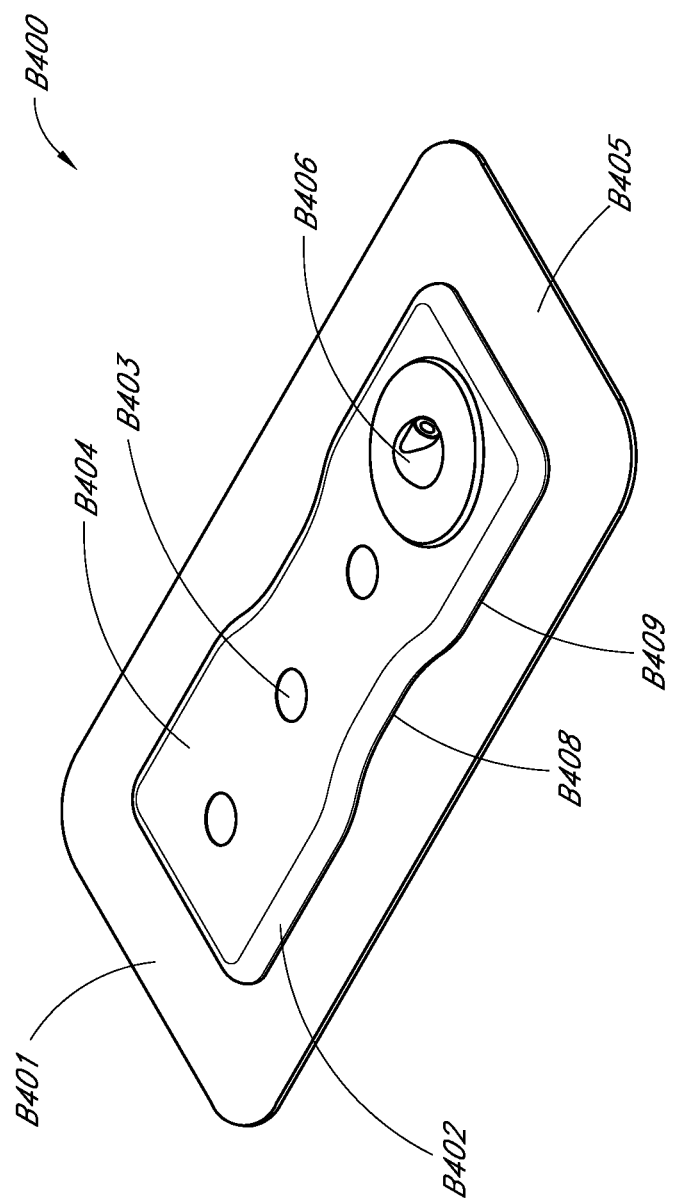
Figure 227B:
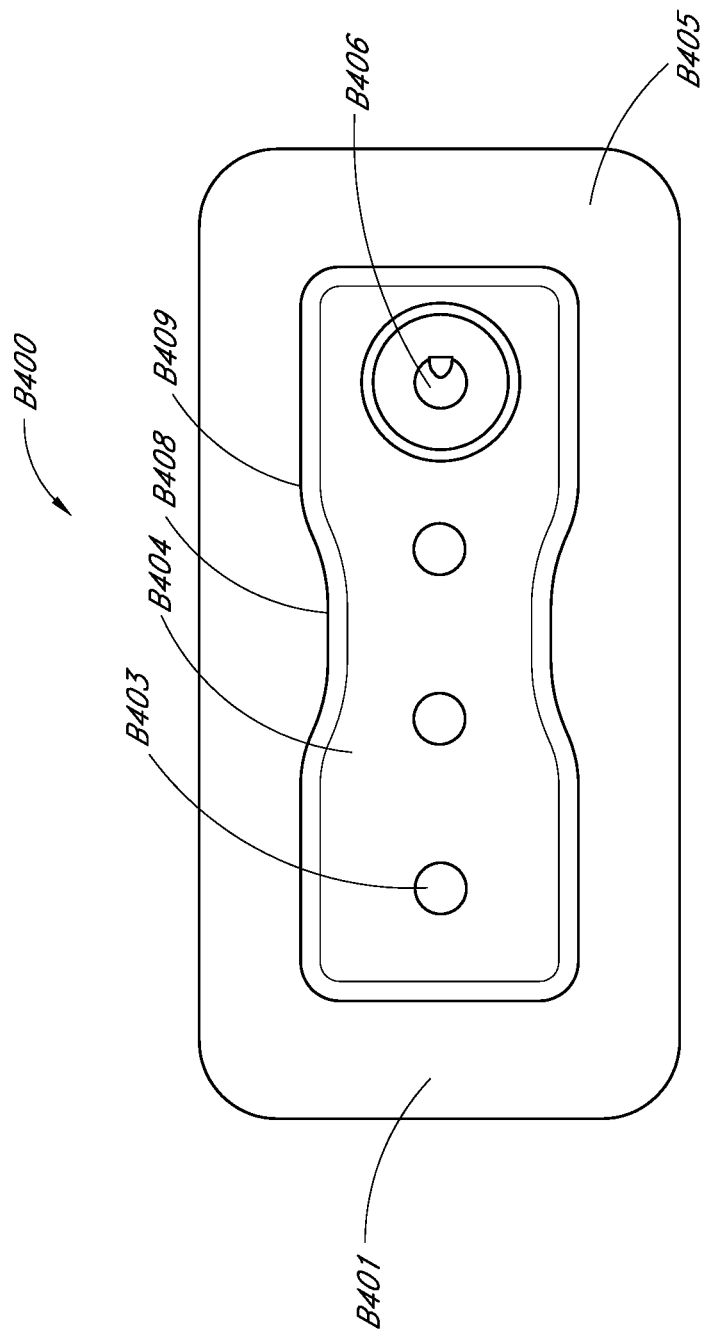
Figure 227C:
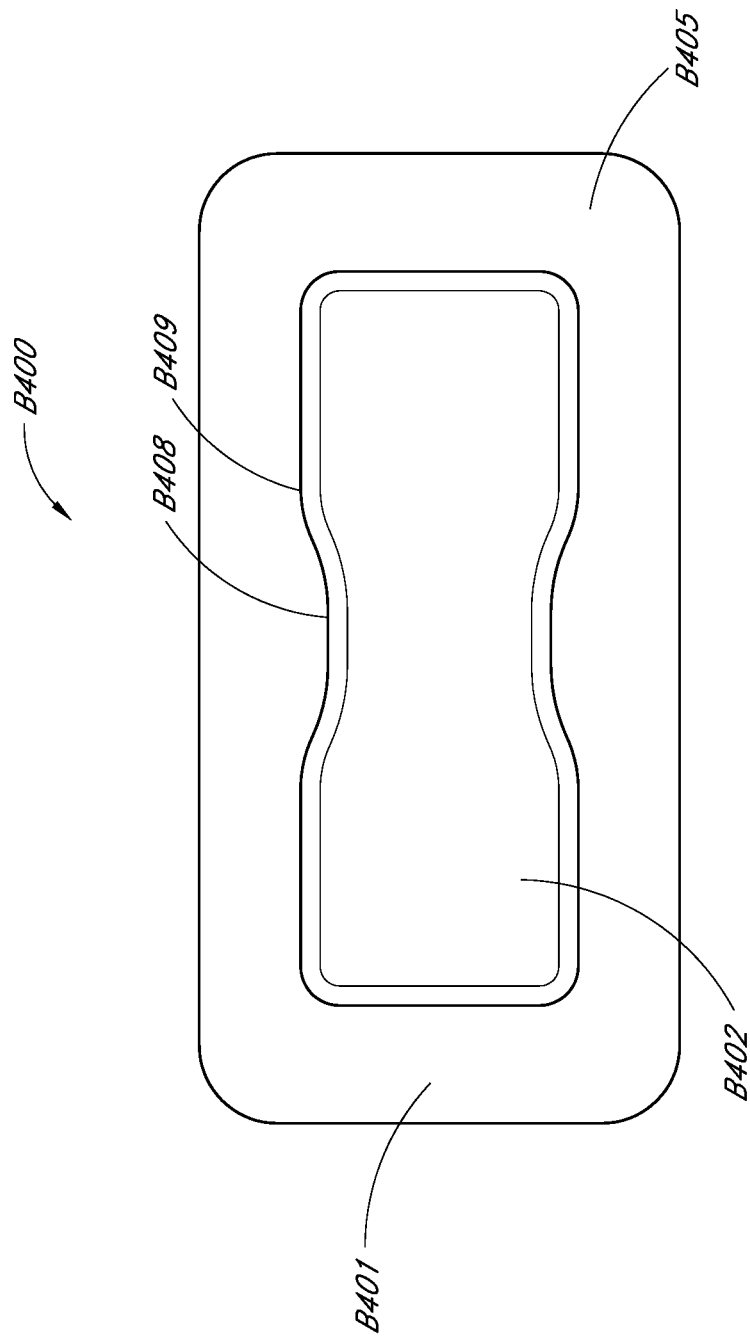
Figure 228A:
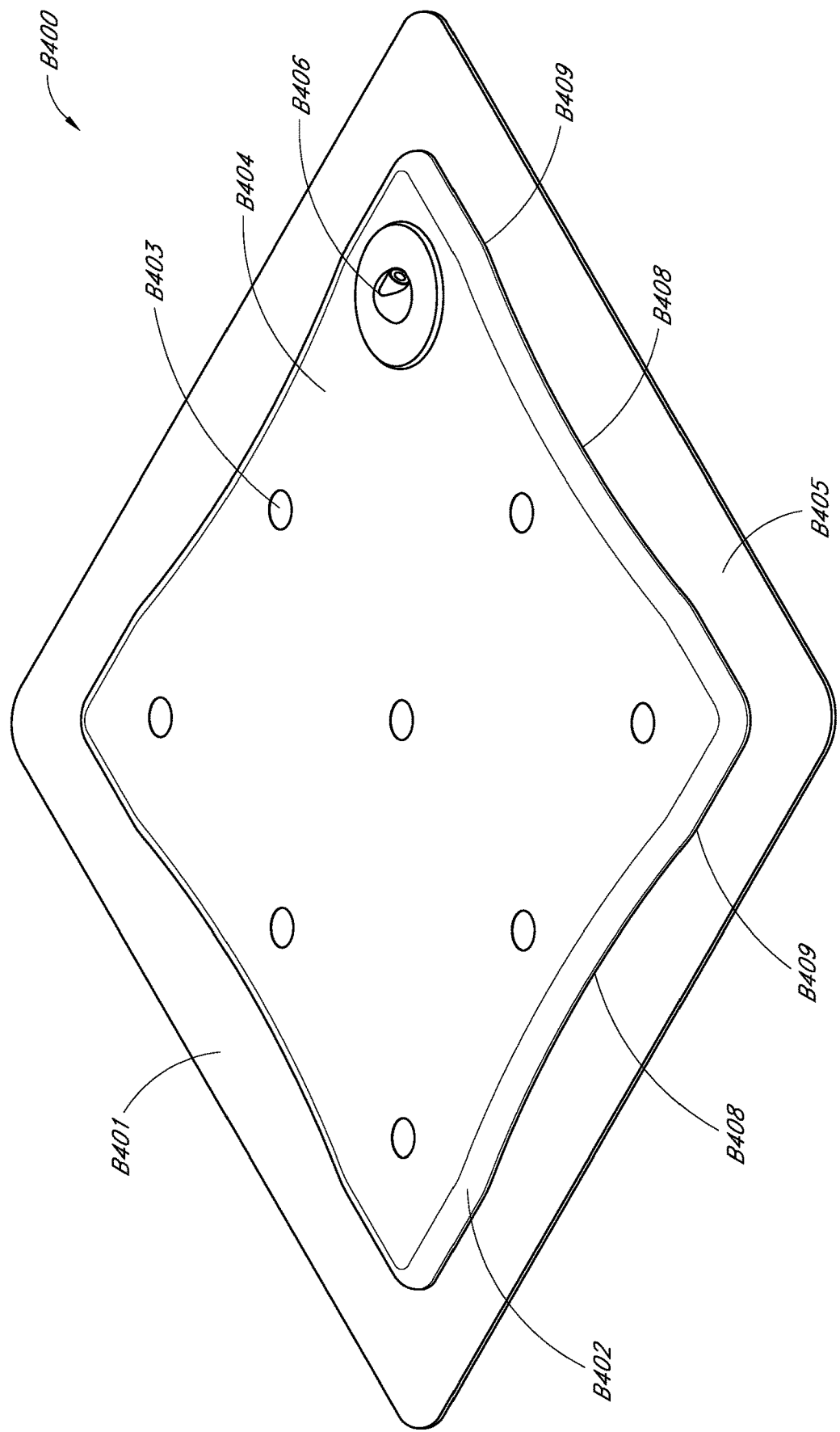
Figure 228B:
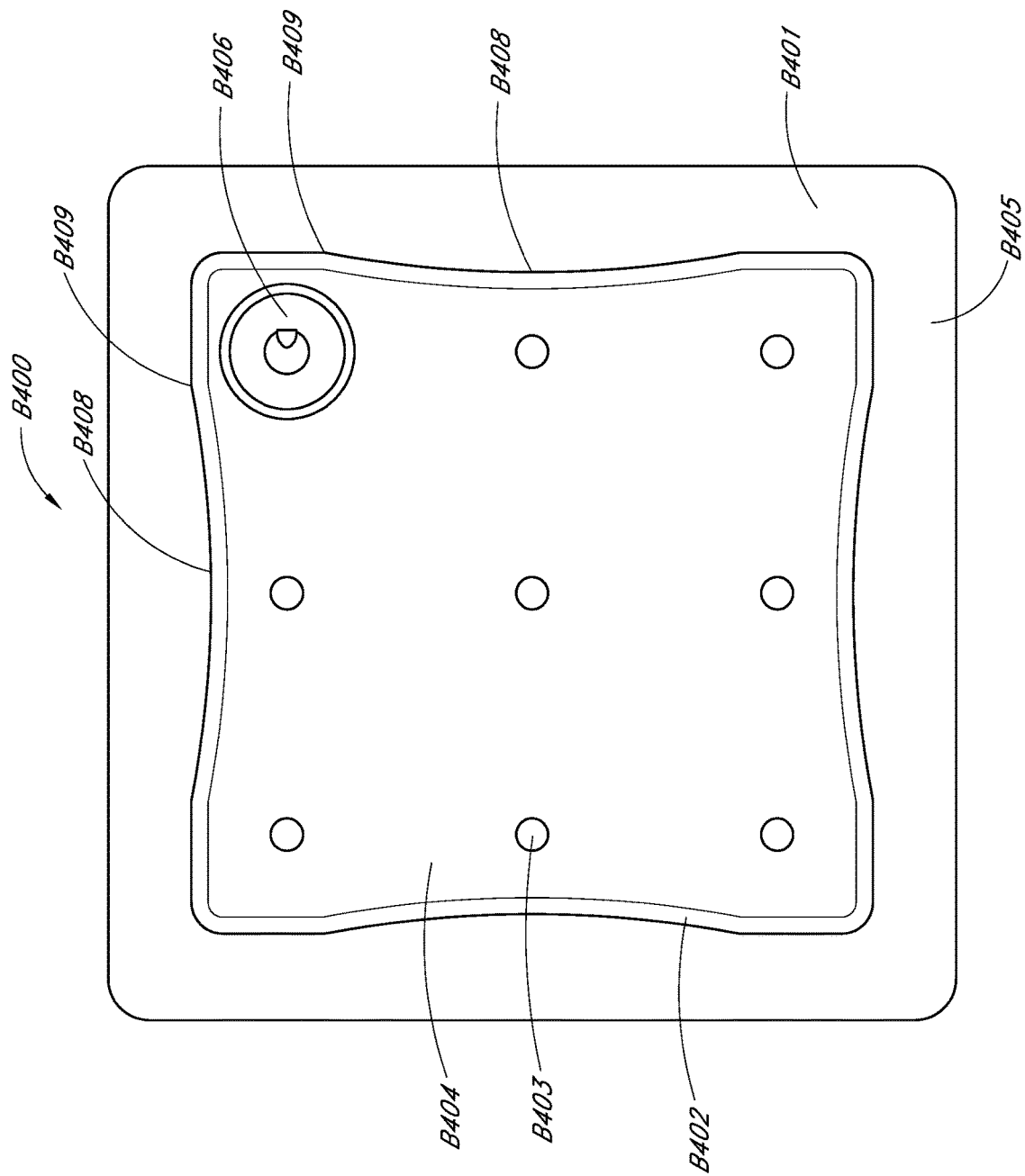
Figure 228C:
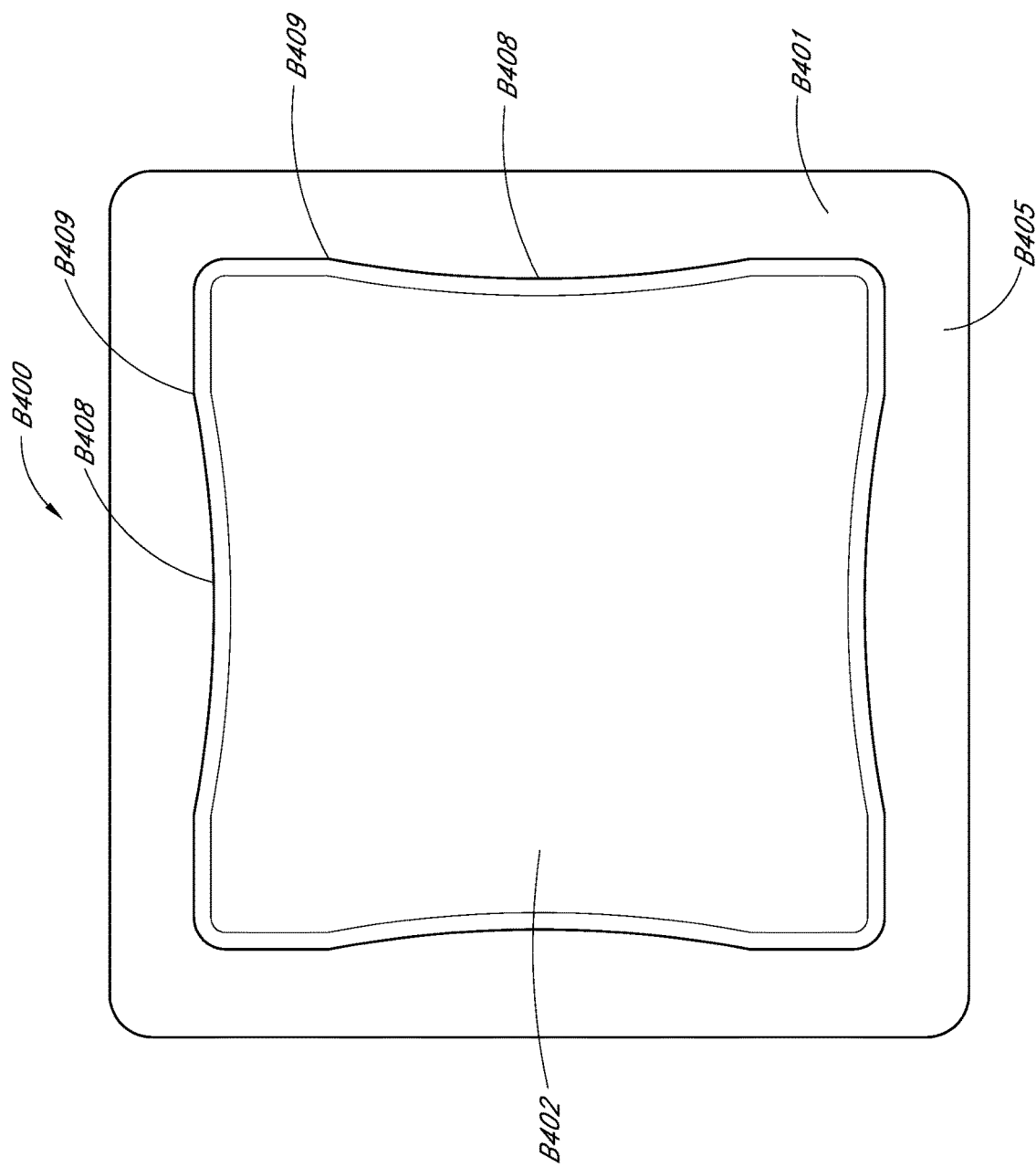
Figure 229A:
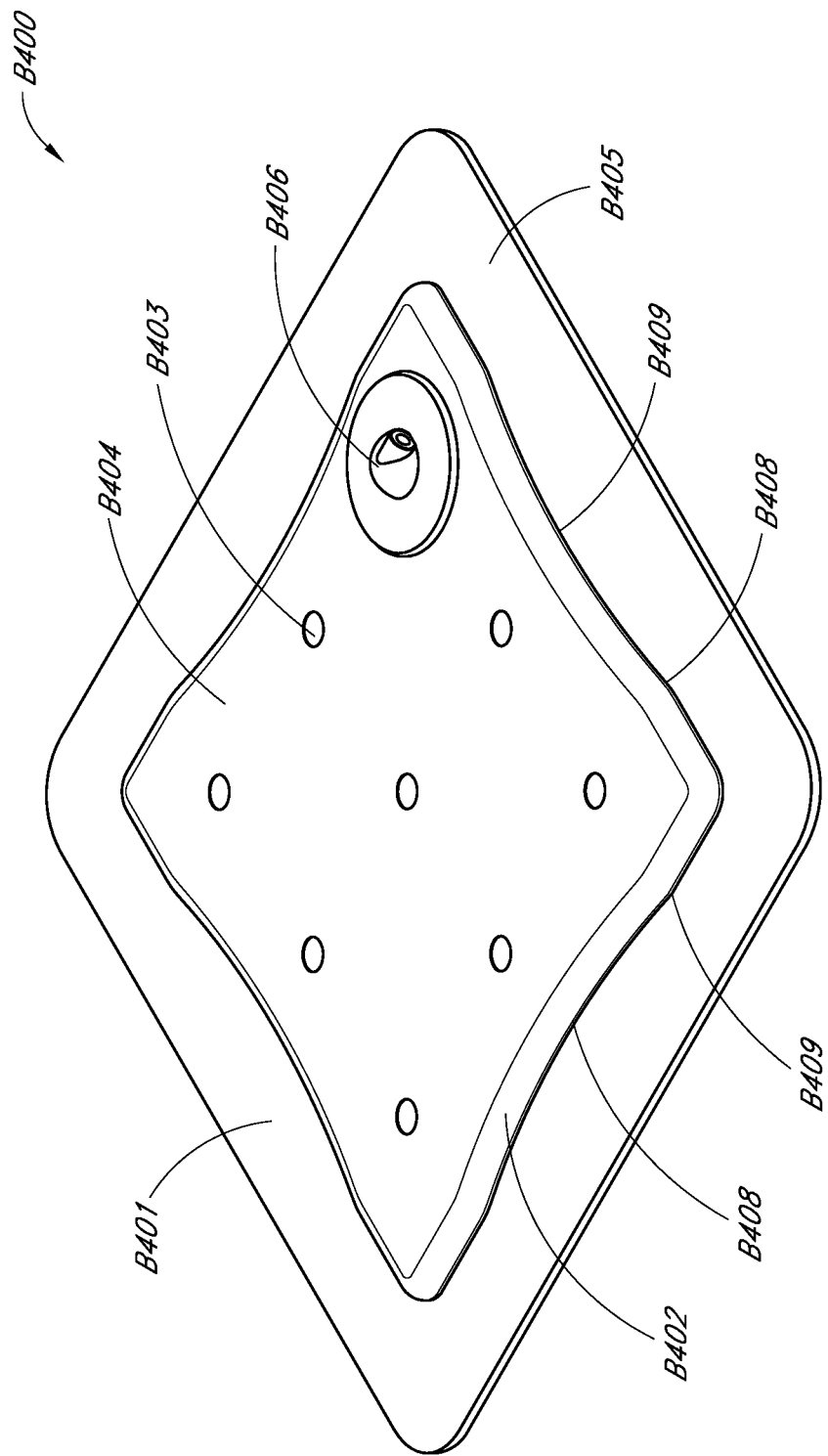
Figure 229B:
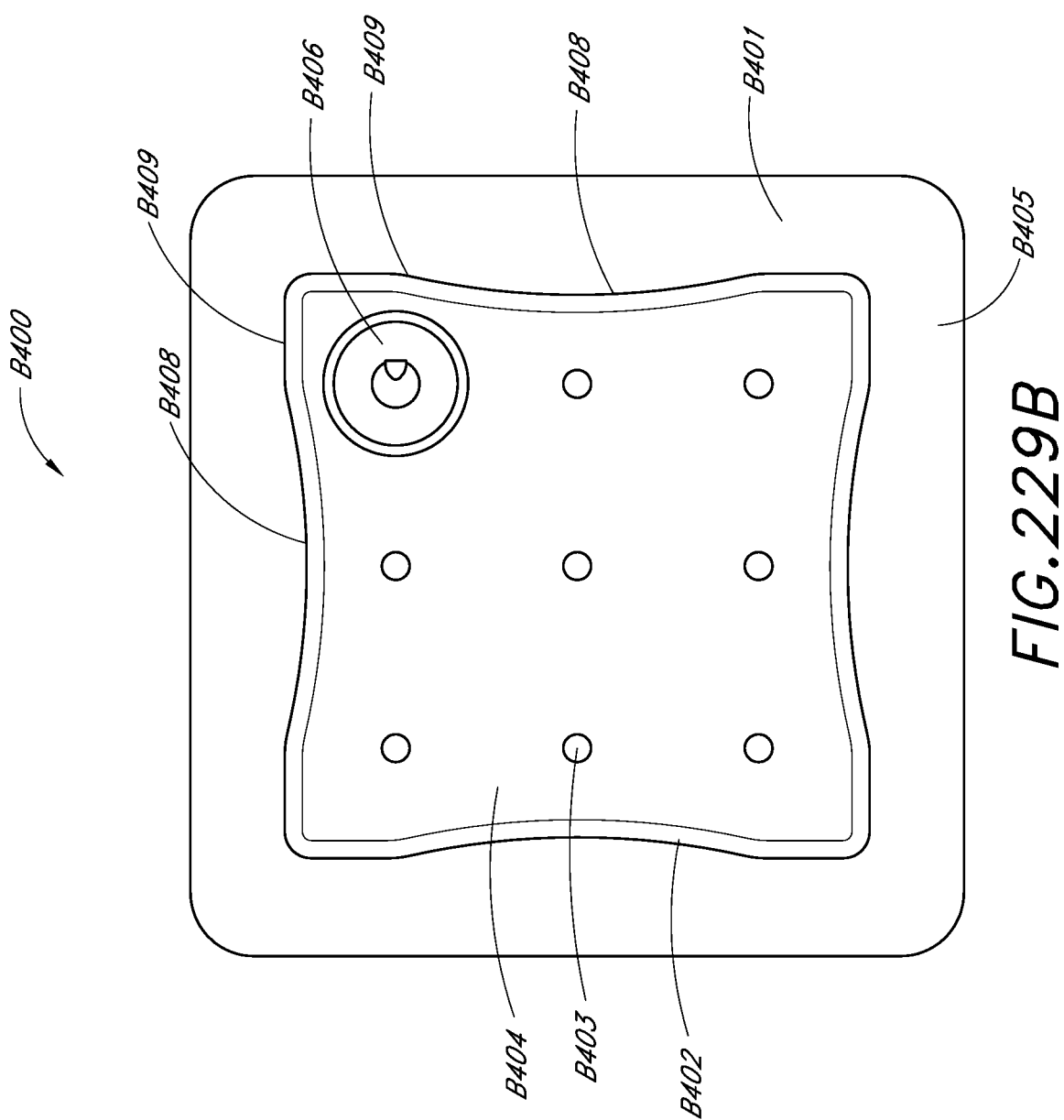
Figure 229C:
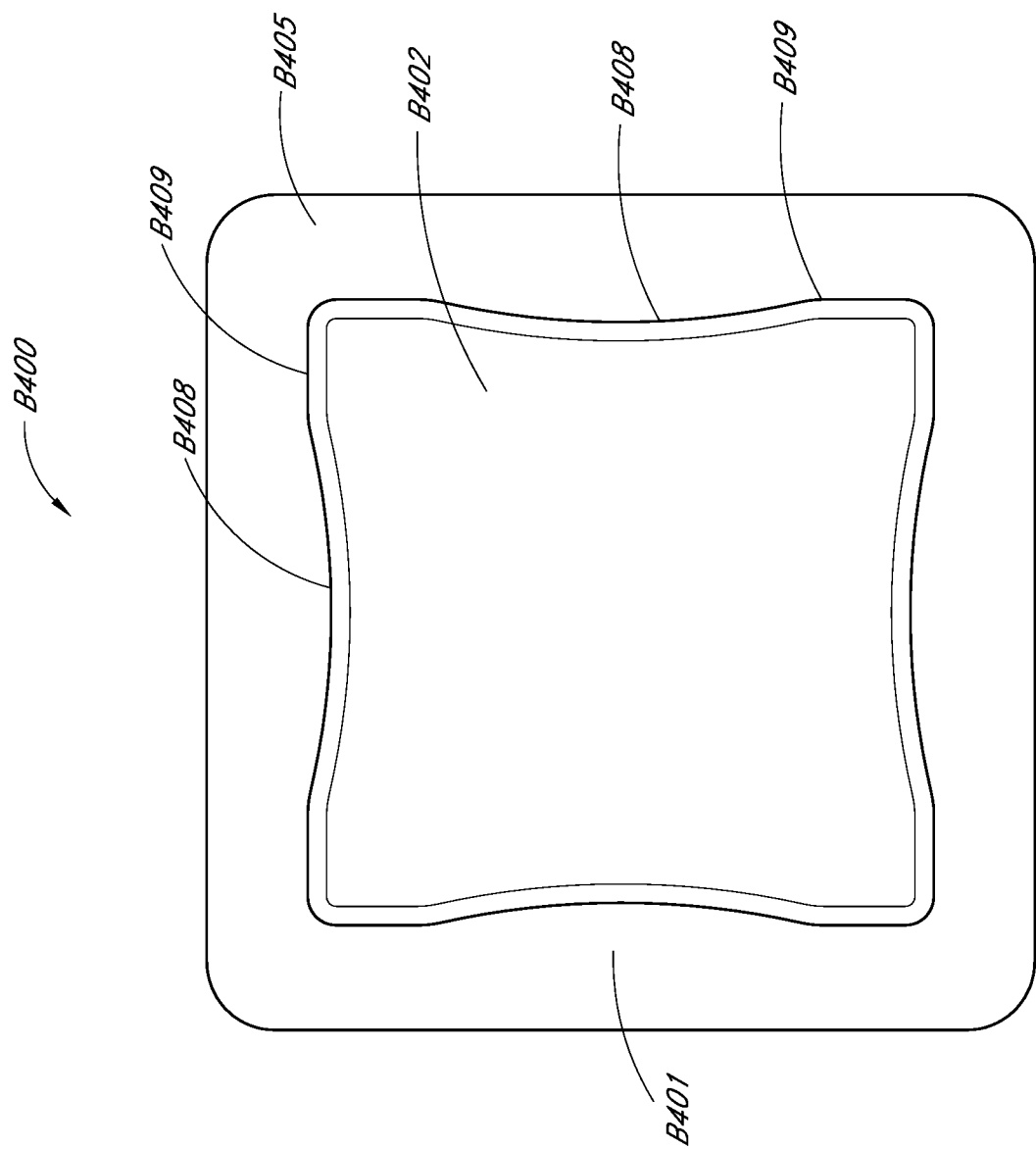
Figure 230A:
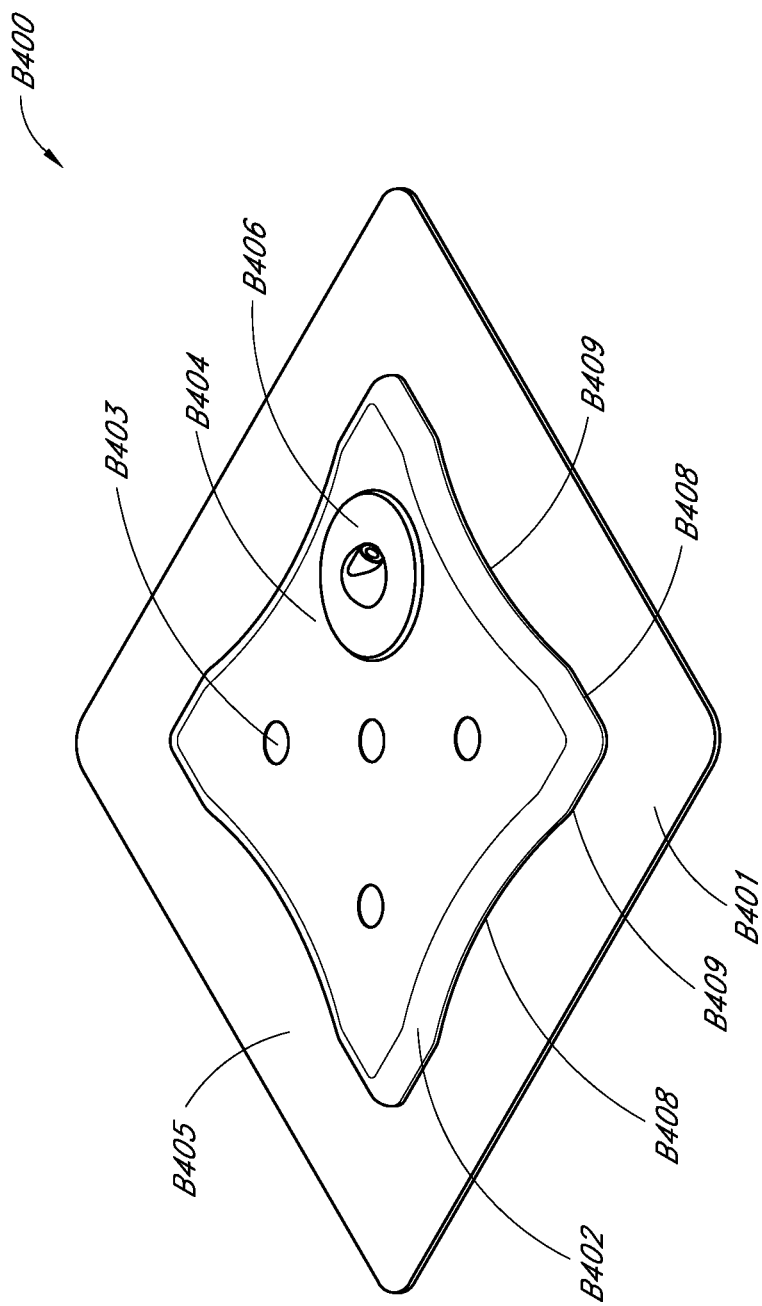
Figure 230B:
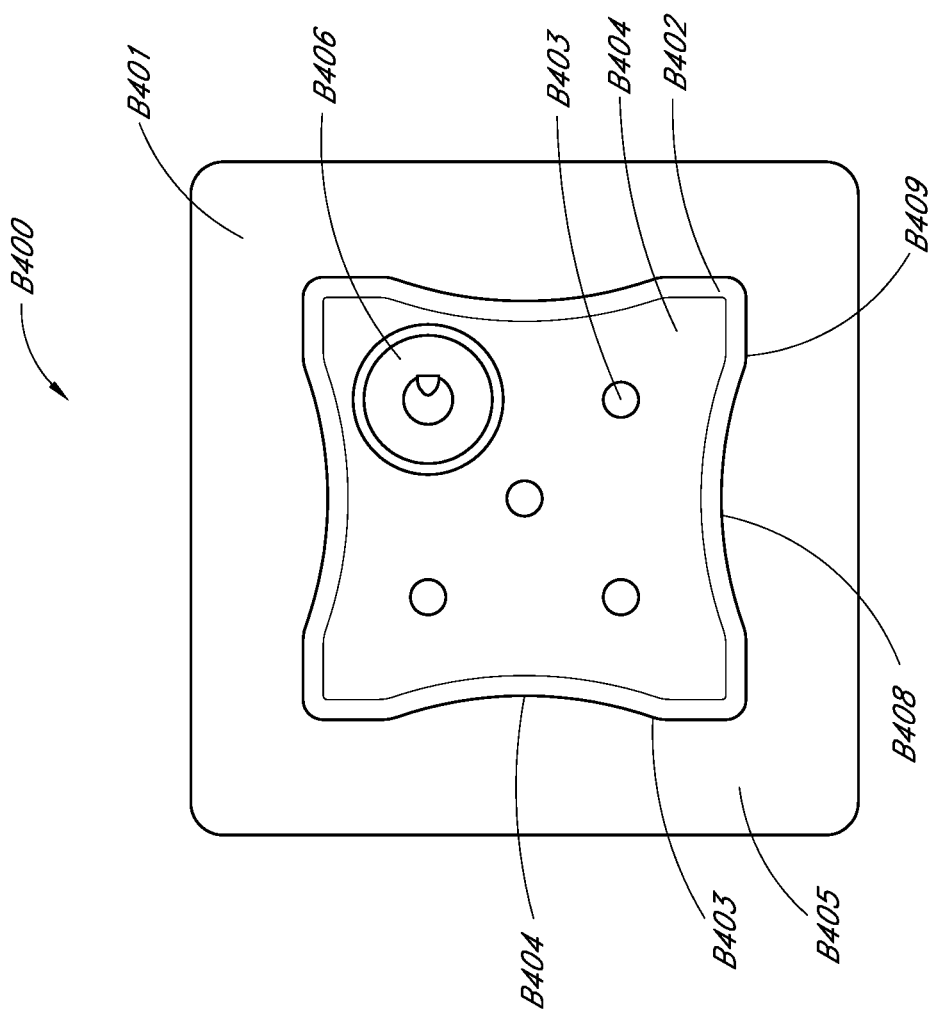
Figure 230F:
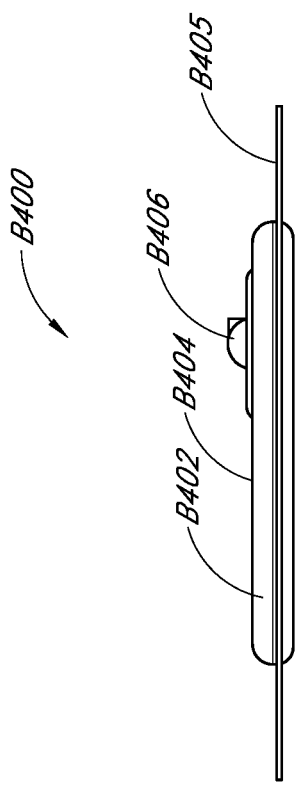

FIGS. 223A-F illustrate multiple views of the wound dressing B400. FIG. 223A illustrates a perspective view of a wound dressing with the dimensions of 300 mm×150 mm. FIGS. 223B and 223C illustrate a top view and bottom view of the embodiment of a wound dressing described in FIG. 223A. FIGS. 223D and 223E illustrate a front and back view respectively of the wound dressing B400 described in FIG. 223A. FIG. 223F illustrates a side view of the wound dressing as described in FIG. 223A.

Embodiments of the wound dressings described herein may be arranged such that each embodiment may have enhanced compatibility with body movement. This can be achieved by using a different shape for different wound types or areas of the body. Wound dressing embodiments can be of any suitable shape or form or size as illustrated in FIGS. 223A-F, 224A-F, 225A-F, 226A-F, 227A-F, 228A-F, 229A-F, 230A-F, and 242A-F. The overall dimensions of the dressings as illustrated in FIGS. 223A-F, 224A-F, 225A-F, 226A-F, 227A-F, 228A-F, 229A-F, and 230A-F may be, for example but without limitation, 300 mm×150 mm, 200 mm×150 mm, 400 mm×100 mm, 300 mm×100 mm, 200 mm×100 mm, 250 mm×250 mm, 200 mm×200 mm, and 150 mm×150 mm, respectively, although any total size may be used, and the size may be determined to match particular wound sizes. The oval-shaped dressing in FIGS. 242A-F may, in some embodiments, measure 190 mm×230 mm, or 145.5 mm×190 mm. Again, it will be understood that the embodiments described in the foregoing are simply illustrative embodiments illustrating possible sizes, dimensions, and configurations of wound dressings, and that other configurations are possible.

As noted above, the preceding embodiments illustrated in FIGS. 223A-F, 224A-F, 225A-F, 226A-F, 227A-F, 228A-F, 229A-F, and 230A-F may comprise a waisted portion B408 located inwardly with reference to an edge B409 of the absorbent layer B402. The contour of the absorbent layer to the waisted portion B408 is preferably rounded and smooth. In the embodiments of FIGS. 223A-F, 224A-F, 225A-F, 226A-F, and 227A-F, the inward distance between the edge B409 and the waisted portion B408 may range from 1 mm, 5 mm, 10 mm, 15 mm, 20 mm, and 30 mm. Preferably, the inward distance is 10 mm. In the embodiments of FIGS. 228A-F, 229A-F, and 230A-F the inward distance between the edge B409 and the waisted portion B408 may range from 5 mm, 10 mm, 20 mm, 30 mm, 40 mm, 45 mm, 50 mm, 60 mm, and 75 mm. FIGS. 224A-F illustrate a perspective view, a top view, a bottom view, a front view, a back view, and a side view, respectively, of an embodiment of a wound dressing B400. In some embodiments, the dressing may measure 200 mm×150 mm. The wound dressing B400 of FIGS. 224A-F can have a similar configuration and components as described above for FIGS. 223A-F, except the embodiments of FIG. 224A-F are of a smaller size. Additionally, in contrast to the embodiment of FIGS. 223A-F which comprises a 5×2 configuration of an array of dots viewing windows, the embodiment of FIGS. 224A-F comprises a viewing window configuration comprising a 3×2 array of dots.

FIGS. 225A-F illustrate a perspective view, a top view, a bottom view, a front view, a back view, and a side view, respectively, of an embodiment of a wound dressing B400. In some embodiments, the dressing may measure 400 mm×100 mm. The wound dressing B400 of FIGS. 225A-F can have a similar configuration and components as described above for FIGS. 223A-F, except the embodiments of FIG. 225A-F are of a different size. Additionally, in contrast to the embodiment of FIGS. 223A-F, the embodiment of FIGS. 225A-F comprises a viewing window configuration comprising an 8×1 array of dots.

FIGS. 226A-F illustrate a perspective view, a top view, a bottom view, a front view, a back view, and a side view, respectively, of an embodiment of a wound dressing B400. In some embodiments, the dressing may measure 300 mm×100 mm. The wound dressing B400 of FIGS. 226A-F can have a similar configuration and components as described above for FIGS. 223A-F, except the embodiments of FIG. 226A-F are of a different size. Additionally, in contrast to the embodiment of FIGS. 223A-F, the embodiment of FIGS. 226A-F comprises a viewing window configuration comprising a 5×1 array of dots.

FIGS. 227A-F illustrate a perspective view, a top view, a bottom view, a front view, a back view, and a side view, respectively, of an embodiment of a wound dressing B400. In some embodiments, the dressing may measure 200 mm×100 mm. The wound dressing B400 of FIGS. 227A-F can have a similar configuration and components as described above for FIGS. 223A-F, except the embodiments of FIG. 227A-F are of a different size. Additionally, in contrast to the embodiment of FIGS. 223A-F, the embodiment of FIGS. 227A-F comprises a viewing window configuration comprising a 3×1 array of dots.

FIGS. 230A-F illustrate a perspective view, a top view, a bottom view, a front view, a back view, and a side view, respectively, of an embodiment of a wound dressing B400. In some embodiments, the dressing may measure 150 mm×150 mm. The wound dressing B400 of FIGS. 230A-F can have a similar configuration and components as described above for FIGS. 223A-F, except the embodiments of FIGS. 227A-F are of a different size. Additionally, in contrast to the embodiment of FIGS. 223A-F, the embodiment of FIGS. 230A-F comprises a viewing window configuration comprising a quincunx array of dots. The quincunx array of dots configuration consists of five dots arranged in a cross, with four of the dots forming a square or rectangle where one dot is positioned at each of the four corners of the square or rectangle shaped wound dressing and a fifth dot in the center. However, one corner of the wound dressing preferably has the fluidic connector or port B406 in place of a dot in the quincunx dot array.

FIGS. 228A-F illustrate a perspective view, a top view, a bottom view, a front view, a back view, and a side view, respectively, of an embodiment of a wound dressing B400. In some embodiments, the dressing may measure 250 mm×250 mm. The wound dressing B400 of FIGS. 228A-F can have a similar configuration and components as described above for FIGS. 223A-F, except the embodiments of FIG. 228A-F are of a different size. Additionally, in contrast to the embodiment of FIGS. 223A-F, the embodiment of FIGS. 228A-F comprises a viewing window configuration comprising a 3×3 array of dots with an absent at a corner position of the wound dressing and in its place is a domed port or a fluidic connector B406 completing the 3×3 array.

FIGS. 229A-F illustrate a perspective view, a top view, a bottom view, a front view, a back view, and a side view, respectively, of an embodiment of a wound dressing B400. In some embodiments, the dressing may measure 200 mm×200 mm. The wound dressing B400 of FIGS. 229A-F can have a similar configuration and components as described above for FIGS. 223A-F, except the embodiments of FIGS. 229A-F are of a different size. Additionally, in contrast to the embodiment of FIGS. 223A-F, the embodiment of FIGS. 229A-F comprises a viewing window configuration comprising a 3×3 array of dots with an absent dot at a corner position of the wound dressing and in its place is a domed port or a fluidic connector completing the 3×3 array.

The additional sizes and shapes illustrated in FIGS. 223A-F, 224A-F, 225A-F, 226A-F, 227A-F, 228A-F, 229A-F, 230A-F, and 242 may incorporate the waisted portion B408, obscuring layer B404, viewing windows B403, and other components and embodiments described herein.

FIGS. 231A, 231B, and 232 illustrate embodiments of a dressing B500 comprising one or more orifice viewing windows B502 at, near, or adjacent to the port. The orifice viewing windows B502 can be provided at, near, adjacent to the port B504 in the backing layer for viewing of the absorbent material B503 present in proximity to the port B504. The orifice viewing windows B502 can have the same structure and/or function as the viewing windows herein described. In some embodiments, the orifice viewing window B502 can be formed from a cross-shaped or Maltese-cross-shaped aperture or cut-out B501 in the obscuring layer. The arms of the cross-shaped cut-out B501 can be aligned with the longitudinal length and transverse width of the absorbent material B503 as shown in FIG. 231A. Alternatively, the arms of the cross-shaped cut-out B501 can be offset from the longitudinal length and transverse width of the absorbent material, at an angle, for example, a 45° angle, as illustrated in FIG. 231B. The arms of the cross-shaped cut-out may span a larger dimension than a hole in the absorbent material below the cut-out B501. For example, the arms may span a dimension of about 25 mm, while the through-hole in the absorbent material may have a diameter of 10 mm.

Additionally, FIG. 232 illustrates an embodiment of a wound dressing B600 in which the arms of the cross-shaped aperture can have flared edges B601. The orifice viewing windows B502 at, near, or adjacent to the port B604 may be used to indicate that fluid is approaching the port B604 or that the dressing B600 is otherwise becoming saturated. This can assist the clinician or patient in maintaining the wound dressing and determining when to change the dressing, because once fluid contacts the center of the port, such fluid contact may at least partially occlude the hydrophobic filter that may be contained therein so as to interrupt or at least partially block the application of negative pressure. The orifice viewing windows B502 can be used with the fluidic connector as well as the domed port or any other suitable connector.

As with FIGS. 233A and 233B, the wound dressing may also be provided with one or more slits B2150 to aid the dressing in conforming to a non-planar area. FIG. 233A illustrates an embodiment of a wound dressing B2100 with a narrowed central portion or waisted portion B2120 and concentric slits B2150. This embodiment may be useful for the treatment of wounds on non-planar surfaces or otherwise contoured wounds, including, for example, feet, knees, sacral regions, or other such areas. In some embodiments, the wound dressing B2100 may provide for one or more slits B2150 cut into the dressing, preferably into the absorbent layer, that may enhance the conformability of the dressing. In this embodiment, the slits B2150 are cut in concentric ovoid arcs, although other configurations (as discussed below) are possible. Preferably, the area under the port B2130 or fluidic connector disposed at the top of the device is free from the slits B2150, as this may interfere with fluid transfer from the dressing. In some embodiments, the slits B2150 may be formed as part of, in addition to, or instead of baffles that may be present within the absorbent layer so as to may aid in distribution of wound exudate. In these embodiments, and with all other embodiments described herein, although a domed connector is shown attached to the dressing, this may be interchanged with any other suitable connector, including for example embodiments of the fluidic connectors described in FIGS. 241A and 241B (as described below).

FIG. 233B illustrates an embodiment of a wound dressing B2100 with a narrow central portion B2120. Here, however, one or more slits B2150 extending across the width of the dressing may be present. Preferably, these slits B2150 do not extend entirely across the width of the dressing, in order to promote fluid transfer within the absorbent layer. The slits B2150 may enhance conformability of the dressing, possibly in conjunction with the waisted configuration of the dressing, when applied to a non-planar or contoured wound area. For example, such a dressing B2100 may be useful when applied so as to wrap around an arm or a leg.

FIGS. 241A and 241B illustrate embodiments of white and black fluidic connectors B2410, B2420, respectively, that may be used to connect an embodiment of a wound dressing described herein to a source of negative pressure. In some embodiments, the domed port used in other embodiments discussed herein (e.g., as illustrated above in FIG. 219) may be replaced by the fluidic connector B2410, B2420, for example as illustrated in FIGS. 234-237. The fluidic connector B2410, B2420 may be flexible and/or enhance the comfort of the patient. The fluidic connector B2410, B2420 preferably comprises a fluidic connector body configured to transmit fluid through itself, including, for example, negative pressure and/or wound exudate. The fluidic connector body is preferably encapsulated within one or more layers of fluid-impermeable material. In some embodiments, the fluid-impermeable material is heat-sealed together to enclose the fluid connector body.

With reference now to FIG. 241A, the body of the fluidic connector B2410 is preferably be constructed from a material configured to transmit fluids therethrough, including fabrics such as 3D fabric. In some embodiments, the thickness of the fluidic connector body may measure between 0.5 to 4 mm, preferably 0.7 to 3 mm, and even more preferably between 1 and 2 mm; in a preferred embodiment the fluid connector body is 1.5 mm thick. Suitable materials that may be used for the fluidic connector body, including the 3D fabric, are disclosed in U.S. application Ser. No. 13/381,885, filed Dec. 30, 2011, published as US2012/0116334, titled "APPARATUSES AND METHODS FOR NEGATIVE PRESSURE WOUND THERAPY," and which is hereby incorporated by reference in its entirety. Use of the 3D fabric in the fluidic connector body may help alleviate fluid blockage when the connector is kinked, and may further provide for a soft fluidic connector that alleviates contact pressure onto a patient, for example when the patient's weight is pressed against the fluidic connector. This may enhance patient comfort and reduce the likelihood of pressure ulcers.

Testing of various weights in various configurations on embodiments of fluidic connectors comprising a 3D fabric was completed. The testing included weights above those believed to be likely to be encountered by a patient, as maximal pressure on a heel for a patient using dressings was found to be 1.3 kg/cm$^2$ in some studies. Preferably, embodiments of the fluidic connectors described herein, especially when comprising 3D fabric, can transmit therapeutic levels of negative pressure (i.e., in an amount sufficient to heal a wound) while a weight is pressed down thereupon. For example, embodiments are preferably able to transmit therapeutic levels of negative pressure while an external pressure applied on the dressing and/or 3D fabric of up to 1 kg/cm$^2$, preferably up to 2 kg/cm$^2$, and even more preferably up to 4 kg/cm$^2$. Certain embodiments, as described below, have been tested as being capable of transmitting therapeutic levels of negative pressure while an external pressure applied on the dressing and/or 3D fabric is above 6 kg/cm$^2$.

In the testing, a 400 ml wound cavity was used, and pressure was measured both at the wound and at the pump. Embodiments of a fluidic connector comprising 3D fabric were tested when laid flat with a weight placed thereupon. Testing indicated that when no pressure was applied to the fluidic connector, the pressure differential between the pressure at the pump and at the cavity was approximately 2 mmHg. Various different weights were applied, ranging between 2 and 12 kg/cm$^2$, in 2 kg increments, and the resulting pressure difference was approximately linear, with the pressure difference at 12 kg/cm$^2$ being calculated at 33 mmHg, while the pressure difference at 2 kg/cm$^2$ being only 16 mmHg. The relation between the pressure difference in mmHg was found to equal approximately 4.5 times the applied load in kg/cm$^2$. Testing also indicated that the relative pressure difference between the pressure at the pump and the pressure at the wound after five minutes was less than 10 mmHg when measured at the pump for loads under 4 kg/cm$^2$, and under 20 mmHg when measured at the wound for loads under 4 kg/cm$^2$.

Testing was also performed with a weight laid on an embodiment of a fluidic connector, while being bent at a 90° angle. Various different weights were applied, ranging between 2 and 12 kg/cm$^2$, in 2 kg increments, and the resulting pressure difference was approximately linear, with the pressure difference at 12 kg/cm$^2$ being calculated at 51 mmHg, while the pressure difference at 2 kg/cm$^2$ being 17 mmHg. The relation between the pressure difference in mmHg was found to equal approximately 8 times the applied load in kg/cm$^2$. Testing also indicated that the relative pressure difference between the pressure at the pump and the pressure at the wound after five minutes was approximately 20 mmHg when measured at the pump for loads under 4 kg/cm$^2$, and under 30 mmHg when measured at the wound for loads under 4 kg/cm$^2$.

Further testing was performed with a weight laid on an embodiment of a fluidic connector, while being bent at a 180° angle (i.e., folded over itself). Various different weights were applied, ranging between 2 and 12 kg/cm$^2$, in 2 kg increments, and the resulting pressure difference was approximately linear, with the pressure difference at 12 kg/cm$^2$ being calculated at 76 mmHg, while the pressure difference at 2 kg/cm$^2$ being 25 mmHg. The relation between the pressure difference in mmHg was found to equal approximately 10.7 times the applied load in kg/cm$^2$. Testing also indicated that the relative pressure difference between the pressure at the pump and the pressure at the wound after five minutes was approximately 20 mmHg when measured at the pump for loads under 4 kg/cm$^2$, and under 30 mmHg when measured at the wound for loads under 4 kg/cm$^2$.

Testing was also performed on different widths and thicknesses of 3D fabric that may be used in embodiments of fluidic connectors described herein. In a particular example, the maximum negative pressure that could be applied using 3D fabric measuring 1, 1.25, 1.5, 1.75, and 2 cm in width was found to be between 85 and 92 mmHg, respectively. Upon application of an applied load of 1 kg/cm$^2$, however, the maximum negative pressure applied for a 1 cm-width embodiment dropped to 75 mmHg, while the 1.25 and 1.5 cm-width embodiments were essentially unchanged, exhibiting pressures between 85 and 90 mmHg. Application of a 1 kg/cm$^2$ weight made the 1 cm-width embodiment maximum negative pressure drop to about 73 mmHg, while the 1.25 cm-width embodiment dropped to about 84 mmHg. The 1.5 cm-width embodiment showed a minimal maximum negative pressure change down to approximately 86 mmHg. As tested, the greatest increases in flow rate (as evidenced by the maximal negative pressures applied) were greatest when increasing the width of the 3D fabric from 1 cm to 1.25 cm, and stabilized above 1.5 cm. Similarly, increasing the width of the 3D fabric (i.e., above 1 cm) was found to slightly reduce the amount of time required to pump a wound cavity down to a target negative pressure.

Further testing with single and double layers of Baltex 3540 3D fabric, either single or double thickness, indicated that while the maximum negative pressure applied using a single thickness fabric dropped from about 88 mmHg with no applied weight to about 73 mmHg with a 2 kg/cm$^2$ weight. However, a double thickness fabric showed minimal change in the maximum amount of negative pressure applied, dropping from 90 mmHg with no weight applied to about 87 mmHg with an applied load of 2 kg/cm$^2$.

Depending on the particular application, using wider and/or thicker 3D fabric may permit improved air flow, together with greater pressure and kink resistance in some context; this may be useful especially if higher absolute negative pressure need to be applied to the wound. However, the greater kink and pressure resistance may need to be balanced with other concerns such as perceived bulk and size of the fluidic connector, aesthetics, and comfort, which may require use of a thinner 3D fabric.

In some embodiments, the proximal end B2411 of the fluidic connector B2410 is configured to be connected to a tube or other conduit that is in fluid communication with a source of negative pressure via the fluid connector body, although some embodiments may provide for the fluidic connector B2410 to be directly connectable to a source of negative pressure without needing a conventional tube. The distal end B2412 of the fluidic connector B2410 may be enlarged, and is configured to be attached and/or adhered to a dressing, for example via an aperture in the backing layer of the dressing and/or in the fluidic connector B2410, so that the fluid connector body is in fluid communication therewith.

In one configuration and as illustrated in FIG. 241A, the distal end B2412 of the fluidic connector B2410 may be convex on one side and flat on the opposite side. As illustrated in FIGS. 234-236 below, the flat side may be aligned with the edge of the absorbent layer with the convex side extending over the aperture in the backing layer. The fluidic connector B2410 may be provided preattached to the dressing portion, or may be provided in an unattached format so as to be connectable to the dressing portion by the patient or caregiver. The enlarged distal end B2412 may aid in providing a larger area capable of transmitting negative pressure to the dressing, although the distal end may be provided without any enlargement. Although preferred embodiments of the fluidic connector B2410 are used in dressings that contain substantially all wound exudate within the absorbent material, such that the fluidic connector transmits essentially only air, some embodiments of the fluidic connector may be configured so as to transfer exudate in addition to air. In embodiments of the fluidic connector that are configured to transfer essentially only air (while wound exudate remains substantially within the absorbent material), the distal end of the fluidic connector is preferably provided with a filter configured to block fluid transport beyond itself, such as a hydrophobic filter. An example of such a configuration is described in U.S. Provisional Application Ser. No. 61/650,904, filed May 23, 2012, titled "APPARATUSES AND METHODS FOR NEGATIVE PRESSURE WOUND THERAPY," and which is hereby incorporated into this present application in its entirety.

In embodiments of the fluidic connector that are configured to transfer exudate in addition to air, the fluidic connector may be provided with a secondary air leak channel configured to provide a flow of ambient air to the wound site. Preferably, the secondary air leak channel is provided with a filter to prevent contamination of the wound.

Turning now to FIG. 241B, this figure shows an embodiment similar to FIG. 241A, but where the fluidic connector B2420 may appear colored, for example as a result of an obscuring layer similar to that previously described. In some embodiments, obscuring coloration may be provided by dyeing the material used in the fluidic connector B2420, for example the 3D fabric that may be used therein. In some embodiments, the obscuring layer may be placed above the 3D fabric, either above or below the fluid-impermeable material. In some embodiments, the encapsulating fluid-impermeable material may be colored or tinted. Coloring the fluidic connector B2420 (e.g., via the obscuring layer) may enhance the aesthetic appeal of the device, help in disguising or making the device less obtrusive (in particular when the fluidic connector is visible to others), and, when the fluidic connector is used to transfer exudates away from the wound, may hide the presence of the exudates therein.

In some embodiments, the fluidic connector body may be colored as a result of an auxiliary compound such as activated charcoal. Further, some embodiments may provide for text or images to be printed thereon, for example for instructional or advertising purposes. Such improvements may enhance patient comfort and minimize embarrassment, thereby increasing patient compliance and satisfaction with the device. The obscuring layer in the fluidic connector can have all features described with reference to the obscuring layer of the wound dressing as herein described.

FIG. 235 illustrates an embodiment of a wound dressing B720 that comprises a hexagonal backing layer and a three-lobed configuration for the absorbent material and the obscuring layer. This wound dressing B720, as with several other embodiments described herein, may be advantageously applied to wounds or areas surrounding wounds that are located in non-planar areas. The embodiment illustrated here may be particularly advantageous when applied to protruding body portions, for example elbows and heels.

FIG. 236 illustrates a wound dressing B730 with a three-lobed configuration similar in some respects to the embodiment illustrated in FIG. 235. Here, however, the dressing is smaller and comprises more rounded projections. FIGS. 234-236 illustrate a fluidic connector B721, B731 similar to those described in FIGS. 241A and 241B attached to the device, with the flat end aligned with the edge of the absorbent material and the convex end extending over an aperture in the backing layer. This fluidic connector may enhance comfort and prevent pressure ulcers or other complications that may result from extended pressure of a conventional tube onto the wound or skin surrounding the wound (as described above). Of course, different connectors may be used, such as the domed port illustrated in FIG. 219.

FIGS. 237-238 also illustrate additional embodiments of wound dressings B740, B750 with three-lobed configurations for the absorbent material and a hexagonal backing layer. The wound dressing B750 illustrated in FIG. 238 is larger where the lobes of the absorbent material comprises flared ends, while the wound dressing B740 illustrated in FIG. 237 is smaller and the absorbent material does not have flared ends. All suitable fluidic connectors or conduits may be used, and the domed port connector of FIG. 238 may be used in place of the fluidic connector of FIG. 237, and vice versa. As with the preceding embodiments, the absorbent layers may be colored or obscured, and one or more slits may be formed onto the absorbent layers to enhance conformability to non-planar surfaces. It will be appreciated that in the embodiments of FIGS. 235-238, the number of lobes may be varied, and the backing layer can have other shapes, and is not limited to being hexagonal.

Additionally, FIGS. 239A-C and 240 illustrate embodiments of a wound dressing B760, B770, B780, B790 that comprises a four-lobed configuration. Although these embodiments are illustrated without a port or fluidic connector attached thereto, it will of course be understood that such ports and fluidic connectors are envisioned and may be attached in a similar fashion as described previously herein. FIGS. 239A-C comprise embodiments of a four-lobed wound dressing comprising an obscuring layer and viewing windows extending through the obscuring layer. The viewing windows can be used as discussed above for visualization of wound exudate in the absorbent layer. Examples of such viewing windows are illustrated in FIGS. 239A and 239B. The dressing B760 shown in FIG. 239A includes an obscuring layer B762 and crescent-shaped viewing windows B764 provided in the obscuring layer to extend through the obscuring layer allowing visibility of the dressing therebelow. The dressing B770 of FIG. 239B includes an obscuring layer B772 and a number of holes B774 therethrough acting as viewing windows for viewing the state of the dressing therebelow. FIG. 239C shows another dressing B780 including an obscuring layer B782 with viewing windows B784. With the dressings B760, B770, B780 the progress of exudate spread over the dressing and towards the edge of the dressing can be monitored.

FIG. 240 illustrates a perspective view of an embodiment of a wound dressing B790 according to an embodiment of the four-lobe configuration. FIG. 240 shows a possible four-lobe configuration of a dressing, useful for enhanced compatibility with body movement, where each layer is shaped to reduce the incident angle of the pad edge, and to provide somewhat independently moving sub-sections of the dressing. The dressing border, including the wound contact layer B791 and the backing layer B792 can also comprise slits, provided to further enhance the conformability on application by allowing the borders to overlap if needed. The wound dressing with a four-lobe configuration, as well as other configurations, are described in detail in International Application PCT/GB2012/000587, titled "WOUND DRESSING AND METHOD OF TREATMENT" and filed on Jul. 12, 2012. which is incorporated by reference herein.

Additionally, FIGS. 242A-F illustrate an embodiment of a wound dressing B2300 with an oval shaped absorbent layer B2308 having multiple lobes B2301. FIGS. 242A-F illustrate, respectively, perspective, top, bottom, left, right, and side views of an embodiment of the dressing B2300. In some embodiments, the absorbent layer B2308 can have six lobes. Preferably, two or more lobes B2301 (e.g., six lobes) are provided on the wound dressing B2300; the lobes B2301, and specifically, the gaps between the lobes B2301, aid the wound dressing B2300 in conforming to nonplanar wounds. For example, it may be advantageous to use the dressing B2300 to conform around joints such as elbows and knees.

Figure 242A:
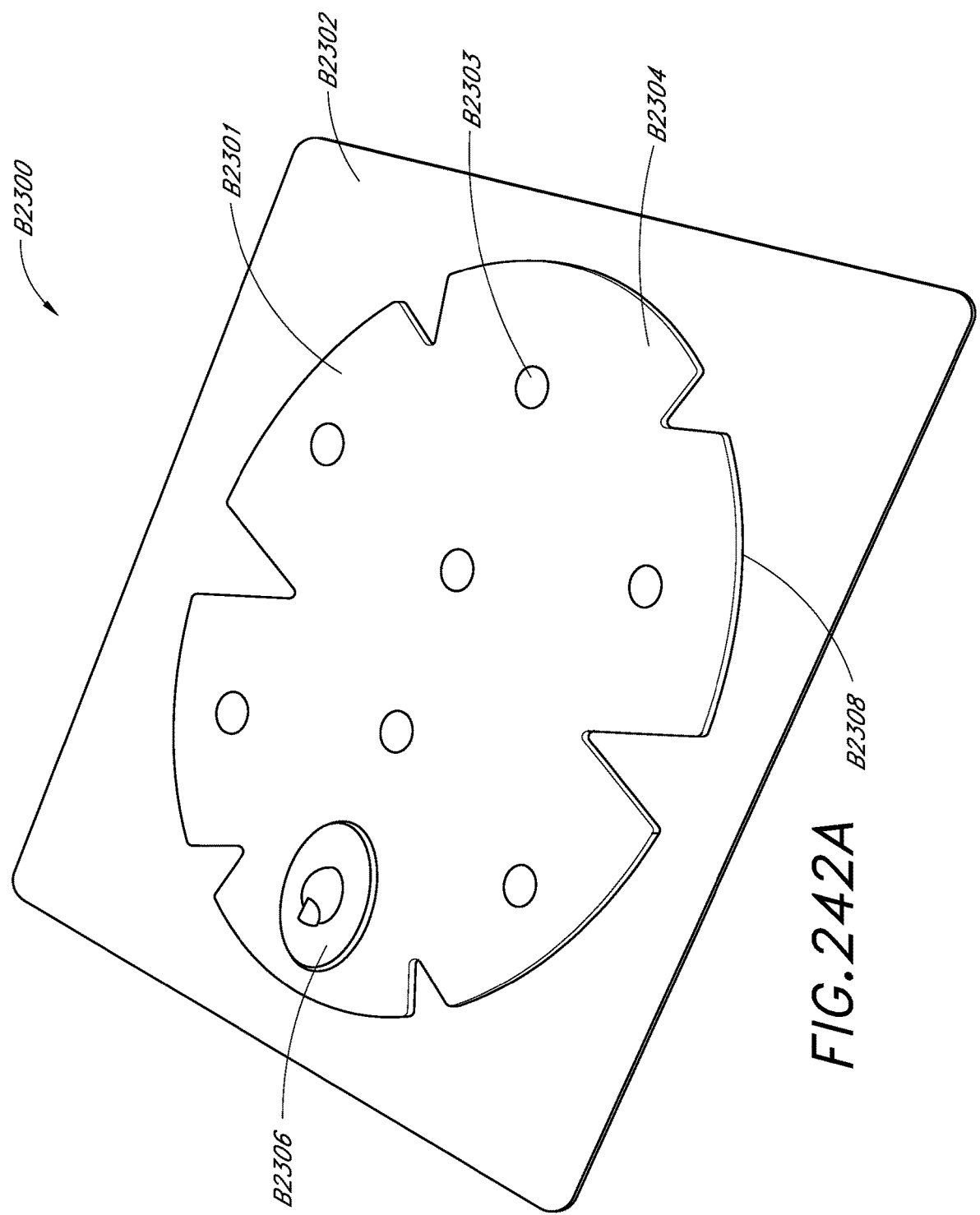
Figure 242B:
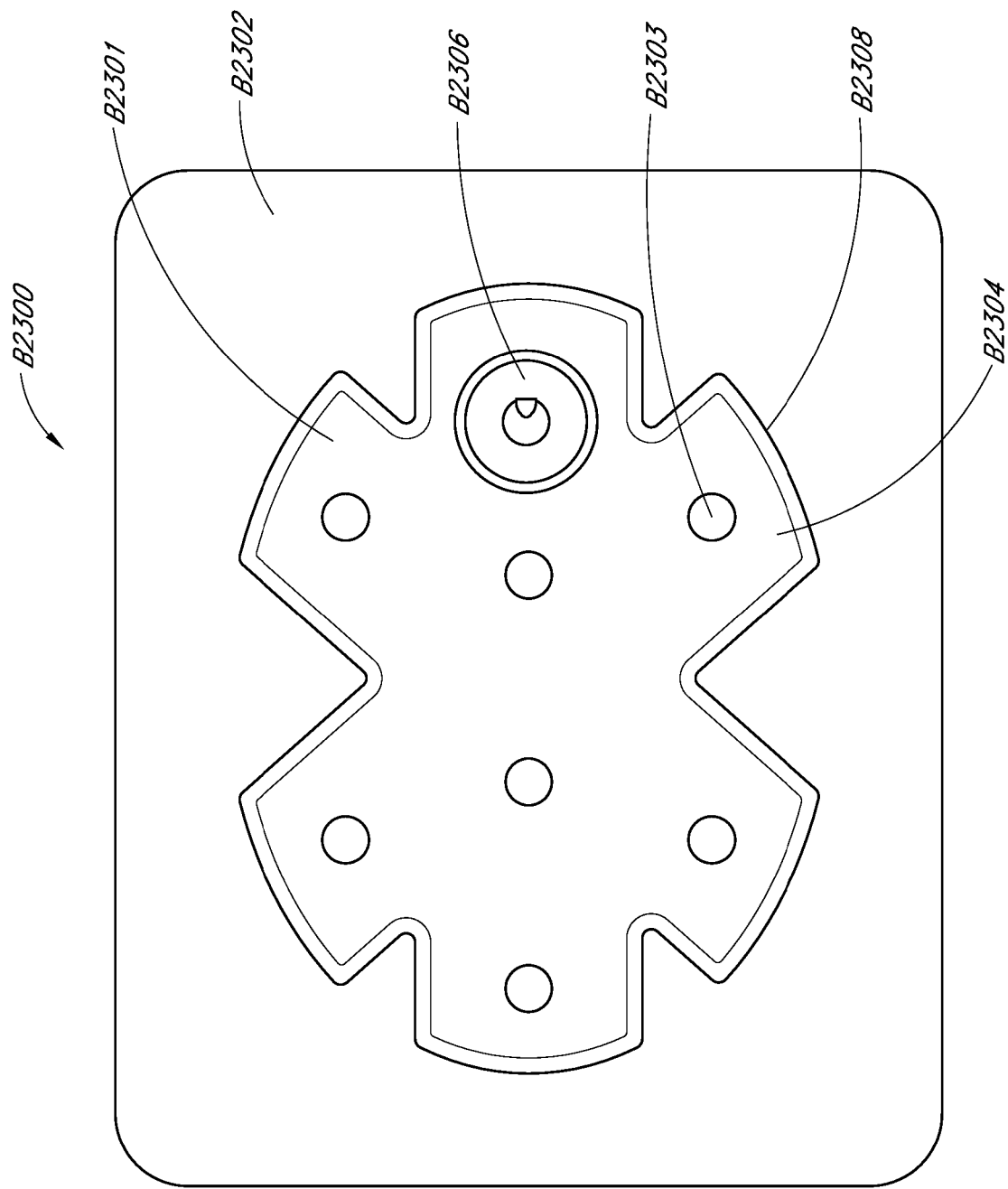
Figure 242C:
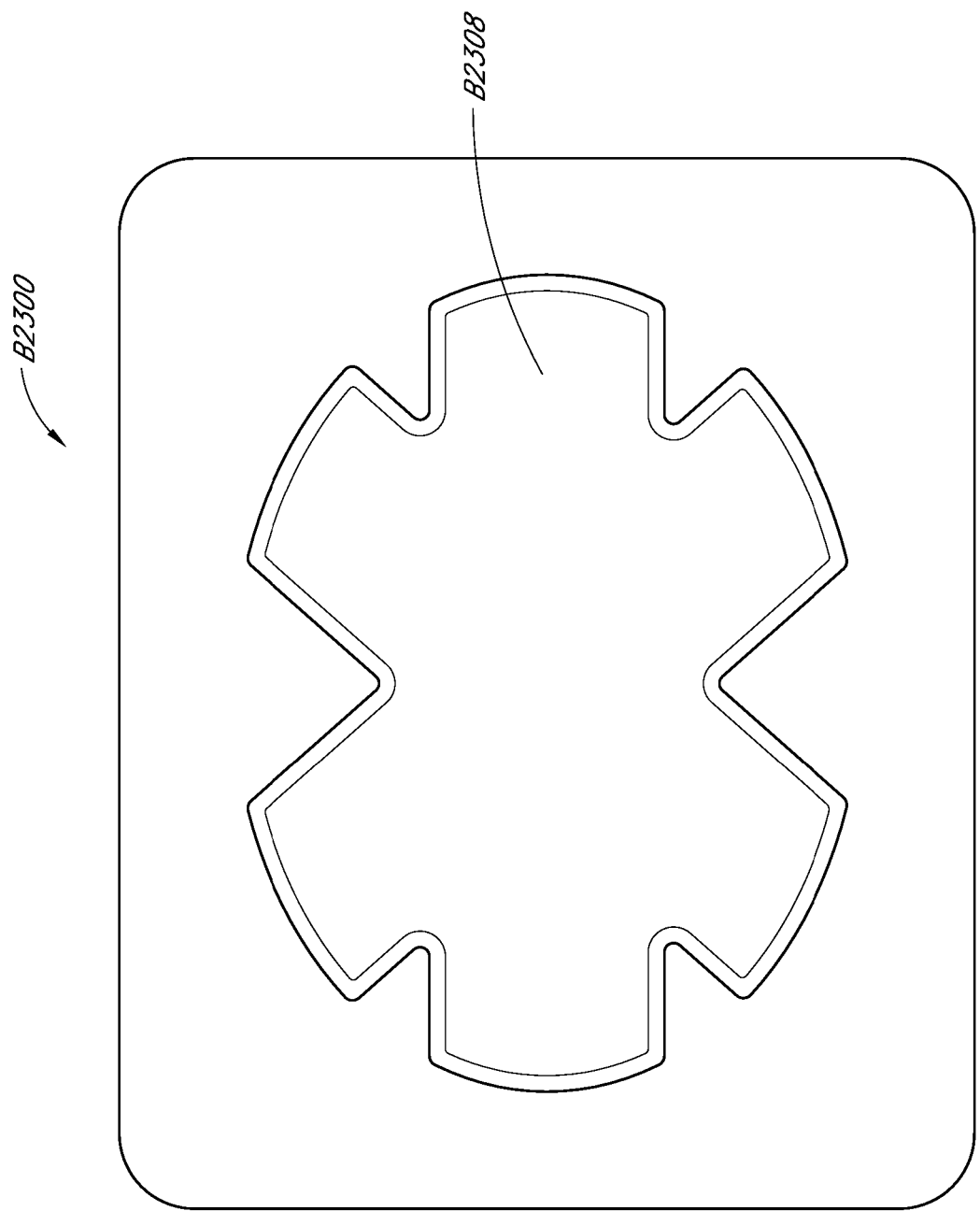
Figure 242F:

The dressing B2300 can have a rectangular or square shaped backing layer B2302, and in some embodiments, the overall dressing B2300 may measure 190 mm×230 mm, or 145.5 mm×190 mm. Preferably, a fluidic connector such as a port B2306 is attached to the dressing B2300, although it will of be recognized that the fluidic connector of FIGS. 241A-B may be used instead or in addition. Additionally, in some embodiments, the dressing B2300 can have an obscuring layer B2304 and one or more viewing windows B2303 similar to that described for other embodiments herein. FIG. 242A illustrates a perspective view of the dressing B2300, while FIG. 242B illustrates a top view, 242C a bottom view, and 242D-F represent views of the four sides of the dressing B2300.

Figure 243:
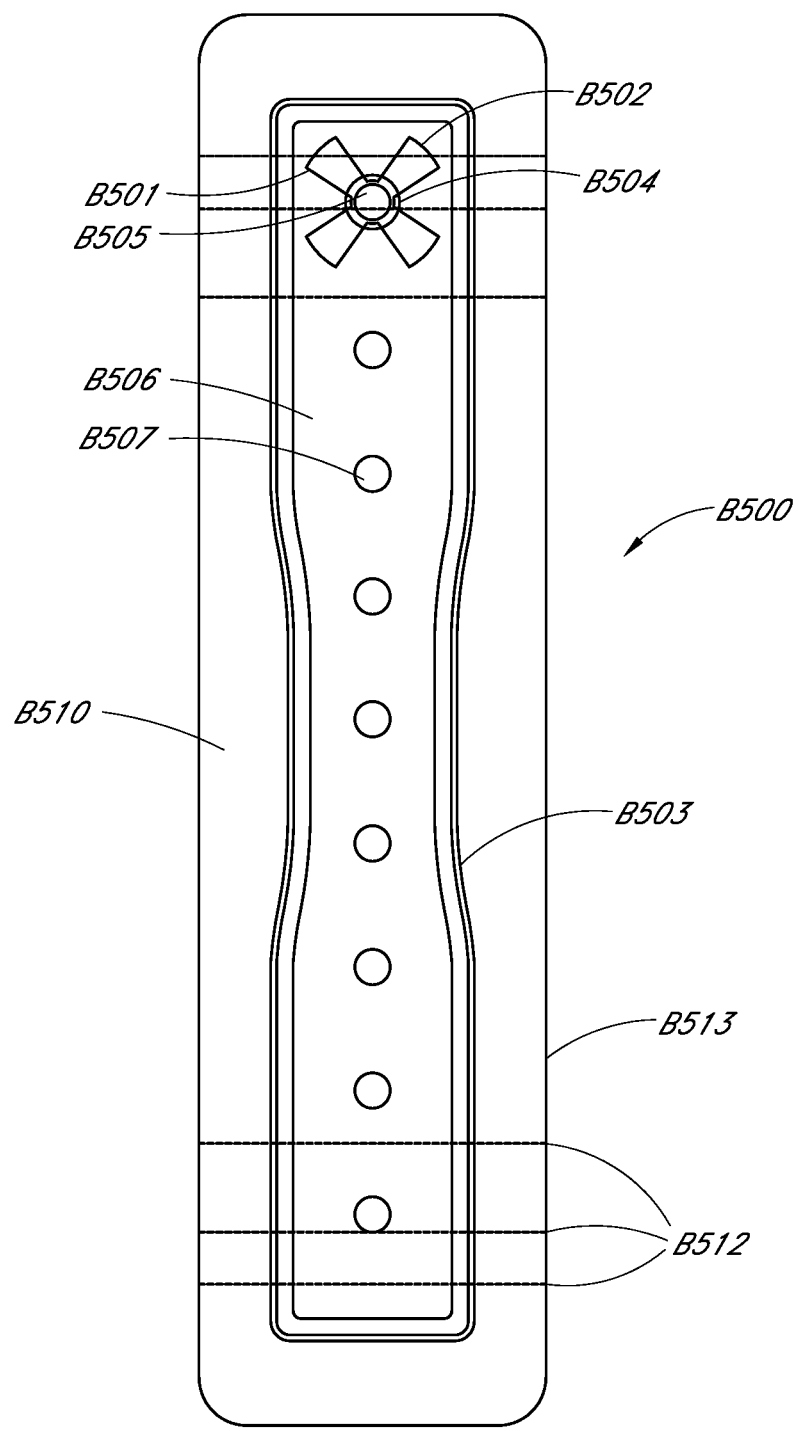

FIG. 243 illustrates an embodiment similar in shape and overall configuration to the embodiments illustrated above in FIGS. 225A-F. Here, however, the dressing B500 comprises an orifice viewing window B502 similar to that described in relation to FIGS. 231A-B and 232. The orifice viewing window B502 is preferably formed from a cross-shaped or Maltese-cross shaped aperture or cutout B501 in the obscuring layer B506. The backing layer B510 provided over the obscuring layer preferably has an orifice B504 located at the center of the orifice viewing window B502. Reference number B504 can also be considered to designate a port that may be provided in or over the backing layer B510 to provide a connection to a source of negative pressure, for example, a port provided over the orifice in the backing layer as described above. A smaller orifice B505 may be located in the absorbent layer B503 that is provided below the obscuring layer B506. The dressing B500 may comprise one or more viewing windows B507; here, eight viewing windows B507 are provided in a linear arrangement. The bottom side of the dressing B500 optionally comprises a layer of adhesive, over which a release layer B513 may be placed. Lines B512 illustrate possible locations where breaks in the release liner B513 may be provided.

In a preferred embodiment, the dressing B500 illustrated here has a longitudinal length of approximately 400 mm, and a transverse width of approximately 100 mm. The central axis of each arm of the cutout B501 of the orifice viewing window B502 is preferably offset from the longitudinal length and transverse width of the absorbent material, at an angle, for example, a 45° angle, as illustrated. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500. Although the location may be changed, it may be preferable to locate the port B504 near or along a side, edge, or corner of the dressing B500, which is then preferably elevated with respect to the remainder of the dressing. This configuration may extend the life of the dressing, as fluid would be slower in saturating the absorbent layer below or near the orifice or port B504.

Figure 244:
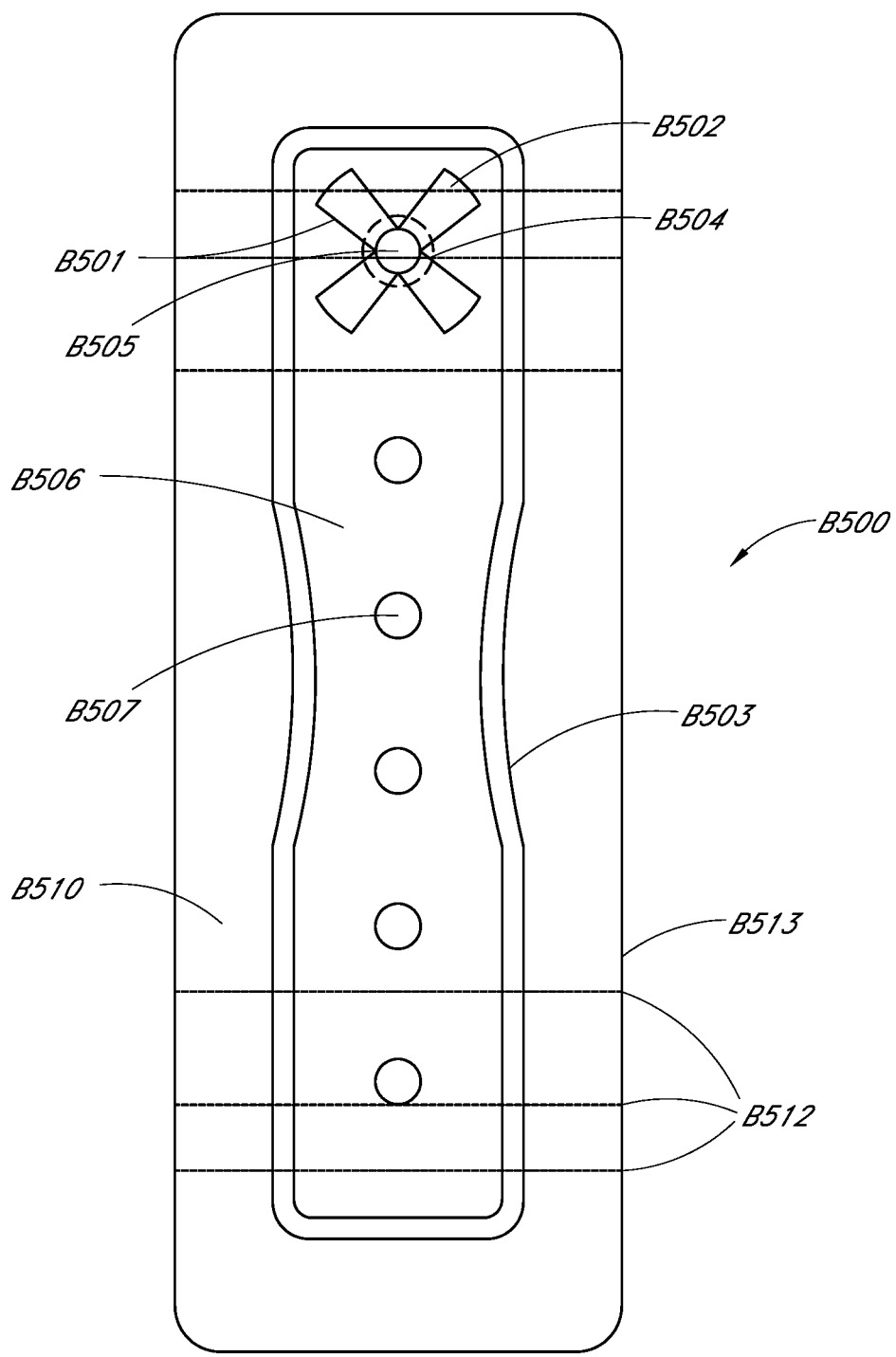

FIG. 244 illustrates an embodiment similar in shape and overall configuration to the embodiments illustrated above in FIGS. 226A-F. Here, however, the dressing B500 comprises an orifice viewing window B502 and cutout B501, with for example five linearly arranged viewing windows B507, among other parts, that are similar to that described above in relation to FIG. 243. In a preferred embodiment, the dressing B500 illustrated here has a longitudinal length of approximately 300 mm, and a transverse width of approximately 100 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500.

Figure 245:
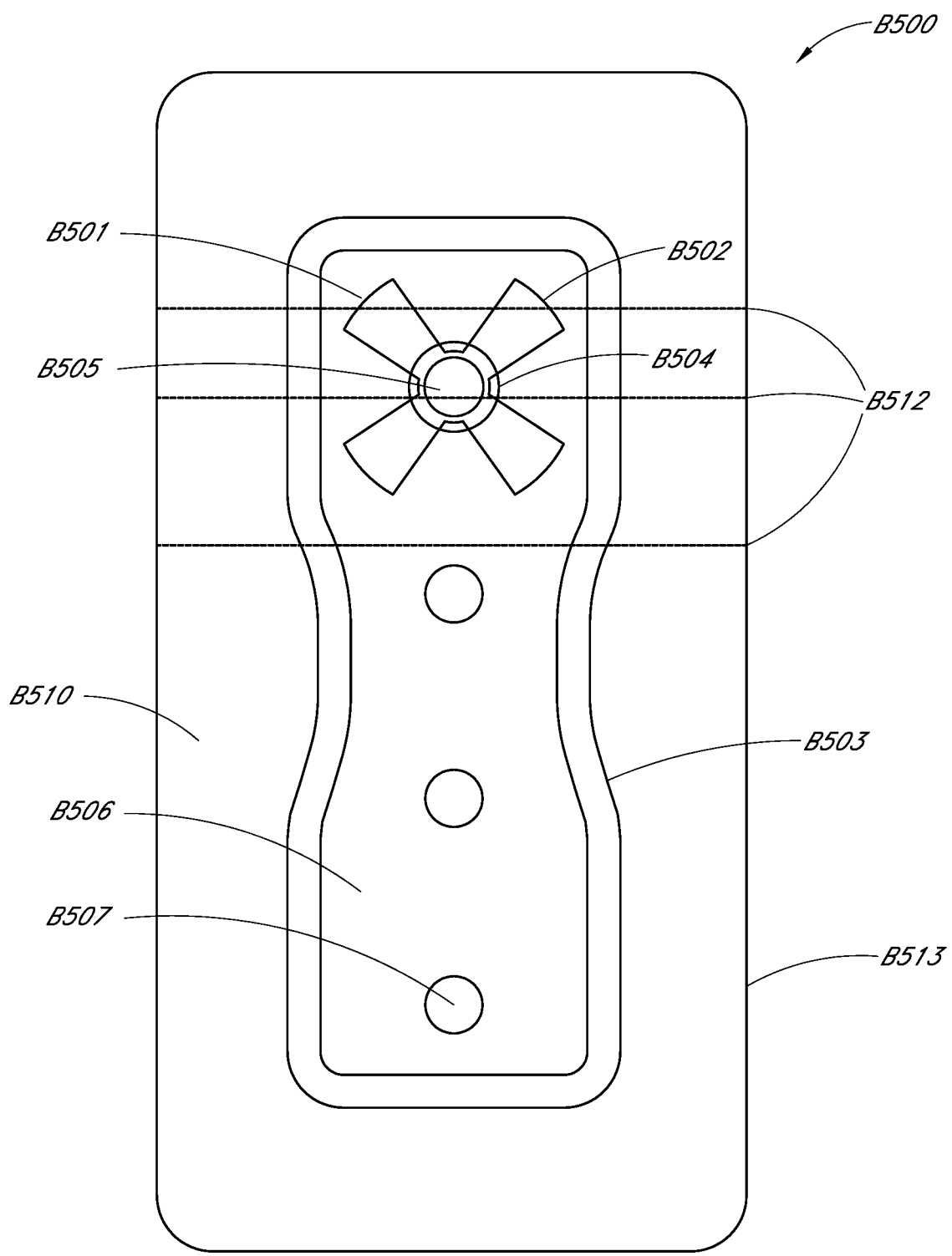

FIG. 245 illustrates an embodiment similar in shape and overall configuration to the embodiments illustrated above in FIGS. 227A-F. Here, however, the dressing B500 comprises an orifice viewing window B502 and cutout B501, with for example three linearly arranged viewing windows B507, among other parts, that are similar to that described above in relation to FIG. 243. In a preferred embodiment, the dressing B500 illustrated here has a longitudinal length of approximately 200 mm, and a transverse width of approximately 100 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500.

Figure 246:
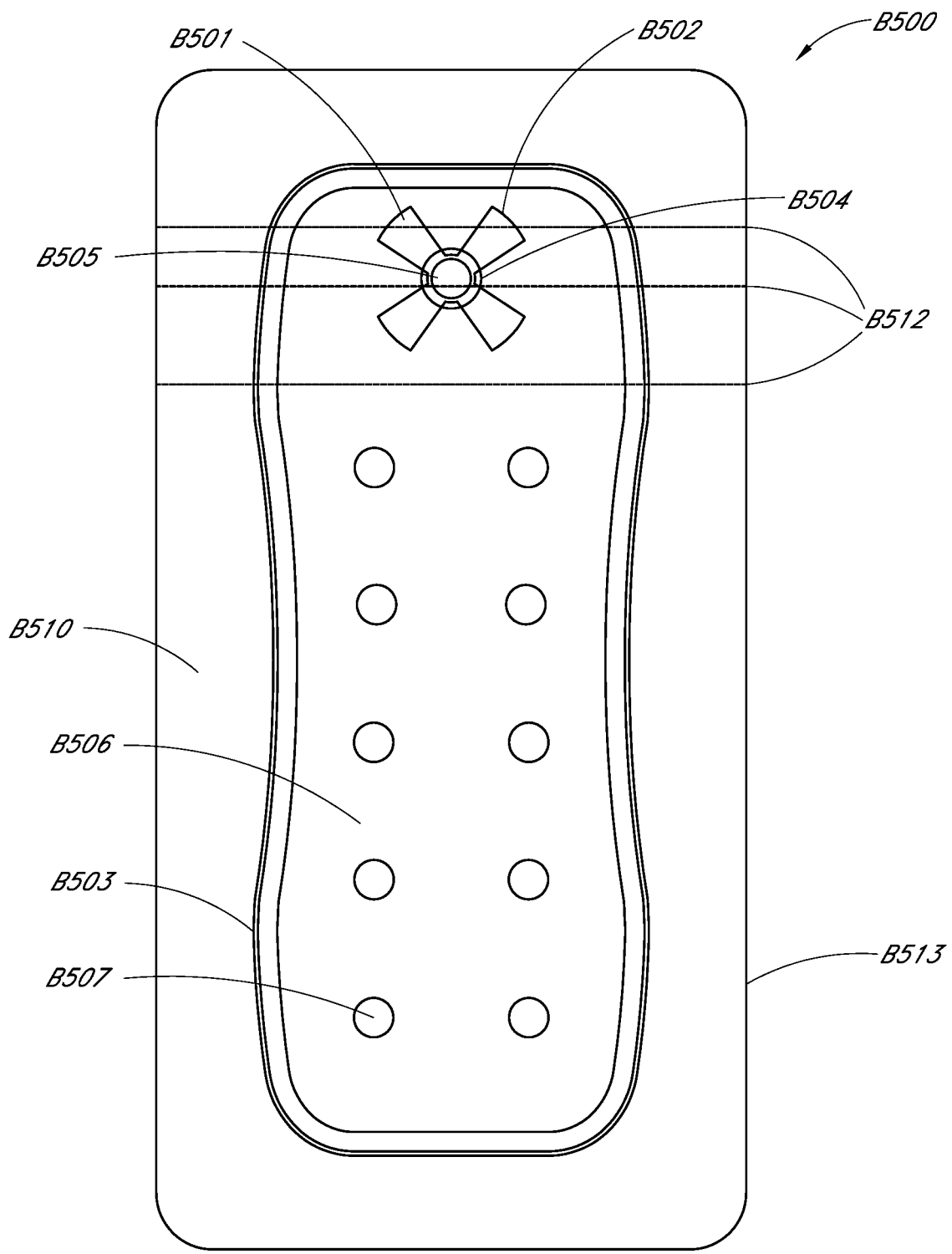

FIG. 246 illustrates an embodiment similar in shape and overall configuration to the embodiments illustrated above in FIGS. 223A-F. Here, however, the dressing B500 comprises an orifice viewing window B502 and cutout B501, with for example two rows of five linearly arranged viewing windows B507, among other parts, that are similar to that described above in relation to FIG. 243. In a preferred embodiment, the dressing B500 illustrated here has a longitudinal length of approximately 300 mm, and a transverse width of approximately 150 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500.

Figure 247:
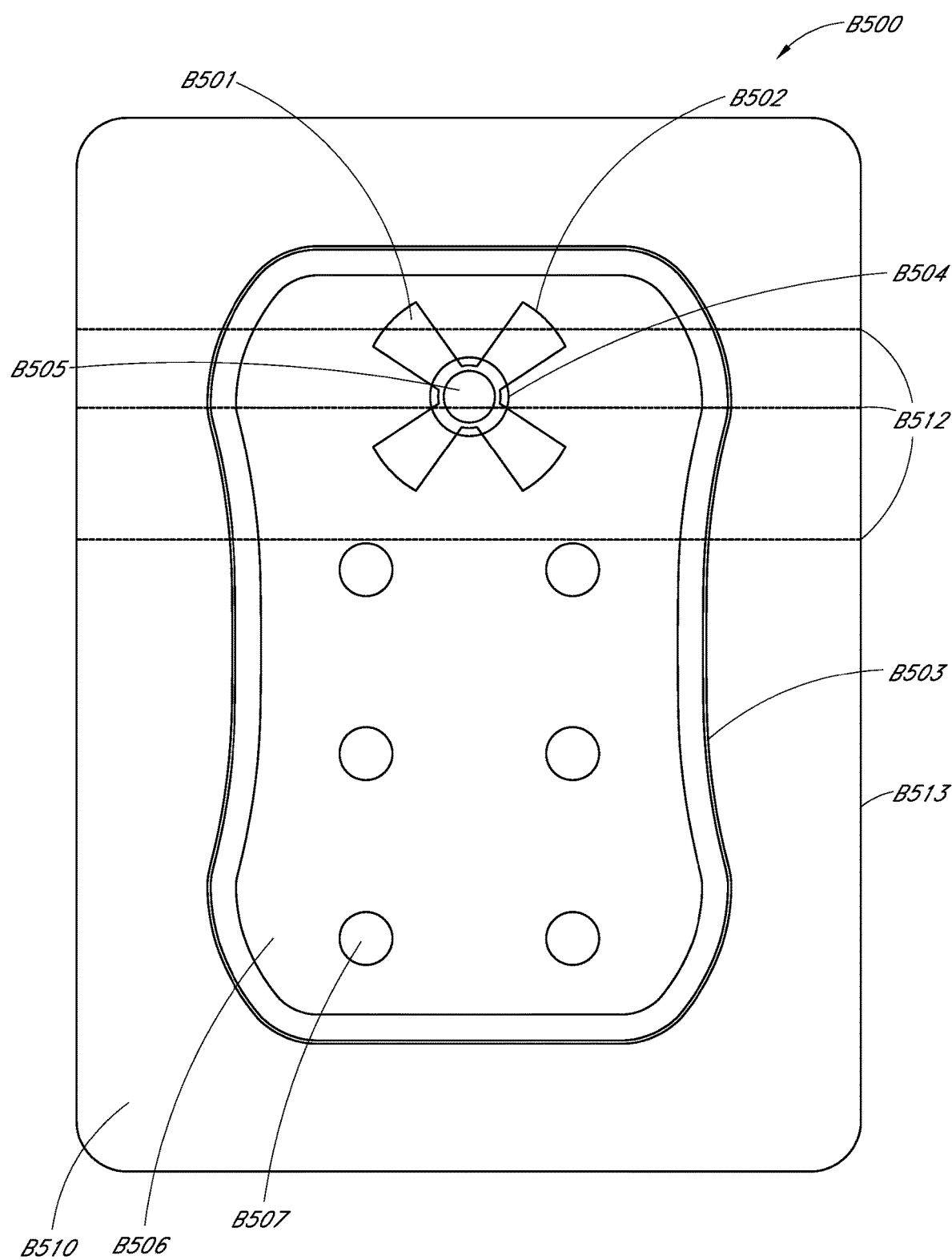

FIG. 247 illustrates an embodiment similar in shape and overall configuration to the embodiments illustrated above in FIGS. 224A-F. Here, however, the dressing B500 comprises an orifice viewing window B502 and cutout B501, with for example two rows of three linearly arranged viewing windows B507, among other parts, that are similar to that described above in relation to FIG. 243. In a preferred embodiment, the dressing B500 illustrated here has a longitudinal length of approximately 300 mm, and a transverse width of approximately 100 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on the transverse midline of the dressing B500, and situated approximately 52-55 mm from the top edge of the dressing B500.

Figure 248:
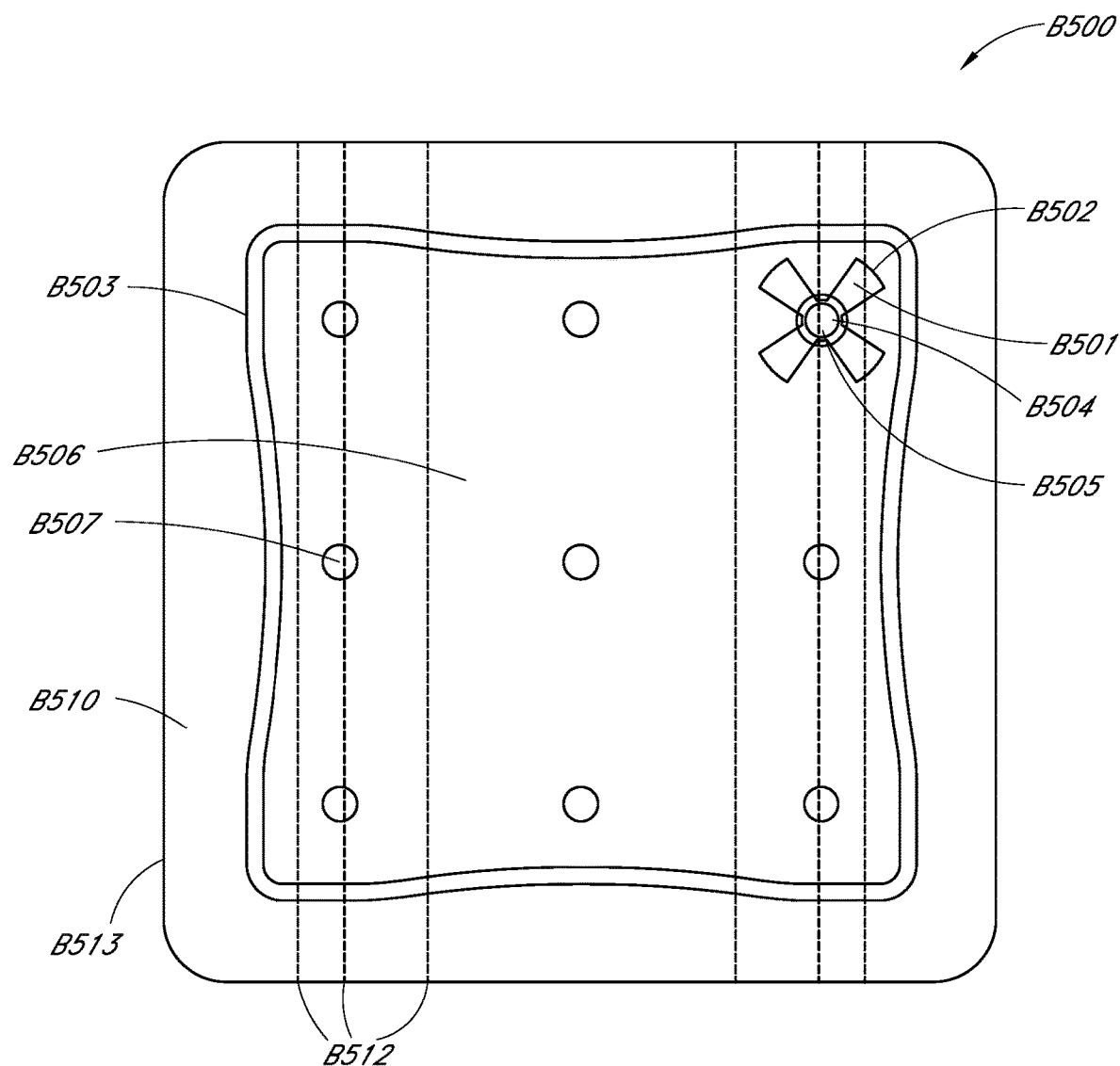

FIG. 248 illustrates an embodiment similar in shape and overall configuration to the embodiments illustrated above in FIGS. 228A-F. Here, however, the dressing B500 comprises an orifice viewing window B502 and cutout B501, with a 3×3 array of viewing windows absent a viewing window at a corner position of the wound dressing, among other parts, that are similar to that described above in relation to FIG. 243 but located in a corner of the dressing B500. In a preferred embodiment, the dressing B500 illustrated here is approximately square, with each side measuring approximately 250 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on a corner of the dressing B500, and situated approximately 52-55 mm from the top edge of the dressing B500.

Figure 249:
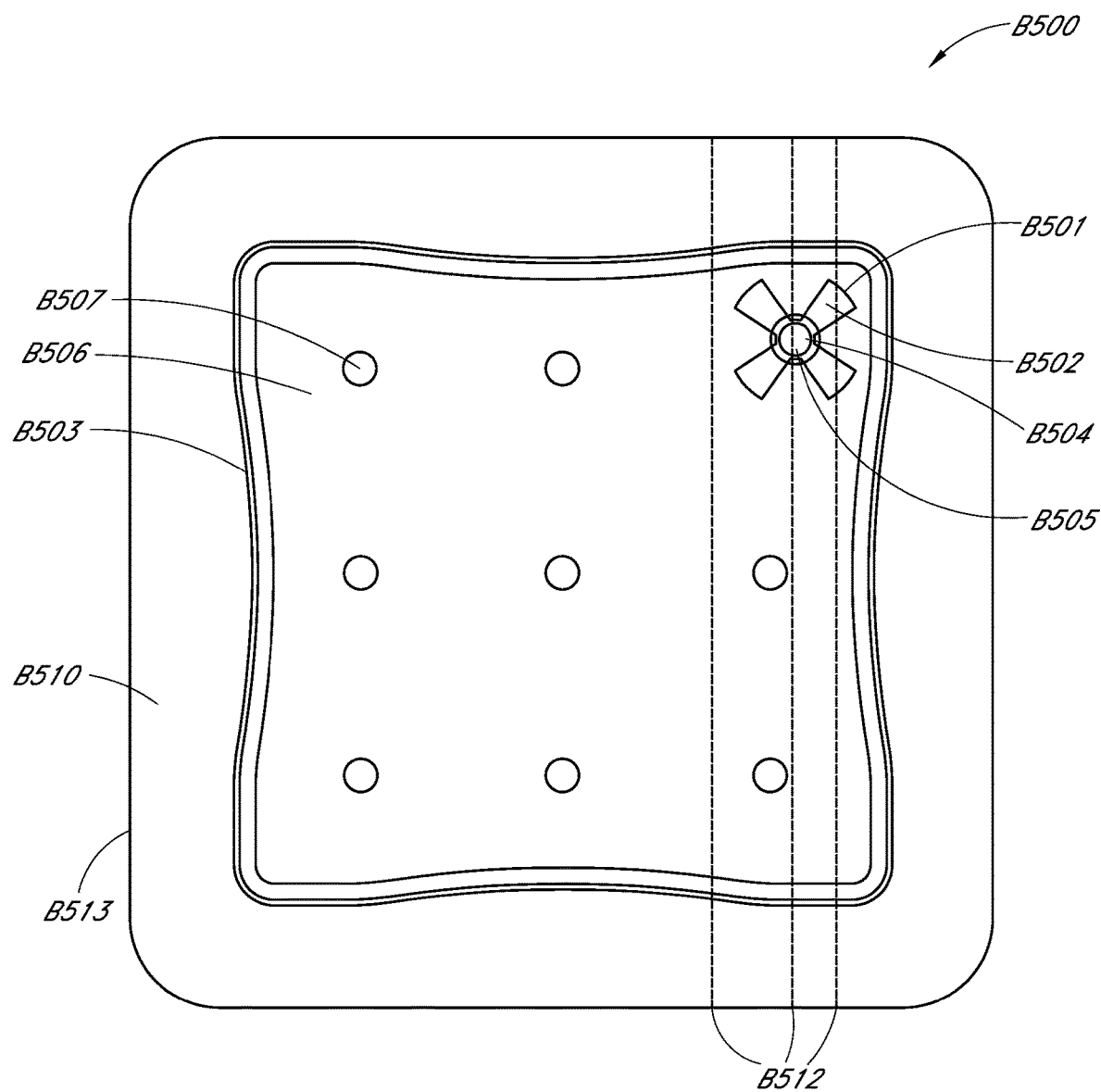

FIG. 249 illustrates an embodiment similar in shape and overall configuration to the embodiments illustrated above in FIGS. 229A-F. Here, however, the dressing B500 comprises an orifice viewing window B502 and cutout B501, with a 3×3 array of viewing windows absent a viewing window at a corner position of the wound dressing, among other parts, that are similar to that described above in relation to FIG. 243 but located in a corner of the dressing B500. In a preferred embodiment, the dressing B500 illustrated here is approximately square, with each side measuring approximately 200 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, 40±4 mm, and 25±4 mm from each of the top and bottom edges of the dressing B500. As illustrated, the orifice or port B504 (and cutout B501) are preferably centered on a corner of the dressing B500, and situated approximately 52-55 mm from the top edge of the dressing B500.

Figure 250:
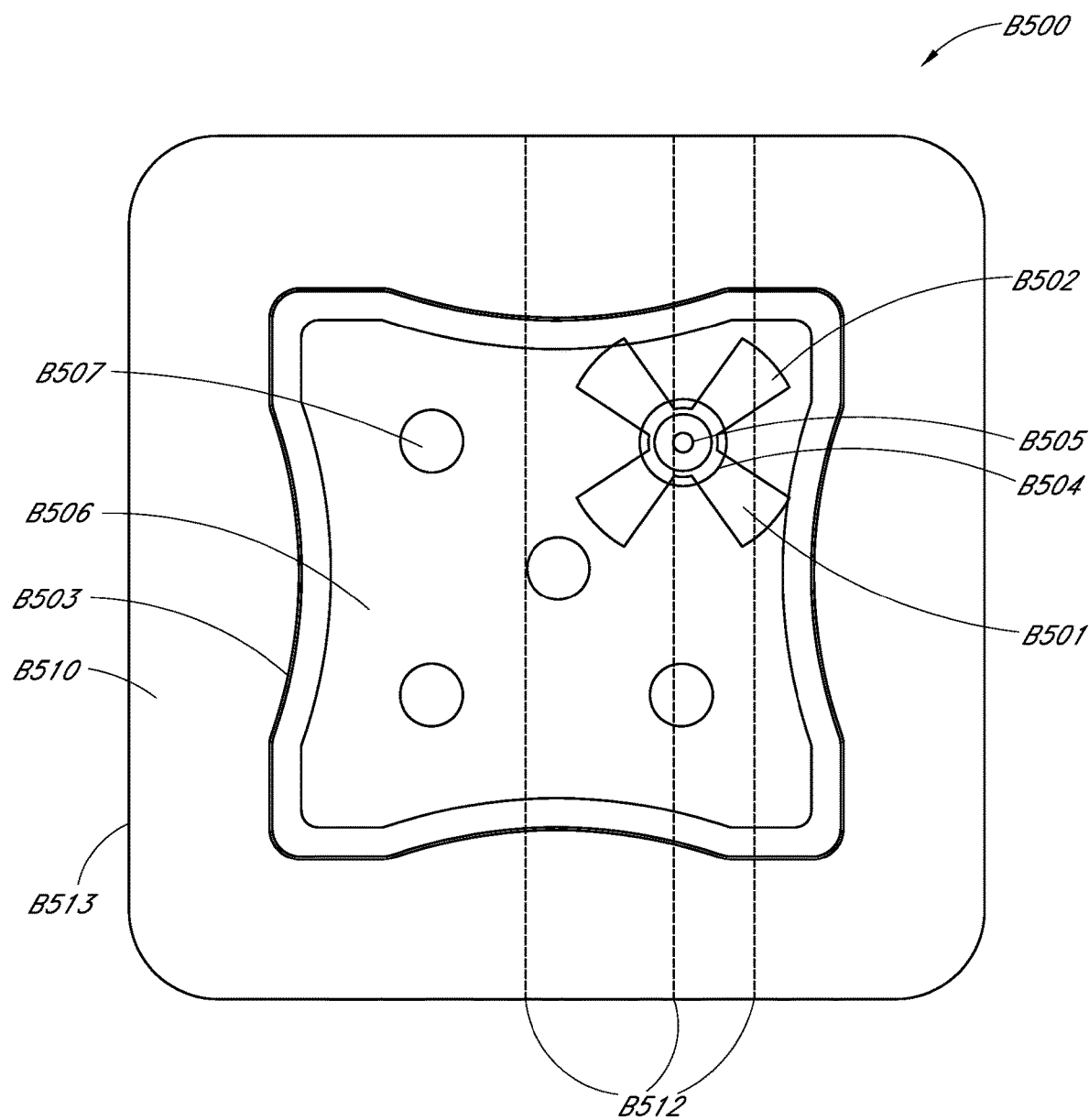

FIG. 250 illustrates an embodiment similar in shape and overall configuration to the embodiments illustrated above in FIGS. 230A-F. Here, however, the dressing B500 comprises an orifice viewing window B502 and cutout B501, with a quincunx array of viewing windows absent a viewing window at a corner position of the wound dressing, among other parts, that are similar to that described above in relation to FIG. 243 but located in a corner of the dressing B500. In a preferred embodiment, the dressing B500 illustrated here is approximately square, with each side measuring approximately 150 mm. The spacing between each arm of the cutout B501 may be, as illustrated here, 72°, although it will of course be recognized that other angles and configurations are possible. Lines B512, indicating possible locations where breaks in the release liner B513 may be provided, can be located, for example, at 80 mm, B40±4 mm, and 25±4 mm from each of the top and bottom edges of the dressing B500. As illustrated, the port B504 (and cutout B501) are preferably centered on a corner of the dressing B500, and situated approximately 52-55 mm from the top edge of the dressing B500.

FIG. 251A-B illustrates an embodiment somewhat similar in shape and overall configuration to the embodiments illustrated above in FIGS. 242A-F. Here, however, the oval-shaped dressing B500 comprises an orifice viewing window B502 and cutout B501, among other parts, that are similar to that described above in relation to FIG. 243. Viewing windows are not shown, but may be provided as in one embodiment as described above. In a preferred embodiment, the dressing B500 illustrated in FIG. 251A has a longitudinal length of approximately 250 mm, and a transverse width of approximately 200 mm. The longitudinal length of the absorbent layer B503 (and corresponding obscuring layer, if so provided) measures approximately 200 mm, with a transverse width of approximately 150 mm. The embodiment of the dressing B500 illustrated in FIG. 33B has a longitudinal length of approximately 200 mm, and a transverse width of approximately 150 mm. The longitudinal length of the absorbent layer B503 (and corresponding obscuring layer, if so provided) measures approximately 150 mm, with a transverse width of approximately 100 mm. Although no viewing windows B507 are illustrated, it will of course be understood that one or more such windows B507 may be provided on the dressing B500. The spacing between each arm of the cutout B501 may be 72°, although it will of course be recognized that other angles and configurations are possible. As illustrated, the orifice or port B504 (and cutout B501) are preferably centered on the transverse midline of the dressing B500, and situated approximately 52-55 mm from the top edge of the dressing B500.

FIG. 252A illustrates an exploded view of a dressing B3400 for use in negative pressure wound therapy. Although this figure illustrates a dressing having one particular shape, the construction of the layers can be applied to any of the embodiments identified above, including FIGS. 222A-232, 234-240, and 242A-251B. The dressing B3400 comprises a release layer B3480, wound contact layer B3460, a transmission layer B3450, an acquisition distribution layer B3440, an absorbent layer B3430, an obscuring layer B3420, and a backing layer B3410. The dressing B3400 may be connected to a port, such as described below with respect to FIGS. 253 and 254. At least the wound contact layer B3460, transmission layer B3450, absorbent layer B3430, obscuring layer B3420, and backing layer B3410 may have properties as described with respect to particular embodiments above, such as the embodiments of FIGS. 221A-240, and 242A-251B, as well as or instead of the properties described below.

The dressing B3400 may comprise a wound contact layer B3460 for sealing the dressing B3400 to the healthy skin of a patient surrounding a wound area. Certain embodiments of the wound contact layer may comprise three layers: a polyurethane film layer, a lower adhesive layer and an upper adhesive layer. The upper adhesive layer may assist in maintaining the integrity of the dressing B3400, and the lower adhesive layer may be employed for sealing the dressing B3400 to the healthy skin of a patient around a wound site. As described above, in some embodiments with respect to FIGS. 221A-C, some embodiments of the polyurethane film layer may be perforated. Some embodiments of the polyurethane film layer and upper and lower adhesive layers may be perforated together after the adhesive layers have been applied to the polyurethane film. In some embodiments a pressure sensitive adhesive, which may be a silicone, hot melt, hydrocolloid or acrylic based adhesive or other such adhesives, may be formed on both sides or optionally on a selected one side of the wound contact layer. In certain embodiments, the upper adhesive layer may comprise an acrylic pressure sensitive adhesive, and the lower adhesive layer may comprise a silicone pressure sensitive adhesive. In other embodiments the wound contact layer B3460 may not be provided with adhesive. In some embodiments, the wound contact layer B3460 may be transparent or translucent. The film layer of the wound contact layer B3460 may define a perimeter with a rectangular or a square shape. A release layer B3480 may be removably attached to the underside of the wound contact layer B3460, for example covering the lower adhesive layer, and may be peeled off using flaps B3481. Some embodiments of the release layer B3480 may have a plurality of flaps extending along the length of the layer B3480.

Some embodiments of the dressing B3400 may comprise an optional spacer or transmission layer B3450. The transmission layer B3450 may comprise a porous material or 3D fabric configured to allow for the passage of fluids therethrough away from the wound site and into the upper layers of the dressing B3400. In particular, the transmission layer B3450 can ensure that an open air channel can be maintained to communicate negative pressure over the wound area even when the absorbent layer B3430 has absorbed substantial amounts of exudates. The transmission layer B3450 should remain open under the typical pressures that will be applied during negative pressure wound therapy as described above, so that the whole wound site sees an equalized negative pressure.

Some embodiments of the transmission layer B3450 may be formed of a material having a three dimensional structure. For example, a knitted or woven spacer fabric (for example Baltex 7970 weft knitted polyester) or a non-woven fabric can be used. In some embodiments, the transmission layer B3450 can have a 3D polyester spacer fabric layer. This layer can have a top layer which is a 84/144 textured polyester, and a bottom layer which can be a 100 denier flat polyester and a third layer formed sandwiched between these two layers which is a region defined by a knitted polyester viscose, cellulose or the like monofilament fiber. In use, this differential between filament counts in the spaced apart layers tends to draw liquid away from the wound bed and into a central region of the dressing B3400 where the absorbent layer B3430 helps lock the liquid away or itself wicks the liquid onwards towards the cover layer B3410 where it can be transpired. Other materials can be utilized, and examples of such materials are described in U.S. Patent Pub. No. 2011/0282309, which are hereby incorporated by reference and made part of this disclosure. However, the transmission layer B3450 may be optional, and for example may be optional in embodiments of the dressing B3400 which comprise the acquisition distribution layer B3440, described below.

Some embodiments may comprise a wicking or acquisition distribution layer (ADL) B3440 to horizontally wick fluid such as wound exudate as it is absorbed upward through the layers of the dressing B3400. Lateral wicking of fluid may allow maximum distribution of the fluid through the absorbent layer B3430 and may enable the absorbent layer B3430 to reach its full holding capacity. This may advantageously increase moisture vapor permeation and efficient delivery of negative pressure to the wound site. Some embodiments of the ADL B3440 may comprise viscose, polyester, polypropylene, cellulose, or a combination of some or all of these, and the material may be needle-punched. Some embodiments of the ADL B3440 may comprise polyethylene in the range of 40-150 grams per square meter (gsm).

The dressing B3400 may further comprise an absorbent or superabsorbent layer B3430. The absorbent layer can be manufactured from ALLEVYN™ foam, Freudenberg 114-224-4 and/or Chem-Posite™11C-450, or any other suitable material. In some embodiments, the absorbent layer B3430 can be a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid.

For example, some embodiments of the absorbent layer B3430 may comprise a layered construction of an upper layer of non-woven cellulose fibers, superabsorbent particles (SAP), and a lower layer of cellulose fibers with 40-80% SAP. In some embodiments, the absorbent layer B3430 may be an air-laid material. Heat fusible fibers can optionally be used to assist in holding the structure of the pad together. Some embodiments may combine cellulose fibers and air-laid materials, and may further comprise up to 60% SAP. Some embodiments may comprise 60% SAP and 40% cellulose. Other embodiments of the absorbent layer may comprise between 60% and 90% (or between about 60% and about 90%) cellulose matrix and between 10% and 40% (or between about 10% and about 40%) superabsorbent particles. For example, the absorbent layer may have about 20% superabsorbent material and about 80% cellulose fibers. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc. The absorbent layer B3430 can have one or more through holes B3431 located so as to underlie the suction port.

Some embodiments of the present disclosure may employ a masking or obscuring layer B3420 to help reduce the unsightly appearance of a dressing B3400 during use due to the absorption of wound exudate. The obscuring layer B3420 may be a colored portion of the absorbent material, or may be a separate layer that covers the absorbent material. The obscuring layer B3420 may be one of a variety of colors such as blue, orange, yellow, green, or any color suitable for masking the presence of wound exudate in the dressing B3400. For example, a blue obscuring layer B3420 may be a shade of blue similar to the shade of blue commonly used for the material of medical gowns, scrubs, and drapes. Some embodiments of the obscuring layer B3420 may comprise polypropylene spunbond material. Further, some embodiments of the obscuring layer B3420 may comprise a hydrophobic additive or coating. Other embodiments may comprise a thin fibrous sheet of B60, 70, or 80 gsm.

The obscuring layer may comprise at least one viewing window B3422 configured to allow a visual determination of the saturation level of the absorbent layer. The at least one viewing window B3422 may comprise at least one aperture made through the obscuring layer. The at least one viewing window B3422 may comprise at least one uncolored region of the obscuring layer. Some embodiments of the obscuring layer may comprise a plurality of viewing windows or an array of viewing windows, as discussed above with respect to FIGS. 243-250.

The masking capabilities of the obscuring layer B3420 should preferably only be partial, to allow clinicians to access the information they require by observing the spread of exudate across the dressing surface. An obscuring layer B3420 may be partial due to material properties allowing wound exudate to slightly alter the appearance of the dressing or due to the presence of at least one viewing window B3422 in a completely obscuring material. The partial masking nature of the obscuring layer B3420 enables a skilled clinician to perceive a different colour caused by exudate, blood, by-products etc. in the dressing allowing for a visual assessment and monitoring of the extent of spread across the dressing. However, since the change in colour of the dressing from its clean state to a state with exudate contained is only a slight change, the patient is unlikely to notice any aesthetic difference. Reducing or eliminating a visual indicator of wound exudate from a patient is likely to have a positive effect on their health, reducing stress for example.

Tests performed upon various dressings with respect to the transmittance properties of the dressing indicate the ability of various samples to mask colour. The ability to mask colour may be calculated, for example, by measuring the reduction in absorption of light radiation at particular wavelengths. The tests utilized a UV-Vis spectrophotometer Jasco with integrating sphere, with a scanning range 340 to 800 nm, bandwidth 5 nm and B1000 nm/sec scanning speed. The data labelled black background represents the extreme of exudate colour (the most colour an exudate might have)—the highest level of radiation absorbed and the least amount of radiation reflected from the sample. The data for white background represents the upper limit for total masking—generally the lowest level of radiation absorbed and the highest level of reflection. Sample 1 was a tinted polymer film placed over a black background, which was judged not to sufficiently mask the black background (representing wound exudate) satisfactorily. Sample 2 was a sheet of 3-dimensional spacer fabric (Baltex 3D) placed over a black background, and was judged to provide adequate masking of the black background. Sample 3 was a sheet of non-woven material dyed green placed over a black background, and provided complete masking of the black background.

Wound exudate may have dark yellow, red and/or brown tones. Therefore, to appropriately mask these colours, an obscuring layer B3420 would preferably shield light wavelengths of below 600 nm.

Measuring the reduction in absorption of light radiation at particular wavelengths may be performed by calculating:

$$\% \text{ reduction} = (A_{background} - A_{sample\ placed\ on\ background}) / (A_{background}) \times 100$$

where A is the absorption of light radiation at the particular wavelength.

Using this formula, using light at a wavelength of 460 nm, the percentage of absorption reduction was calculated as shown in Table 3 below.

TABLE 3

| Sample | Absorption reduction at 460 nm | Appropriate masking observed |
|---|---|---|
| Sample 1 | 34% | No |
| Sample 2 | 77% | Yes - partial |
| Sample 3 | 69% | Yes - complete |

It has been found that materials that reduce light absorption by about 50% or more will provide enough partial or complete masking of wound exudate (as judged by the inventors). Of course a complete masking element would preferably require a means for a clinician to judge the spread of wound exudate in the dressing below the obscuring layer B3420, e.g. the masking element not completely covering the entire dressing. For example, as described above with respect to FIGS. 243-251, a plurality of viewing windows may be provided in the obscuring layer B3420 such that the spread of exudate in the dressing below may be adequately assessed. Alternatively a partial masking element may allow a clinician to judge the spread of exudate in the dressing below without additional means.

It will be understood that the wetting of a masking material (by exudate for example) will also affect the masking performance of the masking element, since hydrophilic materials will allow chromophore-carrying species to travel through them more easily. As such, the absorption reduction rate should also be tested on wet materials.

The above-mentioned Samples 1, 2 and 3 were also tested for their masking properties by measuring CIE L*a*b* values (a known 3-dimensional model for representing colour space). The analysis employed Jasco software using the range 380 to 780 nm, stard observed 2 (deg), lightsource D65, colour matching JIS Z8701-1999.

Table 4 below shows the L*a*b* values found when Samples 1, 2 and 3 were respectively placed over a black background. The results for the black background alone and a white background are also shown.

TABLE 4

| Sample | CIE L*a*b* values recorded | | | Appropriate masking observed? |
|---|---|---|---|---|
| | L* | a* | b* | |
| Black background | 0 | 0 | 0 | n/a |
| Sample 1 (on black) | 36.59 | 3.76 | −1.80 | No |
| Sample 2 (on black) | 71.76 | −0.20 | −1.08 | Yes - partial |
| Sample 3 (on black) | 70.64 | −0.25 | −1.23 | Yes - complete |
| White background | 100 | 0 | 0 | n/a |

Generally, samples which lead to an increase in L* value will provide a lighter colour tone than the reference surface, which is the main contributor to masking a dark colour. From the values above, apt partial masking materials will yield an L* value above 50, or more aptly above 70.

However, completely opaque masking layers, such as for example a tinted polymeric film, may cover the area to be masked with a darker tone altogether, in which case the measure of L* is not relevant. Once again these values should also be considered on wet material, for the reasons stated above.

In addition to transmittance properties, the color of the obscuring layer B3420 may affect the masking ability of the layer. In liquid permeable embodiments of the obscuring layer, various colors are suitable for masking the usual colors of wound exudate, while other colors may not provide optimal masking of the exudate. For example, with reference to the CIE chromacity diagram illustrated in FIG. 256, some embodiments of the obscuring layer, in a dry state, may be configured to yield a CIE y value of 0.4 or less and a CIE x value of 0.5 or less. Some embodiments of the obscuring layer, in a dry state, may have a color of Bg, gB, B, pB, bP, P, rP, pPk, RP, O, rO, or yO on the CIE x, y chromacity diagram. It will be appreciated that liquid impermeable embodiments of the obscuring layer may be configured with any color.

The obscuring layer B3420 can have one or more through holes located so as to underlie the suction port. Some embodiments may have a maltese cross B3421 or other shaped cutout underlying the suction port, wherein the diameter of the maltese cross B3421 is greater than the diameter of the port. This may allow a clinician to easily assess the amount of wound exudate absorbed into the layers beneath the port.

The dressing B3400 may also comprise a backing layer, or cover layer B3410 extending across the width of the wound dressing. The cover layer B3410 may be gas impermeable but moisture vapor permeable. Some embodiments may employ a polyurethane film (for example, Elastollan SP9109) or any other suitable material. For example, certain embodiments may comprise translucent or transparent 30 gsm EU33 film. The cover layer B3410 may have a pressure sensitive adhesive on the lower side, thereby creating a substantially sealed enclosure over the wound in which negative pressure may be established. The cover layer can protect the wound as a bacterial barrier from external contamination, and may allow liquid from wound exudates to be transferred through the layer and evaporated from the film outer surface.

The cover layer B3410 can have an orifice B3411 located so as to underlie the suction port. The orifice B3411 may allow transmission of negative pressure through the cover layer B3410 to the wound enclosure. The port may be adhered and sealed to the cover film using an adhesive such as an acrylic, cyanoacrylate, epoxy, UV curable or hot melt adhesive. Some embodiments may have a plurality of orifices for the attachment of multiple ports or other sources of negative pressure or other mechanisms for distributing fluid.

FIG. 252B illustrates a cross sectional view of the wound dressing B3400, displaying an embodiment of the relative thicknesses of layers of the dressing B3400. In some embodiments, the wound contact layer B3460 may be flat and the top film layer B3410 may be contoured over the inner layers of the dressing B3400. The spacer layer B3450 may be half as thick as the acquisition distribution layer B3440 in some embodiments. In some embodiments, the absorbent layer B3430 may be about 1.5 times thicker than the spacer layer B3450. The obscuring layer B3420 may be about half the thickness of the spacer layer B3450.

FIG. 253 illustrates a perspective exploded view of an embodiment of a flexible port or fluidic connector B3500 that may be used to connect any of the wound dressings described herein to a source of negative pressure. The port B3500 comprises a top layer B3510, a spacer layer B3520, a filter element B3530, a bottom layer B3540, and a conduit B3550. The conduit optionally comprises a connector B3560. The distal end of the port B3500 (the end connectable to the dressing B3400) is depicted as having an enlarged circular shape, although it will be appreciated that any suitable shape may be used and that the distal end need not be enlarged. For example, the distal end can have any of the shapes shown in FIGS. 241A and 241B above. The distal end can also have the shape shown in FIGS. 221A-221C of Provisional Application Ser. No. 61/785,927, filed Mar. 14, 2013, incorporated by reference herein.

The bottom layer B3540 may comprise an elongate bridge portion B3544, an enlarged (e.g., rounded or circular) sealing portion B3545, and an orifice B3541. In some embodiments a plurality of orifices may be provided in the bottom layer. Some embodiments of the rounded sealing portion B3545 may comprise a layer of adhesive, for example a pressure sensitive adhesive, on the lower surface for use in sealing the port B3500 to a dressing. For example, the port may be sealed to the cover layer B3410 of the dressing in FIG. 252. The orifice B3541 in the bottom layer B3540 of the port B3500 may be aligned with the orifice B3411 in the cover layer B3410 of the dressing B3400 in order to transmit negative pressure through the dressing B3400 and into a wound site.

The top layer B3515 may be substantially the same shape as the bottom layer in that it comprises an elongate bridge B3514 and an enlarged (e.g., rounded or circular) portion B3515. The top layer B3515 and the bottom layer B3545 may be sealed together, for example by heat welding. In some embodiments, the bottom layer B3545 may be substantially flat and the top layer B3515 may be slightly larger than the bottom layer B3545 in order to accommodate the height of the spacer layer B3520 and seal to the bottom layer B3545. In other embodiments, the top layer B3515 and bottom layer B3545 may be substantially the same size, and the layers may be sealed together approximately at the middle of the height of the spacer layer B3520. In some embodiments, the elongate bridge portions B3544, B3514 may have a length of 10 cm (or about 10 cm) or more, more preferably a length of 20 cm (or about 20 cm) or more and in some embodiments, may be about 27 cm long. In some embodiments, the elongate bridge portions may have a width of between 1 cm and 4 cm (or between about 1 cm and about 4 cm), and in one embodiment, is about 2.5 cm wide. The ratio of the length of the elongate bridge portions B3544, B3514 to their widths may in some embodiments exceed 6:1, and may more preferably exceed 8:1 or even 10:1. The diameter of the circular portion B3545, B3515 may be about 3.5 cm in some embodiments.

The bottom and top layers may comprise at least one layer of a flexible film, and in some embodiments may be transparent. Some embodiments of the bottom layer B3540 and top layer B3515 may be polyurethane, and may be liquid impermeable.

The port B3500 may comprise a spacer layer B3520, such as the 3D fabric discussed above, positioned between the lower layer B3540 and the top layer B3510. The spacer layer B3520 may be made of any suitable material, for example material resistant to collapsing in at least one direction, thereby enabling effective transmission of negative pressure therethrough. The spacer layer B3520 may comprise an enlarged (e.g., rounded or circular) portion B3525, and may optionally include a fold B3521. In some embodiments, the elongate bridge portion may have dimensions in the same ranges as the bridge portions of the upper and lower layers described above though slightly smaller, and in one embodiment is about 25.5 cm long and 1.5 cm wide. Similarly, the diameter of the circular portion B3525 may be slightly smaller than the diameters of the enlarged ends B3545, B3515, and in one embodiment is about 2 cm. Some embodiments of the spacer layer B3520 may have adhesive on one or both of its proximal and distal ends (e.g., one or more dabs of adhesive) in order to secure the spacer layer B3520 to the top layer B3510 and/or the bottom layer B3540. Adhesive may also be provided along a portion or the entire length of the spacer layer. In other embodiments, the spacer layer B3520 may be freely movable within the sealed chamber of the top and bottom layers.

The fold B3521 of the spacer fabric may make the end of the port B3500 softer and therefore more comfortable for a patient, and may also help prevent the conduit B3550 from blockage. The fold B3521 may further protect the end of the conduit B3550 from being occluded by the top or bottom layers. The fold B3521 may, in some embodiments, be between 1 cm and 3 cm (or between about 1 cm and about 3 cm) long, and in one embodiment is 2 cm (or about 2 cm) long. The spacer fabric may be folded underneath itself, that is toward the bottom layer B3540, and in other embodiments may be folded upward toward the top layer B3510. Other embodiments of the spacer layer B3520 may contain no fold. A slot or channel 3522 may extend perpendicularly away from the proximal end of the fold B3521, and the conduit B3550 may rest in the slot or channel B3522. In some embodiments the slot B3522 may extend through one layer of the fold, and in others it may extend through both layers of the fold. The slot B3522 may, in some embodiments, be 1 cm (or about 1 cm) long. Some embodiments may instead employ a circular or elliptical hole in the fold B3521. The hole may face proximally so that the conduit B3550 may be inserted into the hole and rest between the folded layers of spacer fabric. In some embodiments, the conduit B3550 may be adhered to the material of the fold B3521, while in other embodiments it may not.

The port B3500 may have a filter element B3530 located adjacent the orifice B3541, and as illustrated is located between the lower layer B3540 and the spacer layer B3520. As illustrated, the filter element B3530 may have a round or disc shape. The filter element B3530 is impermeable to liquids, but permeable to gases. The filter element B3530 can act as a liquid barrier, to substantially prevent or inhibit liquids from escaping from the wound dressing, as well as an odor barrier. The filter element B3530 may also function as a bacterial barrier. In some embodiments, the pore size of the filter element B3530 can be approximately 0.2 μm. Suitable materials for the filter material of the filter element include 0.2 micron Gore™ expanded PTFE from the MMT range, PALL Versapore™ B200R, and Donaldson™ TX6628. The filter element B3530 thus enables gas to be exhausted through the orifice. Liquid, particulates and pathogens however are contained in the dressing. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. In some embodiments, the filter element B3530 may be adhered to one or both of top surface of the bottom layer B3540 and the bottom surface of the spacer layer B3520 using an adhesive such as, but not limited to, a UV cured adhesive. In other embodiments, the filter B3530 may be welded to the inside of the spacer layer B3520 and to the top surface of the bottom layer B3540. The filter may also be provided adjacent the orifice on a lower surface of the bottom layer B3540. Other possible details regarding the filter are disclosed in U.S. Patent Pub. No. 2011/0282309 and incorporated by reference herein.

The proximal end of the port B3500 may be connected to the distal end of a conduit B3550. The conduit B3550 may comprise one or more circular ribs B3551. The ribs B3551 may be formed in the conduit B3550 by grooves in a mold during the manufacturing of the conduit. During heat welding of the upper and lower layers B3515, B3545 melted material from those layers may flow around the ribs B3551, advantageously providing a stronger connection between the conduit B3550 and the layers. As a result, it may be more difficult to dislodge the conduit B3550 out from between the layers during use of the port B3500.

The proximal end of the conduit B3550 may be optionally attached to a connector B3560. The connector B3560 may be used to connect the port B3500 to a source of negative pressure, or in some embodiments to an extension conduit which may in turn be connected to a source of negative pressure. The distal end of the conduit B3550, which is inserted into the spacer layer B3520, may be shaped in such a way to reduce the possibility of occlusion.

FIG. 254 illustrates an embodiment of a wound dressing B3610 with a flexible port B3620 such as described with respect to FIG. 253 attached. The port B3620 comprises a conduit 3630 and a connector 3640 for connecting the port to a source of negative pressure or to an extension conduit. The dressing B3610 comprises an obscuring layer with one row of eight holes in a linear arrangement, and is described above in more detail with respect to FIG. 243. Although in this depiction the port B3620 is connected over a circular window in the obscuring layer of the dressing B3610, in other embodiments the port B3620 may be connected over a maltese cross in the obscuring layer. In some embodiments, the maltese cross may be of a larger diameter than the port and may be at least partially viewable after the port is attached to the dressing.

FIG. 255A illustrates a perspective view of an embodiment of the dressing. Although the configuration as depicted is similar to the embodiment of FIG. 29B, the dressing can have any of the constructions of different layers previously described. Conduit B3710 is connected to the dressing B3700 via port B3720, however other embodiments of ports may be connected to the dressing, for example the flexible port of FIG. 253.

FIG. 255B illustrates a bottom view of the dressing B3700. The view illustrates a transmission layer B3730 and an acquisition distribution layer B3740, which may be similar to the transmission layer B3450 and acquisition distribution layer B3440 of FIGS. 252A and 252B. In some embodiments, the perimeter of the transmission layer B3730 may be slightly smaller than the perimeter of the acquisition distribution layer B3740. The view also illustrates one embodiment of a release layer B3750 similar to release layer B3480 previously described for use in protecting the adhesive side of the wound contact layer. The release layer B3750 as illustrated is made of two separate layers of material that can be removed from the adhesive side of the wound contact layer by pulling on flaps attached to the release layer.

FIG. 257A illustrates another embodiment of a wound dressing B3900. The wound dressing may comprise a release layer B3980, wound contact layer B3960, a transmission layer B3950, an acquisition distribution layer B3940, an adhesive layer B3970, an absorbent layer B3930, an obscuring layer B3920, and a backing layer B3910. Although this figure illustrates a dressing having one particular shape, the construction of the layers can be applied to any of the embodiments identified above, including FIGS. 222A-232, 234-240, and 242A-251B. At least the wound contact layer B3960, transmission layer B3950, absorbent layer B3930, obscuring layer B3920, and backing layer B3910 may have properties as described with respect to particular embodiments above, such as the embodiments of FIGS. 221A-240, and 242A-251B, and these layers as well as the acquisition distribution layer B3940 may have properties similar to those described for the layers of the dressing embodiment of FIG. 252A, as well as or instead of the properties described below.

The dressing B3900 may be connected to a port, such as described above with respect to FIGS. 253 and 254 and as illustrated in FIG. 257B (shown without the release layer B3980). At least the backing layer B3910, obscuring layer B3920, absorbent layer B3930, and acquisition distribution layer B3940 may have openings underlying the port B3990, and the port B3990 may comprise a filter element B3995 overlying the openings. In some embodiments, the opening B3921 in the obscuring layer may be cross-shaped. As illustrated, the cross-shaped opening B3921 may comprise four arms of roughly equal length extending outward from a central point of intersection of the arms, wherein the sides of each arm are angled or arced such that the far end of each arm is wider than the end closest to the intersection. The far ends of the four arms may comprise arcs, for example four arcs from a single circle, giving the cross a rounded shape. The opening B3911 in the backing layer B3910, opening B3931 in the absorbent layer B3930, and opening B3941 in the acquisition distribution layer B3940 may be aligned with the central intersection point of the cross-shaped opening B3921. The openings B3911, B3931, and B3941 may be the same size or of varying sizes.

The backing layer B3910 (as well as the backing layer of previously described embodiments) may comprise, in some embodiments, EU33 film and may optionally have a pressure-sensitive adhesive provided on a lower surface thereof. For example, the adhesive may be a water dispersible acrylic adhesive, for example K5. The adhesive may be able to be pattern spread, and may be hydrophilic.

The obscuring layer B3920 may be provided to increase patient comfort by masking the presence of wound exudate absorbed by the inner layers of the dressing. The obscuring layer B3920 may be provided with a plurality of viewing windows B3922 which may be used to assess the spread of exudate across the dressing B3900. The cross-shaped opening B3921 may be used as a viewing window to ascertain the level of saturation of the layer or layers underlying an attached port. The width of the cross-shaped opening B3921 may be greater than the width of an attached port to enable such assessment. Some embodiments of the obscuring layer B3920 (including other embodiments of the obscuring layer previously described) may comprise polypropylene spunbond material of suitable colors such as described above, including medical blue. Further, some embodiments of the obscuring layer B3420 may comprise a hydrophobic additive or coating.

The absorbent layer B3930 may be configured to absorb and retain exudate from a patient's wound. The absorbent layer B3930 will preferably be constructed from a material which has good absorbent qualities under negative pressure. In some embodiments (including any of the earlier described embodiments), the absorbent layer may comprise cellulose fibers or air-laid materials. Some embodiments may comprise a layered construction of an upper layer of non-woven cellulose fibers, superabsorbent particles (SAP), and a lower layer of cellulose fibers with 40-80% SAP. Heat fusible fibers can optionally be used to assist in holding the structure of the absorbent pad together. Some embodiments may combine cellulose fibers and air-laid materials, for example as a hybrid bonded airlaid composite in the range of 400-500 gsm (or about 400 to about 500 gsm), for example 460 (or about 460) gsm. The absorbent layer B3930 may include polyacrylate superabsorber powder to increase the absorbent capabilities of the material. Some embodiments of the absorbent layer B3930 comprise a tissue dispersant layer. This may, in some embodiments, be provided along the lower surface of the layer, resulting in an asymmetric construction of the absorbent layer. The tissue dispersant layer may comprise a heat fusible binder to aid in holding the layer structure together. The tissue dispersant layer may provide the advantage of enabling fluid transport. In some embodiments, the tissue dispersant layer may comprise a hot melt adhesive such as ethylene vinyl acetate (EVA), for example applied as a solution to cellulose fibers of the layer.

The adhesive layer B3970 may bond an upper surface of the acquisition distribution layer B3940 to a lower surface of the absorbent layer B3930. As illustrated, in some embodiments the adhesive layer B3970 may comprise an adhesive web or net. In other embodiments, the adhesive layer B3970 may comprise adhesive tape. Yet other embodiments may employ a hot melt adhesive, for example EVA. In some embodiments the acquisition distribution layer B3940 and the absorbent layer B3930 may be sewn together, and the adhesive layer B3970 may comprise suitable fibers, strands, or threads. Preferred embodiments of the adhesive layer B3970 are hydrophilic so as not to affect the transport of water and/or water-based solutions between the acquisition distribution layer B3940 and absorbent layer B3930. In some embodiments, the adhesive layer may comprise a fine sprinkle of adhesive powder such that the acquisition distribution layer B3940 and absorbent layer B3930 are not bonded together across the entire upper and lower surfaces, respectively, but may be merely tacked together in a number of locations. However, some embodiments of the dressing may be constructed without the use of an adhesive between the acquisition distribution layer B3940 and absorbent layer B3930.

The acquisition distribution layer (ADL) B3940 may be constructed so as to advantageously horizontally wick fluid, such as wound exudate, as it is absorbed upward through the layers of the dressing B3900. Such lateral wicking of fluid may allow maximum distribution of the fluid through the absorbent layer B3930, enabling the absorbent layer B3930 to reach its full holding capacity. Some embodiments of the ADL B3440 (including any embodiments of the ADL previously described) may comprise cellulose in the range of 40-160 gsm (or about 40 to about 160 gsm), for example 80 (or about 80) gsm. The ADL may be constructed from a material which resists compression under the levels of negative pressure commonly applied during negative pressure therapy.

Some embodiments of the dressing B3900 may optionally comprise a spacer or transmission layer B3950. The transmission layer B3950 may comprise a porous material or 3D fabric configured to allow for the passage of fluids therethrough away from the wound site and into the upper layers of the dressing B3400. In particular, the transmission layer B3450 should remain open under the typical pressures that will be applied during negative pressure wound therapy as described above, so that the whole wound site sees an equalized negative pressure. In some embodiments, the acquisition distribution layer B3940 may be sufficient to maintain even transmission of negative pressure throughout the dressing B3900 and the transmission layer B3950 may be excluded.

The dressing B3900 may further comprise a wound contact layer B3960 for sealing the dressing B3900 to the healthy skin of a patient surrounding a wound area. As discussed above with respect to FIG. 252A, the wound contact layer B3960 may comprise flexible polyurethane film, and may be provided with a silicone adhesive on a lower surface thereof. The wound contact layer B3960 may be perforated to allow for the transmission of fluids such as wound exudate therethrough, so that the fluids may be passed through or retained by the inner layers of the dressing B3900. Prior to use, the wound contact layer B3960 may be protected by a protective release layer B3980, which may be provided with at least one set of flaps B3981 for removing or peeling off the release layer B3980.

It will be of course appreciated that other dressing configurations are possible other than a narrow central portion configuration, a three-lobed configuration, a four-lobed configuration, including, for example, hexagonal or circular shaped backing layers for use in dressings. As illustrated in FIGS. 233A-B, these embodiments may also comprise various configurations of slits, described previously, so as to enhance conformability of the dressing in non-planar wounds. Also, as described previously, the absorbent layers of these embodiments may be colored or obscured with an obscuring layer, and optionally provided with one or more viewing windows. Further, the domed ports of these embodiments may also be replaced with one or more fluidic connectors of the type described below in FIGS. 241A-B, and vice versa. Additionally, all features and structures described for wound dressings with the waisted portion configuration can be incorporated into any shape or dressing configuration as described herein.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future. Finally, as used herein and unless otherwise stated, the term approximately is meant to represent a range of +/-10% of the stated value.

What is claimed is:

1. A pump assembly apparatus comprising:
a magnetic circuit comprising a magnet;
an electrically conductive coil;
a diaphragm; and
a valve assembly comprising:
one or more valves configured to control a flow of fluid through the pump assembly,
a first valve member comprising one or more recesses configured to receive the one or more valves therein,
a second valve member, the one or more valves configured to be supported between the first valve member and the second valve member, and
one or more protrusions, wherein at least a portion of the one or more valves is configured to deflect relative to the one or more protrusions to facilitate the flow of fluid through the pump assembly, wherein the one or more protrusions are configured to bias at least the portion of the one or more valves toward an open position that permits the flow of fluid through the one or more valves,
wherein the coil is directly or indirectly coupled with the diaphragm and is configured to move at least a portion of the diaphragm to pump a fluid through the pump assembly.

2. The apparatus of claim 1, wherein the one or more valves comprises a first valve and a second valve, wherein the first valve and the second valve are positioned within the one or more recesses.

3. The apparatus of claim 2, wherein the first valve is preloaded against the first valve member and the second valve is preloaded against the second valve member.

4. The apparatus of claim 1, wherein the first valve member further comprises one or more ports in fluid communication with the one or more recesses.

5. The apparatus of claim 4, wherein the one or more ports comprises an inlet port and an exhaust port.

6. The apparatus of claim 1, wherein the second valve member comprises one or more recesses and one or more ports in fluid communication with the one or more recesses of the second valve member.

7. The apparatus of claim 6, wherein the one or more ports comprises an inlet port and an exhaust port.

8. The apparatus of claim 1, wherein the valve assembly further comprises a barrier separating the one or more recesses.

9. The apparatus of claim 1, wherein the one or more valves comprises a flap portion and a frame portion, the flap portion configured to deflect relative to the frame portion.

10. The apparatus of claim 1, wherein the one or more valves further comprises one or more alignment tabs configured to facilitate positioning of the one or more valves within the one or more recesses.

11. The apparatus of claim 10, wherein the one or more recesses comprises one or more cutouts configured to receive the one or more alignment tabs.

12. The apparatus of claim 1, wherein at least the portion of the one or more valves are configured to transition between the open position and away from the one or more protrusions toward a closed position that inhibits the flow of fluid through the one or more valves.

13. The apparatus of claim 1, wherein the one or more protrusions are disposed between at least a portion of the first valve member and at least a portion of the second valve member.

14. An apparatus for applying negative pressure to a wound, comprising:
a pump operatively coupled to a dressing and configured to apply negative pressure to the wound via the dressing, comprising:
a magnetic circuit comprising a magnet;
an electrically conductive coil;
a diaphragm; and
a valve assembly comprising:
one or more valves configured to control a flow of fluid through the pump assembly,
a first valve member comprising one or more recesses configured to receive the one or more valves therein,
a second valve member, the one or more valves configured to be supported between the first valve member and the second valve member, and
one or more protrusions configured to facilitate the flow of fluid around at least a portion of the one or more valves, wherein the one or more protrusions are configured to bias at least the portion of the one or more valves toward an open position that permits the flow of fluid through the one or more valves, wherein the coil is directly or indirectly coupled with the diaphragm and is configured to move at least a portion of the diaphragm to pump a fluid through the pump assembly.

15. The apparatus of claim 14, wherein the one or more valves comprises a first valve and a second valve, wherein the first valve and the second valve are positioned within the one or more recesses, and wherein the first valve is preloaded against the first valve member and the second valve is preloaded against the second valve member.

16. The apparatus of claim 14, wherein the first valve member further comprises one or more ports in fluid communication with the one or more recesses.

17. The apparatus of claim 16, wherein the one or more ports comprises an inlet port and an exhaust port.

18. The apparatus of claim 14, wherein the second valve member comprises one or more recesses and one or more ports in fluid communication with the one or more recesses of the second valve member.

19. The apparatus of claim 18, wherein the one or more ports comprises an inlet port and an exhaust port.

20. The apparatus of claim 14, wherein the valve assembly further comprises a barrier separating the one or more recesses.

21. The apparatus of claim 14, wherein the one or more valves comprises a flap portion and a frame portion, the flap portion configured to deflect relative to the frame portion.

22. The apparatus of claim 14, wherein the one or more valves further comprises one or more alignment tabs configured to facilitate positioning of the one or more valves within the one or more recesses, and wherein the one or more recesses comprises one or more cutouts configured to receive the one or more alignment tabs.

23. The apparatus of claim 9, wherein the one or more protrusions are located on the frame portion of the one or more valves.

24. The apparatus of claim 21, wherein the one or more protrusions are located on the frame portion of the one or more valves.

25. The apparatus of claim 14, wherein at least the portion of the one or more valves are configured to transition between the open position and away from the one or more protrusions toward a closed position that inhibits the flow of fluid around at least the portion of the one or more valves.

26. The apparatus of claim 14, wherein the one or more protrusions are disposed between at least a portion of the first valve member and at least a portion of the second valve member.

* * * * *